US011178870B2

(12) United States Patent
Umetani et al.

(10) Patent No.: US 11,178,870 B2
(45) Date of Patent: Nov. 23, 2021

(54) PYRIDONE COMPOUNDS AND AGRICULTURAL AND HORTICULTURAL FUNGICIDES CONTAINING THE SAME AS ACTIVE INGREDIENTS

(71) Applicant: MITSUI CHEMICALS AGRO, INC., Tokyo (JP)

(72) Inventors: Hideki Umetani, Ritto (JP); Shun Okaya, Mobara (JP); Hideaki Ikishima, Chiba (JP); Takeshi Fukumoto, Chiba (JP); Akihiro Nishida, Chiba (JP); Masanori Yanagi, Mobara (JP); Ryohei Naito, Kusatsu (JP); Koji Masutomi, Mobara (JP); Tomomi Shirakawa, Ritto (JP); Akane Sakurada, Mobara (JP); Satoshi Yutani, Ratchaburi (TH)

(73) Assignee: MITSUI CHEMICALS AGRO, INC., Chuo (JP)

( * ) Notice: Subject to any disclaimer, the term of this patent is extended or adjusted under 35 U.S.C. 154(b) by 0 days.

(21) Appl. No.: 16/496,701

(22) PCT Filed: Apr. 10, 2018

(86) PCT No.: PCT/JP2018/015142

§ 371 (c)(1),
(2) Date: Sep. 23, 2019

(87) PCT Pub. No.: WO2018/190352

PCT Pub. Date: Oct. 18, 2018

(65) Prior Publication Data

US 2020/0045968 A1 Feb. 13, 2020

(30) Foreign Application Priority Data

Apr. 11, 2017 (JP) ............................ JP2017-078492
Oct. 13, 2017 (JP) ............................ JP2017-199795

(51) Int. Cl.

| | |
|---|---|
| ***A01N 43/653*** | (2006.01) |
| ***A01N 43/10*** | (2006.01) |
| ***A01N 43/40*** | (2006.01) |
| ***A01N 43/50*** | (2006.01) |
| ***A01N 43/56*** | (2006.01) |
| ***A01N 43/76*** | (2006.01) |
| ***C07D 203/04*** | (2006.01) |
| ***C07D 231/12*** | (2006.01) |
| ***C07D 235/00*** | (2006.01) |
| ***C07D 249/08*** | (2006.01) |
| ***C07D 333/22*** | (2006.01) |
| ***C07D 401/04*** | (2006.01) |
| ***C07D 405/04*** | (2006.01) |
| ***C07D 409/04*** | (2006.01) |
| ***C07D 413/04*** | (2006.01) |
| ***C07D 471/10*** | (2006.01) |

(52) U.S. Cl.

CPC ........... *A01N 43/653* (2013.01); *A01N 43/10* (2013.01); *A01N 43/40* (2013.01); *A01N 43/50* (2013.01); *A01N 43/56* (2013.01); *A01N 43/76* (2013.01); *C07D 203/04* (2013.01); *C07D 231/12* (2013.01); *C07D 235/00* (2013.01); *C07D 249/08* (2013.01); *C07D 333/22* (2013.01); *C07D 401/04* (2013.01); *C07D 405/04* (2013.01); *C07D 409/04* (2013.01); *C07D 413/04* (2013.01); *C07D 471/10* (2013.01)

(58) Field of Classification Search

CPC .................................................... A01N 43/653
USPC ...................................................... 546/275.4
See application file for complete search history.

(56) References Cited

U.S. PATENT DOCUMENTS

| | | | | |
|---|---|---|---|---|
| 6,200,982 | B1 * | 3/2001 | Collins | C07D 213/64 514/277 |
| 6,403,596 | B1 | 6/2002 | Liverton et al. | |
| 2001/0018438 | A1 | 8/2001 | Collins et al. | |
| 2002/0156087 | A1 * | 10/2002 | Nuss | C07D 213/74 514/256 |
| 2005/0038010 | A1 | 2/2005 | Cao et al. | |
| 2015/0080362 | A1 | 3/2015 | Branstrom et al. | |
| 2018/0279614 | A1 | 10/2018 | Umetani et al. | |

(Continued)

FOREIGN PATENT DOCUMENTS

| | | | |
|---|---|---|---|
| CL | 2020000886 | A1 | 10/2020 |
| EP | 0308020 | A2 | 3/1989 |
| EP | 3 575 286 | A1 | 12/2019 |

(Continued)

OTHER PUBLICATIONS

Zhang, ACS Appl. Mater. Interfaces 2013, 5, 10953-10959.*

(Continued)

*Primary Examiner* — Nizal S Chandrakumar
(74) *Attorney, Agent, or Firm* — Buchanan, Ingersoll & Rooney PC

(57) ABSTRACT

Pyridine compounds of Formula (1) are provided:

(1)

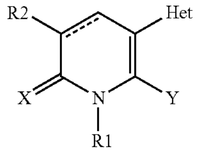

wherein R1, R2, X, Y and Het are defined. The pyridine compounds can be used to treat or prevent plant diseases.

6 Claims, No Drawings

(56) References Cited

U.S. PATENT DOCUMENTS

| | | | |
|---|---|---|---|
| 2019/0210978 | A1 | 7/2019 | Cai et al. |
| 2019/0380340 | A1 | 12/2019 | Umetani et al. |

FOREIGN PATENT DOCUMENTS

| | | | | |
|---|---|---|---|---|
| JP | 01128969 | A | 5/1989 | |
| JP | H01-261371 | A | 10/1989 | |
| JP | 2005530810 | A | 10/2005 | |
| JP | 2014525452 | A | 9/2014 | |
| WO | 9855480 | A1 | 12/1998 | |
| WO | 0100208 | A1 | 1/2001 | |
| WO | WO 2004022540 | * | 3/2004 | ........... C07D 213/73 |
| WO | 2010/093595 | A1 | 8/2010 | |
| WO | 2017061525 | A1 | 4/2017 | |

OTHER PUBLICATIONS

Linda Hall, How Herbicides Work, Biology to Application, 2014.*

Venkatesh, J. Pharm. Sci. 89, 145-154 (2000).*

J. G. Cannon, Chapter Nineteen in Burger's Medicinal Chemistry and Drug Discovery, Fifth Edition, vol. I: Principles and Practice, Wiley-Interscience 1995, pp. 783-802, 784.*

Dorwald (Side Reactions in Organic Synthesis, 2005, Wiley: VCH, Weinheim p. IX of Preface p. 1-15).*

El-Nawawy, Journal of Microbiology of the United Arab Republic (1967), 2(2), 115-33.*

International Search Report (PCT/ISA/210) dated Jun. 12, 2018, by the Japanese Patent Office as the International Searching Authority for International Application No. PCT/JP2018/015142.

Extended European Search Report dated Oct. 30, 2020, by the European Patent Office in corresponding European Patent Application No. 18783750.5. (6 pages).

Office Action dated Nov. 16, 2020, by the Chilean Patent Office in corresponding Chilean Patent Application No. 201902877 and an English translation of the Office Action. (22 pages).

* cited by examiner

PYRIDONE COMPOUNDS AND AGRICULTURAL AND HORTICULTURAL FUNGICIDES CONTAINING THE SAME AS ACTIVE INGREDIENTS

TECHNICAL FIELD

The present invention relates to pyridone compounds and agricultural chemicals containing the compounds as active ingredients.

BACKGROUND ART

The protection of agricultural and horticultural crops from diseases is important to ensure stable agricultural production. Therefore, various fungicides are used for this purpose, but use of fungicides over years causes appearance of fungi resistant to drugs and thus novel fungicides that are effective not only to drug-sensitive fungi but also to drug-resistant fungi are demanded.

By the way, regarding 1,3,5,6-substituted-2-pyridone compounds, for example, 1,3,5,6-substituted-2-pyridone compounds having an aryl group or a heteroaryl group at the 3-position are disclosed as GABA alpha 2/3 ligands (for example, see WO 98/55480). Further, 1,3,5,6-substituted-2-pyridone compounds having a carboxyl group at the 3-position are disclosed as bacterial infection treatment agents (for example, see EP Patent No. 0308020).

CITATION LIST

Patent Literature

Patent Literature 1: WO 98/55480

Patent Literature 2: EP Patent No. 0308020

SUMMARY OF INVENTION

Technical Problem

However, the uses of the compounds disclosed in WO 98/55480 and EP Patent No. 0308020 are each medicine and differ from the technical field to which the agricultural and horticultural fungicides according to the present invention belongs.

An object of the present invention is to provide novel compounds effective as agricultural and horticultural fungicides.

Solution to Problem

To achieve the above object, the present inventors have extensively studied 1,3,5,6-substituted-2-pyridone compounds and a 1,5,6-substituted-2-pyridone compounds and as a result, they have found that novel compounds in which an aryl group or a heteroaryl group each having a substituent at the ortho position is introduced at the 6-position in the 2-pyridone skeleton exhibit an excellent activity in the treatment or prevention of plant diseases, thus completing the present invention.

Specifically, the present invention resides in the following aspects.

[1] A compound represented by Formula (1):

[Chem. 1]

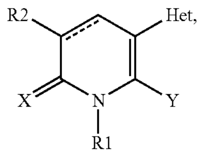

(1)

or a salt thereof
[wherein R1 represents
a hydroxyl group,
a cyano group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group,
or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group);
R2 represents
a hydrogen atom,
a nitro group,
a halogen atom,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A, a C3-C6 haloalkynyloxy group, Rc-L- (wherein Rc represents a C1-C6 alkyl group or a C1-C6 haloalkyl group and L represents S, SO or $SO_2$), or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove));

Het represents a 5 to 6-membered heterocyclic group or a 8 to 10-membered heterocyclic group, and the 5 to 6-membered heterocyclic group or the 8 to 10-membered heterocyclic group is optionally substituted with 0 to 6 substituents R3 (with the proviso that when two or more substituents R3 are present, each R3 represents an independent substituent), R3 represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group), Rx4Rx5C═N—O— (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)), or a 3 to 6-membered ring group containing 1 to 2 oxygen atoms;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, the phenyl group is substituted with R4 at the ortho position and further optionally substituted with 0 to 4 substituents R5 (with the proviso that when two or more substituents R5 are present, each R5 represents an independent substituent), the pyridyl group, the pyridazinyl group, the pyrimidinyl group, the pyrazinyl group, the triazinyl group or the tetrazinyl group is substituted with R4 at the ortho position and further optionally substituted with 0 to 3 substituents R5 (with the proviso that when two or more substituents R5 are present, each R5 represents an independent substituent), the thienyl group, the thiazolyl group, the isothiazolyl group or the thiadiazolyl group is substituted with R4 at the ortho position and further optionally substituted with 0 to 2 substituents R5 (with the proviso that when two substituents R5 are present, each R5 represents an independent substituent), R4 represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group), Rx4Rx5C═N—O— (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)), or a 3 to 6-membered ring group containing 1 to 2 oxygen atoms, R5 is defined the same as R4 described hereinabove;

X represents an oxygen atom or a sulfur atom;

a bond containing the broken line represents a double bond or a single bond;

and the substituent(s) A is at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, RaRbN— (wherein Ra and Rb are the same as defined hereinabove.) and Rc-L- (wherein Rc and L are the same as defined hereinabove);

the substituent(s) B is at least one kind selected from the group consisting of a cyano group, a C1-C6 alkoxy group, a C1-C6 haloalkoxy group and a C3-C8 cycloalkoxy group;

the substituent(s) C is at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), Rx1C(═O)— (wherein Rx1 is the same as defined hereinabove.) and a 3 to 6-membered ring group containing 1 to 2 oxygen atoms; the substituent(s) D is at least one kind selected from the group consisting of a hydroxyl group, a cyano group, a nitro group, a halogen atom, a C1-C6 alkyl group which may be substituted with substituent(s) B, a C1-C6 haloalkyl group, a C3-C8 cycloalkyl group, a C1-C6 alkoxy group, a C1-C6 haloalkoxy group and a C3-C8 cycloalkoxy group.].

[2] The compound or a salt thereof described in [1], wherein Het represents a pyridyl group, a pyridazinyl group, a pyrimidinyl group, a pyrazinyl group, a triazinyl group, a tetrazinyl group, a thienyl group, a thiazolyl group, an isothiazolyl group, a thiadiazolyl group, a thiatriazolyl group, a pyrrolyl group, a pyrazolyl group, an imidazolyl group, a triazolyl group, a tetrazolyl group, a pentazolyl group, a furyl group, an oxazolyl group, an indolyl group, an isoindolyl group, an indazolyl group, a benzimidazolyl group, a benzotriazolyl group, a benzofuryl group, an isobenzofuryl group, a benzoxazolyl group, a benzothienyl group, a benzothiazolyl group, a benzisothiazolyl group, a benzothiadiazolyl group, an indolidinyl group, an imidazopyridyl group, a pyrazolopyridyl group, a triazolopyridyl group, a pyrrolopyrimidinyl group, an imidazopyrimidinyl group, a pyrazolopyrimidinyl group, a triazolopyrimidinyl group, a pyrrolopyrazinyl group, an imidazopyrazinyl group, a pyrazolopyrazinyl group, a triazolopyrazinyl group, a quinolyl group, an isoquinolyl group, a cinnolyl group, a phthalazinyl group, a quinoxalynyl group, a quinazolynyl group, a naphthylidinyl group or a 3 to 6-membered ring group containing 1 to 2 oxygen atoms, the pyridyl group, the pyridazinyl group, the pyrimidinyl group, the pyrazinyl group, the triazinyl group or the tetrazinyl group is optionally substituted with 0 to 4 substituents R3 (with the proviso that when two or more substituents R3 are present, each R3 represents an independent substituent), the thienyl group, the thiazolyl group, the isothiazolyl group, the thiadiazolyl group or the thiatriazolyl group is optionally substituted with 0 to 3 substituents R3 (with the proviso that when two or more substituents R3 are present, each R3 represents an independent substituent), the pyrrolyl group, the pyrazolyl group, the imidazolyl group, the triazolyl group, the tetrazolyl group or the pentazolyl group is optionally substituted with 0 to 4 substituents R3 (with the proviso that when two or more substituents R3 are present, each R3 represents an independent substituent), the furyl group or the oxazolyl group is optionally substituted with 0 to 3 substituents R3 (with the proviso that when two or more substituents R3 are present, each R3 represents an independent substituent), the indolyl group, the isoindolyl group, the indazolyl group, the benzimidazolyl group or the benzotriazolyl group is optionally substituted with 0 to 6 substituents R3 (with the proviso that when two or more substituents R3 are present, each R3 represents an independent substituent), the benzofuryl group, the isobenzofuryl group or the benzoxazolyl group is optionally substituted with 0 to 5 substituents R3 (with the proviso that when two or more substituents R3 are present, each R3 represents an independent substituent), the benzothienyl group, the benzothiazolyl group, the benzisothiazolyl group or the benzothiadiazolyl group is optionally substituted with 0 to 5 substituents R3 (with the proviso that when two or more substituents R3 are present, each R3 represents an independent substituent), the indolidinyl group, the imidazopyridyl group, the pyrazolopyridyl group or the triazolopyridyl group is optionally substituted with 0 to 6 substituents R3 (with the proviso that when two or more substituents R3 are present, each R3 represents an independent substituent), the pyrrolopyrimidinyl group, the imidazopyrimidinyl group, the pyrazolopyrimidinyl group, the triazolopyrimidinyl group, the pyrrolopyrazinyl group, the imidazopyrazinyl group, the pyrazolopyrazinyl group or the triazolopyrazinyl group is optionally substituted with 0 to 5 substituents R3 (with the proviso that when two or more substituents R3 are present, each R3 represents an independent substituent), the quinolyl group, the isoquinolyl group, the cinnolyl group, the phthalazinyl group, the quinoxalynyl group, the quinazolynyl group or the naphthylidinyl group is optionally substituted with 0 to 6 substituents R3 (with the proviso that when two or more substituents R3 are present, each R3 represents an independent substituent).

[3] The compound or a salt thereof described in [2], wherein R1 represents
a C1-C6 alkyl group optionally substituted with substituent(s) A,
a C1-C6 haloalkyl group,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group);
R2 represents
a hydrogen atom,
a halogen atom,
a C1-C6 alkyl group optionally substituted with substituent(s) A,
a C1-C6 haloalkyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C2-C6 alkenyloxy group optionally substituted with substituent(s) A,
a C3-C6 alkynyloxy group optionally substituted with substituent(s) A,
Rc-L- (wherein Rc represents a C1-C6 alkyl group or a C1-C6 haloalkyl group and L represents S, SO or $SO_2$),
or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove));
Het represents
a pyridyl group, a pyridazinyl group, a pyrimidinyl group, a pyrazinyl group, a triazinyl group, a tetrazinyl group, a thienyl group, a thiazolyl group, an isothiazolyl group, a thiadiazolyl group, a thiatriazolyl group, a pyrrolyl group, a pyrazolyl group, an imidazolyl group, a triazolyl group, a tetrazolyl group, a pentazolyl group, a furyl group, an oxazolyl group or a 3 to 6-membered ring group containing 1 to 2 oxygen atoms,
the pyridyl group, the pyridazinyl group, the pyrimidinyl group, the pyrazinyl group, the triazinyl group or the tetrazinyl group is optionally substituted with 0 to 4 substituents R3 (with the proviso that when two or more substituents R3 are present, each R3 represents an independent substituent),
the thienyl group, the thiazolyl group, the isothiazolyl group, the thiadiazolyl group or the thiatriazolyl group is optionally substituted with 0 to 3 substituents R3 (with the proviso that when two or more substituents R3 are present, each R3 represents an independent substituent),
the pyrrolyl group, the pyrazolyl group, the imidazolyl group, the triazolyl group, the tetrazolyl group or the pentazolyl group is optionally substituted with 0 to 4 substituents R3 (with the proviso that when two or more substituents R3 are present, each R3 represents an independent substituent),
the furyl group or the oxazolyl group is optionally substituted with 0 to 3 substituents R3 (with the proviso that when two or more substituents R3 are present, each R3 represents an independent substituent),
R3 represents
a cyano group,
a nitro group,
a halogen atom,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 alkynyl group optionally substituted with substituent(s) C,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C3-C6 alkynyloxy group optionally substituted with substituent(s) C,
RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group),
Rc-L- (wherein Rc and L are the same as defined hereinabove),
Rx1C(═O)— (wherein Rx1 is the same as defined hereinabove),
Rx1C(═O)O— (wherein Rx1 is the same as defined hereinabove),
Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group);
Y represents
a phenyl group or a pyridyl group,
the phenyl group is substituted with R4 at the ortho position and further optionally substituted with 0 to 4 substituents R5 (with the proviso that when two or more substituents R5 are present, each R5 represents an independent substituent),
the pyridyl group is substituted with R4 at the ortho position and further optionally substituted with 0 to 3 substituents R5 (with the proviso that when two or more substituents R5 are present, each R5 represents an independent substituent),
R4 represents
a cyano group,
a nitro group,
a halogen atom,
a C1-C6 alkyl group optionally substituted with substituent(s) C, a C1-C6 haloalkyl group,
a C1-C6 alkoxy group optionally substituted with substituent(s) C,
or C1-C6 haloalkoxy group,
R5 represents
a hydroxyl group,
a cyano group,
a halogen atom,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 alkynyl group optionally substituted with substituent(s) C,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C3-C6 alkynyloxy group optionally substituted with substituent(s) C,
RaRbN— (wherein Ra and Rb are the same as defined hereinabove),
Rc-L- (wherein Rc and L are the same as defined hereinabove),
or Rx1C(═O)O— (wherein Rx1 is the same as defined hereinabove).

[4] The compound or a salt thereof described in [3], wherein R1 represents
a C1-C6 alkyl group optionally substituted with substituent(s) A,
a C1-C6 haloalkyl group,
or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group);
R2 represents
a hydrogen atom,
a halogen atom,
a C1-C6 alkyl group optionally substituted with substituent(s) A,
a C1-C6 haloalkyl group,
a C2-C6 alkynyl group optionally substituted with substituent(s) A,
a C1-C6 alkoxy group optionally substituted with substituent(s) A,
or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove));
Het represents
a pyridyl group, a thienyl group, a pyrrolyl group, a pyrazolyl group, an imidazolyl group, a triazolyl group, a tetrazolyl group, an oxazolyl group or a 3 to 6-membered ring group containing 1 to 2 oxygen atoms,
the pyridyl group is optionally substituted with 0 to 4 substituents R3 (with the proviso that when two or more substituents R3 are present, each R3 represents an independent substituent),
the thienyl group is optionally substituted with 0 to 3 substituents R3 (with the proviso that when two or more substituents R3 are present, each R3 represents an independent substituent),
the pyrrolyl group, the pyrazolyl group, the imidazolyl group, the triazolyl group or the tetrazolyl group is each independently and optionally substituted with 0 to 4 substituents R3 (with the proviso that when two or more substituents R3 are present, each R3 represents an independent substituent),
the oxazolyl group is optionally substituted with 0 to 2 substituents R3 (with the proviso that when two substituents R3 are present, each R3 represents an independent substituent),
R3 represents
a cyano group,
a nitro group,
a halogen atom,
a C1-C6 alkyl group optionally substituted with substituent(s) C,
a C1-C6 haloalkyl group,
a C1-C6 alkoxy group optionally substituted with substituent(s) C,
RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group),
Rx1C(═O)— (wherein Rx1 is the same as defined hereinabove),
Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group);
Y represents
a phenyl group,
the phenyl group is substituted with R4 at the ortho position and further optionally substituted with 0 to 4 substituents R5 (with the proviso that when two or more substituents R5 are present, each R5 represents an independent substituent),
R4 represents
a cyano group,
a nitro group,
a halogen atom,
a C1-C6 alkyl group optionally substituted with substituent(s) C,
a C1-C6 haloalkyl group,
or a C1-C6 alkoxyl group optionally substituted with substituent(s) C,
R5 represents
a hydroxyl group,
a cyano group,
a halogen atom,
a C1-C6 alkyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb are the same as defined hereinabove), Rc-L- (wherein Rc and L are the same as defined hereinabove), or Rx1C(═O)O— (wherein Rx1 is the same as defined hereinabove).

[5] A compound represented by Formula (2)

[Chem. 2]

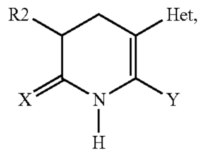

(2)

or a salt thereof

[wherein R2 represents a hydrogen atom, a nitro group, a halogen atom, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc represents a C1-C6 alkyl group or a C1-C6 haloalkyl group and L represents S, SO or $SO_2$), or Rx1C(═O)— (wherein Rx1 represents a hydrogen, atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group));

Het represents a 5 to 6-membered heterocyclic group or a 8 to 10-membered heterocyclic group, and the 5 to 6-membered heterocyclic group or the 8 to 10-membered heterocyclic group is optionally substituted with 0 to 6 substituents R3 (with the proviso that when two or more substituents R3 are present, each R3 represents an independent substituent), R3 represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group), Rx4Rx5C═N—O— (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)), or a 3 to 6-membered ring group containing 1 to 2 oxygen atoms;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, the phenyl group is substituted with R4 at the ortho position and further optionally substituted with 0 to 4 substituents R5 (with the proviso that when two or more substituents R5 are present, each R5 represents an independent substituent), the pyridyl group, the pyridazinyl group, the pyrimidinyl group, the pyrazinyl group, the triazinyl group or the tetrazinyl group is substituted with R4 at the ortho position and further optionally substituted with 0 to 3 substituents R5 (with the proviso that when two or more substituents R5 are present, each R5 represents an independent substituent), the thienyl group, the thiazolyl group, the isothiazolyl group or the thiadiazolyl group is substituted with R4 at the ortho position and further optionally substituted with 0 to 2 substituents R5 (with the proviso that when two R5 are present, each R5 represents an independent substituent), R4 represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group), Rx4Rx5C═N—O— (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)), or a 3 to 6-membered ring group containing 1 to 2 oxygen atoms, R5 is defined the same as R4 described hereinabove;

X represents an oxygen atom or a sulfur atom;

and the substituent(s) A is at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, RaRbN— (wherein Ra and Rb are the same as defined hereinabove.) and Rc-L- (wherein Rc and L are the same as defined hereinabove);

the substituent(s) B is at least one kind selected from the group consisting of a cyano group, a C1-C6 alkoxy group, a C1-C6 haloalkoxy group and a C3-C8 cycloalkoxy group;

the substituent(s) C is at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), Rx1C(═O)— (wherein Rx1 is the same as defined hereinabove.) and a 3 to 6-membered ring group containing 1 to 2 oxygen atoms; the substituent(s) D is at least one kind selected from the group consisting of a hydroxyl group, a cyano group, a nitro group, a halogen atom, a C1-C6 alkyl group which may be substituted with substituent(s) B, a C1-C6 haloalkyl group, a C3-C8 cycloalkyl group, a C1-C6 alkoxy group, a C1-C6 haloalkoxy group and a C3-C8 cycloalkoxy group.].

[6] The compound or a salt thereof described in any one of [1] to [4], wherein R1 represents a C1-C6 alkyl group, a C1-C6 haloalkyl group or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group).

[7] The compound or a salt thereof described in any one of [1] to [4], wherein

R1 represents a methyl group, an ethyl group, a propyl group, a 2-fluoroethyl group, a 2,2-difluoroethyl group, a 2,2,2-trifluoroethyl group, an amino group, a methylamino group, a dimethylamino group, an ethylmethylamino group or a diethylamino group.

[8] The compound or a salt thereof described in any one of [1] to [4], wherein

R1 represents a methyl group, an ethyl group, a 2,2-difluoroethyl group, a 2,2,2-trifluoroethyl group, an amino group, a methylamino group or a dimethylamino group.

[9] The compound or a salt thereof described in any one of [1] to [4] and [6] to [8], wherein R2 represents a hydrogen atom, a halogen atom, a C1-C6 alkyl group optionally substituted with substituent(s) A, a C1-C6 haloalkyl group, a C2-C6 alkynyl group optionally substituted with substituent(s) A or a C1-C6 alkoxy group optionally substituted with substituent(s) A.

[10] The compound or a salt thereof described in any one of [1] to [4] and [6] to [8], wherein R2 represents a hydrogen atom, a fluorine atom, a chlorine atom, a bromine atom, an iodine atom, a methyl group, an ethyl group, a difluoromethyl group, a trifluoromethyl group, a 2,2-difluoroethyl group, a 2,2,2-trifluoroethyl group, an ethynyl group, a 1-propynyl group, a propargyl group, a methoxy group, an ethoxy group, a propyloxy group, an isopropyloxy group, a formyl group, an acetyl group, a methoxyacetyl group, a cyanoacetyl group, a methoxycarbonyl group or an ethoxycarbonyl group.

[11] The compound or a salt thereof described in any one of [1] to [4] and [6] to [8], wherein R2 represents a hydrogen atom, a chlorine atom, a bromine atom, an iodine atom, a methyl group, a difluoromethyl group, a trifluoromethyl group, an ethynyl group or a methoxy group.

[12] The compound or a salt thereof described in any one of [1] to [4] and [6] to [11], wherein Het represents a partial structure represented by Formula (a-1), Formula (a-2), Formula (a-3), Formula (b-1-1), Formula (b-2-1), Formula (c-1-1), Formula (c-1-2), Formula (c-1-3), Formula (c-1-4), Formula (c-1-5), Formula (c-1-6), Formula (c-1-7), Formula (c-1-8), Formula (c-2-1), Formula (c-2-2), Formula (c-2-3), Formula (c-2-4), Formula (c-2-5), Formula (c-2-6), Formula (c-2-7), Formula (c-2-8), Formula (c-3-1), Formula (c-3-2), Formula (c-3-3), Formula (c-3-4), Formula (c-3-5), Formula (c-3-6), Formula (c-3-7), Formula (c-3-8), Formula (d-1-2), Formula (d-1-3), Formula (d-2-2), Formula (n-1-1) or Formula (n-1-2)

[Chem. 3]

(a-1)

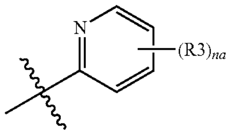

(a-2)

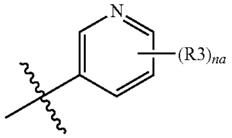

(a-3)

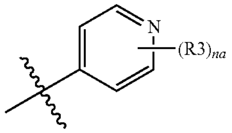

(b-1-1)

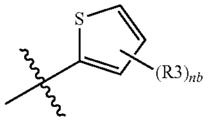

-continued (b-2-1)

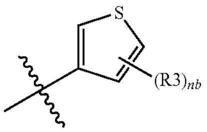

(c-1-1)

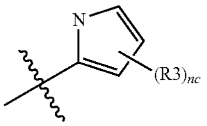

(c-1-2)

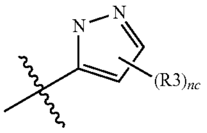

(c-1-3)

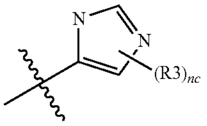

(c-1-4)

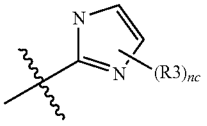

(c-1-5)

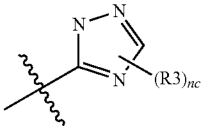

(c-1-6)

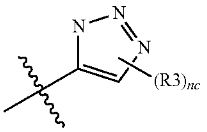

(c-1-7)

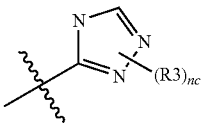

(c-1-8)

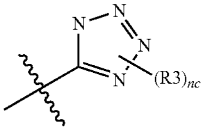

(c-2-1)

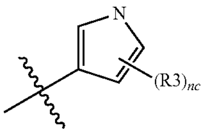

(c-2-2)

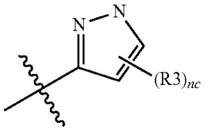

-continued (c-2-3)

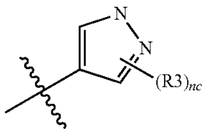

(c-2-4)

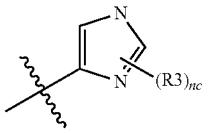

(c-2-5)

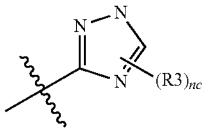

(c-2-6)

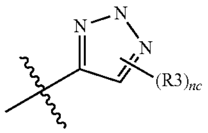

(c-2-7)

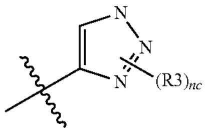

(c-2-8)

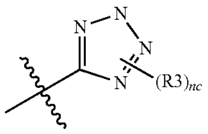

(c-3-1)

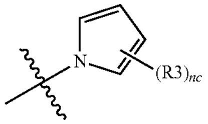

(c-3-2)

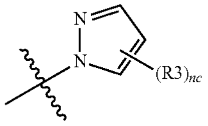

(c-3-3)

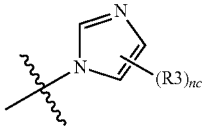

(c-3-4)

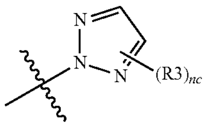

(c-3-5)

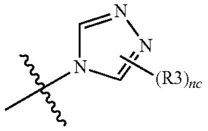

-continued (c-3-6)

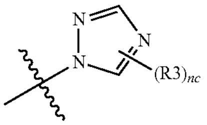

(c-3-7)

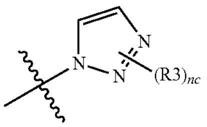

(c-3-8)

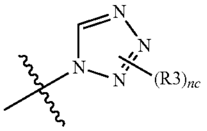

(d-1-2)

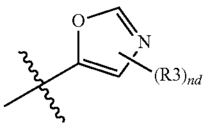

(d-1-3)

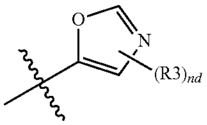

(d-2-2)

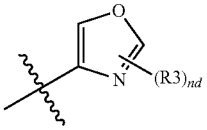

(n-1-1)

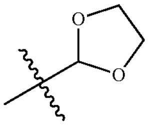

(n-1-2)

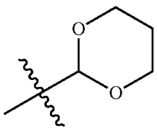

(wherein R3 is the same as defined hereinabove, na represents an integer of 0 to 4, nb represents an integer of 0 to 3, nc represents an integer of 0 to 4 and nd represents an integer of 0 to 2).

[13] The compound or a salt thereof described in any one of [1] to [4] and [6] to [11], wherein Het represents a partial structure represented by Formula (a-1), Formula (a-2), Formula (a-3), Formula (b-1-1), Formula (b-2-1), Formula (c-1-1), Formula (c-1-2), Formula (c-1-3), Formula (c-1-4), Formula (c-2-1), Formula (c-2-2), Formula (c-2-3), Formula (c-2-4), Formula (c-3-1), Formula (c-3-2), Formula (c-3-3), Formula (c-3-4), Formula (c-3-5), Formula (c-3-6), Formula (c-3-8), Formula (d-1-2), Formula (d-1-3), Formula (d-2-2), Formula (n-1-1) or Formula (n-1-2)

[Chem. 4]
(a-1)
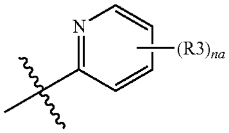
(a-2)
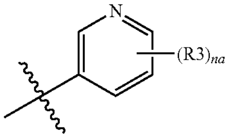
(a-3)
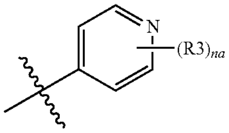
(b-1-1)
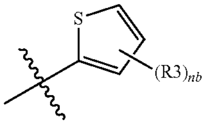
(b-2-1)
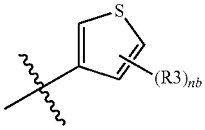
(c-1-1)
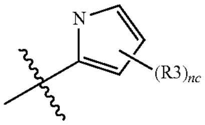
(c-1-2)
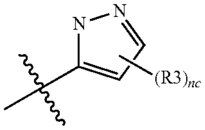
(c-1-3)
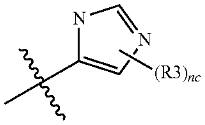
(c-1-4)
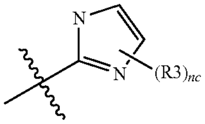
(c-2-1)
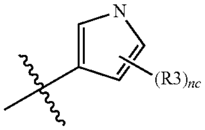
-continued
(c-2-2)
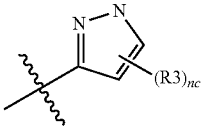
(c-2-3)
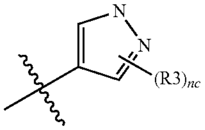
(c-2-4)
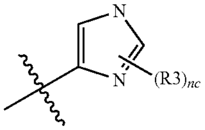
(c-3-1)
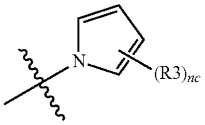
(c-3-2)
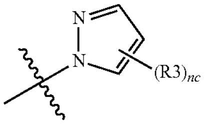
(c-3-3)
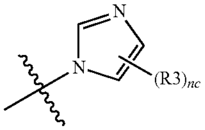
(c-3-4)
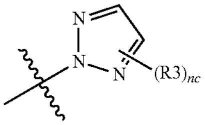
(c-3-5)
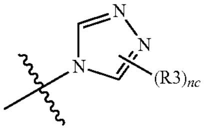
(c-3-6)
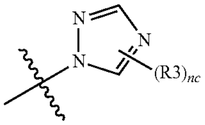
(c-3-8)
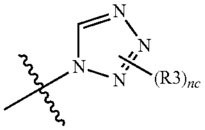
(d-1-2)
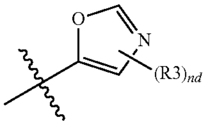
(d-1-3)
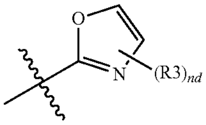

-continued (d-2-2)

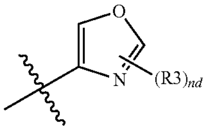

(n-1-1)

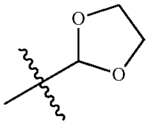

(n-1-2)

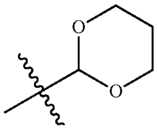

(wherein R3 is the same as defined hereinabove, na represents an integer of 0 to 4, nb represents an integer of 0 to 3, nc represents an integer of 0 to 4 and nd represents an integer of 0 to 2).

[14] The compound or a salt thereof described in any one of [1] to [4] and [6] to [11], wherein Het represents a partial structure represented by Formula (a-1), Formula (a-2), Formula (a-3), Formula (b-1-1), Formula (b-2-1), Formula (c-1-2), Formula (c-1-3), Formula (c-1-4), Formula (c-2-1), Formula (c-2-2), Formula (c-2-3), Formula (c-3-1), Formula (c-3-2), Formula (c-3-3), Formula (c-3-6), Formula (c-3-8), Formula (d-1-2), Formula (d-1-3), Formula (n-1-1) or Formula (n-1-2)

[Chem. 5]

(a-1)

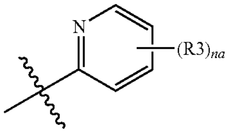

(a-2)

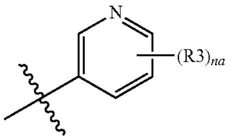

(a-3)

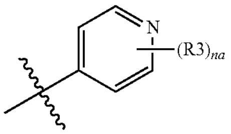

(b-1-1)

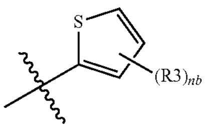

(b-2-1)

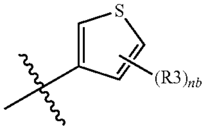

-continued (c-1-2)

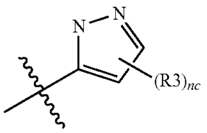

(c-1-3)

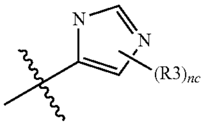

(c-1-4)

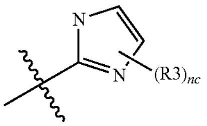

(c-2-1)

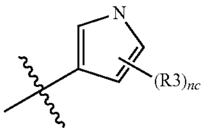

(c-2-2)

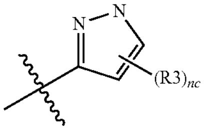

(c-2-3)

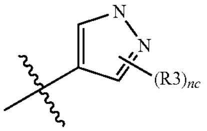

(c-3-1)

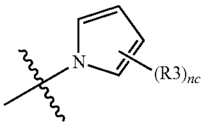

(c-3-2)

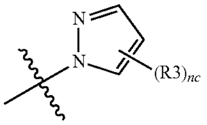

(c-3-3)

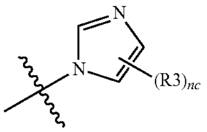

(c-3-6)

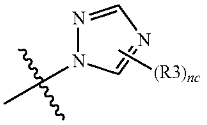

(c-3-8)

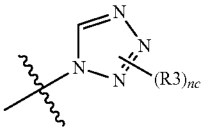

-continued (d-1-2)

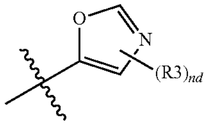

(d-1-3)

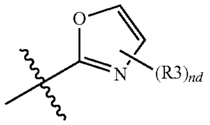

(n-1-1)

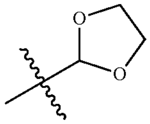

(n-1-2)

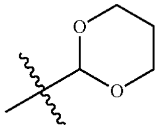

(wherein R3 is the same as defined hereinabove, na represents an integer of 0 to 4, nb represents an integer of 0 to 3, nc represents an integer of 0 to 4 and nd represents an integer of 0 to 2).

[15] The compound or a salt thereof described in any one of [1] to [4] and [6] to [11], wherein Het represents a partial structure represented by Formula (a-2), Formula (b-1-1), Formula (b-2-1), Formula (c-1-2), Formula (c-2-1), Formula (c-2-2), Formula (c-3-1), Formula (c-3-2), Formula (c-3-3), Formula (c-3-6), Formula (c-3-8), Formula (d-1-2), Formula (d-1-3), Formula (n-1-1) or Formula (n-1-2)

[Chem. 6]

(a-2)

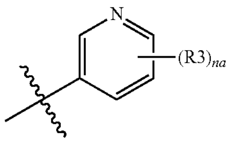

(b-1-1)

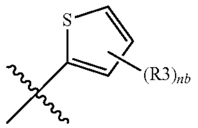

(b-2-1)

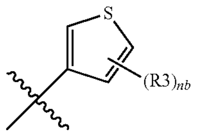

(c-1-2)

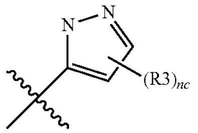

-continued (c-2-1)

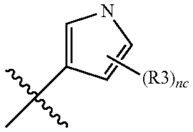

(c-2-2)

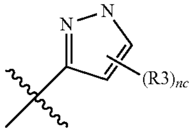

(c-3-1)

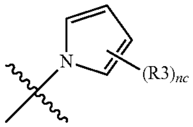

(c-3-2)

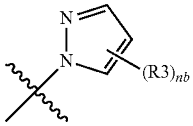

(c-3-3)

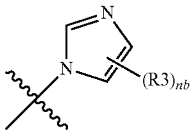

(c-3-6)

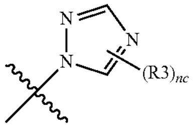

(c-3-8)

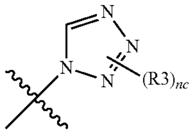

(d-1-2)

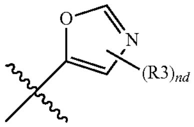

(d-1-3)

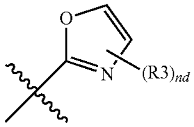

(n-1-2)

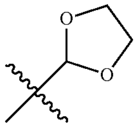

(n-1-2)

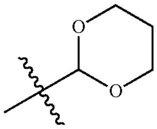

(wherein R3 is the same as defined hereinabove, na represents an integer of 0 to 4, nb represents an integer of 0 to 3, nc represents an integer of 0 to 4 and nd represents an integer of 0 to 2).

[16] The compound or a salt thereof described in any one of [1] to [4] and [6] to [11], wherein Het represents
a partial structure represented by Formula (c-1-2), Formula (c-2-2) or Formula (c-3-2)

[Chem. 7]

(c-1-2)

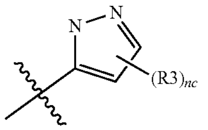

(c-2-2)

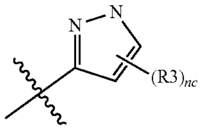

(c-3-2)

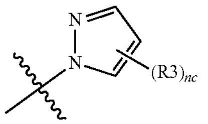

(wherein R3 is the same as defined hereinabove and nc represents an integer of 0 to 3).

[17] The compound or a salt thereof described in any one of [1] to [4] and [6] to [11], wherein Het represents
a partial structure represented by Formula (b-1-1) or Formula (b-2-1)

[Chem. 8]

(b-1-1)

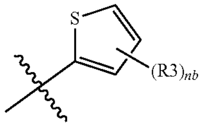

(b-2-1)

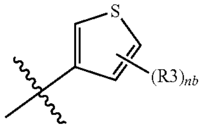

(wherein R3 is the same as defined hereinabove and nb represents an integer of 0 to 3).

[18] The compound or a salt thereof described in any one of [1] to [4] and [6] to [17], wherein R3 represents
a cyano group, a nitro group, a halogen atom, a C1-C6 alkyl group optionally substituted with substituent(s) C, a C1-C6 haloalkyl group, a C1-C6 alkoxy group optionally substituted with substituent(s) C, RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group.) or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)).

[19] The compound or a salt thereof described in any one of [1] to [4] and [6] to [17], wherein R3 represents
a cyano group, a nitro group, a fluorine atom, a chlorine atom, a bromine atom, an iodine atom, a methyl group, an ethyl group, a propyl group, a monobromomethyl group, a difluoromethyl group, a trifluoromethyl group, a 2,2-difluoroethyl group, a 2,2,2-trifluoroethyl group, a methoxy group, an ethoxy group, a propyloxy group, an isopropyloxy group, an amino group, a methylamino group, a dimethylamino group, an ethylmethylamino group, a diethylamino group, a formyl group, an acetyl group, a methoxyacetyl group, a cyanoacetyl group, a propionyl group, a methoxycarbonyl group, an ethoxycarbonyl group or an acetylamide group.

[20] The compound or a salt thereof described in any one of [1] to [4] and [6] to [17], wherein R3 represents
a cyano group, a nitro group, a fluorine atom, a chlorine atom, a bromine atom, an iodine atom, a methyl group, a monobromomethyl group, a difluoromethyl group, a trifluoromethyl group, a methoxy group, an amino group, a methylamino group, a dimethylamino group, a formyl group or an ethoxycarbonyl group.

[21] The compound or a salt thereof described in any one of [1] to [4], [6] to [15] and [18] to [20], wherein Het represents
an oxazol-5-yl group, a 4-methoxy-oxazol-5-yl group, a 4-methyl-oxazol-5-yl group, a 4-iodo-oxazol-5-yl group, a 4-fluoro-oxazol-5-yl group, a 4-chloro-oxazol-5-yl group, a 4-bromo-oxazol-5-yl group, a 2-methoxy-oxazol-5-yl group, a 2-methylamino-oxazol-5-yl group, a 2-dimethylamino-oxazol-5-yl group, a 2-iodo-oxazol-5-yl group, a 2-amino-oxazol-5-yl group, a 2-chloro-oxazol-5-yl group, a 2,4-diiodo-oxazol-5-yl group, a 2,4-dichloro-oxazol-5-yl group, a 2,4-dibromo-oxazol-5-yl group, a 5-methoxy-oxazol-2-yl group, a thiophen-2-yl group, a 5-chloro-thiophen-2-yl group, a thiophen-3-yl group, a 2-chloro-thiophen-3-yl group, a 2-bromo-thiophen-3-yl group, a 2,5-dichloro-thiophen-3-yl group, a 3-methyl-thiophen-2-yl group, a 3-chloro-thiophen-2-yl group, a 3-bromo-thiophen-2-yl group, a 3,5-dichloro-thiophen-2-yl group, a 5-bromo-3-chloro-thiophen-2-yl group, a 5-bromo-3-methyl-thiophen-2-yl group, a 3,5-dibromo-thiophen-2-yl group, a 3-bromo-5-chloro-thiophen-2-yl group, a 2-methyl-thiophen-3-yl group, a 2,5-dibromo-thiophen-3-yl group, a 2-bromo-5-chloro-thiophen-3-yl group, a 5-bromo-2-chloro-thiophen-3-yl group, a 5-bromo-2-methyl-thiophen-3-yl group, a 5-bromo-2-bromomethyl-thiophen-3-yl group, a 1H-1,2,4-triazol-1-yl group, a 5-iodo-1H-1,2,4-triazol-1-yl group, a 5-bromo-1H-1,2,4-triazol-1-yl group, a 3-chloro-1H-1,2,4-triazol-1-yl group, a 5-ethoxycarbonyl-1H-imidazol-1-yl group, a 4,5-dichloro-1H-imidazol-1-yl group, a 2,4,5-trichloro-1H-imidazol-1-yl group, a 3-cyano-1H-pyrrol-4-yl group, a 1H-pyrrol-1-yl group, a 2,5-dimethyl-1H-pyrrol-1-yl group, a 2,5-dichloro-1H-pyrrol-1-yl group, a 1H-tetrazol-1-yl group, a 2-chloro-pyridin-3-yl group, a 1,3-dioxolan-2-yl group, a 1,3-dioxan-2-yl group, a 1H-pyrazol-1-yl group, a 5-chloro-4-methyl-1H-pyrazol-1-yl group, a 5-bromo-4-methyl-H-pyrazol-1-yl group, a 4-nitro-1H-pyrazol-1-yl group, a 4-methoxy-1H-pyrazol-1-yl group, a 4-methyl-1H-pyrazol-1-yl group, a 4-iodo-1H-pyrazol-1-yl group, a 4-formyl-1H-pyrazol-1-yl group, a 4-trifluoromethyl-1H-pyrazol-1-yl group, a 4-difluoromethyl-1H-pyrazol-1-yl group, a 4-fluoro-1H-pyrazol-1-yl group, a 4-chloro-1H-pyrazol-1-yl group, a 4-bromo-1 I-pyrazol-1-yl group, a 4-acetylamino-1H-pyrazol-1-yl group, a 4-chloro-3-methyl-1H-pyrazol-1-yl group, a 4-chloro-3,5-dimethyl-1H-pyrazol-1-yl group, a 4-bromo-3-methyl-1H-pyrazol-1-yl group, a 4-bromo-3,5-dimethyl-1H-pyrazol-1-yl group, a 3,5-dimethyl-1H-pyrazol-1-yl group, a 3,4-dimethyl-1H-pyrazol-1-yl group, a 4-bromo-1-methyl-1H-pyrazol-3-yl group, a 1,4-dimethyl-1H-pyrazol-3-yl group, a 1-methyl-1H-pyrazol-5-yl group, a 4-chloro-1-methyl-1H-pyrazol-5-yl group or a 4-bromo-1-methyl-1H-pyrazol-5-yl group.

[22] The compound or a salt thereof described in any one of [1] to [4], [6] to [16] and [18] to [20], wherein Het represents a 1H-pyrazol-1-yl group, a 5-chloro-4-methyl-1H-pyrazol-1-yl group, a 5-bromo-4-methyl-1H-pyrazol-1-yl group, a 4-nitro-1H-pyrazol-1-yl group, a 4-methoxy-1H-pyrazol-1-yl group, a 4-methyl-1H-pyrazol-1-yl group, a 4-iodo-1H-pyrazol-1-yl group, a 4-formyl-1H-pyrazol-1-yl group, a 4-trifluoromethyl-1H-pyrazol-1-yl group, a 4-difluoromethyl-1H-pyrazol-1-yl group, a 4-fluoro-1H-pyrazol-1-yl group, a 4-chloro-1H-pyrazol-1-yl group, a 4-bromo-1H-pyrazol-1-yl group, a 4-acetylamino-1H-pyrazol-1-yl group, a 4-chloro-3-methyl-1H-pyrazol-1-yl group, a 4-chloro-3,5-dimethyl-1H-pyrazol-1-yl group, a 4-bromo-3-methyl-1H-pyrazol-1-yl group, a 4-bromo-3,5-dimethyl-1H-pyrazol-1-yl group, a 3,5-dimethyl-1H-pyrazol-1-yl group, a 3,4-dimethyl-1H-pyrazol-1-yl group, a 4-bromo-1-methyl-1H-pyrazol-3-yl group, a 1,4-dimethyl-1H-pyrazol-3-yl group, a 1-methyl-1H-pyrazol-5-yl group, a 4-chloro-1-methyl-1H-pyrazol-5-yl group or a 4-bromo-1-methyl-1H-pyrazol-5-yl group.

[23] The compound or a salt thereof described in any one of [1] to [4], [6] to [15] and [17] to [20], wherein Het represents a thiophen-2-yl group, a 5-chloro-thiophen-2-yl group, a thiophen-3-yl group, a 2-chloro-thiophen-3-yl group, a 2-bromo-thiophen-3-yl group, a 2,5-dichloro-thiophen-3-yl group, a 3-methyl-thiophen-2-yl group, a 3-chloro-thiophen-2-yl group, a 3-bromo-thiophen-2-yl group, a 3,5-dichloro-thiophen-2-yl group, a 5-bromo-3-chloro-thiophen-2-yl group, a 5-bromo-3-methyl-thiophen-2-yl group, a 3,5-dibromo-thiophen-2-yl group, a 3-bromo-5-chloro-thiophen-2-yl group, a 2-methyl-thiophen-3-yl group, a 2,5-dibromo-thiophen-3-yl group, a 2-bromo-5-chloro-thiophen-3-yl group, a 5-bromo-2-chloro-thiophen-3-yl group, a 5-bromo-2-methyl-thiophen-3-yl group, a or 5-bromo-2-bromomethyl-thiophen-3-yl group.

[24] The compound or a salt thereof described in any one of [1] to [4] and [6] to [23], wherein Y represents a partial structure represented by Formula (k-1), Formula (k-2), Formula (k-3), Formula (k-4), Formula (k-5) or Formula (k-6)

[Chem. 9]

(k-1)

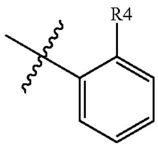

(k-2)

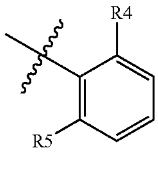

-continued (k-3)

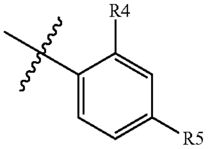

(k-4)

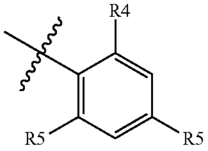

(k-5)

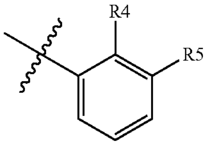

(k-6)

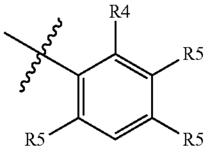

[25] The compound or a salt thereof described in any one of [1] to [4] and [6] to [23], wherein Y represents a partial structure represented by Formula (k-1), Formula (k-2), Formula (k-3), Formula (k-4) or Formula (k-6)

[Chem. 10]

(k-1)

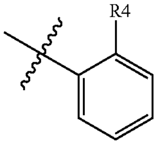

(k-2)

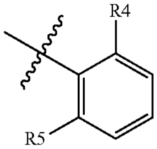

(k-3)

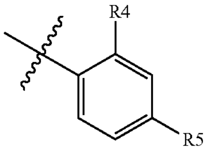

(k-4)

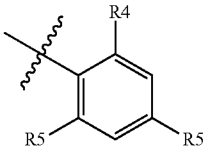

-continued

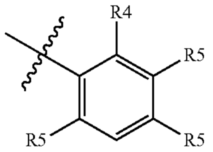

(k-6)

[26] The compound or a salt thereof described in any one of [l] to [4] and [6] to [25], wherein R4 represents a cyano group, a halogen atom, a C1-C6 alkyl group optionally substituted with substituent(s) C, a C1-C6 haloalkyl group or a C1-C6 alkoxyl group optionally substituted with substituent(s) C.

[27] The compound or a salt thereof described in any one of [1] to [4] and [6] to [25], wherein R4 represents a cyano group, a nitro group, a fluorine atom, a chlorine atom, a bromine atom, an iodine atom, a methyl group, an ethyl group, a propyl group, a difluoromethyl group, a trifluoromethyl group, a methoxy group or an ethoxy group.

[28] The compound or a salt thereof described in any one of [1] to [4] and [6] to [25], wherein R4 represents a cyano group, a fluorine atom, a chlorine atom, a bromine atom, a methyl group, an ethyl group, a trifluoromethyl group, a methoxy group.

[29] The compound or a salt thereof described in any one of [1] to [4] and [6] to [28], wherein R5 represents a hydroxyl group, a cyano group, a halogen atom, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group), Rc-L- (wherein Rc represents a C1-C6 alkyl group or a C1-C6 haloalkyl group and L represents S, SO or $SO_2$.) or Rx1C(═O)O— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)).

[30] The compound or a salt thereof described in any one of [1] to [4] and [6] to [28], wherein R5 represents a hydroxyl group, a cyano group, a fluorine atom, a chlorine atom, a bromine atom, an iodine atom, a methyl group, an ethyl group, a methoxy group, an ethoxy group, a propyloxy group, an isopropyloxy group, a cyanomethoxy group, a methoxymethoxy group, a methoxyethoxy group, a vinyloxy group, a 1-propenyloxy group, an allyloxy group, a propargyloxy group, a 2-butynyloxy group, an amino group, a methylamino group, a dimethylamino group, an ethylmethylamino group, a diethylamino group, a pyrrolidinyl group, a piperidinyl group, a methylthio group, a methanesulfinyl group, a methanesulfonyl group, an acetyloxy group, a methoxyacetyloxy group, a cyanoacetyloxy group, a difluoroacetyloxy group, a trifluoroacetyloxy group, a methoxycarbonyloxy group, an ethoxycarbonyloxy group, an aminocarbonyloxy group, a dimethylaminocarbonyloxy group, an ethylmethylaminocarbonyloxy group or a diethylaminocarbonyloxy group.

[31] The compound or a salt thereof described in any one of [1] to [4] and [6] to [28], wherein R5 represents a hydroxyl group, a cyano group, a fluorine atom, an iodine atom, a methoxy group, an ethoxy group, a methoxymethoxy group, a methoxyethoxy group, allyloxy group, a propargyloxy group, a methylamino group, a pyrrolidinyl group, a piperidinyl group, a methylthio group or an acetyloxy group.

[32] The compound or a salt thereof described in any one of [1] to [4] and [6] to [23], wherein Y represents a 2,6-difluoro-phenyl group, a 2,4,6-trifluoro-phenyl group, a 2,6-difluoro-4-methoxy-phenyl group, a 2-chloro-4-fluoro-phenyl group, a 2-chloro-4-methoxy-phenyl group, a 2,6-difluoro-4-(methylamino)-phenyl group, a 2,4-difluoro-phenyl group, a 2-fluoro-4-methoxy-phenyl group, a 2-bromo-4-fluoro-phenyl group, a 2-bromo-4-methoxy-phenyl group, a 4-fluoro-2-methyl-phenyl group, a 2-chloro-phenyl group, a 2-bromo-phenyl group, a 2,6-difluoro-4-hydroxy-phenyl group, a 2-chloro-6-fluoro-phenyl group, a 2,6-difluoro-4-ethoxy-phenyl group, a 2,6-difluoro-4-(propargyloxy)-phenyl group, a 2,6-difluoro-4-(allyloxy)-phenyl group, a 2,6-difluoro-4-(methoxymethoxy)-phenyl group, a 2,6-difluoro-4-(2-methoxyethoxy)-phenyl group, a 2,6-difluoro-4-(acetyloxy)-phenyl group, a 2-bromo-6-fluoro-phenyl group, a 2-fluoro-phenyl group, a 2-methyl-phenyl group, a 2-methoxy-phenyl group, a 2,6-difluoro-3-iodo-4-methoxy-phenyl group, a 2-nitro-phenyl group, a 4-cyano-2-fluoro-phenyl group, a 2-ethyl-phenyl group, a 2-fluoro-4-(methylamino)-phenyl group, a 2-trifluoromethyl-phenyl group, a 2-fluoro-4-(methylthio)-phenyl group, a 2-fluoro-4-(pyrrolidin-1-yl)-phenyl group, a 2-fluoro-4-(piperidin-1-yl)-phenyl group, a 2-cyano-phenyl group, a 4-bromo-2-fluoro-phenyl group or a 2-cyano-4-fluoro-phenyl group.

[33] The compound or a salt thereof described in any one of [1] to [4] and [6] to [32], wherein X is an oxygen atom.

[34] The compound or a salt thereof described in any one of [1] to [4] and [6] to [32], wherein X is a sulfur atom.

[35] The compound or a salt thereof described in any one of [1] to [4] and [6] to [34], wherein the bond containing the broken line is a double bond.

[36] The compound or a salt thereof described in any one of [1] to [4] and [6] to [34], wherein the bond containing the broken line is a single bond.

[37] An agricultural and horticultural pest control agent containing the compound or a salt thereof described in [1] to [4] and [6] to [36] as an active ingredient.

[38] An agricultural and horticultural fungicide containing the compound or a salt thereof described in [1] to [4] and [6] to [36] as an active ingredient.

[39] A method for preventing and/or treating a plant disease, which comprises applying the agricultural and horticultural pest control agent described in [37] to a plant, a plant seed or a soil for plant cultivation.

[40] A method for preventing and/or treating a plant disease, which comprises applying the agricultural and horticultural fungicide described in [38] to a plant, a plant seed or a soil for plant cultivation,

[41] Use of the compound described in any one of [1] to [4] and [6] to [36] as an agricultural and horticultural pest control agent.

[42] Use of the compound described in any one of [1] to [4] and [6] to [36] as an agricultural and horticultural fungicide.

Advantageous Effects of Invention

According to the present invention, novel compounds effective as agricultural and horticultural fungicides can be provided.

DESCRIPTION OF EMBODIMENTS

Hereinbelow, embodiments for carrying out the present invention will be described in detail.

The terminologies used in the claims and the specification are understood in accordance with the definitions which are generally used in the art unless otherwise specified.

In the present specification, the abbreviations used are explained below.

DMF: N,N-dimethylformamide, THF: tetrahydrofuran, Me: methyl group, Et: ethyl group, Pr: propyl group, Bu: butyl group, Ac: acetyl group, Ph: phenyl group, Py: pyridyl group, Thio: thienyl group, Pyrrolyl: pyrrolyl group, Pyra: pyrazolyl group, Imida: imidazolyl group, Triazolyl: triazolyl group, Tetrazolyl: tetrazolyl group, Oxa: oxazolyl group, i: iso, sec: secondary, t: tertiary, =: double bond and ≡: triple bond. In the columns in the tables, Pr and Bu used without any prefix indicate that the respective groups have a normal form.

The definitions of the terminologies used in the present specification will be explained below.

The expression Cx-Cy means that the number of carbon atoms that are possessed range from x to y. Here, x and y each represent an integer and are also understood to disclose all individual integers between x and y inclusive. For example, C1-C6 means that the number of carbon atoms that are possessed is 1, 2, 3, 4, 5 or 6; C2-C6 means that the number of carbon atoms that are possessed is 2, 3, 4, 5 or 6; C3-C8 means that the number of carbon atoms that are possessed is 3, 4, 5, 6, 7 or 8; C3-C6 means that the number of carbon atoms that are possessed is 3, 4, 5 or 6; and C1-C3 means that the number of carbon atoms that are possessed is 1, 2 or 3.

The terms "optionally substituted" means it is to be substituted or unsubstituted. When this terms are used and a number of the substituent(s) is not clearly shown, the number of the substituent(s) indicates to be 1. On the other hand, for example, when a number of the substituent(s) is designated to as "optionally substituted with 0 to 6", it is to be understood to disclose all individual integers between 0 to 6 inclusive. That is, it means that a number of substituent(s) is 0, 1, 2, 3, 4, 5 or 6. Similarly, "optionally substituted with 0 to 5" means that a number of substituent(s) is 0, 1, 2, 3, 4 or 5; "optionally substituted with 0 to 4" means that a number of substituent(s) is 0, 1, 2, 3 or 4; "optionally substituted with 0 to 3" means that a number of substituent(s) is 0, 1, 2 or 3; and "optionally substituted with 0 to 2" means that a number of substituent(s) of 0, 1 or 2.

C1-C6 alkyl group may be a linear or branched and may include a methyl group, an ethyl group, a propyl group, an isopropyl group, a butyl group, an isobutyl group, a sec-butyl group, a t-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a 1-isopropylpropyl group, a 1,1,2-trimethylpropyl group, a, 1,2,2-trimethylpropyl group and the like.

The halogen atom may include a fluorine atom, a chlorine atom, a bromine atom, an iodine atom and the like.

The C1-C6 haloalkyl group represents a group resulting from the substitution of the above-mentioned C11-C6 alkyl group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C1-C6 haloalkyl group may include a monofluoromethyl group, a difluoromethyl group, a trifluoromethyl group, a monochloromethyl group, a monobromomethyl group, a monoiodomethyl group, a chlorodifluoromethyl group, a bromodifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2-tetrafluoroethyl group, a pentafluoroethyl group, a 2,2,2-trichloroethyl group, a 3,3-difluoropropyl group, a 3,3,3-trifluoropropyl group, a heptafluoropropyl group, a heptafluoroisopropyl group, a 2,2,2-trifluoro-1-(trifluoromethyl)ethyl group, a nonafluorobutyl group, a nonafluoro-sec-butyl group, a 3,3,4,4,5,5,5-heptafluoropentyl group, a undecafluoropentyl group, a tridecafluorohexyl group and the like.

The C3-C8 cycloalkyl group includes a cyclopropyl group, a cyclobutyl group, a cyclopentyl group, a cyclohexyl group, a cycloheptyl group, a cyclooctyl group and the like.

The C2-C6 alkenyl group represents a linear or branched, unsaturated hydrocarbon group having 1 or 2 or more double bonds. When the group has geometric isomeric forms, the group may be either one of the E-isomer or the Z-isomer, or may be a mixture of the E-isomer and the Z-isomer in an appropriate ratio without limitation as long as the number of carbon atoms falls in the designated range. Specific examples of the C2-C6 alkenyl group may include a vinyl group, a 1-propenyl group, an allyl group, a 1-butenyl group, a 2-butenyl group, a 3-butenyl group, a 1-pentenyl group, a 2-pentenyl group, a 3-pentenyl group, a 4-pentenyl group, a 3-methyl-2-butenyl group, a 1-hexenyl group, a 2-hexenyl group, a 3-hexenyl group, a 4-hexenyl group, a 5-hexenyl group, a 4-methyl-3-pentenyl group, a 3-methyl-2-pentenyl group and the like.

The C2-C6 haloalkenyl group represents a group resulting from the substitution of the above-mentioned C2-C6 alkenyl group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C2-C6 haloalkenyl group may include a 2-fluorovinyl group, a 2,2-difluorovinyl group, a 2,2-dichlorovinyl group, a 3-fluoroallyl group, a 3,3-difluoroallyl group, a 3,3-dichloroallyl group, a 4,4-difluoro-3-butenyl group, a 5,5-difluoro-4-pentenyl group, a 6,6-difluoro-5-hexenyl group and the like.

The C2-C6 alkynyl group represents a linear or branched, unsaturated hydrocarbon group having 1 or 2 or more triple bonds. Specific examples of the C2-C6 alkynyl group may include an ethynyl group, a 1-propynyl group, a propargyl group, a 1-butynyl group, a 2-butynyl group, a 3-butynyl group, a 1-pentynyl group, a 2-pentynyl group, a 3-pentynyl group, a 4-pentynyl group, a 1,1-dimethyl-2-propynyl group, a 1-hexynyl group, a 2-hexynyl group, a 3-hexynyl group, a 4-hexynyl group, a 5-hexynyl group and the like.

The C2-C6 haloalkynyl group represents a group resulting from the substitution of the above-mentioned C2-C6 alkynyl group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C2-C6 haloalkynyl group may include a 2-fluoroethynyl group, a 2-chloroethynyl group, a 2-bromoethynyl group, a 2-iodoethynyl group, a 3,3-difluoro-1-propynyl group, a 3-chloro-3,3-difluoro-1-propynyl group, a 3-bromo-3,3-difluoro-1-propynyl group, a 3,3,3-trifluoro-1-propynyl group, a 4,4-difluoro-1-butynyl group, a 4,4-difluoro-2-butynyl group, a 4-chloro-4,4-difluoro-1-butynyl group, a 4-chloro-4,4-difluoro-2-butynyl group, a 4-bromo-4,4-difluoro-1-butynyl group, a 4-bromo-4,4-difluoro-2-butynyl group, a 4,4,4-trifluoro-1-butynyl group, a 4,4,4-trifluoro-2-butynyl group, a 5,5-difluoro-3-pentynyl group, a 5-chloro-5,5-difluoro-3-pentynyl group, a 5-bromo-5,5-difluoro-3-pentynyl group, a 5,5,5-trifluoro-3-pentynyl group, a 6,6-difluoro-4-hexynyl group, a 6-chloro-6,6-difluoro-4-hexynyl group, a 6-bromo-6,6-difluoro-4-hexynyl group, a 6,6,6-trifluoro-4-hexynyl group and the like.

The C1-C6 alkoxy group represents a combination of the above-mentioned C1-C6 alkyl group and an oxygen atom as a bonding site. Specific examples of the C1-C6 alkoxy group may include a methoxy group, an ethoxy group, a propyloxy group, an isopropyloxy group, a butoxy group, an isobutoxy group, a sec-butoxy group, a t-butoxy group, a pentyloxy group, an isopentyloxy group, a 1-methylbutoxy group, a 2-methylbutoxy group, a neopentyloxy group, a 1-ethylpropyloxy group, a 1,2-dimethylpropyloxy group, a hexyloxy group, a 1-methylpentyloxy group, a 2-methylpentyloxy group, a 3-methylpentyloxy group, a 4-methylpentyloxy group, a 1,1-dimethylbutoxy group, a 2,2-dimethylbutoxy group, a 3,3-dimethylbutoxy group, a 1,2-dimethylbutoxy group, a 1,3-dimethylbutoxy group, a 2,3-dimethylbutoxy group, a 2-ethylbutoxy group, a 1-isopropylpropyloxy group, a 1,1,2-trimethylpropyloxy group, a 1,2,2-trimethylpropyloxy group and the like.

The C1-C6 haloalkoxy group represents a group resulting from the substitution of the above-mentioned C1-C6 alkoxy group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C1-C6 haloalkoxy group may include a difluoromethoxy group, a trifluoromethoxy group, a chlorodifluoromethoxy group, a bromodifluoromethoxy group, a 2-fluoroethoxy group, a 2,2-difluoroethoxy group, a 2,2,2-trifluoroethoxy group, a 1,1,2,2-tetrafluoroethoxy group, a pentafluoroethoxy group, a 2,2,2-trichloroethoxy group, a 3,3-difluoropropyloxy group, a 3,3,3-trifluoropropyloxy group, a heptafluoropropyloxy group, a heptafluoroisopropyloxy group, a 2,2,2-trifluoro-1-(trifluoromethyl)-ethoxy group, a nonafluorobutoxy group, a nonafluoro-sec-butoxy group, a 3,3,4,4,5,5,5-heptafluoropentyloxy group, a undecafluoropentyloxy group, a tridecafluorohexyloxy group and the like.

The C3-C8 cycloalkoxy group represents a combination of the above-mentioned C3-C8 cycloalkyl group and an oxygen atom as a bonding site. Specific examples of the C3-C8 cycloalkoxy group may include a cyclopropyloxy group, a cyclobutoxy group, a cyclopentyloxy group, a cyclohexyloxy group, a cycloheptyloxy group, a cyclooctyloxy group and the like.

The C2-C6 alkenyloxy group represents a combination of the above-mentioned C2-C6 alkenyl group and an oxygen atom as a bonding site. When the group has geometric isomeric forms, the group may be either one of the E-isomer or the Z-isomer, or may be a mixture of the E-isomer and the Z-isomer in an appropriate ratio without limitation as long as the number of carbon atoms falls in the designated range. Specific examples of the C2-C6 alkenyloxy group may include a vinyloxy group, a 1-propenyloxy group, an allyloxy group, a 1-butenyloxy group, a 2-butenyloxy group, a 3-butenyloxy group, a 1-pentenyloxy group, a 2-pentenyloxy group, a 3-pentenyloxy group, a 4-pentenyloxy group, a 3-methyl-2-butenyloxy group, a 1-hexenyloxy group, a 2-hexenyloxy group, a 3-hexenyloxy group, a 4-hexenyloxy group, a 5-hexenyloxy group, a 4-methyl-3-pentenyloxy group, a 3-methyl-2-pentenyloxy group and the like.

The C2-C6 haloalkenyloxy group represents a group resulting from the substitution of the above-mentioned C2-C6 alkenyloxy group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C2-C6 haloalkenyloxy group may include a 2-fluorovinyloxy group, a 2,2-difluorovinyloxy group, a 2,2-dichlorovinyloxy group, a 3-fluoroallyloxy group, a 3,3-difluoroallyloxy group, a 3,3-dichloroallyloxy group, a 4,4-difluoro-3-butenyloxy group, a 5,5-difluoro-4-pentenyloxy group, a 6,6-difluoro-5-hexenyloxy group and the like.

The C3-C6 alkynyloxy group represents a combination of a C3-C6 alkynyl group belonging to the above-mentioned C2-C6 alkynyl group, and an oxygen atom as a bonding site. Specific examples of the C3-C6 alkynyloxy group may include a propargyloxy group, a 2-butynyloxy group, a 3-butynyloxy group, a 2-pentynyloxy group, a 3-pentynyloxy group, a 4-pentynyloxy group, a 1,1-dimethyl-2-propynyloxy group, a 2-hexynyloxy group, a 3-hexynyloxy group, a 4-hexynyloxy group, a 5-hexynyloxy group and the like.

The C3-C6 haloalkynyloxy group represents a group resulting from the substitution of the above-mentioned C3-C6 alkynyloxy group with 1 or 2 or more halogen atoms in place of any hydrogen atom(s). When the group is substituted with two or more halogen atoms, these halogen atoms may be the same as or different from one another and the number of the substituents is not particularly limited as long as they can exist as a substituent. Specific examples of the C3-C6 haloalkynyloxy group may include a 1,1-difluoro-2-propynyloxy group, a 4,4-difluoro-2-butynyloxy group, a 4-chloro-4,4-difluoro-2-butynyloxy group, a 4-bromo-4,4-difluoro-2-butynyloxy group, a 4,4,4-trifluoro-2-butynyloxy group, a 5,5-difluoro-3-pentynyloxy group, a 5-chloro-5,5-difluoro-3-pentynyloxy group, a 5-bromo-5,5-difluoro-3-pentynyloxy group, a 5,5,5-trifluoro-3-pentynyloxy group, a 6,6-difluoro-4-hexynyloxy group, a 6-chloro-6,6-difluoro-4-hexynyloxy group, a 6-bromo-6,6-difluoro-4-hexynyloxy group, a 6,6,6-trifluoro-4-hexynyloxy group and the like.

The C2-C6 alkoxyalkoxy group represents a group resulting from the substitution of a C1-C5 alkoxy group belonging to the above-mentioned C1-C6 alkoxy group with 1 or 2 or more C1-C5 alkoxy groups in place of any hydrogen atom(s). It is not particularly limited as long as the total number of the carbon atoms is within the range of the designated number of the carbon atoms. Specific examples of the C2-C6 alkoxyalkoxy group may include a methoxymethoxy group, an ethoxymethoxy group, a propyloxymethoxy group, isopropyloxymethoxy group, a methoxyethoxy group, ethoxyethoxy group, a propyloxyethoxy group, isopropyloxyethoxy group, a methoxypropyloxy group, an ethoxypropyloxy group, a propyloxypropyloxy group, an isopropyloxypropyloxy group and the like.

The aryl group represents a cyclic aromatic substituent constituted by a hydrogen atom(s) and a carbon atom(s). Specific examples of the aryl group may include a phenyl group, a naphthyl group and the like.

The heteroaryl group represents a cyclic aromatic substituent containing at least one hetero atom selected from the group consisting of a nitrogen atom, an oxygen atom and a sulfur atom as a constitutional atom of the ring. Specific examples of the heteroaryl group may include a pyridyl group, a pyridazinyl group, a pyrimidinyl group, a pyrazinyl group, a triazinyl group, a tetrazinyl group, a thienyl group, a thiazolyl group, an isothiazolyl group, a thiadiazolyl group, furyl group, a pyrrolyl group, an imidazolyl group, a pyrazolyl group, oxazolyl group, an isoxazolyl group, a triazolyl group, an oxadiazolyl group, a thiadiazolyl group, tetrazolyl group and the like.

The aryloxy group represents a combination of the above-mentioned aryl group and an oxygen atoms a bonding site. Specific examples of the aryloxy group may include a phenoxy group, a naphthyloxy group and the like.

The heteroaryloxy group represents a combination of the above-mentioned heteroaryl group and an oxygen atoms a bonding site. Specific examples of the heteroaryloxy group may include a pyridyloxy group, a pyridazinyloxy group, a pyrimidinyloxy group, a pyrazinyloxy group, a triazinyloxy group, a tetrazinyloxy group, a thienyloxy group, a thiazolyloxy group, an isothiazolyloxy group, a thiadiazolyloxy group, a furyloxy group, a pyrrolyloxy group, an imidazolyloxy group, a pyrazolyloxy group, an oxazolyloxy group, an isoxazolyloxy group, a triazolyloxy group, an oxadiazolyloxy group, a thiadiazolyloxy group, a tetrazolyloxy group and the like.

The aralkyloxy group represents a combination of an aralkyl group resulting from the substitution of the C1-C3 alkyl group with an aryl group such as a phenyl group, a naphthyl group and the like in place of hydrogen atom(s), and an oxygen atom as a bonding site. Specific examples of the aralkyloxy group may include a benzyloxy group, a phenethyloxy group, a phenylpropyloxy group, a naphthalenylmethoxy group, a naphthalenylethoxy group, a naphthalenylpropoxy group and the like.

Specific examples of the 3 to 6 membered ring group containing 1 to 2 oxygen atoms may include a 1,2-epoxyethanyl group, an oxetanyl group, a oxolanyl group, an oxanyl group, a 1,3-dioxolanyl group, a 1,3-dioxanyl group, a 1,4-dioxanyl group and the like.

The pyridone compound of the present invention include those compounds represented by Formula (1) below and salts thereof.

[Chem. 11]

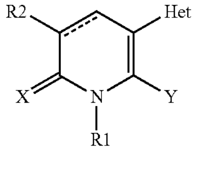

(1)

In the following, Formula (1) will be described.

R1 in Formula (1) is a hydroxyl group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent (s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group).

Above all, R1 is preferably a C1-C6 alkyl group optionally substituted with substituent(s) A, a C1-C6 haloalkyl group, a C2-C6 alkenyl group optionally substituted with substituent(s) A, a C2-C6 haloalkenyl group, a C2-C6 alkynyl group optionally substituted with substituent(s) A, a C2-C6 haloalkynyl group or RaRbN— (wherein Ra and Rb are the same as defined hereinabove);

R1 is particularly preferably a C1-C6 alkyl group optionally substituted with substituent(s) A, a C1-C6 haloalkyl group or RaRbN— (wherein Ra and Rb are the same as defined hereinabove);

and R1 is further preferably a C1-C6 alkyl group, a C1-C6 haloalkyl group or RaRbN— (wherein Ra and Rb are the same as defined hereinabove).

In R1 of Formula (1), a hydroxyl group and a cyano group are contained.

The C1-C6 alkyl group of the "C1-C6 alkyl group optionally substituted with substituent(s) A" in R1 of Formula (1) is the same as defined hereinabove and preferably a methyl group, an ethyl group, a propyl group, an isopropyl group, a butyl group or an isobutyl group, further preferably a methyl group, an ethyl group or a propyl group and particularly preferably a methyl group or an ethyl group. When it has the substituent(s) A, the C1-C6 alkyl group is optionally substituted with the substituent(s) A in place of hydrogen atom(s).

The "C1-C6 haloalkyl group" in R1 of Formula (1) is the same as defined hereinabove, preferably a 2-fluoroethyl group, a 2,2-difluoroethyl group, a 2,2,2-trifluoroethyl group, a 3,3-difluoropropyl group or a 3,3,3-trifluoropropyl group, further preferably a 2-fluoroethyl group, a 2,2-difluoroethyl group or a 2,2,2-trifluoroethyl group and particularly preferably a 2,2-difluoroethyl group or a 2,2,2-trifluoroethyl group.

The C3-C8 cycloalkyl group of the "C3-C8 cycloalkyl group optionally substituted with substituent(s) A" in R1 of Formula (1) is the same as defined hereinabove, preferably a cyclopropyl group, a cyclobutyl group, a cyclopentyl group or a cyclohexyl group and further preferably a cyclopropyl group or a cyclobutyl group. When it has the substituent(s) A, the C3-C8 cycloalkyl group is optionally substituted with the substituent(s) A in place of hydrogen atom(s).

The C2-C6 alkenyl group of the "C2-C6 alkenyl group optionally substituted with substituent(s) A" in R1 of Formula (1) is the same as defined hereinabove, preferably a vinyl group, a 1-propenyl group or an allyl group and further preferably a vinyl group or an allyl group. When it has the substituent(s) A, the C2-C6 alkenyl group is optionally substituted with the substituent(s) A in place of hydrogen atom(s).

The "C2-C6 haloalkenyl group" in R1 of Formula (1) is the same as defined hereinabove, preferably a 2-fluorovinyl group, a 2,2-difluorovinyl group, a 3-fluoroallyl group or a 3,3-difluoroallyl group and further preferably a 2-fluorovinyl group or a 2,2-difluorovinyl group.

The C2-C6 alkynyl group of "C2-C6 alkynyl group optionally substituted with substituent(s) A" in R1 of Formula (1) is the same as defined hereinabove, preferably a propargyl group, a 2-butynyl group or a 3-butynyl group and further preferably a propargyl group. When it has the substituent(s) A, the C2-C6 alkynyl group is optionally substituted with the substituent(s) A in place of hydrogen atom(s).

The "C2-C6 haloalkynyl group" in R1 of Formula (1) is the same as defined hereinabove, preferably 4,4-difluoro-2-butynyl group, a 4-chloro-4,4-difluoro-2-butynyl group, a 4-bromo-4,4-difluoro-2-butynyl group or a 4,4,4-trifluoro-2-butynyl group, further preferably a 4,4-difluoro-2-butynyl group or a 4,4,4-trifluoro-2-butynyl group.

The C1-C6 alkoxy group of "C1-C6 alkoxy group optionally substituted with substituent(s) A" in R1 of Formula (1) is the same as defined hereinabove, preferably a methoxy group, an ethoxy group, a propyloxy group, an isopropyloxy group, a butoxy group or an isobutoxy group and further preferably a methoxy group or an ethoxy group.

When it has the substituent(s) A, the C1-C6 alkoxy group is optionally substituted with the substituent(s) A in place of hydrogen atom(s).

The "C1-C6 haloalkoxy group" in R1 of Formula (1) is the same as defined hereinabove, preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group and further preferably a difluoromethoxy group, a trifluoromethoxy group, a 2,2-difluoroethoxy group or a 2,2,2-trifluoroethoxy group.

The C3-C8 cycloalkoxy group of the "C3-C8 cycloalkoxy group optionally substituted with substituent(s) A" in R1 of Formula (1) is the same as defined hereinabove, preferably a cyclopropyloxy group, a cyclobutoxy group, a cyclopentyloxy group or a cyclohexyloxy group and further preferably a cyclopropyloxy group or a cyclobutoxy group. When it has the substituent(s) A, the C3-C8 cycloalkoxy group is optionally substituted with the substituent(s) A in place of hydrogen atom(s).

The C2-C6 alkenyloxy group of the "C2-C6 alkenyloxy group optionally substituted with substituent(s) A" in R1 of Formula (1) is the same as defined hereinabove, preferably a vinyloxy group, a 1-propenyloxy group or an allyloxy group and further preferably an allyloxy group. When it has the substituent(s) A, a hydrogen atom in the C2-C6 alkenyloxy group is optionally substituted with the substituent(s) A in place of hydrogen atom(s).

The "C2-C6 haloalkenyloxy group" in R1 of Formula (1) is the same as defined hereinabove, preferably a 2-fluorovinyloxy group, a 2,2-difluorovinyloxy group, a 3-fluoroallyloxy group or a 3,3-difluoroallyloxy group and further preferably a 2-fluorovinyloxy group or a 2,2-difluorovinyloxy group.

The C3-C6 alkynyloxy group of the "C3-C6 alkynyloxy group optionally substituted with substituent(s) A" in R1 of Formula (1) is the same as defined hereinabove, preferably a propargyloxy group, a 2-butynyloxy group or a 3-butynyloxy group and further preferably a propargyloxy group. When it has the substituent(s) A, a hydrogen atom of the C3-C6 alkynyloxy group is optionally substituted with the substituent(s) A in place of hydrogen atom(s).

The "C3-C6 haloalkynyloxy group" in R1 of Formula (1) is the same as defined hereinabove, preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group and further preferably a 4,4-difluoro-2-butynyloxy group or a 4,4,4-trifluoro-2-butynyloxy group.

Each term of the "RaRbN—" (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group.) in R1 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s). Ra and Rb are each preferably a hydrogen atom, a C1-C6 alkyl group optionally substituted with substituent(s) B, a C1-C6 haloalkyl group, a C3-C8 cycloalkyl group, a pyrrolidinyl group or a piperidinyl group and further preferably a hydrogen atom or a C1-C6 alkyl group optionally substituted with substituent(s) B. The "RaRbN—" is preferably an amino group, a methylamino group, an ethylamino group, a (methoxymethyl)amino group, a (2-methoxyethyl) amino group, a (cyanomethyl)amino group, a (2-cyanoethyl) amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, further preferably an amino group, a methylamino group, a dimethylamino group, an ethylmethylamino group or a diethylamino group and particularly preferably an amino group, a methylamino group or a dimethylamino group.

R2 in Formula (1) represents a hydrogen atom, a nitro group, a halogen atom, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc represents a C1-C6 alkyl group or a C1-C6 haloalkyl group and L represents S, SO or $SO_2$.) or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)).

Above all, R2 is preferably a hydrogen atom, a halogen atom, a C1-C6 alkyl group optionally substituted with substituent(s) A, a C1-C6 haloalkyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C2-C6 alkenyloxy group optionally substituted with substituent(s) A, a C3-C6 alkynyloxy group optionally substituted with substituent(s) A, Rc-L- (wherein Rc and L are the same as defined hereinabove.) or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove));

R2 is particularly preferably a hydrogen atom, a halogen atom, a C1-C6 alkyl group optionally substituted with substituent(s) A, a C1-C6 haloalkyl group, a C2-C6 alkynyl group optionally substituted with substituent(s) A, a C1-C6 alkoxy group optionally substituted with substituent(s) A or Rx1C(═O)— (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove));

and R2 is further preferably a hydrogen atom, a halogen atom, a C1-C6 alkyl group optionally substituted with substituent(s) A, a C1-C6 haloalkyl group, a C2-C6 alkynyl group optionally substituted with substituent(s) A or a C1-C6 alkoxy group optionally substituted with substituent(s) A.

In R2 of Formula (1), a hydrogen atom and a nitro group are contained.

The halogen atom in R2 of Formula (1) is the same as defined hereinabove, preferably a fluorine atom, a chlorine atom, a bromine atom or an iodine atom.

The C1-C6 alkyl group of the "C1-C6 alkyl group optionally substituted with substituent(s) A" in R2 of Formula (1) is the same as defined hereinabove, preferably a methyl group, an ethyl group, a propyl group, an isopropyl group, a butyl group or an isobutyl group, further preferably a methyl group or an ethyl group and particularly preferably a methyl group. When it has the substituent(s) A, the C1-C6 alkyl group is optionally substituted with the substituent(s) A in place of hydrogen atom(s).

The "C1-C6 haloalkyl group" in R2 of Formula (1) is the same as defined hereinabove, preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, further preferably a difluoromethyl group, a trifluoromethyl group, a 2,2-difluoroethyl group or a 2,2,2-trifluoroethyl group and particularly preferably a difluoromethyl group or a trifluoromethyl group.

The C3-C8 cycloalkyl group of the "C3-C8 cycloalkyl group optionally substituted with substituent(s) A" in R2 of Formula (1) is the same as defined hereinabove, preferably a cyclopropyl group, a cyclobutyl group, a cyclopentyl group or a cyclohexyl group, and further preferably a cyclopropyl group or a cyclobutyl group. When it has the substituent(s) A, the C3-C8 cycloalkyl group is optionally substituted with the substituent(s) A in place of hydrogen atom(s).

The C2-C6 alkenyl group of the "C2-C6 alkenyl group optionally substituted with substituent(s) A" in R2 of Formula. (1) is the same as defined hereinabove, preferably a vinyl group, a 1-propenyl group, an allyl group, a 1-butenyl group, a 2-butenyl group or a 3-butenyl group and further preferably a vinyl group, a 1-propenyl group or an allyl group. When it has the substituent(s) A, the C2-C6 alkenyl group is optionally substituted with the substituent(s) A in place of hydrogen atom(s).

The "C2-C6 haloalkenyl group" in R2 of Formula (1) is the same as defined hereinabove, preferably a 2-fluorovinyl group, a 2,2-difluorovinyl group, a 2,2-dichlorovinyl group, a 3-fluoroallyl group, a 3,3-difluoroallyl group or a 3,3-dichloroallyl group and further preferably a 2-fluorovinyl group or a 2,2-difluorovinyl group.

The C2-C6 alkynyl group of the "C2-C6 alkynyl group optionally substituted with substituent(s) A" in R2 of Formula (1) is the same as defined hereinabove, preferably an ethynyl group, a 1-propynyl group, a propargyl group, a 1-butynyl group, a 2-butynyl group or a 3-butynyl group, further preferably an ethynyl group, a 1-propynyl group or a propargyl group and particularly preferably an ethynyl group. When it has the substituent(s) A, the C2-C6 alkynyl group is optionally substituted with the substituent(s) A in place of hydrogen atom(s).

The "C2-C6 haloalkynyl group" in R2 of Formula (1) is the same as defined hereinabove, preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group and further preferably a 3,3-difluoro-1-propynyl group or a 3,3,3-trifluoro-1-propynyl group.

The C1-C6 alkoxy group of the "C1-C6 alkoxy group optionally substituted with substituent(s) A" in R2 of Formula (1) is the same as defined hereinabove, preferably a methoxy group, an ethoxy group, a propyloxy group, an isopropyloxy group, a butoxy group or an isobutoxy group, further preferably a methoxy group, an ethoxy group, a propyloxy group or an isopropyloxy group and particularly preferably a methoxy group. When it has the substituent(s) A, the C1-C6 alkoxy group is optionally substituted with the substituent(s) A in place of hydrogen atom(s).

The "C1-C6 haloalkoxy group" in R2 of Formula (1) is the same as defined hereinabove, preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group and further preferably a difluoromethoxy group, a trifluoromethoxy group, a 2,2-difluoroethoxy group or a 2,2,2-trifluoroethoxy group.

The C3-C8 cycloalkoxy group of the "C3-C8 cycloalkoxy group optionally substituted with substituent(s) A" in R2 of Formula (1) is the same as defined hereinabove, preferably a cyclopropyloxy group, a cyclobutoxy group, a cyclopentyloxy group or a cyclohexyloxy group and further preferably a cyclopropyloxy group or a cyclobutoxy group. When it has the substituent(s) A, the C3-C8 cycloalkoxy group is optionally substituted with the substituent(s) A in place of hydrogen atom(s).

The C2-C6 alkenyloxy group of the "C2-C6 alkenyloxy group optionally substituted with substituent(s) A" in R2 of Formula (1) is the same as defined hereinabove, preferably a vinyloxy group, a 1-propenyloxy group, an allyloxy group, a 1-butenyloxy group, a 2-butenyloxy group or a 3-butenyloxy group and further preferably a vinyloxy group, a 1-propenyloxy group or an allyloxy group. When it has the substituent(s) A, the C2-C6 alkenyloxy group is optionally substituted with the substituent(s) A in place of hydrogen atom(s).

The "C2-C6 haloalkenyloxy group" in R2 of Formula (1) is the same as defined hereinabove and is a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, further preferably a 2-fluorovinyloxy group or a 2,2-difluorovinyloxy group.

The C3-C6 alkynyloxy group of the "C3-C6 alkynyloxy group optionally substituted with substituent(s) A" in R2 of Formula (1) is the same as defined hereinabove, preferably a propargyloxy group, a 2-butynyloxy group or a 3-butynyloxy group and further preferably a propargyloxy group. When it has the substituent(s) A, the C3-C6 alkynyloxy group is optionally substituted with the substituent(s) A in place of hydrogen atom(s).

The "C3-C6 haloalkynyloxy group" in R2 of Formula (1) is the same as defined hereinabove, preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group and further preferably a 4,4-difluoro-2-butynyloxy group or a 4,4,4-trifluoro-2-butynyloxy group.

Each term of the "Rc-L-" (wherein Rc represents a C1-C6 alkyl group or a C1-C6 haloalkyl group and L represents S, SO or $SO_2$.) in R2 of Formula (1) is the same as defined hereinabove. The "Rc-L-" is preferably a methylthio group, a methanesulfinyl group, a methanesulfonyl group, a trifluoromethylthio group, a trifluoromethanesulfinyl group or a trifluoromethanesulfonyl group and further preferably a methylthio group, a methanesulfinyl group or a methanesulfonyl group.

Each term of the "Rx1C(=O)—" (wherein Rx1 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) in R2 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s). The Rx1 is preferably a hydrogen atom, a C1-C6 alkyl group optionally substituted with substituent(s) B, a C1-C6 haloalkyl group or C1-C6 alkoxy group, further preferably a hydrogen atom, a C1-C6 alkyl group optionally substituted with substituent(s) B or C1-C6 alkoxy group and particularly preferably a hydrogen atom. The "Rx1C(=O)—" is a formyl group, an acetyl group, a methoxyacetyl group, a cyanoacetyl group, a propionyl group, a difluoroacetyl group, a trifluoroacetyl group, a cyclopropancarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)-methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, a piperidinylcarbonyl group and the like. The "Rx1C(=O)—" is preferably a formyl group, an acetyl group, a methoxyacetyl group, a cyanoacetyl group, a propionyl group, a difluoroacetyl group, a trifluoroacetyl group, a methoxycarbonyl group or an ethoxycarbonyl group, further preferably a formyl group, an acetyl group, a methoxyacetyl group, a cyanoacetyl group, a methoxycarbonyl group or an ethoxycarbonyl group and particularly preferably a formyl group.

In Formula (1), Het represents a 5 to 6-membered heterocyclic group or the 8 to 10-membered heterocyclic group.

The 5 to 6-membered heterocyclic group or the 8 to 10-membered heterocyclic group is optionally substituted with 0 to 6 substituents R3 (with the proviso that when two or more substituents R3 are present, each R3 represents an independent substituent).

Specific examples of the 5 to 6-membered heterocyclic group may include a pyridyl group, a pyridazinyl group, a pyrimidinyl group, a pyrazinyl group, a triazinyl group, a tetrazinyl group, a thienyl group, a thiazolyl group, an isothiazolyl group, a thiadiazolyl group, a thiatriazolyl group, a pyrrolyl group, a pyrazolyl group, an imidazolyl group, a triazolyl group, a tetrazolyl group, a pentazolyl group, a furyl group, an oxazolyl group or a 3 to 6-membered ring group containing 1 to 2 oxygen atoms and the like.

Specific examples of the 8 to 10-membered heterocyclic group may include an indolyl group, an isoindolyl group, an indazolyl group, a benzimidazolyl group, a benzotriazolyl group, a benzofuryl group, an isobenzofuryl group, a benzoxazolyl group, a benzothienyl group, benzothiazolyl group, a benzisothiazolyl group, a benzothiadiazolyl group, an indolidinyl group, an imidazopyridyl group, a pyrazolopyridyl group, a triazolopyridyl group, a pyrrolopyrimidinyl group, an imidazopyrimidinyl group, a pyrazolopyrimidinyl group, a triazolopyrimidinyl group, a pyrrolopyrazinyl group, an imidazopyrazinyl group, a pyrazolopyrazinyl group, a triazolopyrazinyl group, a quinolyl group, an isoquinolyl group, a cinnolyl group, a phthalazinyl group, a quinoxalynyl group, a quinazolynyl group or a naphthylidinyl group and the like.

Above all, Het is preferably a 5 to 6-membered heterocyclic group, and is specifically preferably a pyridyl group, a pyridazinyl group, a pyrimidinyl group, a pyrazinyl group, a triazinyl group, a tetrazinyl group, a thienyl group, a thiazolyl group, an isothiazolyl group, a thiadiazolyl group, a thiatriazolyl group, a pyrrolyl group, a pyrazolyl group, an imidazolyl group, a triazolyl group, a tetrazolyl group, a pentazolyl group, a furyl group, an oxazolyl group or a 3 to 6-membered ring group containing 1 to 2 oxygen atoms; and Het is particularly preferably a pyridyl group, a thienyl group, a pyrrolyl group, a pyrazolyl group, an imidazolyl group, a triazolyl group, a tetrazolyl group, an oxazolyl group or a 3 to 6-membered ring, group containing 1 to 2 oxygen atoms.

Het is further preferably a pyridyl group, a thienyl group, a pyrrolyl group, a pyrazolyl group, an imidazolyl group, a triazolyl group, an oxazolyl group or a 3 to 6-membered ring group containing 1 to 2 oxygen atoms.

The pyridyl group, the pyridazinyl group, the pyrimidinyl group, the pyrazinyl group, the triazinyl group or the tetrazinyl group is optionally substituted with 0 to 4 substituents R3. (with the proviso that when two or more substituents R3 are present, each R3 represents an independent substituent.)

The thienyl group, the thiazolyl group, the isothiazolyl group, the thiadiazolyl group or the thiatriazolyl group is optionally substituted with 0 to 3 substituents R3. (with the proviso that when two or more substituents R3 are present, each R3 represents an independent substituent.)

The pyrrolyl group, the pyrazolyl group, the imidazolyl group, the triazolyl group, the tetrazolyl group or the pentazolyl group is optionally substituted with 0 to 4 substituents R3. (with the proviso that when two or more substituents R3 are present, each R3 represents an independent substituent.)

The furyl group or the oxazolyl group is optionally substituted with 0 to 3 substituents R3. (with the proviso that when two or more substituents R3 are present, each R3 represents an independent substituent.)

The indolyl group, the isoindolyl group, the indazolyl group, the benzimidazolyl group or the benzotriazolyl group is optionally substituted with 0 to 6 substituents R3. (with the proviso that when two or more substituents R3 are present, each R3 represents an independent substituent.)

The benzofuryl group, the isobenzofuryl group or the benzoxazolyl group is optionally substituted with 0 to 5 substituents R3. (with the proviso that when two or more substituents R3 are present, each R3 represents an independent substituent.)

The benzothienyl group, the benzothiazolyl group, the benzisothiazolyl group or the benzothiadiazolyl group is optionally substituted with 0 to 5 substituents R3. (with the proviso that when two or more substituents R3 are present, each R3 represents an independent substituent.)

The indolidinyl group, the imidazopyridyl group, the pyrazolopyridyl group or the triazolopyridyl group is optionally substituted with 0 to 6 substituents R3. (with the proviso that when two or more substituents R3 are present, each R3 represents an independent substituent.)

The pyrrolopyrimidinyl group, the imidazopyrimidinyl group, the pyrazolopyrimidinyl group, the triazolopyrimidinyl group, the pyrrolopyrazinyl group, the imidazopyrazinyl group, the pyrazolopyrazinyl group or the triazolopyrazinyl group is optionally substituted with 0 to 5 substituents R3. (with the proviso that when two or more substituents R3 are present, each R3 represents an independent substituent.)

The quinolyl group, the isoquinolyl group, the cinnolyl group, the phthalazinyl group, the quinoxalynyl group, the quinazolynyl group or the naphthylidinyl group is optionally substituted with 0 to 6 substituents R3. (with the proviso that when two or more substituents R3 are present, each R3 represents an independent substituent.)

R3 represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a CL-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group), Rx4Rx5C═N—O— (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) or a 3 to 6-membered ring group containing 1 to 2 oxygen atoms.

Above all, R3 is preferably a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove.) or Rx2C(═O)N(Rx3)- (wherein Rx2 and Rx3 are the same as defined hereinabove); R3 is particularly preferably a cyano group, a nitro group, a halogen atom, a C1-C6 alkyl group optionally substituted with substituent(s) C, a C1-C6 haloalkyl group, a C1-C6 alkoxy group optionally substituted with substituent(s) C, RaRbN— (wherein Ra and Rb are the same as defined hereinabove), Rx1C(═O)— (wherein Rx1 is the same as defined hereinabove.) or Rx2C(═O)N(Rx3)- (wherein Rx2 and Rx3 are the same as defined hereinabove);

and R3 is further preferably a cyano group, a nitro group, a halogen atom, a C1-C6 alkyl group optionally substituted with substituent(s) C, a C1-C6 haloalkyl group, a C1-C6 alkoxy group optionally substituted with substituent(s) C, RaRbN— (wherein Ra and Rb are the same as defined hereinabove), or Rx1C(═O)— (wherein Rx1 is the same as defined hereinabove).

In R3 of Formula (1), a hydroxyl group, a cyano group and a nitro group are contained.

The halogen atom in R3 of Formula (1) is the same as defined hereinabove, preferably a fluorine atom, a chlorine atom, a bromine atom or an iodine atom.

The C1-C6 alkyl group of the "C1-C6 alkyl group optionally substituted with substituent(s) C" in R3 of Formula (I) is the same as defined hereinabove, preferably a methyl group, an ethyl group, a propyl group, an isopropyl group, a butyl group or an isobutyl group, further preferably a methyl group, an ethyl group or a propyl group and particularly preferably a methyl group. When it has the substituent(s) C, the C1-C6 alkyl group is optionally substituted with the substituent(s) C in place of hydrogen atom(s).

The "C1-C6 haloalkyl group" in R3 of Formula (1) is the same as defined hereinabove, preferably a monofluoromethyl group, a monochloromethyl group, a monobromomethyl group, a difluoromethyl group, a trifluoromethyl group, a 2,2-difluoroethyl group, a 2,2,2-trifluoroethyl group, a 3,3-difluoropropyl group or a 3,3,3-trifluoropropyl group, further preferably a monobromomethyl group, a difluoromethyl group, a trifluoromethyl group, a 2,2-difluoroethyl group or a 2,2,2-trifluoroethyl group and particularly preferably monobromomethyl group, a difluoromethyl group or a trifluoromethyl group.

The C3-C8 cycloalkyl group of the "C3-C8 cycloalkyl group optionally substituted with substituent(s) C" in R3 of Formula (1) is the same as defined hereinabove, preferably a cyclopropyl group, a cyclobutyl group, a cyclopentyl group or a cyclohexyl group, further preferably a cyclopropyl group or a cyclobutyl group. When it has the substituent(s) C, the C3-C8 cycloalkyl group is optionally substituted with the substituent(s) C in place of hydrogen atom(s).

The C2-C6 alkenyl group of the "C2-C6 alkenyl group optionally substituted with substituent(s) C" in R3 of Formula (1) is the same as defined hereinabove, preferably a vinyl group, a 1-propenyl group, an allyl group, a 1-butenyl group, a 2-butenyl group or a 3-butenyl group and further preferably a vinyl group, a 1-propenyl group or an allyl group. When it has the substituent(s) C, the C2-C6 alkenyl group is optionally substituted with the substituent(s) C in place of hydrogen atom(s).

The "C2-C6 haloalkenyl group" in R3 of Formula (1) is the same as defined hereinabove, preferably a 2-fluorovinyl group, a 2,2-difluorovinyl group, a 2,2-dichlorovinyl group, a 3-fluoroallyl group, a 3,3-difluoroallyl group or a 3,3-dichloroallyl group and further preferably a 2-fluorovinyl group or a 2,2-difluorovinyl group.

The C2-C6 alkynyl group of the "C2-C6 alkynyl group optionally substituted with substituent(s) C" in R3 of Formula (1) is the same as defined hereinabove, preferably an ethynyl group, a 1-propynyl group, a propargyl group, a 1-butynyl group, a 2-butynyl group or a 3-butynyl group and further preferably an ethynyl group, a 1-propynyl group or a propargyl group. When it has the substituent(s) C, the C2-C6 alkynyl group is optionally substituted with the substituent(s) C in place of hydrogen atom(s).

The "C2-C6 haloalkynyl group" in R3 of Formula (1) is the same as defined hereinabove, preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group and further preferably a 3,3-difluoro-1-propynyl group or a 3,3,3-trifluoro-1-propynyl group.

The C1-C6 alkoxy group of the "C1-C6 alkoxyl group optionally substituted with substituent(s) C" in R3 of Formula (1) is the same as defined hereinabove, preferably a methoxy group, an ethoxy group, a propyloxy group, an isopropyloxy group, a butoxy group or an isobutoxy group, further preferably a methoxy group, an ethoxy group, a propyloxy group or an isopropyloxy group and particularly preferably a methoxy group. When it has the substituent(s) C, the C1-C6 alkoxy group is optionally substituted with the substituent(s) C in place of hydrogen atom(s).

The "C1-C6 haloalkoxy group" in R3 of Formula (1) is the same as defined hereinabove, preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group and further preferably a difluoromethoxy group, a trifluoromethoxy group, a 2,2-difluoroethoxy group or a 2,2,2-trifluoroethoxy group.

The C3-C8 cycloalkoxy group of the "C3-C8 cycloalkoxy group optionally substituted with substituent(s) C" in R3 of Formula (1) is the same as defined hereinabove, preferably a cyclopropyloxy group, a cyclobutoxy group, a cyclopentyloxy group or a cyclohexyloxy group and further preferably a cyclopropyloxy group or a cyclobutoxy group. When it has the substituent(s) C, the C3-C8 cycloalkoxy group is optionally substituted with the substituent(s) C in place of hydrogen atom(s).

The C2-C6 alkenyloxy group of the "C2-C6 alkenyloxy group optionally substituted with substituent(s) C" in R3 of Formula (1) is the same as defined hereinabove, preferably a vinyloxy group, a 1-propenyloxy group, an allyloxy group, a 1-butenyloxy group, a 2-butenyloxy group or a 3-butenyloxy group and further preferably a vinyloxy group, a 1-propenyloxy group or an allyloxy group. When it has the substituent(s) C, the C2-C6 alkenyloxy group is optionally substituted with the substituent(s) C in place of hydrogen atom(s).

The "C2-C6 haloalkenyloxy group" in R3 of Formula (1) is the same as defined hereinabove, preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group and further preferably a 2-fluorovinyloxy group or a 2,2-difluorovinyloxy group.

The C3-C6 alkynyloxy group of the "C3-C6 alkynyloxy group optionally substituted with substituent(s) C" in R3 of Formula (1) is the same as defined hereinabove, preferably a propargyloxy group, a 2-butynyloxy group or a 3-butynyloxy group and further preferably a propargyloxy group. When it has the substituent(s) C, the C3-C6 alkynyloxy group is optionally substituted with the substituent(s) C in place of hydrogen atom(s).

The "C3-C6 haloalkynyloxy group" in R3 of Formula (1) is the same as defined hereinabove, preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group and further preferably a 4,4-difluoro-2-butynyloxy group or a 4,4,4-trifluoro-2-butynyloxy group.

The aryl group of the "aryl group optionally substituted with substituent(s) D" in R3 of Formula (1) is the same as defined hereinabove, preferably phenyl group. When it has the substituent(s) D, the aryl group is optionally substituted with the substituent(s) D in place of hydrogen(s).

The heteroaryl group of the "heteroaryl group optionally substituted with substituent(s) D" in R3 of Formula (1) is the same as defined hereinabove, preferably a pyridyl group, a pyrazinyl group, a thienyl group, a thiazolyl group, an isothiazolyl group, furyl group, an imidazolyl group, a pyrazolyl group, oxazolyl group, an isoxazolyl group, a triazolyl group, an oxadiazolyl group or a tetrazolyl group and further preferably a pyridyl group, an imidazolyl group, a pyrazolyl group, triazolyl group or a tetrazolyl group. When it has the substituent(s) D, the heteroaryl group is optionally substituted with the substituent(s) D in place of hydrogen(s).

The aryloxy group of the "aryloxy group optionally substituted with substituent(s) D" in R3 of Formula (1) is the same as defined hereinabove, preferably a phenoxy group or a naphthyloxy group and further preferably a phenoxy group. When it has the substituent(s) D, the aryloxy group is optionally substituted with the substituent(s) D in place of hydrogen atom(s).

The heteroaryloxy group of the "heteroaryloxy group optionally substituted with substituent(s) D" in R3 of Formula (1) is the same as defined hereinabove, preferably a pyridyloxy group, a pyridazinyloxy group, a pyrimidinyloxy group, a pyrazinyloxy group, a pyrazolyloxy group, a triazinyloxy group, a tetrazinyloxy group, a thienyloxy group, a thiazolyloxy group, an isothiazolyloxy group or a thiadiazolyloxy group and further preferably a pyridyloxy group, a pyridazinyloxy group, a pyrimidinyloxy group, a pyrazinyloxy group or a pyrazolyloxy group. When it has the substituent(s) D, the heteroaryloxy group is optionally substituted with the substituent(s) D in place of hydrogen atom(s).

The aralkyloxy group of the "aralkyloxy group optionally substituted with substituent(s) D" in R3 of Formula (1) is the same as defined hereinabove, preferably a benzyloxy group, a phenethyloxy group or a phenylpropyloxy group and further preferably a benzyloxy group or a phenethyloxy group. When it has the substituent(s) D, the aralkyloxy group is optionally substituted with the substituent(s) D in place of hydrogen atom(s).

Ra and Rb of "RaRbN—" in R3 of Formula (1) are the same as defined hereinabove. Ra and Rb are each preferably a hydrogen atom, a C1-C6 alkyl group optionally substituted with substituent(s) B, a C1-C6 haloalkyl group, a C3-C8 cycloalkyl group, pyrrolidinyl group or a piperidinyl group and further preferably a hydrogen atom or a C1-C6 alkyl group optionally substituted with substituent(s) B. The "RaRbN—" is preferably an amino group, a methylamino group, an ethylamino group, a (methoxymethyl)amino group, a (2-methoxyethyl)amino group, a (cyanomethyl) amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, further preferably an amino group, a methylamino group, a dimethylamino group, an ethylmethylamino group or a diethylamino group and particularly preferably an amino group, a methylamino group or a dimethylamino group.

Rc and L of "Rc-L-" in R3 of Formula (1) are the same as defined hereinabove. The "Rc-L-" is preferably a methylthio group, a methanesulfinyl group, a methanesulfonyl group, a trifluoromethylthio group, a trifluoromethanesulfinyl group or a trifluoromethanesulfonyl group and further preferably a methylthio group, a methanesulfinyl group or a methanesulfonyl group.

Rx1 of "Rx1C(═O)—" in R3 of Formula (1) is the same as defined hereinabove. Rx1 is preferably a hydrogen atom, a C1-C6 alkyl group optionally substituted with substituent(s) B, a C1-C6 haloalkyl group or C1-C6 alkoxy group, further preferably a hydrogen atom, a C1-C6 alkyl group optionally substituted with substituent(s) B or C1-C6 alkoxy group and particularly preferably a hydrogen atom. The "Rx1C(═O)—" is preferably a formyl group, an acetyl group, a methoxyacetyl group, a cyanoacetyl group, a propionyl group, a difluoroacetyl group, a trifluoroacetyl group, a cyclopropancarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, further preferably a formyl group, an acetyl group, a methoxyacetyl group, a cyanoacetyl group, a propionyl group, a difluoroacetyl group, a trifluoroacetyl group, a methoxycarbonyl group, an ethoxycarbonyl group and particularly preferably a formyl group or an ethoxycarbonyl group.

Rx1 of "Rx1C(═O)O—" in R3 of Formula (1) is the same as defined hereinabove. The "Rx1C(═O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropancarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl) methylaminocarbonyloxy group, a (cyanomethyl)methylamino-carbonyloxy group, a (2-cyanoethyl) methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group and further preferably a formyloxy group, an acetyloxy group or a trifluoroacetyloxy group.

Each term of "Rx2C(═O)N(Rx3)-" (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group.) in R3 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s). The Rx2 is preferably a hydrogen atom, a C1-C6 alkyl group optionally substituted with substituent(s) B, a C1-C6 haloalkyl group, a C1-C6 alkoxy group or RaRbN— (wherein Ra and Rb are the same as defined hereinabove.) and further preferably a C1-C6 alkyl group optionally substituted with substituent(s) B. The Rx3 is preferably a hydrogen atom, a C1-C6 alkyl group optionally substituted with substituent(s) B or C1-C6 haloalkyl group and further preferably a hydrogen atom. Specific examples of the Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl) amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, further preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group and particularly preferably a methyl group. Also, specific examples of the Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, further preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group and particularly preferably a hydrogen atom. Further, the "Rx2C(═O)N(Rx3)-" is preferably an acetylamide group, a 2,2,2-trifluoroacetylamide group, a methylcarbamate group or an ethylcarbamate group and further preferably an acetylamide group.

Each term of the "Rx4Rx5C═N—O—" (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) in R3 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s).

Rx4 and Rx5 are each preferably a methyl group, an ethyl group, a propyl group, an isopropyl group, a trifluoromethyl group, a 2,2,2-trifluoroethyl group, a cyclopropyl group, a cyclopentyl group, a cyclohexyl group, a methoxy group, an ethoxy group, isopropyloxy group, a difluoromethoxy group, a trifluoromethoxy group, a 2,2-difluoroethoxy group, a 2,2,2-trifluoroethoxy group, a cyclopropyloxy group, a cyclobutyloxy group, a cyclopentyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl) methylamino group, a pyrrolidinyl group or a piperidinyl group and further preferably a methyl group, an ethyl group, a trifluoromethyl group, a 2,2,2-trifluoroethyl group, a methoxy group, an ethoxy group, a 2,2,2-trifluoroethoxy group, a dimethylamino group, an ethylmethylamino group or a diethylamino group.

The "3 to 6 membered ring group containing 1 to 2 oxygen atoms" in R3 of Formula (1) is the same as defined hereinabove, preferably an oxolanyl group, an oxanyl group, a 1,3-dioxolanyl group or a 1,3-dioxanyl group and further preferably a 1,3-dioxolanyl group or a 1,3-dioxanyl group.

In the following, Het in Formula (1) will be described in detail.

A) When Het is a pyridyl group, a pyridazinyl group, a pyrimidinyl group, a pyrazinyl group, a triazinyl group or tetrazinyl group, Het represents a partial structure represented by Formula (a)

[Chem. 12]

(a)

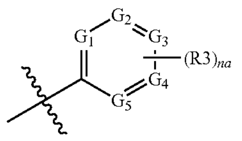

(wherein R3 is the same as defined hereinabove and "na" represents an integer of 0 to 4).

G1, G2, G3, G4 and G5 in Formula (a) are each independent and represent a carbon atom or a nitrogen atom. With the proviso that at least one among G1, G2, G3, G4 and G5 is a nitrogen atom. Preferred G1, G2, G3, G4 and G5 are that any one of G1, G2, G3, G4 and G5 is a nitrogen atom. That is, it is a pyridyl group.

"na" in Formula (a) represents an integer of 0 to 4.

When "na" in Formula (a) is 2 or more, the two or more substituents R3 are independent of one another and may be selected appropriately to be the same as or different from one another.

Specific examples of the partial structures of Formula (a) are illustrated below.

[Chem. 13]

(a-1)

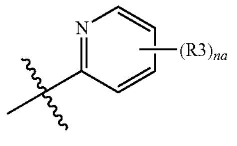

(a-2)

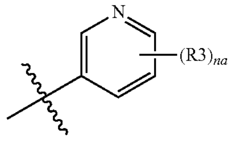

(a-3)

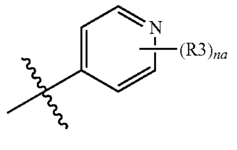

-continued
(a-4)
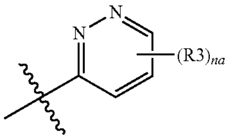
(a-5)
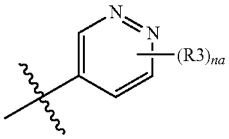
(a-6)
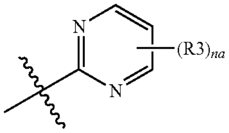
(a-7)
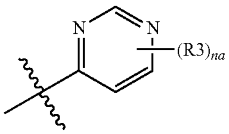
(a-8)
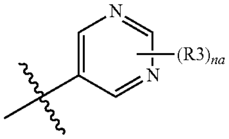
(a-9)
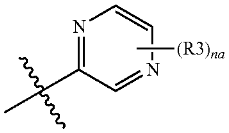
(a-10)
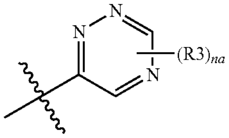
(a-11)
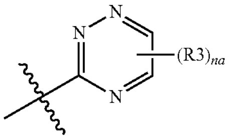
(a-12)
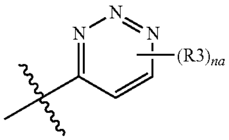
(a-13)
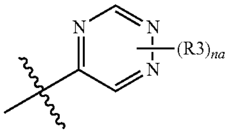
-continued
(a-14)
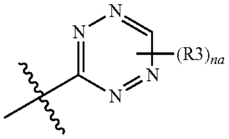
(a-15)
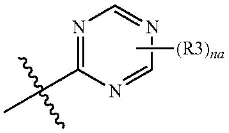
(a-16)
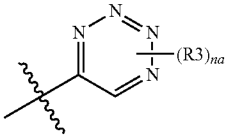
(a-17)
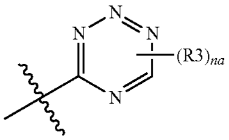
Among the partial structures of Formula (a), preferable specific examples are shown below.
[Chem. 14]
(a-1)
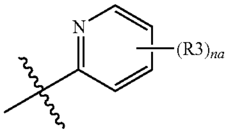
(a-2)
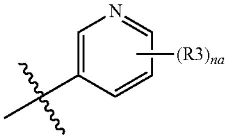
(a-3)
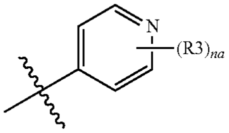
(a-4)
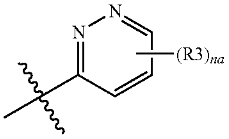
(a-5)
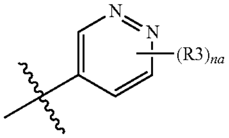

-continued (a-6)

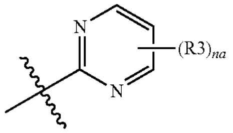

(a-7)

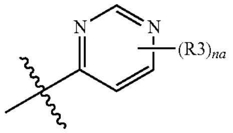

(a-8)

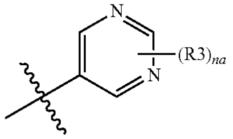

(a-9)

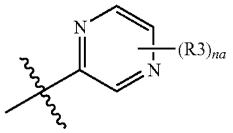

Among the partial structures of Formula (a), more preferable specific examples are shown below.

[Chem. 15]

(a-1)

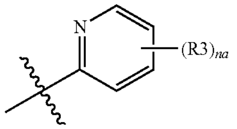

(a-2)

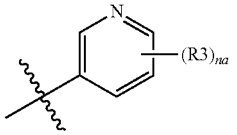

(a-3)

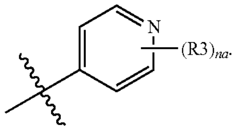

Among the partial structures of Formula (a), particularly preferable specific examples are shown below.

[Chem. 16]

(a-2)

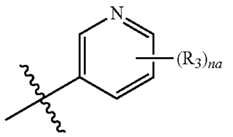

B) When Het is a thienyl group, a thiazolyl group, an isothiazolyl group, a thiadiazolyl group or a thiatriazolyl group, Het represents a partial structure represented by Formula (b-1)

[Chem. 17]

(b-1)

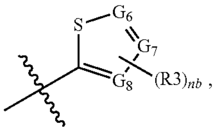

or Formula (b-2)

[Chem. 18]

(b-2)

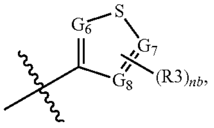

(wherein R3 is the same as defined hereinabove and "nb" represents an integer of 0 to 3).

G6, G7 and G8 in Formula (b-1) and Formula (b-2) are each independent and represent a carbon atom or a nitrogen atom.

"nb" in Formula (b-1) and Formula (b-2) represents an integer of 0 to 3.

When "nb" in Formula (b-1) and Formula (b-2) is 2 or more, the two or more substituents R3 are independent of one another and may be selected appropriately to be the same as or different from one another.

Specific examples of the partial structure of Formula (b-1) are shown below.

(b-1-1)

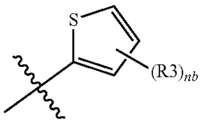

(b-1-2)

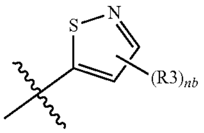

(b-1-3)

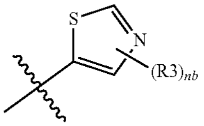

(b-1-4)

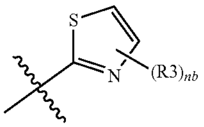

(b-1-5)

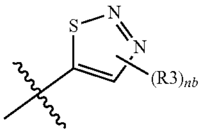

-continued (b-1-6)

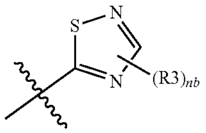

(b-1-7)

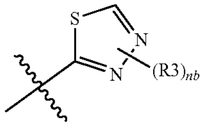

(b-1-8)

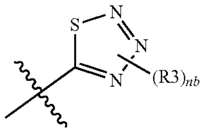

Among the partial structures of Formula (b-1), preferable specific examples are shown below.

[Chem. 20]

(b-1-1)

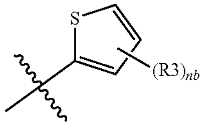

(b-1-2)

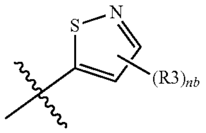

(b-1-3)

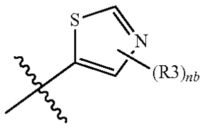

(b-1-5)

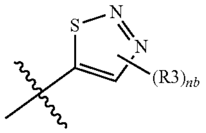

Among the partial structures of Formula (b-1), more preferable specific examples are shown below.

[Chem, 21]

(b-1-1)

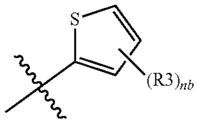

Specific examples of the partial structure of Formula (b-2) are shown below.

[Chem. 22]

(b-2-1)

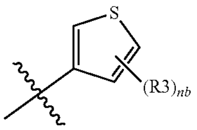

(b-2-2)

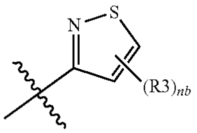

(b-2-3)

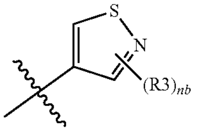

(b-2-4)

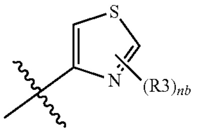

(b-2-5)

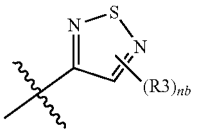

(b-2-6)

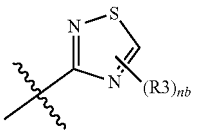

(b-2-7)

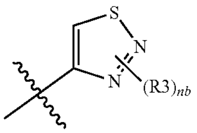

(b-2-8)

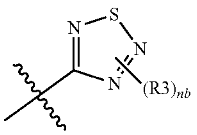

Among the partial structures of Formula (b-2), preferable specific examples are shown below.

[Chem. 23]

(b-2-1)

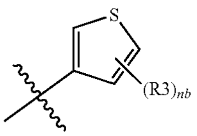

-continued (b-2-2)

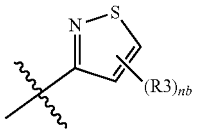

(b-2-4)

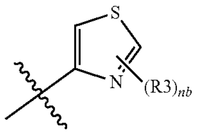

(b-2-7)

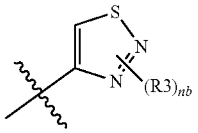

Among the partial structures of Formula (b-2), more preferable specific examples are shown below.

[Chem. 24]

(b-2-1)

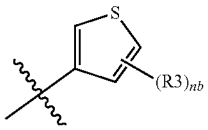

C) When Het is a pyrrolyl group, a pyrazolyl group, an imidazolyl group, a triazolyl group, a tetrazolyl group or a pentazolyl group, Het represents a partial structure represented by Formula (c-1)
[Chem. 25]

(c-1)

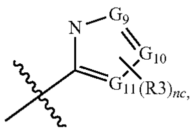

Formula (c-2)
[Chem. 26]

(c-2)

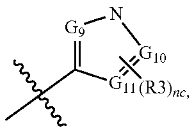

or

Formula (c-3)
[Chem. 27]

(c-3)

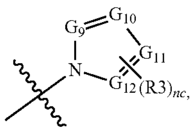

(wherein R3 is the same as defined hereinabove and "nc" represents an integer of 0 to 4).

G9, G10, G11 and G12 in Formula (c-1), Formula (c-2) and Formula (c-3) are each independent and represent a carbon atom or a nitrogen atom.

"nc" in Formula (c-1), Formula (c-2) and Formula (c-3) represents an integer of 0 to 4.

When "nc" in Formula (c-1), Formula (c-2) and Formula (c-3) is 2 or more, the two or more substituents R3 are independent of one another and may be selected appropriately to be the same as or different from one another.

Specific examples of the partial structure of Formula (c-1) are shown below.

[Chem. 28]

(c-1-1)

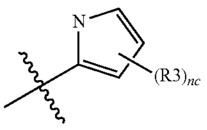

(c-1-2)

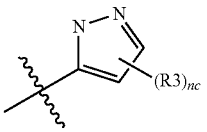

(c-1-3)

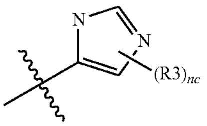

(c-1-4)

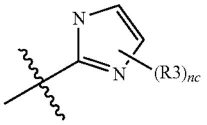

(c-1-5)

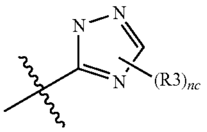

(c-1-6)

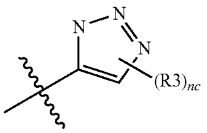

(c-1-7)

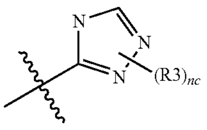

(c-1-8)

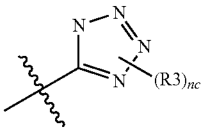

Among the partial structures of Formula (c-1), preferable specific examples are shown below.

[Chem. 29]

(c-1-1)

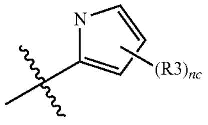

(c-1-2)

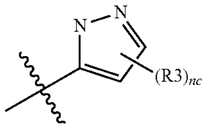

(c-1-3)

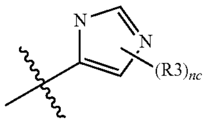

(c-1-4)

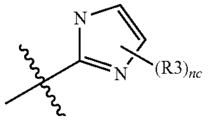

Among the partial structures of Formula (c-1), more preferable specific examples are shown below.

[Chem. 30]

(c-1-2)

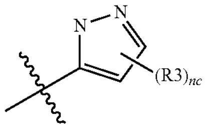

(c-1-3)

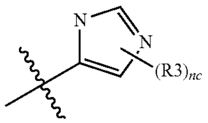

(c-1-4)

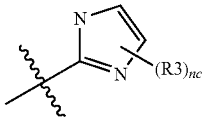

Among the partial structures of Formula (c-1), particularly preferable specific examples are shown below.

[Chem. 31]

(c-1-2)

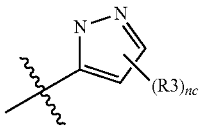

Specific examples of the partial structure of Formula (c-2) are shown below.

[Chem. 32]

(c-2-1)

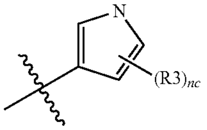

(c-2-2)

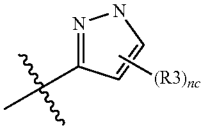

(c-2-3)

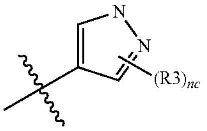

(c-2-4)

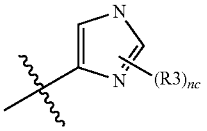

(c-2-5)

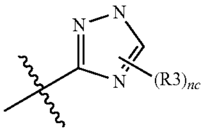

(c-2-6)

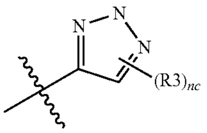

(c-2-7)

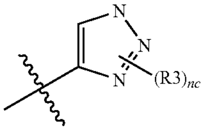

(c-2-8)

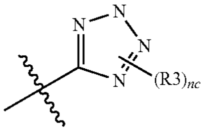

Among the partial structures of Formula (c-2), preferable specific examples are shown below.

[Chem. 33]

(c-2-1)

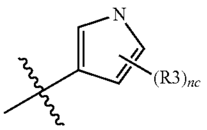

-continued (c-2-2)

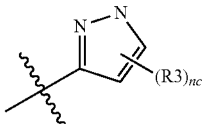

(c-2-3)

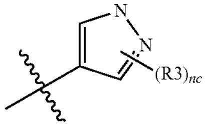

(c-2-4)

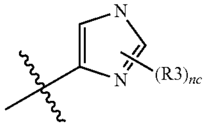

Among the partial structures of Formula (c-2), more preferable specific examples are shown below.

[Chem. 34]

(c-2-1)

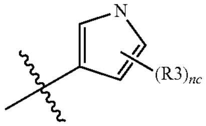

(c-2-2)

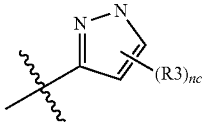

(c-2-3)

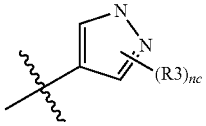

Among the partial structures of Formula (c-2), particularly preferable specific examples are shown below.

[Chem. 35]

(c-2-1)

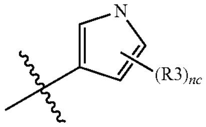

(c-2-2)

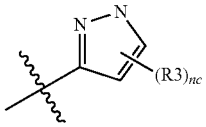

Specific examples of the partial structure of Formula (c-3) are shown below.

[Chem. 36]

(c-3-1)

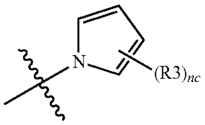

(c-3-2)

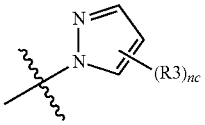

(c-3-3)

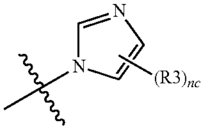

(c-3-4)

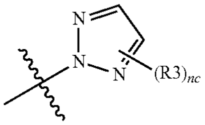

(c-3-5)

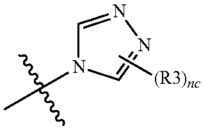

(c-3-6)

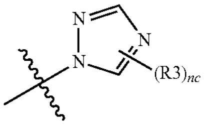

(c-3-7)

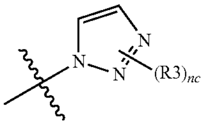

(c-3-8)

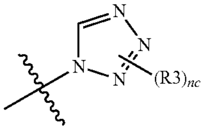

(c-3-9)

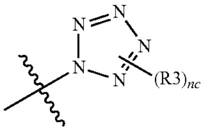

Among the partial structures of Formula (c-3), preferable specific examples are shown below.

[Chem. 37]

(c-3-1)

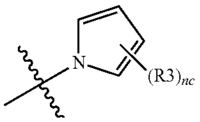

-continued (c-3-2)

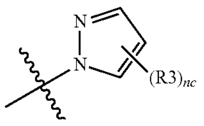

(c-3-3)

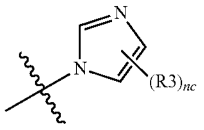

(c-3-4)

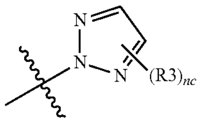

(c-3-5)

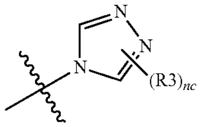

(c-3-6)

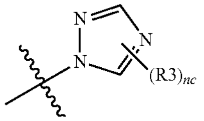

(c-3-8)

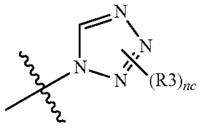

Among the partial structures of Formula (c-3), more preferable specific examples are shown below.

[Chem. 38]

(c-3-1)

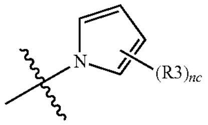

(c-3-2)

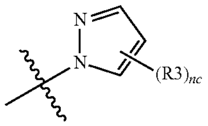

(c-3-3)

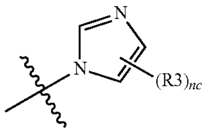

(c-3-6)

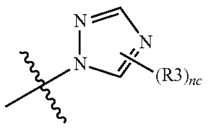

-continued (c-3-8)

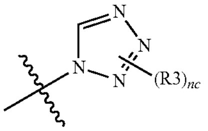

Among the partial structures of Formula (c-3), particularly preferable specific examples are shown below.

[Chem. 39]

(c-3-1)

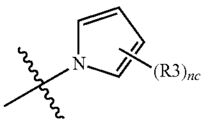

(c-3-2)

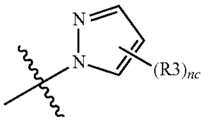

(c-3-3)

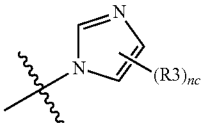

(c-3-6)

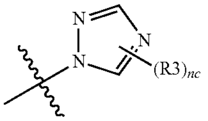

D) When Het is a furyl group or an oxazolyl group, Het represents a partial structure represented by Formula (d-1)

[Chem. 40]

(d-1)

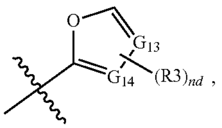

or Formula (d-2)

[Chem. 41]

(d-2)

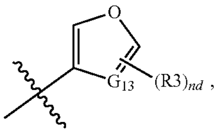

(wherein R3 is the same as defined hereinabove and "nd" represents an integer of 0 to 3).

G13 and G14 in Formula (d-1) and Formula (d-2) are each independent and represent a carbon atom or a nitrogen atom.

"nd" in Formula (d-1) and Formula (d-2) represents an integer of 0 to 3.

When "nd" in Formula (d-1) and Formula (d-2) is 2 or more, the two or more substituents R3 are independent of one another and may be selected appropriately to be the same as or different from one another.

Specific examples of the partial structure of Formula (d-1) are shown below.

[Chem. 42]

(d-1-1)

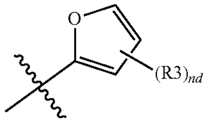

(d-1-2)

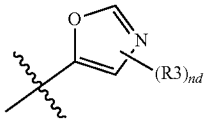

(d-1-3)

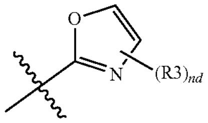

Among the partial structures of Formula (d-1), preferable specific examples are shown below.

[Chem. 43]

(d-1-2)

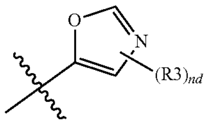

(d-1-3)

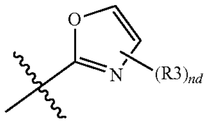

Among the partial structures of Formula (d-1), more preferable specific examples are shown below.

[Chem. 44]

(d-1-2)

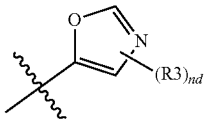

Specific examples of the partial structure of Formula (d-2) are shown below.

[Chem. 45]

(d-2-1)

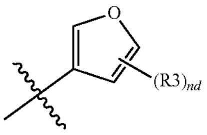

(d-2-2)

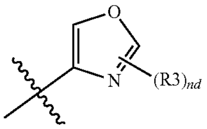

Among the partial structures of Formula (d-2), preferable specific examples are shown below.

[Chem. 46]

(d-2-2)

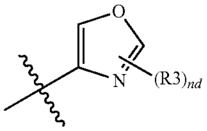

E) When Het is an indolyl group, an isoindolyl group, an indazolyl group, a benzimidazolyl group or a benzotriazolyl group, Het represents a partial structure represented by Formula (e-1)

[Chem. 47]

(e-1)

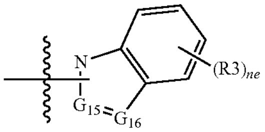

or Formula (e-2)

[Chem. 48]

(e-2)

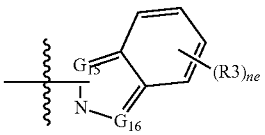

(wherein R3 is the same as defined hereinabove and "ne" represents an integer of 0 to 6).

G15 and G16 in Formula (e-1) and Formula (e-2) are each independent and represent a carbon atom or a nitrogen atom.

"ne" in Formula (e-1) and Formula (e-2) represents an integer of 0 to 6.

When "ne" in Formula (e-1) and Formula (e-2) is 2 or more, the two or more substituents R3 are independent of one another and may be selected appropriately to be the same as or different from one another.

Specific examples of the partial structure of Formula (e-1) are shown below.

[Chem. 49]
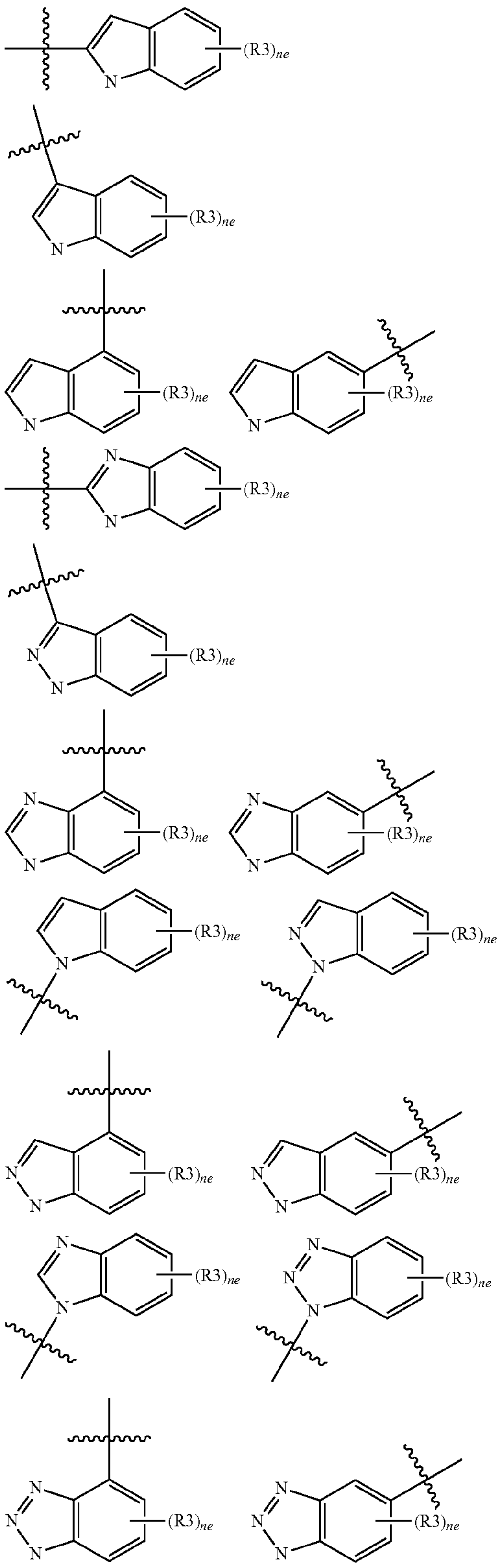
-continued
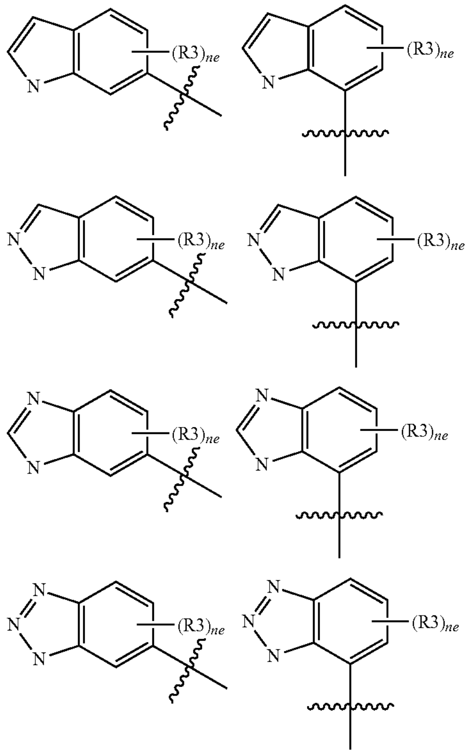
Specific examples of the partial structure of Formula (e-2) are shown below.
[Chem. 50]
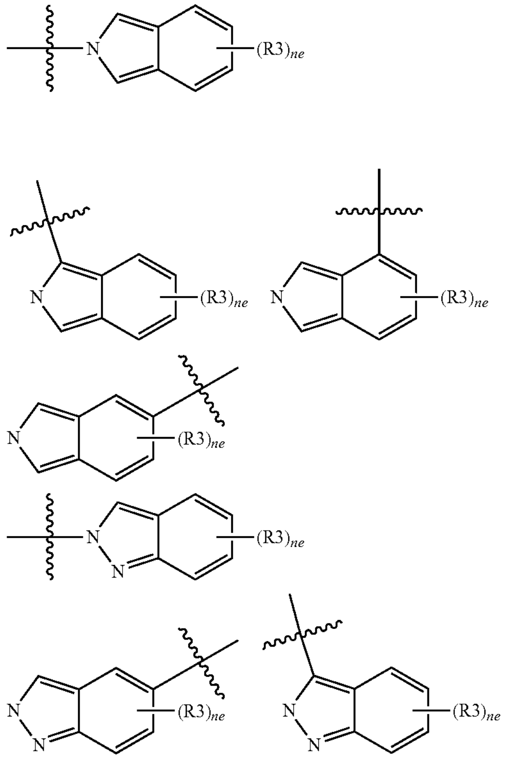

-continued

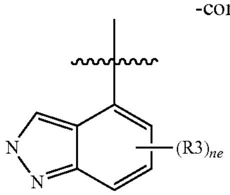

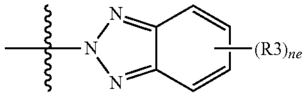

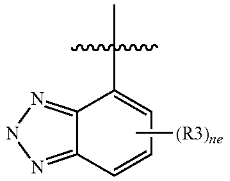

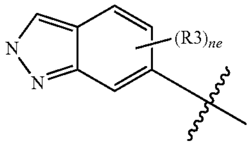

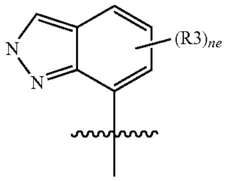

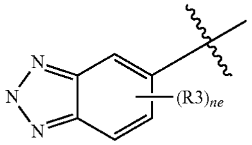

F) when Het is a benzofuryl group, an isobenzofuryl group or a benzoxazolyl group, Het represents a partial structure represented by Formula (f-1)

[Chem. 51]

(f-1)

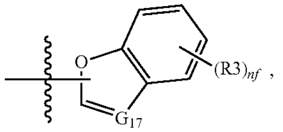

or Formula (f-2)

[Chem. 52]

(f-2)

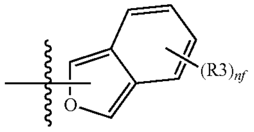

(wherein R3 is the same as defined hereinabove and "nf" represents an integer of 0 to 5).

G17 in Formula (f-1) represents a carbon atom or a nitrogen atom.

"nf" in Formula (f-1) and Formula (f-2) represents an integer of 0 to 5.

When "nf" in Formula (f-1) and Formula (f-2) is 2 or more, the two or more substituents R3 are independent of one another and may be selected appropriately to be the same as or different from one another.

Specific examples of the partial structure of Formula (f-1) are shown below.

[Chem. 53]

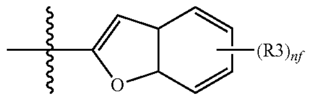

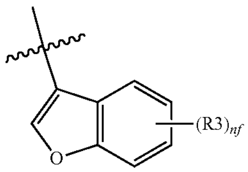

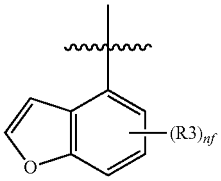

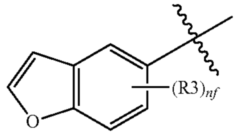

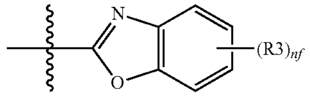

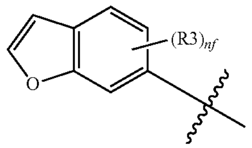

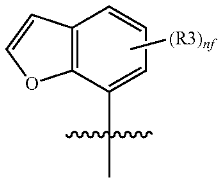

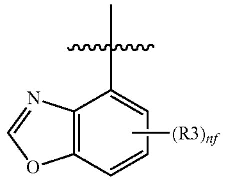

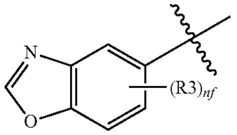

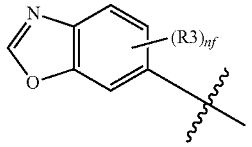

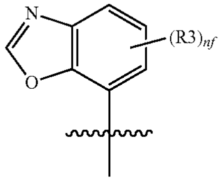

Specific examples of the partial structure of Formula (f-2) are shown below.

[Chem. 54]

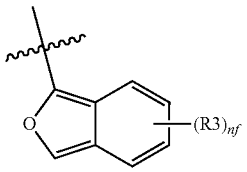

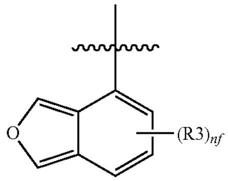

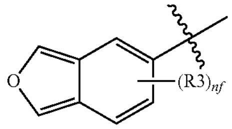

G) When Het is a benzothienyl group, benzothiazolyl group, a benzisothiazolyl group or a benzothiadiazolyl group, Het represents a partial structure represented by Formula (g-1)

[Chem. 55]

(g-1)

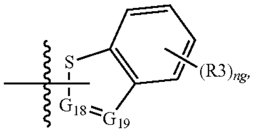

or Formula (g-2)

[Chem. 56]

(g-2)

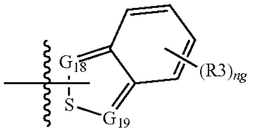

(wherein R3 is the same as defined hereinabove and "ng" represents an integer of 0 to 5).

G18 and G19 in Formula (g-1) and Formula (g-2) are each independent and represent a carbon atom or a nitrogen atom.

"ng" in Formula (g-1) and Formula (g-2) represents an integer of 0 to 5.

When "ng" in Formula (g-1) and Formula (g-2) is 2 or more, the two or more substituents R3 are independent of one another and may be selected appropriately to be the same as or different from one another.

Specific examples of the partial structure of Formula (g-1) are shown below.

[Chem. 57]

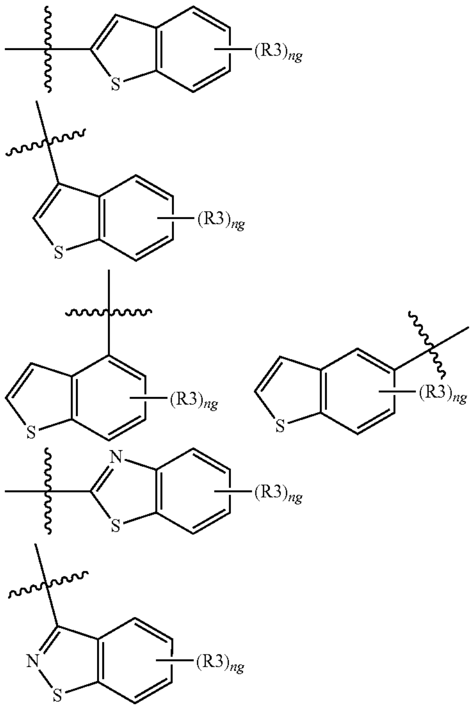

-continued

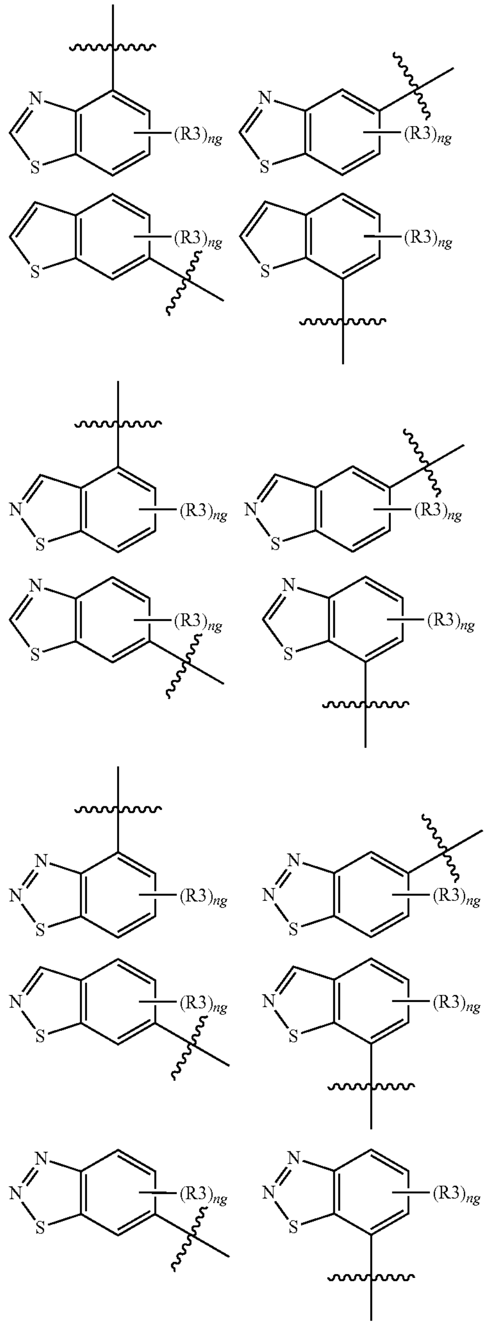

Specific examples of the partial structure of Formula (g-2) are shown below.

[Chem. 58]

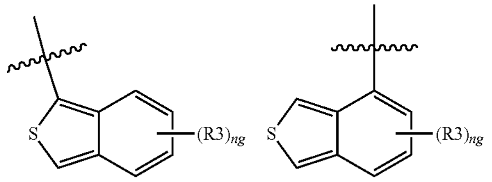

-continued

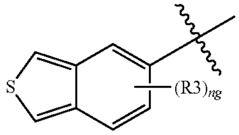
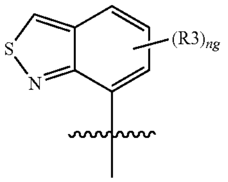
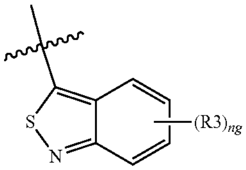
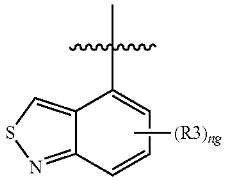
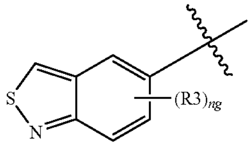
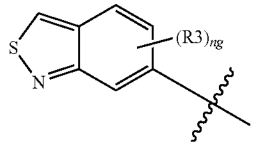
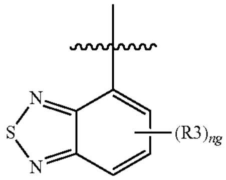
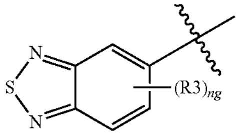

H) When Het is an indolidinyl group, an imidazopyridyl group, a pyrazolopyridyl group or a triazolopyridyl group, Het represents a partial structure represented by Formula (h-1)

[Chem. 59]

(h-1)

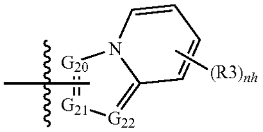

(wherein R3 is the same as defined hereinabove and "nh" represents an integer of 0 to 6).

G20, G21 and G22 in Formula (h-1) are each independent and represent a carbon atom or a nitrogen atom.

"nh" in Formula (h-1) represents an integer of 0 to 6.

When "nh" in Formula (h-1) is 2 or more, the two or more substituents R3 are independent of one another and may be selected appropriately to be the same as or different from one another.

Specific examples of the partial structure of Formula (h-1) are shown below.

[Chem. 60]

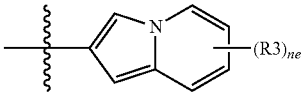

-continued

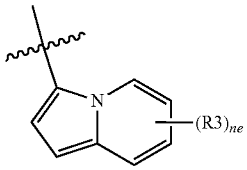
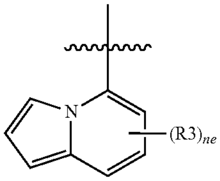
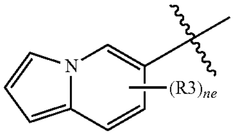
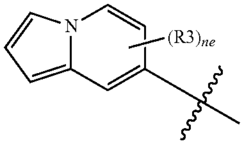
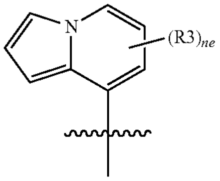
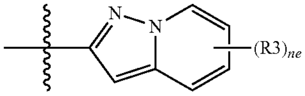
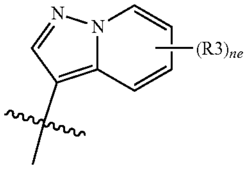
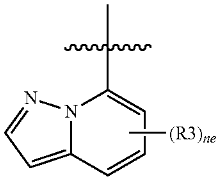
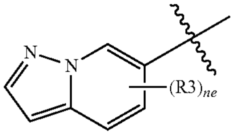
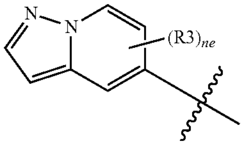
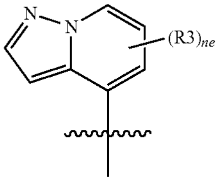
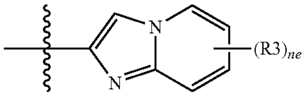
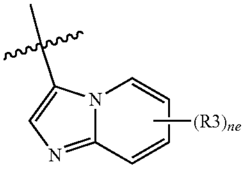
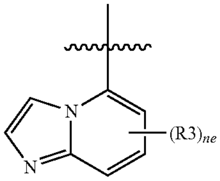
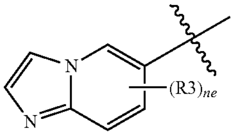
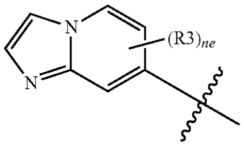

-continued
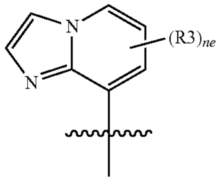
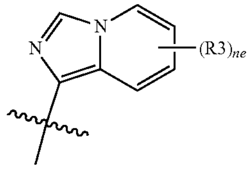
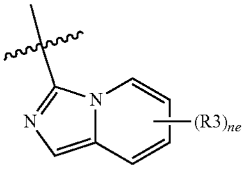
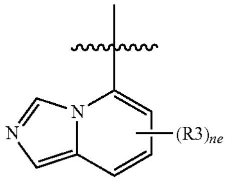
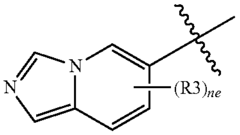
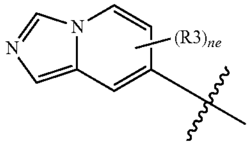
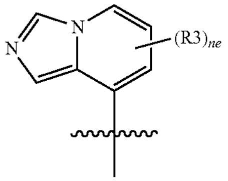
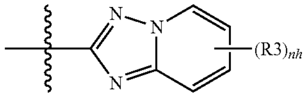
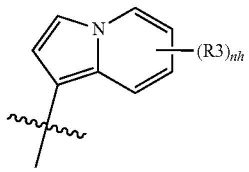
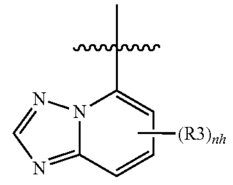
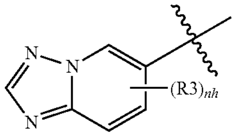
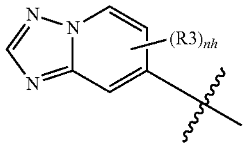
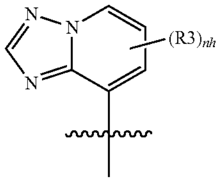
-continued
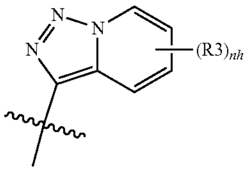
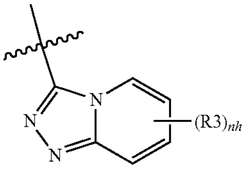
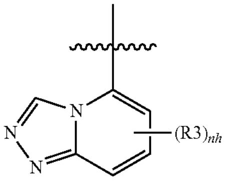
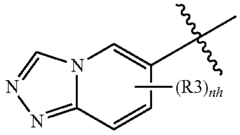
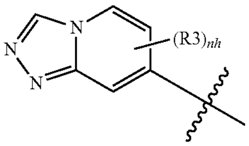
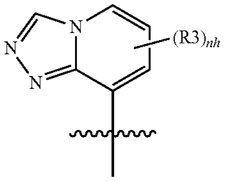
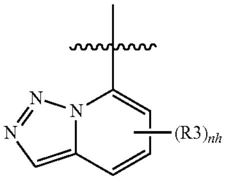
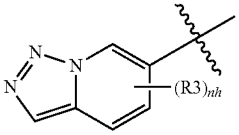
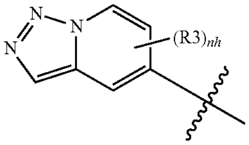
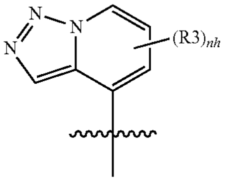
I) When Het is a pyrrolopyrimidinyl group, an imidazopyrimidinyl group, a pyrazolopyrimidinyl group, a triazolopyrimidinyl group, a pyrrolopyrazinyl group, an imidazopyrazinyl group, a pyrazolopyrazinyl group or a triazolopyrazinyl group, Het represents a partial structure represented by
Formula (i-1)
[Chem. 61]
(i-1)
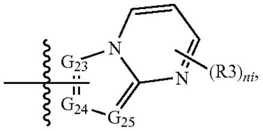
Formula (i-2)
[Chem. 62]
(i-2)
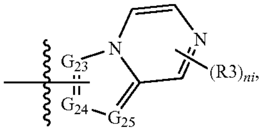
or -continued Formula (i-3)
[Chem. 63]

(i-3)

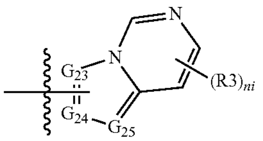

(wherein R3 is the same as defined hereinabove and "ni" represents an integer of 0 to 5).

G23, G24 and G25 in Formula (i-1), Formula (i-2) and Formula (i-3) are each independent and represent a carbon atom or a nitrogen atom.

"ni" in Formula (i-1), Formula (i-2) and Formula (i-3) represents an integer of 0 to 5.

When "ni" in Formula (i-1), Formula (i-2) and Formula (i-3) is 2 or more, the two or more substituents R3 are independent of one another and may be selected appropriately to be the same as or different from one another.

Specific examples of the partial structure of Formula (i-1) are shown below.

[Chem. 64]

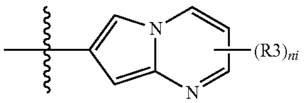

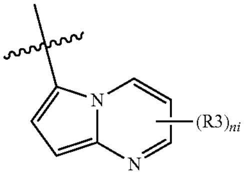

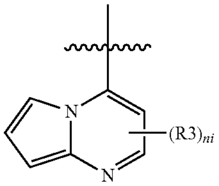

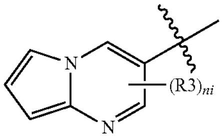

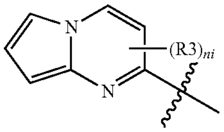

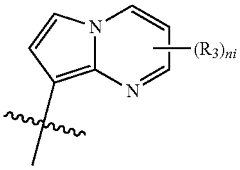

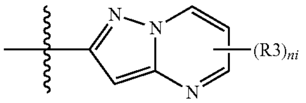

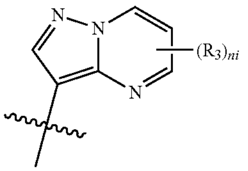

-continued

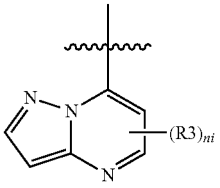

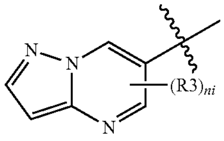

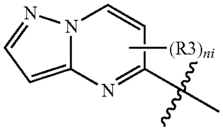

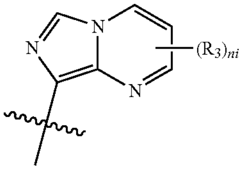

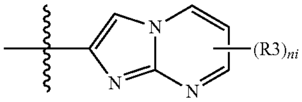

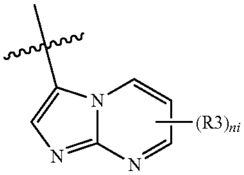

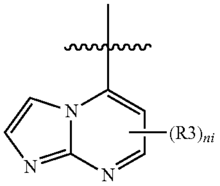

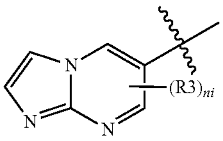

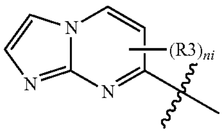

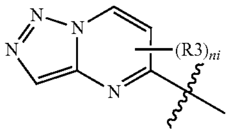

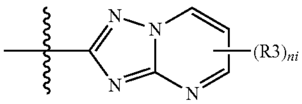

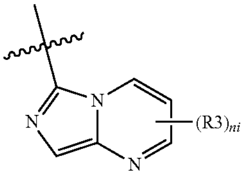

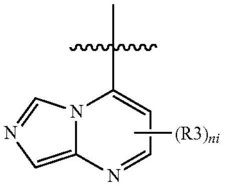

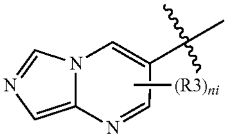

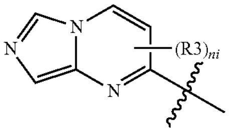

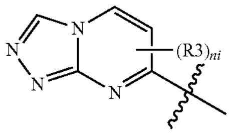

-continued
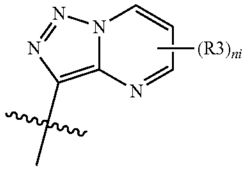
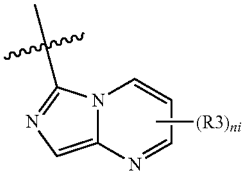
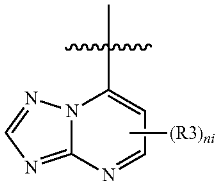
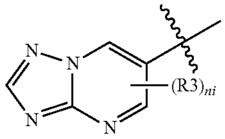
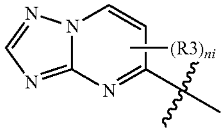
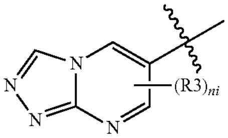
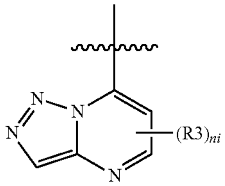
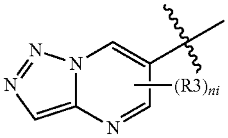
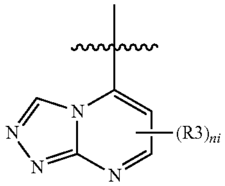
Specific examples of the partial structure of Formula (i-2) are shown below.
[Chem. 65]
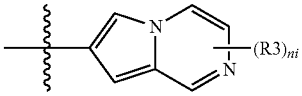
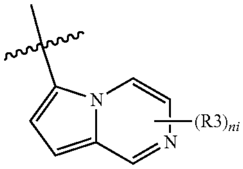
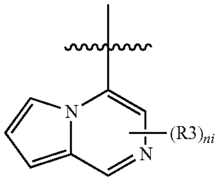
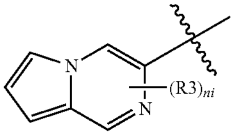
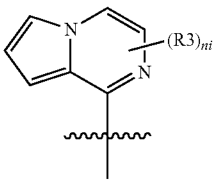
-continued
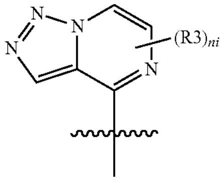
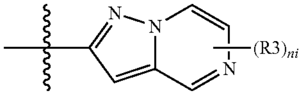
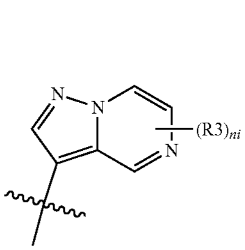
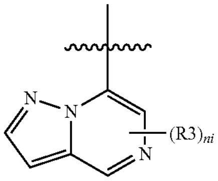
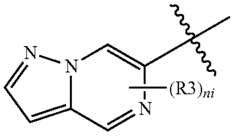
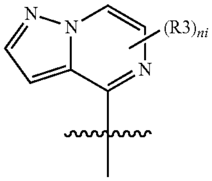
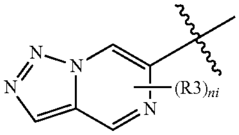
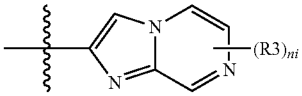
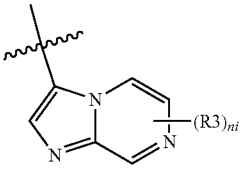
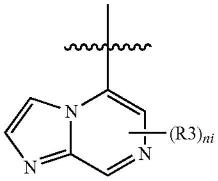
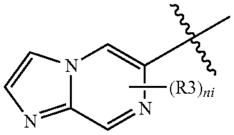
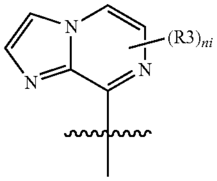
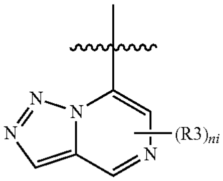

-continued
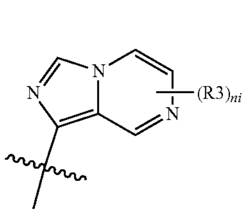
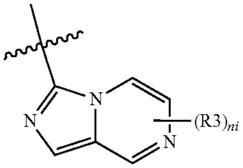
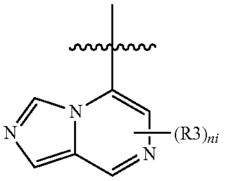
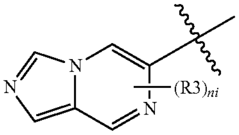
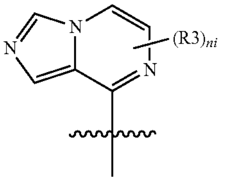
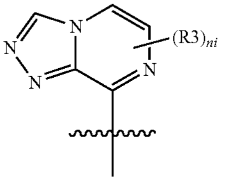
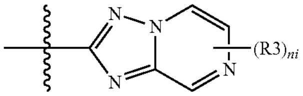
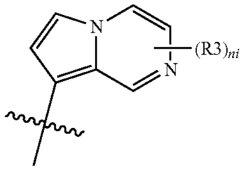
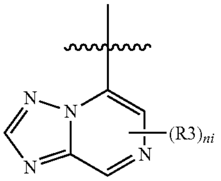
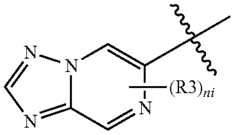
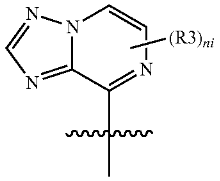
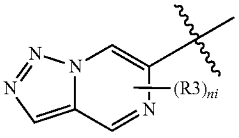
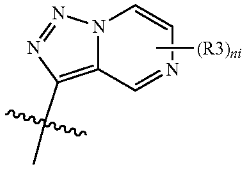
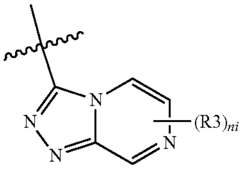
-continued
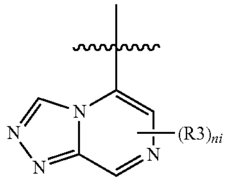
Specific examples of the partial structure of Formula (i-3) are shown below.
[Chem. 66]
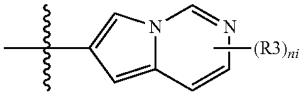
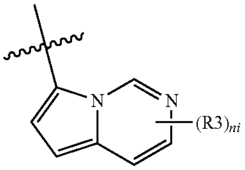
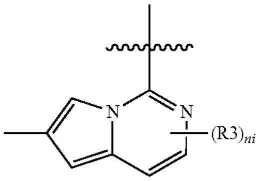
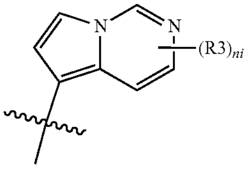
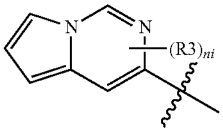
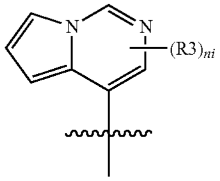
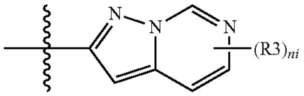
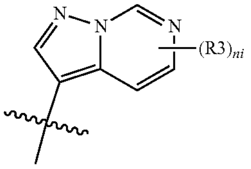
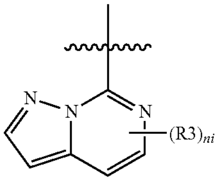
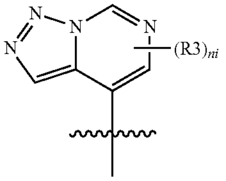

-continued

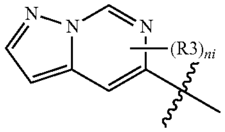

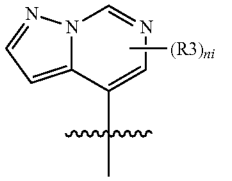

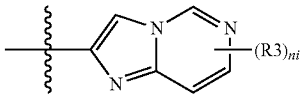

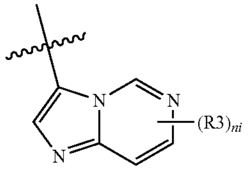

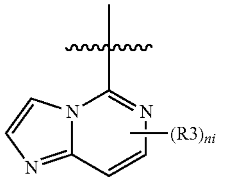

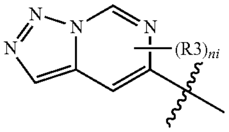

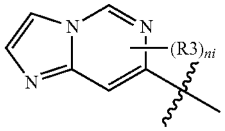

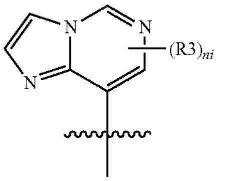

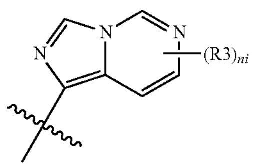

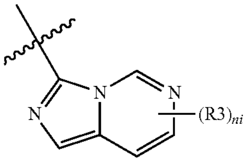

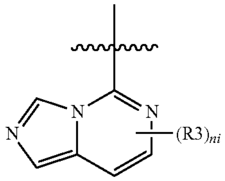

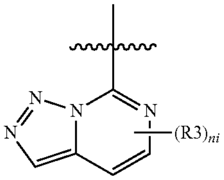

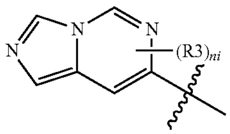

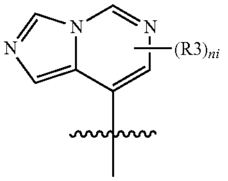

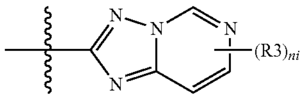

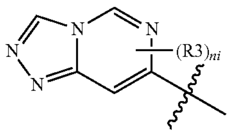

-continued

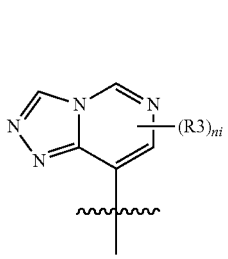

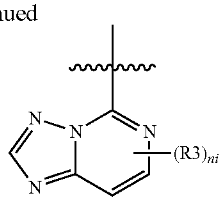

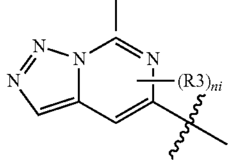

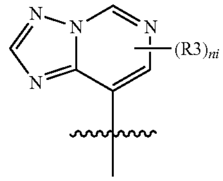

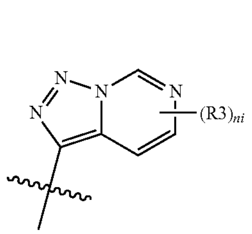

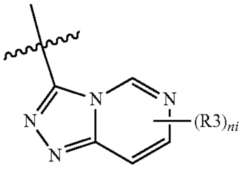

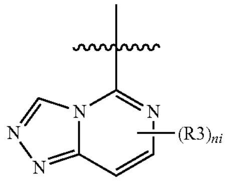

J) When Het is a quinolyl group, an isoquinolyl group, a cinnolyl group, a phthalazinyl group, a quinoxalynyl group, a quinazolynyl group or a naphthylidinyl group, Het represents a partial structure represented by Formula (j-1)

[Chem. 67]

(j-1)

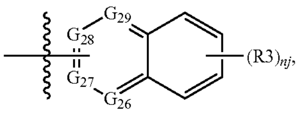

or Formula (j-2)

[Chem. 68]

(j-2)

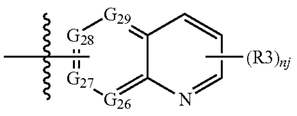

(wherein R3 is the same as defined hereinabove and "nj" represents an integer of 0 to 6).

G26, G27, G28 and G29 in Formula (j-1) and Formula (j-2) are each independent and represent a carbon atom or a nitrogen atom. With the proviso that at least one among G26, G27, G28 and G29 is a nitrogen atom. Preferred G26, G27, G28 and G29 are that any one of G26, G27, G28 and G29 is a nitrogen atom. That is, it is a quinolyl group.

"nj" in Formula (j-1) and Formula (j-2) represents an integer of 0 to 6.
When "nj" in Formula (j-1) and Formula (j-2) is 2 or more, the two or more substituents R3 are independent of one another and may be selected appropriately to be the same as or different from one another.
Specific examples of the partial structures of Formula (j-1) are illustrated below.
[Chem. 69]
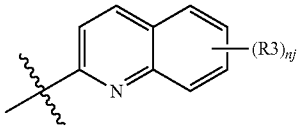
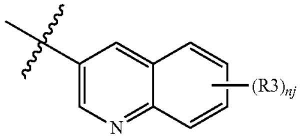
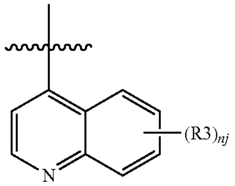
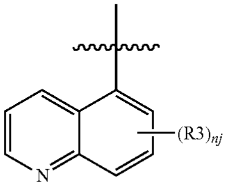
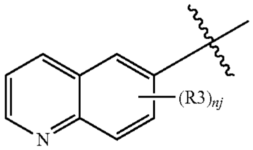
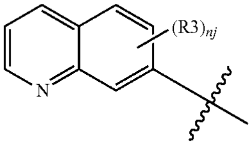
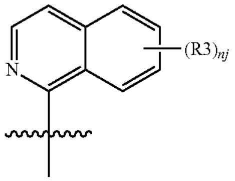
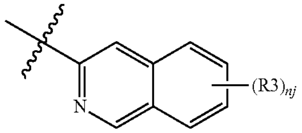
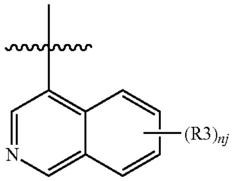
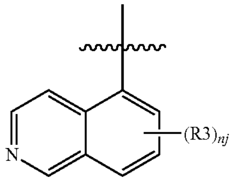
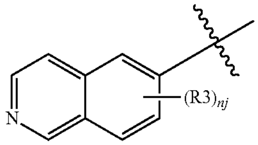
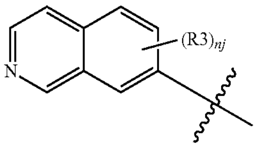
-continued
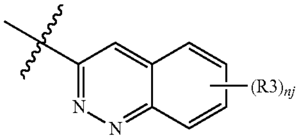
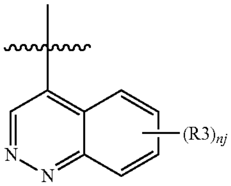
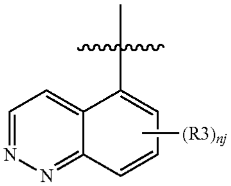
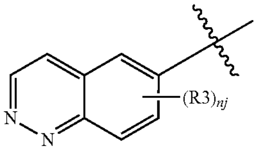
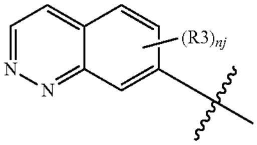
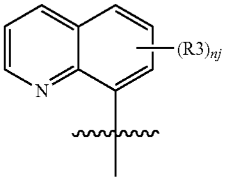
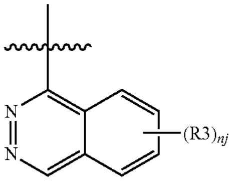
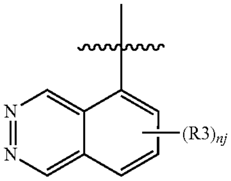
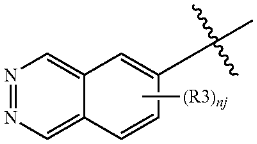
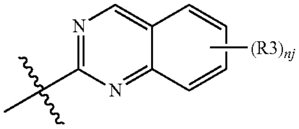
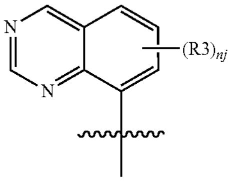
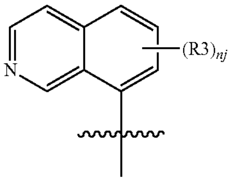
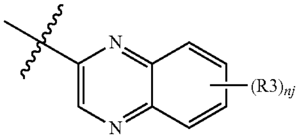
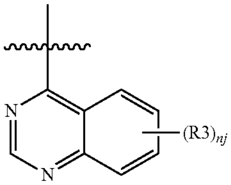
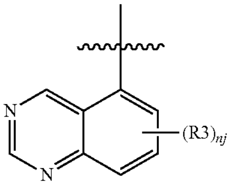

-continued

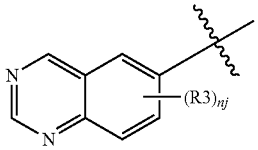
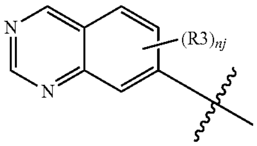
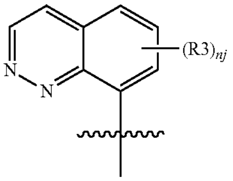
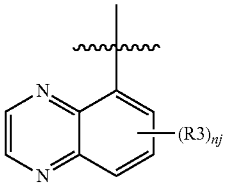
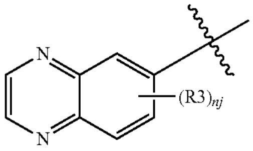

Specific examples of the partial structures of Formula (j-2) are illustrated below.

[Chem. 70]

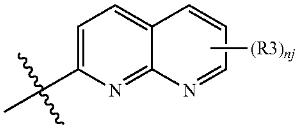
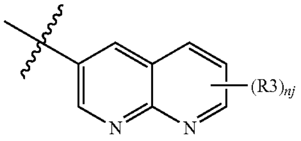
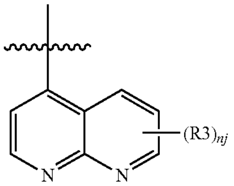
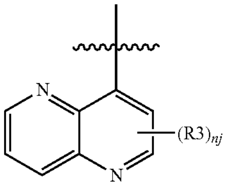
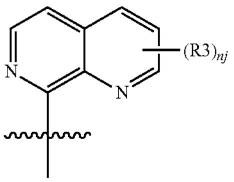
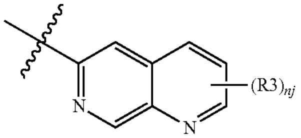

-continued

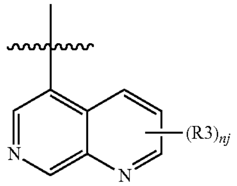
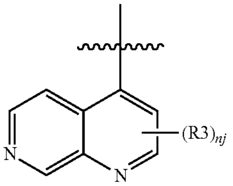
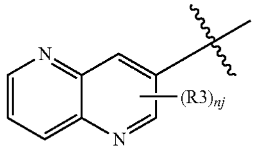
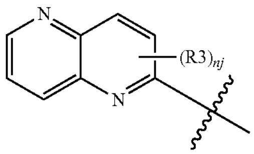
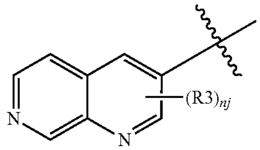
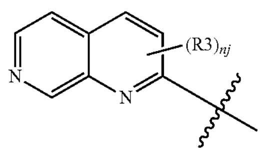

N) When. Het is the "3 to 6 membered ring group containing 1 to 2 oxygen atoms", Het represents a 1,2-epoxyethanyl group, an oxetanyl group, a oxolanyl group, an oxanyl group, a 1,3-dioxolanyl group, a 1,3-dioxanyl group or a 1,4-dioxanyl group. Above all, an oxolanyl group, an oxanyl group, a 1,3-dioxolanyl group, a 1,3-dioxanyl group or a 1,4-dioxanyl group is preferable, and in particular, a 1,3-dioxolanyl group or a 1,3-dioxanyl group is preferable.

Y in Formula (1) represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group. Above all, a phenyl group or a pyridyl group is preferable, and in particular, a phenyl group is preferable.

The phenyl group is substituted with R4 at an ortho position and is further optionally substituted with 0 to 4 substituents R5. (with the proviso that when two or more substituents R5 are present, each R5 represents an independent substituent.)

the pyridyl group, the pyridazinyl group, the pyrimidinyl group, the pyrazinyl group, the triazinyl group or the tetrazinyl group is substituted with R4 at an ortho position and is further optionally substituted with 0 to 3 substituents R5. (with the proviso that when two or more substituents R5 are present, each R5 represents an independent substituent.)

the thienyl group, the thiazolyl group, the isothiazolyl group or the thiadiazolyl group is substituted with R4 at an ortho position and is further optionally substituted with 0 to 2 substituents R5. (with the proviso that when two substituents R5 are present, each R5 represents an independent substituent.)

R4 in Formula (1) represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx1C(═O)O— (wherein Rx1 is the same as defined hereinabove), Rx2C(═O)N(Rx3)- (wherein Rx2 and Rx3 are the same as defined hereinabove), Rx4Rx5C═N—O— (wherein Rx4 and Rx5 are the same as defined hereinabove.) or a 3 to 6-membered ring group containing 1 to 2 oxygen atoms.

Above all, R4 is preferably a cyano group, a nitro group, a halogen atom, a C1-C6 alkyl group optionally substituted with substituent(s) C, a C1-C6 haloalkyl group, a C1-C6 alkoxy group optionally substituted with substituent(s) C or C1-C6 haloalkoxy group;

R4 is particularly preferably a cyano group, a nitro group, a halogen atom, a C1-C6 alkyl group optionally substituted with substituent(s) C, a C1-C6 haloalkyl group or a C1-C6 alkoxyl group optionally substituted with substituent(s) C;

and R4 is further preferably a cyano group, a halogen atom, a C1-C6 alkyl group optionally substituted with substituent(s) C, a C1-C6 haloalkyl group or a C1-C6 alkoxyl group optionally substituted with substituent(s) C.

In R4 of Formula (1), a hydroxyl group, a cyano group and a nitro group are contained.

The halogen atom in R4 of Formula (1) is the same as defined hereinabove, preferably a fluorine atom, a chlorine atom, a bromine atom or an iodine atom, and further preferably a fluorine atom, a chlorine atom or a bromine atom.

The C1-C6 alkyl group of the "C1-C6 alkyl group optionally substituted with substituent(s) C" in R4 of Formula (1) is the same as defined hereinabove, preferably a methyl group, an ethyl group, a propyl group or an isopropyl group, further preferably a methyl group, an ethyl group or a propyl group, and particularly preferably a methyl group or an ethyl group. When it has the substituent(s) C, the C1-C6 alkyl group is optionally substituted with the substituent(s) C in place of hydrogen atom(s).

The "C1-C6 haloalkyl group" in R4 of Formula (1) is the same as defined hereinabove, preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, further preferably a difluoromethyl group or a trifluoromethyl group, and particularly preferably a trifluoromethyl group.

The C3-C8 cycloalkyl group of the "C3-C8 cycloalkyl group optionally substituted with substituent(s) C" in R4 of Formula (1) is the same as defined hereinabove, preferably a cyclopropyl group, a cyclobutyl group, a cyclopentyl group or a cyclohexyl group, and further preferably a cyclopropyl group or a cyclobutyl group. When it has the substituent(s) C, the C3-C8 cycloalkyl group is optionally substituted with the substituent(s) C in place of hydrogen atom(s).

The C2-C6 alkenyl group of the "C2-C6 alkenyl group optionally substituted with substituent(s) C" in R4 of Formula (1) is the same as defined hereinabove, preferably a vinyl group, a 1-propenyl group, an allyl group, a 1-butenyl group, a 2-butenyl group or a 3-butenyl group, and further preferably a vinyl group. When it has the substituent(s) C, the C2-C6 alkenyl group is optionally substituted with the substituent(s) C in place of hydrogen atom(s).

The "C2-C6 haloalkenyl group" in R4 of Formula (1) is the same as defined hereinabove, preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and further preferably a 2-fluorovinyl group or a 2,2-difluorovinyl group.

The C2-C6 alkynyl group of the "C2-C6 alkynyl group optionally substituted with substituent(s) C" in R4 of Formula (1) is the same as defined hereinabove, preferably an ethynyl group, a 1-propynyl group or a propargyl group, and further preferably a ethynyl group. When it has the substituent(s) C, the C2-C6 alkynyl group is optionally substituted with the substituent(s) C in place of hydrogen atom(s).

The "C2-C6 haloalkynyl group" in R4 of Formula (1) is the same as defined hereinabove, preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and further preferably a 3,3-difluoro-1-propynyl group or a 3,3,3-trifluoro-1-propynyl group.

The C1-C6 alkoxy group of the "C1-C6 alkoxyl group optionally substituted with substituent(s) C" in R4 of Formula (1) is the same as defined hereinabove, preferably a methoxy group, an ethoxy group, a propyloxy group or an isopropyloxy group, further preferably a methoxy group or an ethoxy group, and particularly preferably a methoxy group. When it has the substituent(s) C, the C1-C6 alkoxy group is optionally substituted with the substituent(s) C in place of hydrogen atom(s).

The "C1-C6 haloalkoxy group" in R4 of Formula (1) is the same as defined hereinabove, preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and further preferably a difluoromethoxy group or a trifluoromethoxy group.

The C3-C8 cycloalkoxy group of the "C3-C8 cycloalkoxy group optionally substituted with substituent(s) C" in R4 of Formula (1) is the same as defined hereinabove, preferably a cyclopropyloxy group, a cyclobutoxy group, a cyclopentyloxy group or a cyclohexyloxy group, and further preferably a cyclopropyloxy group or a cyclobutoxy group. When it has the substituent(s) C, the C3-C8 cycloalkoxy group is optionally substituted with the substituent(s) C in place of hydrogen atom(s).

The C2-C6 alkenyloxy group of the "C2-C6 alkenyloxy group optionally substituted with substituent(s) C" in R4 of Formula (1) is the same as defined hereinabove, preferably a vinyloxy group, a 1-propenyloxy group or an allyloxy group, and further preferably an allyloxy group. When it has the substituent(s) C, the C2-C6 alkenyloxy group is optionally substituted with the substituent(s) C in place of hydrogen atom(s).

The "C2-C6 haloalkenyloxy group" in R4 of Formula (1) is the same as defined hereinabove, preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and further preferably a 2-fluorovinyloxy group or a 2,2-difluorovinyloxy group.

The C3-C6 alkynyloxy group of the "C3-C6 alkynyloxy group optionally substituted with substituent(s) C" in R4 of Formula (1) is the same as defined hereinabove, preferably a propargyloxy group, a 2-butynyloxy group or a 3-butynyloxy group, and further preferably a propargyloxy group. When it has the substituent(s) C, the C3-C6 alkynyloxy group is optionally substituted with the substituent(s) C in place of hydrogen atom(s).

The "C3-C6 haloalkynyloxy group" in R4 of Formula (1) is the same as defined hereinabove, preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and further preferably a 4,4-difluoro-2-butynyloxy group or a 4,4,4-trifluoro-2-butynyloxy group.

The aryl group of the "aryl group optionally substituted with substituent(s) D" in R4 of Formula (1) is the same as defined hereinabove, and preferably a phenyl group. When it has the substituent(s) D, the aryl group is optionally substituted with the substituent(s) D in place of hydrogen(s).

The heteroaryl group of the "heteroaryl group optionally substituted with substituent(s) D" in R4 of Formula (1) is the same as defined hereinabove, preferably a pyridyl group, a pyrazinyl group, a thienyl group, a thiazolyl group, an isothiazolyl group, furyl group, an imidazolyl group, a pyrazolyl group, oxazolyl group, an isoxazolyl group, a triazolyl group, an oxadiazolyl group or a tetrazolyl group, and further preferably a pyridyl group, an imidazolyl group, a pyrazolyl group, triazolyl group or a tetrazolyl group. When it has the substituent(s) D, the heteroaryl group is optionally substituted with the substituent(s) D in place of hydrogen(s).

The aryloxy group of the "aryloxy group optionally substituted with substituent(s) D" in R4 of Formula (1) is the same as defined hereinabove, preferably a phenoxy group or a naphthyloxy group, and further preferably a phenoxy group. When it has the substituent(s) D, the aryloxy group is optionally substituted with the substituent(s) D in place of hydrogen atom(s).

The heteroaryloxy group of the "heteroaryloxy group optionally substituted with substituent(s) D" in R4 of Formula (1) is the same as defined hereinabove, preferably a pyridyloxy group, a pyridazinyloxy group, a pyrimidinyloxy group, a pyrazinyloxy group, a pyrazolyloxy group, a triazinyloxy group, a tetrazinyloxy group, a thienyloxy group, a thiazolyloxy group, an isothiazolyloxy group or a thiadiazolyloxy group, and further preferably a pyridyloxy group, a pyridazinyloxy group, a pyrimidinyloxy group, a pyrazinyloxy group or a pyrazolyloxy group. When it has the substituent(s) D, the heteroaryloxy group is optionally substituted with the substituent(s) D in place of hydrogen atom(s).

The aralkyloxy group of the "aralkyloxy group optionally substituted with substituent(s) D" in R4 of Formula (1) is the same as defined hereinabove, preferably a benzyloxy group, a phenethyloxy group or a phenylpropyloxy group, and further preferably a benzyloxy group. When it has the substituent(s) D, the aralkyloxy group is optionally substituted with the substituent(s) D in place of hydrogen atom(s).

Ra and Rb of "RaRbN—" in R4 of Formula (1) are the same as defined hereinabove. The "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and further preferably an amino group, a dimethylamino group, an ethylmethylamino group or a diethylamino group.

Rc and L of the "Rc-L-" in R4 of Formula (1) is the same as defined hereinabove. The "Rc-L-" is preferably a methylthio group, a methanesulfinyl group, a methanesulfonyl group, a trifluoromethylthio group, a trifluoromethanesulfinyl group or a trifluoromethanesulfonyl group, and further preferably a methylthio group, a methanesulfinyl group or a methanesulfonyl group.

Rx1 of the "Rx1C(═O)—" in R4 of Formula (1) is the same as defined hereinabove. The "Rx1C(═O)—" is preferably an acetyl group, a methoxyacetyl group, a cyanoacetyl group, a propionyl group, a difluoroacetyl group, a trifluoroacetyl group, a cyclopropancarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and further preferably an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethylmethylaminocarbonyl group or a diethylaminocarbonyl group.

Rx1 of "Rx1C(═O)O—" in R4 of Formula (1) is the same as defined hereinabove. The "Rx1C(═O)O—" is preferably an acetyloxy group, a methoxyacetyloxy group, a cyanoacetyloxy group, a propionyloxy group, a difluoroacetyloxy group, a trifluoroacetyloxy group, a cyclopropancarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)-aminocarbonyloxy group, a (2-methoxyethyl)aminocarbonyloxy group, a (cyano-methyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylamino-carbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, further preferably an acetyloxy group, a methoxyacetyloxy group, a cyanoacetyloxy group, a difluoroacetyloxy group, a trifluoroacetyloxy group, a methoxycarbonyloxy group, an ethoxycarbonyloxy group, an aminocarbonyloxy group, a dimethylaminocarbonyloxy group, an ethylmethylaminocarbonyloxy group or a diethylaminocarbonyloxy group.

Each term of "Rx2C(═O)N(Rx3)-" (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group.) in R4 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s). The Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl)amino group, a (2-methoxyethyl) amino group, a (cyanomethyl)amino group, a (2-cyanoethyl) amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and further preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group. Also, the Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, and further preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group.

Each term in the "Rx4Rx5C═N—O—" (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) in R4 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s).

Rx4 and Rx5 are each preferably a methyl group, an ethyl group, a propyl group, an isopropyl group, a trifluoromethyl group, a 2,2,2-trifluoroethyl group, a cyclopropyl group, a cyclopentyl group, a cyclohexyl group, a methoxy group, an ethoxy group, isopropyloxy group, a difluoromethoxy group, a trifluoromethoxy group, a 2,2-difluoroethoxy group, a 2,2,2-trifluoroethoxy group, a cyclopropyloxy group, a cyclobutyloxy group, a cyclopentyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl) methylamino group, a pyrrolidinyl group or a piperidinyl group, and further preferably a methyl group, an ethyl group, a trifluoromethyl group, a 2,2,2-trifluoroethyl group, a methoxy group, an ethoxy group, a 2,2,2-trifluoroethoxy group, a dimethylamino group, an ethylmethylamino group or a diethylamino group.

The "3 to 6 membered ring group containing 1 to 2 oxygen atoms" in R4 of Formula (1) is the same as defined hereinabove, preferably an oxolanyl group, an oxanyl group, a 1,3-dioxolanyl group or a 1,3-dioxanyl group, and further preferably a 1,3-dioxolanyl group or a 1,3-dioxanyl group.

R5 in Formula (1) is defined the same as R4 described hereinabove. That is, it represents a hydroxyl group, a cyano group, a nitro group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (wherein Ra and Rb are the same as defined hereinabove), Rc-L- (wherein Rc and L are the same as defined hereinabove), Rx1C(═O)— (wherein Rx1 is the same as defined hereinabove), Rx C(═O)O— (wherein Rx1 is the same as defined hereinabove), Rx2C(═O)N(Rx3)- (wherein Rx2 and Rx3 are the same as defined hereinabove), Rx4Rx5C═N—O— (wherein Rx4 and Rx5 are the same as defined hereinabove.) or a 3 to 6-membered ring group containing 1 to 2 oxygen atoms.

Above all, R5 is preferably a hydroxyl group, a cyano group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb are the same as defined hereinabove), Rc-L- (wherein Rc and L are the same as defined hereinabove.) or Rx1C(═O)O— (wherein Rx1 is the same as defined hereinabove);

R5 is particularly preferably a hydroxyl group, a cyano group, a halogen atom, a C1-C6 alkyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb are the same as defined hereinabove), Rc-L- (wherein Rc and L are the same as defined hereinabove.) or Rx1C(═O)O— (wherein Rx1 is the same as defined hereinabove);

and R5 is further preferably a hydroxyl group, a cyano group, a halogen atom, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RaRbN— (wherein Ra and Rb are the same as defined hereinabove), Rc-L- (wherein Rc and L are the same as defined hereinabove.) or Rx1C(═O)O— (wherein Rx1 is the same as defined hereinabove).

In R5 of Formula (1), a hydroxyl group, a cyano group and a nitro group are contained.

The halogen atom in R5 of Formula (1) is the same as defined hereinabove, preferably a fluorine atom, a chlorine atom, a bromine atom or an iodine atom, and further preferably a fluorine atom or an iodine atom.

The C1-C6 alkyl group of the "C1-C6 alkyl group optionally substituted with substituent(s) C" in R5 of Formula (1) is the same as defined hereinabove, preferably a methyl group, an ethyl group, a propyl group, an isopropyl group, a butyl group or an isobutyl group, further preferably a methyl group or an ethyl group. When it has the substituent(s) C, the C1-C6 alkyl group is optionally substituted with the substituent(s) C in place of hydrogen atom(s).

The "C1-C6 haloalkyl group" in R5 of Formula (1) is the same as defined hereinabove, preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and further preferably a difluoromethyl group, a trifluoromethyl group, a 2,2-difluoroethyl group or a 2,2,2-trifluoroethyl group.

The C3-C8 cycloalkyl group of the "C3-C8 cycloalkyl group optionally substituted with substituent(s) C" in R5 of Formula (1) is the same as defined hereinabove, preferably a cyclopropyl group, a cyclobutyl group, a cyclopentyl group or a cyclohexyl group, and further preferably a cyclopropyl group or a cyclobutyl group. When it has the substituent(s) C, the C3-C8 cycloalkyl group is optionally substituted with the substituent(s) C in place of hydrogen atom(s).

The C2-C6 alkenyl group in the "C2-C6 alkenyl group optionally substituted with substituent(s) C" in R5 of Formula (1) is the same as defined hereinabove, preferably a vinyl group, a 1-propenyl group, an allyl group, a 1-butenyl group, a 2-butenyl group or a 3-butenyl group, and further preferably a vinyl group, a 1-propenyl group or an allyl group. When it has the substituent(s) C, C2-C6 alkenyl group is optionally substituted with the substituent(s) C in place of hydrogen atom(s).

The "C2-C6 haloalkenyl group" in R5 of Formula (1) is the same as defined hereinabove, preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and further preferably a 2-fluorovinyl group or a 2,2-difluorovinyl group.

The C2-C6 alkynyl group of the "C2-C6 alkynyl group optionally substituted with substituent(s) C" in R5 of Formula (1) is the same as defined hereinabove, preferably an ethynyl group, a 1-propynyl group, a propargyl group, a 1-butynyl group, a 2-butynyl group or a 3-butynyl group, and further preferably an ethynyl group, a 1-propynyl group or a propargyl group. When it has the substituent(s) C, the C2-C6 alkynyl group is optionally substituted with the substituent(s) C in place of hydrogen atom(s).

The "C2-C6 haloalkynyl group" in R5 of Formula (1) is the same as defined hereinabove, preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and further preferably a 3,3-difluoro-1-propynyl group or a 3,3,3-trifluoro-1-propynyl group.

The C1-C6 alkoxy group in the "C1-C6 alkoxyl group optionally substituted with substituent(s) C" in R5 of Formula (1) is the same as defined hereinabove, preferably a methoxy group, an ethoxy group, a propyloxy group, an isopropyloxy group, a butoxy group or an isobutoxy group, further preferably a methoxy group, an ethoxy group, a propyloxy group or an isopropyloxy group, and particularly preferably a methoxy group or an ethoxy group. When it has the substituent(s) C, the C1-C6 alkoxy group is optionally substituted with the substituent(s) C in place of hydrogen atom(s). The substituent(s) C is preferably a cyano group, a C3-C8 cycloalkyl group, a C1-C6 alkoxy group, a C1-C6 haloalkoxy group, a C2-C6 alkoxyalkoxy group, Rc-L- (wherein Rc and L are the same as defined hereinabove), Rx1C(═O)— (wherein Rx1 is the same as defined hereinabove.) or a 3 to 6-membered ring group containing 1 to 2 oxygen atoms, and further preferably a cyano group, a C1-C6 alkoxy group or Rc-L- (wherein Rc and L are the same as defined hereinabove). The C1-C6 alkoxy group substituted with the substituent(s) C is preferably a cyanomethoxy group, a cyanoethoxy group, a methoxymethoxy group, a methoxyethoxy group, an ethoxymethoxy group or an ethoxyethoxy group, further preferably a cyanomethoxy group, a methoxymethoxy group or a methoxyethoxy group, and particularly preferably a methoxymethoxy group or a methoxyethoxy group.

The "C1-C6 haloalkoxy group" in R5 of Formula (1) is the same as defined hereinabove, preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and further preferably a difluoromethoxy group, a trifluoromethoxy group, a 2,2-difluoroethoxy group or a 2,2,2-trifluoroethoxy group.

The C3-C8 cycloalkoxy group of the "C3-C8 cycloalkoxy group optionally substituted with substituent(s) C" in R5 of Formula (1) is the same as defined hereinabove, preferably a cyclopropyloxy group, a cyclobutoxy group, a cyclopentyloxy group or a cyclohexyloxy group, and further preferably a cyclopropyloxy group or a cyclobutoxy group. When it has the substituent(s) C, the C3-C8 cycloalkoxy group is optionally substituted with the substituent(s) C in place of hydrogen atom(s).

The C2-C6 alkenyloxy group of the "C2-C6 alkenyloxy group optionally substituted with substituent(s) C" in R5 of Formula (1) is the same as defined hereinabove, preferably a vinyloxy group, a 1-propenyloxy group, an allyloxy group, a 1-butenyloxy group, a 2-butenyloxy group or a 3-butenyloxy group, further preferably a vinyloxy group, a 1-propenyloxy group or an allyloxy group, and particularly preferably an allyloxy group. When it has the substituent(s) C, the C2-C6 alkenyloxy group is optionally substituted with the substituent(s) C in place of hydrogen atom(s).

The "C2-C6 haloalkenyloxy group" in R5 of Formula (1) is the same as defined hereinabove, preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and further preferably a 2-fluorovinyloxy group or a 2,2-difluorovinyloxy group.

The C3-C6 alkynyloxy group of the "C3-C6 alkynyloxy group optionally substituted with substituent(s) C" in R5 of Formula (1) is the same as defined hereinabove, preferably a propargyloxy group, a 2-butynyloxy group or a 3-butynyloxy group, further preferably a propargyloxy group or a 2-butynyloxy group, and particularly preferably a propargyloxy group. When it has the substituent(s) C, the C3-C6 alkynyloxy group is optionally substituted with the substituent(s) C in place of hydrogen atom(s).

The "C3-C6 haloalkynyloxy group" in R5 of Formula (1) is the same as defined hereinabove, preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and further preferably a 4,4-difluoro-2-butynyloxy group or a 4,4,4-trifluoro-2-butynyloxy group.

The aryl group of the "aryl group optionally substituted with substituent(s) D" in R5 of Formula (1) is the same as defined hereinabove, and preferably a phenyl group. When it has, the substituent(s) D, the aryl group is optionally substituted with the substituent(s) D in place of hydrogen(s).

The heteroaryl group of the "heteroaryl group optionally substituted with substituent(s) D" in R5 of Formula (1) is the same as defined hereinabove, preferably a pyridyl group, a pyrazinyl group, a thienyl group, a thiazolyl group, an isothiazolyl group, furyl group, an imidazolyl group, a pyrazolyl group, oxazolyl group, an isoxazolyl group, a triazolyl group, an oxadiazolyl group or a tetrazolyl group, and further preferably a pyridyl group, an imidazolyl group, a pyrazolyl group, triazolyl group or a tetrazolyl group. When it has the substituent(s) D, the heteroaryl group is optionally substituted with the substituent(s) D in place of hydrogen(s).

The aryloxy group of the "aryloxy group optionally substituted with substituent(s) D" in R5 of Formula (1) is the same as defined hereinabove, preferably a phenoxy group or a naphthyloxy group, and further preferably a phenoxy group. When it has the substituent(s) D, the aryloxy group is optionally substituted with the substituent(s) D in place of hydrogen atom(s).

The heteroaryloxy group of the "heteroaryloxy group optionally substituted with substituent(s) D" in R5 of Formula (1) is the same as defined hereinabove, preferably a pyridyloxy group, a pyridazinyloxy group, a pyrimidinyloxy group, a pyrazinyloxy group, a pyrazolyloxy group, a triazinyloxy group, a tetrazinyloxy group, a thienyloxy group, a thiazolyloxy group, an isothiazolyloxy group or a thiadiazolyloxy group, and further preferably a pyridyloxy group, a pyridazinyloxy group, a pyrimidinyloxy group, a pyrazinyloxy group or a pyrazolyloxy group. When it has the substituent(s) D, the heteroaryloxy group is optionally substituted with the substituent(s) D in place of hydrogen atom(s).

The aralkyloxy group of the "aralkyloxy group optionally substituted with substituent(s) D" in R5 of Formula (1) is the same as defined hereinabove, preferably a benzyloxy group, a phenethyloxy group or a phenylpropyloxy group, and further preferably a benzyloxy group or a phenethyloxy group. When it has the substituent(s) D, the aralkyloxy group is optionally substituted with the substituent(s) D in place of hydrogen atom(s).

Ra and Rb of the "RaRbN—" in R5 of Formula (1) are the same as defined hereinabove. Ra and Rb are each preferably a hydrogen atom, a C1-C6 alkyl group optionally substituted with substituent(s) B, a C1-C6 haloalkyl group, a C3-C8 cycloalkyl group, pyrrolidinyl group or a piperidinyl group, and further preferably a hydrogen atom, a C1-C6 alkyl group optionally substituted with substituent(s) B, a pyrrolidinyl group or a piperidinyl group. The "RaRbN—" is-preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, further preferably an amino group, a methylamino group, a dimethylamino group, an ethylmethylamino group, a diethylamino group, a pyrrolidinyl group or a piperidinyl group, and particularly preferably a methylamino group, a pyrrolidinyl group or a piperidinyl group.

Rc and L of the "Rc-L-" in R5 of Formula (1) is the same as defined hereinabove. The Rc is preferably a C1-C6 alkyl group. The L is preferably S. The "Rc-L-" is preferably a methylthio group, a methanesulfinyl group, a methanesulfonyl group, a trifluoromethylthio group, a trifluoromethanesulfinyl group or a trifluoromethanesulfonyl group, further preferably a methylthio group, a methanesulfinyl group or a methanesulfonyl group, and particularly preferably a methylthio group.

Rx1 in the "Rx1C(═O)—" in R5 of Formula (1) is the same as defined hereinabove. The "Rx1C(═O)—" is preferably an acetyl group, a methoxyacetyl group, a cyanoacetyl group, a propionyl group, a difluoroacetyl group, a trifluoroacetyl group, a cyclopropancarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and further preferably an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethylmethylaminocarbonyl group or a diethylaminocarbonyl group.

Rx1 of the "Rx1C(═O)O—" in R5 of Formula (1) is the same as defined hereinabove. The Rx1 is preferably a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), further preferably a C1-C6 alkyl group optionally substituted with substituent(s) B, a C1-C6 haloalkyl group, a C1-C6 alkoxy group or RaRbN— (wherein Ra and Rb are the same as defined hereinabove), and particularly preferably a C1-C6 alkyl group optionally substituted with substituent(s) B. The "Rx1C(═O)O—" is preferably an acetyloxy group, a methoxyacetyloxy group, a cyanoacetyloxy group, a propionyloxy group, a difluoroacetyloxy group; a trifluoroacetyloxy group, a cyclopropancarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxy-methyl)methylaminocarbonyloxy group, a (2-methoxyethyl)methylaminocarbonyloxy group, a (cyanomethyl)methylaminocarbonyloxy group, a (2-cyanoethyl) methylamino-carbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, further preferably an acetyloxy group, a methoxyacetyloxy group, a cyanoacetyloxy group, a difluoroacetyloxy group, a trifluoroacetyloxy group, a methoxycarbonyloxy group, an ethoxycarbonyloxy group, an aminocarbonyloxy group, a dimethylaminocarbonyloxy group, an ethylmethylaminocarbonyloxy group or a diethylaminocarbonyloxy group, and particularly preferably an acetyloxy group.

Each term of the "Rx2C(═O)N(Rx3)-" (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), Rx3 represents a hydrogen atom, a C1-C6 alkyl group optionally substituted with substituent(s) B, a C1-C6 haloalkyl group or a C3-C8 cycloalkyl group.) in R5 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s). The Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl)amino group, a (2-methoxyethyl) amino group, a (cyanomethyl)amino group, a (2-cyanoethyl) amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, further preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group. Also, Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, and further preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group.

Each term of the "Rx4Rx5C═N—O—" (wherein Rx4 and Rx5 each independently represent a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) in R5 of Formula (1) is the same as defined hereinabove. Incidentally, with regard to the "C1-C6 alkyl group optionally substituted with substituent(s) B", when it has the substituent(s) B, the C1-C6 alkyl group is optionally substituted with the substituent(s) B in place of hydrogen atom(s).

Rx4 and Rx5 are each preferably a methyl group, an ethyl group, a propyl group, an isopropyl group, a trifluoromethyl group, a 2,2,2-trifluoroethyl group, a cyclopropyl group, a cyclopentyl group, a cyclohexyl group, a methoxy group, an ethoxy group, isopropyloxy group, a difluoromethoxy group, a trifluoromethoxy group, a 2,2-difluoroethoxy group, a 2,2,2-trifluoroethoxy group, a cyclopropyloxy group, a cyclobutyloxy group, a cyclopentyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl) methylamino group, a pyrrolidinyl group or a piperidinyl group, and further preferably a methyl group, an ethyl group, a trifluoromethyl group, a 2,2,2-trifluoroethyl group, a methoxy group, an ethoxy group, a 2,2,2-trifluoroethoxy group, a dimethylamino group, an ethylmethylamino group or a diethylamino group.

The "3 to 6 membered ring group containing 1 to 2 oxygen atoms in R5 of Formula (1) is the same as defined hereinabove, preferably an oxolanyl group, an oxanyl group, a 1,3-dioxolanyl group or a 1,3-dioxanyl group, and further preferably a 1,3-dioxolanyl group or a 1,3-dioxanyl group.

In the following, Y in Formula (1) will be described in detail.

A) When Y is a phenyl group, Y represents a partial structure represented by Formula (k)

[Chem. 71]

(k)

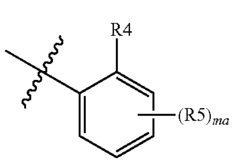

(wherein R4 and R5 is the same as defined hereinabove and "ma" represents an integer of 0 to 4).

"ma" in Formula (k) represents an integer of 0 to 4.

When "ma" of Formula (k) is 2 or more, the two or more substituents R5 are independent of one another and may be optionally selected to be the same as or different from one another.

In the present specification, when Y is a phenyl group, the ortho position indicates the position in the phenyl group at which there is the substituent R4 as illustrated in Formula (k).

The phenyl group in which the substituent R4 is positioned at the ortho position constitutes the characteristics of the present invention.

Preferred combination of the substituents of Formula (k) is a 2-R4-phenyl group, a 2-R4-6-R5-phenyl group, a 2-R4-4-R5-phenyl group, a 2-R4-4-R5-6-R5-phenyl group, a 2-R4-3-R5-phenyl group or a 2-R4-3-R5-4-R5-6-R5-phenyl group, and more preferred combination of the substituents is a 2-R4-phenyl group, a 2-R4-6-R5-phenyl group, a 2-R4-4-R5-phenyl group, a 2-R4-4-R5-6-R5-phenyl group or a 2-R4-3-R5-4-R5-6-R5-phenyl group. Here, for example, the "2-R4-6-R5-phenyl group" indicates a di-substituted phenyl group having the substituent R4 at the 2-position and the substituent R5 at the 6-position, and the same applies hereinafter.

B) When Y is a pyridyl group, a pyridazinyl group, a pyrimidinyl group, a pyrazinyl group, a triazinyl group or tetrazinyl group, Y represents a partial structure represented by Formula (L)

[Chem. 72]

(L)

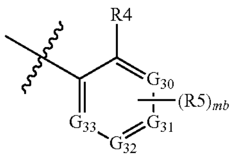

(wherein R4, R5 are the same as defined hereinabove and "mb" represents an integer of 0 to 3).

G30, G31, G32 and G33 in Formula (L) are each independent and represent a carbon atom or a nitrogen atom. With the proviso that at least one among G30, G31, G32 and G33 is a nitrogen atom. Preferred G30, G31, G32 and G33 are that any one of G30, G31, G32 and G33 is a nitrogen atom. That is, it is a pyridyl group.

"mb" in Formula (L) represents an integer of 0 to 3.

When "mb" of Formula (L) is 2 or more, the two or more substituents R5 are independent of one another and may be optionally selected to be the same as or different from one another.

In the present specification, when Y is a pyridyl group, a pyridazinyl group, a pyrimidinyl group, a pyrazinyl group, a triazinyl group or a tetrazinyl group, the ortho position indicates the position in the 6-membered ring at which there is the substituent R4 as illustrated in Formula (L).

Specific examples of the partial structures represented by Formula (L) are illustrated below.

[Chem. 73]

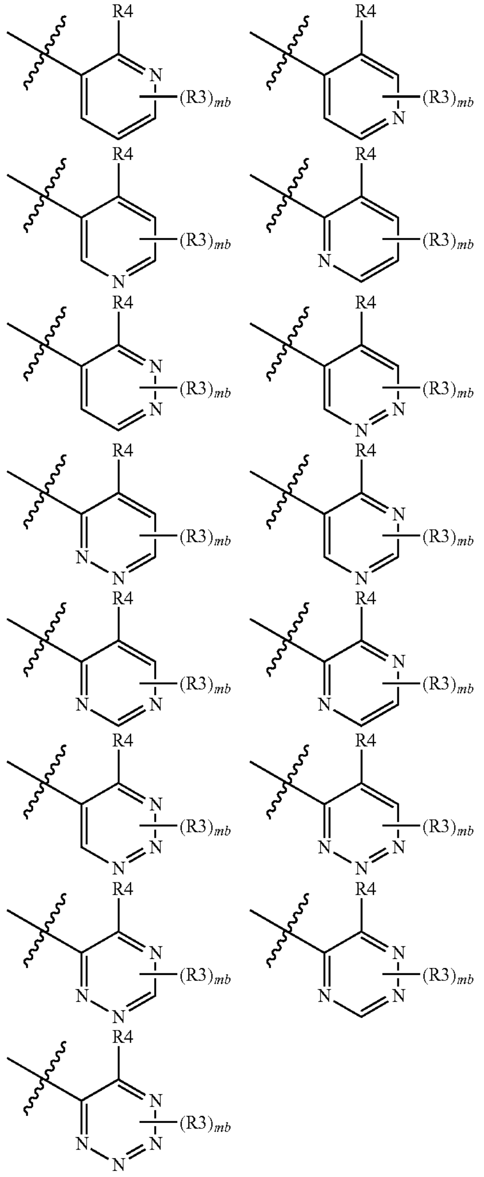

The pyridyl group, the pyridazinyl group, the pyrimidinyl group, the pyrazinyl group, the triazinyl group or the tetrazinyl group in which the substituent R4 is positioned at the ortho position constitute the characteristics of the present invention.

Preferred specific examples of Formula (L) are a 3-R4-pyridin-2-yl group, a 3-R4-5-R5-pyridin-2-yl group, a 2-R4- pyridin-3-yl group, a 2-R4-4-R5-pyridin-3-yl group, a 2-R4-6-R5-pyridin-3-yl group, a 2-R4-4-R5-6-R5-pyridin-3-yl group, a 4-R4-pyridin-3-yl group, a 4-R4-2-R5-pyridin-3-yl group, a 4-R4-6-R5-pyridin-3-yl group, a 4-R4-2-R5-6-R5-pyridin-3-yl group, a 3-R4-pyridin-4-yl group or a 3-R4-5-R5-pyridin-4-yl group.

C) When Y is a thienyl group, a thiazolyl group, an isothiazolyl group or a thiadiazolyl group, Y represents a partial structure represented by Formula (m-1)
[Chem. 74]

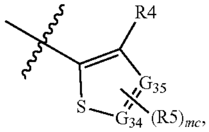

(m-1)

Formula (m-2)
[Chem. 75]

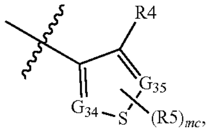

(m-2)

or

Formula (m-3)
[Chem. 76]

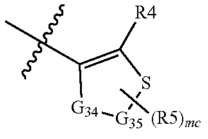

(m-3)

(wherein R4 and R5 are the same as defined hereinabove and "mc" represents an integer of 0 to 2).

G34 and G35 in Formula (m-1), Formula (m-2) and Formula (m-3) are each independent and represent a carbon atom or a nitrogen atom.

"mc" in Formula (m-1), Formula (m-2) and Formula (m-3) represents an integer of 0 to 2.

When "mc" in Formula (m-1), Formula (m-2) and Formula (m-3) is 2, the two substituents R5 are independent of one another and may be optionally selected to be the same as or different from one another.

In the present specification, when Y is a thienyl group, a thiazolyl group, an isothiazolyl group or a thiadiazolyl group, the ortho position indicates the position in the 5-membered ring at which there is the subsistent R4 as illustrated in Formula (m-1), Formula (m-2) and Formula (m-3).

Specific examples of the partial structures represented by Formula (m-1) are illustrated below.

[Chem. 77]

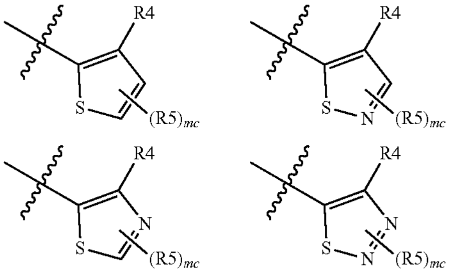

Specific examples of the partial structures represented by Formula (m-2) are illustrated below.

[Chem. 78]

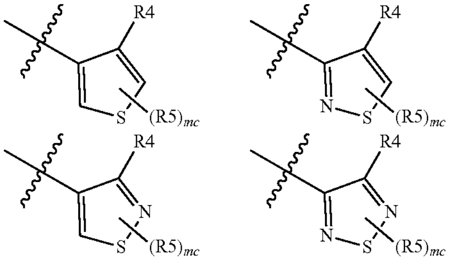

Specific examples of the partial structures represented by Formula (m-3) are illustrated below.

[Chem. 79]

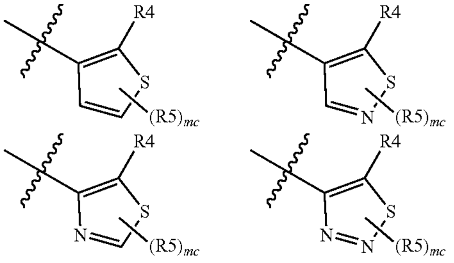

The thienyl group, the thiazolyl group, the isothiazolyl group or the thiadiazolyl group in which the substituent R4 is positioned at the ortho position constitute the characteristics of the present invention.

X in Formula (1) represents an oxygen atom or a sulfur atom. Preferable X is an oxygen atom.

A bond containing the broken line in Formula (1) represents the portion represented by

[Chem. 80]

The bond containing the broken line in Formula (1) represents a double bond or a single bond.

When the bond containing the a broken line in Formula (1) is a double bond, the compound represented by Formula (1a)

[Chem. 81]

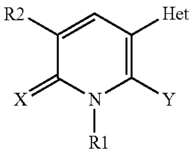

(1a)

(wherein R1, R2, Het, X and Y are the same as defined in Formula (1)) or a salt thereof is represented.

When the bond containing the broken line in Formula (1) is a single bond, the compound represented by Formula (1b)

[Chem. 82]

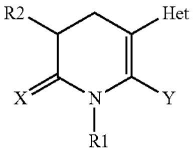

(1b)

(wherein R1, R2, Het, X and Y are the same as defined in Formula (1).) or a salt thereof is represented.

When R2 in Formula (1b) is a substituent other than hydrogen, the compound is either one of the R-isomer or the S-isomer, or a mixture of the R-isomer and the S-isomer with an optional ratio.

The "substituent(s) A" in Formula (1) represents at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, RaRbN— (wherein Ra and Rb are the same as defined hereinabove.) and Rc-L- (wherein Rc and L are the same as defined hereinabove).

Above all, the substituent(s) A is preferably a cyano group, a C1-C6 alkoxy group or Rc-L- (wherein Rc and L are the same as defined hereinabove), and particularly preferably a cyano group or a C1-C6 alkoxy group.

Preferred specific examples of the substituent(s) A may include a hydroxyl group; a cyano group;

a cyclopropyl group, a cyclobutyl group, a cyclopentyl group and a cyclohexyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoro-propyloxy group as the C1-C6 haloalkoxy group;

a cyclopropyloxy group, a cyclobutoxy group, a cyclopentyloxy group and a cyclohexyloxy group as the C3-C8 cycloalkoxy group;

an amino group, a methylamino group, an ethylamino group, a (methoxymethyl)amino group, a (2-methoxyethyl)amino group, a (cyanomethyl)amino group, a (2-cyanoethyl)-amino group, a dimethylamino group, an ethylmethylamino group, a diethylamino group, a (methoxymethyl)methyl-amino group, a (2-methoxyethyl)methylamino group, a (cyanomethyl)methylamino group, a (2-cyanoethyl)methyl-amino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined hereinabove);

and a methylthio group, a methanesulfinyl group, a methanesulfonyl group, a trifluoromethylthio group, a trifluoromethanesulfinyl group and a trifluoromethanesulfonyl group as the Rc-L- (wherein Rc and L are the same as defined hereinabove).

More preferred specific examples of the substituent(s) A may include a hydroxyl group; a cyano group;

a cyclopropyl group and a cyclobutyl group as the C3-C8 cycloalkyl group, a methoxy group and an ethoxy group as the C1-C6 alkoxy group, a difluoromethoxy group, a trifluoromethoxy group, a 2,2-difluoroethoxy group and a 2,2,2-trifluoroethoxy group as the C1-C6 haloalkoxy group, a cyclopropyloxy group and a cyclobutoxy group as the C3-C8 cycloalkoxy group, a dimethylamino group, an ethylmethylamino group and a diethylamino group as the RaRbN— (wherein Ra and Rb are the same as defined hereinabove), and a methylthio group, a methanesulfinyl group and a methanesulfonyl group as the Rc-L- (wherein Rc and L are the same as defined hereinabove).

The "substituent(s) B" in Formula (1) represents at least one kind selected from the group consisting of a cyano group, a C1-C6 alkoxy group, a C1-C6 haloalkoxy group and a C3-C8 cycloalkoxy group.

Above all, the substituent(s) B is preferably a cyano group or a C1-C6 alkoxy group.

Preferred specific examples of the substituent(s) B may include a cyano group; a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoro-propyloxy group as the C1-C6 haloalkoxy group;

and a cyclopropyloxy group, a cyclobutoxy group, a cyclopentyloxy group and a cyclohexyloxy group as the C3-C8 cycloalkoxy group.

More preferred specific examples of the substituent(s) B may include a cyano group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

and a cyclopropyloxy group and a cyclobutoxy group as the C3-C8 cycloalkoxy group.

The "substituent(s) C" in Formula (1) represents at least one kind selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), Rx1C(═O)— (wherein Rx1 is the same as defined hereinabove.) and a 3 to 6-membered ring group containing 1 to 2 oxygen atoms;

above all, the substituent(s) C is preferably a cyano group, a C3-C8 cycloalkyl group, a C1-C6 alkoxy group, a C1-C6 haloalkoxy group, a C2-C6 alkoxyalkoxy group, Rc-L- (wherein Rc and L are the same as defined hereinabove), Rx1C(═O)— (wherein Rx1 is the same as defined hereinabove.) or a 3 to 6-membered ring group containing 1 to 2 oxygen atoms, and particularly preferably a cyano group, a C1-C6 alkoxy group or Rc-L- (wherein Rc and L are the same as defined hereinabove).

Preferred specific examples of the substituent(s) C may include a hydroxyl group; a cyano group;

a cyclopropyl group, a cyclobutyl group, a cyclopentyl group and a cyclohexyl group as the C3-C8 cycloalkyl group;

a methoxy group, an ethoxy group, a propyloxy group, an isopropyloxy group, a butoxy group, an isobutoxy group and a t-butoxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoro-propyloxy group as the C1-C6 haloalkoxy group;

a cyclopropyloxy group, a cyclobutoxy group, a cyclopentyloxy group and a cyclohexyloxy group as the C3-C8 cycloalkoxy group;

a methoxymethoxy group, an ethoxymethoxy group, a methoxyethoxy group, an ethoxyethoxy group and a methoxypropyloxy group as the C2-C6 alkoxyalkoxy group;

an amino group, a methylamino group, an ethylamino group, a (methoxymethyl)amino group, a (2-methoxyethyl)amino group, a (cyanomethyl)amino group, a (2-cyanoethyl)-amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined hereinabove);

a methylthio group, a methanesulfinyl group, a methanesulfonyl group, a trifluoromethylthio group, a trifluoromethanesulfinyl group and a trifluoromethanesulfonyl group as the Rc-L- (wherein Rc and L are the same as defined hereinabove);

a formyl group, an acetyl group, a methoxyacetyl group, a cyanoacetyl group, a propionyl group, a difluoroacetyl group, a trifluoroacetyl group, a cyclopropancarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)-aminocarbonyl group, a (2-methoxyethyl)aminocarbonyl group, a (cyanomethyl)-aminocarbonyl group, a (2-cyanoethyl)aminocarbonyl group, a dimethylaminocarbonyl group, an ethylmethylaminocarbonyl group, a diethylaminocarbonyl group, a (methoxymethyl) methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group and a piperidinylcarbonyl group as the Rx1C(═O)— (wherein Rx1 is the same as defined hereinabove);

and an oxolanyl group, an oxanyl group, a 1,3-dioxolanyl group and a 1,3-dioxanyl group as the 3 to 6 membered ring group containing 1 to 2 oxygen atoms.

More preferred specific examples of the substituent(s) C may include a hydroxyl group; a cyano group;

a cyclopropyl group and a cyclobutyl group as the C3-C8 cycloalkyl group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

a cyclopropyloxy group and a cyclobutoxy group as the C3-C8 cycloalkoxy group;

a methoxymethoxy group, an ethoxymethoxy group, a methoxyethoxy group and an ethoxyethoxy group as the C2-C6 alkoxyalkoxy group;

a dimethylamino group, an ethylmethylamino group and a diethylamino group as the RaRbN— (wherein Ra and Rb are the same as defined hereinabove);

a methylthio group, a methanesulfinyl group and a methanesulfonyl group as the Rc-L- (wherein Rc and L are the same as defined hereinabove);

a formyl group, an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethylmethylaminocarbonyl group and a diethylaminocarbonyl group as the Rx1C(═O)— (wherein Rx1 is the same as defined hereinabove);

and a 1,3-dioxolanyl group and a 1,3-dioxanyl group as the 3 to 6-membered ring group containing 1 to 2 oxygen atoms.

The "substituent(s) D" in Formula (1) represents at least one kind selected from the group consisting of a hydroxyl group, a cyano group, a nitro group, a halogen atom, a C1-C6 alkyl group optionally substituted with substituent(s) B, a C1-C6 haloalkyl group, a C3-C8 cycloalkyl group, a C1-C6 alkoxy group, C1-C6 haloalkoxy group and a C3-C8 cycloalkoxy group.

Above all, the substituent(s) D is preferably a cyano group, a halogen atom, a C1-C6 alkyl group optionally substituted with substituent(s) B, a C1-C6 haloalkyl group, a C1-C6 alkoxy group or C1-C6 haloalkoxy group.

Preferred specific examples of the substituent(s) D may include a hydroxyl group; a cyano group; a nitro group;

a fluorine atom, a chlorine atom, a bromine atom and an iodine atom as the halogen atom;

a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, an isopropyl group, a butyl group and an isobutyl group as the C1-C6 alkyl group optionally substituted with substituent(s) B;

a difluoromethyl group, a trifluoromethyl group, a 2,2-difluoroethyl group, a 2,2,2-trifluoroethyl group, a 3,3-difluoropropyl group and a 3,3,3-trifluoropropyl group as the C1-C6 haloalkyl group;

a cyclopropyl group, a cyclobutyl group, a cyclopentyl group and a cyclohexyl group as the C3-C8 cycloalkyl group;

a methoxy group, an ethoxy group, a propyloxy group, an isopropyloxy group, a butoxy group, an isobutoxy group and a t-butoxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;

and a cyclopropyloxy group, a cyclobutoxy group, a cyclopentyloxy group and a cyclohexyloxy group as the C3-C8 cycloalkoxy group.

More preferred specific examples of the substituent(s) D may include a hydroxyl group; a cyano group; a nitro group; a fluorine atom, a chlorine atom and a bromine atom as the halogen atom;

a methyl group, a methoxymethyl group, an ethoxymethyl group, a cyanomethyl group, an ethyl group, a 2-methoxyethyl group, a 2-ethoxyethyl group and a 2-cyanoethyl group as the C1-C6 alkyl group optionally substituted with substituent(s) B; a difluoromethyl group, a trifluoromethyl group, a 2,2-difluoroethyl group and a 2,2,2-trifluoroethyl group as the C1-C6 haloalkyl group;

a cyclopropyl group and a cyclobutyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

and a cyclopropyloxy group and a cyclobutoxy group as the C3-C8 cycloalkoxy group.

The compound represented by Formula (1) may have one or two axial chirality. A ratio of the isomers at this time is a single isomer or a mixture of isomers with an optional ratio, and is not particularly limited.

The compound represented by Formula (1) may contain an asymmetric atom. A ratio of the isomers at this time is a single isomer or a mixture of isomers with an optional ratio, and is not particularly limited.

The compound represented by Formula (1) may contain geometric isomers. A ratio of the isomers at this time is a single isomer or a mixture of isomers with an optional ratio, and is not particularly limited.

The compound represented by Formula (1) may form a salt. There may be exemplified salts formed with acids such as hydrochloric acid, sulfuric acid, acetic acid, fumaric acid and maleic acid, and salts formed with metals such as sodium, potassium and calcium, but these salts are not particularly limited as long as they are usable as agricultural and horticultural fungicides.

All the scope of the compounds obtainable by optionally combining the preferable scope in R1, R2, Het, R3, Y, R4, R5, X, the bond containing the broken line, the substituent(s) A, the substituent(s) B, the substituent(s) C and the substituent(s) D explained hereinabove are also to be described herein as a scope of Formula (1) of the present invention or its production intermediate compounds.

Next, specific compounds of the present invention are shown by combinations of the structural formulae P-1 to P-77 illustrated in Table 1 (wherein X in Table 1 is an oxygen atom or a sulfur atom, a bond containing a broken line represents a double bond or a single bond), the structural formulae (Y-1 to Y-408) of Y illustrated in Table 2 (wherein Y is the same as defined hereinabove), and the structural formulae (Het-1 to Het-2880) of Het illustrated in Table 3 (wherein Het is the same as defined hereinabove). Those compounds are only illustrative and the scope of the present invention is not limited to these compounds.

TABLE 1

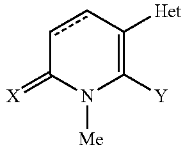

P-1

TABLE 1-continued

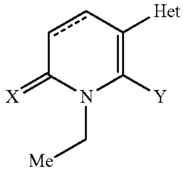

P-2

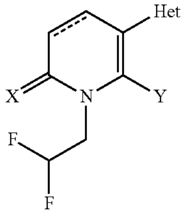

P-3

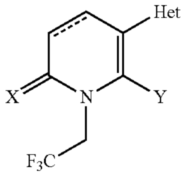

P-4

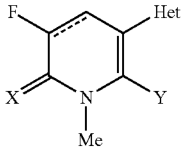

P-5

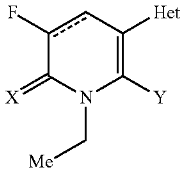

P-6

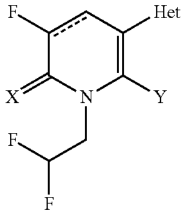

P-7

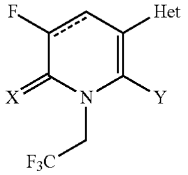

P-8

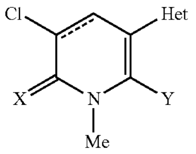

P-9

TABLE 1-continued
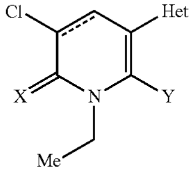
P-10
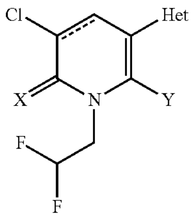
P-11
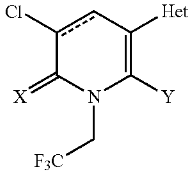
P-12
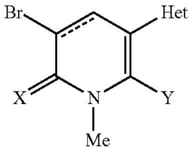
P-13
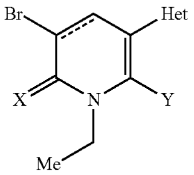
P-14
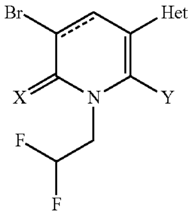
P-15
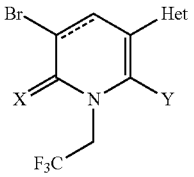
P-16
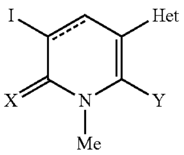
P-17
TABLE 1-continued
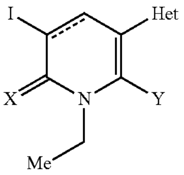
P-18
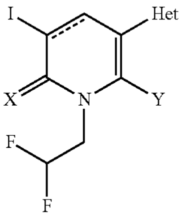
P-19
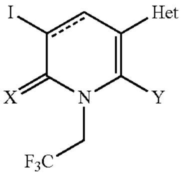
P-20
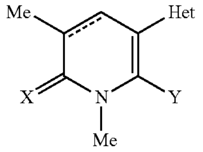
P-21
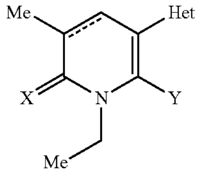
P-22
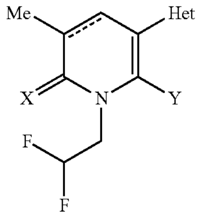
P-23
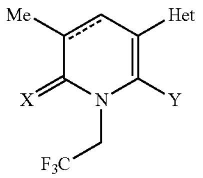
P-24
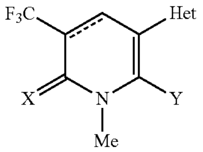
P-25

TABLE 1-continued
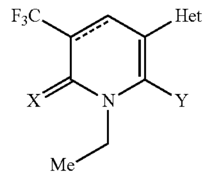
P-26
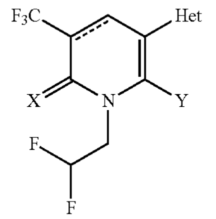
P-27
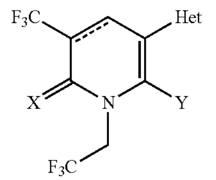
P-28
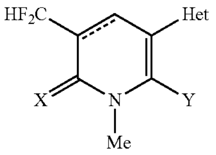
P-29
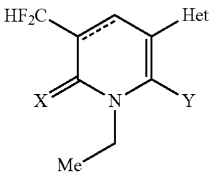
P-30
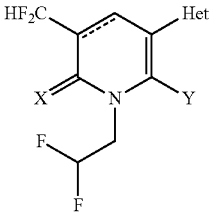
P-31
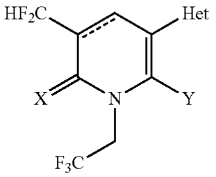
P-32
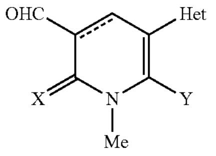
P-33
TABLE 1-continued
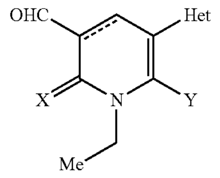
P-34
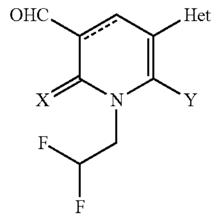
P-35
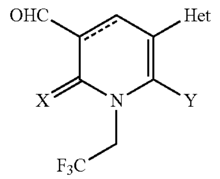
P-36
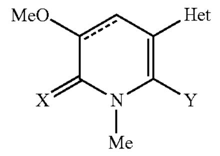
P-37
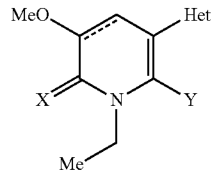
P-38
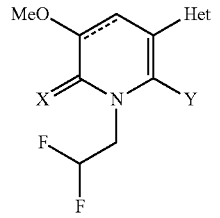
P-39
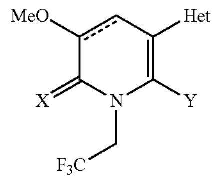
P-40
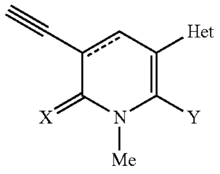
P-41

TABLE 1-continued
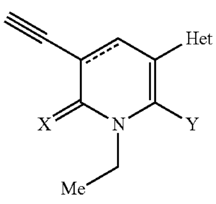
P-42
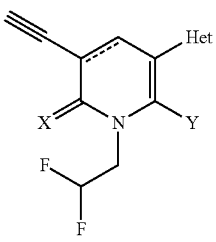
P-43
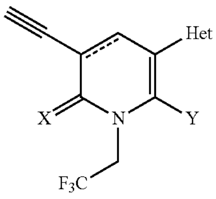
P-44
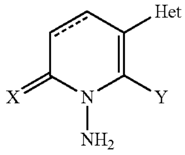
P-45
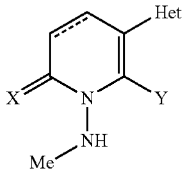
P-46
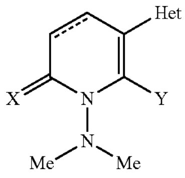
P-47
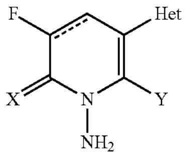
P-48
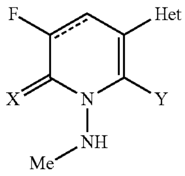
P-49
TABLE 1-continued
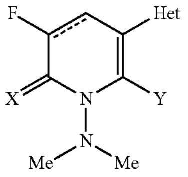
P-50
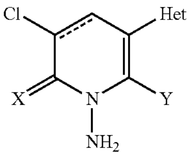
P-51
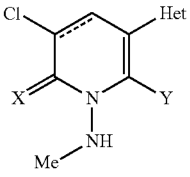
P-52
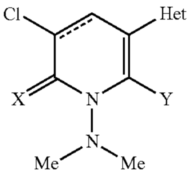
P-53
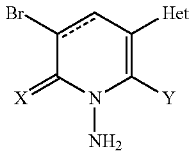
P-54
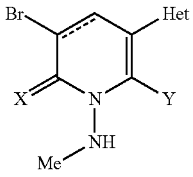
P-55
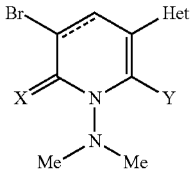
P-56
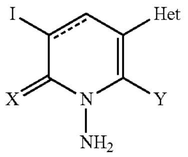
P-57
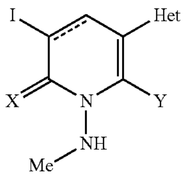
P-58

TABLE 1-continued
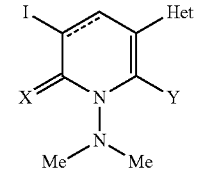
P-59
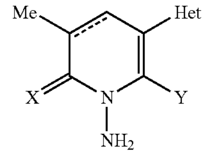
P-60
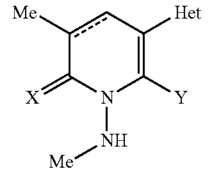
P-61
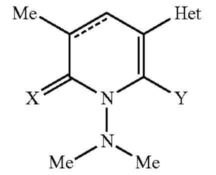
P-62
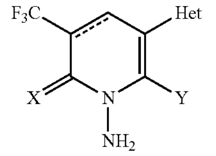
P-63
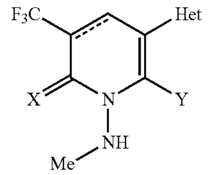
P-64
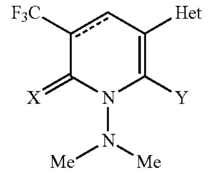
P-65
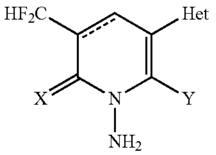
P-66
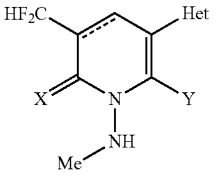
P-67
TABLE 1-continued
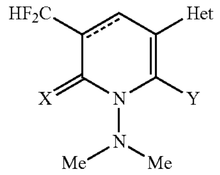
P-68
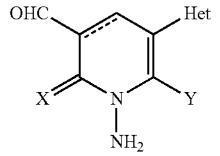
P-69
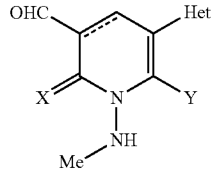
P-70
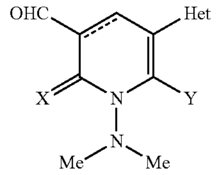
P-71
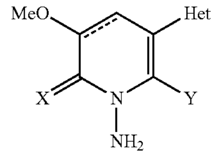
P-72
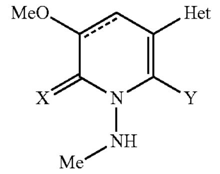
P-73
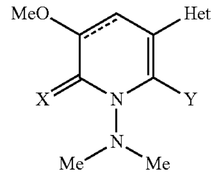
P-74
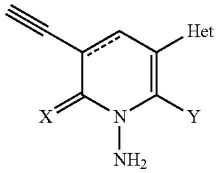
P-75
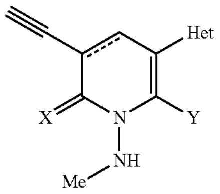
P-76

TABLE 1-continued
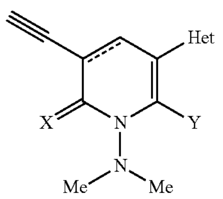
P-77
TABLE 2
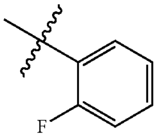 [SMILES: *c1ccccc1F]
Y-1
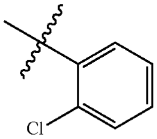
Y-2
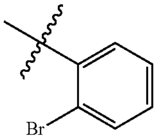 [SMILES: *c1ccccc1Cl]
Y-3
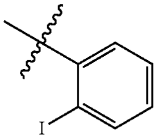 [SMILES: *c1ccccc1I]
Y-4
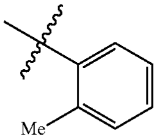 [SMILES: *c1ccccc1C]
Y-5
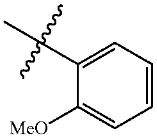 [SMILES: *c1ccccc1OC]
Y-6
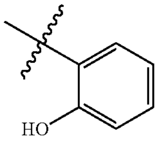 [SMILES: *c1ccccc1O]
Y-7
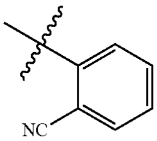 [SMILES: *c1ccccc1C#N]
Y-8
TABLE 2-continued
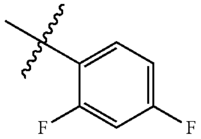
Y-9
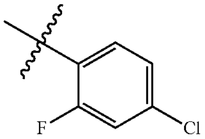 [SMILES: *c1ccc(Cl)cc1F]
Y-10
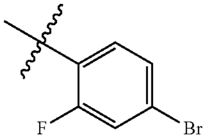
Y-11
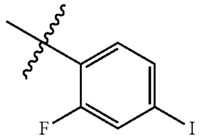
Y-12
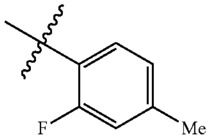
Y-13
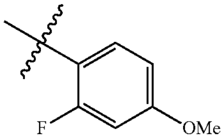
Y-14
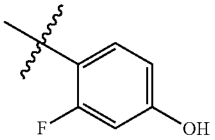 [SMILES: *c1ccc(O)cc1F]
Y-15
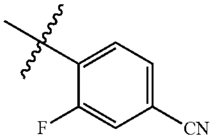
Y-16
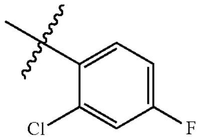 [SMILES: *c1ccc(F)cc1Cl]
Y-17
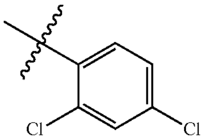 [SMILES: *c1ccc(Cl)cc1Cl]
Y-18

TABLE 2-continued
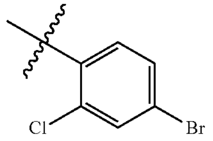 [SMILES: *c1ccc(Br)cc1Cl]
Y-19
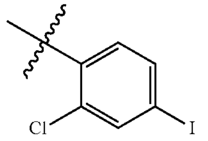 [SMILES: *c1ccc(I)cc1Cl]
Y-20
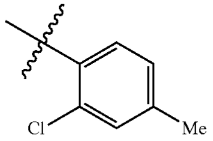 [SMILES: *c1ccc(C)cc1Cl]
Y-21
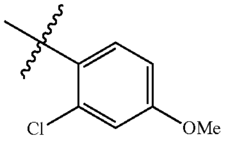 [SMILES: *c1ccc(OC)cc1Cl]
Y-22
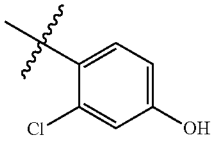 [SMILES: *c1ccc(O)cc1Cl]
Y-23
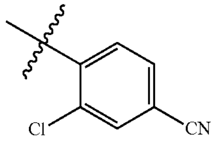 [SMILES: *c1ccc(C#N)cc1Cl]
Y-24
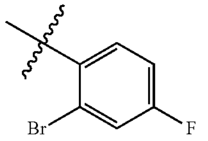 [SMILES: *c1ccc(F)cc1Br]
Y-25
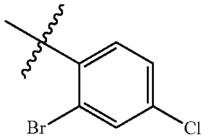
Y-26
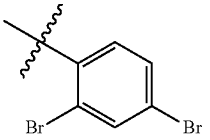 [SMILES: *c1ccc(Br)cc1Br]
Y-27
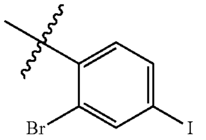
Y-28
TABLE 2-continued
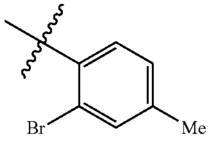
Y-29
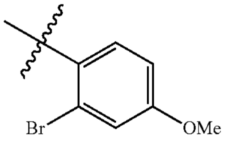
Y-30
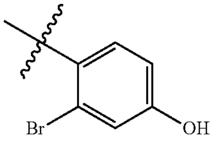 [SMILES: *c1ccc(O)cc1Br]
Y-31
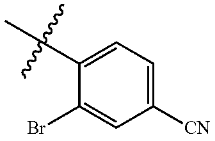
Y-32
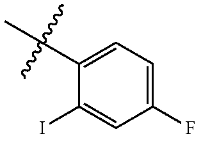 [SMILES: *c1ccc(F)cc1I]
Y-33
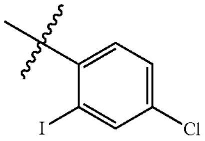 [SMILES: *c1ccc(Cl)cc1I]
Y-34
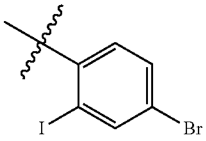 [SMILES: *c1ccc(Br)cc1I]
Y-35
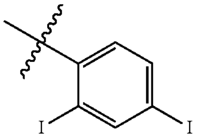 [SMILES: *c1ccc(I)cc1I]
Y-36
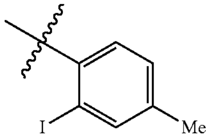 [SMILES: *c1ccc(C)cc1I]
Y-37
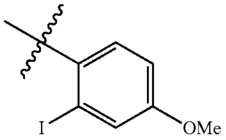 [SMILES: *c1ccc(OC)cc1I]
Y-38

TABLE 2-continued
Y-39
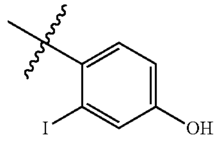 [SMILES: *c1ccc(O)cc1I]
Y-40
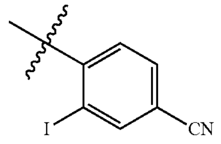 [SMILES: *c1ccc(C#N)cc1I]
Y-41
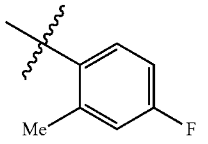
Y-42
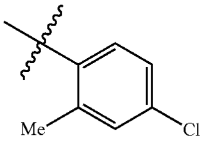 [SMILES: *c1ccc(Cl)cc1C]
Y-43
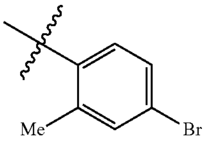 [SMILES: *c1ccc(Br)cc1C]
Y-44
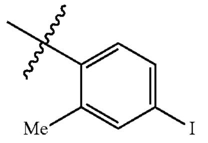 [SMILES: *c1ccc(I)cc1C]
Y-45
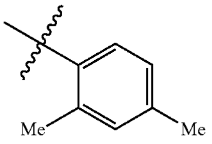 [SMILES: *c1ccc(C)cc1C]
Y-46
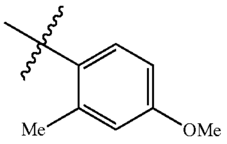 [SMILES: *c1ccc(OC)cc1C]
Y-47
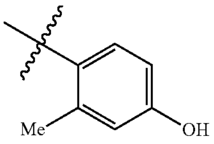 [SMILES: *c1ccc(O)cc1C]
Y-48
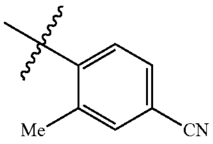 [SMILES: *c1ccc(C#N)cc1C]
TABLE 2-continued
Y-49
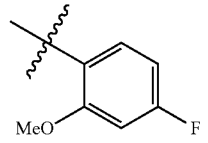 [SMILES: *c1ccc(F)cc1OC]
Y-50
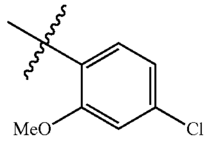 [SMILES: *c1ccc(Cl)cc1OC]
Y-51
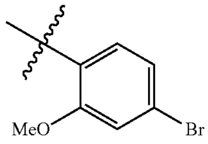 [SMILES: *c1ccc(Br)cc1OC]
Y-52
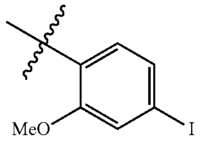 [SMILES: *c1ccc(I)cc1OC]
Y-53
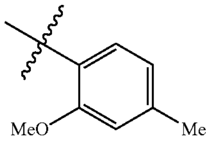 [SMILES: *c1ccc(C)cc1OC]
Y-54
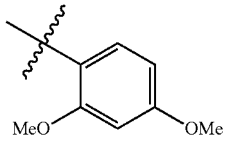 [SMILES: *c1ccc(OC)cc1OC]
Y-55
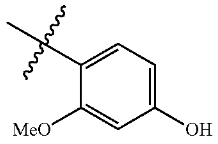 [SMILES: *c1ccc(O)cc1OC]
Y-56
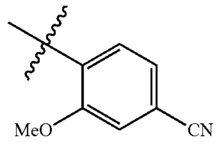 [SMILES: *c1ccc(C#N)cc1OC]
Y-57
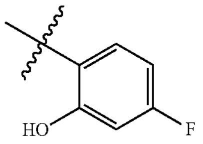
Y-58
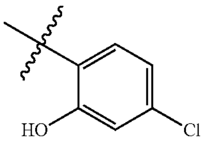 [SMILES: *c1ccc(Cl)cc1O]

TABLE 2-continued
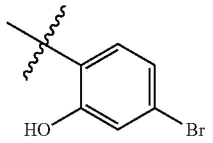 [SMILES: *c1ccc(Br)cc1O]
Y-59
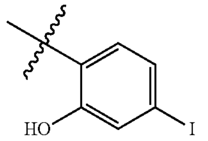
Y-60
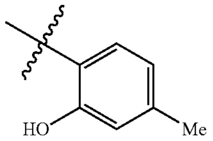 [SMILES: *c1ccc(C)cc1O]
Y-61
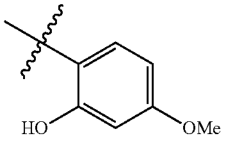 [SMILES: *c1ccc(OC)cc1O]
Y-62
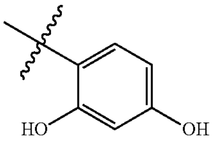
Y-63
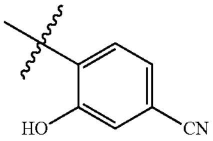
Y-64
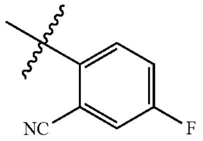 [SMILES: *c1ccc(F)cc1C#N]
Y-65
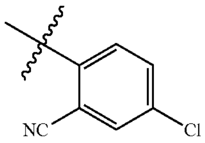 [SMILES: *c1ccc(Cl)cc1C#N]
Y-66
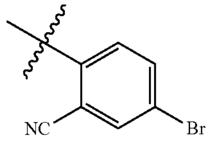 [SMILES: *c1ccc(Br)cc1C#N]
Y-67
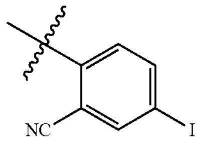 [SMILES: *c1ccc(I)cc1C#N]
Y-68
TABLE 2-continued
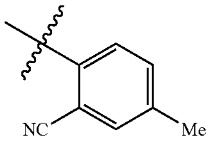 [SMILES: *c1ccc(C)cc1C#N]
Y-69
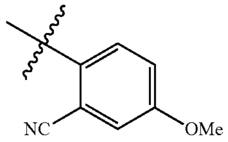 [SMILES: *c1ccc(OC)cc1C#N]
Y-70
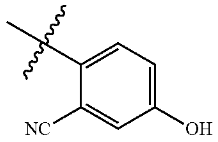 [SMILES: *c1ccc(O)cc1C#N]
Y-71
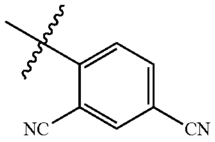 [SMILES: *c1ccc(C#N)cc1C#N]
Y-72
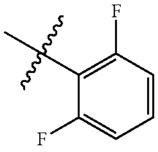
Y-73
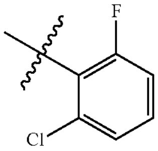 [SMILES: *c1c(F)cccc1Cl]
Y-74
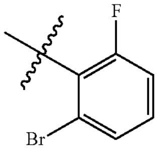 [SMILES: *c1c(F)cccc1Br]
Y-75
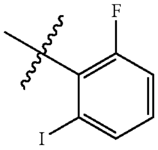 [SMILES: *c1c(F)cccc1I]
Y-76
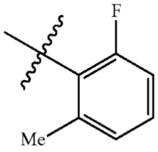 [SMILES: *c1c(C)cccc1F]
Y-77
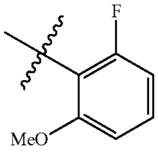 [SMILES: *c1c(F)cccc1OC]
Y-78

TABLE 2-continued
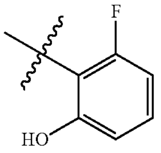 [SMILES: *c1c(O)cccc1F]
Y-79
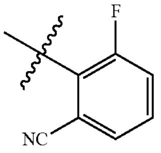 [SMILES: *c1c(F)cccc1C#N]
Y-80
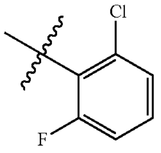 [SMILES: *c1c(F)cccc1Cl]
Y-81
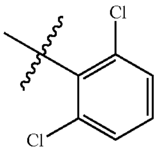
Y-82
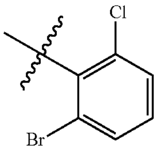
Y-83
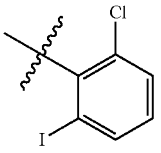 [SMILES: *c1c(Cl)cccc1Cl]
Y-84
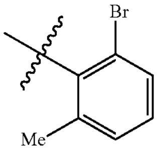 [SMILES: *c1c(C)cccc1Br]
Y-85
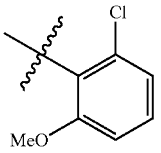 [SMILES: *c1c(Cl)cccc1OC]
Y-86
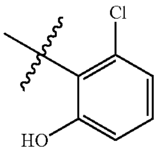
Y-87
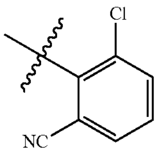 [SMILES: *c1c(Cl)cccc1C#N]
Y-88
TABLE 2-continued
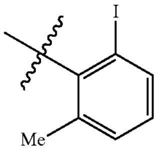 [SMILES: *c1c(C)cccc1I]
Y-89
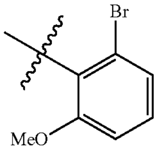 [SMILES: *c1c(Br)cccc1OC]
Y-90
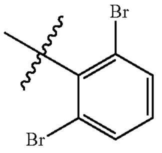 [SMILES: *c1c(Br)cccc1Br]
Y-91
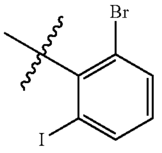 [SMILES: *c1c(Br)cccc1I]
Y-92
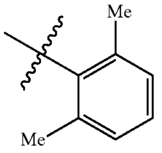 [SMILES: *c1c(C)cccc1C]
Y-93
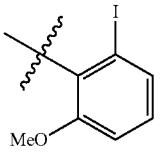 [SMILES: *c1c(I)cccc1OC]
Y-94
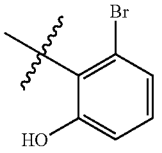 [SMILES: *c1c(O)cccc1Br]
Y-95
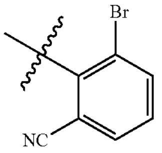 [SMILES: *c1c(Br)cccc1C#N]
Y-96
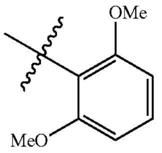 [SMILES: *c1c(OC)cccc1OC]
Y-97
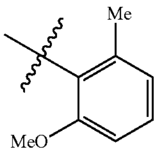 [SMILES: *c1c(C)cccc1OC]
Y-98

TABLE 2-continued
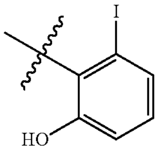 [SMILES: *c1c(O)cccc1I]
Y-99
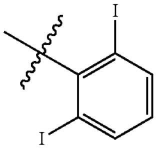 [SMILES: *c1c(I)cccc1I]
Y-100
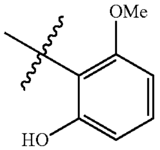 [SMILES: *c1c(O)cccc1OC]
Y-101
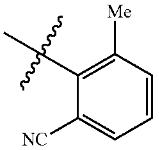 [SMILES: *c1c(C)cccc1C#N]
Y-102
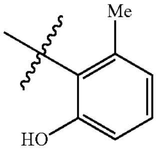 [SMILES: *c1c(C)cccc1O]
Y-103
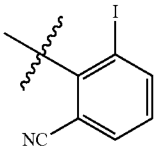 [SMILES: *c1c(I)cccc1C#N]
Y-104
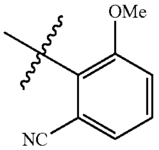 [SMILES: *c1c(C#N)cccc1OC]
Y-105
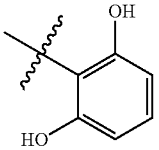 [SMILES: *c1c(O)cccc1O]
Y-106
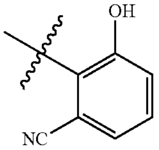 [SMILES: *c1c(O)cccc1C#N]
Y-107
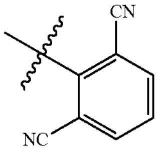 [SMILES: *c1c(C#N)cccc1C#N]
Y-108
TABLE 2-continued
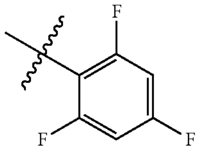 [SMILES: *c1c(F)cc(F)cc1F]
Y-109
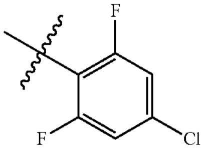 [SMILES: *c1c(F)cc(Cl)cc1F]
Y-110
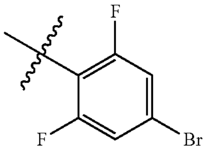 [SMILES: *c1c(F)cc(Br)cc1F]
Y-111
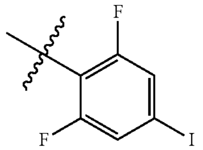 [SMILES: *c1c(F)cc(I)cc1F]
Y-112
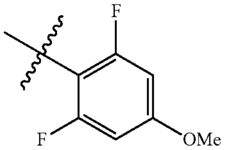 [SMILES: *c1c(F)cc(OC)cc1F]
Y-113
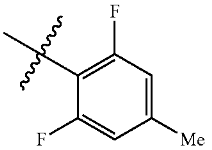 [SMILES: *c1c(F)cc(C)cc1F]
Y-114
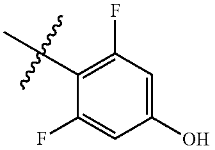 [SMILES: *c1c(F)cc(O)cc1F]
Y-115
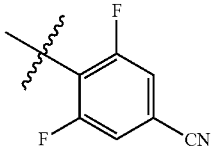 [SMILES: *c1c(F)cc(C#N)cc1F]
Y-116
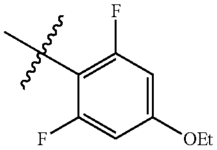 [SMILES: *c1c(F)cc(OCC)cc1F]
Y-117
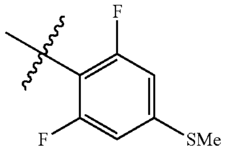 [SMILES: *c1c(F)cc(SC)cc1F]
Y-118

TABLE 2-continued
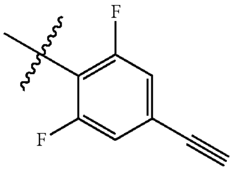 [SMILES: *c1c(F)cc(C#C)cc1F]
Y-119
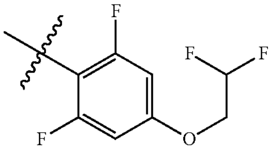 [SMILES: *c1c(F)cc(OCC(F)F)cc1F]
Y-120
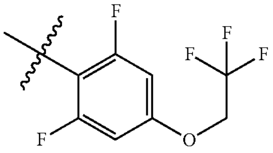 [SMILES: *c1c(F)cc(OCC(F)(F)F)cc1F]
Y-121
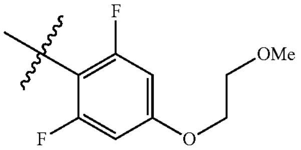 [SMILES: *c1c(F)cc(OCCOC)cc1F]
Y-122
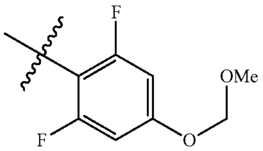 [SMILES: *c1c(F)cc(OCOC)cc1F]
Y-123
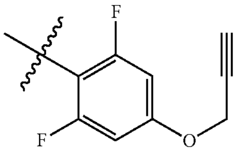 [SMILES: *c1c(F)cc(OCC#C)cc1F]
Y-124
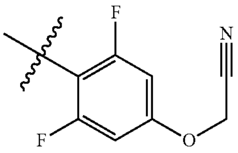 [SMILES: *c1c(F)cc(OCC#N)cc1F]
Y-125
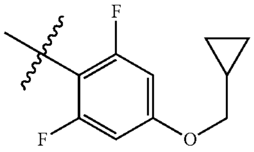 [SMILES: *c1c(F)cc(OCC2CC2)cc1F]
Y-126
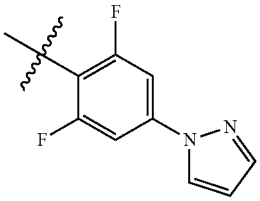 [SMILES: *c1c(F)cc(-n2cccn2)cc1F]
Y-127
TABLE 2-continued
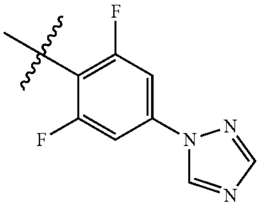 [SMILES: *c1c(F)cc(-n2cncn2)cc1F]
Y-128
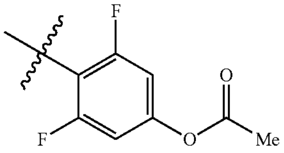 [SMILES: *c1c(F)cc(OC(C)=O)cc1F]
Y-129
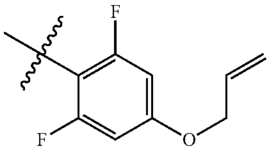 [SMILES: *c1c(F)cc(OCC=C)cc1F]
Y-130
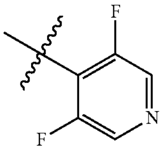
Y-131
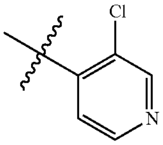 [SMILES: *c1ccncc1Cl]
Y-132
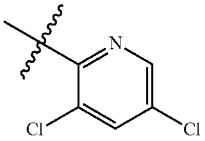 [SMILES: *c1ncc(Cl)cc1Cl]
Y-133
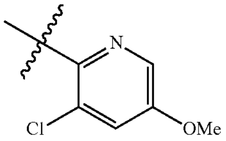 [SMILES: *c1ncc(OC)cc1Cl]
Y-134
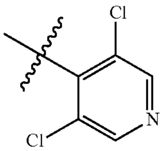 [SMILES: *c1c(Cl)cncc1Cl]
Y-135
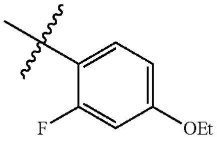
Y-136
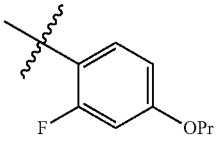
Y-137

TABLE 2-continued
Y-138
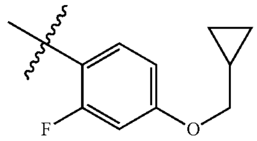 [SMILES: *c1ccc(OCC2CC2)cc1F]
Y-139
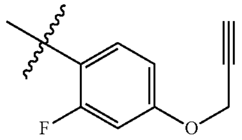
Y-140
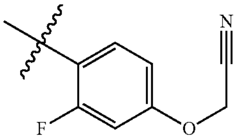 [SMILES: *c1ccc(OCC#N)cc1F]
Y-141
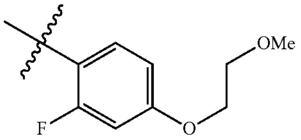
Y-142
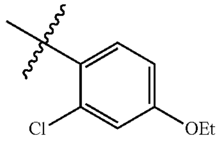 [SMILES: *c1ccc(OCC)cc1Cl]
Y-143
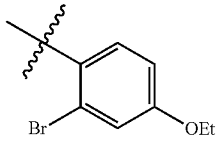 [SMILES: *c1ccc(OCC)cc1Br]
Y-144
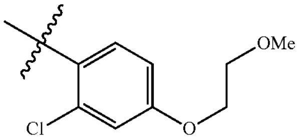 [SMILES: *c1ccc(OCCOC)cc1Cl]
Y-145
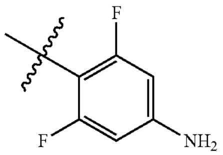
Y-146
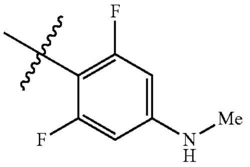 [SMILES: *c1c(F)cc(NC)cc1F]
Y-147
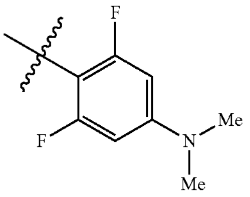
TABLE 2-continued
Y-148
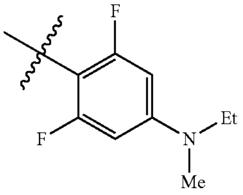 [SMILES: *c1c(F)cc(N(C)CC)cc1F]
Y-149
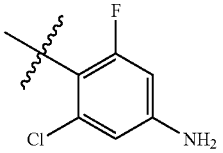
Y-150
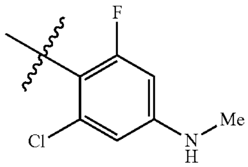 [SMILES: *c1c(F)cc(NC)cc1Cl]
Y-151
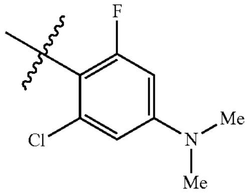 [SMILES: *c1c(F)cc(N(C)C)cc1Cl]
Y-152
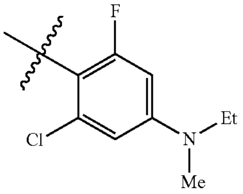 [SMILES: *c1c(F)cc(N(C)CC)cc1Cl]
Y-153
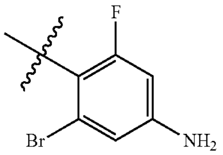 [SMILES: *c1c(F)cc(N)cc1Br]
Y-154
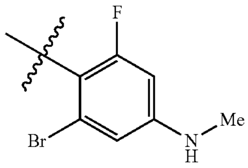 [SMILES: *c1c(F)cc(NC)cc1Br]
Y-155
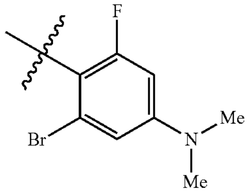 [SMILES: *c1c(F)cc(N(C)C)cc1Br]

TABLE 2-continued
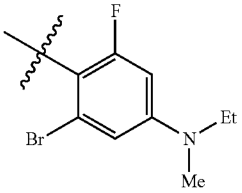 [SMILES: *c1c(F)cc(N(C)CC)cc1Br]
Y-156
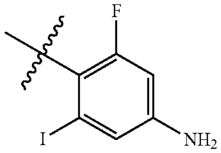
Y-157
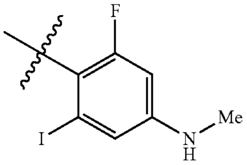 [SMILES: *c1c(F)cc(NC)cc1I]
Y-158
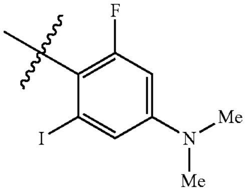 [SMILES: *c1c(F)cc(N(C)C)cc1I]
Y-159
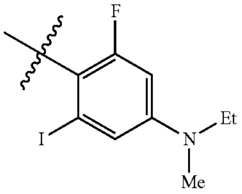 [SMILES: *c1c(F)cc(N(C)CC)cc1I]
Y-160
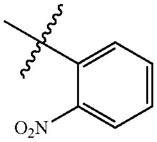 [SMILES: *c1ccccc1[N+](=O)[O-]]
Y-161
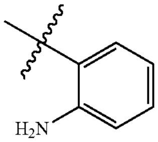
Y-162
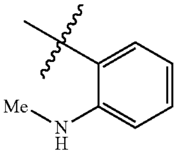 [SMILES: *c1ccccc1NC]
Y-163
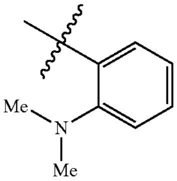 [SMILES: *c1ccccc1N(C)C]
Y-164
TABLE 2-continued
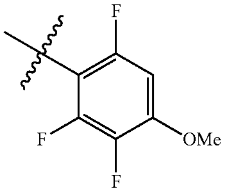 [SMILES: *c1c(F)cc(OC)c(F)c1F]
Y-165
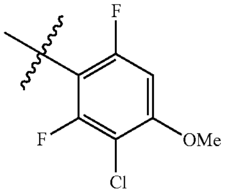 [SMILES: *c1c(F)cc(OC)c(Cl)c1F]
Y-166
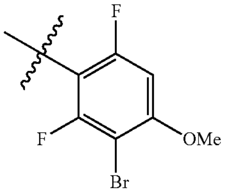
Y-167
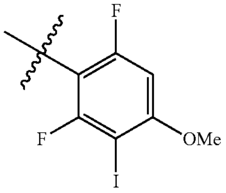 [SMILES: *c1c(F)cc(OC)c(I)c1F]
Y-168
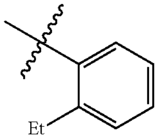 [SMILES: *c1ccccc1CC]
Y-169
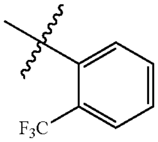
Y-170
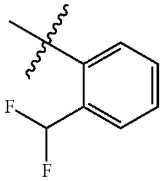 [SMILES: *c1ccccc1C(F)F]
Y-171
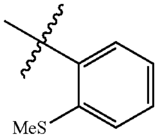 [SMILES: *c1ccccc1SC]
Y-172
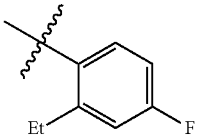
Y-173

TABLE 2-continued
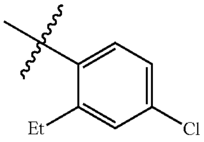 [SMILES: *c1ccc(Cl)cc1CC]
Y-174
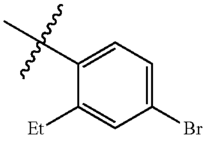
Y-175
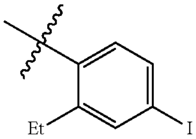
Y-176
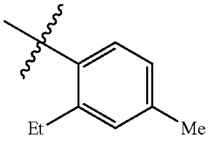
Y-177
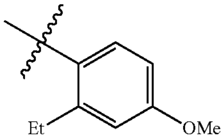
Y-178
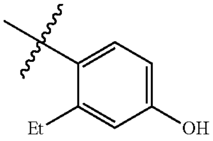
Y-179
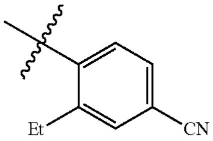
Y-180
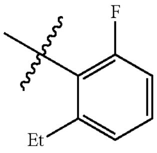 [SMILES: *c1c(F)cccc1CC]
Y-181
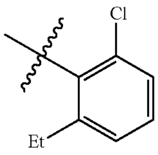
Y-182
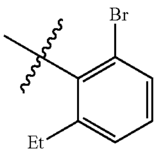 [SMILES: *c1c(Br)cccc1CC]
Y-183
TABLE 2-continued
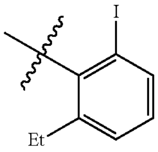 [SMILES: *c1c(I)cccc1CC]
Y-184
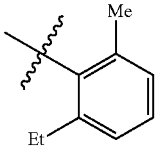 [SMILES: *c1c(C)cccc1CC]
Y-185
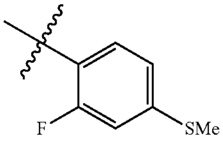 [SMILES: *c1ccc(SC)cc1F]
Y-186
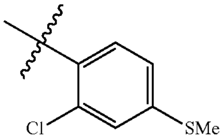 [SMILES: *c1ccc(SC)cc1Cl]
Y-187
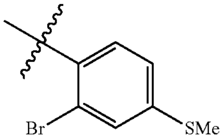
Y-188
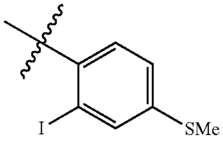 [SMILES: *c1ccc(SC)cc1I]
Y-189
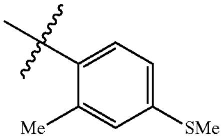 [SMILES: *c1ccc(SC)cc1C]
Y-190
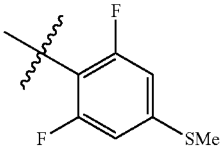 [SMILES: *c1c(F)cc(SC)cc1F]
Y-191
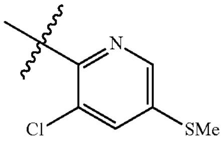 [SMILES: *c1ncc(SC)cc1Cl]
Y-192
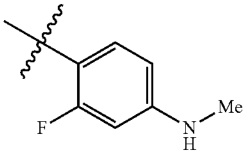
Y-193

TABLE 2-continued
Y-194
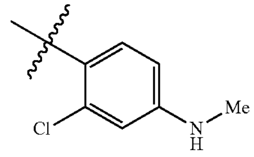
Y-195
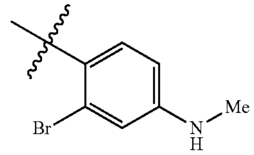 [SMILES: *c1ccc(NC)cc1Br]
Y-196
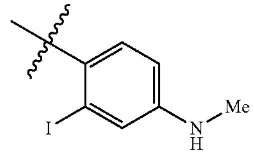 [SMILES: *c1ccc(NC)cc1I]
Y-197
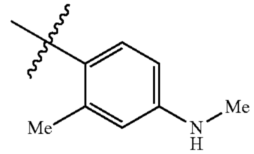 [SMILES: *c1ccc(NC)cc1C]
Y-198
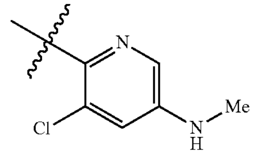 [SMILES: *c1ncc(NC)cc1Cl]
Y-199
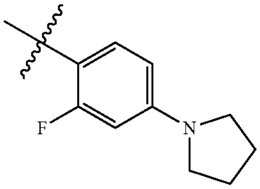
Y-200
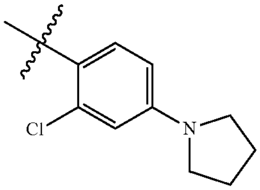 [SMILES: *c1ccc(N2CCCC2)cc1Cl]
Y-201
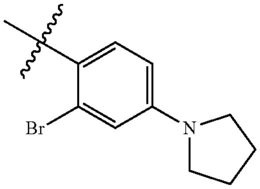 [SMILES: *c1ccc(N2CCCC2)cc1Br]
Y-202
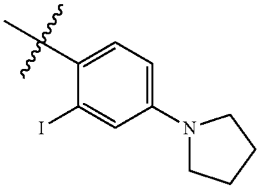 [SMILES: *c1ccc(N2CCCC2)cc1I]
TABLE 2-continued
Y-203
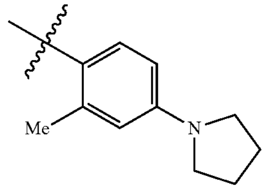 [SMILES: *c1ccc(N2CCCC2)cc1C]
Y-204
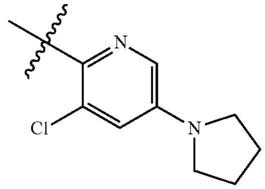 [SMILES: *c1ncc(N2CCCC2)cc1Cl]
Y-205
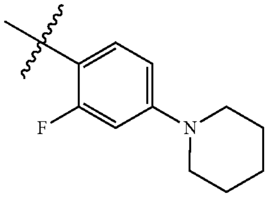
Y-206
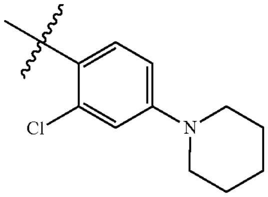 [SMILES: *c1ccc(N2CCCCC2)cc1Cl]
Y-207
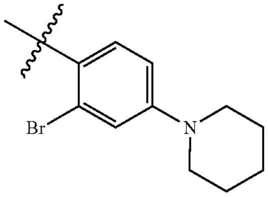 [SMILES: *c1ccc(N2CCCCC2)cc1Br]
Y-208
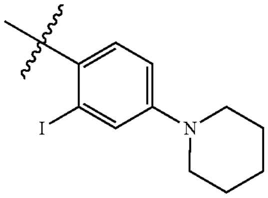 [SMILES: *c1ccc(N2CCCCC2)cc1I]
Y-209
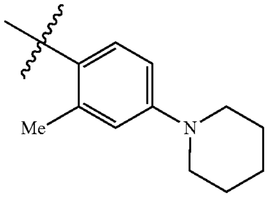 [SMILES: *c1ccc(N2CCCCC2)cc1C]

TABLE 2-continued
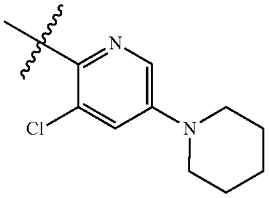 [SMILES: *c1ncc(N2CCCCC2)cc1Cl]
Y-210
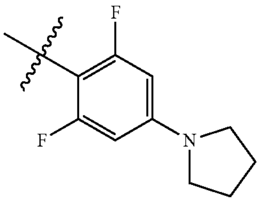 [SMILES: *c1c(F)cc(N2CCCC2)cc1F]
Y-211
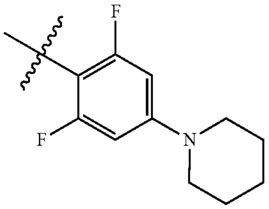 [SMILES: *c1c(F)cc(N2CCCCC2)cc1F]
Y-212
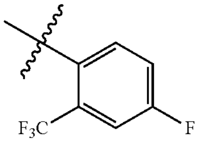
Y-213
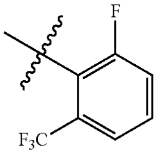 [SMILES: *c1c(F)cccc1C(F)(F)F]
Y-214
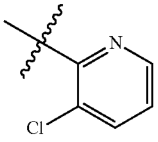 [SMILES: *c1ncccc1Cl]
Y-215
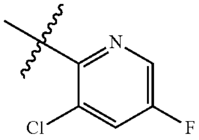 [SMILES: *c1ncc(F)cc1Cl]
Y-216
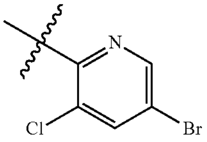 [SMILES: *c1ncc(Br)cc1Cl]
Y-217
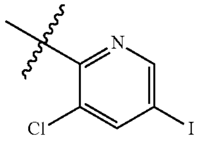 [SMILES: *c1ncc(I)cc1Cl]
Y-218
TABLE 2-continued
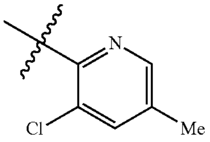 [SMILES: *c1ncc(C)cc1Cl]
Y-219
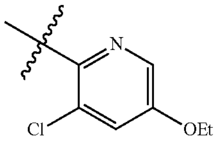
Y-220
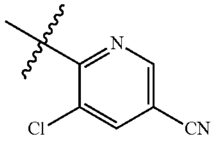 [SMILES: *c1ncc(C#N)cc1Cl]
Y-221
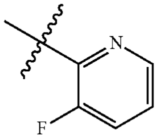 [SMILES: *c1ncccc1F]
Y-222
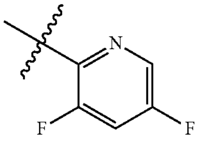 [SMILES: *c1ncc(F)cc1F]
Y-223
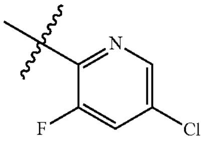 [SMILES: *c1ncc(Cl)cc1F]
Y-224
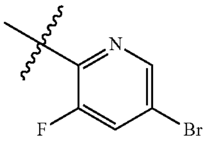 [SMILES: *c1ncc(Br)cc1F]
Y-225
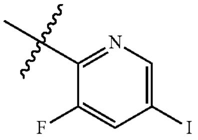 [SMILES: *c1ncc(I)cc1F]
Y-226
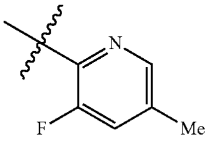 [SMILES: *c1ncc(C)cc1F]
Y-227
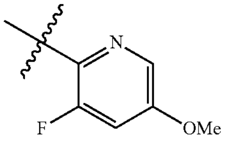 [SMILES: *c1ncc(OC)cc1F]
Y-228

TABLE 2-continued
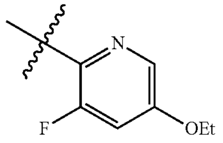 [SMILES: *c1ncc(OCC)cc1F]
Y-229
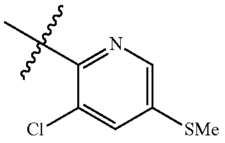 [SMILES: *c1ncc(SC)cc1Cl]
Y-230
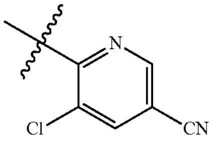 [SMILES: *c1ncc(C#N)cc1Cl]
Y-231
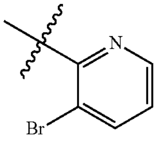
Y-232
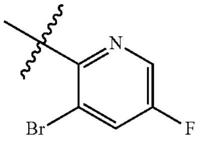 [SMILES: *c1ncc(F)cc1Br]
Y-233
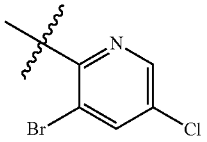
Y-234
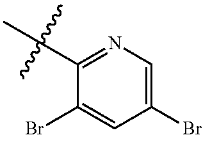 [SMILES: *c1ncc(Br)cc1Br]
Y-235
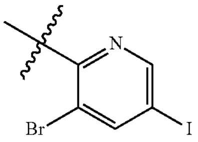
Y-236
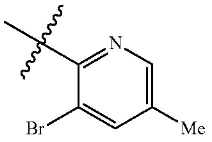
Y-237
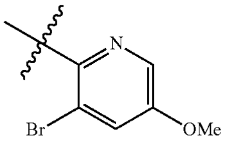 [SMILES: *c1ncc(OC)cc1Br]
Y-238
TABLE 2-continued
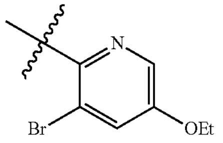
Y-239
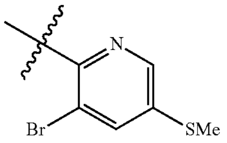
Y-240
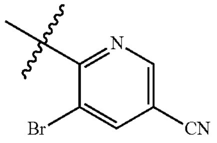
Y-241
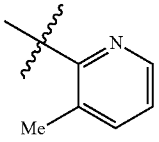 [SMILES: *c1ncccc1C]
Y-242
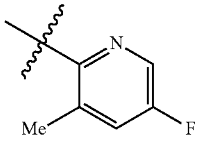 [SMILES: *c1ncc(F)cc1C]
Y-243
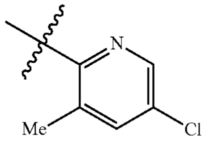 [SMILES: *c1ncc(Cl)cc1C]
Y-244
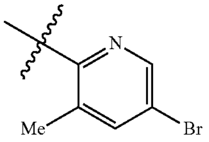 [SMILES: *c1ncc(Br)cc1C]
Y-245
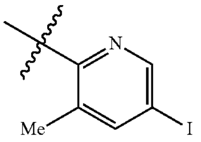 [SMILES: *c1ncc(I)cc1C]
Y-246
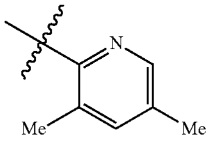 [SMILES: *c1ncc(C)cc1C]
Y-247
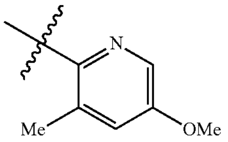 [SMILES: *c1ncc(OC)cc1C]
Y-248

TABLE 2-continued
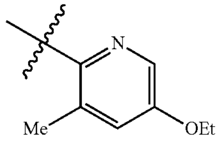 [SMILES: *c1ncc(OCC)cc1C]
Y-249
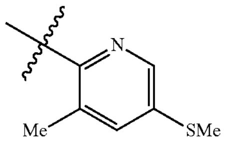 [SMILES: *c1ncc(SC)cc1C]
Y-250
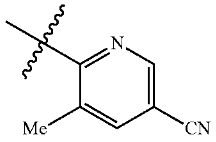 [SMILES: *c1ncc(C#N)cc1C]
Y-251
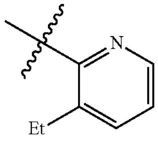 [SMILES: *c1ncccc1CC]
Y-252
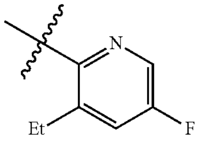 [SMILES: *c1ncc(F)cc1CC]
Y-253
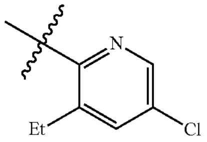 [SMILES: *c1ncc(Cl)cc1CC]
Y-254
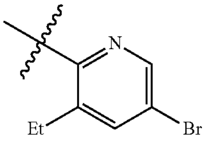 [SMILES: *c1ncc(Br)cc1CC]
Y-255
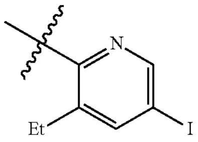 [SMILES: *c1ncc(I)cc1CC]
Y-256
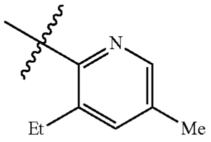 [SMILES: *c1ncc(C)cc1CC]
Y-257
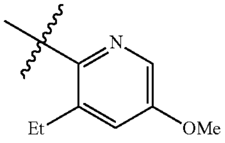 [SMILES: *c1ncc(OC)cc1CC]
Y-258
TABLE 2-continued
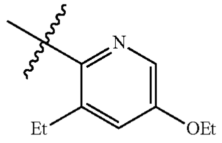 [SMILES: *c1ncc(OCC)cc1CC]
Y-259
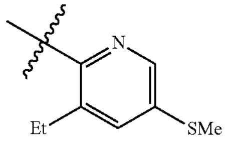 [SMILES: *c1ncc(SC)cc1CC]
Y-260
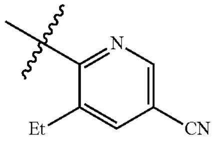 [SMILES: *c1ncc(C#N)cc1CC]
Y-261
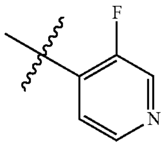
Y-262
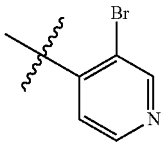
Y-263
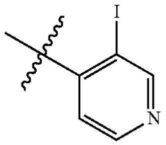 [SMILES: *c1ccncc1I]
Y-264
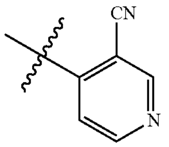 [SMILES: *c1ccncc1C#N]
Y-265
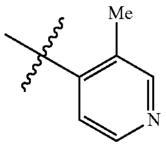 [SMILES: *c1ccncc1C]
Y-266
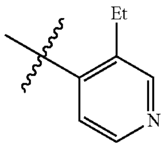 [SMILES: *c1ccncc1CC]
Y-267
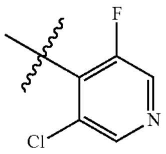 [SMILES: *c1c(F)cncc1Cl]
Y-268

TABLE 2-continued
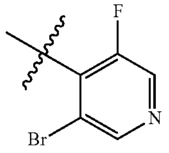
Y-269
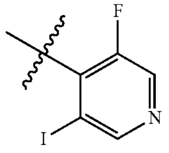
Y-270
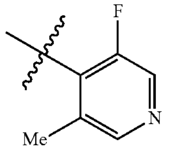
Y-271
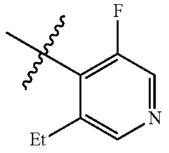
Y-272
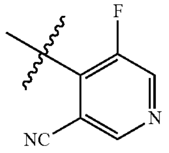
Y-273
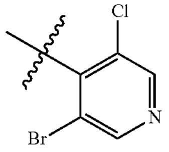 [SMILES: *c1c(Cl)cncc1CC]
Y-274
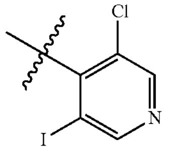
Y-275
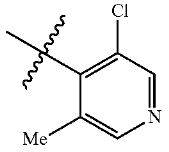
Y-276
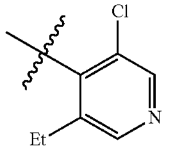
Y-277
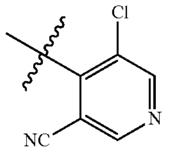 [SMILES: *c1c(Cl)cncc1C#N]
Y-278
TABLE 2-continued
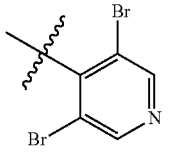
Y-279
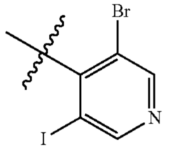 [SMILES: *c1c(Br)cncc1I]
Y-280
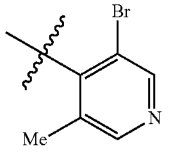
Y-281
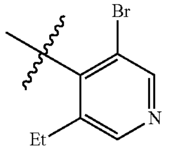 [SMILES: *c1c(Br)cncc1CC]
Y-282
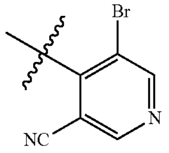 [SMILES: *c1c(Br)cncc1C#N]
Y-283
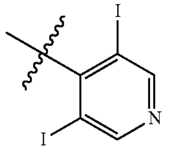 [SMILES: *c1c(I)cncc1I]
Y-284
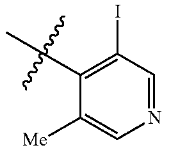
Y-285
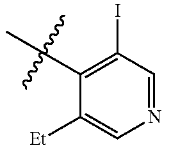
Y-286
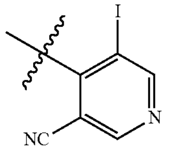 [SMILES: *c1c(I)cncc1C#N]
Y-287
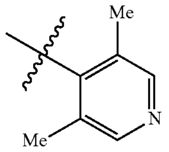
Y-288

TABLE 2-continued
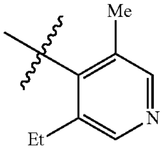 [SMILES: *c1c(C)cncc1CC]
Y-289
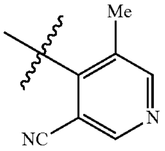 [SMILES: *c1c(C)cncc1C#N]
Y-290
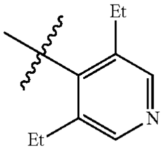
Y-291
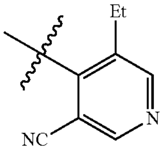 [SMILES: *c1c(C#N)cncc1CC]
Y-292
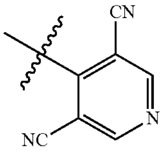 [SMILES: *c1c(C#N)cncc1C#N]
Y-293
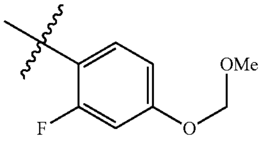
Y-294
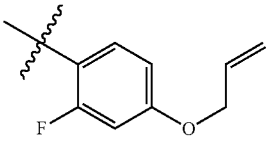
Y-295
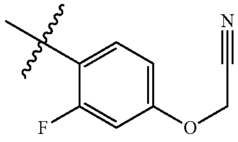 [SMILES: *c1ccc(OCC#N)cc1F]
Y-296
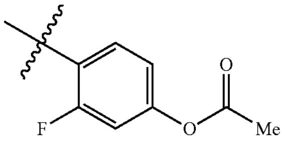
Y-297
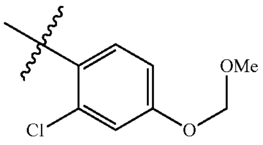 [SMILES: *c1ccc(OCOC)cc1Cl]
Y-298
TABLE 2-continued
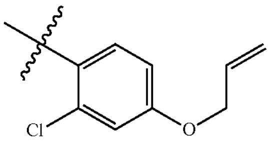 [SMILES: *c1ccc(OCC=C)cc1Cl]
Y-299
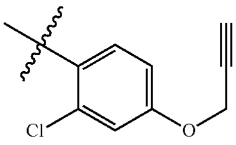 [SMILES: *c1ccc(OCC#C)cc1Cl]
Y-300
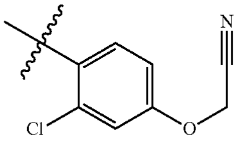 [SMILES: *c1ccc(OCC#N)cc1Cl]
Y-301
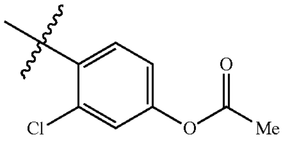 [SMILES: *c1ccc(OC(C)=O)cc1Cl]
Y-302
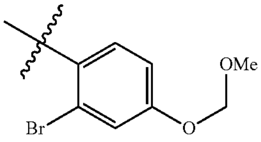 [SMILES: *c1ccc(OCOC)cc1Br]
Y-303
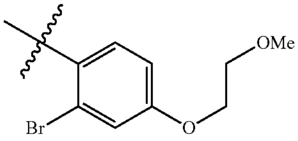 [SMILES: *c1ccc(OCCOC)cc1Br]
Y-304
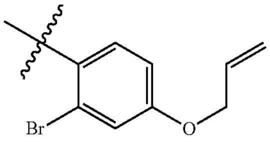
Y-305
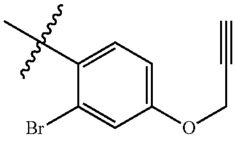 [SMILES: *c1ccc(OCC#C)cc1Br]
Y-306
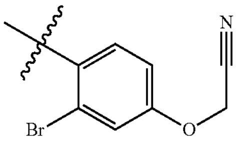 [SMILES: *c1ccc(OCC#N)cc1Br]
Y-307
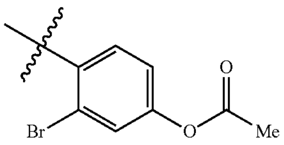 [SMILES: *c1ccc(OC(C)=O)cc1Br]
Y-308

TABLE 2-continued
Y-309
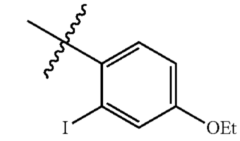 [SMILES: *c1ccc(OCC)cc1I]
Y-310
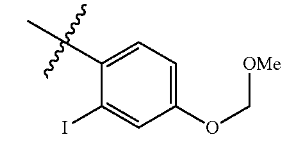 [SMILES: *c1ccc(OCOC)cc1I]
Y-311
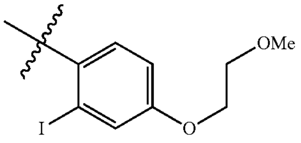
Y-312
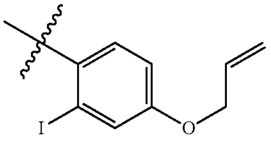 [SMILES: *c1ccc(OCC=C)cc1I]
Y-313
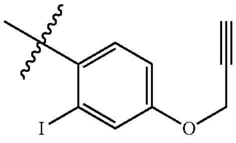 [SMILES: *c1ccc(OCC#C)cc1I]
Y-314
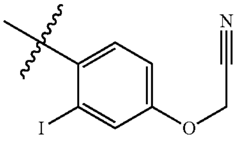 [SMILES: *c1ccc(OCC#N)cc1I]
Y-315
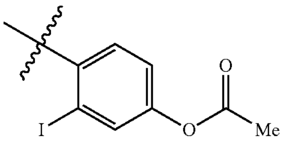 [SMILES: *c1ccc(OC(C)=O)cc1I]
Y-316
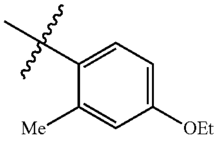 [SMILES: *c1ccc(OCC)cc1C]
Y-317
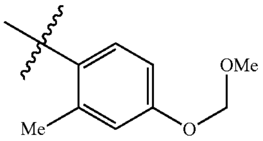
Y-318
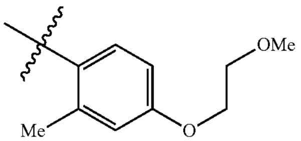
TABLE 2-continued
Y-319
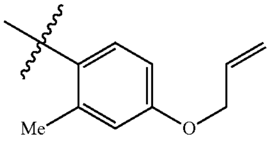 [SMILES: *c1ccc(OCC=C)cc1C]
Y-320
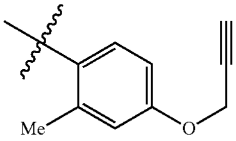 [SMILES: *c1ccc(OCC#C)cc1C]
Y-321
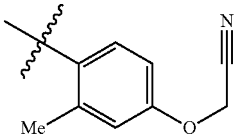 [SMILES: *c1ccc(OCC#N)cc1C]
Y-322
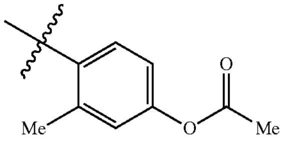 [SMILES: *c1ccc(OC(C)=O)cc1C]
Y-323
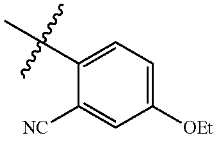 [SMILES: *c1ccc(OCC)cc1C#N]
Y-324
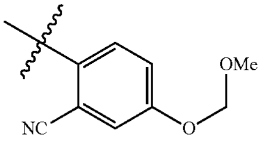 [SMILES: *c1ccc(OCOC)cc1C#N]
Y-325
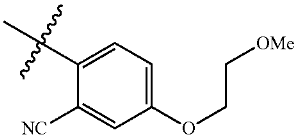 [SMILES: *c1ccc(OCCOC)cc1C#N]
Y-326
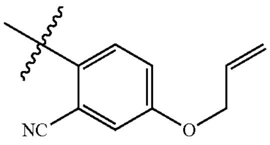
Y-327
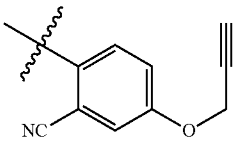 [SMILES: *c1ccc(OCC#C)cc1C#N]
Y-328
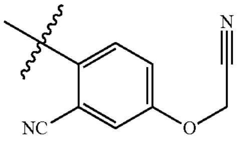 [SMILES: *c1ccc(OCC#N)cc1C#N]

TABLE 2-continued
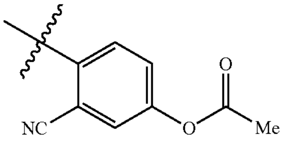 [SMILES: *c1ccc(OC(C)=O)cc1C#N]
Y-329
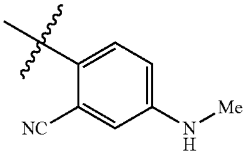 [SMILES: *c1ccc(NC)cc1C#N]
Y-330
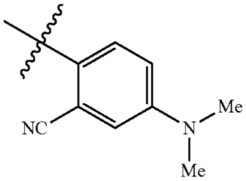 [SMILES: *c1ccc(N(C)C)cc1C#N]
Y-331
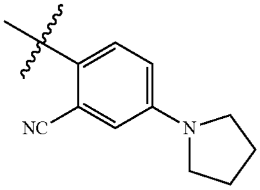 [SMILES: *c1ccc(N2CCCC2)cc1C#N]
Y-332
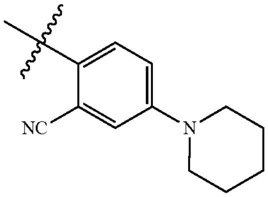 [SMILES: *c1ccc(N2CCCCC2)cc1C#N]
Y-333
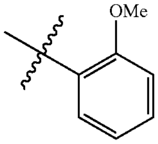 [SMILES: *c1ccccc1OC]
Y-334
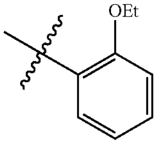 [SMILES: *c1ccccc1OCC]
Y-335
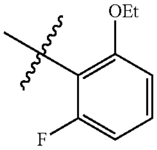 [SMILES: *c1c(F)cccc1OCC]
Y-336
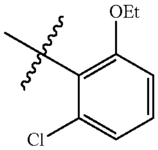 [SMILES: *c1c(Cl)cccc1OCC]
Y-337
TABLE 2-continued
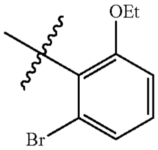 [SMILES: *c1c(Br)cccc1OCC]
Y-338
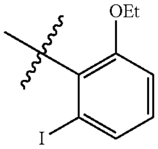 [SMILES: *c1c(I)cccc1OCC]
Y-339
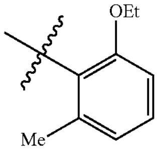 [SMILES: *c1c(C)cccc1OCC]
Y-340
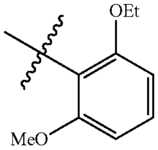 [SMILES: *c1c(OC)cccc1OCC]
Y-341
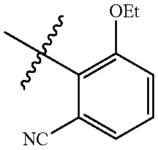 [SMILES: *c1c(C#N)cccc1OCC]
Y-342
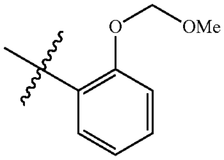 [SMILES: *c1ccccc1OCOC]
Y-343
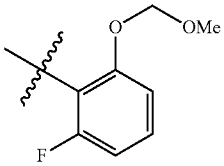
Y-344
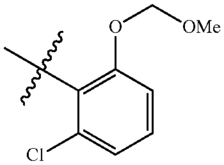 [SMILES: *c1c(Cl)cccc1OCOC]
Y-345
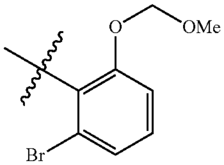 [SMILES: *c1c(Br)cccc1OCOC]
Y-346

TABLE 2-continued
Y-347
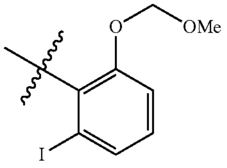 [SMILES: *c1c(I)cccc1OCOC]
Y-348
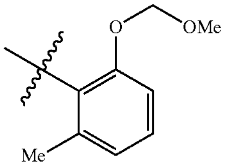 [SMILES: *c1c(C)cccc1OCOC]
Y-349
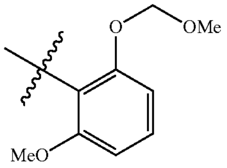 [SMILES: *c1c(OC)cccc1OCOC]
Y-350
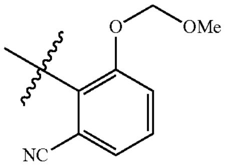 [SMILES: *c1c(C#N)cccc1OCOC]
Y-351
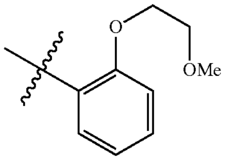 [SMILES: *c1ccccc1OCCOC]
Y-352
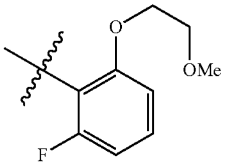
Y-353
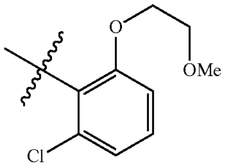 [SMILES: *c1c(Cl)cccc1OCCOC]
Y-354
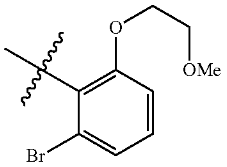 [SMILES: *c1c(Br)cccc1OCCOC]
Y-355
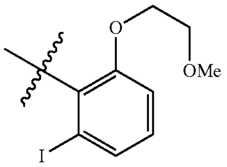 [SMILES: *c1c(I)cccc1OCCOC]
Y-356
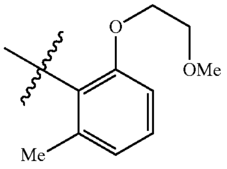 [SMILES: *c1c(C)cccc1OCCOC]
Y-357
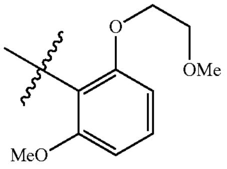 [SMILES: *c1c(OC)cccc1OCCOC]
Y-358
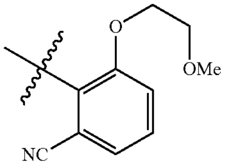 [SMILES: *c1c(C#N)cccc1OCCOC]
Y-359
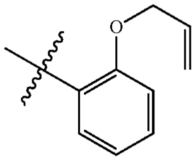 [SMILES: *c1ccccc1OCC=C]
Y-360
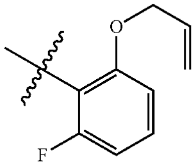 [SMILES: *c1c(F)cccc1OCC=C]
Y-361
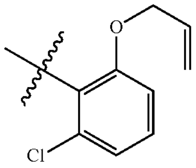 [SMILES: *c1c(Cl)cccc1OCC=C]
Y-362
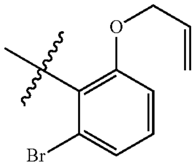 [SMILES: *c1c(Br)cccc1OCC=C]
Y-363
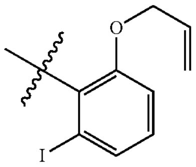 [SMILES: *c1c(I)cccc1OCC=C]
Y-364
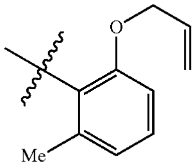 [SMILES: *c1c(C)cccc1OCC=C]

TABLE 2-continued
Y-365
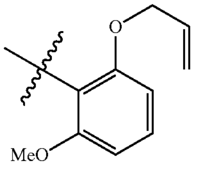 [SMILES: *c1c(OC)cccc1OCC=C]
Y-366
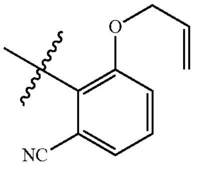 [SMILES: *c1c(C#N)cccc1OCC=C]
Y-367
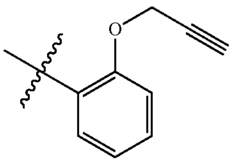 [SMILES: *c1ccccc1OCC#C]
Y-368
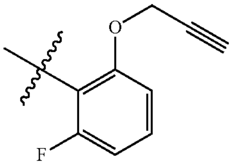
Y-369
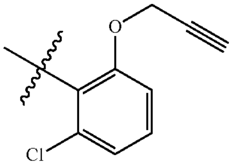 [SMILES: *c1c(Cl)cccc1OCC#C]
Y-370
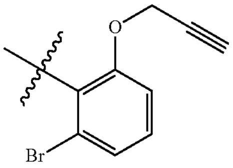 [SMILES: *c1c(Br)cccc1OCC#C]
Y-371
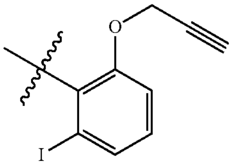 [SMILES: *c1c(I)cccc1OCC#C]
Y-372
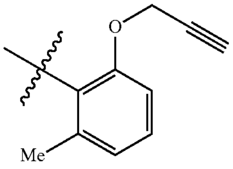 [SMILES: *c1c(C)cccc1OCC#C]
Y-373
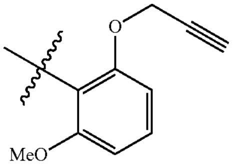 [SMILES: *c1c(OC)cccc1OCC#C]
TABLE 2-continued
Y-374
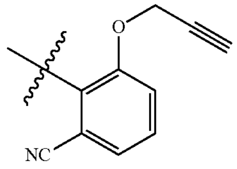 [SMILES: *c1c(C#N)cccc1OCC#C]
Y-375
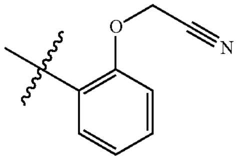 [SMILES: *c1ccccc1OCC#N]
Y-376
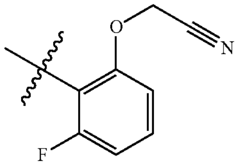 [SMILES: *c1c(F)cccc1OCC#N]
Y-377
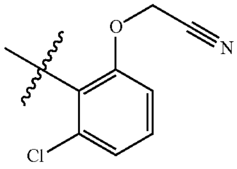 [SMILES: *c1c(Cl)cccc1OCC#N]
Y-378
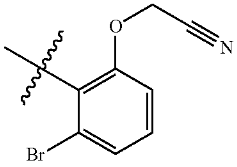 [SMILES: *c1c(Br)cccc1OCC#N]
Y-379
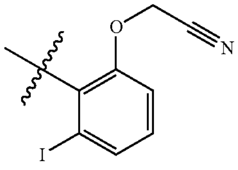 [SMILES: *c1c(I)cccc1OCC#N]
Y-380
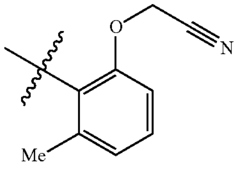 [SMILES: *c1c(C)cccc1OCC#N]
Y-381
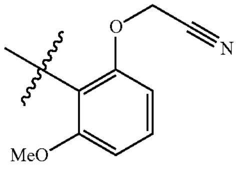 [SMILES: *c1c(OC)cccc1OCC#N]
Y-382
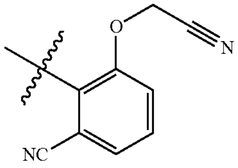 [SMILES: *c1c(C#N)cccc1OCC#N]

TABLE 2-continued
Y-383
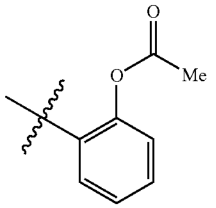 [SMILES: *c1ccccc1OC(C)=O]
Y-384
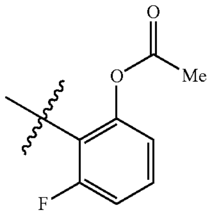
Y-385
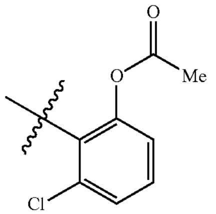 [SMILES: *c1c(Cl)cccc1OC(C)=O]
Y-386
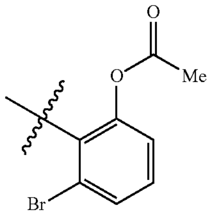 [SMILES: *c1c(Br)cccc1OC(C)=O]
Y-387
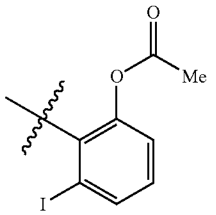 [SMILES: *c1c(I)cccc1OC(C)=O]
Y-388
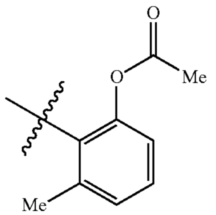 [SMILES: *c1c(C)cccc1OC(C)=O]
Y-389
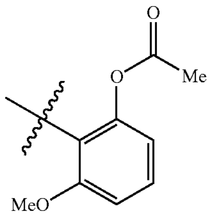 [SMILES: *c1c(OC)cccc1OC(C)=O]
TABLE 2-continued
Y-390
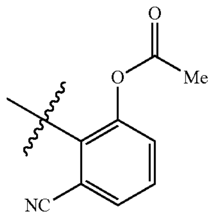 [SMILES: *c1c(C#N)cccc1OC(C)=O]
Y-391
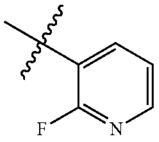 [SMILES: *c1cccnc1F]
Y-392
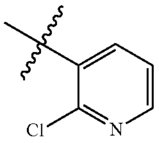 [SMILES: *c1cccnc1Cl]
Y-393
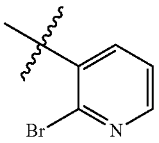 [SMILES: *c1cccnc1Br]
Y-394
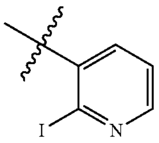
Y-395
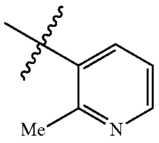 [SMILES: *c1cccnc1C]
Y-396
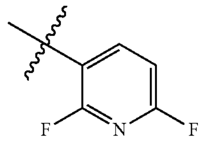
Y-397
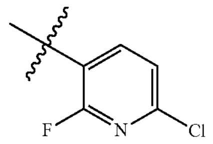 [SMILES: *c1ccc(Cl)nc1F]
Y-398
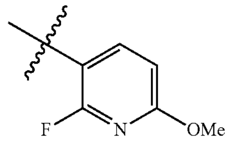 [SMILES: *c1ccc(OC)nc1F]
Y-399
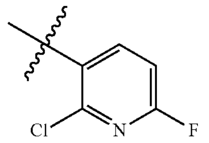 [SMILES: *c1ccc(F)nc1Cl]

TABLE 2-continued
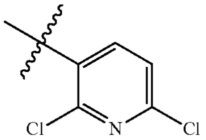 [SMILES: *c1ccc(Cl)nc1Cl]
Y-400
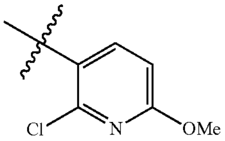 [SMILES: *c1ccc(OC)nc1Cl]
Y-401
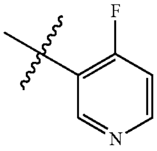 [SMILES: *c1cnccc1F]
Y-402
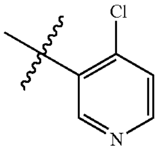
Y-403
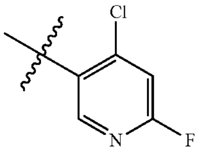 [SMILES: *c1cnc(F)cc1F]
Y-404
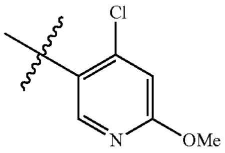
Y-405
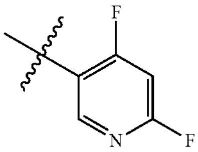
Y-406
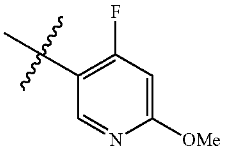 [SMILES: *c1cnc(OC)cc1F]
Y-407
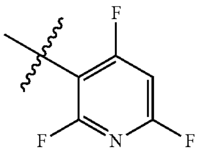 [SMILES: *c1c(F)cc(F)nc1F]
Y-408
TABLE 3
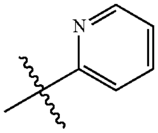 [SMILES: *c1ccccn1]
Het-1
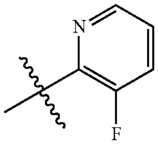 [SMILES: *c1ncccc1F]
Het-2
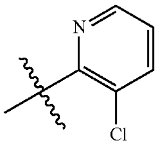 [SMILES: *c1ncccc1Cl]
Het-3
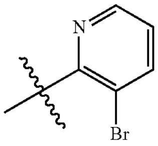 [SMILES: *c1ncccc1Br]
Het-4
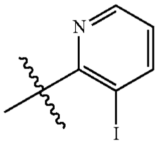 [SMILES: *c1ncccc1I]
Het-5
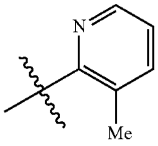 [SMILES: *c1ncccc1C]
Het-6
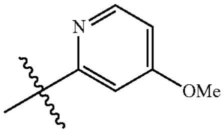 [SMILES: *c1cc(OC)ccn1]
Het-7
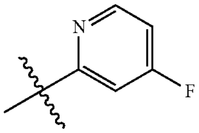 [SMILES: *c1cc(F)ccn1]
Het-8
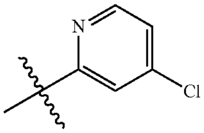 [SMILES: *c1cc(Cl)ccn1]
Het-9
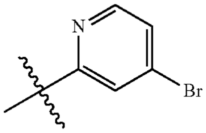 [SMILES: *c1cc(Br)ccn1]
Het-10

TABLE 3-continued
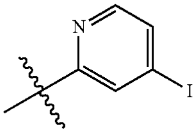 [SMILES: *c1cc(I)ccn1]
Het-11
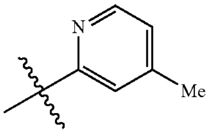 [SMILES: *c1cc(C)ccn1]
Het-12
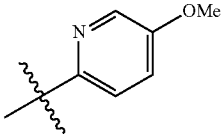 [SMILES: *c1ccc(OC)cn1]
Het-13
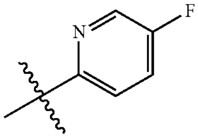 [SMILES: *c1ccc(F)cn1]
Het-14
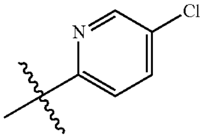 [SMILES: *c1ccc(Cl)cn1]
Het-15
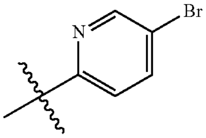 [SMILES: *c1ccc(Br)cn1]
Het-16
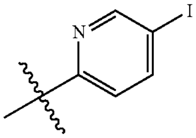 [SMILES: *c1ccc(I)cn1]
Het-17
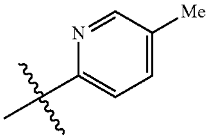 [SMILES: *c1ccc(C)cn1]
Het-18
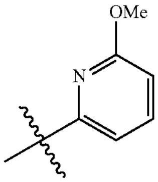 [SMILES: *c1cccc(OC)n1]
Het-19
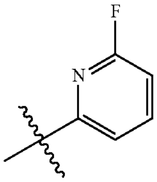 [SMILES: *c1cccc(F)n1]
Het-20
TABLE 3-continued
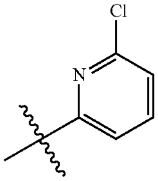 [SMILES: *c1cccc(Cl)n1]
Het-21
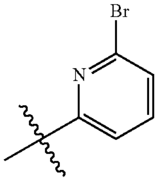 [SMILES: *c1cccc(Br)n1]
Het-22
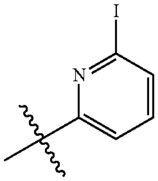 [SMILES: *c1cccc(I)n1]
Het-23
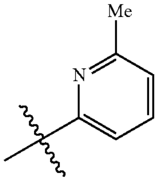 [SMILES: *c1cccc(C)n1]
Het-24
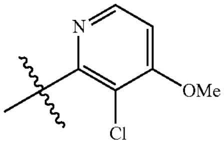 [SMILES: *c1nccc(OC)c1Cl]
Het-25
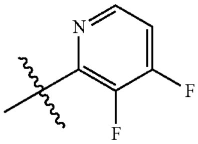
Het-26
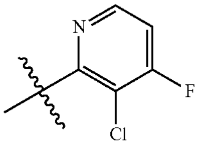 [SMILES: *c1nccc(F)c1Cl]
Het-27
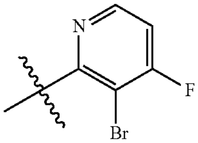
Het-28
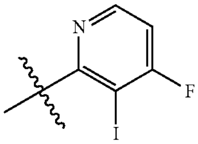 [SMILES: *c1nccc(F)c1I]
Het-29

TABLE 3-continued
Het-30
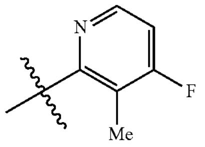 [SMILES: *c1nccc(F)c1C]
Het-31
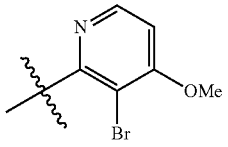 [SMILES: *c1nccc(OC)c1Br]
Het-32
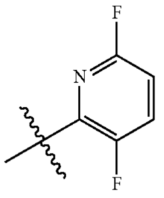 [SMILES: *c1nc(F)ccc1F]
Het-33
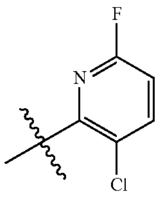 [SMILES: *c1nc(F)ccc1Cl]
Het-34
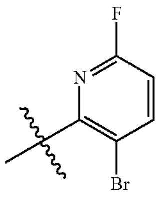 [SMILES: *c1nc(F)ccc1Br]
Het-35
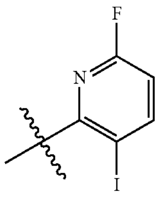 [SMILES: *c1nc(F)ccc1I]
Het-36
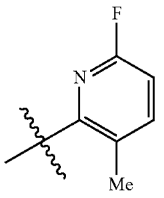 [SMILES: *c1nc(F)ccc1C]
Het-37
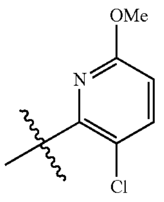 [SMILES: *c1nc(OC)ccc1Cl]
TABLE 3-continued
Het-38
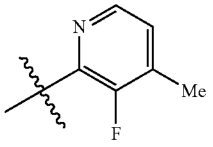
Het-39
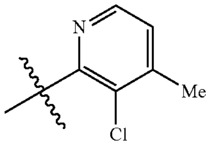 [SMILES: *c1nccc(C)c1Cl]
Het-40
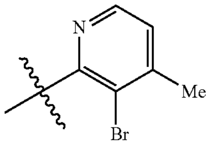 [SMILES: *c1nccc(C)c1Br]
Het-41
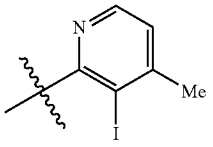 [SMILES: *c1nccc(C)c1I]
Het-42
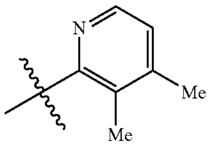 [SMILES: *c1nccc(C)c1C]
Het-43
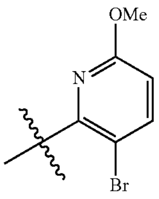 [SMILES: *c1nc(OC)ccc1Br]
Het-44
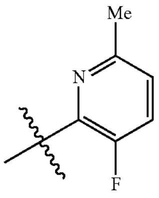 [SMILES: *c1nc(C)ccc1F]
Het-45
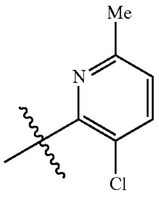 [SMILES: *c1nc(C)ccc1Cl]
Het-46
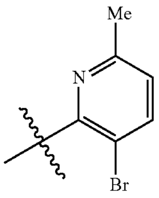

TABLE 3-continued
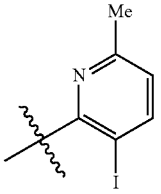 [SMILES: *c1nc(C)ccc1I]
Het-47
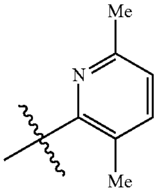 [SMILES: *c1nc(C)ccc1C]
Het-48
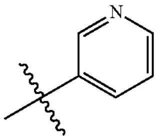 [SMILES: *c1cccnc1]
Het-49
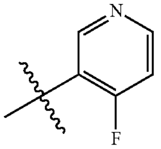 [SMILES: *c1cnccc1F]
Het-50
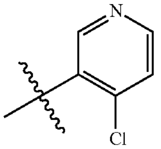 [SMILES: *c1cnccc1Cl]
Het-51
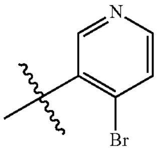 [SMILES: *c1cnccc1Br]
Het-52
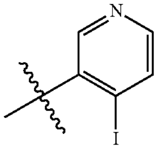 [SMILES: *c1cnccc1I]
Het-53
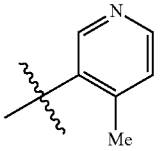 [SMILES: *c1cnccc1C]
Het-54
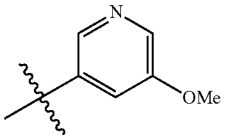 [SMILES: *c1cncc(OC)c1]
Het-55
TABLE 3-continued
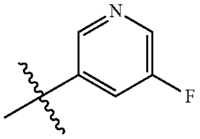 [SMILES: *c1cncc(F)c1]
Het-56
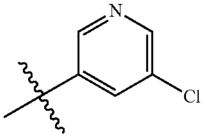 [SMILES: *c1cncc(Cl)c1]
Het-57
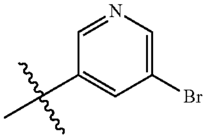 [SMILES: *c1cncc(Br)c1]
Het-58
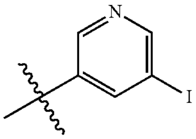 [SMILES: *c1cncc(I)c1]
Het-59
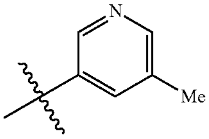 [SMILES: *c1cncc(C)c1]
Het-60
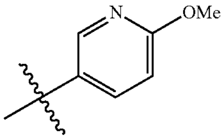 [SMILES: *c1ccc(OC)nc1]
Het-61
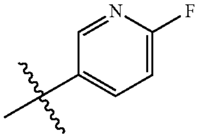 [SMILES: *c1ccc(F)nc1]
Het-62
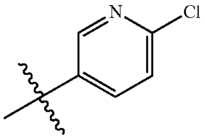 [SMILES: *c1ccc(Cl)nc1]
Het-63
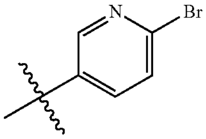
Het-64
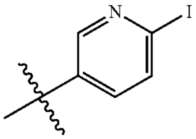 [SMILES: *c1ccc(I)nc1]
Het-65

TABLE 3-continued
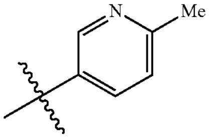 [SMILES: *c1ccc(C)nc1]
Het-66
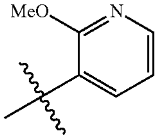 [SMILES: *c1cccnc1OC]
Het-67
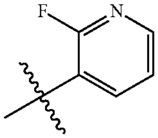 [SMILES: *c1cccnc1F]
Het-68
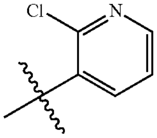 [SMILES: *c1cccnc1Cl]
Het-69
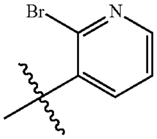 [SMILES: *c1cccnc1Br]
Het-70
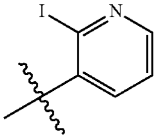 [SMILES: *c1cccnc1I]
Het-71
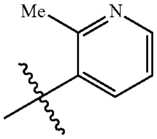 [SMILES: *c1cccnc1C]
Het-72
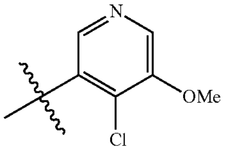 [SMILES: *c1cncc(OC)c1Cl]
Het-73
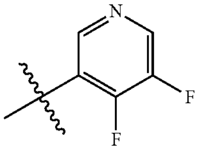
Het-74
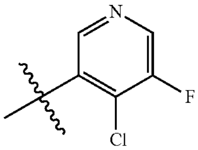 [SMILES: *c1cncc(F)c1Cl]
Het-75
TABLE 3-continued
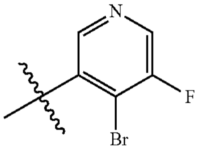 [SMILES: *c1cncc(F)c1Br]
Het-76
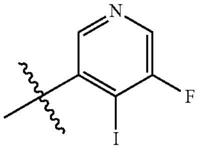 [SMILES: *c1cncc(F)c1I]
Het-77
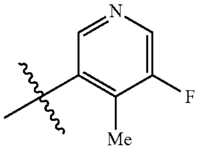 [SMILES: *c1cncc(F)c1C]
Het-78
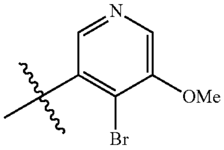
Het-79
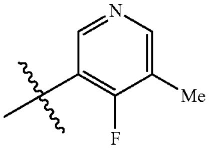
Het-80
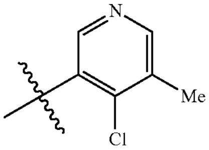 [SMILES: *c1cncc(C)c1Cl]
Het-81
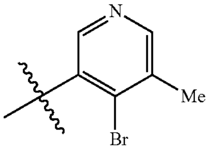 [SMILES: *c1cncc(C)c1Br]
Het-82
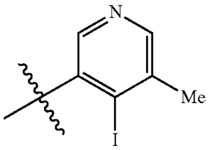 [SMILES: *c1cncc(C)c1I]
Het-83
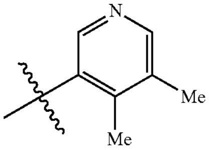 [SMILES: *c1cncc(C)c1C]
Het-84
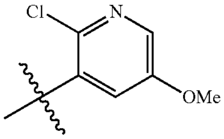 [SMILES: *c1cc(OC)cnc1Cl]
Het-85

TABLE 3-continued
| | |
|---|---|
| 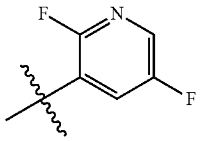 | Het-86 |
| 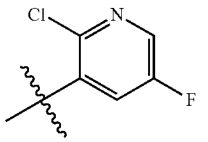 | Het-87 |
| 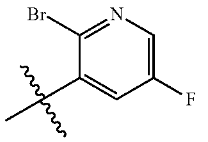 [SMILES: *c1cc(F)cnc1Br] | Het-88 |
| 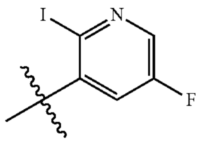 | Het-89 |
| 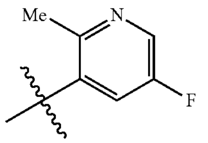 [SMILES: *c1cc(F)cnc1C] | Het-90 |
| 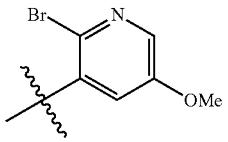 | Het-91 |
| 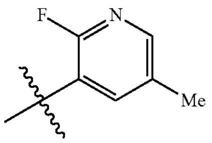 | Het-92 |
| 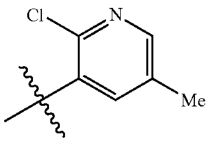 [SMILES: *c1cc(C)cnc1Cl] | Het-93 |
| 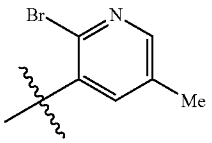 [SMILES: *c1cc(C)cnc1Br] | Het-94 |
| 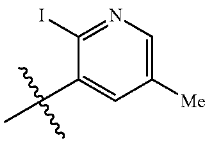 [SMILES: *c1cc(C)cnc1I] | Het-95 |
TABLE 3-continued
| | |
|---|---|
| 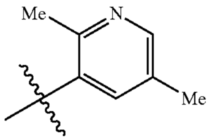 [SMILES: *c1cc(C)cnc1C] | Het-96 |
| 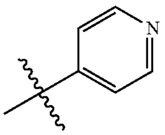 [SMILES: *c1ccncc1] | Het-97 |
| 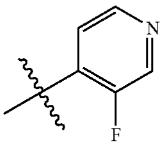 | Het-98 |
| 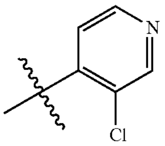 [SMILES: *c1ccncc1Cl] | Het-99 |
| 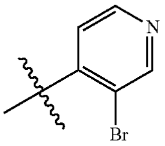 [SMILES: *c1ccncc1Br] | Het-100 |
| 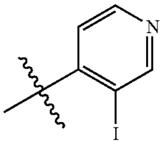 [SMILES: *c1ccncc1I] | Het-101 |
| 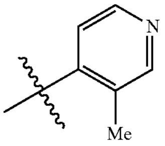 [SMILES: *c1ccncc1C] | Het-102 |
| 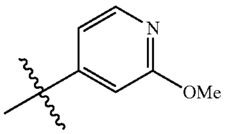 [SMILES: *c1ccnc(OC)c1] | Het-103 |
| 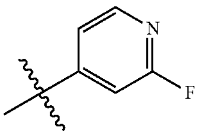 [SMILES: *c1ccnc(F)c1] | Het-104 |
| 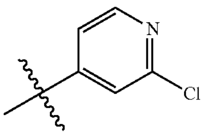 [SMILES: *c1ccnc(Cl)c1] | Het-105 |

TABLE 3-continued
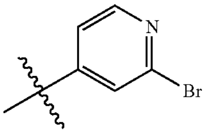 [SMILES: *c1ccnc(Br)c1]
Het-106
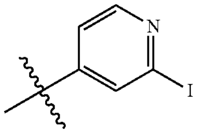 [SMILES: *c1ccnc(I)c1]
Het-107
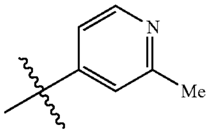 [SMILES: *c1ccnc(C)c1]
Het-108
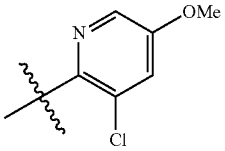 [SMILES: *c1ncc(OC)cc1Cl]
Het-109
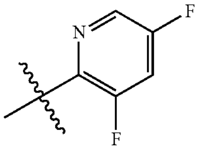
Het-110
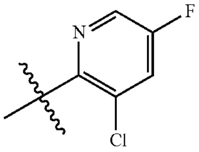 [SMILES: *c1ncc(F)cc1Cl]
Het-111
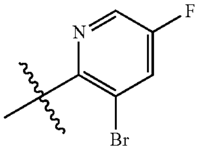
Het-112
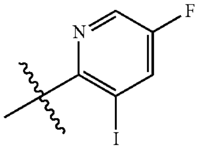 [SMILES: *c1ncc(F)cc1I]
Het-113
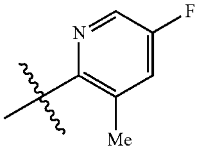 [SMILES: *c1ncc(F)cc1C]
Het-114
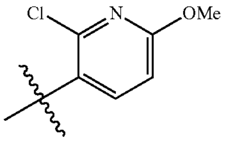 [SMILES: *c1ccc(OC)nc1Cl]
Het-115
TABLE 3-continued
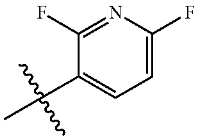
Het-116
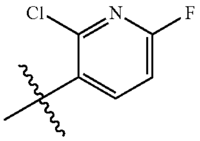 [SMILES: *c1ccc(F)nc1Cl]
Het-117
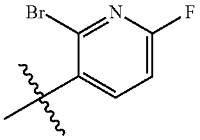 [SMILES: *c1ccc(F)nc1Br]
Het-118
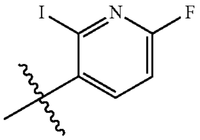 [SMILES: *c1ccc(F)nc1I]
Het-119
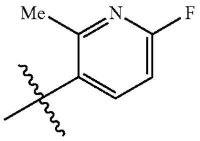 [SMILES: *c1ccc(F)nc1C]
Het-120
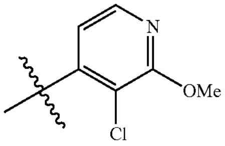 [SMILES: *c1ccnc(OC)c1Cl]
Het-121
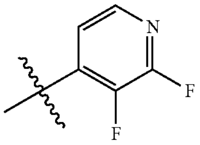
Het-122
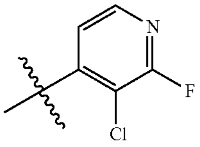 [SMILES: *c1ccnc(F)c1Cl]
Het-123
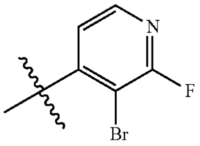
Het-124
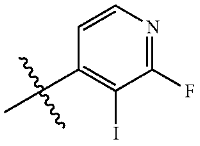 [SMILES: *c1ccnc(F)c1I]
Het-125

TABLE 3-continued
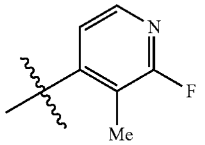 [SMILES: *c1ccnc(F)c1C]
Het-126
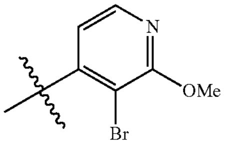 [SMILES: *c1ccnc(OC)c1Br]
Het-127
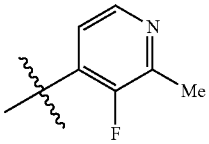
Het-128
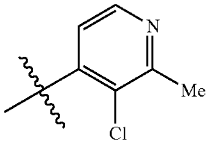 [SMILES: *c1ccnc(C)c1Cl]
Het-129
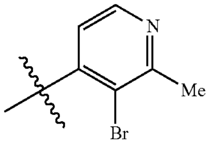 [SMILES: *c1ccnc(C)c1Br]
Het-130
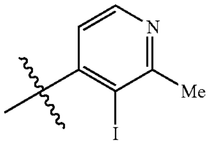 [SMILES: *c1ccnc(C)c1I]
Het-131
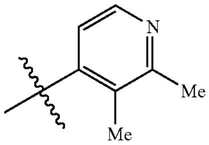 [SMILES: *c1ccnc(C)c1C]
Het-132
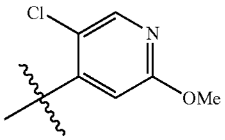 [SMILES: *c1cc(OC)ncc1Cl]
Het-133
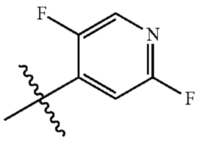
Het-134
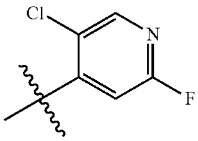 [SMILES: *c1cc(F)ncc1Cl]
Het-135
TABLE 3-continued
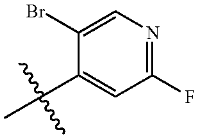 [SMILES: *c1cc(F)ncc1Br]
Het-136
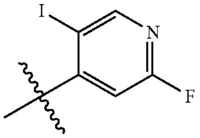 [SMILES: *c1cc(F)ncc1I]
Het-137
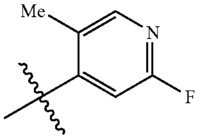 [SMILES: *c1cc(F)ncc1C]
Het-138
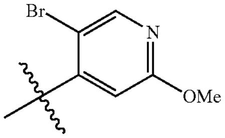 [SMILES: *c1cc(OC)ncc1Br]
Het-139
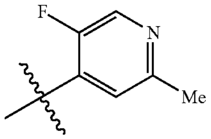
Het-140
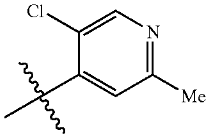 [SMILES: *c1cc(C)ncc1Cl]
Het-141
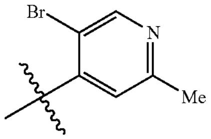 [SMILES: *c1cc(C)ncc1Br]
Het-142
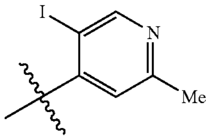 [SMILES: *c1cc(C)ncc1I]
Het-143
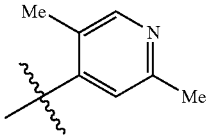 [SMILES: *c1cc(C)ncc1C]
Het-144
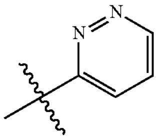 [SMILES: *c1cccnn1]
Het-145

TABLE 3-continued
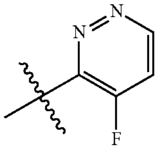 [SMILES: *c1nnccc1F]
Het-146
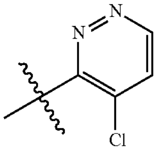 [SMILES: *c1nnccc1Cl]
Het-147
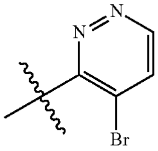
Het-148
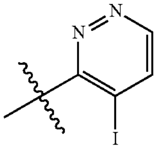 [SMILES: *c1nnccc1I]
Het-149
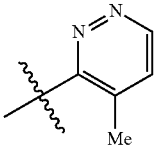
Het-150
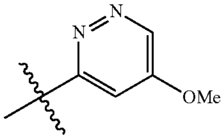 [SMILES: *c1cc(OC)cnn1]
Het-151
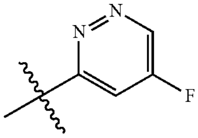 [SMILES: *c1cc(F)cnn1]
Het-152
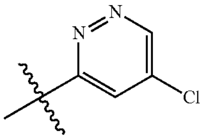 [SMILES: *c1cc(Cl)cnn1]
Het-153
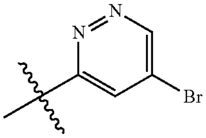 [SMILES: *c1cc(Br)cnn1]
Het-154
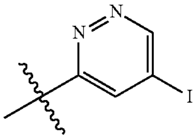 [SMILES: *c1cc(I)cnn1]
Het-155
TABLE 3-continued
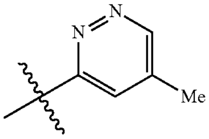 [SMILES: *c1cc(C)cnn1]
Het-156
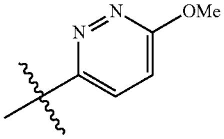 [SMILES: *c1ccc(OC)nn1]
Het-157
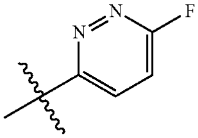 [SMILES: *c1ccc(F)nn1]
Het-158
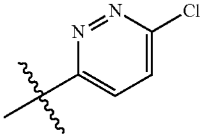 [SMILES: *c1ccc(Cl)nn1]
Het-159
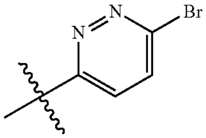 [SMILES: *c1ccc(Br)nn1]
Het-160
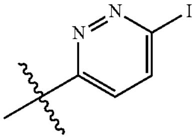 [SMILES: *c1ccc(I)nn1]
Het-161
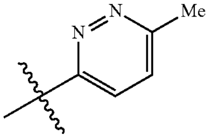 [SMILES: *c1ccc(C)nn1]
Het-162
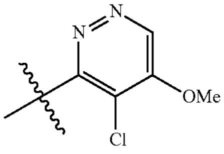 [SMILES: *c1nncc(OC)c1Cl]
Het-163
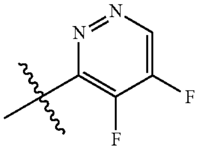
Het-164
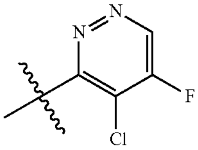 [SMILES: *c1nncc(F)c1Cl]
Het-165

TABLE 3-continued
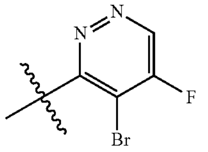
Het-166
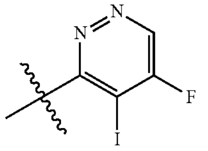 [SMILES: *c1nncc(F)c1I]
Het-167
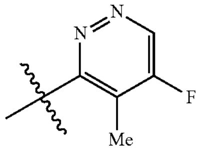
Het-168
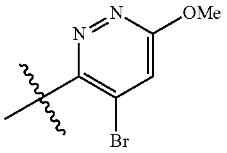 [SMILES: *c1nnc(OC)cc1Br]
Het-169
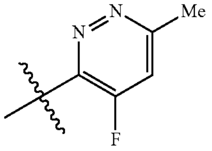
Het-170
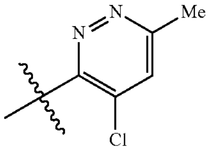 [SMILES: *c1nnc(C)cc1Cl]
Het-171
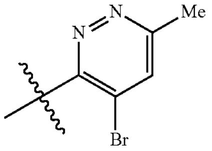 [SMILES: *c1nnc(C)cc1Br]
Het-172
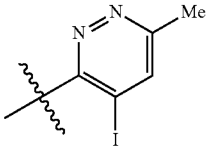 [SMILES: *c1nnc(C)cc1I]
Het-173
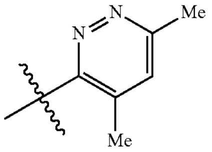 [SMILES: *c1nnc(C)cc1C]
Het-174
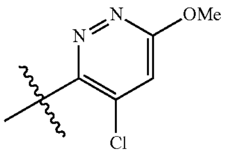 [SMILES: *c1nnc(OC)cc1Cl]
Het-175
TABLE 3-continued
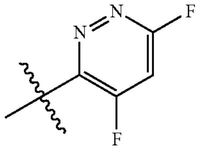
Het-176
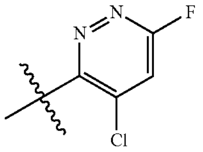 [SMILES: *c1nnc(F)cc1Cl]
Het-177
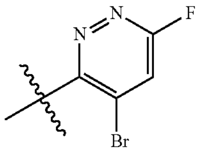 [SMILES: *c1nnc(F)cc1Br]
Het-178
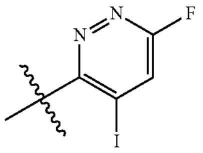 [SMILES: *c1nnc(F)cc1I]
Het-179
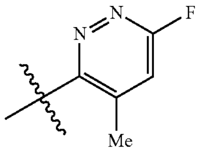 [SMILES: *c1nnc(F)cc1C]
Het-180
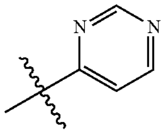 [SMILES: *c1ccncn1]
Het-181
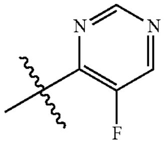
Het-182
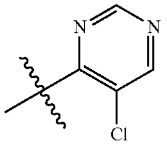 [SMILES: *c1ncncc1Cl]
Het-183
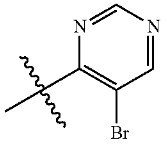 [SMILES: *c1ncncc1Br]
Het-184
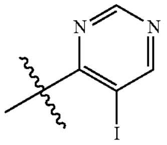 [SMILES: *c1ncncc1I]
Het-185

TABLE 3-continued
Het-186
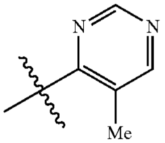 [SMILES: *c1ncncc1C]
Het-187
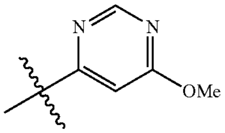 [SMILES: *c1cc(OC)ncn1]
Het-188
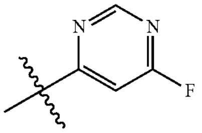 [SMILES: *c1cc(F)ncn1]
Het-189
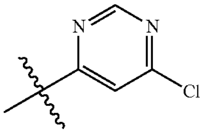
Het-190
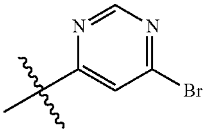
Het-191
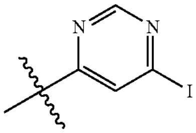 [SMILES: *c1cc(I)ncn1]
Het-192
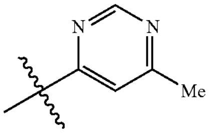 [SMILES: *c1cc(C)ncn1]
Het-193
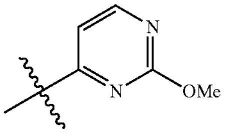 [SMILES: *c1ccnc(OC)n1]
Het-194
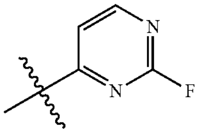 [SMILES: *c1ccnc(F)n1]
Het-195
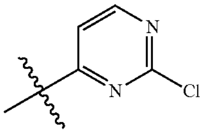 [SMILES: *c1ccnc(Cl)n1]
Het-196
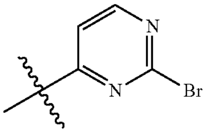 [SMILES: *c1ccnc(Br)n1]
TABLE 3-continued
Het-197
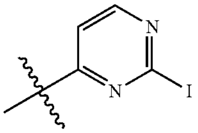 [SMILES: *c1ccnc(I)n1]
Het-198
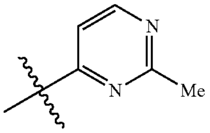
Het-199
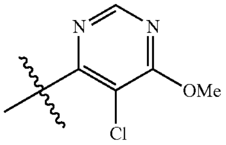 [SMILES: *c1ncnc(OC)c1Cl]
Het-200
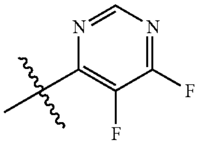
Het-201
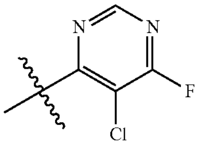 [SMILES: *c1ncnc(F)c1Cl]
Het-202
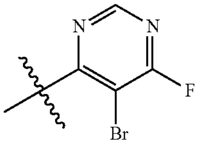 [SMILES: *c1ncnc(F)c1Br]
Het-203
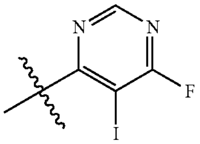 [SMILES: *c1ncnc(F)c1I]
Het-204
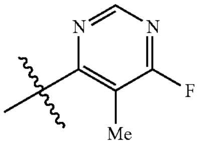 [SMILES: *c1ncnc(F)c1C]
Het-205
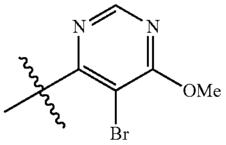 [SMILES: *c1ncnc(OC)c1Br]
Het-206
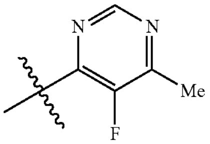

TABLE 3-continued
Het-207
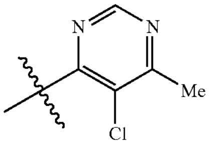 [SMILES: *c1ncnc(C)c1Cl]
Het-208
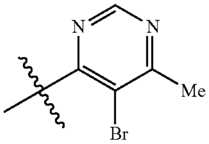 [SMILES: *c1ncnc(C)c1Br]
Het-209
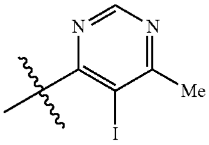 [SMILES: *c1ncnc(C)c1I]
Het-210
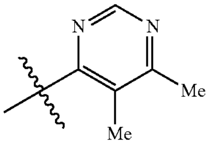 [SMILES: *c1ncnc(C)c1C]
Het-211
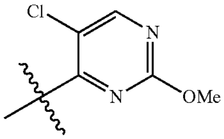
Het-212
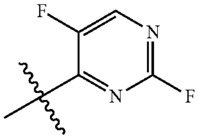
Het-213
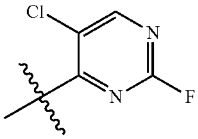
Het-214
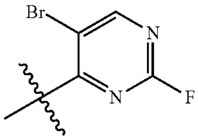 [SMILES: *c1nc(F)ncc1Br]
Het-215
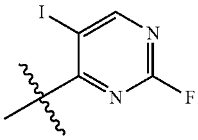 [SMILES: *c1nc(F)ncc1I]
Het-216
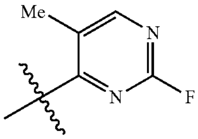 [SMILES: *c1nc(F)ncc1C]
TABLE 3-continued
Het-217
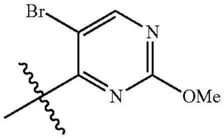 [SMILES: *c1nc(OC)ncc1Br]
Het-218
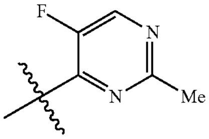
Het-219
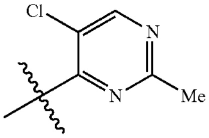
Het-220
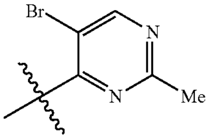 [SMILES: *c1nc(C)ncc1Br]
Het-221
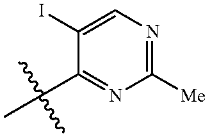 [SMILES: *c1nc(C)ncc1I]
Het-222
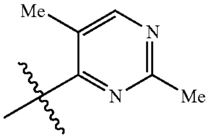 [SMILES: *c1nc(C)ncc1C]
Het-223
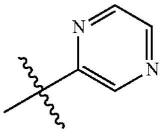 [SMILES: *c1cnccn1]
Het-224
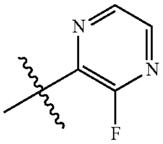
Het-225
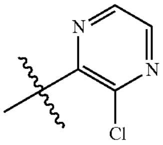 [SMILES: *c1nccnc1Cl]
Het-226
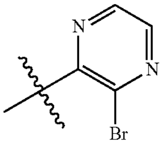 [SMILES: *c1nccnc1Br]

TABLE 3-continued
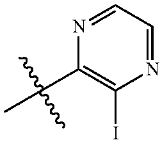 [SMILES: *c1nccnc1I]
Het-227
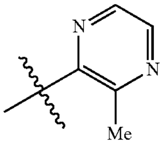 [SMILES: *c1nccnc1C]
Het-228
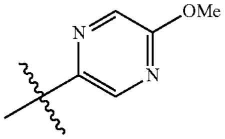 [SMILES: *c1cnc(OC)cn1]
Het-229
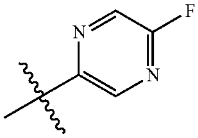 [SMILES: *c1cnc(F)cn1]
Het-230
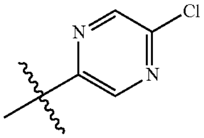 [SMILES: *c1cnc(Cl)cn1]
Het-231
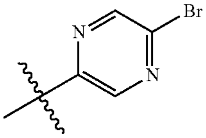 [SMILES: *c1cnc(Br)cn1]
Het-232
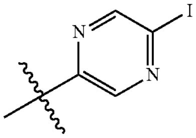 [SMILES: *c1cnc(I)cn1]
Het-233
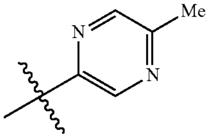 [SMILES: *c1cnc(C)cn1]
Het-234
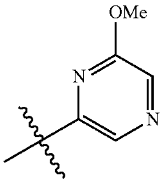 [SMILES: *c1cncc(OC)n1]
Het-235
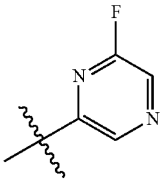
Het-236
TABLE 3-continued
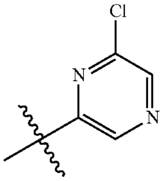 [SMILES: *c1cncc(Cl)n1]
Het-237
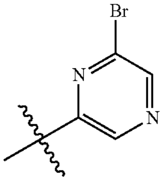 [SMILES: *c1cncc(Br)n1]
Het-238
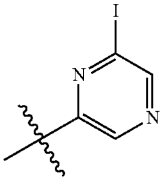 [SMILES: *c1cncc(I)n1]
Het-239
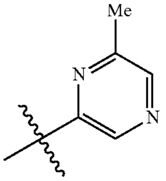
Het-240
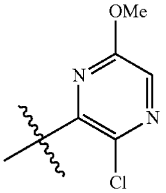 [SMILES: *c1nc(OC)cnc1Cl]
Het-241
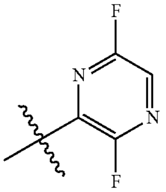
Het-242
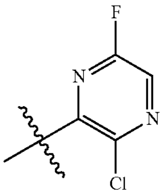 [SMILES: *c1nc(F)cnc1Cl]
Het-243
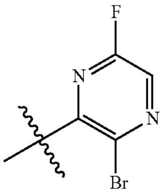 [SMILES: *c1nc(F)cnc1Br]
Het-244

TABLE 3-continued
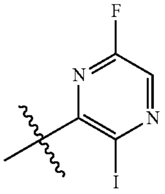 [SMILES: *c1nc(F)cnc1I]
Het-245
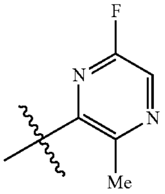 [SMILES: *c1nc(F)cnc1C]
Het-246
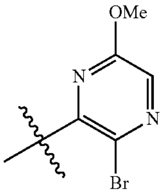 [SMILES: *c1nc(OC)cnc1Br]
Het-247
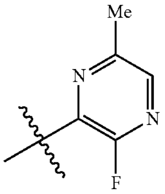
Het-248
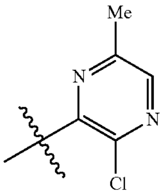 [SMILES: *c1nc(C)cnc1Cl]
Het-249
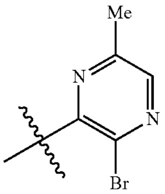 [SMILES: *c1nc(C)cnc1Br]
Het-250
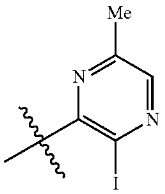 [SMILES: *c1nc(C)cnc1I]
Het-251
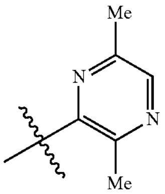 [SMILES: *c1nc(C)cnc1C]
Het-252
TABLE 3-continued
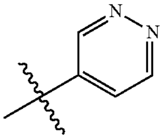 [SMILES: *c1ccnnc1]
Het-253
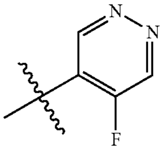
Het-254
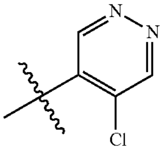 [SMILES: *c1cnncc1Cl]
Het-255
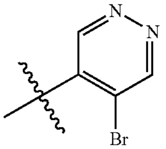
Het-256
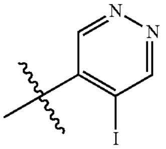 [SMILES: *c1cnncc1I]
Het-257
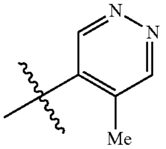 [SMILES: *c1cnncc1C]
Het-258
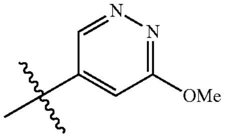 [SMILES: *c1cnnc(OC)c1]
Het-259
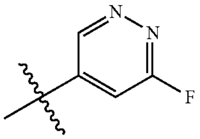 [SMILES: *c1cnnc(F)c1]
Het-260
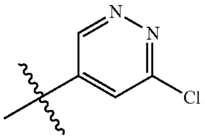 [SMILES: *c1cnnc(Cl)c1]
Het-261
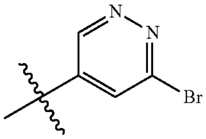 [SMILES: *c1cnnc(Br)c1]
Het-262

TABLE 3-continued
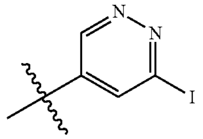 [SMILES: *c1cnnc(I)c1]
Het-263
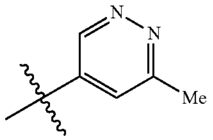 [SMILES: *c1cnnc(C)c1]
Het-264
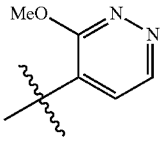 [SMILES: *c1ccnnc1OC]
Het-265
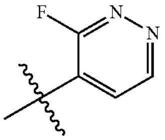
Het-266
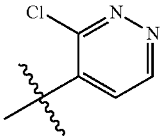 [SMILES: *c1ccnnc1Cl]
Het-267
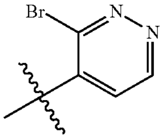 [SMILES: *c1ccnnc1Br]
Het-268
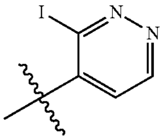 [SMILES: *c1ccnnc1I]
Het-269
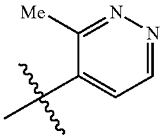 [SMILES: *c1ccnnc1C]
Het-270
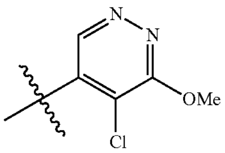 [SMILES: *c1cnnc(OC)c1Cl]
Het-271
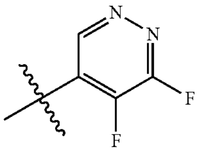
Het-272
TABLE 3-continued
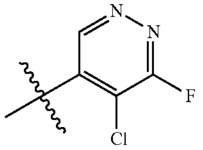 [SMILES: *c1cnnc(F)c1Cl]
Het-273
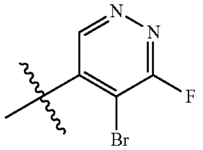
Het-274
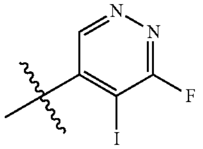 [SMILES: *c1cnnc(F)c1I]
Het-275
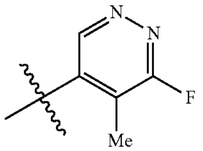 [SMILES: *c1cnnc(F)c1C]
Het-276
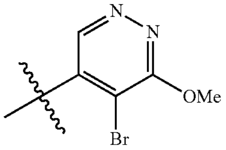 [SMILES: *c1cnnc(OC)c1Br]
Het-277
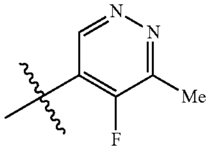
Het-278
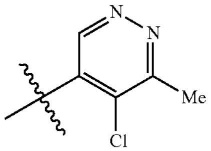 [SMILES: *c1cnnc(C)c1Cl]
Het-279
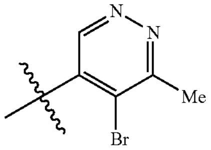 [SMILES: *c1cnnc(C)c1Br]
Het-280
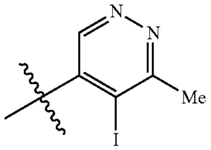 [SMILES: *c1cnnc(C)c1I]
Het-281
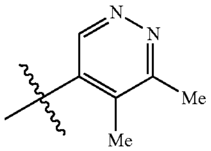 [SMILES: *c1cnnc(C)c1C]
Het-282

TABLE 3-continued
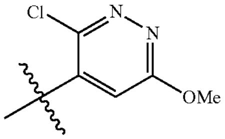 [SMILES: *c1cc(OC)nnc1Cl]
Het-283
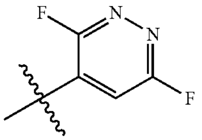
Het-284
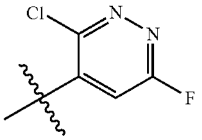 [SMILES: *c1cc(F)nnc1Cl]
Het-285
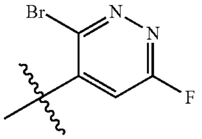 [SMILES: *c1cc(F)nnc1Br]
Het-286
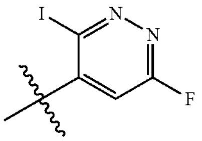
Het-287
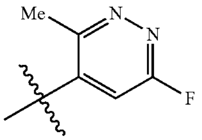 [SMILES: *c1cc(F)nnc1C]
Het-288
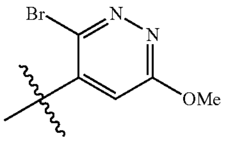 [SMILES: *c1cc(OC)nnc1Br]
Het-289
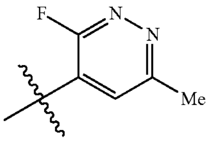
Het-290
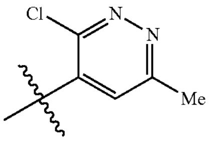 [SMILES: *c1cc(C)nnc1Cl]
Het-291
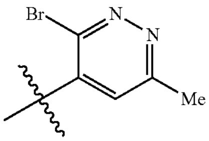 [SMILES: *c1cc(C)nnc1Br]
Het-292
TABLE 3-continued
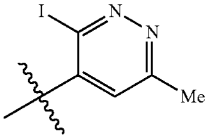 [SMILES: *c1cc(C)nnc1I]
Het-293
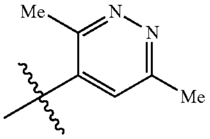 [SMILES: *c1cc(C)nnc1C]
Het-294
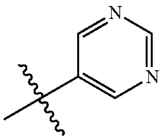 [SMILES: *c1cncnc1]
Het-295
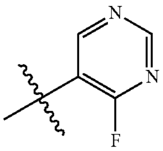
Het-296
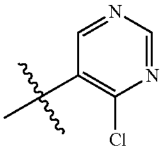 [SMILES: *c1cncnc1Cl]
Het-297
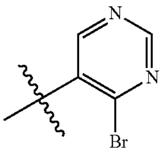 [SMILES: *c1cncnc1Br]
Het-298
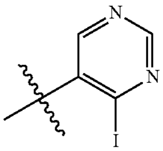 [SMILES: *c1cncnc1I]
Het-299
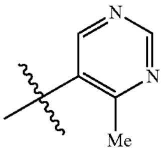 [SMILES: *c1cncnc1C]
Het-300
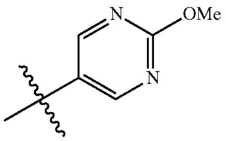 [SMILES: *c1cnc(OC)nc1]
Het-301
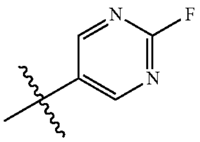 [SMILES: *c1cnc(F)nc1]
Het-302

TABLE 3-continued
| | |
|---|---|
| 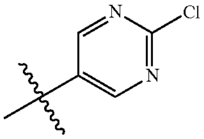 [SMILES: *c1cnc(Cl)nc1] | Het-303 |
| 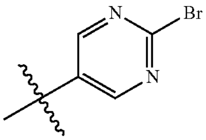 [SMILES: *c1cnc(Br)nc1] | Het-304 |
| 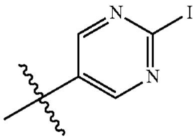 [SMILES: *c1cnc(I)nc1] | Het-305 |
| 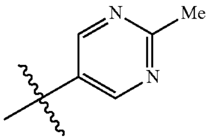 [SMILES: *c1cnc(C)nc1] | Het-306 |
| 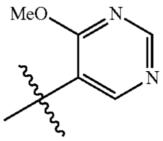 [SMILES: *c1cncnc1OC] | Het-307 |
| 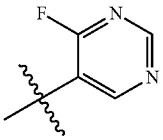 | Het-308 |
| 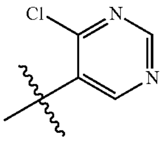 [SMILES: *c1cncnc1Cl] | Het-309 |
| 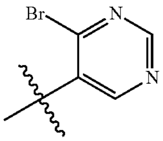 [SMILES: *c1cncnc1Br] | Het-310 |
| 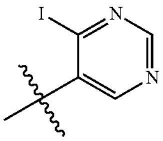 | Het-311 |
| 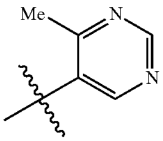 [SMILES: *c1cncnc1C] | Het-312 |
TABLE 3-continued
| | |
|---|---|
| 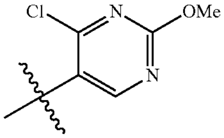 | Het-313 |
| 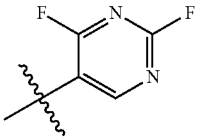 | Het-314 |
| 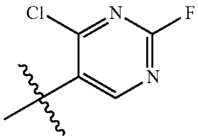 | Het-315 |
| 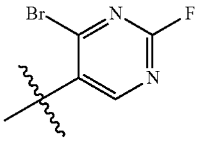 [SMILES: *c1cnc(F)nc1Br] | Het-316 |
| 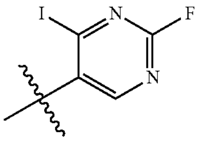 [SMILES: *c1cnc(F)nc1I] | Het-317 |
| 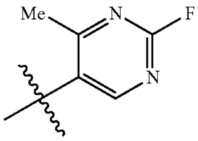 [SMILES: *c1cnc(F)nc1C] | Het-318 |
| 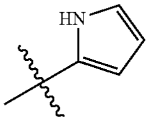 [SMILES: *c1ccc[nH]1] | Het-319 |
| 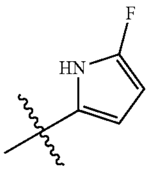 [SMILES: *c1ccc(F)[nH]1] | Het-320 |
| 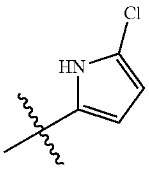 [SMILES: *c1ccc(Cl)[nH]1] | Het-321 |
| 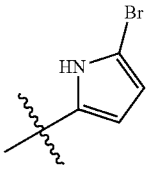 [SMILES: *c1ccc(Br)[nH]1] | Het-322 |

TABLE 3-continued
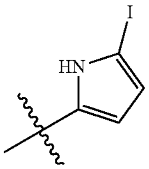 [SMILES: *c1ccc(I)[nH]1]
Het-323
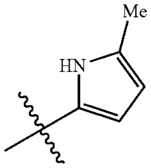 [SMILES: *c1ccc(C)[nH]1]
Het-324
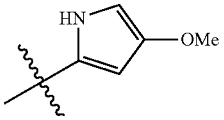 [SMILES: *c1cc(OC)c[nH]1]
Het-325
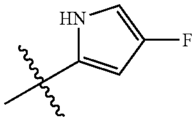 [SMILES: *c1cc(F)c[nH]1]
Het-326
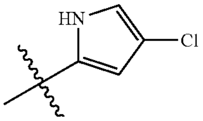 [SMILES: *c1cc(Cl)c[nH]1]
Het-327
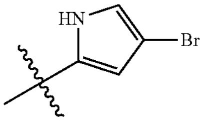 [SMILES: *c1cc(Br)c[nH]1]
Het-328
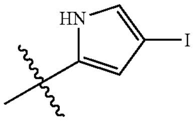 [SMILES: *c1cc(I)c[nH]1]
Het-329
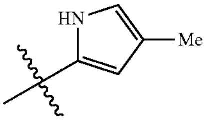 [SMILES: *c1cc(C)c[nH]1]
Het-330
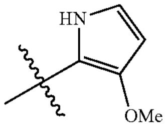 [SMILES: *c1[nH]ccc1OC]
Het-331
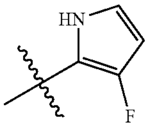 [SMILES: *c1[nH]ccc1F]
Het-332
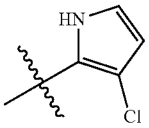
Het-333
TABLE 3-continued
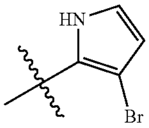 [SMILES: *c1[nH]ccc1Br]
Het-334
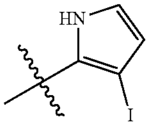 [SMILES: *c1[nH]ccc1I]
Het-335
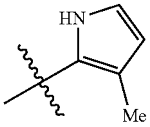
Het-336
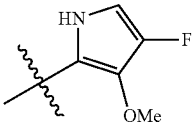 [SMILES: *c1[nH]cc(F)c1OC]
Het-337
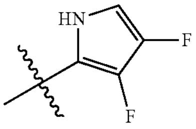
Het-338
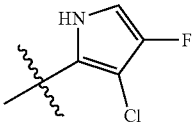 [SMILES: *c1[nH]cc(F)c1Cl]
Het-339
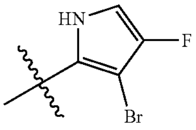 [SMILES: *c1[nH]cc(F)c1Br]
Het-340
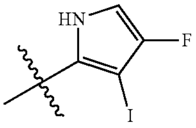 [SMILES: *c1[nH]cc(F)c1I]
Het-341
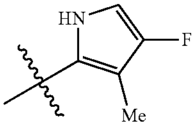 [SMILES: *c1[nH]cc(F)c1C]
Het-342
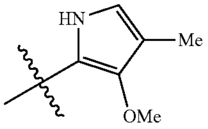 [SMILES: *c1[nH]cc(C)c1OC]
Het-343
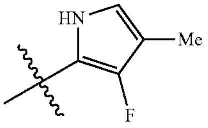
Het-344

TABLE 3-continued
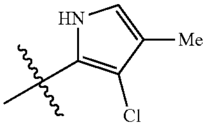 [SMILES: *c1[nH]cc(C)c1Cl]
Het-345
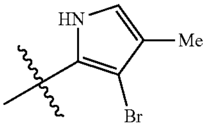 [SMILES: *c1[nH]cc(C)c1Br]
Het-346
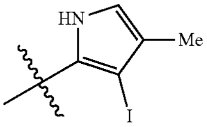 [SMILES: *c1[nH]cc(C)c1I]
Het-347
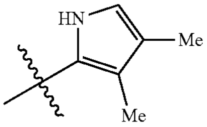 [SMILES: *c1[nH]cc(C)c1C]
Het-348
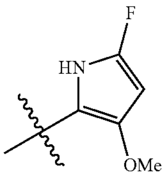 [SMILES: *c1[nH]c(F)cc1OC]
Het-349
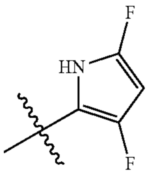 [SMILES: *c1[nH]c(F)cc1F]
Het-350
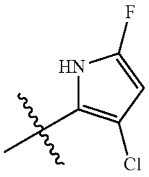 [SMILES: *c1[nH]c(F)cc1Cl]
Het-351
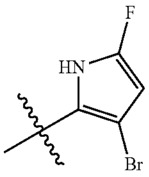
Het-352
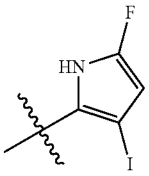 [SMILES: *c1[nH]c(F)cc1I]
Het-353
TABLE 3-continued
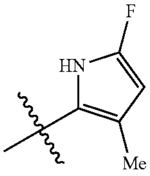 [SMILES: *c1[nH]c(F)cc1C]
Het-354
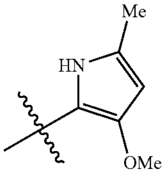 [SMILES: *c1[nH]c(C)cc1OC]
Het-355
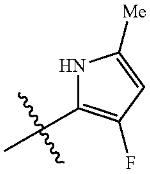
Het-356
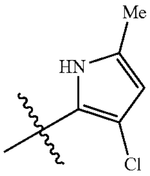 [SMILES: *c1[nH]c(C)cc1Cl]
Het-357
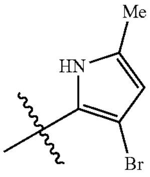
Het-358
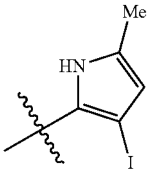 [SMILES: *c1[nH]c(C)cc1I]
Het-359
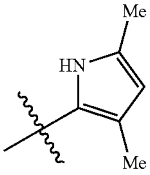 [SMILES: *c1[nH]c(C)cc1C]
Het-360
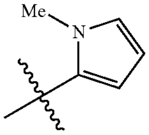 [SMILES: *c1cccn1C]
Het-361
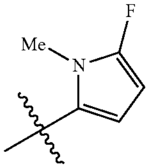 [SMILES: *c1ccc(F)n1C]
Het-362

TABLE 3-continued
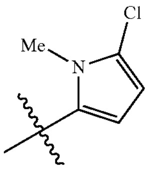 [SMILES: *c1ccc(Cl)n1C]
Het-363
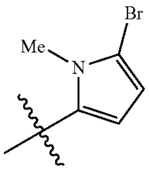 [SMILES: *c1ccc(Br)n1C]
Het-364
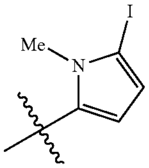 [SMILES: *c1ccc(I)n1C]
Het-365
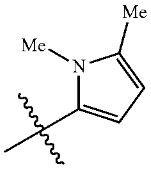 [SMILES: *c1ccc(C)n1C]
Het-366
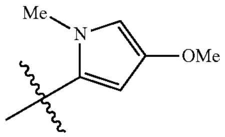 [SMILES: *c1cc(OC)cn1C]
Het-367
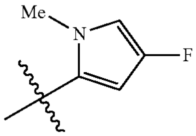 [SMILES: *c1cc(F)cn1C]
Het-368
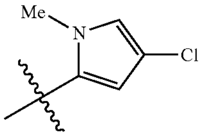 [SMILES: *c1cc(Cl)cn1C]
Het-369
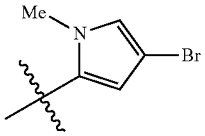 [SMILES: *c1cc(Br)cn1C]
Het-370
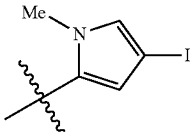 [SMILES: *c1cc(I)cn1C]
Het-371
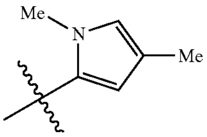 [SMILES: *c1cc(C)cn1C]
Het-372
TABLE 3-continued
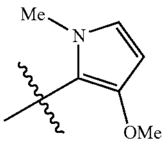 [SMILES: *c1c(OC)ccn1C]
Het-373
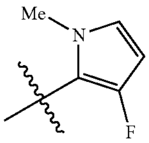 [SMILES: *c1c(F)ccn1C]
Het-374
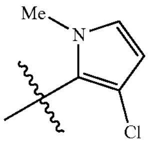 [SMILES: *c1c(Cl)ccn1C]
Het-375
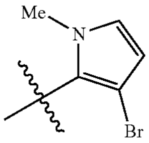 [SMILES: *c1c(Br)ccn1C]
Het-376
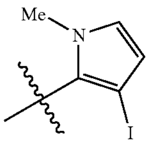
Het-377
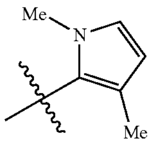 [SMILES: *c1c(C)ccn1C]
Het-378
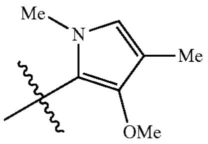 [SMILES: *c1c(OC)c(C)cn1C]
Het-379
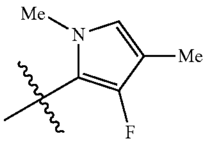
Het-380
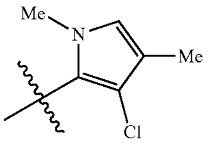 [SMILES: *c1c(Cl)c(C)cn1C]
Het-381
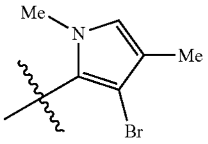 [SMILES: *c1c(Br)c(C)cn1C]
Het-382

TABLE 3-continued
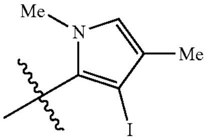 [SMILES: *c1c(I)c(C)cn1C] Het-383
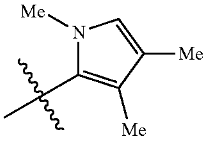 Het-384
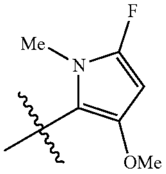 [SMILES: *c1c(OC)cc(F)n1C] Het-385
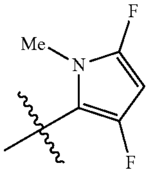 [SMILES: *c1c(F)cc(F)n1C] Het-386
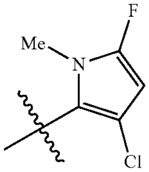 [SMILES: *c1c(Cl)cc(F)n1C] Het-387
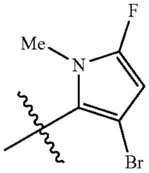 [SMILES: *c1c(Br)cc(F)n1C] Het-388
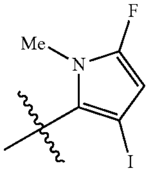 [SMILES: *c1c(I)cc(F)n1C] Het-389
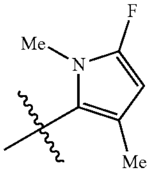 [SMILES: *c1c(C)cc(F)n1C] Het-390
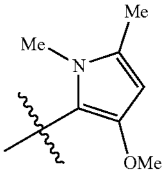 [SMILES: *c1c(OC)cc(C)n1C] Het-391
TABLE 3-continued
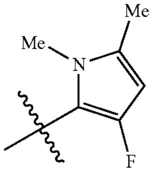 [SMILES: *c1c(F)cc(C)n1C] Het-392
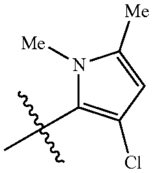 [SMILES: *c1c(Cl)cc(C)n1C] Het-393
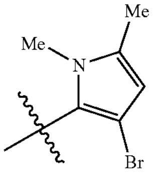 [SMILES: *c1c(Br)cc(C)n1C] Het-394
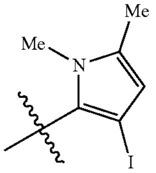 [SMILES: *c1c(I)cc(C)n1C] Het-395
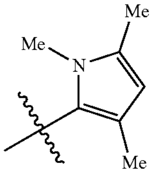 [SMILES: *c1c(C)cc(C)n1C] Het-396
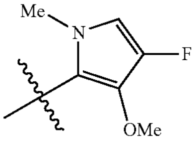 [SMILES: *c1c(OC)c(F)cn1C] Het-397
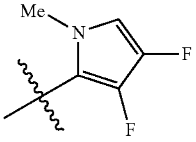 Het-398
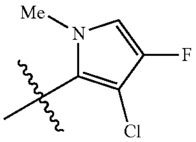 [SMILES: *c1c(Cl)c(F)cn1C] Het-399
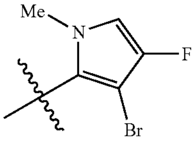 Het-400

TABLE 3-continued
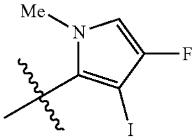 [SMILES: *c1c(I)c(F)cn1C]
Het-401
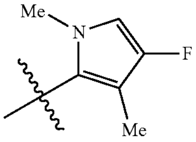
Het-402
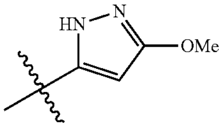 [SMILES: *c1cc(OC)n[nH]1]
Het-403
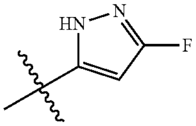 [SMILES: *c1cc(F)n[nH]1]
Het-404
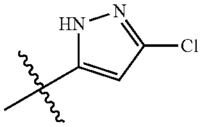 [SMILES: *c1cc(Cl)n[nH]1]
Het-405
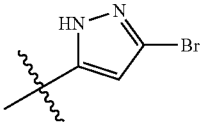 [SMILES: *c1cc(Br)n[nH]1]
Het-406
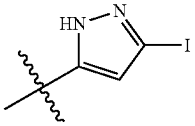 [SMILES: *c1cc(I)n[nH]1]
Het-407
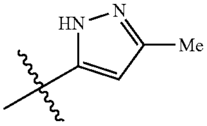 [SMILES: *c1cc(C)n[nH]1]
Het-408
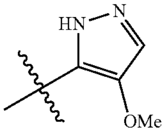 [SMILES: *c1[nH]ncc1OC]
Het-409
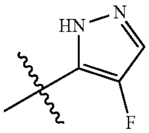 [SMILES: *c1[nH]ncc1F]
Het-410
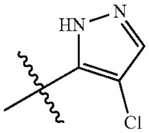 [SMILES: *c1[nH]ncc1Cl]
Het-411
TABLE 3-continued
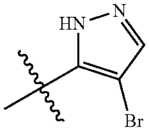 [SMILES: *c1[nH]ncc1Br]
Het-412
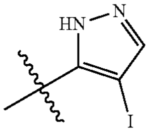 [SMILES: *c1[nH]ncc1I]
Het-413
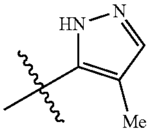 [SMILES: *c1[nH]ncc1C]
Het-414
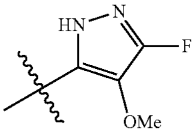
Het-415
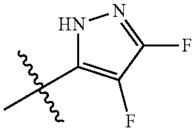
Het-416
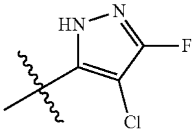
Het-417
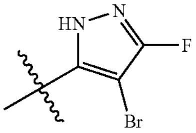 [SMILES: *c1[nH]nc(F)c1Br]
Het-418
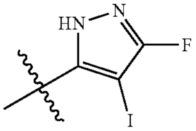 [SMILES: *c1[nH]nc(F)c1I]
Het-419
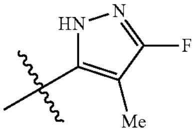 [SMILES: *c1[nH]nc(F)c1C]
Het-420
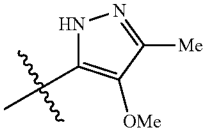
Het-421
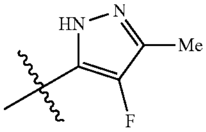
Het-422

TABLE 3-continued
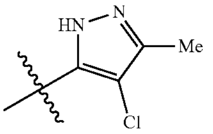 [SMILES: *c1[nH]nc(C)c1Cl]
Het-423
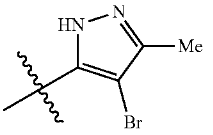 [SMILES: *c1[nH]nc(C)c1Br]
Het-424
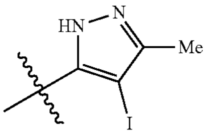 [SMILES: *c1[nH]nc(C)c1I]
Het-425
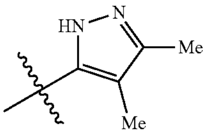
Het-426
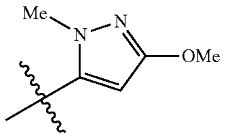 [SMILES: *c1cc(OC)nn1C]
Het-427
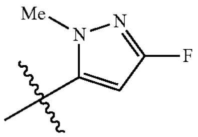 [SMILES: *c1cc(F)nn1C]
Het-428
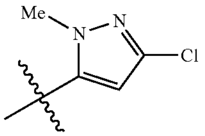 [SMILES: *c1cc(Cl)nn1C]
Het-429
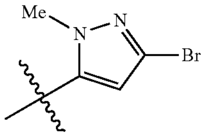 [SMILES: *c1cc(Br)nn1C]
Het-430
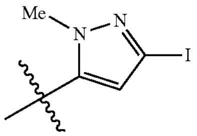 [SMILES: *c1cc(I)nn1C]
Het-431
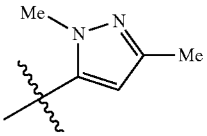 [SMILES: *c1cc(C)nn1C]
Het-432
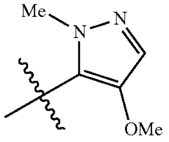 [SMILES: *c1c(OC)cnn1C]
Het-433
TABLE 3-continued
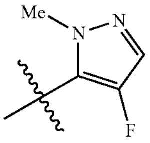 [SMILES: *c1c(F)cnn1C]
Het-434
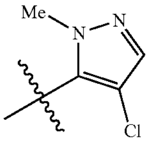 [SMILES: *c1c(Cl)cnn1C]
Het-435
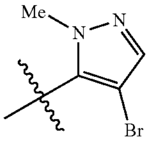 [SMILES: *c1c(Br)cnn1C]
Het-436
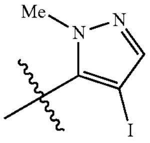 [SMILES: *c1c(I)cnn1C]
Het-437
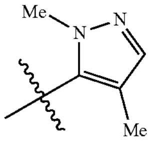 [SMILES: *c1c(C)cnn1C]
Het-438
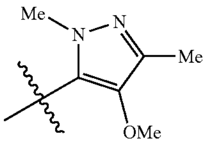 [SMILES: *c1c(OC)c(C)nn1C]
Het-439
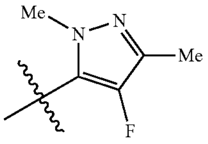
Het-440
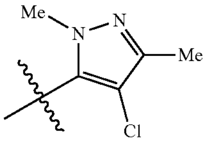 [SMILES: *c1c(Cl)c(C)nn1C]
Het-441
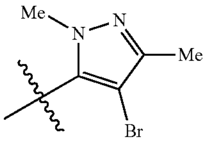 [SMILES: *c1c(Br)c(C)nn1C]
Het-442
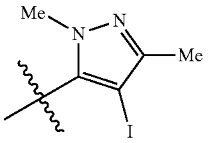 [SMILES: *c1c(I)c(C)nn1C]
Het-443

TABLE 3-continued
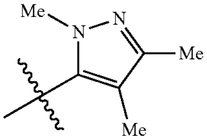 [SMILES: *c1c(C)c(C)nn1C]
Het-444
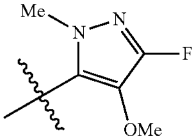 [SMILES: *c1c(OC)c(F)nn1C]
Het-445
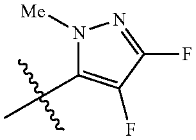
Het-446
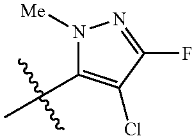 [SMILES: *c1c(Cl)c(F)nn1C]
Het-447
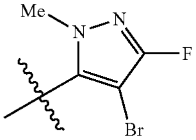
Het-448
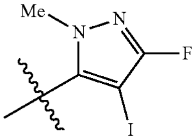 [SMILES: *c1c(I)c(F)nn1C]
Het-449
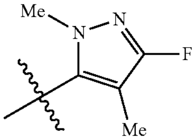
Het-450
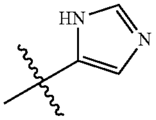 [SMILES: *c1cnc[nH]1]
Het-451
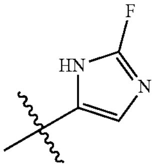 [SMILES: *c1cnc(F)[nH]1]
Het-452
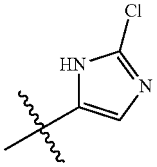 [SMILES: *c1cnc(Cl)[nH]1]
Het-453
TABLE 3-continued
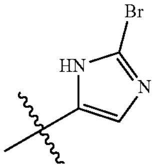 [SMILES: *c1cnc(Br)[nH]1]
Het-454
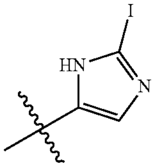
Het-455
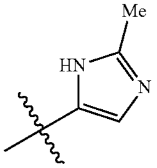 [SMILES: *c1cnc(C)[nH]1]
Het-456
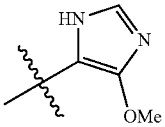 [SMILES: *c1[nH]cnc1OC]
Het-457
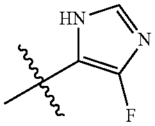
Het-458
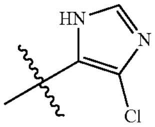 [SMILES: *c1[nH]cnc1Cl]
Het-459
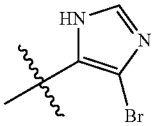 [SMILES: *c1[nH]cnc1Br]
Het-460
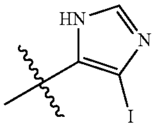 [SMILES: *c1[nH]cnc1I]
Het-461
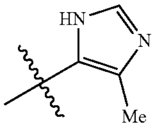 [SMILES: *c1[nH]cnc1C]
Het-462
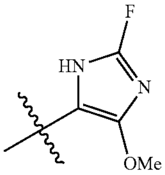 [SMILES: *c1[nH]c(F)nc1OC]
Het-463

TABLE 3-continued
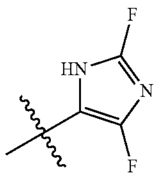 [SMILES: *c1[nH]c(F)nc1F]
Het-464
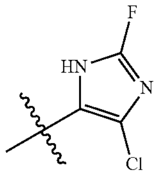 [SMILES: *c1[nH]c(F)nc1Cl]
Het-465
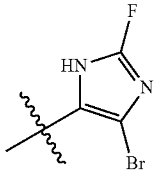 [SMILES: *c1[nH]c(F)nc1Br]
Het-466
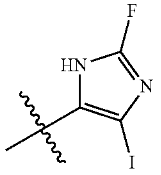 [SMILES: *c1[nH]c(F)nc1I]
Het-467
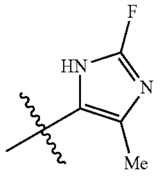 [SMILES: *c1[nH]c(F)nc1C]
Het-468
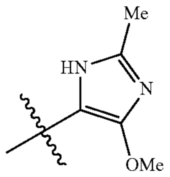 [SMILES: *c1[nH]c(C)nc1OC]
Het-469
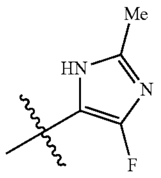 [SMILES: *c1[nH]c(C)nc1F]
Het-470
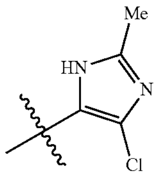 [SMILES: *c1[nH]c(C)nc1Cl]
Het-471
TABLE 3-continued
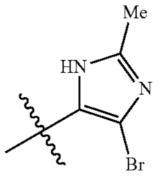 [SMILES: *c1[nH]c(C)nc1Br]
Het-472
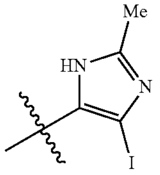 [SMILES: *c1[nH]c(C)nc1I]
Het-473
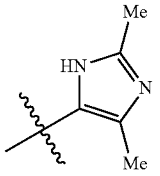 [SMILES: *c1[nH]c(C)nc1C]
Het-474
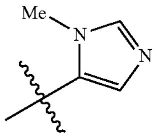 [SMILES: *c1cncn1C]
Het-475
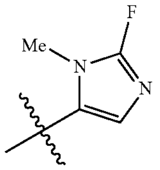
Het-476
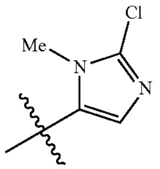 [SMILES: *c1cnc(Cl)n1C]
Het-477
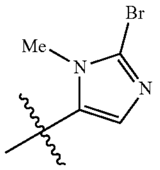 [SMILES: *c1cnc(Br)n1C]
Het-478
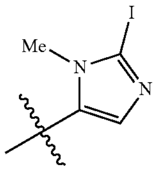 [SMILES: *c1cnc(I)n1C]
Het-479
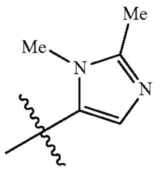 [SMILES: *c1cnc(C)n1C]
Het-480

TABLE 3-continued
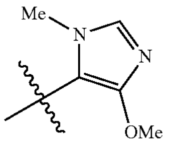 [SMILES: *c1c(OC)ncn1C]
Het-481
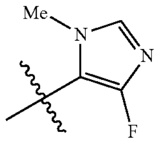 [SMILES: *c1c(F)ncn1C]
Het-482
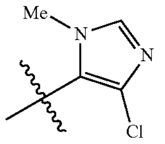 [SMILES: *c1c(Cl)ncn1C]
Het-483
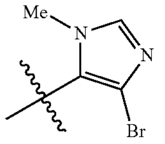 [SMILES: *c1c(Br)ncn1C]
Het-484
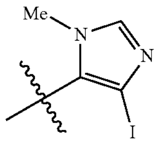 [SMILES: *c1c(I)ncn1C]
Het-485
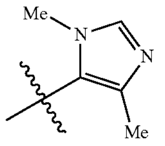 [SMILES: *c1c(C)ncn1C]
Het-486
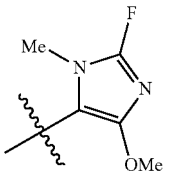 [SMILES: *c1c(OC)nc(F)n1C]
Het-487
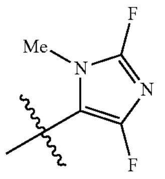 [SMILES: *c1c(F)nc(F)n1C]
Het-488
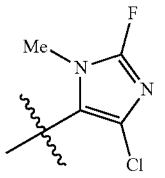 [SMILES: *c1c(Cl)nc(F)n1C]
Het-489
TABLE 3-continued
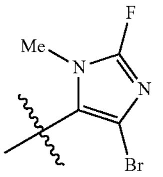 [SMILES: *c1c(Br)nc(F)n1C]
Het-490
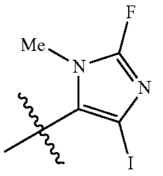 [SMILES: *c1c(I)nc(F)n1C]
Het-491
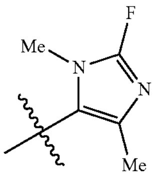 [SMILES: *c1c(C)nc(F)n1C]
Het-492
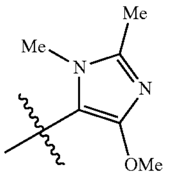 [SMILES: *c1c(OC)nc(C)n1C]
Het-493
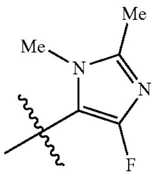
Het-494
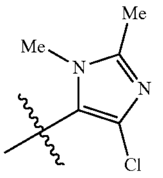 [SMILES: *c1c(Cl)nc(C)n1C]
Het-495
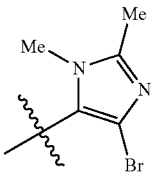 [SMILES: *c1c(Br)nc(C)n1C]
Het-496
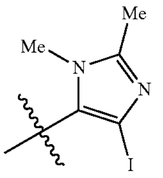 [SMILES: *c1c(I)nc(C)n1C]
Het-497

TABLE 3-continued
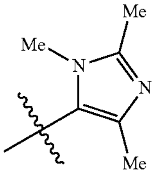 [SMILES: *c1c(C)nc(C)n1C]
Het-498
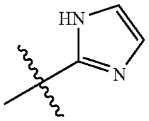 [SMILES: *c1ncc[nH]1]
Het-499
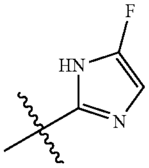 [SMILES: *c1ncc(F)[nH]1]
Het-500
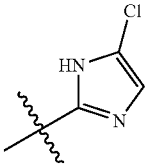 [SMILES: *c1ncc(Cl)[nH]1]
Het-501
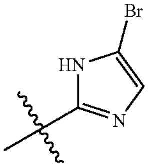 [SMILES: *c1ncc(Br)[nH]1]
Het-502
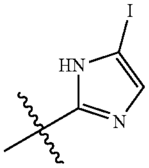 [SMILES: *c1ncc(I)[nH]1]
Het-503
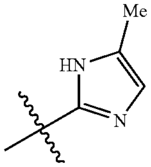 [SMILES: *c1ncc(C)[nH]1]
Het-504
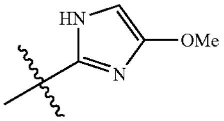 [SMILES: *c1nc(OC)c[nH]1]
Het-505
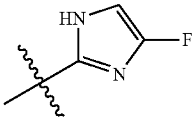 [SMILES: *c1nc(F)c[nH]1]
Het-506
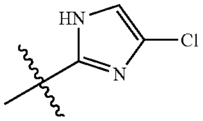 [SMILES: *c1nc(Cl)c[nH]1]
Het-507
TABLE 3-continued
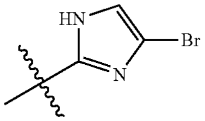 [SMILES: *c1nc(Br)c[nH]1]
Het-508
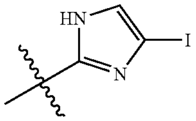 [SMILES: *c1nc(I)c[nH]1]
Het-509
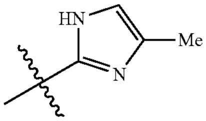 [SMILES: *c1nc(C)c[nH]1]
Het-510
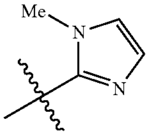 [SMILES: *c1nccn1C]
Het-511
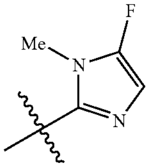 [SMILES: *c1ncc(F)n1C]
Het-512
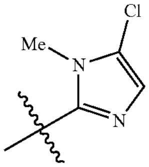 [SMILES: *c1ncc(Cl)n1C]
Het-513
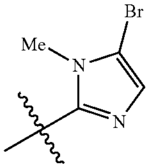 [SMILES: *c1ncc(Br)n1C]
Het-514
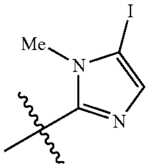 [SMILES: *c1ncc(I)n1C]
Het-515
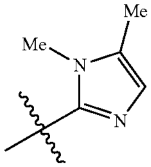 [SMILES: *c1ncc(C)n1C]
Het-516
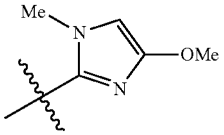 [SMILES: *c1nc(OC)cn1C]
Het-517

TABLE 3-continued
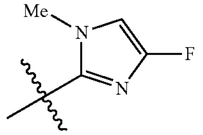 [SMILES: *c1nc(F)cn1C]
Het-518
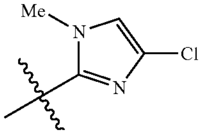 [SMILES: *c1nc(Cl)cn1C]
Het-519
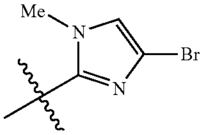 [SMILES: *c1nc(Br)cn1C]
Het-520
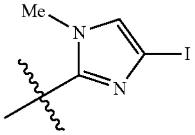 [SMILES: *c1nc(I)cn1C]
Het-521
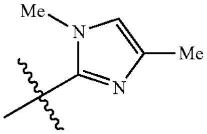 [SMILES: *c1nc(C)cn1C]
Het-522
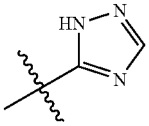 [SMILES: *c1ncn[nH]1]
Het-523
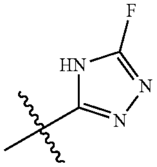 [SMILES: *c1nnc(F)[nH]1]
Het-524
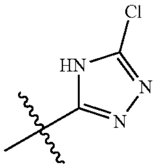 [SMILES: *c1nnc(Cl)[nH]1]
Het-525
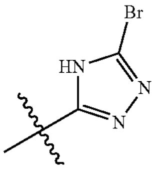 [SMILES: *c1nnc(Br)[nH]1]
Het-526
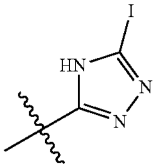 [SMILES: *c1nnc(I)[nH]1]
Het-527
TABLE 3-continued
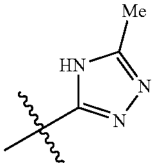 [SMILES: *c1nnc(C)[nH]1]
Het-528
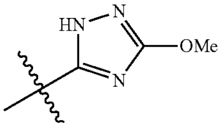 [SMILES: *c1nc(OC)n[nH]1]
Het-529
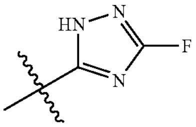
Het-530
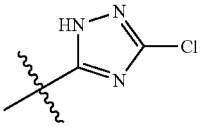 [SMILES: *c1nc(Cl)n[nH]1]
Het-531
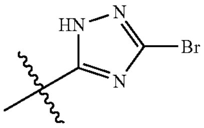 [SMILES: *c1nc(Br)n[nH]1]
Het-532
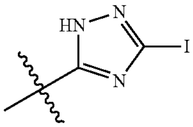 [SMILES: *c1nc(I)n[nH]1]
Het-533
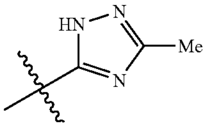
Het-534
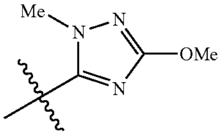 [SMILES: *c1nc(OC)nn1C]
Het-535
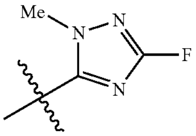 [SMILES: *c1nc(F)nn1C]
Het-536
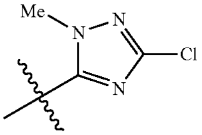 [SMILES: *c1nc(Cl)nn1C]
Het-537

TABLE 3-continued
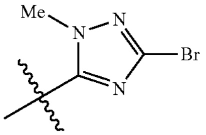 [SMILES: *c1nc(Br)nn1C]
Het-538
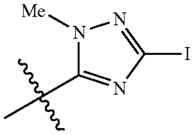 [SMILES: *c1nc(I)nn1C]
Het-539
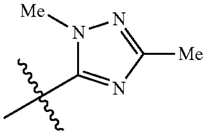 [SMILES: *c1nc(C)nn1C]
Het-540
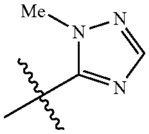 [SMILES: *c1ncnn1C]
Het-541
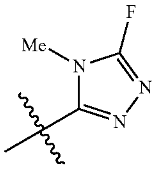 [SMILES: *c1nnc(F)n1C]
Het-542
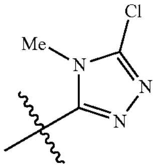
Het-543
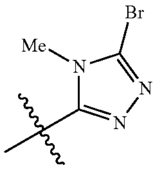 [SMILES: *c1nnc(Br)n1C]
Het-544
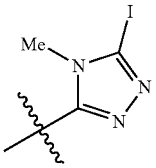 [SMILES: *c1nnc(I)n1C]
Het-545
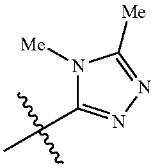 [SMILES: *c1nnc(C)n1C]
Het-546
TABLE 3-continued
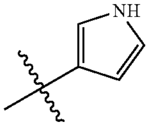 [SMILES: *c1cc[nH]c1]
Het-547
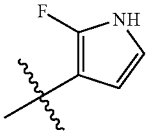
Het-548
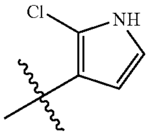 [SMILES: *c1cc[nH]c1Cl]
Het-549
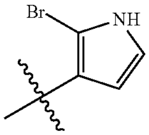 [SMILES: *c1cc[nH]c1Br]
Het-550
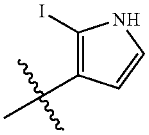 [SMILES: *c1cc[nH]c1I]
Het-551
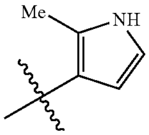 [SMILES: *c1cc[nH]c1C]
Het-552
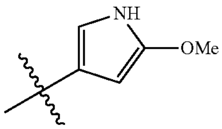 [SMILES: *c1c[nH]c(OC)c1]
Het-553
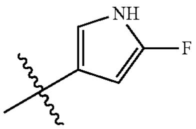 [SMILES: *c1c[nH]c(F)c1]
Het-554
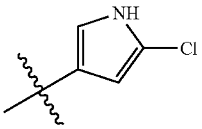 [SMILES: *c1c[nH]c(Cl)c1]
Het-555
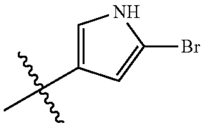 [SMILES: *c1c[nH]c(Br)c1]
Het-556
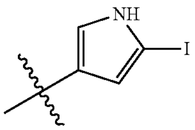 [SMILES: *c1c[nH]c(I)c1]
Het-557

TABLE 3-continued
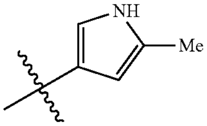 [SMILES: *c1c[nH]c(C)c1]
Het-558
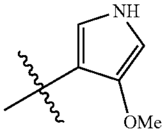 [SMILES: *c1c[nH]cc1OC]
Het-559
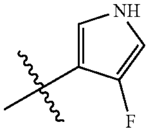 [SMILES: *c1c[nH]cc1F]
Het-560
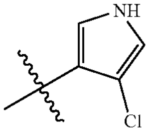 [SMILES: *c1c[nH]cc1Cl]
Het-561
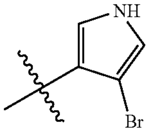 [SMILES: *c1c[nH]cc1Br]
Het-562
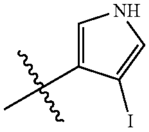
Het-563
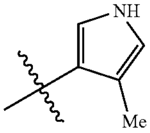 [SMILES: *c1c[nH]cc1C]
Het-564
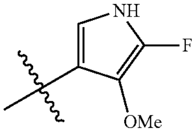 [SMILES: *c1c[nH]c(F)c1OC]
Het-565
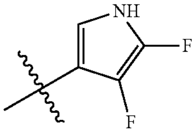
Het-566
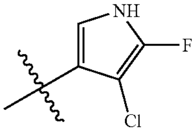 [SMILES: *c1c[nH]c(F)c1Cl]
Het-567
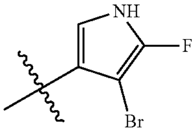
Het-568
TABLE 3-continued
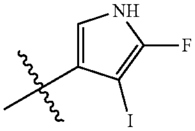 [SMILES: *c1c[nH]c(F)c1I]
Het-569
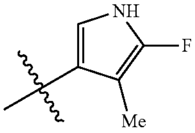
Het-570
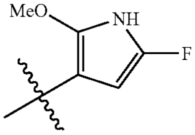 [SMILES: *c1cc(F)[nH]c1OC]
Het-571
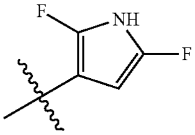
Het-572
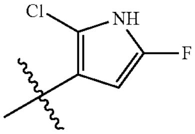 [SMILES: *c1cc(F)[nH]c1Cl]
Het-573
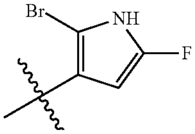 [SMILES: *c1cc(F)[nH]c1Br]
Het-574
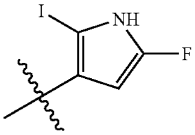 [SMILES: *c1cc(F)[nH]c1I]
Het-575
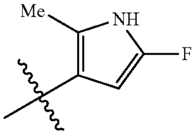 [SMILES: *c1cc(F)[nH]c1C]
Het-576
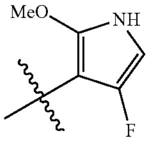 [SMILES: *c1c(F)c[nH]c1OC]
Het-577
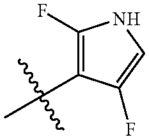
Het-578
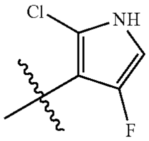
Het-579

TABLE 3-continued
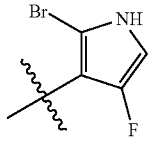
Het-580
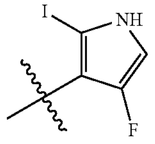 [SMILES: *c1c(F)c[nH]c1I]
Het-581
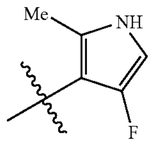 [SMILES: *c1c(F)c[nH]c1C]
Het-582
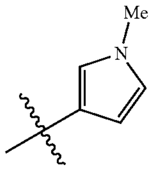 [SMILES: *c1ccn(C)c1]
Het-583
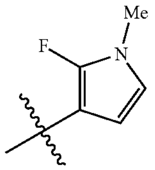
Het-584
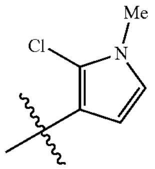 [SMILES: *c1ccn(C)c1Cl]
Het-585
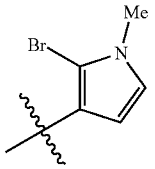 [SMILES: *c1ccn(C)c1Br]
Het-586
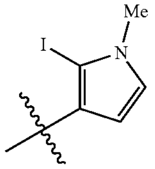 [SMILES: *c1ccn(C)c1I]
Het-587
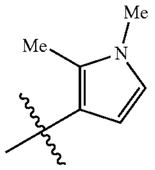 [SMILES: *c1ccn(C)c1C]
Het-588
TABLE 3-continued
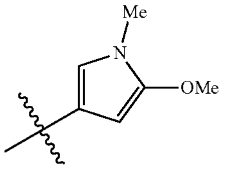 [SMILES: *c1cc(OC)n(C)c1]
Het-589
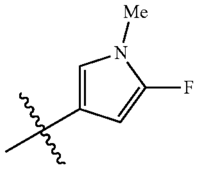 [SMILES: *c1cc(F)n(C)c1]
Het-590
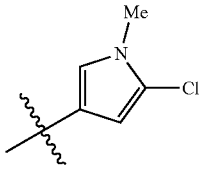 [SMILES: *c1cc(Cl)n(C)c1]
Het-591
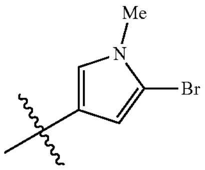 [SMILES: *c1cc(Br)n(C)c1]
Het-592
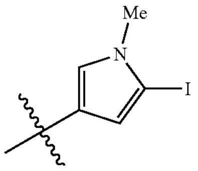 [SMILES: *c1cc(I)n(C)c1]
Het-593
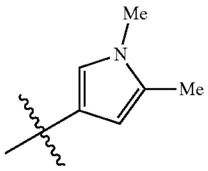 [SMILES: *c1cc(C)n(C)c1]
Het-594
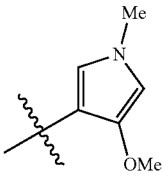 [SMILES: *c1cn(C)cc1OC]
Het-595
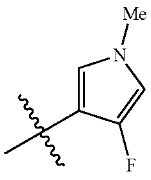
Het-596

TABLE 3-continued
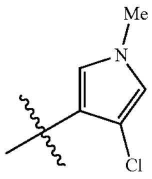 [SMILES: *c1cn(C)cc1Cl]
Het-597
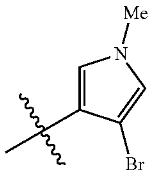 [SMILES: *c1cn(C)cc1Br]
Het-598
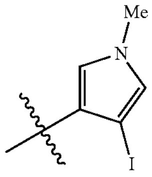 [SMILES: *c1cn(C)cc1I]
Het-599
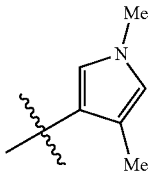 [SMILES: *c1cn(C)cc1C]
Het-600
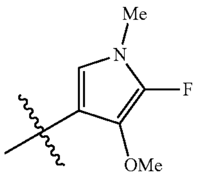 [SMILES: *c1cn(C)c(F)c1OC]
Het-601
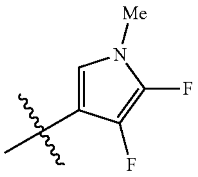
Het-602
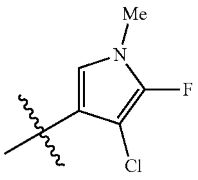 [SMILES: *c1cn(C)c(F)c1Cl]
Het-603
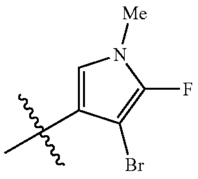 [SMILES: *c1cn(C)c(F)c1Br]
Het-604
TABLE 3-continued
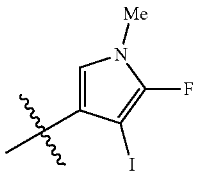 [SMILES: *c1cn(C)c(F)c1I]
Het-605
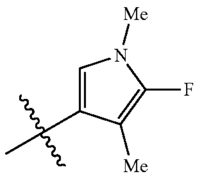 [SMILES: *c1cn(C)c(F)c1C]
Het-606
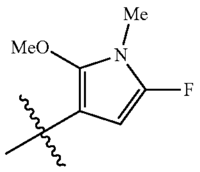 [SMILES: *c1cc(F)n(C)c1OC]
Het-607
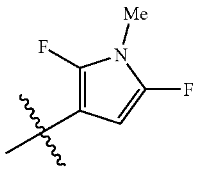
Het-608
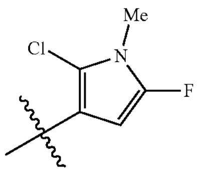 [SMILES: *c1cc(F)n(C)c1Cl]
Het-609
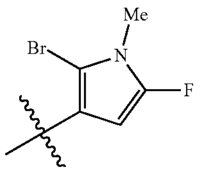
Het-610
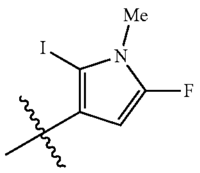 [SMILES: *c1cc(F)n(C)c1I]
Het-611
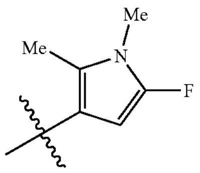 [SMILES: *c1cc(F)n(C)c1C]
Het-612

TABLE 3-continued
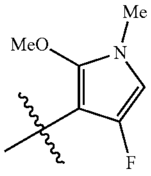 [SMILES: *c1c(F)cn(C)c1OC]
Het-613
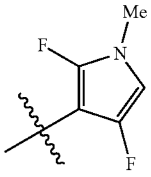
Het-614
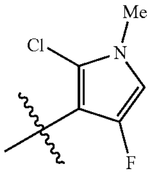 [SMILES: *c1c(F)cn(C)c1Cl]
Het-615
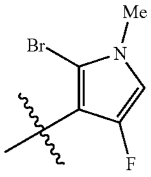 [SMILES: *c1c(F)cn(C)c1Br]
Het-616
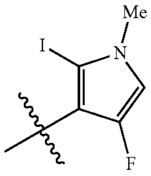 [SMILES: *c1c(F)cn(C)c1I]
Het-617
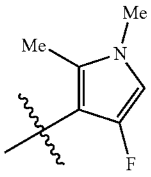 [SMILES: *c1c(F)cn(C)c1C]
Het-618
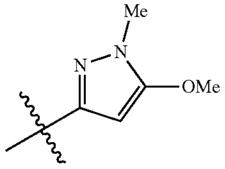 [SMILES: *c1cc(OC)n(C)n1]
Het-619
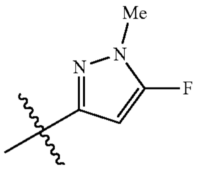 [SMILES: *c1cc(F)n(C)n1]
Het-620
TABLE 3-continued
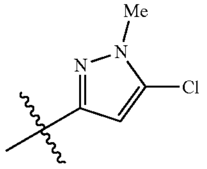 [SMILES: *c1cc(Cl)n(C)n1]
Het-621
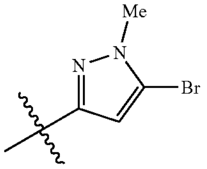 [SMILES: *c1cc(Br)n(C)n1]
Het-622
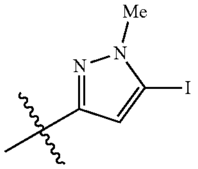 [SMILES: *c1cc(I)n(C)n1]
Het-623
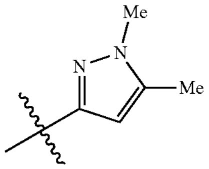 [SMILES: *c1cc(C)n(C)n1]
Het-624
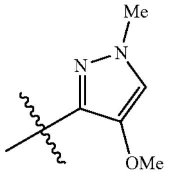 [SMILES: *c1nn(C)cc1OC]
Het-625
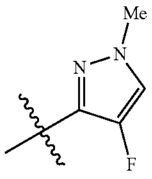
Het-626
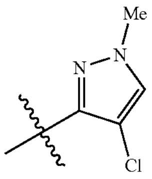 [SMILES: *c1nn(C)cc1Cl]
Het-627
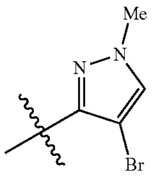 [SMILES: *c1nn(C)cc1Br]
Het-628
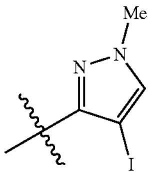 [SMILES: *c1nn(C)cc1I]
Het-629

TABLE 3-continued
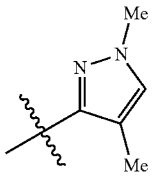 [SMILES: *c1nn(C)cc1C]
Het-630
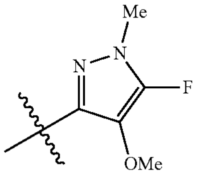 [SMILES: *c1nn(C)c(F)c1OC]
Het-631
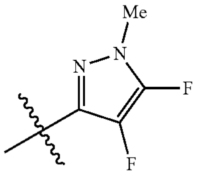
Het-632
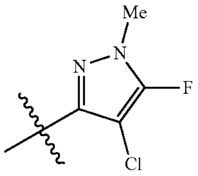 [SMILES: *c1nn(C)c(F)c1Cl]
Het-633
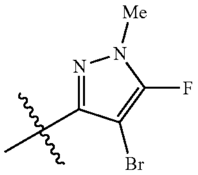
Het-634
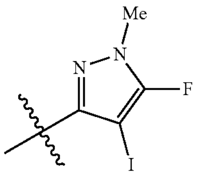 [SMILES: *c1nn(C)c(F)c1I]
Het-635
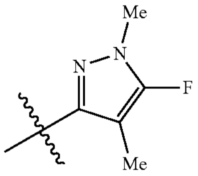 [SMILES: *c1nn(C)c(F)c1C]
Het-636
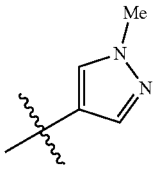 [SMILES: *c1cnn(C)c1]
Het-637
TABLE 3-continued
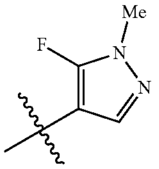
Het-638
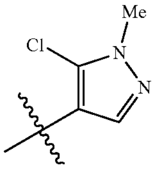 [SMILES: *c1cnn(C)c1Cl]
Het-639
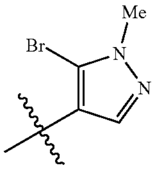 [SMILES: *c1cnn(C)c1Br]
Het-640
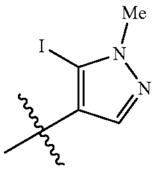 [SMILES: *c1cnn(C)c1I]
Het-641
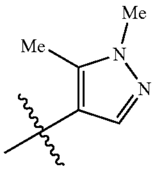 [SMILES: *c1cnn(C)c1C]
Het-642
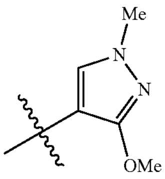 [SMILES: *c1cn(C)nc1OC]
Het-643
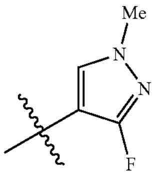
Het-644
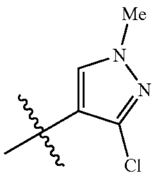 [SMILES: *c1cn(C)nc1Cl]
Het-645

TABLE 3-continued
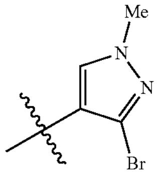 [SMILES: *c1cn(C)nc1Br]
Het-646
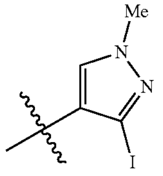 [SMILES: *c1cn(C)nc1I]
Het-647
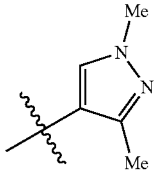 [SMILES: *c1cn(C)nc1C]
Het-648
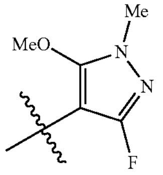 [SMILES: *c1c(F)nn(C)c1OC]
Het-649
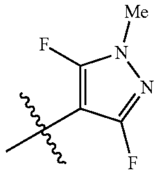 [SMILES: *c1c(F)nn(C)c1F]
Het-650
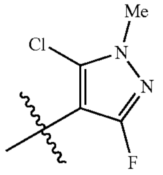 [SMILES: *c1c(F)nn(C)c1Cl]
Het-651
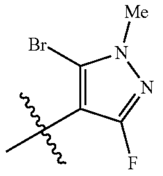 [SMILES: *c1c(F)nn(C)c1Br]
Het-652
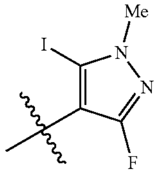
Het-653
TABLE 3-continued
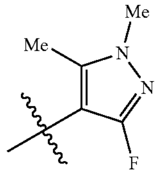
Het-654
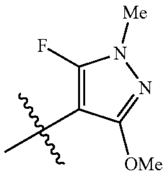
Het-655
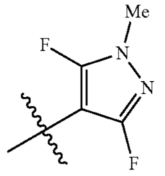
Het-656
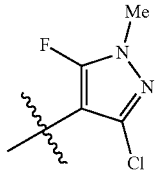
Het-657
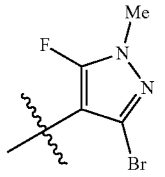 [SMILES: *c1c(Br)nn(C)c1F]
Het-658
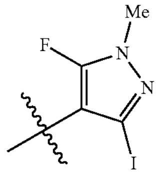 [SMILES: *c1c(I)nn(C)c1F]
Het-659
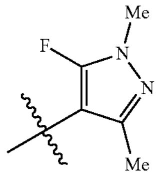
Het-660
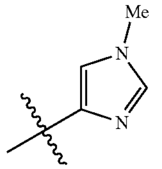 [SMILES: *c1cn(C)cn1]
Het-661

TABLE 3-continued
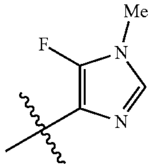
Het-662
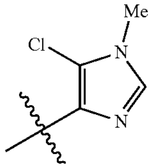 [SMILES: *c1ncn(C)c1Cl]
Het-683
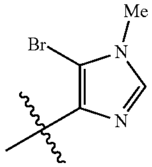 [SMILES: *c1ncn(C)c1Br]
Het-664
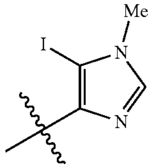 [SMILES: *c1ncn(C)c1I]
Het-665
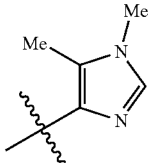 [SMILES: *c1ncn(C)c1C]
Het-666
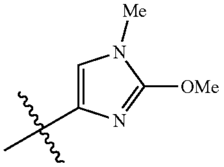 [SMILES: *c1cn(C)c(OC)n1]
Het-667
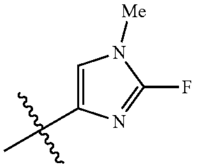 [SMILES: *c1cn(C)c(F)n1]
Het-688
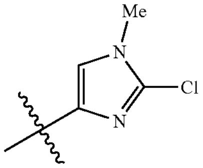 [SMILES: *c1cn(C)c(Cl)n1]
Het-669
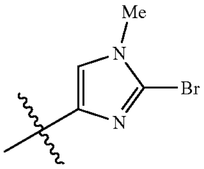 [SMILES: *c1cn(C)c(Br)n1]
Het-670
TABLE 3-continued
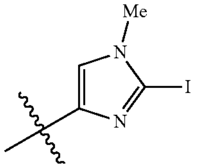 [SMILES: *c1cn(C)c(I)n1]
Het-671
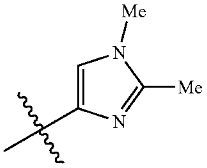 [SMILES: *c1cn(C)c(C)n1]
Het-672
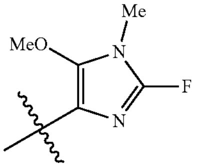 [SMILES: *c1nc(F)n(C)c1OC]
Het-673
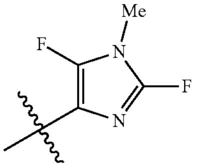
Het-674
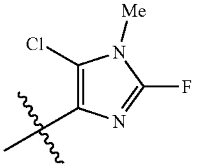 [SMILES: *c1nc(F)n(C)c1Cl]
Het-675
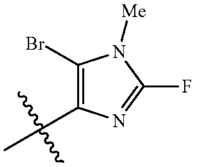 [SMILES: *c1nc(F)n(C)c1Br]
Het-676
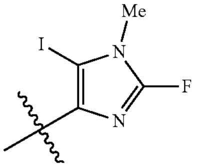 [SMILES: *c1nc(F)n(C)c1I]
Het-677
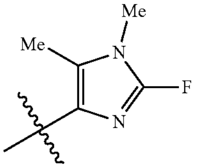 [SMILES: *c1nc(F)n(C)c1C]
Het-678

TABLE 3-continued
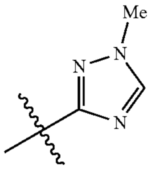 [SMILES: *c1ncn(C)n1]
Het-679
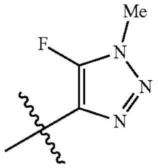 [SMILES: *c1nnn(C)c1F]
Het-680
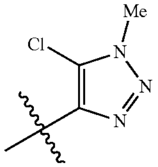 [SMILES: *c1nnn(C)c1Cl]
Het-681
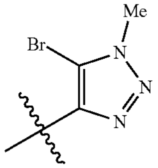
Het-682
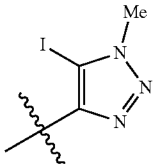 [SMILES: *c1nnn(C)c1I]
Het-683
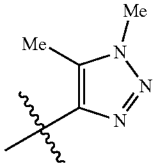 [SMILES: *c1nnn(C)c1C]
Het-684
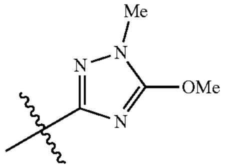 [SMILES: *c1nc(OC)n(C)n1]
Het-685
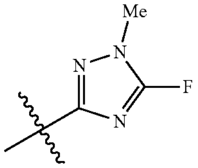 [SMILES: *c1nc(F)n(C)n1]
Het-686
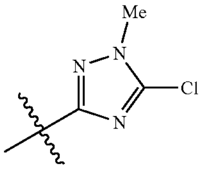 [SMILES: *c1nc(Cl)n(C)n1]
Het-687
TABLE 3-continued
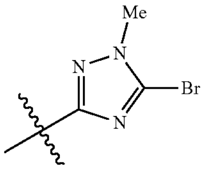 [SMILES: *c1nc(Br)n(C)n1]
Het-688
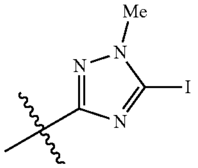 [SMILES: *c1nc(I)n(C)n1]
Het-689
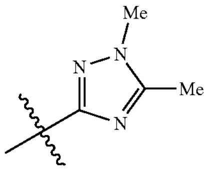 [SMILES: *c1nc(C)n(C)n1]
Het-690
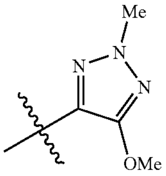 [SMILES: *c1nn(C)nc1OC]
Het-691
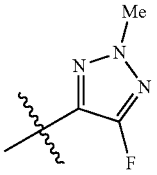
Het-692
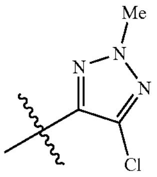 [SMILES: *c1nn(C)nc1Cl]
Het-693
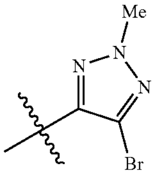
Het-694
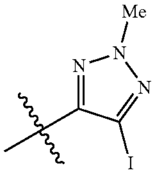 [SMILES: *c1nn(C)nc1I]
Het-695

TABLE 3-continued
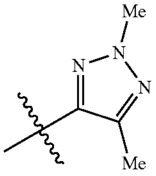 [SMILES: *c1nn(C)nc1C]
Het-696
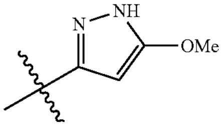 [SMILES: *c1cc(OC)[nH]n1]
Het-697
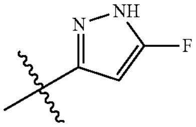 [SMILES: *c1cc(F)[nH]n1]
Het-698
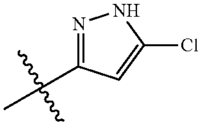 [SMILES: *c1cc(Cl)[nH]n1]
Het-699
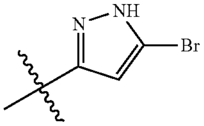 [SMILES: *c1cc(Br)[nH]n1]
Het-700
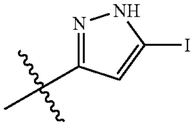 [SMILES: *c1cc(I)[nH]n1]
Het-701
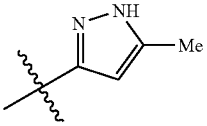 [SMILES: *c1cc(C)[nH]n1]
Het-702
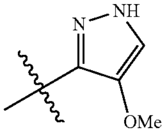 [SMILES: *c1n[nH]cc1OC]
Het-703
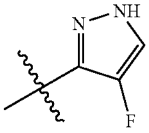
Het-704
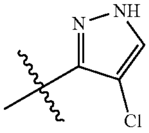 [SMILES: *c1n[nH]cc1Cl]
Het-705
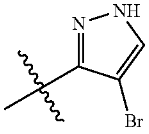
Het-706
TABLE 3-continued
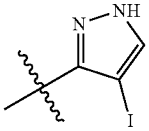 [SMILES: *c1n[nH]cc1I]
Het-707
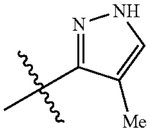 [SMILES: *c1n[nH]cc1C]
Het-708
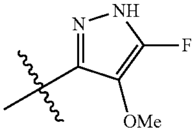 [SMILES: *c1n[nH]c(F)c1OC]
Het-709
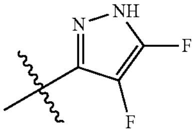
Het-710
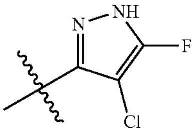 [SMILES: *c1n[nH]c(F)c1Cl]
Het-711
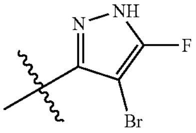
Het-712
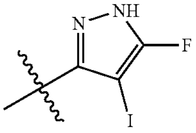 [SMILES: *c1n[nH]c(F)c1I]
Het-713
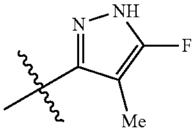
Het-714
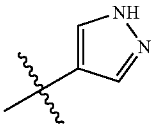 [SMILES: *c1cn[nH]c1]
Het-715
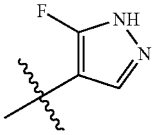 [SMILES: *c1cn[nH]c1F]
Het-716
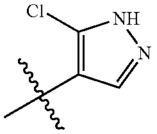 [SMILES: *c1cn[nH]c1Cl]
Het-717

TABLE 3-continued
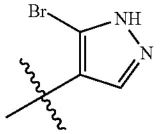
Het-718
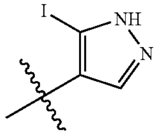 [SMILES: *c1cn[nH]c1I]
Het-719
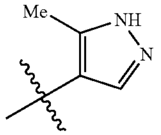 [SMILES: *c1cn[nH]c1C]
Het-720
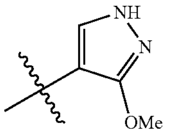 [SMILES: *c1c[nH]nc1OC]
Het-721
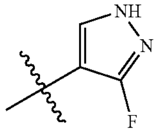 [SMILES: *c1c[nH]nc1F]
Het-722
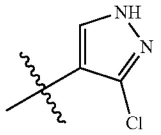
Het-723
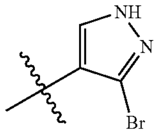 [SMILES: *c1c[nH]nc1Cl]
Het-724
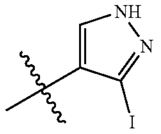 [SMILES: *c1c[nH]nc1I]
Het-725
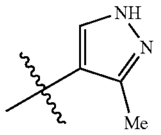 [SMILES: *c1c[nH]nc1C]
Het-726
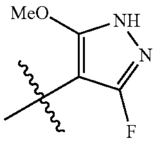 [SMILES: *c1c(F)n[nH]c1OC]
Het-727
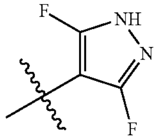 [SMILES: *c1c(F)n[nH]c1F]
Het-728
TABLE 3-continued
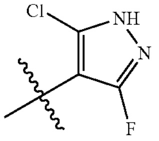 [SMILES: *c1c(F)n[nH]c1Cl]
Het-729
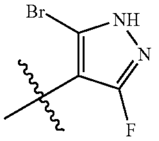 [SMILES: *c1c(F)n[nH]c1Br]
Het-730
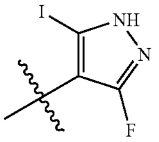 [SMILES: *c1c(F)n[nH]c1I]
Het-731
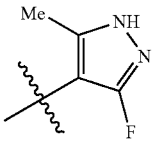 [SMILES: *c1c(F)n[nH]c1C]
Het-732
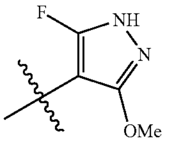 [SMILES: *c1c(OC)n[nH]c1F]
Het-733
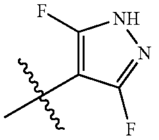
Het-734
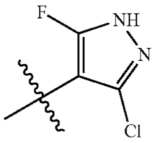 [SMILES: *c1c(Cl)n[nH]c1F]
Het-735
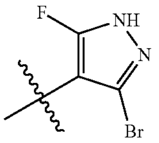 [SMILES: *c1c(Br)n[nH]c1F]
Het-736
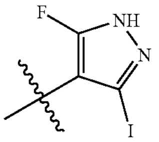 [SMILES: *c1c(I)n[nH]c1F]
Het-737
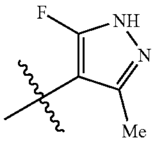 [SMILES: *c1c(C)n[nH]c1F]
Het-738

TABLE 3-continued
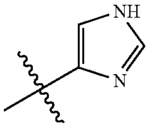 [SMILES: *c1c[nH]cn1]
Het-739
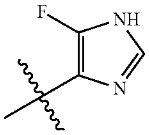 [SMILES: *c1nc[nH]c1F]
Het-740
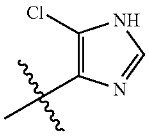 [SMILES: *c1nc[nH]c1Cl]
Het-741
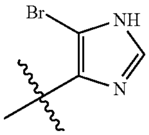 [SMILES: *c1nc[nH]c1Br]
Het-742
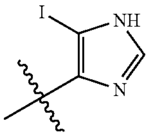 [SMILES: *c1nc[nH]c1I]
Het-743
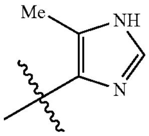 [SMILES: *c1nc[nH]c1C]
Het-744
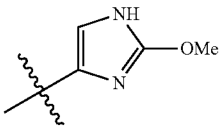 [SMILES: *c1c[nH]c(OC)n1]
Het-745
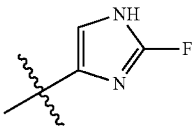 [SMILES: *c1c[nH]c(F)n1]
Het-746
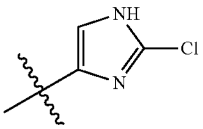 [SMILES: *c1c[nH]c(Cl)n1]
Het-747
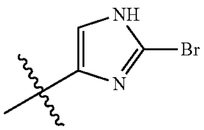 [SMILES: *c1c[nH]c(Br)n1]
Het-748
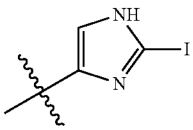 [SMILES: *c1c[nH]c(I)n1]
Het-749
TABLE 3-continued
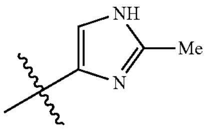 [SMILES: *c1c[nH]c(C)n1]
Het-750
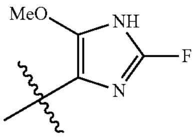 [SMILES: *c1nc(F)[nH]c1OC]
Het-751
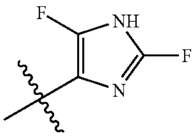
Het-752
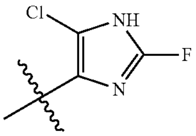 [SMILES: *c1nc(F)[nH]c1Cl]
Het-753
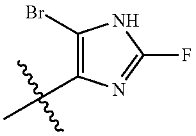 [SMILES: *c1nc(F)[nH]c1Br]
Het-754
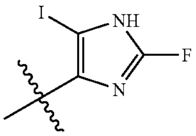 [SMILES: *c1nc(F)[nH]c1I]
Het-755
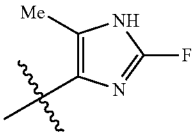 [SMILES: *c1nc(F)[nH]c1C]
Het-756
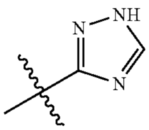 [SMILES: *c1nc[nH]n1]
Het-757
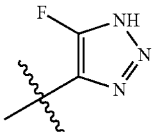
Het-758
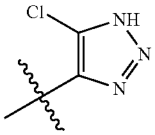
Het-759
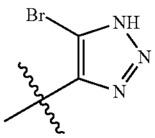 [SMILES: *c1nn[nH]c1Br]
Het-760

TABLE 3-continued
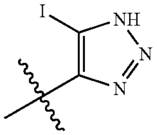 [SMILES: *c1nn[nH]c1I]
Het-761
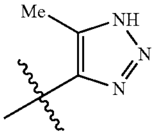 [SMILES: *c1nn[nH]c1C]
Het-762
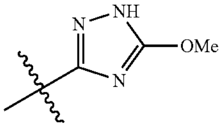 [SMILES: *c1n[nH]c(OC)n1]
Het-763
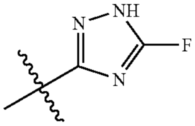 [SMILES: *c1n[nH]c(F)n1]
Het-764
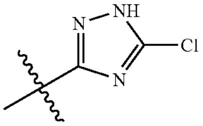 [SMILES: *c1n[nH]c(Cl)n1]
Het-765
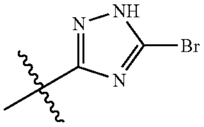 [SMILES: *c1n[nH]c(Br)n1]
Het-766
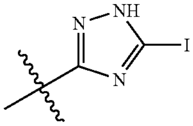 [SMILES: *c1n[nH]c(I)n1]
Het-767
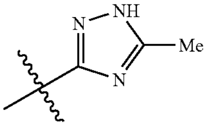 [SMILES: *c1n[nH]c(C)n1]
Het-768
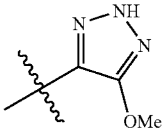 [SMILES: *c1n[nH]nc1OC]
Het-769
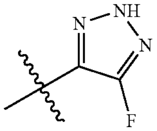 [SMILES: *c1n[nH]nc1F]
Het-770
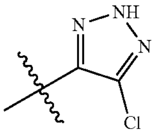 [SMILES: *c1n[nH]nc1Cl]
Het-771
TABLE 3-continued
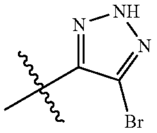 [SMILES: *c1n[nH]nc1Br]
Het-772
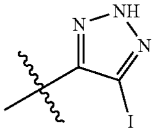 [SMILES: *c1n[nH]nc1I]
Het-773
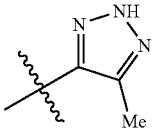 [SMILES: *c1n[nH]nc1C]
Het-774
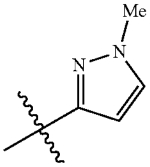 [SMILES: *c1ccn(C)n1]
Het-775
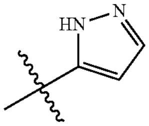 [SMILES: *c1ccn[nH]1]
Het-776
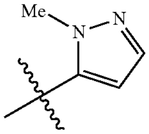 [SMILES: *c1ccnn1C]
Het-777
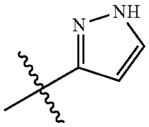 [SMILES: *c1cc[nH]n1]
Het-778
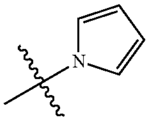 [SMILES: *n1cccc1]
Het-779
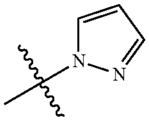 [SMILES: *n1cccn1]
Het-780
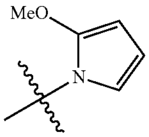 [SMILES: *n1cccc1OC]
Het-781
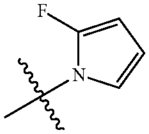
Het-782

TABLE 3-continued
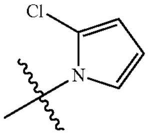
Het-783
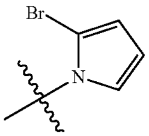 [SMILES: *n1cccc1Br]
Het-784
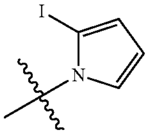 [SMILES: *n1cccc1I]
Het-785
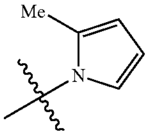 [SMILES: *n1cccc1C]
Het-786
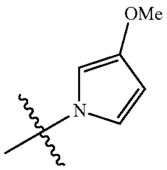 [SMILES: *n1ccc(OC)c1]
Het-787
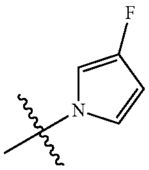 [SMILES: *n1ccc(F)c1]
Het-788
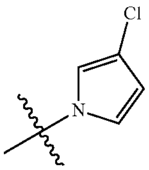
Het-789
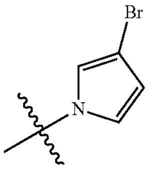 [SMILES: *n1ccc(Br)c1]
Het-790
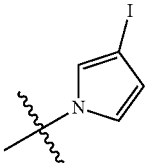 [SMILES: *n1ccc(I)c1]
Het-791
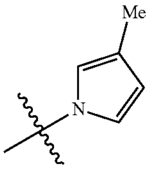 [SMILES: *n1ccc(C)c1]
Het-792
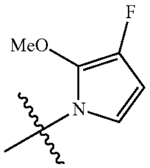 [SMILES: *n1ccc(F)c1OC]
Het-793
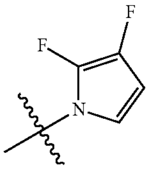
Het-794
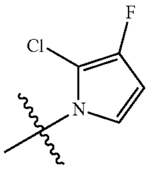 [SMILES: *n1ccc(F)c1Cl]
Het-795
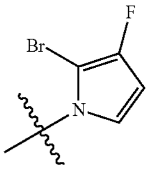 [SMILES: *n1ccc(F)c1Br]
Het-796
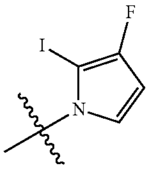 [SMILES: *n1ccc(F)c1I]
Het-797
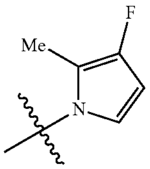 [SMILES: *n1ccc(F)c1C]
Het-798
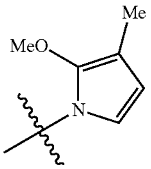 [SMILES: *n1ccc(C)c1OC]
Het-799
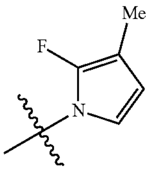
Het-800

TABLE 3-continued
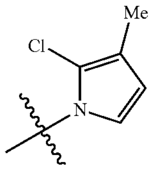 [SMILES: *n1ccc(C)c1Cl]
Het-801
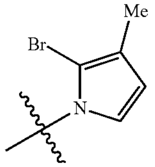 [SMILES: *n1ccc(C)c1Br]
Het-802
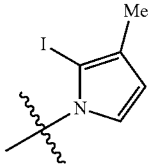 [SMILES: *n1ccc(C)c1I]
Het-803
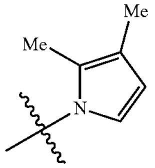 [SMILES: *n1ccc(C)c1C]
Het-804
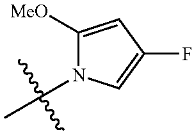 [SMILES: *n1cc(F)cc1OC]
Het-805
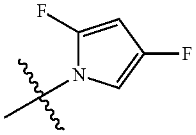
Het-806
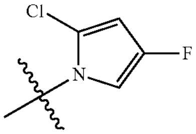
Het-807
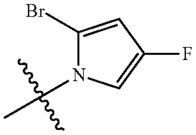 [SMILES: *n1cc(F)cc1Br]
Het-808
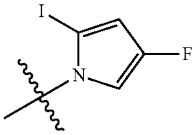 [SMILES: *n1cc(F)cc1I]
Het-809
TABLE 3-continued
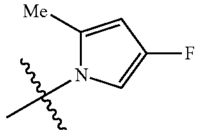 [SMILES: *n1cc(F)cc1C]
Het-810
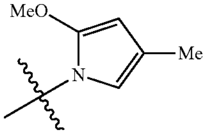 [SMILES: *n1cc(C)cc1OC]
Het-811
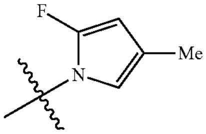
Het-812
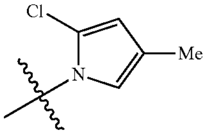
Het-813
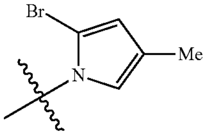 [SMILES: *n1cc(C)cc1Cl]
Het-814
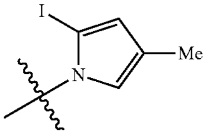 [SMILES: *n1cc(C)cc1I]
Het-815
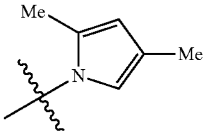 [SMILES: *n1cc(C)cc1C]
Het-816
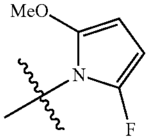 [SMILES: *n1c(F)ccc1OC]
Het-817
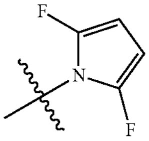
Het-818
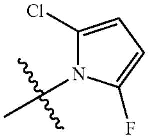
Het-819

TABLE 3-continued
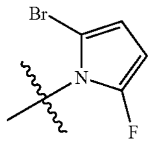 [SMILES: *n1c(F)ccc1Br]
Het-820
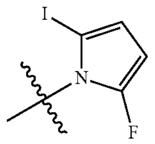 [SMILES: *n1c(F)ccc1I]
Het-821
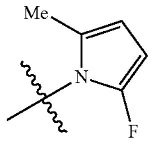 [SMILES: *n1c(C)ccc1F]
Het-822
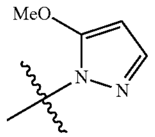 [SMILES: *n1nccc1OC]
Het-823
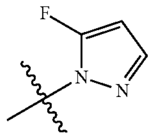 [SMILES: *n1nccc1F]
Het-824
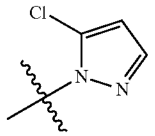
Het-825
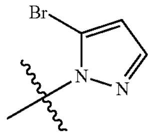 [SMILES: *n1nccc1Br]
Het-826
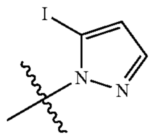 [SMILES: *n1nccc1I]
Het-827
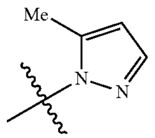 [SMILES: *n1nccc1C]
Het-828
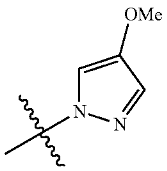 [SMILES: *n1cc(OC)cn1]
Het-829
TABLE 3-continued
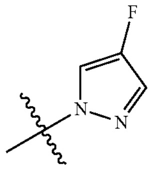 [SMILES: *n1cc(F)cn1]
Het-830
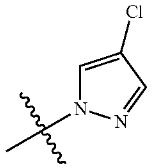 [SMILES: *n1cc(Cl)cn1]
Het-831
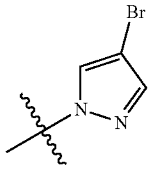 [SMILES: *n1cc(Br)cn1]
Het-832
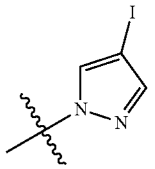 [SMILES: *n1cc(I)cn1]
Het-833
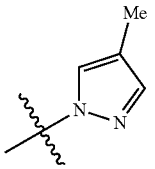 [SMILES: *n1cc(C)cn1]
Het-834
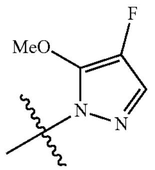 [SMILES: *n1ncc(F)c1OC]
Het-835
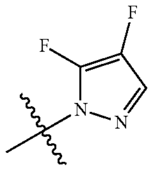
Het-836
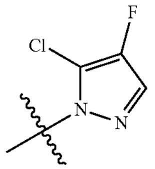 [SMILES: *n1ncc(F)c1Cl]
Het-837
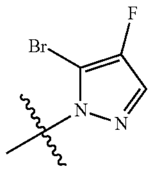 [SMILES: *n1ncc(F)c1Br]
Het-838

TABLE 3-continued
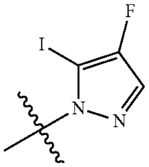 [SMILES: *n1ncc(F)c1I]
Het-839
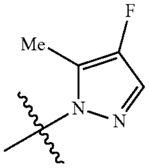 [SMILES: *n1ncc(F)c1C]
Het-840
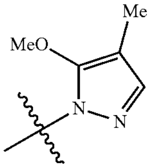 [SMILES: *n1ncc(C)c1OC]
Het-841
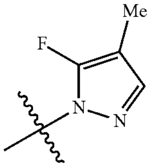
Het-842
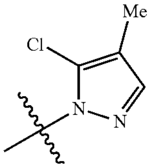 [SMILES: *n1ncc(C)c1Cl]
Het-843
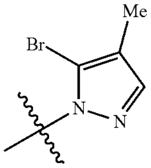 [SMILES: *n1ncc(C)c1Br]
Het-844
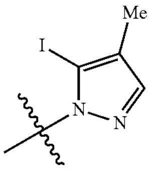 [SMILES: *n1ncc(C)c1I]
Het-845
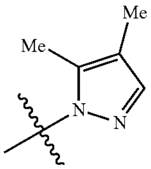 [SMILES: *n1ncc(C)c1C]
Het-846
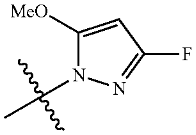 [SMILES: *n1nc(F)cc1OC]
Het-847
TABLE 3-continued
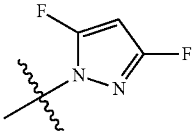
Het-848
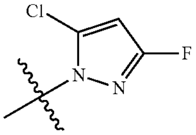 [SMILES: *n1nc(F)cc1Cl]
Het-849
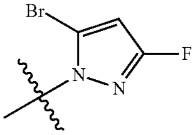 [SMILES: *n1nc(F)cc1Br]
Het-850
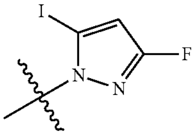 [SMILES: *n1nc(F)cc1I]
Het-851
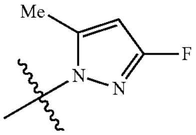 [SMILES: *n1nc(F)cc1C]
Het-852
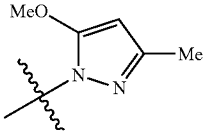 [SMILES: *n1nc(C)cc1OC]
Het-853
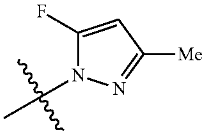
Het-854
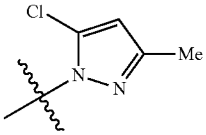 [SMILES: *n1nc(C)cc1Cl]
Het-855
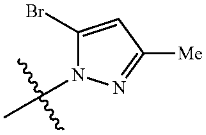 [SMILES: *n1nc(C)cc1Br]
Het-856
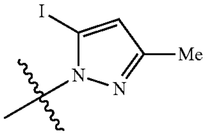 [SMILES: *n1nc(C)cc1I]
Het-857
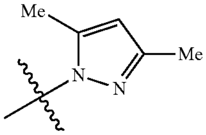 [SMILES: *n1nc(C)cc1C]
Het-858

TABLE 3-continued
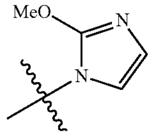 [SMILES: *n1ccnc1OC]
Het-859
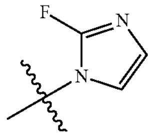 [SMILES: *n1ccnc1F]
Het-860
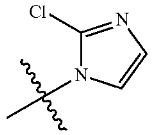 [SMILES: *n1ccnc1Cl]
Het-881
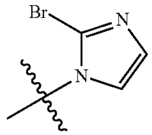 [SMILES: *n1ccnc1Br]
Het-862
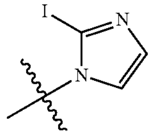 [SMILES: *n1ccnc1I]
Het-863
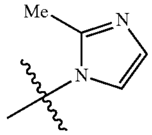 [SMILES: *n1ccnc1C]
Het-864
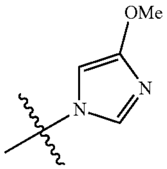 [SMILES: *n1cnc(OC)c1]
Het-865
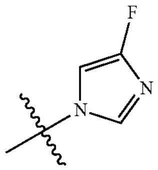 [SMILES: *n1cnc(F)c1]
Het-866
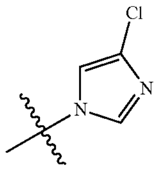 [SMILES: *n1cnc(Cl)c1]
Het-887
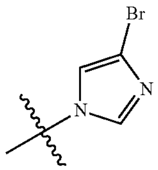 [SMILES: *n1cnc(Br)c1]
Het-868
TABLE 3-continued
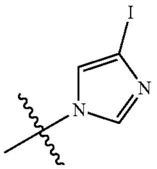 [SMILES: *n1cnc(I)c1]
Het-869
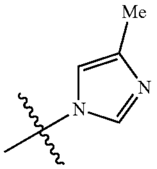 [SMILES: *n1cnc(C)c1]
Het-870
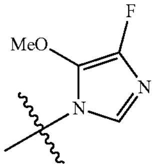
Het-871
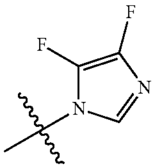
Het-872
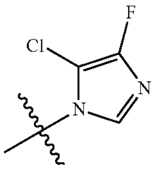
Het-873
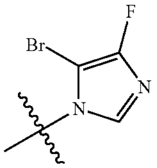
Het-874
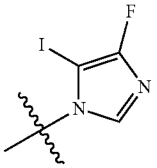
Het-875
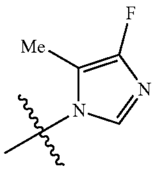
Het-876
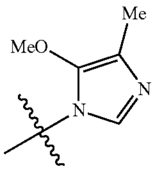 [SMILES: *n1cnc(C)c1OC]
Het-877

TABLE 3-continued
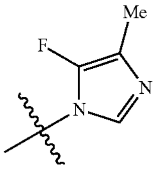
Het-878
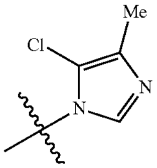 [SMILES: *n1cnc(C)c1Cl]
Het-879
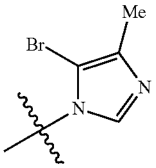
Het-880
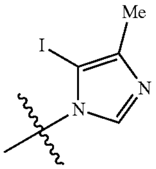 [SMILES: *n1cnc(C)c1I]
Het-881
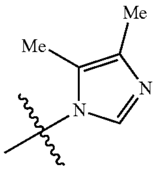 [SMILES: *n1cnc(C)c1C]
Het-882
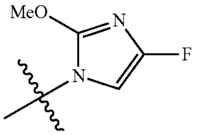 [SMILES: *n1cc(F)nc1OC]
Het-883
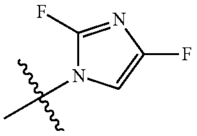
Het-884
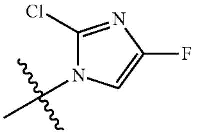 [SMILES: *n1cc(F)nc1Cl]
Het-885
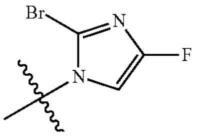 [SMILES: *n1cc(F)nc1Br]
Het-886
TABLE 3-continued
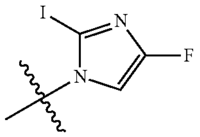 [SMILES: *n1cc(F)nc1I]
Het-887
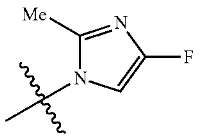 [SMILES: *n1cc(F)nc1C]
Het-888
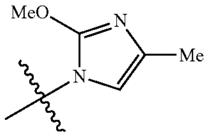 [SMILES: *n1cc(C)nc1OC]
Het-889
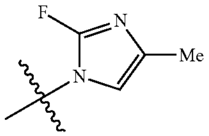
Het-890
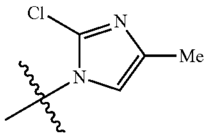 [SMILES: *n1cc(C)nc1Cl]
Het-891
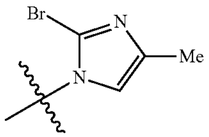 [SMILES: *n1cc(C)nc1Br]
Het-892
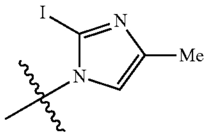 [SMILES: *n1cc(C)nc1I]
Het-893
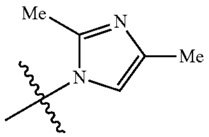 [SMILES: *n1cc(C)nc1C]
Het-894
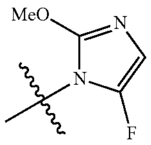 [SMILES: *n1c(F)cnc1OC]
Het-895
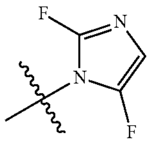 [SMILES: *n1c(F)cnc1F]
Het-896

TABLE 3-continued
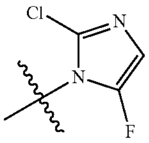 [SMILES: *n1c(F)cnc1Cl]
Het-897
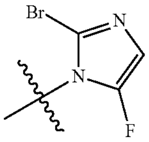 [SMILES: *n1c(F)cnc1Br]
Het-898
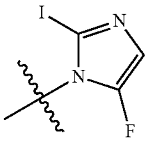 [SMILES: *n1c(F)cnc1I]
Het-899
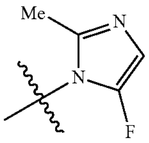 [SMILES: *n1c(F)cnc1C]
Het-900
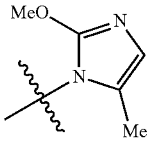 [SMILES: *n1c(C)cnc1OC]
Het-901
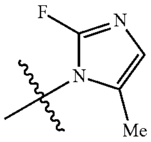
Het-902
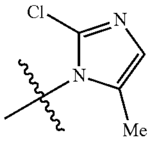 [SMILES: *n1c(C)cnc1Cl]
Het-903
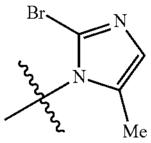 [SMILES: *n1c(C)cnc1Br]
Het-904
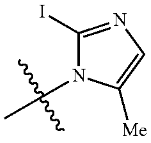 [SMILES: *n1c(C)cnc1I]
Het-905
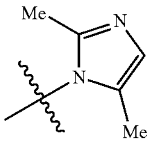 [SMILES: *n1c(C)cnc1C]
Het-906
TABLE 3-continued
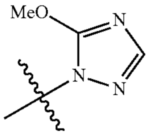 [SMILES: *n1ncnc1OC]
Het-907
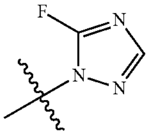
Het-908
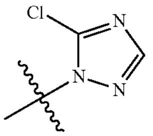 [SMILES: *n1ncnc1Cl]
Het-909
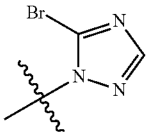 [SMILES: *n1ncnc1Br]
Het-910
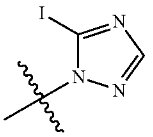 [SMILES: *n1ncnc1I]
Het-911
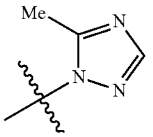 [SMILES: *n1ncnc1C]
Het-912
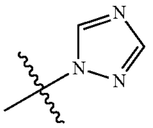 [SMILES: *n1cncn1]
Het-913
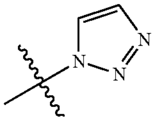 [SMILES: *n1ccnn1]
Het-914
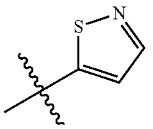 [SMILES: *c1ccns1]
Het-915
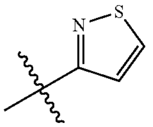 [SMILES: *c1ccsn1]
Het-916
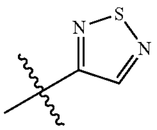 [SMILES: *c1cnsn1]
Het-917

TABLE 3-continued
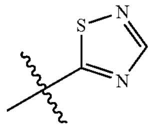 [SMILES: *c1ncns1]
Het-918
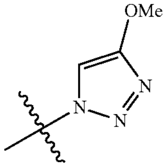 [SMILES: *n1cc(OC)nn1]
Het-919
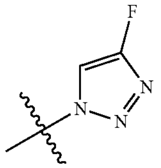 [SMILES: *n1cc(F)nn1]
Het-920
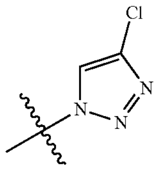
Het-921
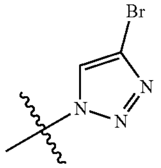 [SMILES: *n1cc(Br)nn1]
Het-922
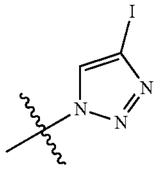 [SMILES: *n1cc(I)nn1]
Het-923
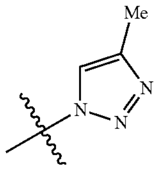 [SMILES: *n1cc(C)nn1]
Het-924
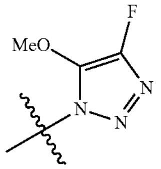 [SMILES: *n1nnc(F)c1OC]
Het-925
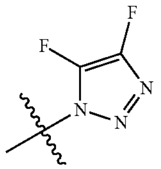 [SMILES: *n1nnc(F)c1F]
Het-926
TABLE 3-continued
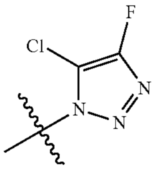 [SMILES: *n1nnc(F)c1Cl]
Het-927
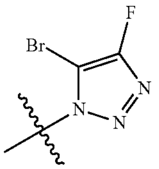 [SMILES: *n1nnc(F)c1Br]
Het-928
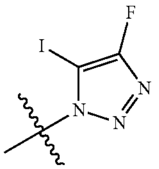 [SMILES: *n1nnc(F)c1I]
Het-929
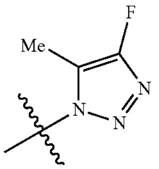 [SMILES: *n1nnc(F)c1C]
Het-930
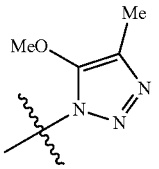 [SMILES: *n1nnc(C)c1OC]
Het-931
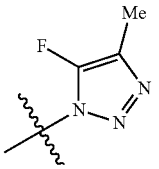 [SMILES: *n1nnc(C)c1F]
Het-932
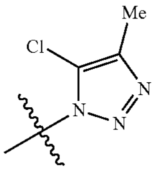 [SMILES: *n1nnc(C)c1Cl]
Het-933
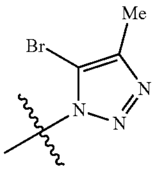 [SMILES: *n1nnc(C)c1Br]
Het-934
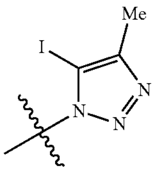 [SMILES: *n1nnc(C)c1I]
Het-935

TABLE 3-continued
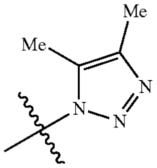 [SMILES: *n1nnc(C)c1C]
Het-936
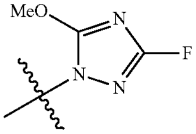 [SMILES: *n1nc(F)nc1OC]
Het-937
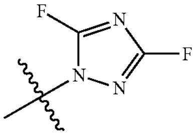
Het-938
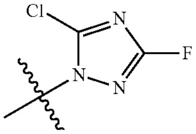
Het-939
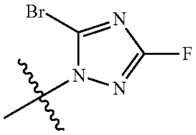 [SMILES: *n1nc(F)nc1Br]
Het-940
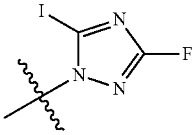
Het-941
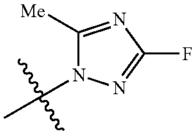
Het-942
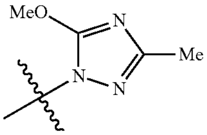 [SMILES: *n1nc(C)nc1OC]
Het-943
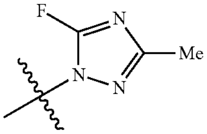
Het-944
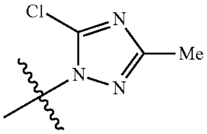
Het-945
TABLE 3-continued
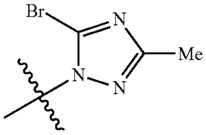 [SMILES: *n1nc(C)nc1Br]
Het-946
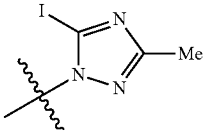 [SMILES: *n1nc(C)nc1I]
Het-947
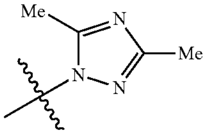 [SMILES: *n1nc(C)nc1C]
Het-948
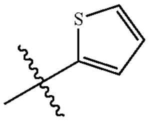 [SMILES: *c1cccs1]
Het-949
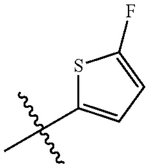 [SMILES: *c1ccc(F)s1]
Het-950
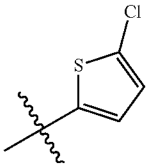 [SMILES: *c1ccc(Cl)s1]
Het-951
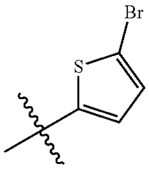 [SMILES: *c1ccc(Br)s1]
Het-952
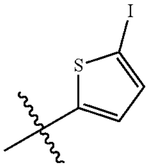 [SMILES: *c1ccc(I)s1]
Het-953
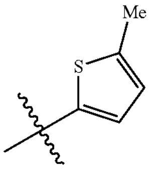 [SMILES: *c1ccc(C)s1]
Het-954
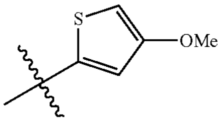 [SMILES: *c1cc(OC)cs1]
Het-955

TABLE 3-continued
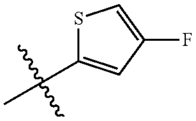 [SMILES: *c1cc(F)cs1]
Het-956
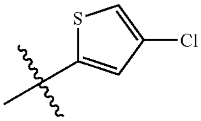 [SMILES: *c1cc(Cl)cs1]
Het-957
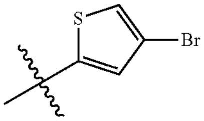 [SMILES: *c1cc(Br)cs1]
Het-958
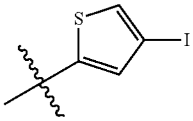 [SMILES: *c1cc(I)cs1]
Het-959
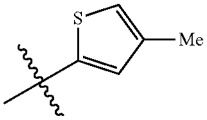 [SMILES: *c1cc(C)cs1]
Het-960
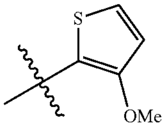 [SMILES: *c1sccc1OC]
Het-961
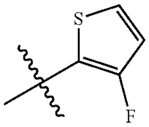 [SMILES: *c1sccc1F]
Het-982
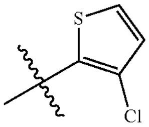 [SMILES: *c1sccc1Cl]
Het-983
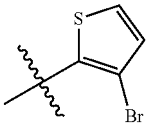 [SMILES: *c1sccc1Br]
Het-964
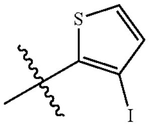 [SMILES: *c1sccc1I]
Het-965
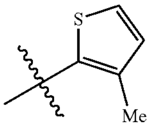 [SMILES: *c1sccc1C]
Het-966
TABLE 3-continued
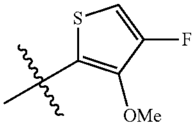 [SMILES: *c1scc(F)c1OC]
Het-967
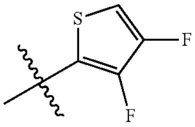
Het-968
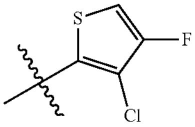 [SMILES: *c1scc(F)c1Cl]
Het-969
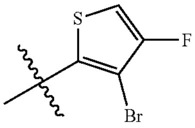 [SMILES: *c1scc(F)c1Br]
Het-970
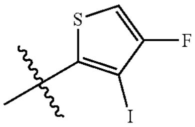 [SMILES: *c1scc(F)c1I]
Het-971
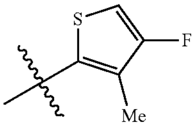 [SMILES: *c1scc(F)c1C]
Het-972
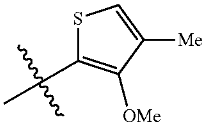
Het-973
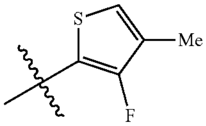
Het-974
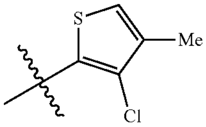 [SMILES: *c1scc(C)c1Cl]
Het-975
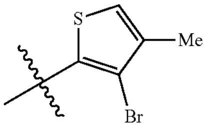 [SMILES: *c1scc(C)c1Br]
Het-976
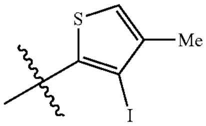 [SMILES: *c1scc(C)c1I]
Het-977

TABLE 3-continued
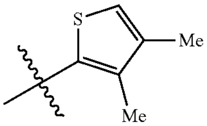 [SMILES: *c1scc(C)c1C]
Het-978
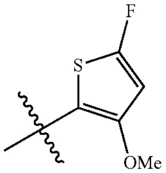 [SMILES: *c1sc(F)cc1OC]
Het-979
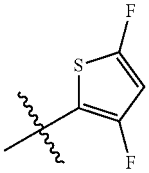
Het-980
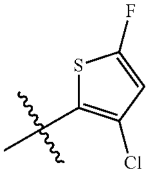 [SMILES: *c1sc(F)cc1Cl]
Het-981
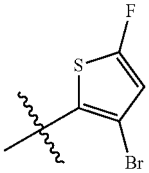 [SMILES: *c1sc(F)cc1Br]
Het-982
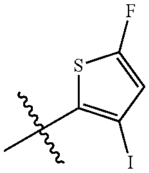 [SMILES: *c1sc(F)cc1I]
Het-983
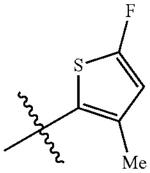 [SMILES: *c1sc(F)cc1C]
Het-984
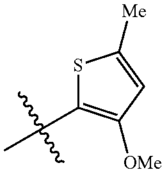 [SMILES: *c1sc(C)cc1OC]
Het-985
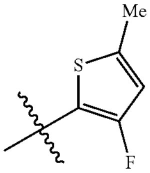 [SMILES: *c1sc(C)cc1F]
Het-986
TABLE 3-continued
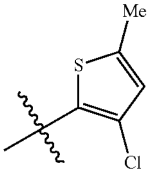 [SMILES: *c1sc(C)cc1Cl]
Het-987
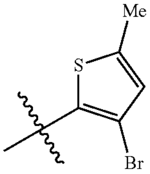 [SMILES: *c1sc(C)cc1Br]
Het-988
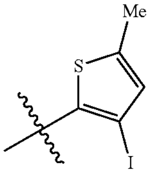 [SMILES: *c1sc(C)cc1I]
Het-989
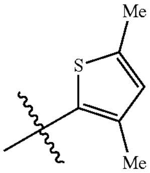 [SMILES: *c1sc(C)cc1C]
Het-990
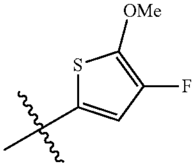 [SMILES: *c1cc(F)c(OC)s1]
Het-991
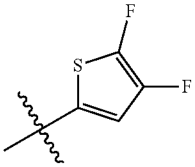
Het-992
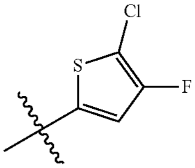 [SMILES: *c1cc(F)c(Cl)s1]
Het-993
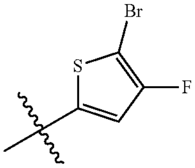
Het-994
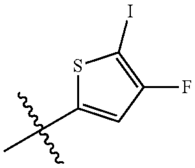 [SMILES: *c1cc(F)c(I)s1]
Het-995

TABLE 3-continued
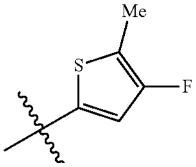 [SMILES: *c1cc(F)c(C)s1]
Het-996
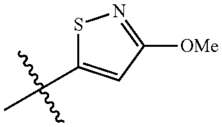 [SMILES: *c1cc(OC)ns1]
Het-997
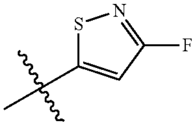 [SMILES: *c1cc(F)ns1]
Het-998
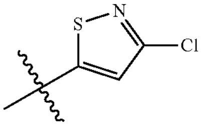 [SMILES: *c1cc(Cl)ns1]
Het-999
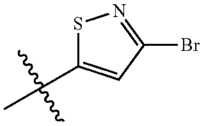 [SMILES: *c1cc(Br)ns1]
Het-1000
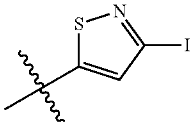 [SMILES: *c1cc(I)ns1]
Het-1001
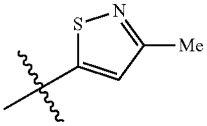 [SMILES: *c1cc(C)ns1]
Het-1002
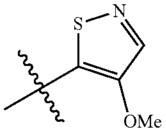 [SMILES: *c1sncc1OC]
Het-1003
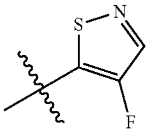
Het-1004
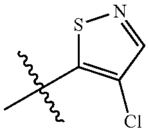 [SMILES: *c1sncc1Cl]
Het-1005
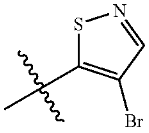
Het-1006
TABLE 3-continued
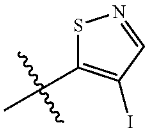 [SMILES: *c1sncc1I]
Het-1007
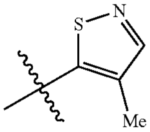 [SMILES: *c1sncc1C]
Het-1008
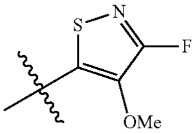 [SMILES: *c1snc(F)c1OC]
Het-1009
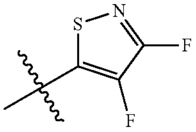
Het-1010
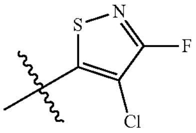 [SMILES: *c1snc(F)c1Cl]
Het-1011
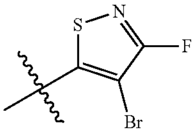 [SMILES: *c1snc(F)c1Br]
Het-1012
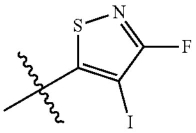 [SMILES: *c1snc(F)c1I]
Het-1013
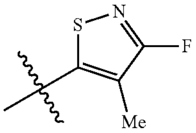 [SMILES: *c1snc(F)c1C]
Het-1014
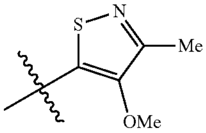 [SMILES: *c1snc(C)c1OC]
Het-1015
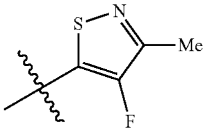
Het-1016
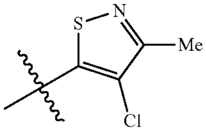 [SMILES: *c1snc(C)c1Cl]
Het-1017

TABLE 3-continued
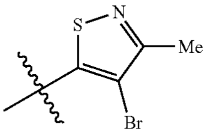
Het-1018
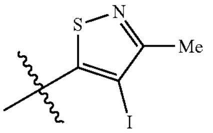 [SMILES: *c1snc(C)c1I]
Het-1019
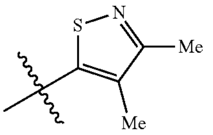 [SMILES: *c1snc(C)c1C]
Het-1020
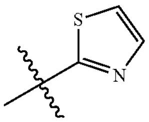 [SMILES: *c1nccs1]
Het-1021
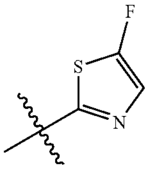 [SMILES: *c1ncc(F)s1]
Het-1022
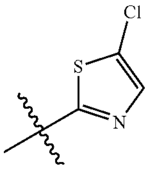 [SMILES: *c1ncc(Cl)s1]
Het-1023
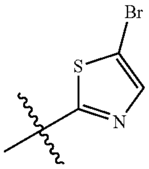 [SMILES: *c1ncc(Br)s1]
Het-1024
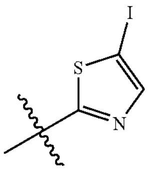 [SMILES: *c1ncc(I)s1]
Het-1025
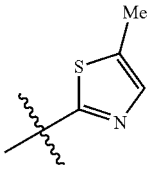 [SMILES: *c1ncc(C)s1]
Het-1026
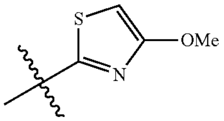 [SMILES: *c1nc(OC)cs1]
Het-1027
TABLE 3-continued
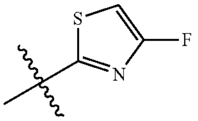 [SMILES: *c1nc(F)cs1]
Het-1028
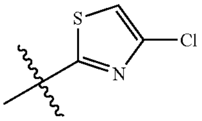 [SMILES: *c1nc(Cl)cs1]
Het-1029
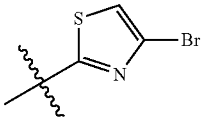 [SMILES: *c1nc(Br)cs1]
Het-1030
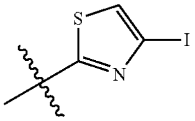 [SMILES: *c1nc(I)cs1]
Het-1031
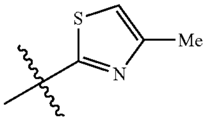 [SMILES: *c1nc(C)cs1]
Het-1032
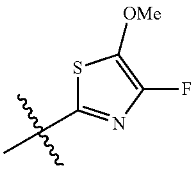 [SMILES: *c1nc(F)c(OC)s1]
Het-1033
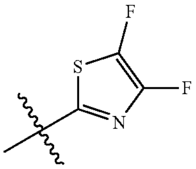
Het-1034
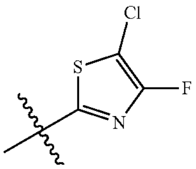 [SMILES: *c1nc(F)c(Cl)s1]
Het-1035
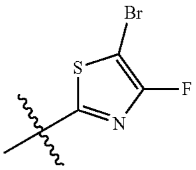 [SMILES: *c1nc(F)c(Br)s1]
Het-1036
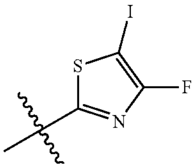 [SMILES: *c1nc(F)c(I)s1]
Het-1037

TABLE 3-continued
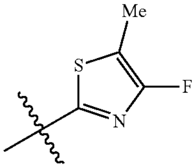 [SMILES: *c1nc(F)c(C)s1]
Het-1038
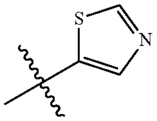 [SMILES: *c1cncs1]
Het-1039
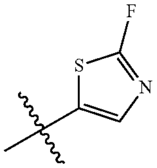 [SMILES: *c1cnc(F)s1]
Het-1040
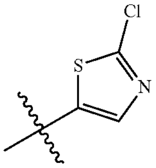 [SMILES: *c1cnc(Cl)s1]
Het-1041
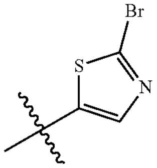 [SMILES: *c1cnc(Br)s1]
Het-1042
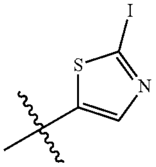 [SMILES: *c1cnc(I)s1]
Het-1043
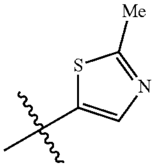 [SMILES: *c1cnc(C)s1]
Het-1044
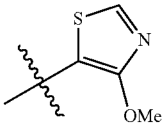 [SMILES: *c1scnc1OC]
Het-1045
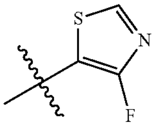 [SMILES: *c1scnc1F]
Het-1046
TABLE 3-continued
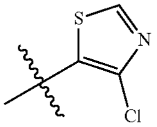 [SMILES: *c1scnc1Cl]
Het-1047
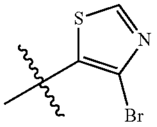 [SMILES: *c1scnc1Br]
Het-1048
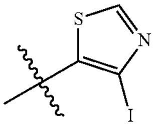 [SMILES: *c1scnc1I]
Het-1049
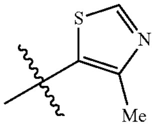 [SMILES: *c1scnc1C]
Het-1050
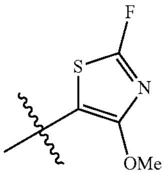 [SMILES: *c1sc(F)nc1OC]
Het-1051
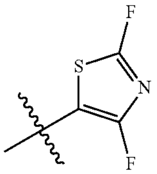
Het-1052
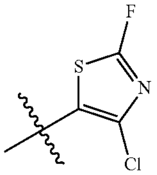
Het-1053
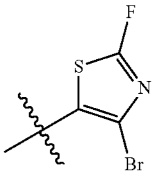
Het-1054
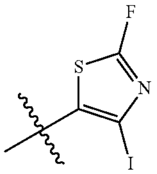
Het-1055

TABLE 3-continued
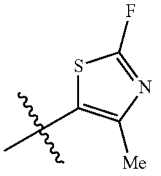 [SMILES: *c1sc(F)nc1C]
Het-1056
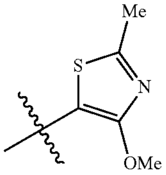
Het-1057
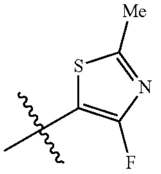 [SMILES: *c1sc(C)nc1F]
Het-1058
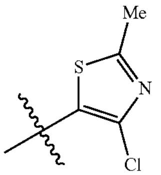
Het-1059
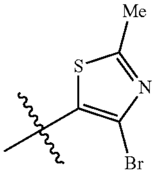 [SMILES: *c1sc(C)nc1Br]
Het-1060
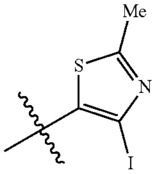 [SMILES: *c1sc(C)nc1I]
Het-1061
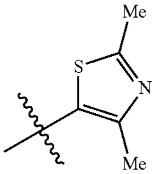 [SMILES: *c1sc(C)nc1C]
Het-1062
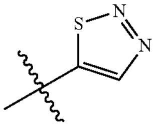 [SMILES: *c1cnns1]
Het-1063
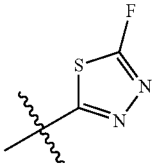 [SMILES: *c1nnc(F)s1]
Het-1064
TABLE 3-continued
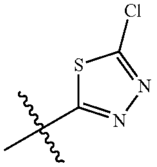 [SMILES: *c1nnc(Cl)s1]
Het-1065
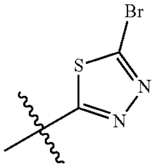 [SMILES: *c1nnc(Br)s1]
Het-1066
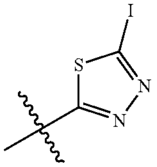 [SMILES: *c1nnc(I)s1]
Het-1067
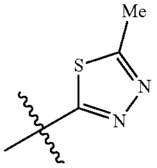 [SMILES: *c1nnc(C)s1]
Het-1068
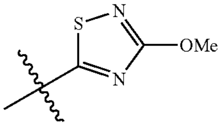 [SMILES: *c1nc(OC)ns1]
Het-1069
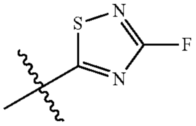 [SMILES: *c1nc(F)ns1]
Het-1070
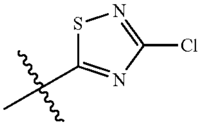 [SMILES: *c1nc(Cl)ns1]
Het-1071
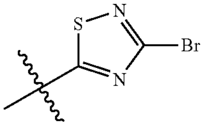 [SMILES: *c1nc(Br)ns1]
Het-1072
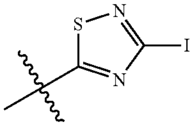 [SMILES: *c1nc(I)ns1]
Het-1073
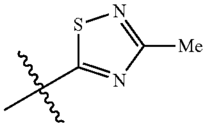 [SMILES: *c1nc(C)ns1]
Het-1074

TABLE 3-continued
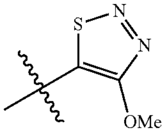 [SMILES: *c1snnc1OC]
Het-1075
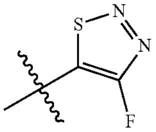 [SMILES: *c1snnc1F]
Het-1076
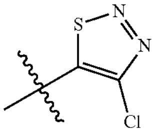 [SMILES: *c1snnc1Cl]
Het-1077
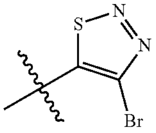 [SMILES: *c1snnc1Br]
Het-1078
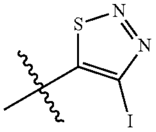 [SMILES: *c1snnc1I]
Het-1079
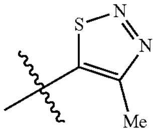 [SMILES: *c1snnc1C]
Het-1080
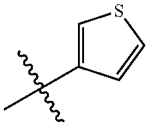 [SMILES: *c1ccsc1]
Het-1081
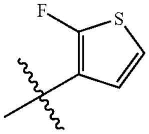 [SMILES: *c1ccsc1F]
Het-1082
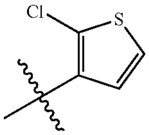
Het-1083
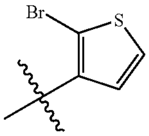 [SMILES: *c1ccsc1Br]
Het-1084
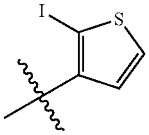 [SMILES: *c1ccsc1I]
Het-1085
TABLE 3-continued
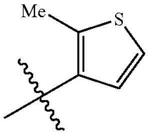 [SMILES: *c1ccsc1C]
Het-1086
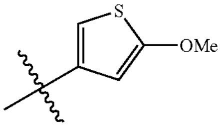 [SMILES: *c1csc(OC)c1]
Het-1087
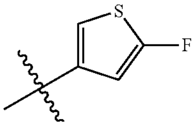 [SMILES: *c1csc(F)c1]
Het-1088
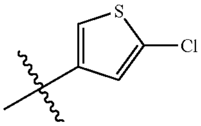 [SMILES: *c1csc(Cl)c1]
Het-1089
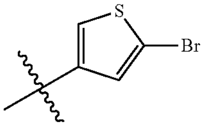 [SMILES: *c1csc(Br)c1]
Het-1090
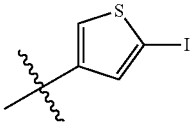 [SMILES: *c1csc(I)c1]
Het-1091
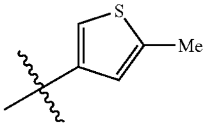 [SMILES: *c1csc(C)c1]
Het-1092
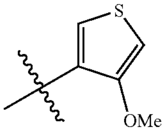 [SMILES: *c1cscc1OC]
Het-1093
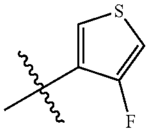 [SMILES: *c1cscc1F]
Het-1094
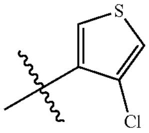 [SMILES: *c1cscc1Cl]
Het-1095
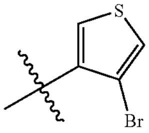 [SMILES: *c1cscc1Br]
Het-1096

TABLE 3-continued
Het-1097
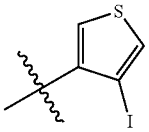 [SMILES: *c1cscc1I]
Het-1098
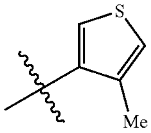 [SMILES: *c1cscc1C]
Het-1099
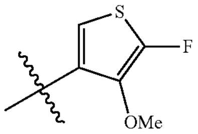 [SMILES: *c1csc(F)c1OC]
Het-1100
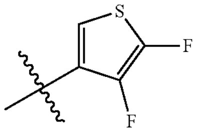
Het-1101
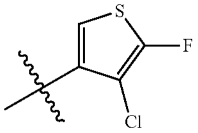 [SMILES: *c1csc(F)c1Cl]
Het-1102
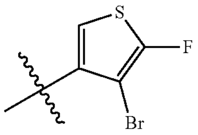
Het-1103
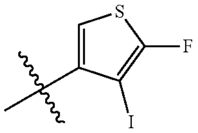 [SMILES: *c1csc(F)c1I]
Het-1104
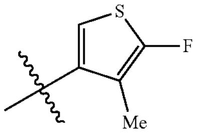 [SMILES: *c1csc(F)c1C]
Het-1105
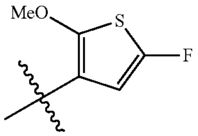 [SMILES: *c1cc(F)sc1OC]
Het-1106
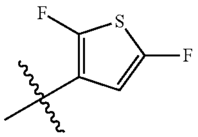
Het-1107
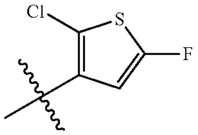
TABLE 3-continued
Het-1108
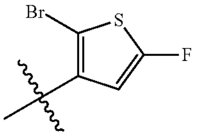 [SMILES: *c1cc(F)sc1Br]
Het-1109
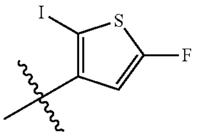 [SMILES: *c1cc(F)sc1I]
Het-1110
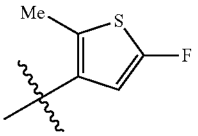 [SMILES: *c1cc(F)sc1C]
Het-1111
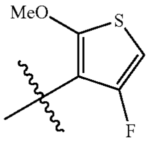 [SMILES: *c1c(F)csc1OC]
Het-1112
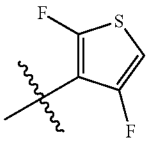
Het-1113
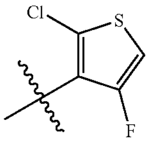 [SMILES: *c1c(F)csc1Cl]
Het-1114
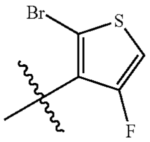
Het-1115
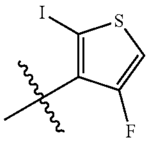
Het-1116
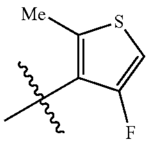 [SMILES: *c1c(F)csc1C]
Het-1117
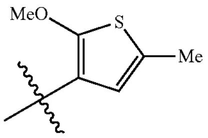 [SMILES: *c1cc(C)sc1OC]

TABLE 3-continued
Het-1118
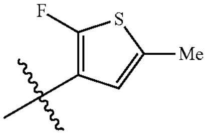
Het-1119
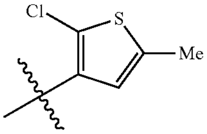
Het-1120
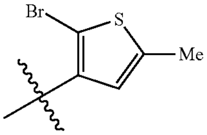 [SMILES: *c1cc(C)sc1Br]
Het-1121
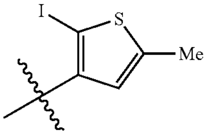 [SMILES: *c1cc(C)sc1I]
Het-1122
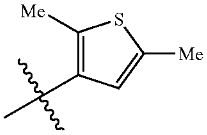 [SMILES: *c1cc(C)sc1C]
Het-1123
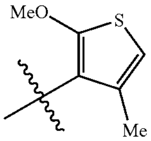 [SMILES: *c1c(C)csc1OC]
Het-1124
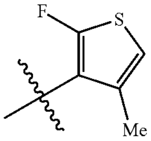
Het-1125
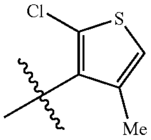
Het-1126
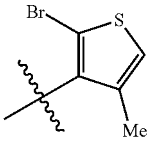 [SMILES: *c1c(C)csc1Cl]
Het-1127
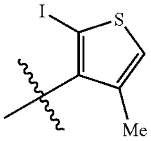 [SMILES: *c1c(C)csc1I]
TABLE 3-continued
Het-1128
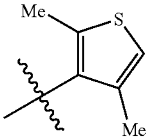 [SMILES: *c1c(C)csc1C]
Het-1129
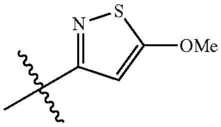 [SMILES: *c1cc(OC)sn1]
Het-1130
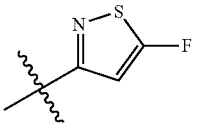 [SMILES: *c1cc(F)sn1]
Het-1131
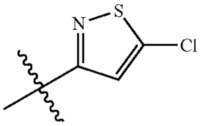 [SMILES: *c1cc(Cl)sn1]
Het-1132
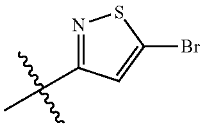 [SMILES: *c1cc(Br)sn1]
Het-1133
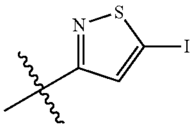 [SMILES: *c1cc(I)sn1]
Het-1134
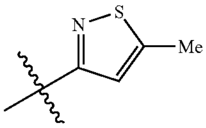 [SMILES: *c1cc(C)sn1]
Het-1135
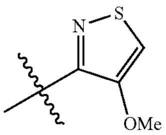 [SMILES: *c1nscc1OC]
Het-1136
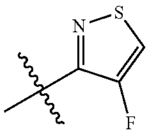 [SMILES: *c1nscc1F]
Het-1137
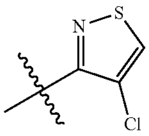 [SMILES: *c1nscc1Cl]
Het-1138
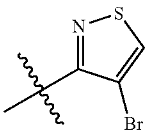 [SMILES: *c1nscc1Br]

TABLE 3-continued
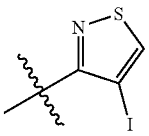 [SMILES: *c1nscc1I]
Het-1139
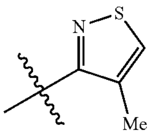 [SMILES: *c1nscc1C]
Het-1140
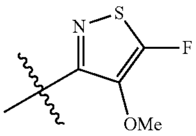 [SMILES: *c1nsc(F)c1OC]
Het-1141
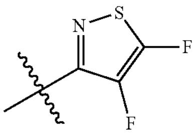
Het-1142
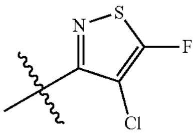 [SMILES: *c1nsc(F)c1Cl]
Het-1143
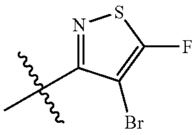 [SMILES: *c1nsc(F)c1Br]
Het-1144
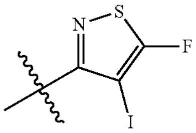 [SMILES: *c1nsc(F)c1I]
Het-1145
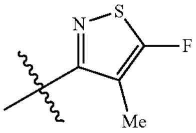 [SMILES: *c1nsc(F)c1C]
Het-1146
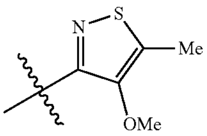 [SMILES: *c1nsc(C)c1OC]
Het-1147
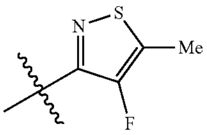 [SMILES: *c1nsc(C)c1F]
Het-1148
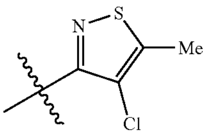 [SMILES: *c1nsc(C)c1Cl]
Het-1149
TABLE 3-continued
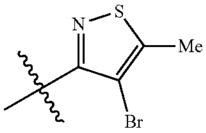 [SMILES: *c1nsc(C)c1Br]
Het-1150
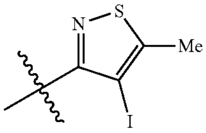 [SMILES: *c1nsc(C)c1I]
Het-1151
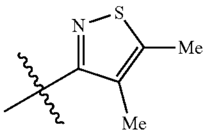 [SMILES: *c1nsc(C)c1C]
Het-1152
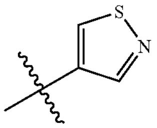 [SMILES: *c1cnsc1]
Het-1153
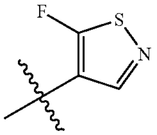
Het-1154
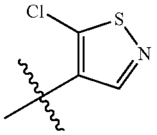 [SMILES: *c1cnsc1Cl]
Het-1155
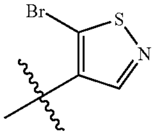 [SMILES: *c1cnsc1Br]
Het-1156
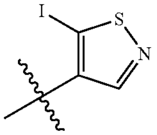 [SMILES: *c1cnsc1I]
Het-1157
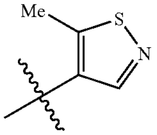 [SMILES: *c1cnsc1C]
Het-1158
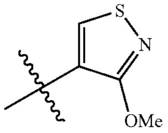 [SMILES: *c1csnc1OC]
Het-1159
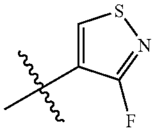
Het-1160

TABLE 3-continued
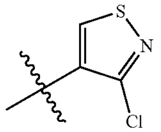 [SMILES: *c1csnc1Cl]
Het-1161
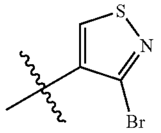 [SMILES: *c1csnc1Br]
Het-1162
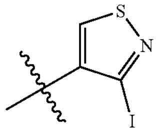 [SMILES: *c1csnc1I]
Het-1163
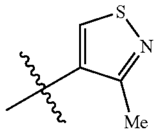 [SMILES: *c1csnc1C]
Het-1164
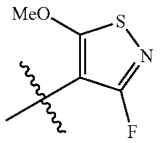 [SMILES: *c1c(F)nsc1OC]
Het-1165
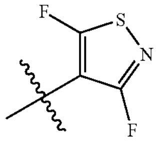
Het-1166
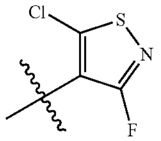
Het-1167
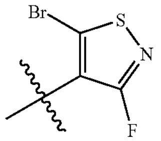 [SMILES: *c1c(F)nsc1Cl]
Het-1168
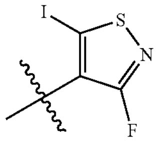 [SMILES: *c1c(F)nsc1I]
Het-1169
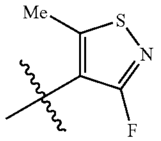 [SMILES: *c1c(F)nsc1C]
Het-1170
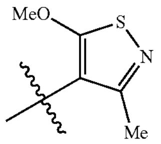 [SMILES: *c1c(C)nsc1OC]
Het-1171
TABLE 3-continued
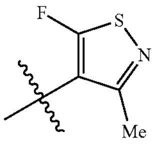
Het-1172
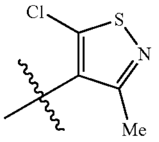 [SMILES: *c1c(C)nsc1Cl]
Het-1173
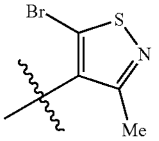
Het-1174
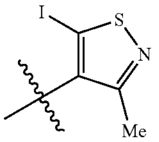 [SMILES: *c1c(C)nsc1I]
Het-1175
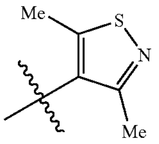 [SMILES: *c1c(C)nsc1C]
Het-1176
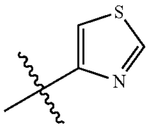 [SMILES: *c1cscn1]
Het-1177
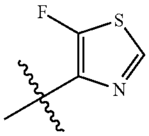
Het-1178
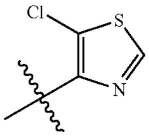
Het-1179
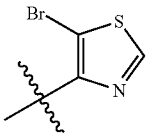 [SMILES: *c1ncsc1Br]
Het-1180
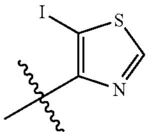 [SMILES: *c1ncsc1I]
Het-1181

TABLE 3-continued
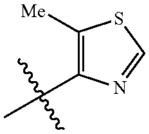 [SMILES: *c1ncsc1C]
Het-1182
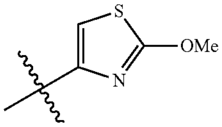 [SMILES: *c1csc(OC)n1]
Het-1183
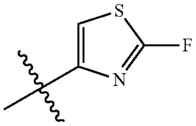 [SMILES: *c1csc(F)n1]
Het-1184
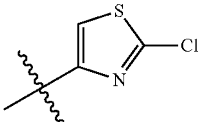 [SMILES: *c1csc(Cl)n1]
Het-1185
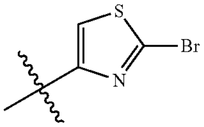 [SMILES: *c1csc(Br)n1]
Het-1186
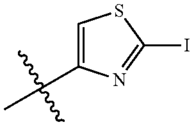 [SMILES: *c1csc(I)n1]
Het-1187
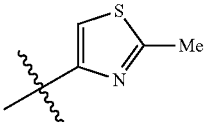 [SMILES: *c1csc(C)n1]
Het-1188
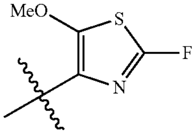 [SMILES: *c1nc(F)sc1OC]
Het-1189
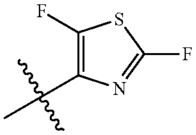
Het-1190
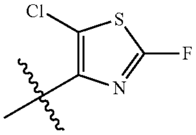
Het-1191
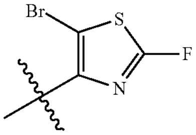 [SMILES: *c1nc(F)sc1Br]
Het-1192
TABLE 3-continued
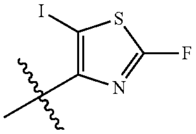 [SMILES: *c1nc(F)sc1I]
Het-1193
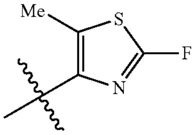 [SMILES: *c1nc(F)sc1C]
Het-1194
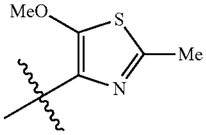 [SMILES: *c1nc(C)sc1OC]
Het-1195
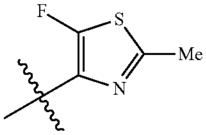
Het-1196
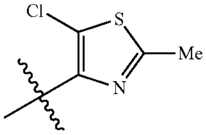
Het-1197
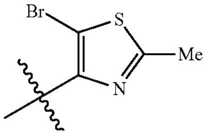 [SMILES: *c1nc(C)sc1Br]
Het-1198
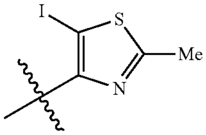 [SMILES: *c1nc(C)sc1I]
Het-1199
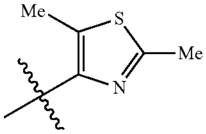 [SMILES: *c1nc(C)sc1C]
Het-1200
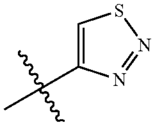 [SMILES: *c1csnn1]
Het-1201
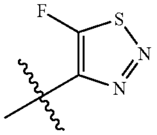
Het-1202
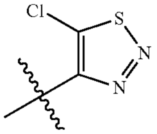 [SMILES: *c1nnsc1Cl]
Het-1203

TABLE 3-continued
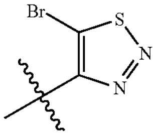 [SMILES: *c1nnsc1Br]
Het-1204
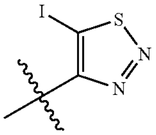 [SMILES: *c1nnsc1I]
Het-1205
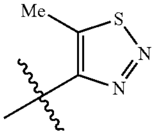 [SMILES: *c1nnsc1C]
Het-1206
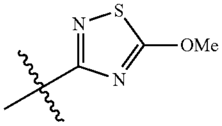 [SMILES: *c1nsc(OC)n1]
Het-1207
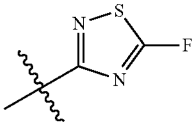 [SMILES: *c1nsc(F)n1]
Het-1208
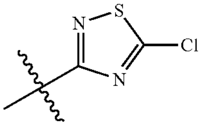 [SMILES: *c1nsc(Cl)n1]
Het-1209
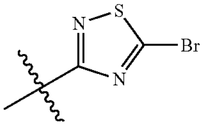 [SMILES: *c1nsc(Br)n1]
Het-1210
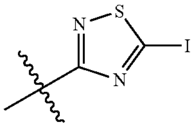 [SMILES: *c1nsc(I)n1]
Het-1211
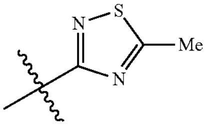 [SMILES: *c1nsc(C)n1]
Het-1212
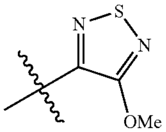 [SMILES: *c1nsnc1OC]
Het-1213
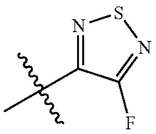 [SMILES: *c1nsnc1F]
Het-1214
TABLE 3-continued
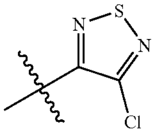 [SMILES: *c1nsnc1Cl]
Het-1215
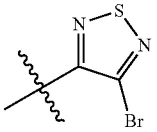 [SMILES: *c1nsnc1Br]
Het-1216
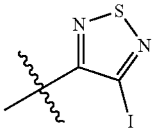 [SMILES: *c1nsnc1I]
Het-1217
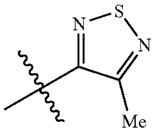 [SMILES: *c1nsnc1C]
Het-1218
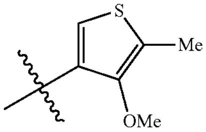 [SMILES: *c1csc(C)c1OC]
Het-1219
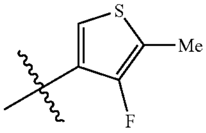
Het-1220
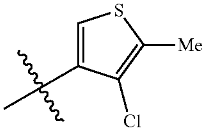 [SMILES: *c1csc(C)c1Cl]
Het-1221
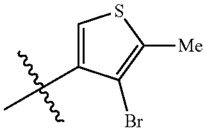
Het-1222
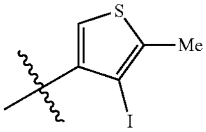 [SMILES: *c1csc(C)c1I]
Het-1223
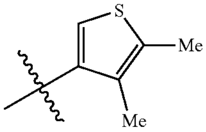 [SMILES: *c1csc(C)c1C]
Het-1224
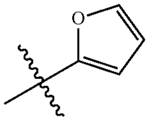 [SMILES: *c1ccco1]
Het-1226

TABLE 3-continued
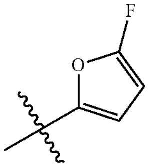 [SMILES: *c1ccc(F)o1]
Het-1226
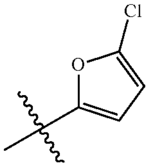
Het-1227
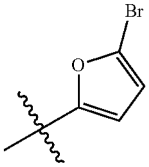 [SMILES: *c1ccc(Br)o1]
Het-1228
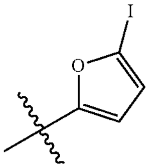 [SMILES: *c1ccc(I)o1]
Het-1229
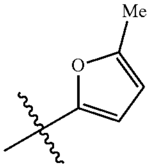 [SMILES: *c1ccc(C)o1]
Het-1230
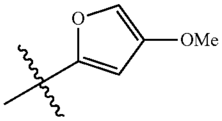 [SMILES: *c1cc(OC)co1]
Het-1231
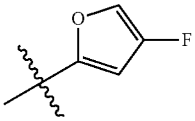 [SMILES: *c1cc(F)co1]
Het-1232
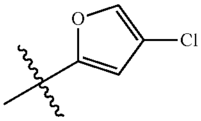 [SMILES: *c1cc(Cl)co1]
Het-1233
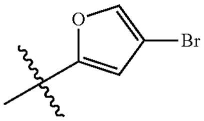 [SMILES: *c1cc(Br)co1]
Het-1234
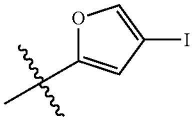 [SMILES: *c1cc(I)co1]
Het-1235
TABLE 3-continued
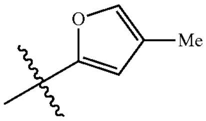 [SMILES: *c1cc(C)co1]
Het-1236
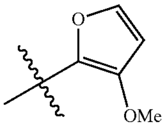
Het-1237
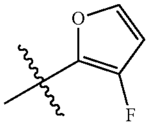 [SMILES: *c1occc1F]
Het-1238
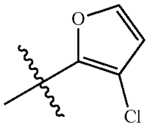 [SMILES: *c1occc1Cl]
Het-1239
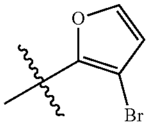 [SMILES: *c1occc1Br]
Het-1240
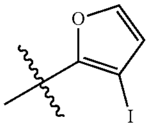 [SMILES: *c1occc1I]
Het-1241
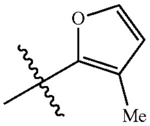 [SMILES: *c1occc1C]
Het-1242
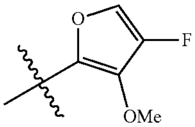 [SMILES: *c1occ(F)c1OC]
Het-1243
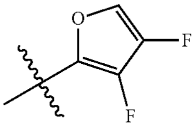
Het-1244
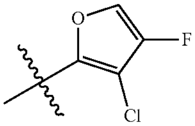 [SMILES: *c1occ(F)c1Cl]
Het-1245
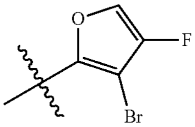
Het-1246

TABLE 3-continued
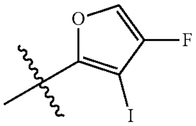 [SMILES: *c1occ(F)c1I]
Het-1247
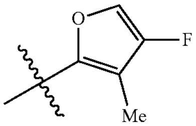 [SMILES: *c1occ(F)c1C]
Het-1248
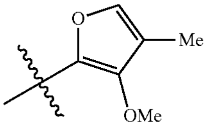 [SMILES: *c1occ(C)c1OC]
Het-1249
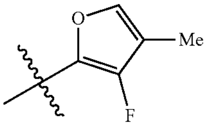
Het-1250
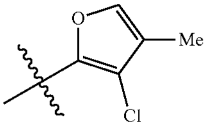 [SMILES: *c1occ(C)c1Cl]
Het-1251
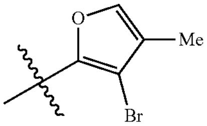
Het-1252
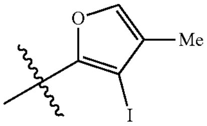 [SMILES: *c1occ(C)c1I]
Het-1253
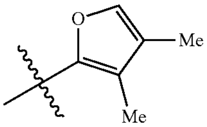 [SMILES: *c1occ(C)c1C]
Het-1254
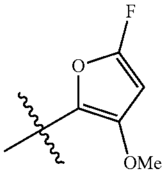
Het-1255
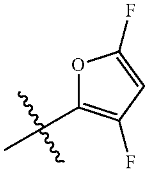 [SMILES: *c1oc(F)cc1F]
Het-1256
TABLE 3-continued
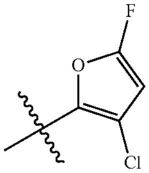 [SMILES: *c1oc(F)cc1Cl]
Het-1257
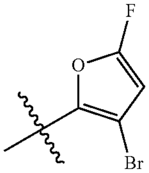 [SMILES: *c1oc(F)cc1Br]
Het-1258
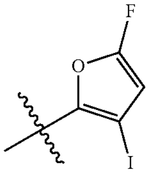 [SMILES: *c1oc(F)cc1I]
Het-1259
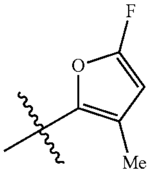 [SMILES: *c1oc(F)cc1C]
Het-1260
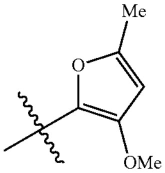 [SMILES: *c1oc(C)cc1OC]
Het-1261
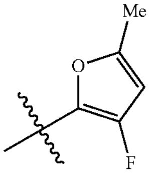
Het-1262
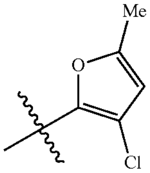 [SMILES: *c1oc(C)cc1Cl]
Het-1263
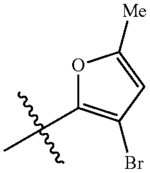 [SMILES: *c1oc(C)cc1Br]
Het-1264
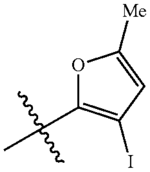 [SMILES: *c1oc(C)cc1I]
Het-1265

TABLE 3-continued
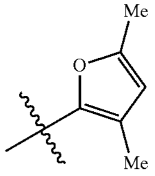 [SMILES: *c1oc(C)cc1C]
Het-1266
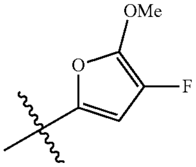 [SMILES: *c1cc(F)c(OC)o1]
Het-1267
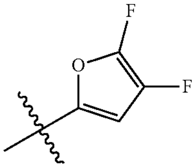
Het-1268
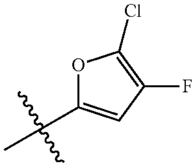 [SMILES: *c1cc(F)c(Cl)o1]
Het-1269
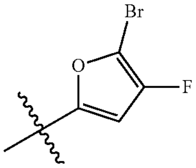 [SMILES: *c1cc(F)c(Br)o1]
Het-1270
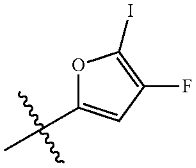 [SMILES: *c1cc(F)c(I)o1]
Het-1271
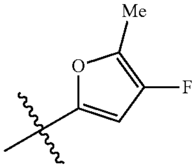 [SMILES: *c1cc(F)c(C)o1]
Het-1272
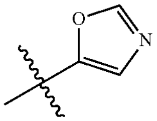 [SMILES: *c1cnco1]
Het-1273
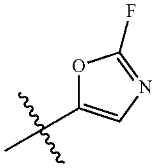
Het-1274
TABLE 3-continued
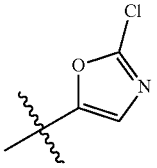 [SMILES: *c1cnc(Cl)o1]
Het-1275
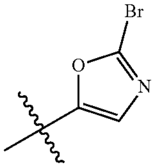 [SMILES: *c1cnc(Br)o1]
Het-1276
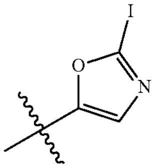 [SMILES: *c1cnc(I)o1]
Het-1277
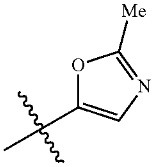 [SMILES: *c1cnc(C)o1]
Het-1278
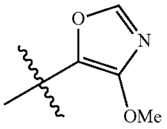
Het-1279
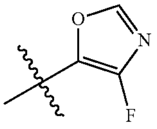
Het-1280
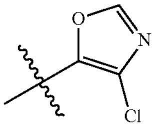 [SMILES: *c1ocnc1Cl]
Het-1281
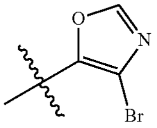 [SMILES: *c1ocnc1Br]
Het-1282
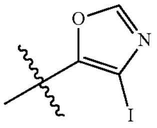 [SMILES: *c1ocnc1I]
Het-1283
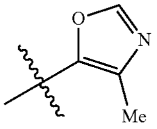 [SMILES: *c1ocnc1C]
Het-1284

TABLE 3-continued
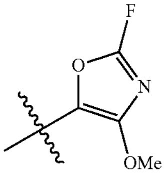
Het-1285
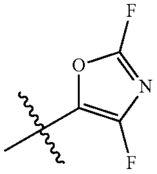
Het-1286
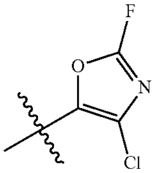
Het-1287
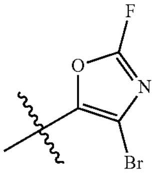 [SMILES: *c1oc(F)nc1Br]
Het-1288
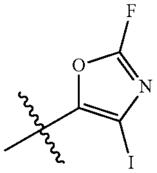
Het-1289
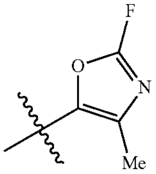 [SMILES: *c1oc(F)nc1C]
Het-1290
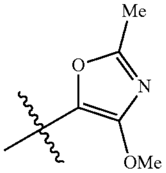 [SMILES: *c1oc(C)nc1OC]
Het-1291
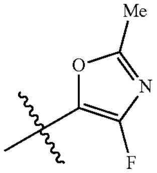 [SMILES: *c1oc(C)nc1F]
Het-1292
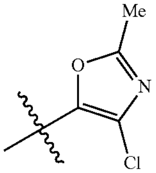 [SMILES: *c1oc(C)nc1Cl]
Het-1293
TABLE 3-continued
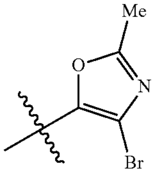 [SMILES: *c1oc(C)nc1Br]
Het-1294
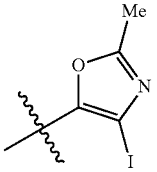 [SMILES: *c1oc(C)nc1I]
Het-1295
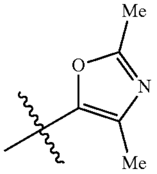 [SMILES: *c1oc(C)nc1C]
Het-1296
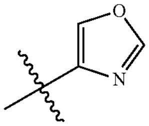 [SMILES: *c1cocn1]
Het-1297
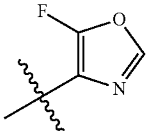
Het-1298
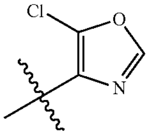
Het-1299
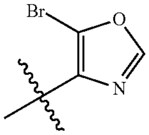 [SMILES: *c1ncoc1Br]
Het-1300
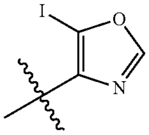 [SMILES: *c1ncoc1I]
Het-1301
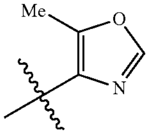 [SMILES: *c1ncoc1C]
Het-1302
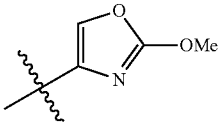 [SMILES: *c1coc(OC)n1]
Het-1303

TABLE 3-continued
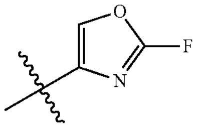 [SMILES: *c1coc(F)n1]
Het-1304
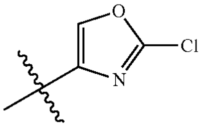 [SMILES: *c1coc(Cl)n1]
Het-1305
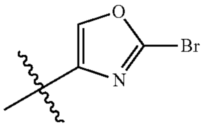 [SMILES: *c1coc(Br)n1]
Het-1306
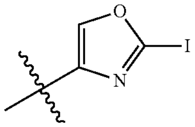 [SMILES: *c1coc(I)n1]
Het-1307
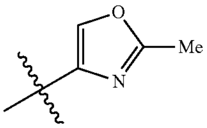 [SMILES: *c1coc(C)n1]
Het-1308
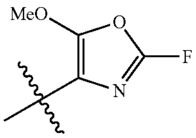 [SMILES: *c1nc(F)oc1OC]
Het-1309
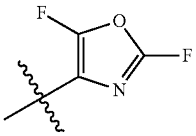
Het-1310
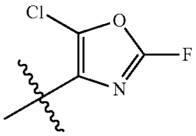
Het-1311
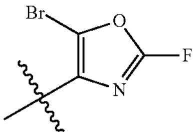 [SMILES: *c1nc(F)oc1Br]
Het-1312
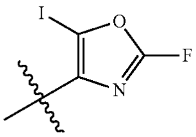 [SMILES: *c1nc(F)oc1I]
Het-1313
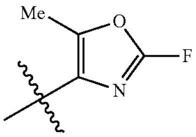 [SMILES: *c1nc(F)oc1C]
Het-1314
TABLE 3-continued
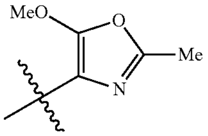 [SMILES: *c1nc(C)oc1OC]
Het-1315
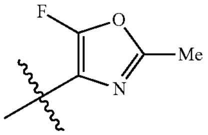
Het-1316
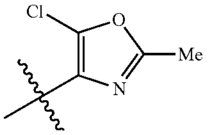
Het-1317
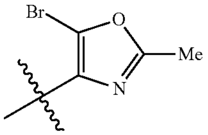 [SMILES: *c1nc(C)oc1Br]
Het-1318
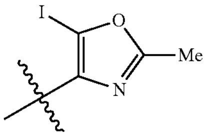 [SMILES: *c1nc(C)oc1I]
Het-1319
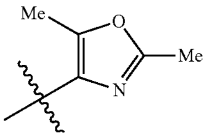 [SMILES: *c1nc(C)oc1C]
Het-1320
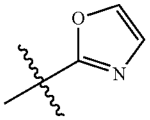 [SMILES: *c1ncco1]
Het-1321
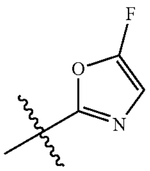 [SMILES: *c1ncc(F)o1]
Het-1322
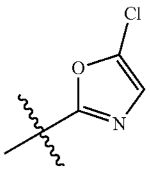 [SMILES: *c1ncc(Cl)o1]
Het-1323
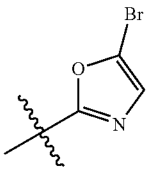 [SMILES: *c1ncc(Br)o1]
Het-1324

TABLE 3-continued
Het-1325
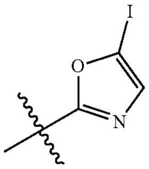 [SMILES: *c1ncc(I)o1]
Het-1326
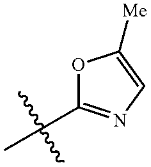 [SMILES: *c1ncc(C)o1]
Het-1327
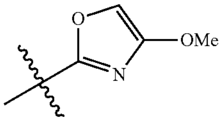 [SMILES: *c1nc(OC)co1]
Het-1328
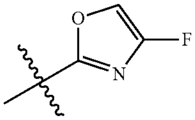 [SMILES: *c1nc(F)co1]
Het-1329
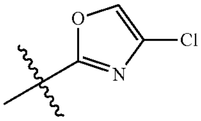 [SMILES: *c1nc(Cl)co1]
Het-1330
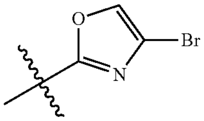 [SMILES: *c1nc(Br)co1]
Het-1331
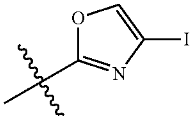 [SMILES: *c1nc(I)co1]
Het-1332
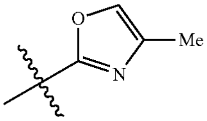 [SMILES: *c1nc(C)co1]
Het-1333
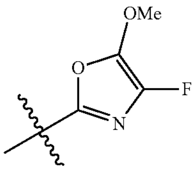
Het-1334
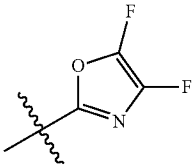
TABLE 3-continued
Het-1335
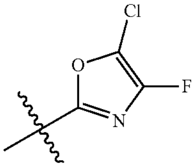 [SMILES: *c1nc(F)c(Cl)o1]
Het-1336
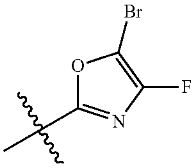 [SMILES: *c1nc(F)c(Br)o1]
Het-1337
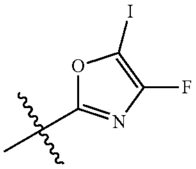 [SMILES: *c1nc(F)c(I)o1]
Het-1338
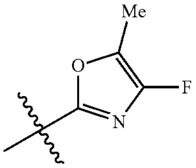 [SMILES: *c1nc(F)c(C)o1]
Het-1339
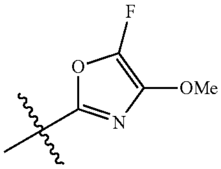
Het-1340
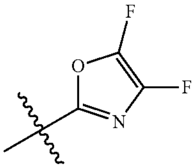
Het-1341
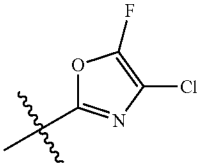 [SMILES: *c1nc(Cl)c(F)o1]
Het-1342
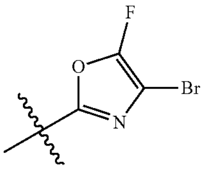
Het-1343
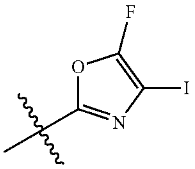

TABLE 3-continued
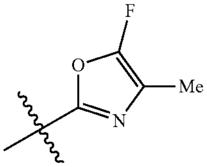
Het-1344
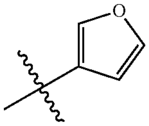 [SMILES: *c1ccoc1]
Het-1345
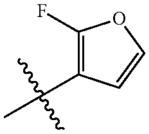 [SMILES: *c1ccoc1F]
Het-1346
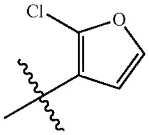
Het-1347
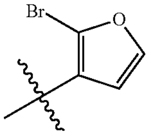 [SMILES: *c1ccoc1Br]
Het-1348
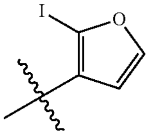 [SMILES: *c1ccoc1I]
Het-1349
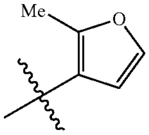 [SMILES: *c1ccoc1C]
Het-1350
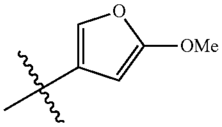 [SMILES: *c1coc(OC)c1]
Het-1351
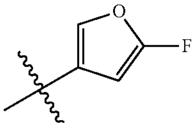
Het-1352
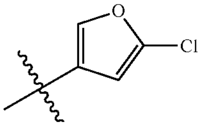 [SMILES: *c1coc(Cl)c1]
Het-1353
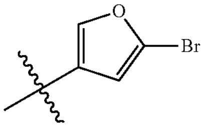 [SMILES: *c1coc(Br)c1]
Het-1354
TABLE 3-continued
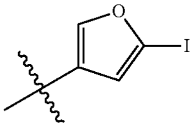 [SMILES: *c1coc(I)c1]
Het-1355
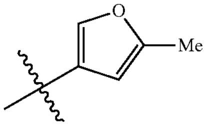 [SMILES: *c1coc(C)c1]
Het-1356
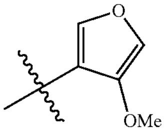 [SMILES: *c1cocc1OC]
Het-1357
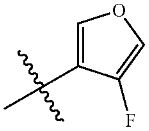 [SMILES: *c1cocc1F]
Het-1358
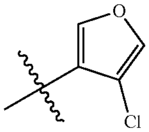 [SMILES: *c1cocc1Cl]
Het-1359
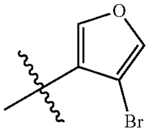 [SMILES: *c1cocc1Br]
Het-1360
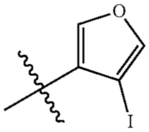 [SMILES: *c1cocc1I]
Het-1361
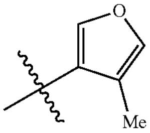 [SMILES: *c1cocc1C]
Het-1362
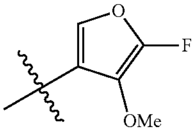 [SMILES: *c1coc(F)c1OC]
Het-1363
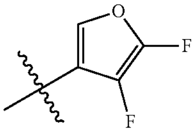
Het-1364
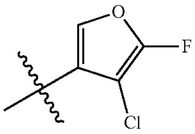 [SMILES: *c1coc(F)c1Cl]
Het-1365

TABLE 3-continued
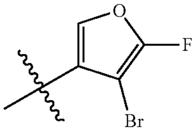 [SMILES: *c1coc(F)c1Br]
Het-1366
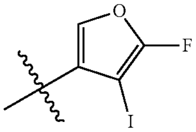
Het-1367
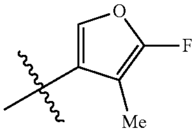 [SMILES: *c1coc(F)c1C]
Het-1368
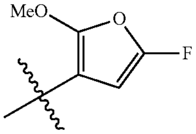 [SMILES: *c1cc(F)oc1OC]
Het-1369
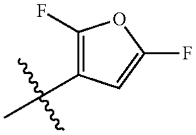
Het-1370
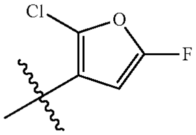
Het-1371
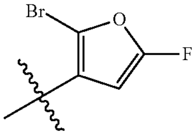 [SMILES: *c1cc(F)oc1Br]
Het-1372
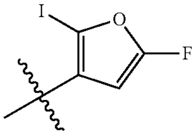 [SMILES: *c1cc(F)oc1I]
Het-1373
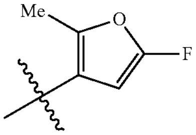 [SMILES: *c1cc(F)oc1C]
Het-1374
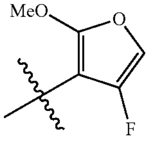 [SMILES: *c1c(F)coc1OC]
Het-1375
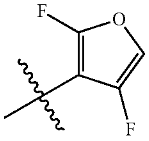 [SMILES: *c1c(F)coc1F]
Het-1376
TABLE 3-continued
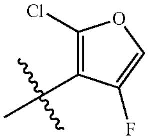
Het-1377
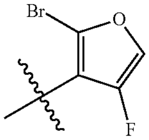 [SMILES: *c1c(F)coc1Cl]
Het-1378
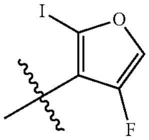
Het-1379
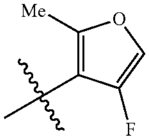
Het-1380
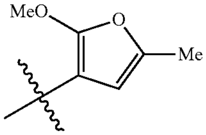 [SMILES: *c1cc(C)oc1OC]
Het-1381
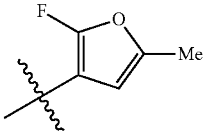
Het-1382
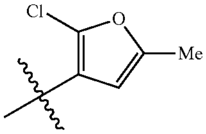
Het-1383
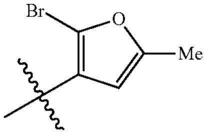 [SMILES: *c1cc(C)oc1Br]
Het-1384
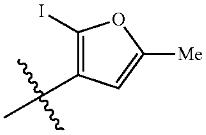 [SMILES: *c1cc(C)oc1I]
Het-1385
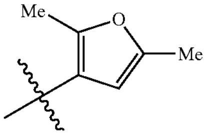 [SMILES: *c1cc(C)oc1C]
Het-1386

TABLE 3-continued
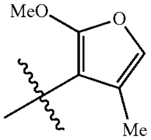 [SMILES: *c1c(C)coc1OC]
Het-1387
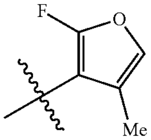
Het-1388
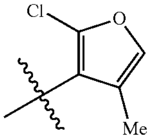 [SMILES: *c1c(C)coc1Cl]
Het-1389
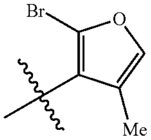 [SMILES: *c1c(C)coc1Br]
Het-1390
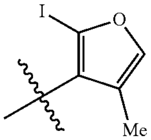 [SMILES: *c1c(C)coc1I]
Het-1391
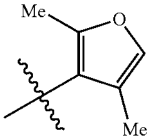 [SMILES: *c1c(C)coc1C]
Het-1392
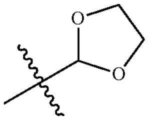 [SMILES: *C1OCCO1]
Het-1393
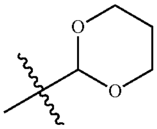 [SMILES: *C1OCCCO1]
Het-1394
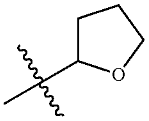 [SMILES: *C1CCCO1]
Het-1395
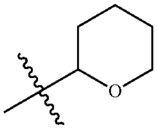 [SMILES: *C1CCCCO1]
Het-1396
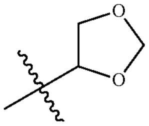 [SMILES: *C1COCO1]
Het-1397
TABLE 3-continued
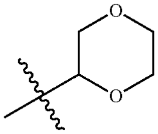 [SMILES: *C1COCCO1]
Het-1398
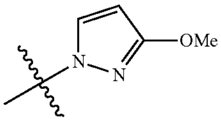 [SMILES: *n1ccc(OC)n1]
Het-1399
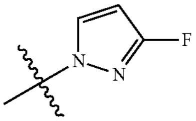 [SMILES: *n1ccc(F)n1]
Het-1400
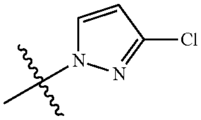 [SMILES: *n1ccc(Cl)n1]
Het-1401
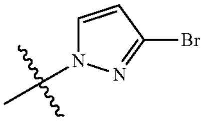 [SMILES: *n1ccc(Br)n1]
Het-1402
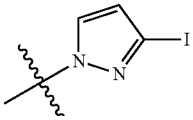 [SMILES: *n1ccc(I)n1]
Het-1403
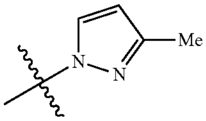 [SMILES: *n1ccc(C)n1]
Het-1404
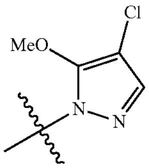 [SMILES: *n1ncc(Cl)c1OC]
Het-1405
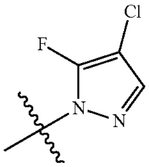
Het-1406
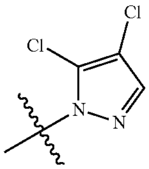 [SMILES: *n1ncc(Cl)c1Cl]
Het-1407

TABLE 3-continued
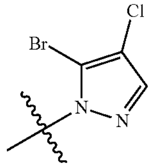
Het-1408
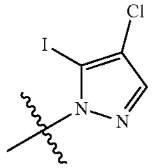 [SMILES: *n1ncc(Cl)c1I]
Het-1409
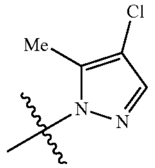 [SMILES: *n1ncc(Cl)c1C]
Het-1410
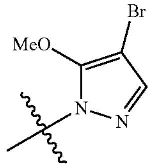 [SMILES: *n1ncc(Br)c1OC]
Het-1411
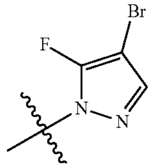 [SMILES: *n1ncc(Br)c1F]
Het-1412
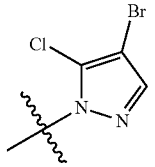 [SMILES: *n1ncc(Br)c1Cl]
Het-1413
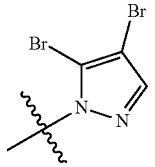 [SMILES: *n1ncc(Br)c1Br]
Het-1414
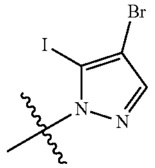 [SMILES: *n1ncc(Br)c1I]
Het-1415
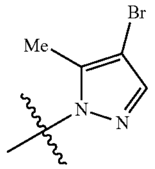 [SMILES: *n1ncc(Br)c1C]
Het-1416
TABLE 3-continued
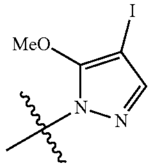 [SMILES: *n1ncc(I)c1OC]
Het-1417
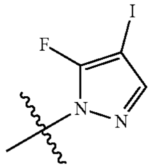 [SMILES: *n1ncc(I)c1F]
Het-1418
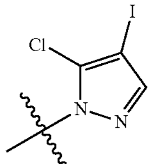 [SMILES: *n1ncc(I)c1Cl]
Het-1419
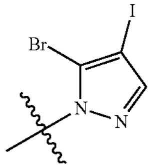 [SMILES: *n1ncc(I)c1Br]
Het-1420
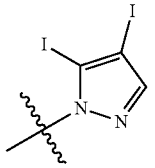
Het-1421
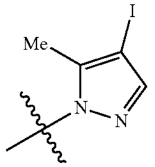 [SMILES: *n1ncc(I)c1C]
Het-1422
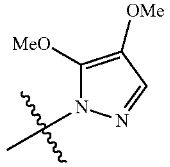 [SMILES: *n1ncc(OC)c1OC]
Het-1423
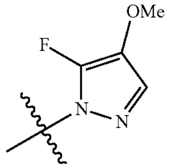 [SMILES: *n1ncc(OC)c1F]
Het-1424
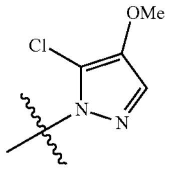 [SMILES: *n1ncc(OC)c1Cl]
Het-1425

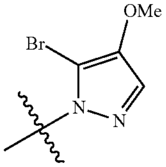 [SMILES: *n1ncc(OC)c1Br]
Het-1426
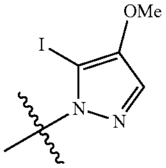 [SMILES: *n1ncc(OC)c1I]
Het-1427
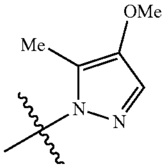 [SMILES: *n1ncc(OC)c1C]
Het-1428
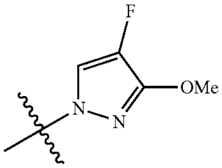
Het-1429
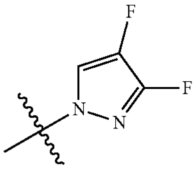
Het-1430
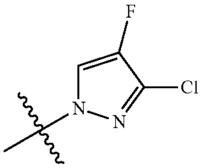 [SMILES: *n1cc(F)c(Cl)n1]
Het-1431
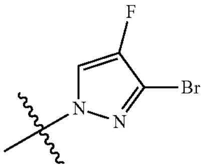
Het-1432
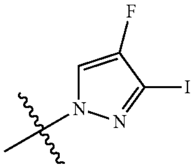
Het-1433
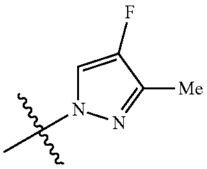 [SMILES: *n1cc(F)c(C)n1]
Het-1434
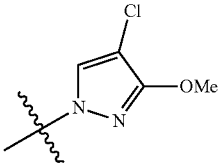 [SMILES: *n1cc(Cl)c(OC)n1]
Het-1435
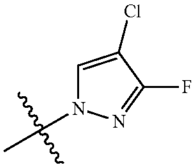 [SMILES: *n1cc(Cl)c(F)n1]
Het-1436
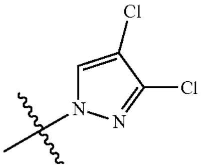 [SMILES: *n1cc(Cl)c(Cl)n1]
Het-1437
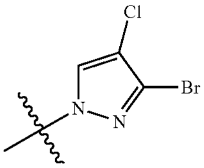
Het-1438
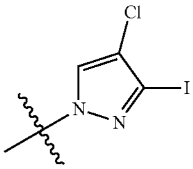
Het-1439
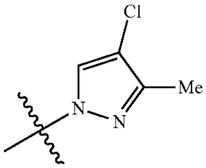 [SMILES: *n1cc(Cl)c(C)n1]
Het-1440
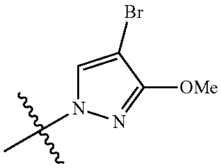 [SMILES: *n1cc(Br)c(OC)n1]
Het-1441
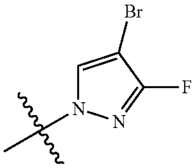 [SMILES: *n1cc(Br)c(F)n1]
Het-1442
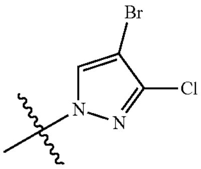 [SMILES: *n1cc(Br)c(Cl)n1]
Het-1443

TABLE 3-continued
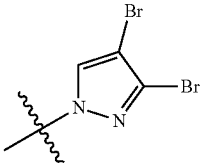 [SMILES: *n1cc(Br)c(Br)n1]
Het-1444
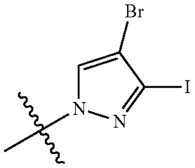 [SMILES: *n1cc(Br)c(I)n1]
Het-1445
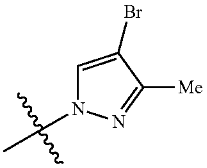 [SMILES: *n1cc(Br)c(C)n1]
Het-1446
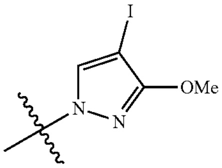 [SMILES: *n1cc(I)c(OC)n1]
Het-1447
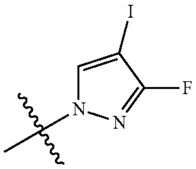 [SMILES: *n1cc(I)c(F)n1]
Het-1448
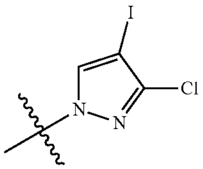 [SMILES: *n1cc(I)c(Cl)n1]
Het-1449
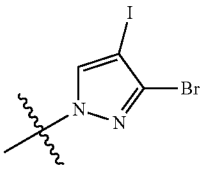 [SMILES: *n1cc(I)c(Br)n1]
Het-1450
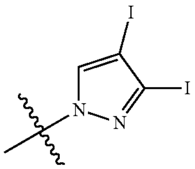 [SMILES: *n1cc(I)c(I)n1]
Het-1451
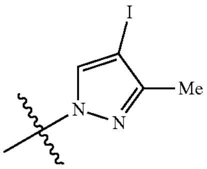 [SMILES: *n1cc(I)c(C)n1]
Het-1452
TABLE 3-continued
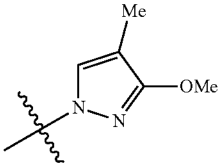 [SMILES: *n1cc(C)c(OC)n1]
Het-1453
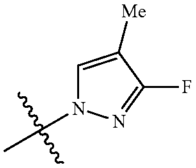 [SMILES: *n1cc(C)c(F)n1]
Het-1454
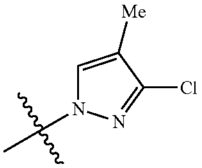 [SMILES: *n1cc(C)c(Cl)n1]
Het-1455
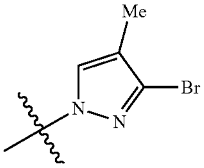 [SMILES: *n1cc(C)c(Br)n1]
Het-1456
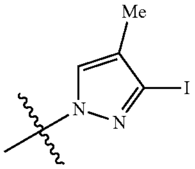 [SMILES: *n1cc(C)c(I)n1]
Het-1457
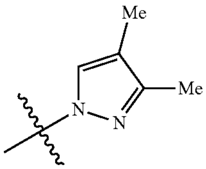 [SMILES: *n1cc(C)c(C)n1]
Het-1458
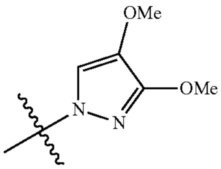 [SMILES: *n1cc(OC)c(OC)n1]
Het-1459
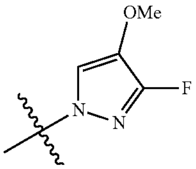 [SMILES: *n1cc(OC)c(F)n1]
Het-1460
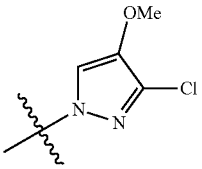 [SMILES: *n1cc(OC)c(Cl)n1]
Het-1461

TABLE 3-continued
| | |
|---|---|
| 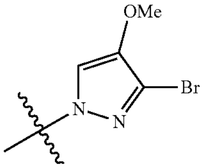 [SMILES: *n1cc(OC)c(Br)n1] | Het-1462 |
| 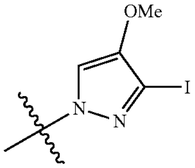 [SMILES: *n1cc(OC)c(I)n1] | Het-1463 |
| 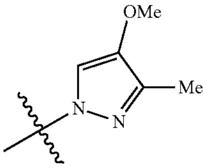 [SMILES: *n1cc(OC)c(C)n1] | Het-1464 |
| 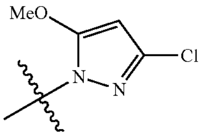 [SMILES: *n1nc(Cl)cc1OC] | Het-1465 |
| 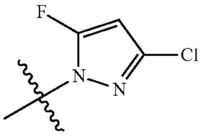 [SMILES: *n1nc(Cl)cc1F] | Het-1466 |
| 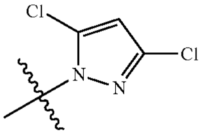 | Het-1467 |
| 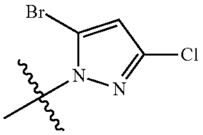 [SMILES: *n1nc(Cl)cc1Br] | Het-1468 |
| 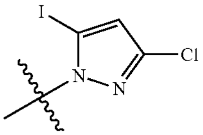 [SMILES: *n1nc(Cl)cc1I] | Het-1469 |
| 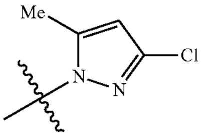 [SMILES: *n1nc(Cl)cc1C] | Het-1470 |
| 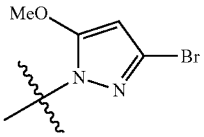 [SMILES: *n1nc(Br)cc1OC] | Het-1471 |
TABLE 3-continued
| | |
|---|---|
| 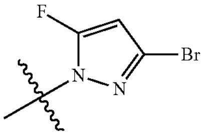 | Het-1472 |
| 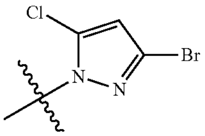 [SMILES: *n1nc(Br)cc1Cl] | Het-1473 |
| 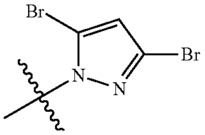 [SMILES: *n1nc(Br)cc1Br] | Het-1474 |
| 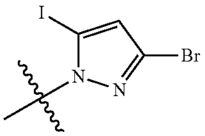 [SMILES: *n1nc(Br)cc1I] | Het-1475 |
| 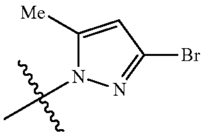 [SMILES: *n1nc(Br)cc1C] | Het-1476 |
| 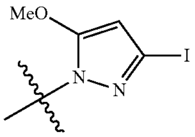 [SMILES: *n1nc(I)cc1OC] | Het-1477 |
| 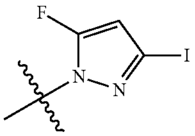 [SMILES: *n1nc(I)cc1F] | Het-1478 |
| 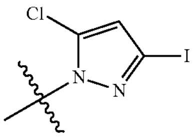 | Het-1479 |
| 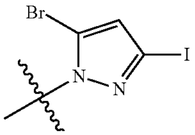 [SMILES: *n1nc(I)cc1Br] | Het-1480 |
| 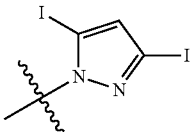 [SMILES: *n1nc(I)cc1I] | Het-1481 |
| 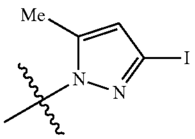 [SMILES: *n1nc(I)cc1C] | Het-1482 |

TABLE 3-continued
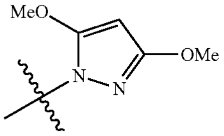 [SMILES: *n1nc(OC)cc1OC]
Het-1483
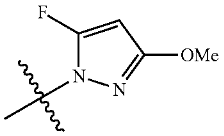
Het-1484
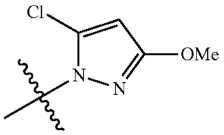
Het-1485
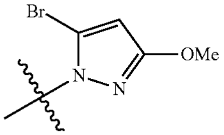 [SMILES: *n1nc(OC)cc1Cl]
Het-1486
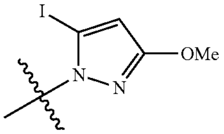 [SMILES: *n1nc(OC)cc1I]
Het-1487
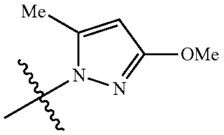 [SMILES: *n1nc(OC)cc1C]
Het-1488
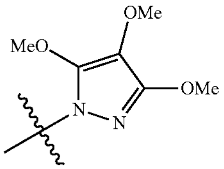 [SMILES: *n1nc(OC)c(OC)c1OC]
Het-1489
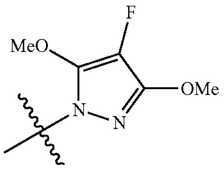
Het-1490
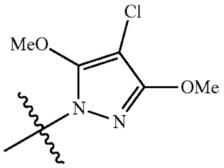
Het-1491
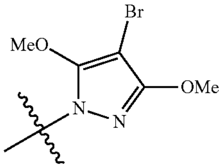 [SMILES: *n1nc(OC)c(Br)c1OC]
Het-1492
TABLE 3-continued
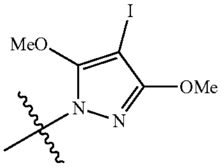 [SMILES: *n1nc(OC)c(I)c1OC]
Het-1493
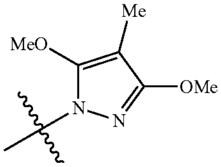 [SMILES: *n1nc(OC)c(C)c1OC]
Het-1494
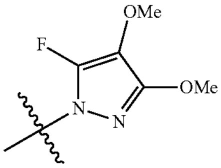 [SMILES: *n1nc(OC)c(OC)c1F]
Het-1495
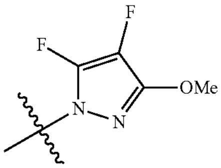
Het-1496
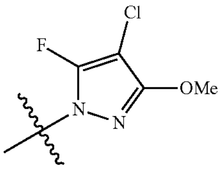 [SMILES: *n1nc(OC)c(Cl)c1F]
Het-1497
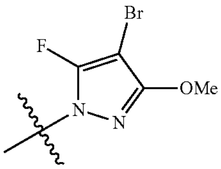 [SMILES: *n1nc(OC)c(Br)c1F]
Het-1498
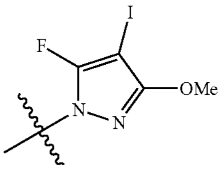 [SMILES: *n1nc(OC)c(I)c1F]
Het-1499
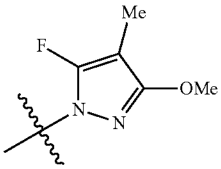
Het-1500
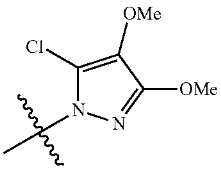 [SMILES: *n1nc(OC)c(OC)c1Cl]
Het-1501

TABLE 3-continued
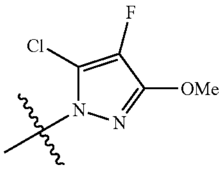
Het-1502
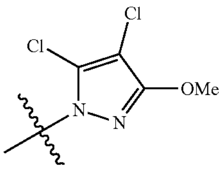 [SMILES: *n1nc(OC)c(Cl)c1Cl]
Het-1503
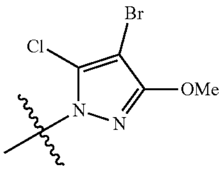 [SMILES: *n1nc(OC)c(Br)c1Cl]
Het-1504
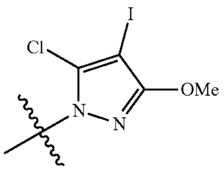 [SMILES: *n1nc(OC)c(I)c1Cl]
Het-1505
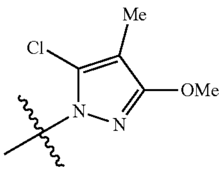 [SMILES: *n1nc(OC)c(C)c1Cl]
Het-1506
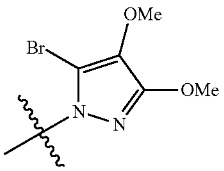 [SMILES: *n1nc(OC)c(OC)c1Br]
Het-1507
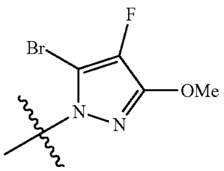
Het-1508
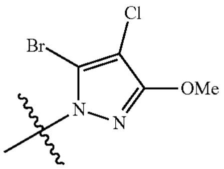
Het-1509
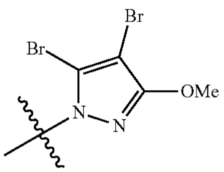 [SMILES: *n1nc(OC)c(Br)c1Br]
Het-1510
TABLE 3-continued
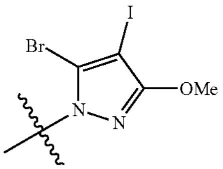 [SMILES: *n1nc(OC)c(I)c1Br]
Het-1511
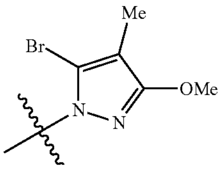 [SMILES: *n1nc(OC)c(C)c1Br]
Het-1512
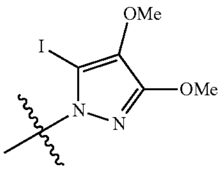 [SMILES: *n1nc(OC)c(OC)c1I]
Het-1513
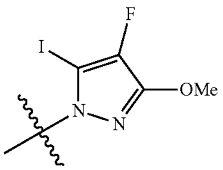
Het-1514
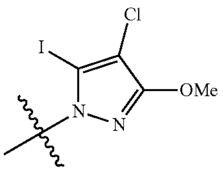 [SMILES: *n1nc(OC)c(Cl)c1I]
Het-1515
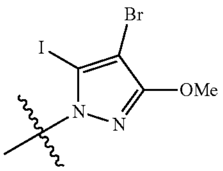 [SMILES: *n1nc(OC)c(Br)c1I]
Het-1516
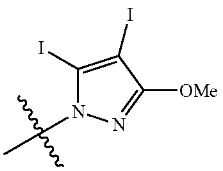 [SMILES: *n1nc(OC)c(I)c1I]
Het-1517
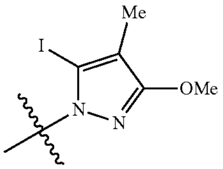 [SMILES: *n1nc(OC)c(C)c1I]
Het-1518
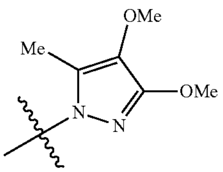 [SMILES: *n1nc(OC)c(OC)c1C]
Het-1519

TABLE 3-continued
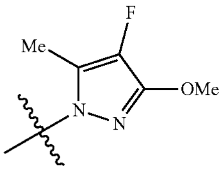
Het-1520
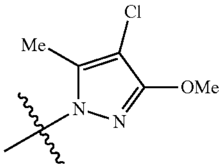 [SMILES: *n1nc(OC)c(Cl)c1C]
Het-1521
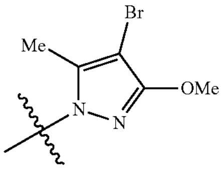 [SMILES: *n1nc(OC)c(Br)c1C]
Het-1522
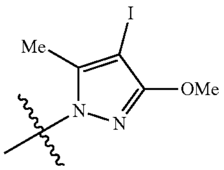 [SMILES: *n1nc(OC)c(I)c1C]
Het-1523
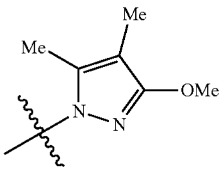 [SMILES: *n1nc(OC)c(C)c1C]
Het-1524
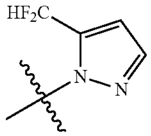 [SMILES: *n1nccc1C(F)F]
Het-1525
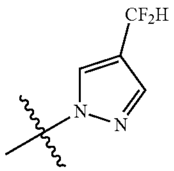 [SMILES: *n1cc(C(F)F)cn1]
Het-1526
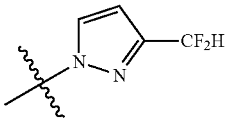 [SMILES: *n1ccc(C(F)F)n1]
Het-1527
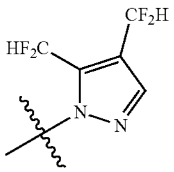 [SMILES: *n1ncc(C(F)F)c1C(F)F]
Het-1528
TABLE 3-continued
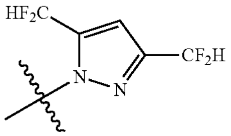 [SMILES: *n1nc(C(F)F)cc1C(F)F]
Het-1529
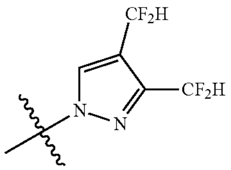 [SMILES: *n1cc(C(F)F)c(C(F)F)n1]
Het-1530
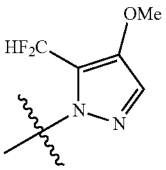
Het-1531
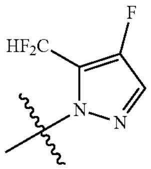 [SMILES: *n1ncc(F)c1C(F)F]
Het-1532
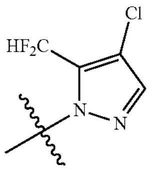
Het-1533
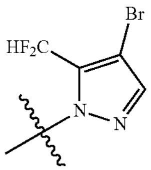 [SMILES: *n1ncc(Br)c1C(F)F]
Het-1534
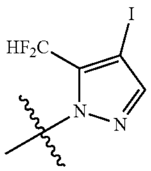 [SMILES: *n1ncc(I)c1C(F)F]
Het-1535
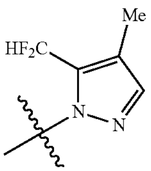
Het-1536
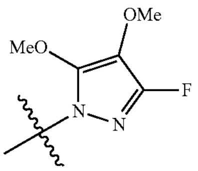
Het-1537

TABLE 3-continued
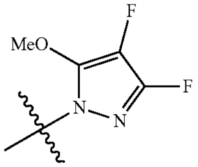
Het-1538
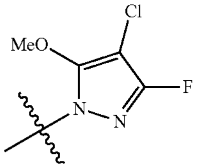
Het-1539
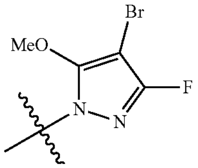
Het-1540
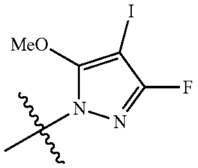
Het-1541
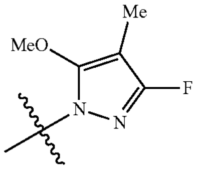
Het-1542
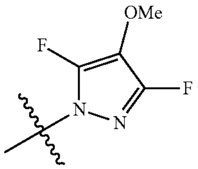
Het-1543
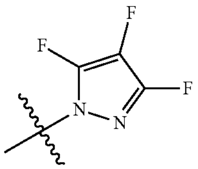
Het-1544
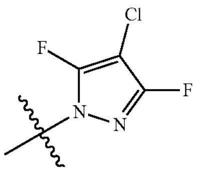
Het-1545
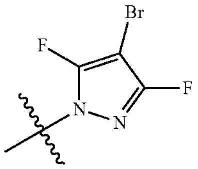
Het-1546
TABLE 3-continued
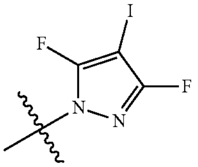
Het-1547
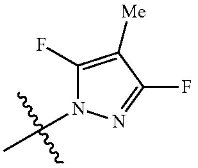
Het-1548
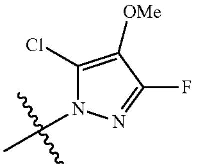 [SMILES: *n1nc(F)c(OC)c1Cl]
Het-1549
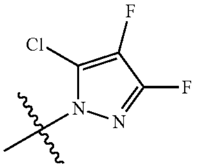
Het-1550
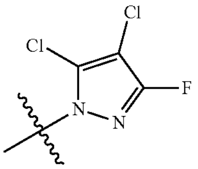
Het-1551
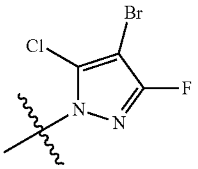
Het-1552
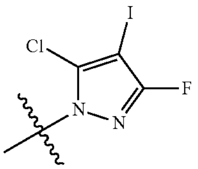
Het-1553
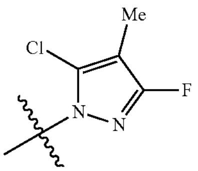 [SMILES: *n1nc(F)c(C)c1Cl]
Het-1554
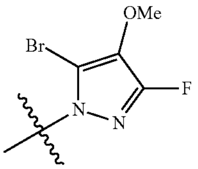
Het-1555

TABLE 3-continued
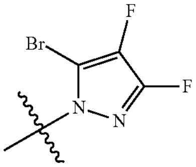
Het-1556
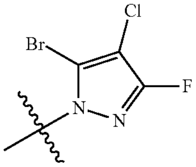
Het-1557
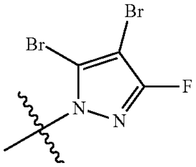 [SMILES: *n1nc(F)c(Br)c1Br]
Het-1558
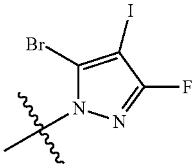
Het-1559
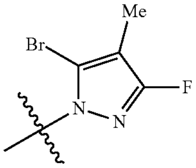
Het-1560
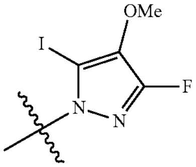
Het-1561
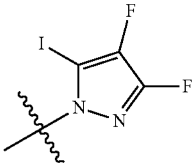
Het-1562
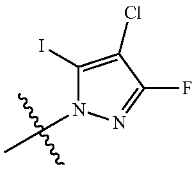
Het-1563
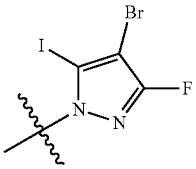
Het-1564
TABLE 3-continued
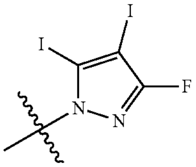 [SMILES: *n1nc(F)c(I)c1I]
Het-1565
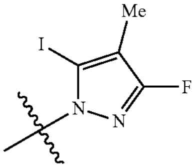 [SMILES: *n1nc(F)c(C)c1I]
Het-1566
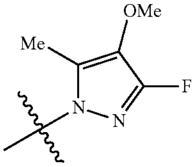
Het-1567
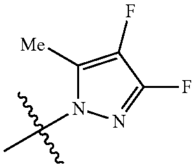
Het-1568
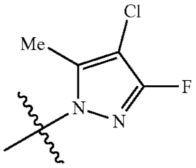 [SMILES: *n1nc(F)c(Br)c1C]
Het-1569
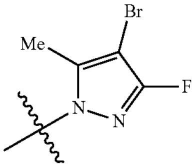
Het-1570
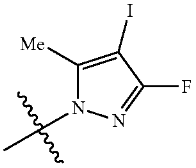 [SMILES: *n1nc(F)c(I)c1C]
Het-1571
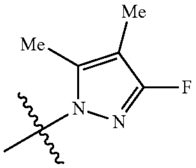 [SMILES: *n1nc(F)c(C)c1C]
Het-1572
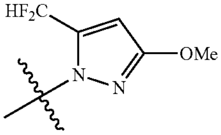 [SMILES: *n1nc(OC)cc1C(F)F]
Het-1573

TABLE 3-continued
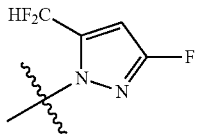
Het-1574
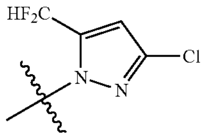 [SMILES: *n1nc(Cl)cc1C(F)F]
Het-1575
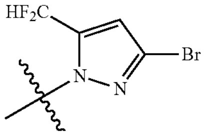 [SMILES: *n1nc(Br)cc1C(F)F]
Het-1576
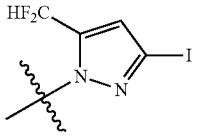 [SMILES: *n1nc(I)cc1C(F)F]
Het-1577
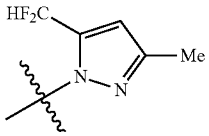 [SMILES: *n1nc(C)cc1C(F)F]
Het-1578
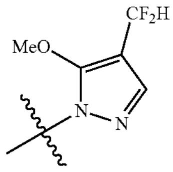 [SMILES: *n1ncc(C(F)F)c1OC]
Het-1579
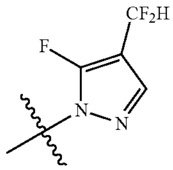
Het-1580
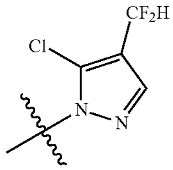 [SMILES: *n1ncc(C(F)F)c1Cl]
Het-1581
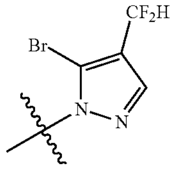 [SMILES: *n1ncc(C(F)F)c1Br]
Het-1582
TABLE 3-continued
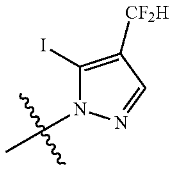 [SMILES: *n1ncc(C(F)F)c1I]
Het-1583
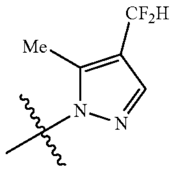 [SMILES: *n1ncc(C(F)F)c1C]
Het-1584
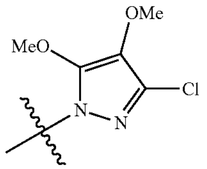 [SMILES: *n1nc(Cl)c(OC)c1OC]
Het-1585
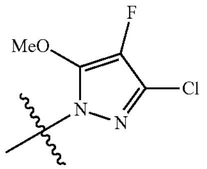 [SMILES: *n1nc(Cl)c(F)c1OC]
Het-1586
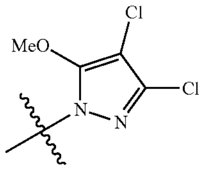 [SMILES: *n1nc(Cl)c(Cl)c1OC]
Het-1587
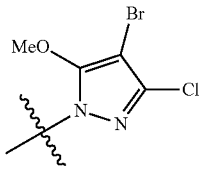 [SMILES: *n1nc(Cl)c(Br)c1OC]
Het-1588
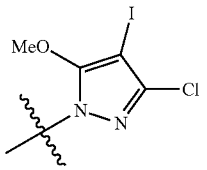 [SMILES: *n1nc(Cl)c(I)c1OC]
Het-1589
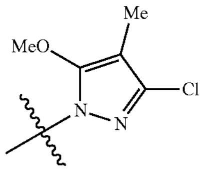 [SMILES: *n1nc(Cl)c(C)c1OC]
Het-1590
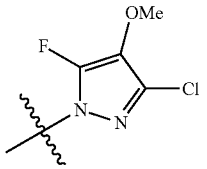 [SMILES: *n1nc(Cl)c(OC)c1F]
Het-1591

TABLE 3-continued
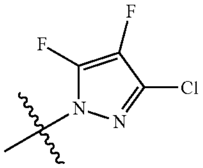 [SMILES: *n1nc(Cl)c(F)c1F]
Het-1592
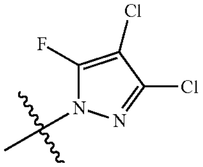 [SMILES: *n1nc(Cl)c(Cl)c1F]
Het-1593
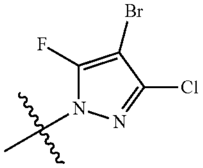
Het-1594
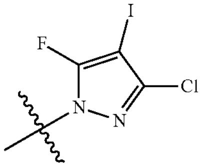 [SMILES: *n1nc(Cl)c(I)c1F]
Het-1595
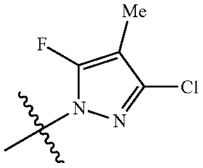 [SMILES: *n1nc(Cl)c(C)c1F]
Het-1596
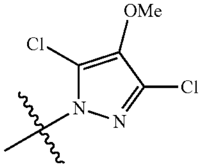 [SMILES: *n1nc(Cl)c(OC)c1Cl]
Het-1597
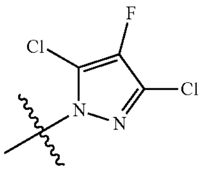 [SMILES: *n1nc(Cl)c(F)c1Cl]
Het-1598
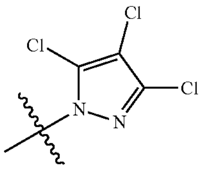
Het-1599
TABLE 3-continued
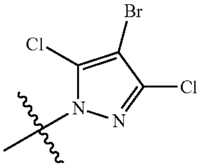 [SMILES: *n1nc(Cl)c(Br)c1Cl]
Het-1600
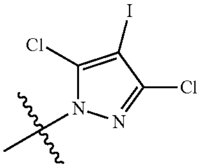 [SMILES: *n1nc(Cl)c(I)c1Cl]
Het-1601
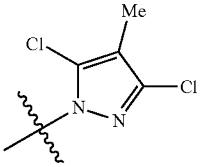 [SMILES: *n1nc(Cl)c(C)c1Cl]
Het-1602
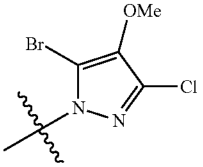 [SMILES: *n1nc(Cl)c(OC)c1Br]
Het-1603
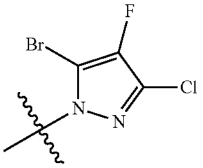 [SMILES: *n1nc(Cl)c(F)c1Br]
Het-1604
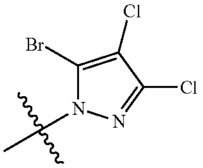 [SMILES: *n1nc(Cl)c(Cl)c1Br]
Het-1605
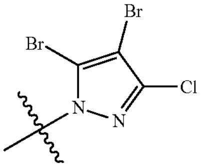 [SMILES: *n1nc(Cl)c(Br)c1Br]
Het-1606
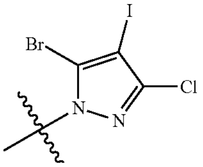 [SMILES: *n1nc(Cl)c(I)c1Br]
Het-1607
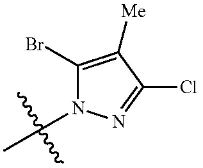 [SMILES: *n1nc(Cl)c(C)c1Br]
Het-1608

TABLE 3-continued
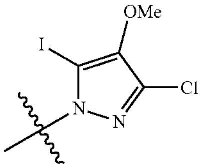 [SMILES: *n1nc(Cl)c(OC)c1I]
Het-1609
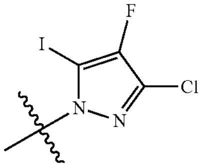 [SMILES: *n1nc(Cl)c(F)c1I]
Het-1610
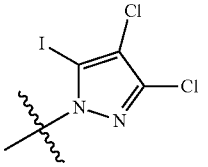 [SMILES: *n1nc(Cl)c(Cl)c1I]
Het-1611
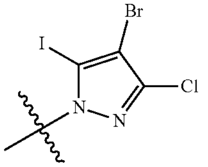 [SMILES: *n1nc(Cl)c(Br)c1I]
Het-1612
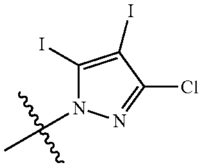 [SMILES: *n1nc(Cl)c(I)c1I]
Het-1613
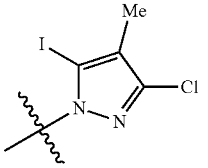 [SMILES: *n1nc(Cl)c(C)c1I]
Het-1614
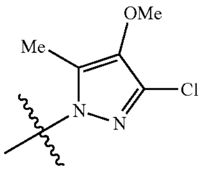 [SMILES: *n1nc(Cl)c(OC)c1C]
Het-1615
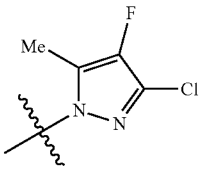 [SMILES: *n1nc(Cl)c(F)c1C]
Het-1616
TABLE 3-continued
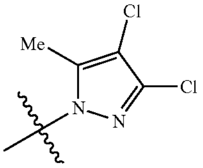
Het-1617
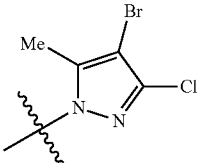 [SMILES: *n1nc(Cl)c(Br)c1C]
Het-1618
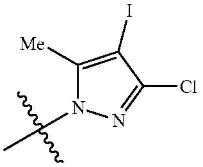 [SMILES: *n1nc(Cl)c(I)c1C]
Het-1619
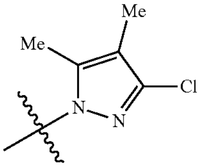 [SMILES: *n1nc(Cl)c(C)c1C]
Het-1620
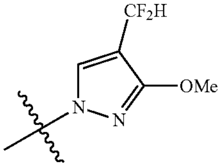 [SMILES: *n1cc(C(F)F)c(OC)n1]
Het-1621
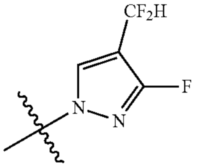 [SMILES: *n1cc(C(F)F)c(F)n1]
Het-1622
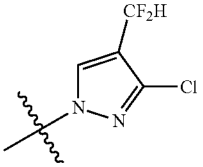 [SMILES: *n1cc(C(F)F)c(Cl)n1]
Het-1623
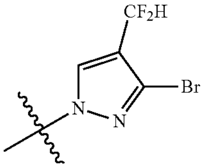 [SMILES: *n1cc(C(F)F)c(Br)n1]
Het-1624
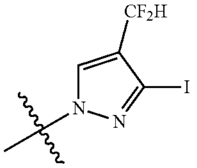 [SMILES: *n1cc(C(F)F)c(I)n1]
Het-1625

TABLE 3-continued
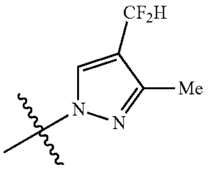 [SMILES: *n1cc(C(F)F)c(C)n1]
Het-1626
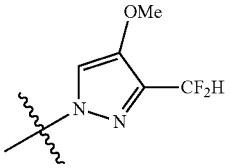 [SMILES: *n1cc(OC)c(C(F)F)n1]
Het-1627
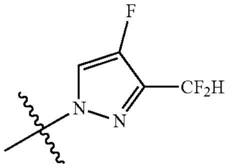 [SMILES: *n1cc(F)c(C(F)F)n1]
Het-1628
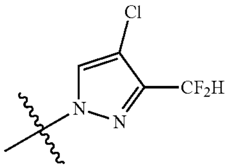 [SMILES: *n1cc(Cl)c(C(F)F)n1]
Het-1629
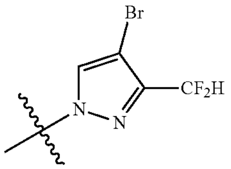 [SMILES: *n1cc(Br)c(C(F)F)n1]
Het-1630
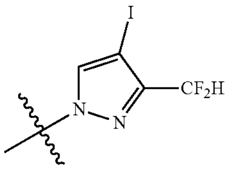 [SMILES: *n1cc(I)c(C(F)F)n1]
Het-1631
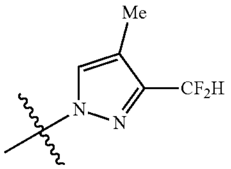 [SMILES: *n1cc(C)c(C(F)F)n1]
Het-1632
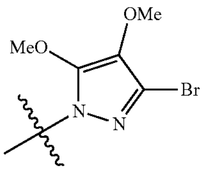 [SMILES: *n1nc(Br)c(OC)c1OC]
Het-1633
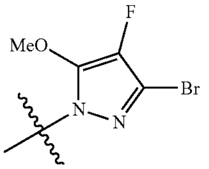
Het-1634
TABLE 3-continued
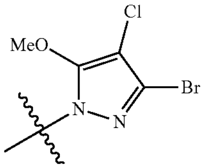 [SMILES: *n1nc(Br)c(Cl)c1OC]
Het-1635
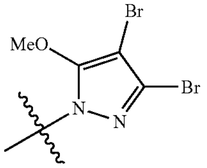 [SMILES: *n1nc(Br)c(Br)c1OC]
Het-1636
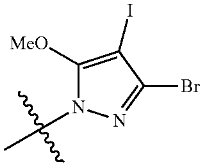 [SMILES: *n1nc(Br)c(I)c1OC]
Het-1637
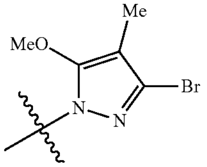 [SMILES: *n1nc(Br)c(C)c1OC]
Het-1638
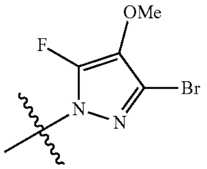 [SMILES: *n1nc(Br)c(OC)c1F]
Het-1639
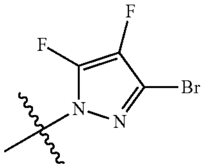 [SMILES: *n1nc(Br)c(F)c1F]
Het-1640
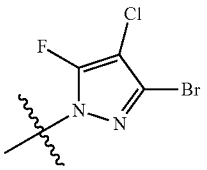 [SMILES: *n1nc(Br)c(Cl)c1F]
Het-1641
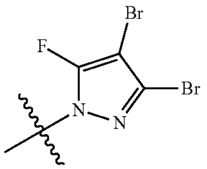 [SMILES: *n1nc(Br)c(Br)c1F]
Het-1642

TABLE 3-continued
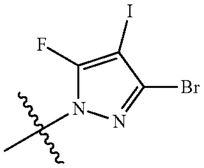 [SMILES: *n1nc(Br)c(I)c1F]
Het-1643
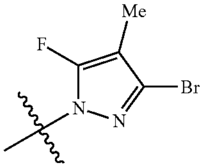
Het-1644
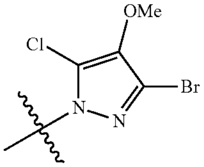 [SMILES: *n1nc(Br)c(OC)c1Cl]
Het-1645
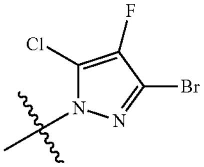
Het-1646
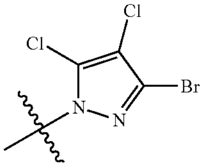
Het-1647
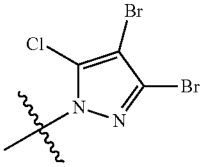 [SMILES: *n1nc(Br)c(Br)c1Cl]
Het-1648
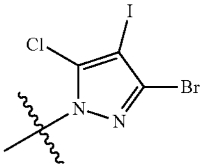 [SMILES: *n1nc(Br)c(I)c1Cl]
Het-1649
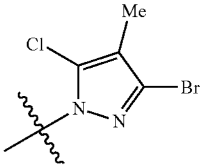 [SMILES: *n1nc(Br)c(C)c1Cl]
Het-1650
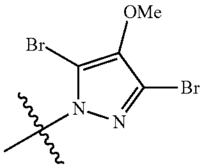
Het-1651
TABLE 3-continued
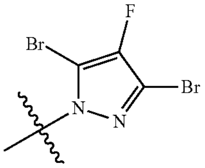 [SMILES: *n1nc(Br)c(F)c1Br]
Het-1652
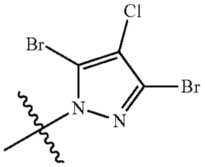 [SMILES: *n1nc(Br)c(Cl)c1Br]
Het-1653
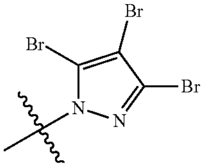 [SMILES: *n1nc(Br)c(Br)c1Br]
Het-1654
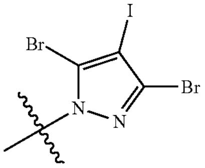 [SMILES: *n1nc(Br)c(I)c1Br]
Het-1655
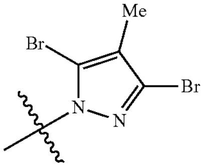 [SMILES: *n1nc(Br)c(C)c1Br]
Het-1656
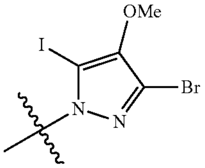 [SMILES: *n1nc(Br)c(OC)c1I]
Het-1657
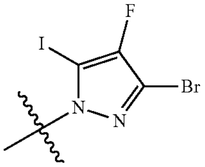 [SMILES: *n1nc(Br)c(F)c1I]
Het-1658
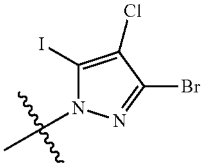 [SMILES: *n1nc(Br)c(Cl)c1I]
Het-1659

TABLE 3-continued
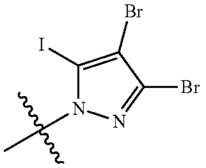 [SMILES: *n1nc(Br)c(Br)c1I]
Het-1660
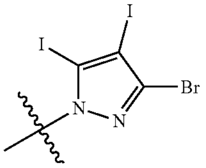 [SMILES: *n1nc(Br)c(I)c1I]
Het-1661
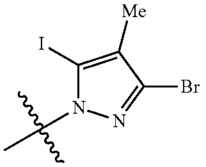 [SMILES: *n1nc(Br)c(C)c1I]
Het-1662
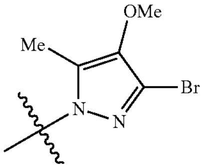 [SMILES: *n1nc(Br)c(OC)c1C]
Het-1683
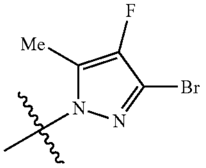
Het-1684
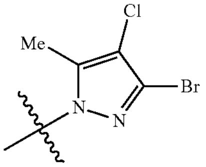 [SMILES: *n1nc(Br)c(Cl)c1C]
Het-1665
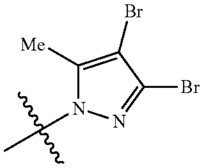 [SMILES: *n1nc(Br)c(Br)c1C]
Het-1666
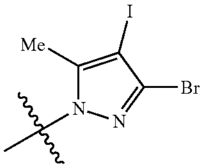 [SMILES: *n1nc(Br)c(I)c1C]
Het-1667
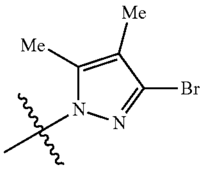 [SMILES: *n1nc(Br)c(C)c1C]
Het-1668
TABLE 3-continued
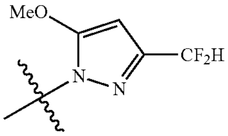 [SMILES: *n1nc(C(F)F)cc1OC]
Het-1669
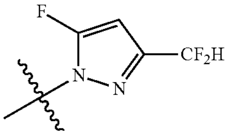 [SMILES: *n1nc(C(F)F)cc1F]
Het-1670
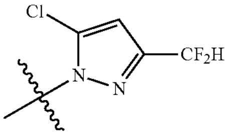 [SMILES: *n1nc(C(F)F)cc1Cl]
Het-1671
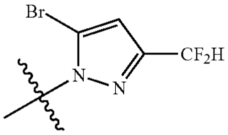 [SMILES: *n1nc(C(F)F)cc1Br]
Het-1672
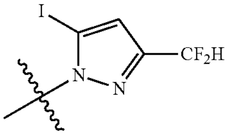 [SMILES: *n1nc(C(F)F)cc1I]
Het-1673
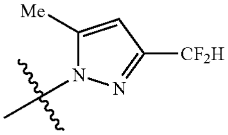 [SMILES: *n1nc(C(F)F)cc1C]
Het-1674
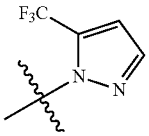 [SMILES: *n1nccc1C(F)(F)F]
Het-1675
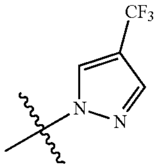 [SMILES: *n1cc(C(F)(F)F)cn1]
Het-1676
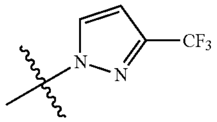 [SMILES: *n1ccc(C(F)(F)F)n1]
Het-1677
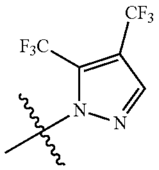 [SMILES: *n1ncc(C(F)(F)F)c1C(F)(F)F]
Het-1678

TABLE 3-continued
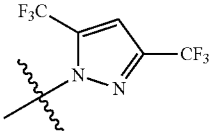 [SMILES: *n1nc(C(F)(F)F)cc1C(F)(F)F]
Het-1679
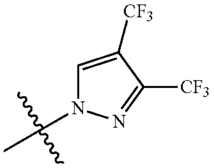 [SMILES: *n1cc(C(F)(F)F)c(C(F)(F)F)n1]
Het-1680
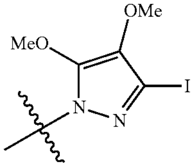 [SMILES: *n1nc(I)c(OC)c1OC]
Het-1681
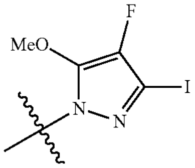
Het-1682
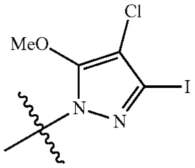 [SMILES: *n1nc(I)c(F)c1OC]
Het-1683
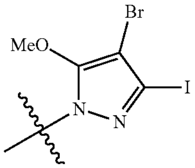 [SMILES: *n1nc(I)c(Br)c1OC]
Het-1684
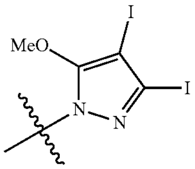 [SMILES: *n1nc(I)c(I)c1OC]
Het-1685
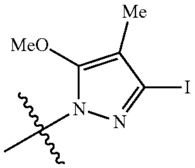 [SMILES: *n1nc(I)c(C)c1OC]
Het-1686
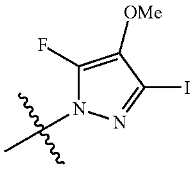 [SMILES: *n1nc(I)c(OC)c1F]
Het-1687
TABLE 3-continued
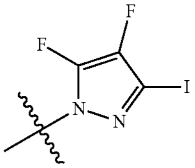
Het-1688
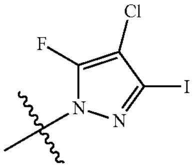
Het-1689
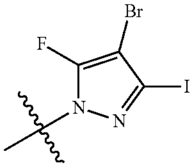 [SMILES: *n1nc(I)c(Br)c1F]
Het-1690
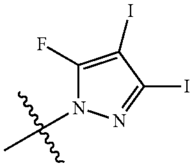 [SMILES: *n1nc(I)c(I)c1F]
Het-1691
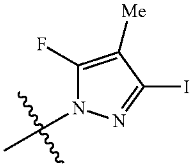 [SMILES: *n1nc(I)c(C)c1F]
Het-1692
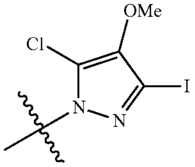 [SMILES: *n1nc(I)c(OC)c1Cl]
Het-1693
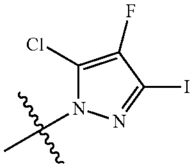
Het-1694
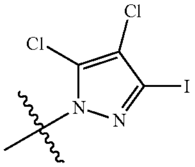 [SMILES: *n1nc(I)c(F)c1Cl]
Het-1695
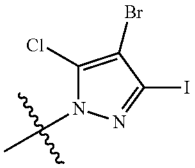 [SMILES: *n1nc(I)c(Br)c1Cl]
Het-1696

TABLE 3-continued
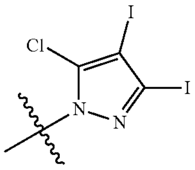 [SMILES: *n1nc(I)c(I)c1Cl]
Het-1697
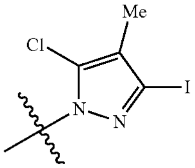 [SMILES: *n1nc(I)c(C)c1Cl]
Het-1698
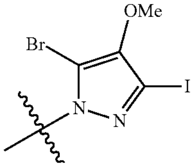 [SMILES: *n1nc(I)c(OC)c1Br]
Het-1699
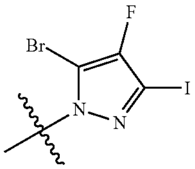
Het-1700
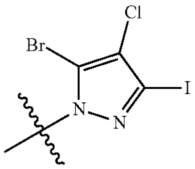 [SMILES: *n1nc(I)c(Cl)c1Br]
Het-1701
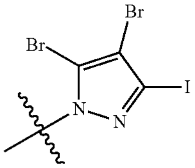 [SMILES: *n1nc(I)c(Br)c1Br]
Het-1702
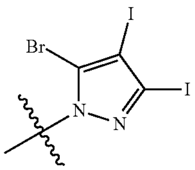 [SMILES: *n1nc(I)c(I)c1Br]
Het-1703
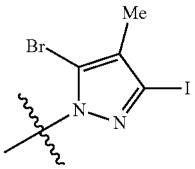 [SMILES: *n1nc(I)c(C)c1Br]
Het-1704
TABLE 3-continued
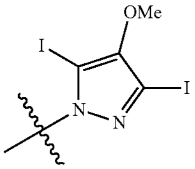 [SMILES: *n1nc(I)c(OC)c1I]
Het-1705
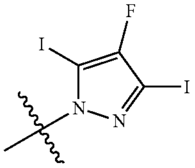
Het-1706
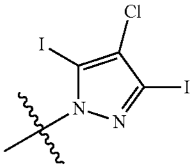 [SMILES: *n1nc(I)c(Cl)c1I]
Het-1707
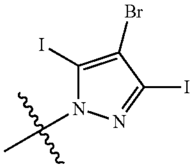 [SMILES: *n1nc(I)c(Br)c1I]
Het-1708
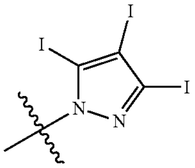 [SMILES: *n1nc(I)c(I)c1I]
Het-1709
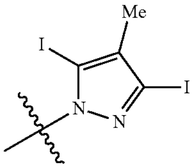 [SMILES: *n1nc(I)c(C)c1I]
Het-1710
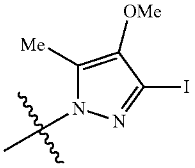 [SMILES: *n1nc(I)c(OC)c1C]
Het-1711
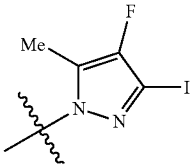
Het-1712
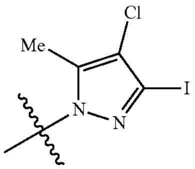 [SMILES: *n1nc(I)c(Cl)c1C]
Het-1713

TABLE 3-continued
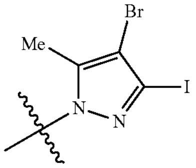 [SMILES: *n1nc(I)c(Br)c1C]
Het-1714
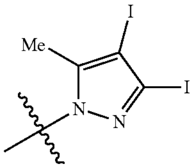 [SMILES: *n1nc(I)c(I)c1C]
Het-1715
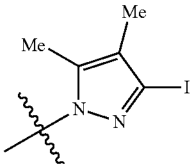 [SMILES: *n1nc(I)c(C)c1C]
Het-1716
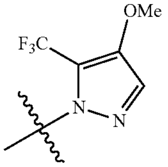 [SMILES: *n1ncc(OC)c1C(F)(F)F]
Het-1717
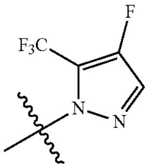 [SMILES: *n1ncc(F)c1C(F)(F)F]
Het-1718
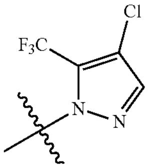 [SMILES: *n1ncc(Cl)c1C(F)(F)F]
Het-1719
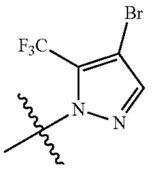 [SMILES: *n1ncc(Br)c1C(F)(F)F]
Het-1720
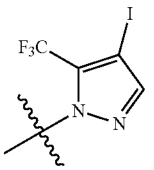 [SMILES: *n1ncc(I)c1C(F)(F)F]
Het-1721
TABLE 3-continued
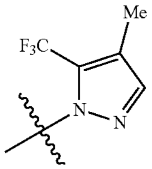 [SMILES: *n1ncc(C)c1C(F)(F)F]
Het-1722
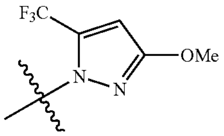 [SMILES: *n1nc(OC)cc1C(F)(F)F]
Het-1723
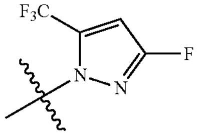 [SMILES: *n1nc(F)cc1C(F)(F)F]
Het-1724
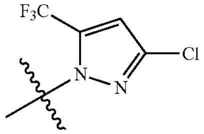 [SMILES: *n1nc(Cl)cc1C(F)(F)F]
Het-1725
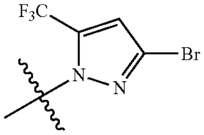 [SMILES: *n1nc(Br)cc1C(F)(F)F]
Het-1726
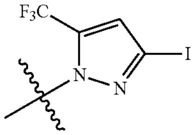 [SMILES: *n1nc(I)cc1C(F)(F)F]
Het-1727
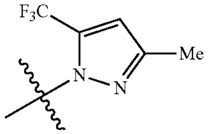
Het-1728
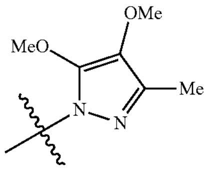 [SMILES: *n1nc(C)c(OC)c1OC]
Het-1729
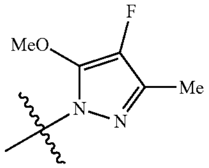
Het-1730
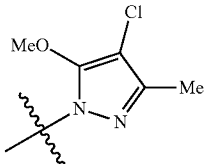 [SMILES: *n1nc(C)c(Cl)c1OC]
Het-1731

TABLE 3-continued
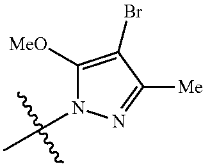 [SMILES: *n1nc(C)c(Br)c1OC]
Het-1732
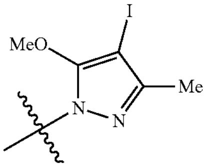 [SMILES: *n1nc(C)c(I)c1OC]
Het-1733
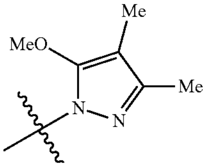 [SMILES: *n1nc(C)c(C)c1OC]
Het-1734
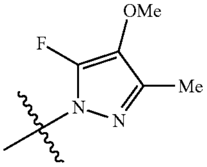
Het-1735
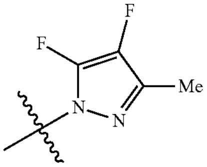
Het-1736
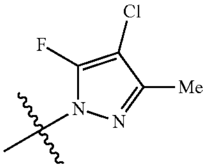
Het-1737
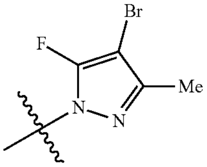
Het-1738
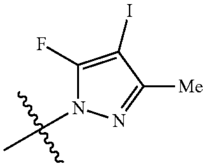
Het-1739
TABLE 3-continued
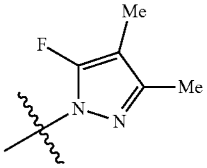
Het-1740
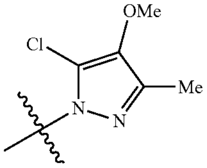 [SMILES: *n1nc(C)c(OC)c1Cl]
Het-1741
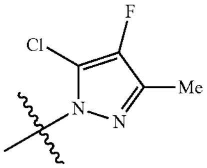
Het-1742
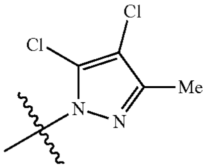 [SMILES: *n1nc(C)c(Cl)c1Cl]
Het-1743
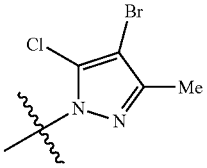 [SMILES: *n1nc(C)c(Br)c1Cl]
Het-1744
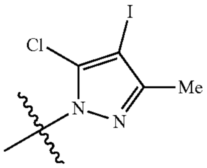 [SMILES: *n1nc(C)c(I)c1Cl]
Het-1745
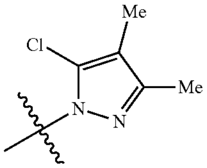 [SMILES: *n1nc(C)c(C)c1Cl]
Het-1746
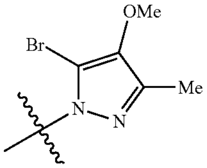 [SMILES: *n1nc(C)c(OC)c1Br]
Het-1747
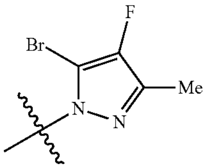
Het-1748

TABLE 3-continued
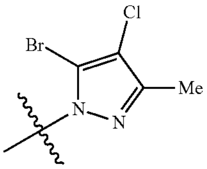
Het-1749
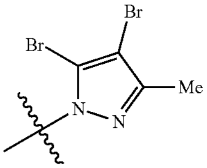 [SMILES: *n1nc(C)c(Br)c1Br]
Het-1750
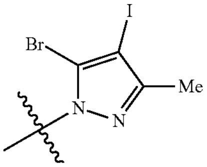 [SMILES: *n1nc(C)c(I)c1Br]
Het-1751
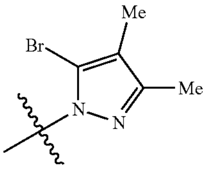 [SMILES: *n1nc(C)c(C)c1Br]
Het-1752
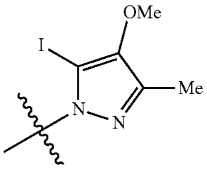 [SMILES: *n1nc(C)c(OC)c1I]
Het-1753
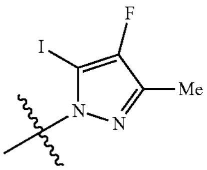 [SMILES: *n1nc(C)c(F)c1I]
Het-1754
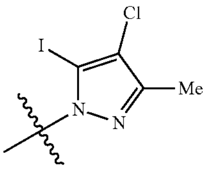
Het-1755
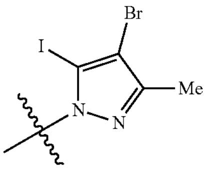 [SMILES: *n1nc(C)c(Br)c1I]
Het-1756
TABLE 3-continued
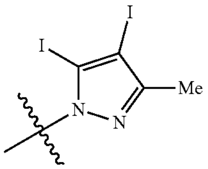 [SMILES: *n1nc(C)c(I)c1I]
Het-1757
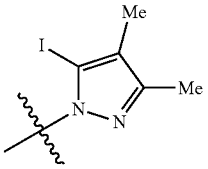 [SMILES: *n1nc(C)c(C)c1I]
Het-1758
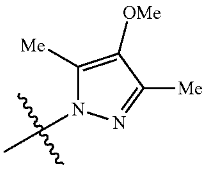 [SMILES: *n1nc(C)c(OC)c1C]
Het-1759
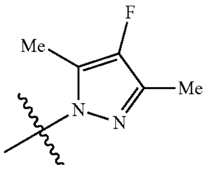
Het-1760
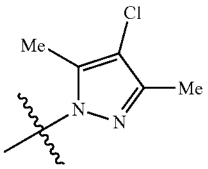 [SMILES: *n1nc(C)c(F)c1C]
Het-1761
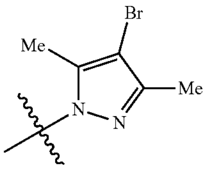 [SMILES: *n1nc(C)c(Br)c1C]
Het-1762
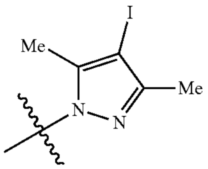 [SMILES: *n1nc(C)c(I)c1C]
Het-1763
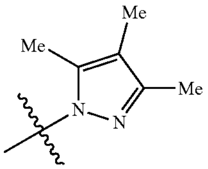 [SMILES: *n1nc(C)c(C)c1C]
Het-1764
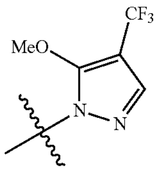 [SMILES: *n1ncc(C(F)(F)F)c1OC]
Het-1765

TABLE 3-continued
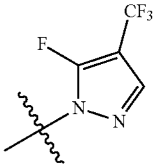
Het-1766
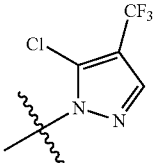 [SMILES: *n1ncc(C(F)(F)F)c1Cl]
Het-1767
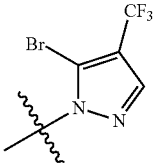 [SMILES: *n1ncc(C(F)(F)F)c1Br]
Het-1768
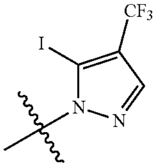 [SMILES: *n1ncc(C(F)(F)F)c1I]
Het-1769
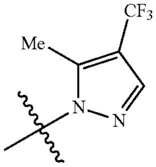 [SMILES: *n1ncc(C(F)(F)F)c1C]
Het-1770
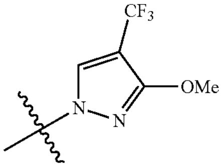 [SMILES: *n1cc(C(F)(F)F)c(OC)n1]
Het-1771
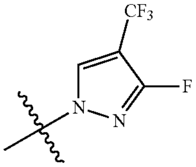
Het-1772
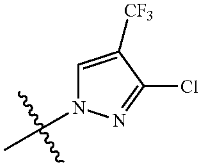 [SMILES: *n1cc(C(F)(F)F)c(Cl)n1]
Het-1773
TABLE 3-continued
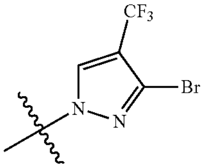 [SMILES: *n1cc(C(F)(F)F)c(Br)n1]
Het-1774
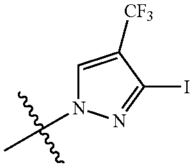 [SMILES: *n1cc(C(F)(F)F)c(I)n1]
Het-1775
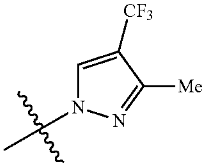 [SMILES: *n1cc(C(F)(F)F)c(C)n1]
Het-1776
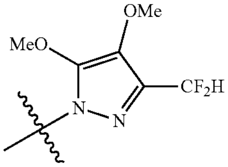 [SMILES: *n1nc(C(F)F)c(OC)c1OC]
Het-1777
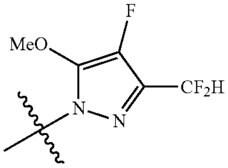 [SMILES: *n1nc(C(F)F)c(F)c1OC]
Het-1778
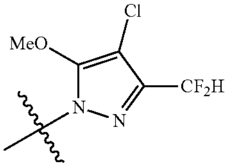
Het-1779
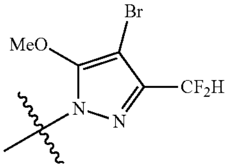 [SMILES: *n1nc(C(F)F)c(Br)c1OC]
Het-1780
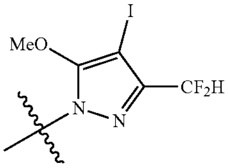 [SMILES: *n1nc(C(F)F)c(I)c1OC]
Het-1781
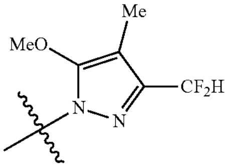 [SMILES: *n1nc(C(F)F)c(C)c1OC]
Het-1782

TABLE 3-continued
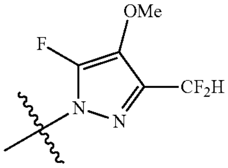 [SMILES: *n1nc(C(F)F)c(OC)c1F]
Het-1783
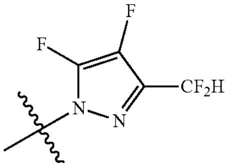 [SMILES: *n1nc(C(F)F)c(F)c1F]
Het-1784
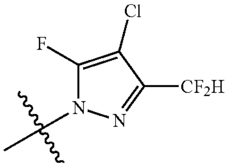
Het-1785
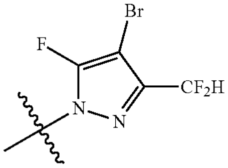 [SMILES: *n1nc(C(F)F)c(Br)c1F]
Het-1786
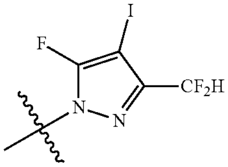 [SMILES: *n1nc(C(F)F)c(I)c1F]
Het-1787
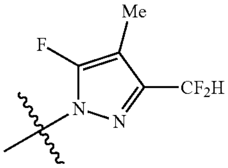 [SMILES: *n1nc(C(F)F)c(C)c1F]
Het-1788
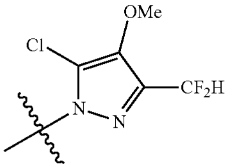 [SMILES: *n1nc(C(F)F)c(OC)c1Cl]
Het-1789
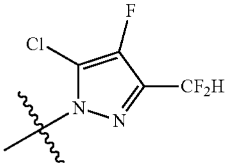 [SMILES: *n1nc(C(F)F)c(F)c1Cl]
Het-1790
TABLE 3-continued
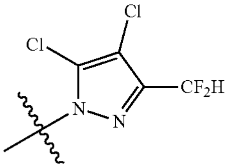 [SMILES: *n1nc(C(F)F)c(Cl)c1Cl]
Het-1791
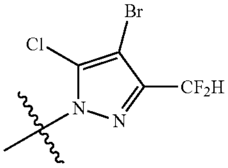 [SMILES: *n1nc(C(F)F)c(Br)c1Cl]
Het-1792
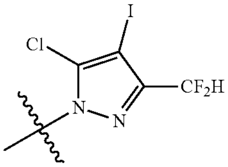 [SMILES: *n1nc(C(F)F)c(I)c1Cl]
Het-1793
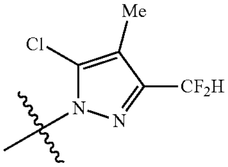 [SMILES: *n1nc(C(F)F)c(C)c1Cl]
Het-1794
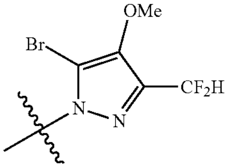 [SMILES: *n1nc(C(F)F)c(OC)c1Br]
Het-1795
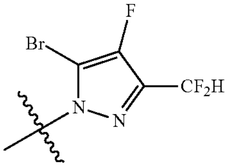 [SMILES: *n1nc(C(F)F)c(F)c1Br]
Het-1796
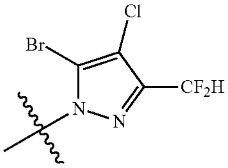 [SMILES: *n1nc(C(F)F)c(Cl)c1Br]
Het-1797
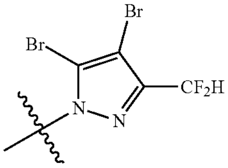 [SMILES: *n1nc(C(F)F)c(Br)c1Br]
Het-1798
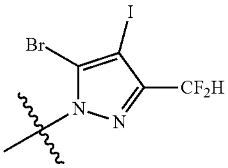 [SMILES: *n1nc(C(F)F)c(I)c1Br]
Het-1799

TABLE 3-continued
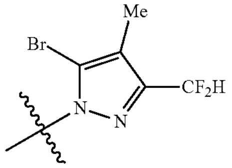 [SMILES: *n1nc(C(F)F)c(C)c1Br]
Het-1800
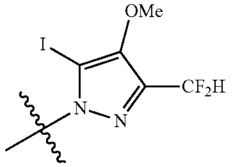 [SMILES: *n1nc(C(F)F)c(OC)c1I]
Het-1801
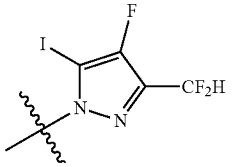 [SMILES: *n1nc(C(F)F)c(F)c1I]
Het-1802
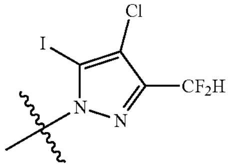
Het-1803
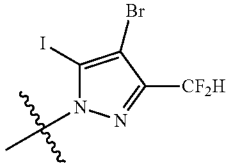 [SMILES: *n1nc(C(F)F)c(Br)c1I]
Het-1804
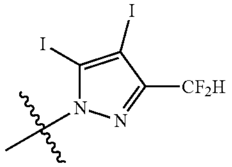 [SMILES: *n1nc(C(F)F)c(I)c1I]
Het-1805
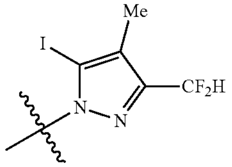 [SMILES: *n1nc(C(F)F)c(C)c1I]
Het-1806
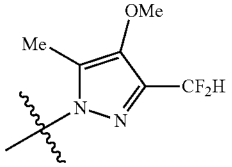 [SMILES: *n1nc(C(F)F)c(OC)c1C]
Het-1807
TABLE 3-continued
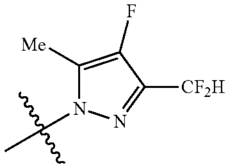 [SMILES: *n1nc(C(F)F)c(F)c1C]
Het-1808
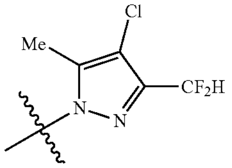
Het-1809
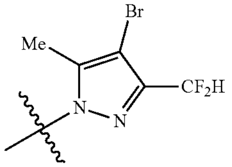 [SMILES: *n1nc(C(F)F)c(Br)c1C]
Het-1810
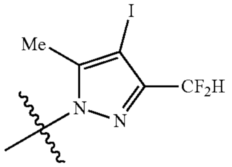 [SMILES: *n1nc(C(F)F)c(I)c1C]
Het-1811
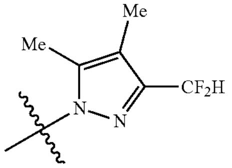 [SMILES: *n1nc(C(F)F)c(C)c1C]
Het-1812
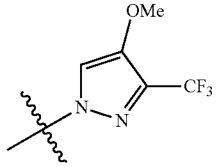 [SMILES: *n1cc(OC)c(C(F)(F)F)n1]
Het-1813
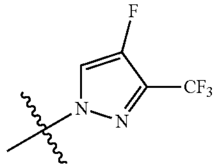
Het-1814
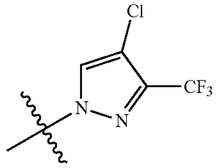 [SMILES: *n1cc(F)c(C(F)(F)F)n1]
Het-1815
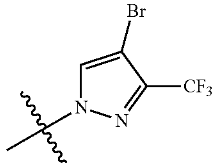 [SMILES: *n1cc(Br)c(C(F)(F)F)n1]
Het-1816

TABLE 3-continued
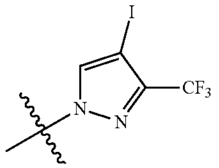 [SMILES: *n1cc(I)c(C(F)(F)F)n1]
Het-1817
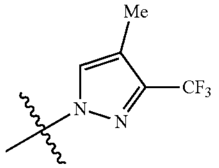 [SMILES: *n1cc(C)c(C(F)(F)F)n1]
Het-1818
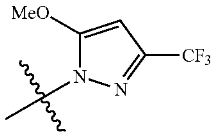 [SMILES: *n1nc(C(F)(F)F)cc1OC]
Het-1819
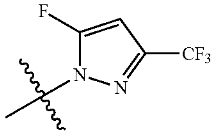 [SMILES: *n1nc(C(F)(F)F)cc1F]
Het-1820
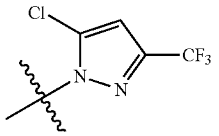 [SMILES: *n1nc(C(F)(F)F)cc1Cl]
Het-1821
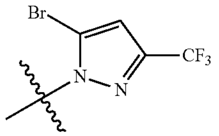 [SMILES: *n1nc(C(F)(F)F)cc1Br]
Het-1822
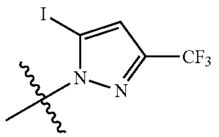 [SMILES: *n1nc(C(F)(F)F)cc1I]
Het-1823
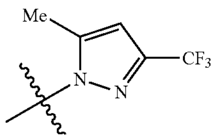 [SMILES: *n1nc(C(F)(F)F)cc1C]
Het-1824
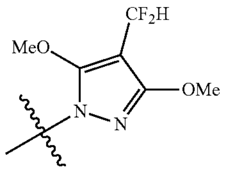 [SMILES: *n1nc(OC)c(C(F)F)c1OC]
Het-1825
TABLE 3-continued
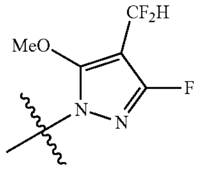 [SMILES: *n1nc(F)c(C(F)F)c1OC]
Het-1826
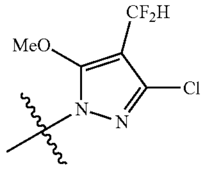 [SMILES: *n1nc(Cl)c(C(F)F)c1OC]
Het-1827
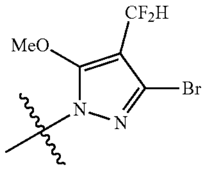 [SMILES: *n1nc(Br)c(C(F)F)c1OC]
Het-1828
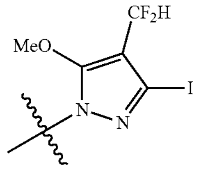 [SMILES: *n1nc(I)c(C(F)F)c1OC]
Het-1829
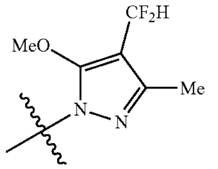 [SMILES: *n1nc(C)c(C(F)F)c1OC]
Het-1830
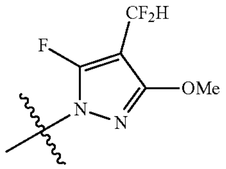 [SMILES: *n1nc(OC)c(C(F)F)c1F]
Het-1831
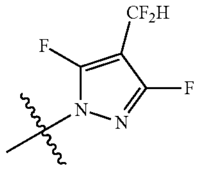
Het-1832
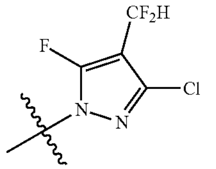 [SMILES: *n1nc(Cl)c(C(F)F)c1F]
Het-1833
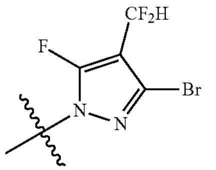 [SMILES: *n1nc(Br)c(C(F)F)c1F]
Het-1834

TABLE 3-continued
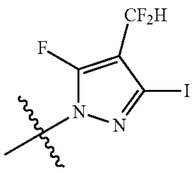 [SMILES: *n1nc(I)c(C(F)F)c1F]
Het-1835
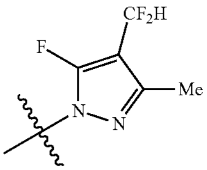
Het-1836
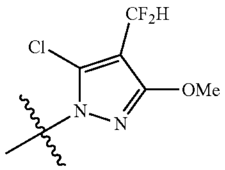 [SMILES: *n1nc(OC)c(C(F)F)c1Cl]
Het-1837
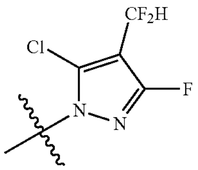
Het-1838
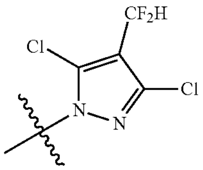 [SMILES: *n1nc(Cl)c(C(F)F)c1Cl]
Het-1839
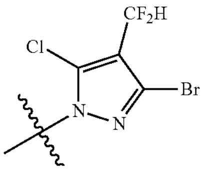 [SMILES: *n1nc(Br)c(C(F)F)c1Cl]
Het-1840
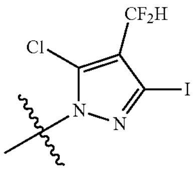 [SMILES: *n1nc(I)c(C(F)F)c1Cl]
Het-1841
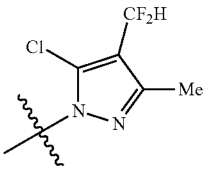 [SMILES: *n1nc(C)c(C(F)F)c1Cl]
Het-1842
TABLE 3-continued
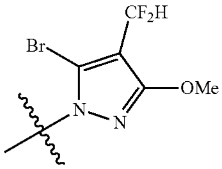 [SMILES: *n1nc(OC)c(C(F)F)c1Br]
Het-1843
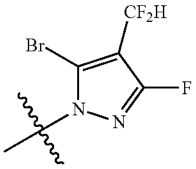 [SMILES: *n1nc(F)c(C(F)F)c1Br]
Het-1844
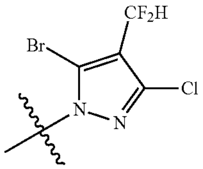 [SMILES: *n1nc(Cl)c(C(F)F)c1Br]
Het-1845
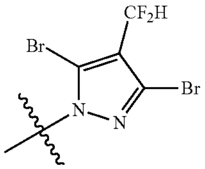 [SMILES: *n1nc(Br)c(C(F)F)c1Br]
Het-1846
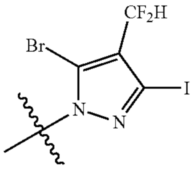 [SMILES: *n1nc(I)c(C(F)F)c1Br]
Het-1847
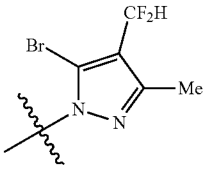 [SMILES: *n1nc(C)c(C(F)F)c1Br]
Het-1848
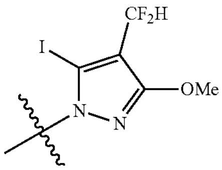 [SMILES: *n1nc(OC)c(C(F)F)c1I]
Het-1849
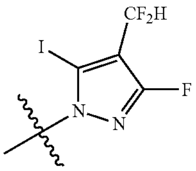 [SMILES: *n1nc(F)c(C(F)F)c1I]
Het-1850
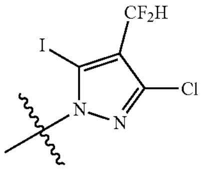 [SMILES: *n1nc(Cl)c(C(F)F)c1I]
Het-1851

TABLE 3-continued
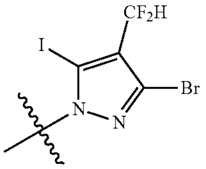 [SMILES: *n1nc(Br)c(C(F)F)c1I]
Het-1852
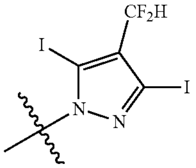 [SMILES: *n1nc(I)c(C(F)F)c1I]
Het-1853
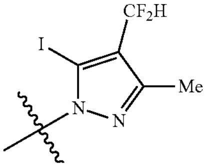 [SMILES: *n1nc(C)c(C(F)F)c1I]
Het-1854
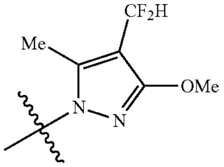 [SMILES: *n1nc(OC)c(C(F)F)c1C]
Het-1855
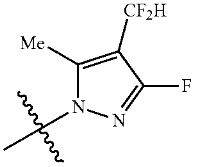
Het-1856
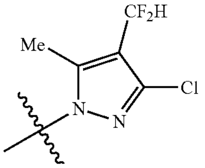 [SMILES: *n1nc(Cl)c(C(F)F)c1C]
Het-1857
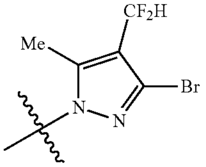 [SMILES: *n1nc(Br)c(C(F)F)c1C]
Het-1858
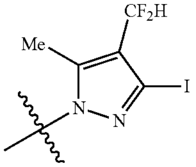 [SMILES: *n1nc(I)c(C(F)F)c1C]
Het-1859
TABLE 3-continued
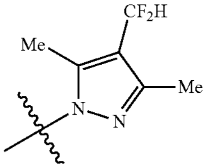 [SMILES: *n1nc(C)c(C(F)F)c1C]
Het-1860
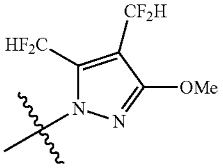
Het-1861
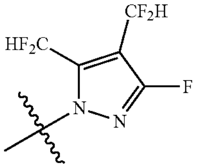 [SMILES: *n1nc(F)c(C(F)F)c1C(F)F]
Het-1862
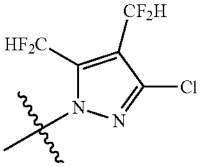 [SMILES: *n1nc(Cl)c(C(F)F)c1C(F)F]
Het-1863
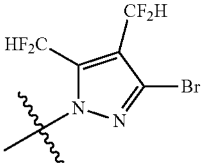 [SMILES: *n1nc(Br)c(C(F)F)c1C(F)F]
Het-1864
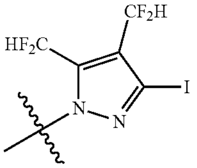 [SMILES: *n1nc(I)c(C(F)F)c1C(F)F]
Het-1865
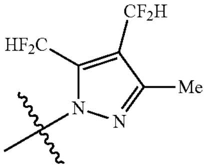 [SMILES: *n1nc(C)c(C(F)F)c1C(F)F]
Het-1866
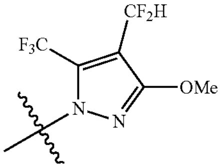
Het-1887
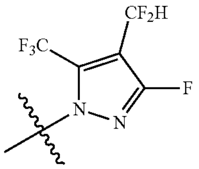 [SMILES: *n1nc(F)c(C(F)F)c1C(F)(F)F]
Het-1868

TABLE 3-continued
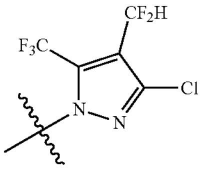 [SMILES: *n1nc(Cl)c(C(F)F)c1C(F)(F)F]
Het-1869
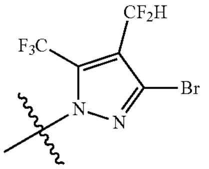 [SMILES: *n1nc(Br)c(C(F)F)c1C(F)(F)F]
Het-1870
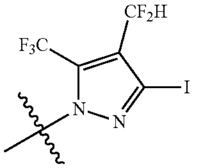
Het-1871
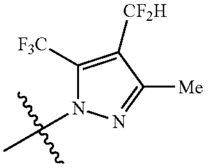 [SMILES: *n1nc(C)c(C(F)F)c1C(F)(F)F]
Het-1872
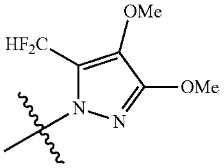 [SMILES: *n1nc(OC)c(OC)c1C(F)F]
Het-1873
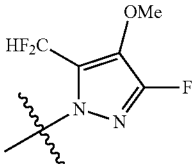
Het-1874
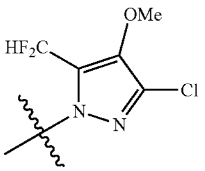 [SMILES: *n1nc(Cl)c(OC)c1C(F)F]
Het-1875
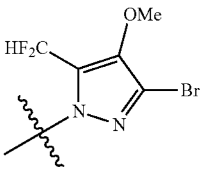 [SMILES: *n1nc(Br)c(OC)c1C(F)F]
Het-1876
TABLE 3-continued
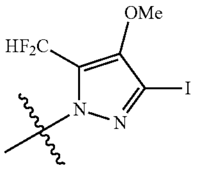 [SMILES: *n1nc(I)c(OC)c1C(F)F]
Het-1877
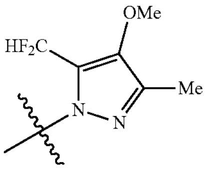 [SMILES: *n1nc(C)c(OC)c1C(F)F]
Het-1878
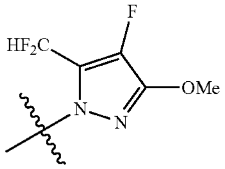
Het-1879
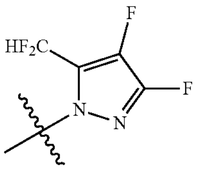
Het-1880
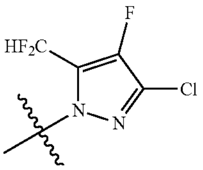
Het-1881
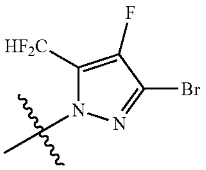 [SMILES: *n1nc(Br)c(F)c1C(F)F]
Het-1882
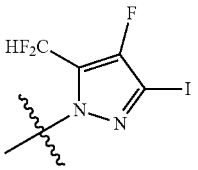
Het-1883
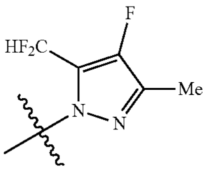
Het-1884
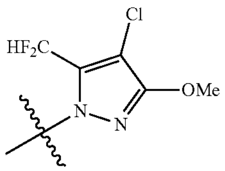 [SMILES: *n1nc(OC)c(Cl)c1C(F)F]
Het-1885

TABLE 3-continued
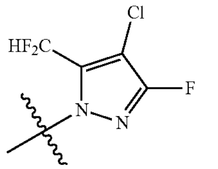
Het-1886
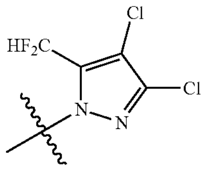 [SMILES: *n1nc(Cl)c(Cl)c1C(F)F]
Het-1887
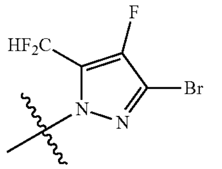
Het-1888
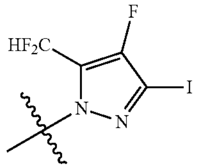
Het-1889
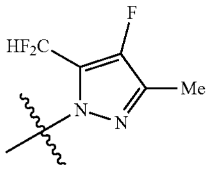 [SMILES: *n1nc(C)c(F)c1C(F)F]
Het-1890
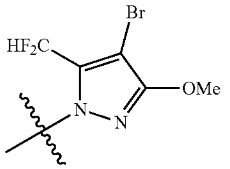
Het-1891
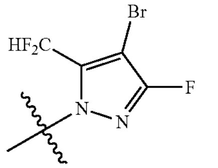
Het-1892
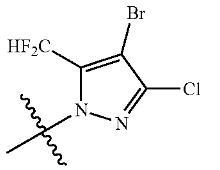 [SMILES: *n1nc(Cl)c(Br)c1C(F)F]
Het-1893
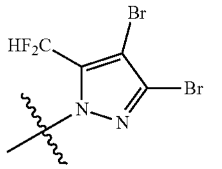 [SMILES: *n1nc(Br)c(Br)c1C(F)F]
Het-1894
TABLE 3-continued
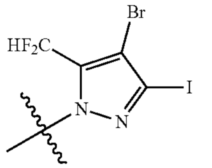 [SMILES: *n1nc(I)c(Br)c1C(F)F]
Het-1895
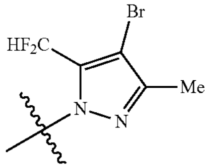 [SMILES: *n1nc(C)c(Br)c1C(F)F]
Het-1896
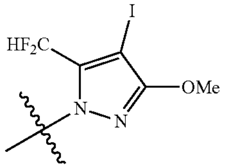 [SMILES: *n1nc(OC)c(I)c1C(F)F]
Het-1897
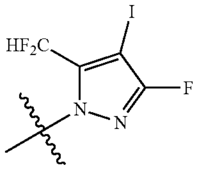 [SMILES: *n1nc(F)c(I)c1C(F)F]
Het-1898
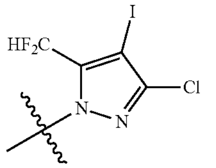 [SMILES: *n1nc(Cl)c(I)c1C(F)F]
Het-1899
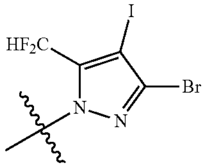
Het-1900
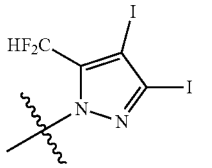 [SMILES: *n1nc(I)c(I)c1C(F)F]
Het-1901
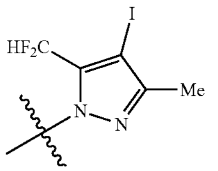 [SMILES: *n1nc(C)c(I)c1C(F)F]
Het-1902
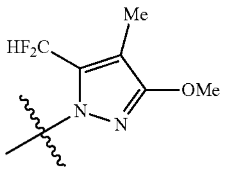 [SMILES: *n1nc(OC)c(C)c1C(F)F]
Het-1903

TABLE 3-continued
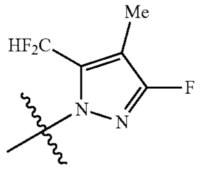
Het-1904
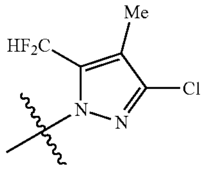 [SMILES: *n1nc(Cl)c(C)c1C(F)F]
Het-1905
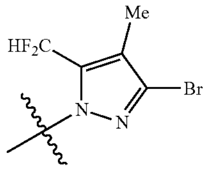 [SMILES: *n1nc(Br)c(C)c1C(F)F]
Het-1906
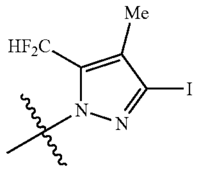 [SMILES: *n1nc(I)c(C)c1C(F)F]
Het-1907
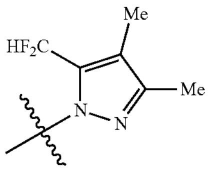 [SMILES: *n1nc(C)c(C)c1C(F)F]
Het-1908
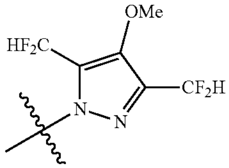 [SMILES: *n1nc(C(F)F)c(OC)c1C(F)F]
Het-1909
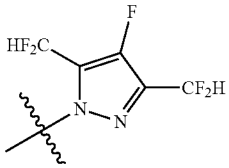 [SMILES: *n1nc(C(F)F)c(F)c1C(F)F]
Het-1910
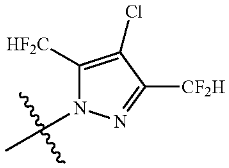 [SMILES: *n1nc(C(F)F)c(Cl)c1C(F)F]
Het-1911
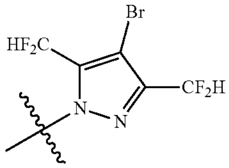 [SMILES: *n1nc(C(F)F)c(Br)c1C(F)F]
Het-1912
TABLE 3-continued
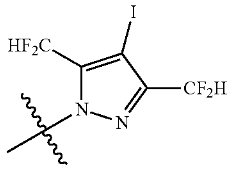 [SMILES: *n1nc(C(F)F)c(I)c1C(F)F]
Het-1913
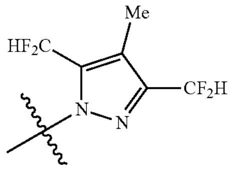 [SMILES: *n1nc(C(F)F)c(C)c1C(F)F]
Het-1914
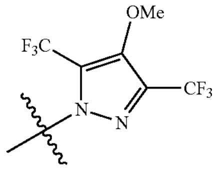 [SMILES: *n1nc(C(F)(F)F)c(OC)c1C(F)(F)F]
Het-1915
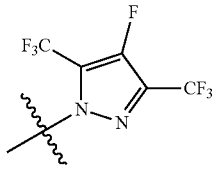
Het-1916
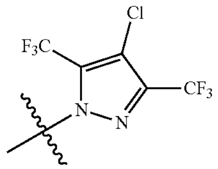 [SMILES: *n1nc(C(F)(F)F)c(Cl)c1C(F)(F)F]
Het-1917
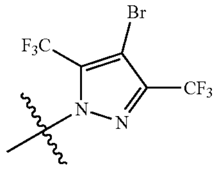 [SMILES: *n1nc(C(F)(F)F)c(Br)c1C(F)(F)F]
Het-1918
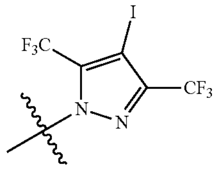 [SMILES: *n1nc(C(F)(F)F)c(I)c1C(F)(F)F]
Het-1919
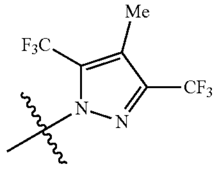 [SMILES: *n1nc(C(F)(F)F)c(C)c1C(F)(F)F]
Het-1920

TABLE 3-continued
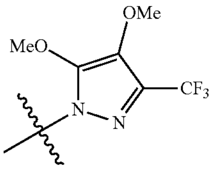 [SMILES: *n1nc(C(F)(F)F)c(OC)c1OC]
Het-1921
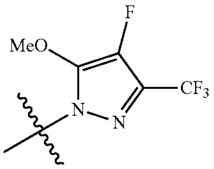 [SMILES: *n1nc(C(F)(F)F)c(F)c1OC]
Het-1922
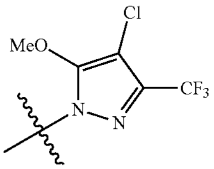 [SMILES: *n1nc(C(F)(F)F)c(Cl)c1OC]
Het-1923
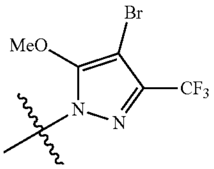 [SMILES: *n1nc(C(F)(F)F)c(Br)c1OC]
Het-1924
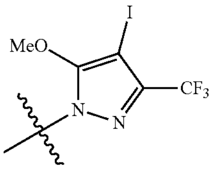 [SMILES: *n1nc(C(F)(F)F)c(I)c1OC]
Het-1925
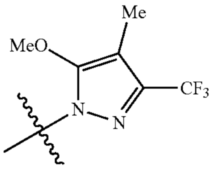 [SMILES: *n1nc(C(F)(F)F)c(C)c1OC]
Het-1926
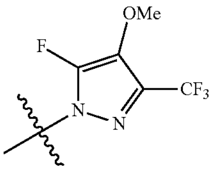
Het-1927
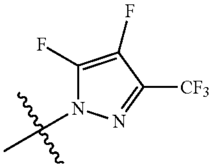
Het-1928
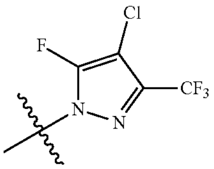
Het-1929
TABLE 3-continued
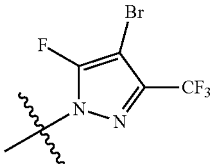
Het-1930
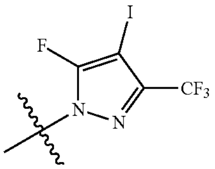 [SMILES: *n1nc(C(F)(F)F)c(I)c1F]
Het-1931
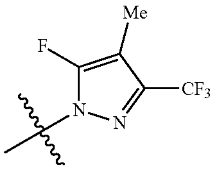
Het-1932
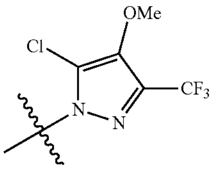 [SMILES: *n1nc(C(F)(F)F)c(OC)c1Cl]
Het-1933
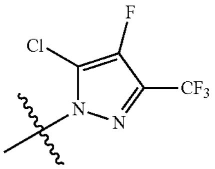
Het-1934
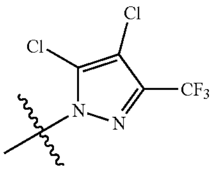 [SMILES: *n1nc(C(F)(F)F)c(Cl)c1Cl]
Het-1935
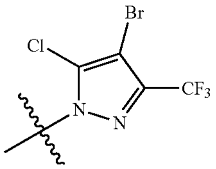 [SMILES: *n1nc(C(F)(F)F)c(Br)c1Cl]
Het-1936
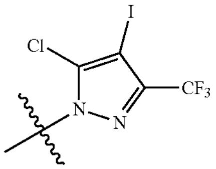 [SMILES: *n1nc(C(F)(F)F)c(I)c1Cl]
Het-1937
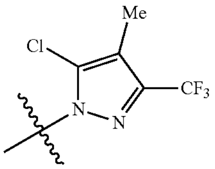 [SMILES: *n1nc(C(F)(F)F)c(C)c1Cl]
Het-1938

TABLE 3-continued
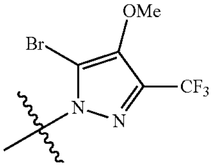 [SMILES: *n1nc(C(F)(F)F)c(OC)c1Br]
Het-1939
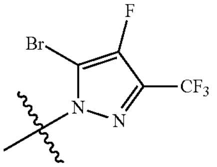
Het-1940
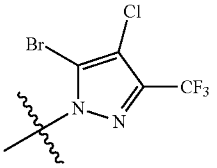 [SMILES: *n1nc(C(F)(F)F)c(Cl)c1Br]
Het-1941
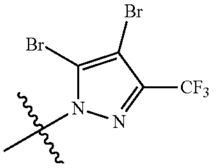 [SMILES: *n1nc(C(F)(F)F)c(Br)c1Br]
Het-1942
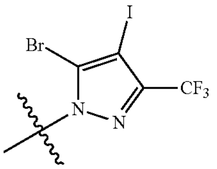 [SMILES: *n1nc(C(F)(F)F)c(I)c1Br]
Het-1943
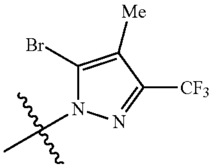 [SMILES: *n1nc(C(F)(F)F)c(C)c1Br]
Het-1944
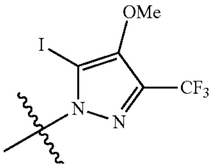 [SMILES: *n1nc(C(F)(F)F)c(OC)c1I]
Het-1945
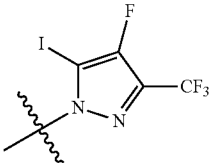
Het-1946
TABLE 3-continued
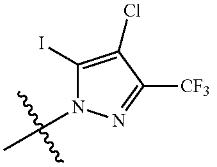 [SMILES: *n1nc(C(F)(F)F)c(Cl)c1I]
Het-1947
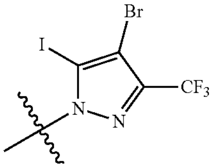 [SMILES: *n1nc(C(F)(F)F)c(Br)c1I]
Het-1948
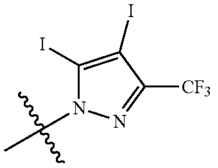 [SMILES: *n1nc(C(F)(F)F)c(I)c1I]
Het-1949
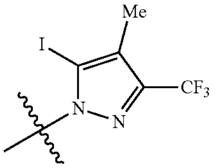 [SMILES: *n1nc(C(F)(F)F)c(C)c1I]
Het-1950
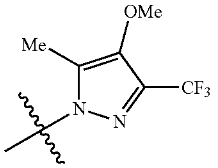 [SMILES: *n1nc(C(F)(F)F)c(OC)c1C]
Het-1951
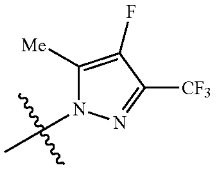
Het-1952
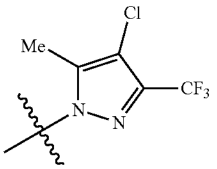 [SMILES: *n1nc(C(F)(F)F)c(Cl)c1C]
Het-1953
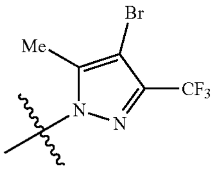 [SMILES: *n1nc(C(F)(F)F)c(Br)c1C]
Het-1954
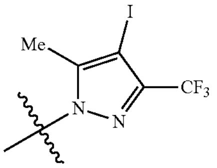 [SMILES: *n1nc(C(F)(F)F)c(I)c1C]
Het-1955

TABLE 3-continued
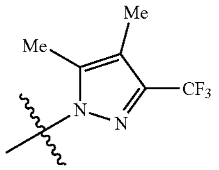 [SMILES: *n1nc(C(F)(F)F)c(C)c1C]
Het-1956
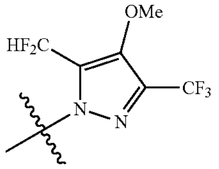 [SMILES: *n1nc(C(F)(F)F)c(OC)c1C(F)F]
Het-1957
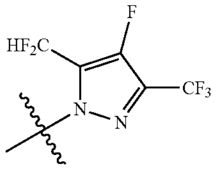
Het-1958
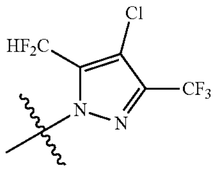
Het-1959
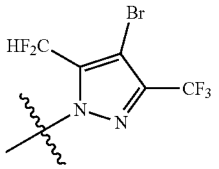 [SMILES: *n1nc(C(F)(F)F)c(Br)c1C(F)F]
Het-1960
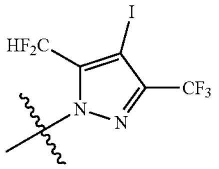 [SMILES: *n1nc(C(F)(F)F)c(I)c1C(F)F]
Het-1961
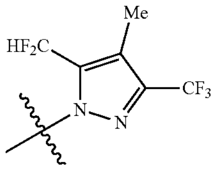 [SMILES: *n1nc(C(F)(F)F)c(C)c1C(F)F]
Het-1962
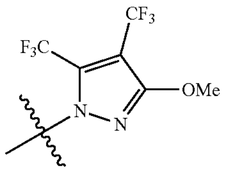 [SMILES: *n1nc(OC)c(C(F)(F)F)c1C(F)(F)F]
Het-1963
TABLE 3-continued
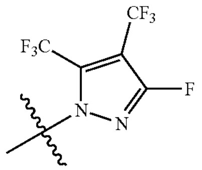 [SMILES: *n1nc(F)c(C(F)(F)F)c1C(F)(F)F]
Het-1964
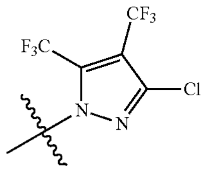 [SMILES: *n1nc(Cl)c(C(F)(F)F)c1C(F)(F)F]
Het-1965
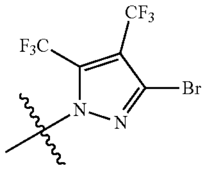 [SMILES: *n1nc(Br)c(C(F)(F)F)c1C(F)(F)F]
Het-1966
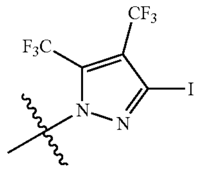 [SMILES: *n1nc(I)c(C(F)(F)F)c1C(F)(F)F]
Het-1967
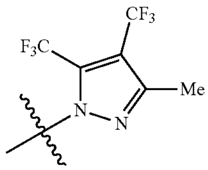 [SMILES: *n1nc(C)c(C(F)(F)F)c1C(F)(F)F]
Het-1968
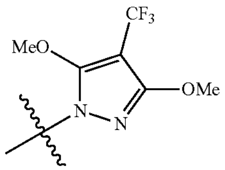 [SMILES: *n1nc(OC)c(C(F)(F)F)c1OC]
Het-1969
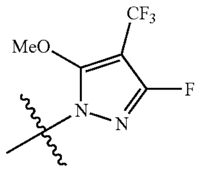 [SMILES: *n1nc(F)c(C(F)(F)F)c1OC]
Het-1970
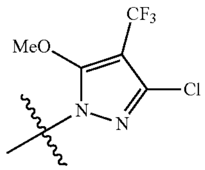 [SMILES: *n1nc(Cl)c(C(F)(F)F)c1OC]
Het-1971
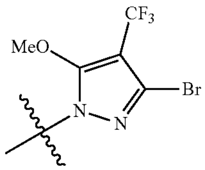 [SMILES: *n1nc(Br)c(C(F)(F)F)c1OC]
Het-1972

TABLE 3-continued
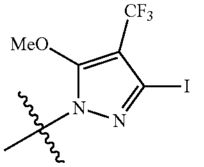 [SMILES: *n1nc(I)c(C(F)(F)F)c1OC]
Het-1973
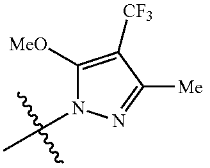 [SMILES: *n1nc(C)c(C(F)(F)F)c1OC]
Het-1974
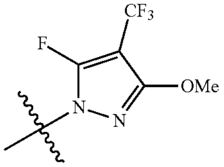
Het-1975
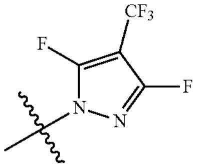
Het-1976
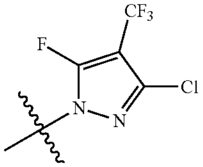 [SMILES: *n1nc(Cl)c(C(F)(F)F)c1F]
Het-1977
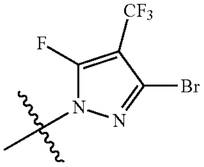 [SMILES: *n1nc(Br)c(C(F)(F)F)c1F]
Het-1978
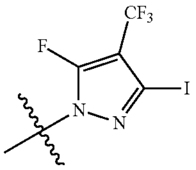 [SMILES: *n1nc(I)c(C(F)(F)F)c1F]
Het-1979
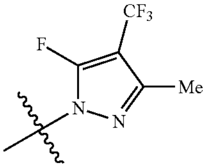
Het-1980
TABLE 3-continued
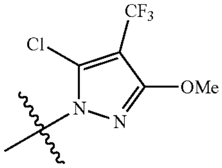 [SMILES: *n1nc(OC)c(C(F)(F)F)c1Cl]
Het-1981
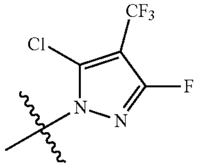
Het-1982
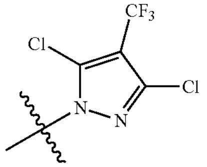
Het-1983
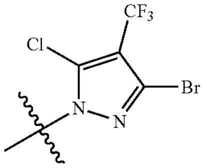 [SMILES: *n1nc(Br)c(C(F)(F)F)c1Cl]
Het-1984
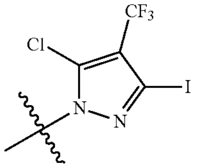
Het-1985
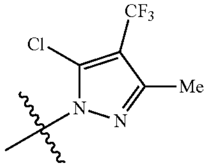
Het-1986
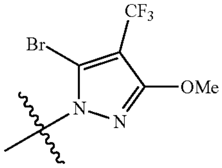 [SMILES: *n1nc(OC)c(C(F)(F)F)c1Br]
Het-1987
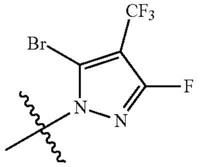 [SMILES: *n1nc(F)c(C(F)(F)F)c1Br]
Het-1988
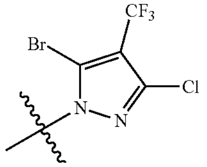
Het-1989

TABLE 3-continued
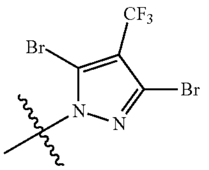
Het-1990
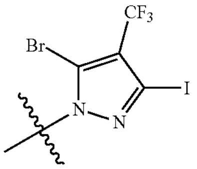 [SMILES: *n1nc(I)c(C(F)(F)F)c1Br]
Het-1991
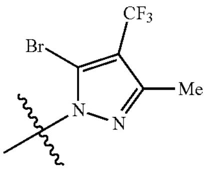 [SMILES: *n1nc(C)c(C(F)(F)F)c1Br]
Het-1992
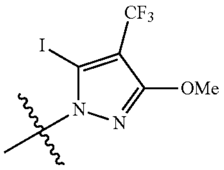 [SMILES: *n1nc(OC)c(C(F)(F)F)c1I]
Het-1993
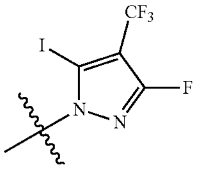
Het-1994
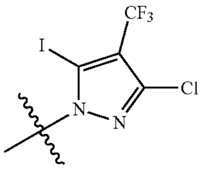 [SMILES: *n1nc(Cl)c(C(F)(F)F)c1I]
Het-1995
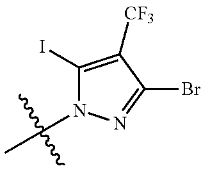
Het-1996
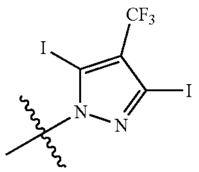
Het-1997
TABLE 3-continued
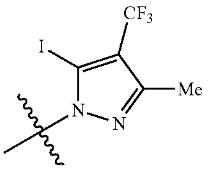
Het-1998
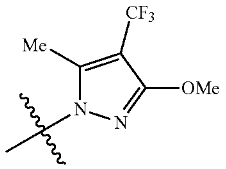 [SMILES: *n1nc(OC)c(C(F)(F)F)c1C]
Het-1999
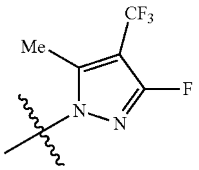 [SMILES: *n1nc(F)c(C(F)(F)F)c1C]
Het-2000
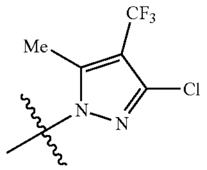 [SMILES: *n1nc(Cl)c(C(F)(F)F)c1C]
Het-2001
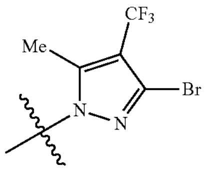
Het-2002
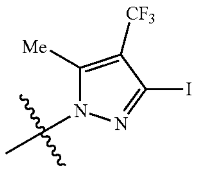
Het-2003
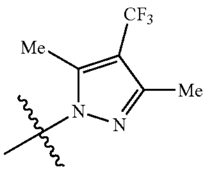
Het-2004
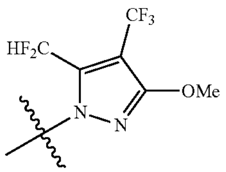
Het-2005
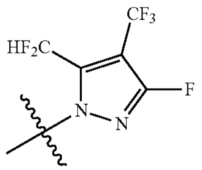 [SMILES: *n1nc(F)c(C(F)(F)F)c1C(F)F]
Het-2006

TABLE 3-continued
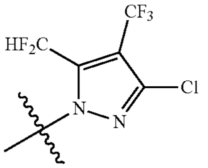 [SMILES: *n1nc(Cl)c(C(F)(F)F)c1C(F)F]
Het-2007
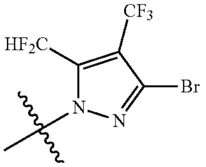 [SMILES: *n1nc(Br)c(C(F)(F)F)c1C(F)F]
Het-2008
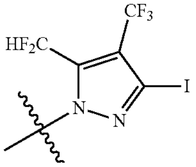 [SMILES: *n1nc(I)c(C(F)(F)F)c1C(F)F]
Het-2009
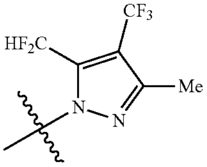 [SMILES: *n1nc(C)c(C(F)(F)F)c1C(F)F]
Het-2010
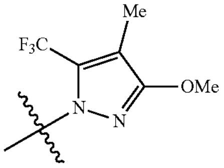 [SMILES: *n1nc(OC)c(C)c1C(F)(F)F]
Het-2011
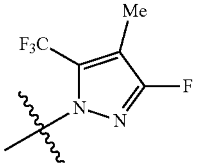 [SMILES: *n1nc(F)c(C)c1C(F)(F)F]
Het-2012
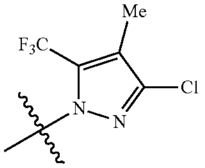
Het-2013
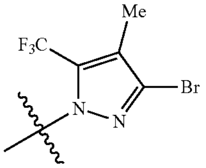 [SMILES: *n1nc(Br)c(C)c1C(F)(F)F]
Het-2014
TABLE 3-continued
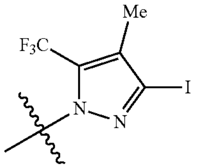 [SMILES: *n1nc(I)c(C)c1C(F)(F)F]
Het-2015
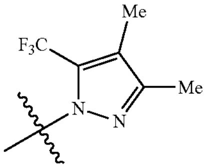 [SMILES: *n1nc(C)c(C)c1C(F)(F)F]
Het-2016
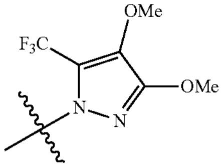
Het-2017
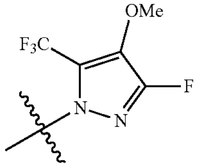 [SMILES: *n1nc(F)c(OC)c1C(F)(F)F]
Het-2018
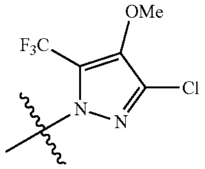 [SMILES: *n1nc(Cl)c(OC)c1C(F)(F)F]
Het-2019
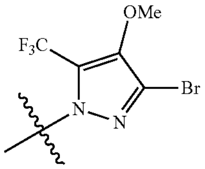
Het-2020
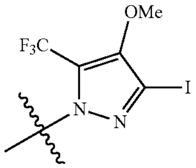 [SMILES: *n1nc(I)c(OC)c1C(F)(F)F]
Het-2021
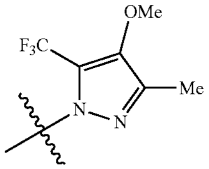 [SMILES: *n1nc(C)c(OC)c1C(F)(F)F]
Het-2022
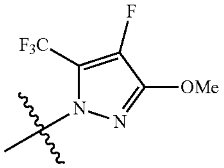
Het-2023

TABLE 3-continued
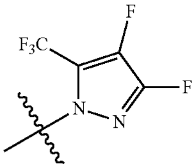
Het-2024
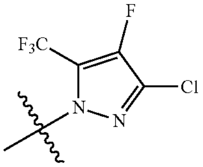 [SMILES: *n1nc(Cl)c(F)c1C(F)(F)F]
Het-2025
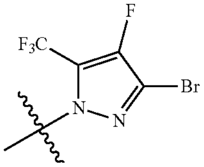
Het-2026
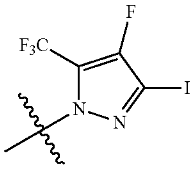
Het-2027
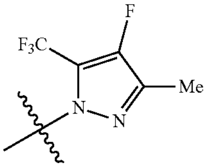 [SMILES: *n1nc(C)c(F)c1C(F)(F)F]
Het-2028
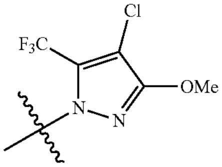 [SMILES: *n1nc(OC)c(Cl)c1C(F)(F)F]
Het-2029
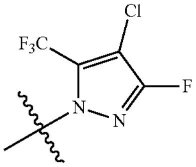
Het-2030
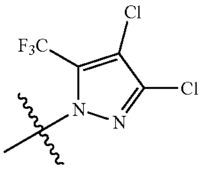 [SMILES: *n1nc(Cl)c(Cl)c1C(F)(F)F]
Het-2031
TABLE 3-continued
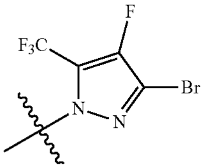 [SMILES: *n1nc(Br)c(F)c1C(F)(F)F]
Het-2032
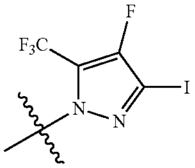
Het-2033
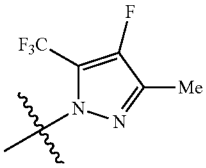
Het-2034
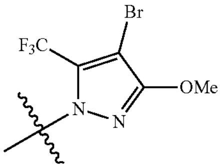
Het-2035
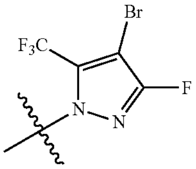
Het-2036
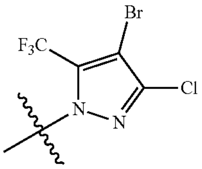 [SMILES: *n1nc(Cl)c(Br)c1C(F)(F)F]
Het-2037
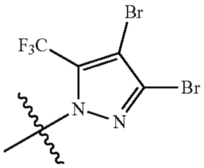 [SMILES: *n1nc(Br)c(Br)c1C(F)(F)F]
Het-2038
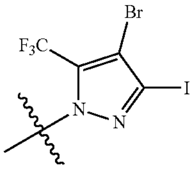
Het-2039
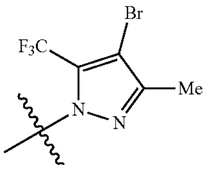
Het-2040

TABLE 3-continued
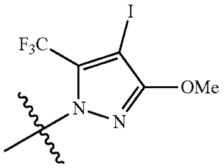 [SMILES: *n1nc(OC)c(I)c1C(F)(F)F]
Het-2041
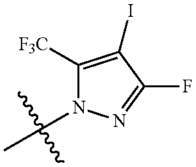
Het-2042
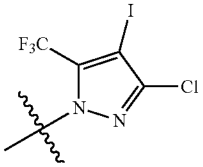 [SMILES: *n1nc(Cl)c(I)c1C(F)(F)F]
Het-2043
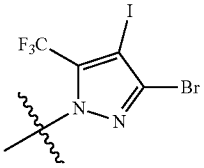 [SMILES: *n1nc(Br)c(I)c1C(F)(F)F]
Het-2044
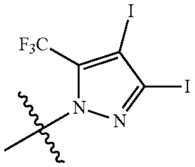 [SMILES: *n1nc(I)c(I)c1C(F)(F)F]
Het-2045
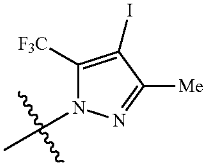 [SMILES: *n1nc(C)c(I)c1C(F)(F)F]
Het-2046
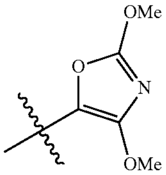 [SMILES: *c1oc(OC)nc1OC]
Het-2047
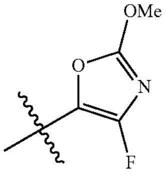
Het-2048
TABLE 3-continued
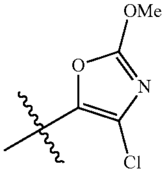 [SMILES: *c1oc(OC)nc1Cl]
Het-2049
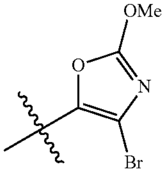 [SMILES: *c1oc(OC)nc1Br]
Het-2050
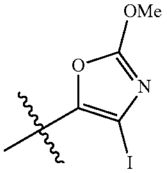 [SMILES: *c1oc(OC)nc1I]
Het-2051
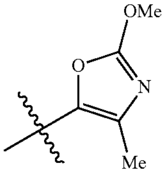 [SMILES: *c1oc(OC)nc1C]
Het-2052
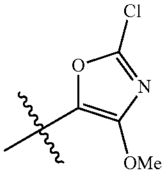
Het-2053
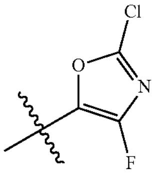
Het-2054
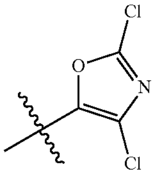
Het-2055
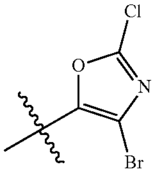
Het-2056
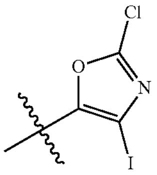
Het-2057

TABLE 3-continued
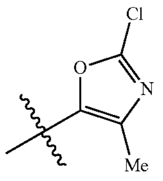
Het-2058
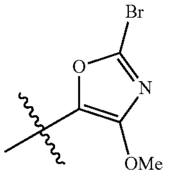 [SMILES: *c1oc(Br)nc1OC]
Het-2059
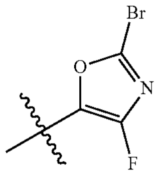 [SMILES: *c1oc(Br)nc1F]
Het-2060
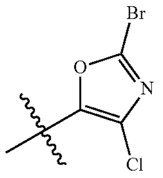 [SMILES: *c1oc(Br)nc1Cl]
Het-2061
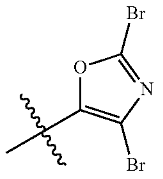 [SMILES: *c1oc(Br)nc1Br]
Het-2062
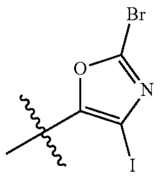 [SMILES: *c1oc(Br)nc1I]
Het-2063
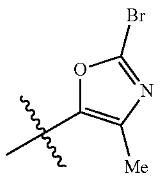 [SMILES: *c1oc(Br)nc1C]
Het-2064
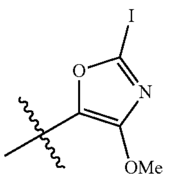 [SMILES: *c1oc(I)nc1OC]
Het-2065
TABLE 3-continued
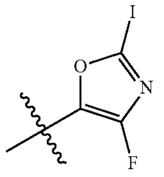
Het-2066
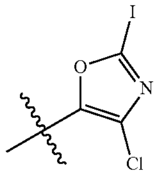 [SMILES: *c1oc(I)nc1Cl]
Het-2067
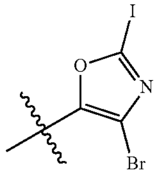 [SMILES: *c1oc(I)nc1Br]
Het-2068
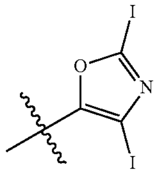 [SMILES: *c1oc(I)nc1I]
Het-2069
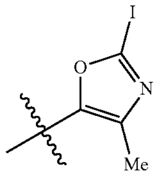 [SMILES: *c1oc(I)nc1C]
Het-2070
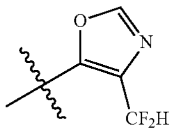 [SMILES: *c1ocnc1C(F)F]
Het-2071
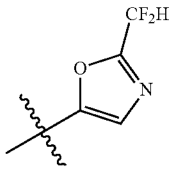 [SMILES: *c1cnc(C(F)F)o1]
Het-2072
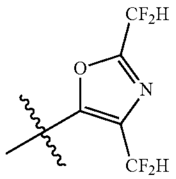 [SMILES: *c1oc(C(F)F)nc1C(F)F]
Het-2073
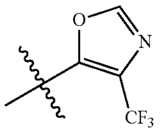 [SMILES: *c1ocnc1C(F)(F)F]
Het-2074

TABLE 3-continued
Het-2075
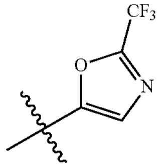 [SMILES: *c1cnc(C(F)(F)F)o1]
Het-2076
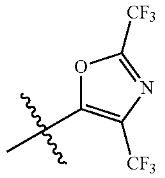
Het-2077
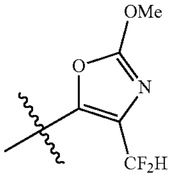 [SMILES: *c1oc(OC)nc1C(F)F]
Het-2078
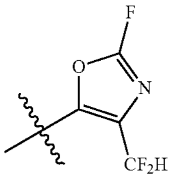 [SMILES: *c1oc(F)nc1C(F)F]
Het-2079
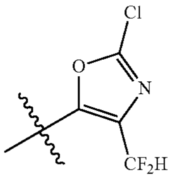 [SMILES: *c1oc(Cl)nc1C(F)F]
Het-2080
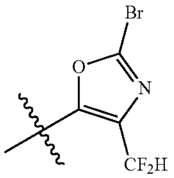 [SMILES: *c1oc(Br)nc1C(F)F]
Het-2081
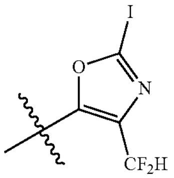 [SMILES: *c1oc(I)nc1C(F)F]
Het-2082
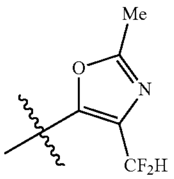 [SMILES: *c1oc(C)nc1C(F)F]
TABLE 3-continued
Het-2083
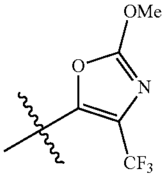 [SMILES: *c1oc(OC)nc1C(F)(F)F]
Het-2084
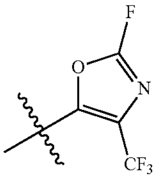
Het-2085
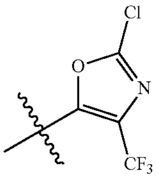 [SMILES: *c1oc(Cl)nc1C(F)(F)F]
Het-2086
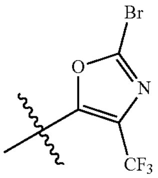
Het-2087
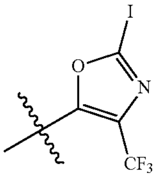
Het-2088
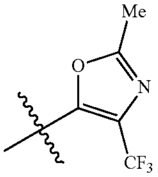
Het-2089
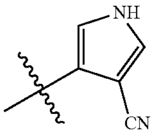 [SMILES: *c1c[nH]cc1C#N]
Het-2090
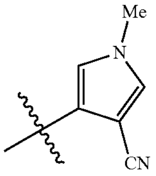 [SMILES: *c1cn(C)cc1C#N]
Het-2091
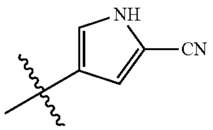 [SMILES: *c1c[nH]c(C#N)c1]

TABLE 3-continued
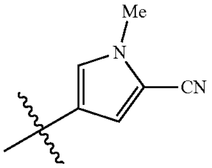 [SMILES: *c1cc(C#N)n(C)c1]
Het-2092
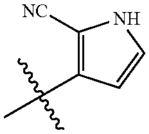 [SMILES: *c1cc[nH]c1C#N]
Het-2093
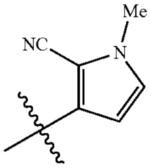 [SMILES: *c1ccn(C)c1C#N]
Het-2094
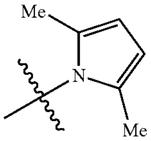 [SMILES: *n1c(C)ccc1C]
Het-2095
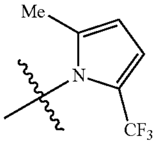
Het-2096
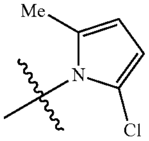 [SMILES: *n1c(C)ccc1Cl]
Het-2097
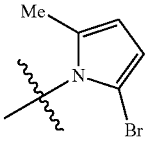 [SMILES: *n1c(C)ccc1Br]
Het-2098
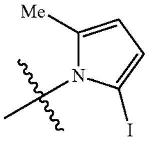 [SMILES: *n1c(C)ccc1I]
Het-2099
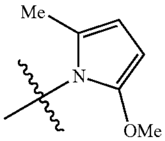 [SMILES: *n1c(C)ccc1OC]
Het-2100
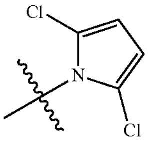
Het-2101
TABLE 3-continued
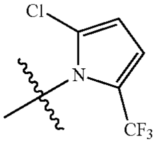 [SMILES: *n1c(Cl)ccc1C(F)(F)F]
Het-2102
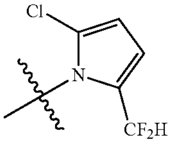 [SMILES: *n1c(Cl)ccc1C(F)F]
Het-2103
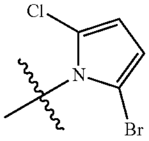 [SMILES: *n1c(Cl)ccc1Br]
Het-2104
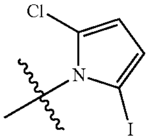 [SMILES: *n1c(Cl)ccc1I]
Het-2105
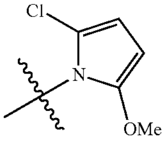
Het-2106
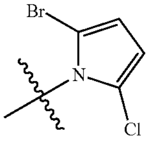 [SMILES: *n1c(Cl)ccc1Br]
Het-2107
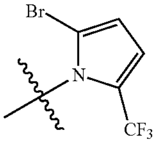
Het-2108
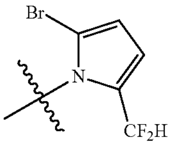
Het-2109
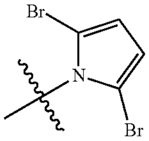 [SMILES: *n1c(Br)ccc1Br]
Het-2110
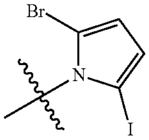
Het-2111

TABLE 3-continued
Het-2112
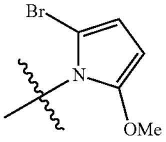
Het-2113
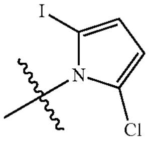 [SMILES: *n1c(Cl)ccc1I]
Het-2114
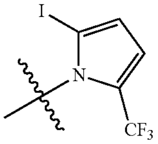
Het-2115
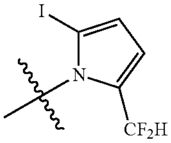
Het-2116
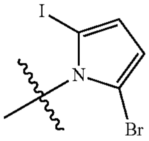
Het-2117
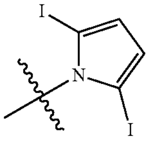 [SMILES: *n1c(I)ccc1I]
Het-2118
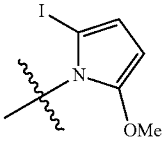 [SMILES: *n1c(I)ccc1OC]
Het-2119
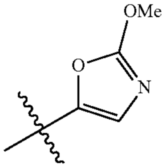 [SMILES: *c1cnc(OC)o1]
Het-2120
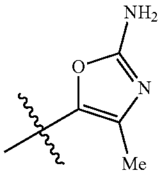 [SMILES: *c1oc(N)nc1C]
Het-2121
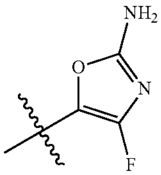
TABLE 3-continued
Het-2122
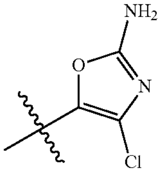 [SMILES: *c1oc(N)nc1Cl]
Het-2123
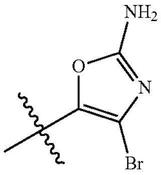 [SMILES: *c1oc(N)nc1Br]
Het-2124
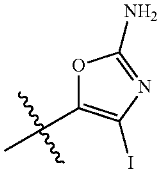 [SMILES: *c1oc(N)nc1I]
Het-2125
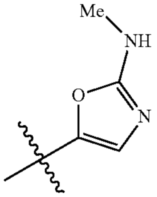 [SMILES: *c1cnc(NC)o1]
Het-2126
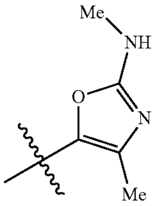 [SMILES: *c1oc(NC)nc1C]
Het-2127
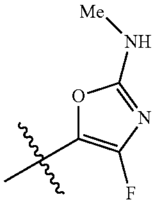
Het-2128
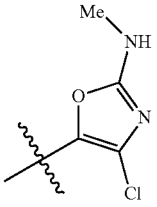 [SMILES: *c1oc(NC)nc1Cl]
Het-2129
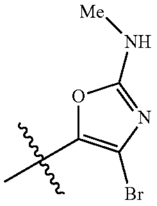 [SMILES: *c1oc(NC)nc1Br]

TABLE 3-continued
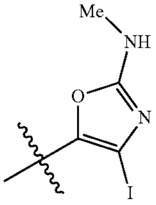 [SMILES: *c1oc(NC)nc1I]
Het-2130
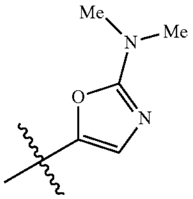 [SMILES: *c1cnc(N(C)C)o1]
Het-2131
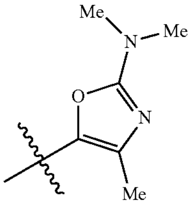 [SMILES: *c1oc(N(C)C)nc1C]
Het-2132
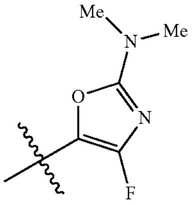
Het-2133
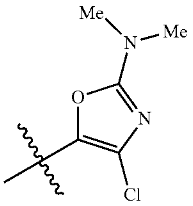 [SMILES: *c1oc(N(C)C)nc1Cl]
Het-2134
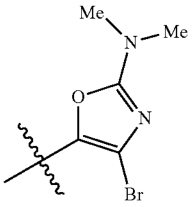 [SMILES: *c1oc(N(C)C)nc1Br]
Het-2135
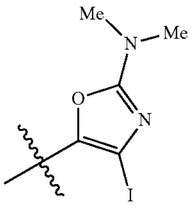 [SMILES: *c1oc(N(C)C)nc1I]
Het-2136
TABLE 3-continued
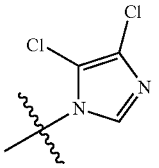
Het-2137
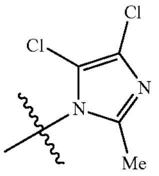 [SMILES: *n1c(C)nc(Cl)c1Cl]
Het-2138
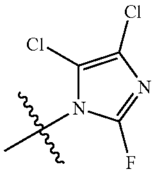
Het-2139
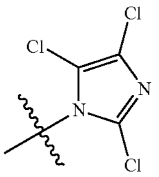 [SMILES: *n1c(Cl)nc(Cl)c1Cl]
Het-2140
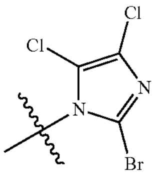 [SMILES: *n1c(Br)nc(Cl)c1Cl]
Het-2141
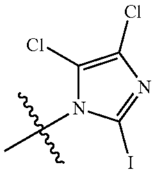 [SMILES: *n1c(I)nc(Cl)c1Cl]
Het-2142
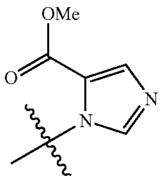 [SMILES: *n1cncc1C(=O)OC]
Het-2143
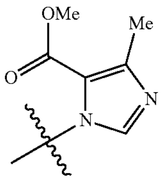 [SMILES: *n1cnc(C)c1C(=O)OC]
Het-2144

TABLE 3-continued
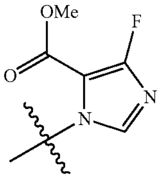
Het-2145
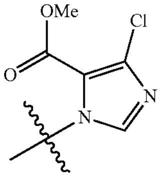 [SMILES: *n1cnc(Cl)c1C(=O)OC]
Het-2146
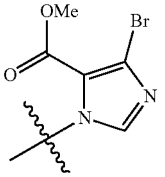 [SMILES: *n1cnc(Br)c1C(=O)OC]
Het-2147
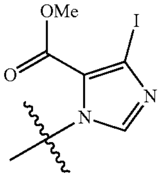 [SMILES: *n1cnc(I)c1C(=O)OC]
Het-2148
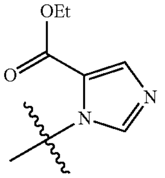 [SMILES: *n1cncc1C(=O)OCC]
Het-2149
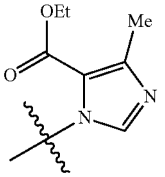 [SMILES: *n1cnc(C)c1C(=O)OCC]
Het-2150
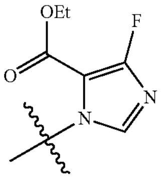
Het-2151
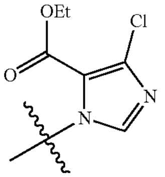 [SMILES: *n1cnc(Cl)c1C(=O)OCC]
Het-2152
TABLE 3-continued
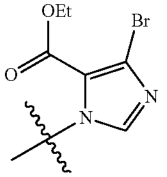 [SMILES: *n1cnc(Br)c1C(=O)OCC]
Het-2153
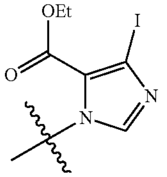 [SMILES: *n1cnc(I)c1C(=O)OCC]
Het-2154
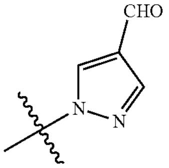 [SMILES: *n1cc(C=O)cn1]
Het-2155
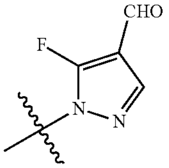
Het-2156
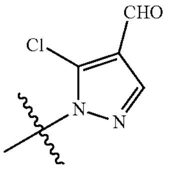 [SMILES: *n1ncc(C=O)c1Cl]
Het-2157
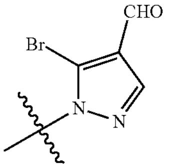
Het-2158
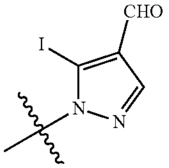 [SMILES: *n1ncc(C=O)c1I]
Het-2159
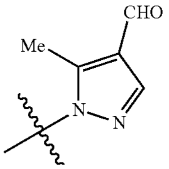 [SMILES: *n1ncc(C=O)c1C]
Het-2160
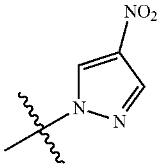 [SMILES: *n1cc([N+](=O)[O-])cn1]
Het-2161

TABLE 3-continued
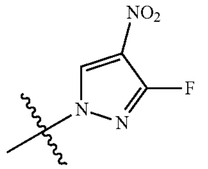 [SMILES: *n1cc([N+](=O)[O-])c(F)n1]
Het-2162
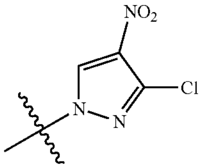 [SMILES: *n1cc([N+](=O)[O-])c(Cl)n1]
Het-2163
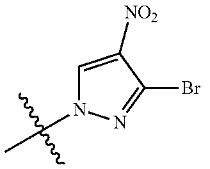 [SMILES: *n1cc([N+](=O)[O-])c(Br)n1]
Het-2164
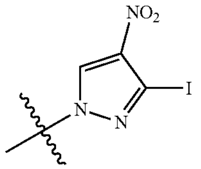 [SMILES: *n1cc([N+](=O)[O-])c(I)n1]
Het-2165
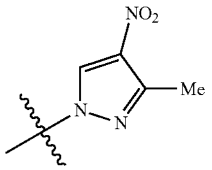 [SMILES: *n1cc([N+](=O)[O-])c(C)n1]
Het-2166
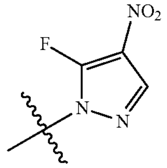 [SMILES: *n1ncc([N+](=O)[O-])c1F]
Het-2167
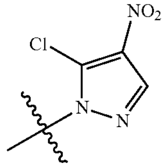 [SMILES: *n1ncc([N+](=O)[O-])c1Cl]
Het-2168
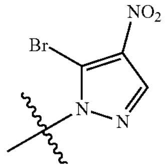 [SMILES: *n1ncc([N+](=O)[O-])c1Br]
Het-2169
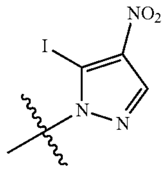 [SMILES: *n1ncc([N+](=O)[O-])c1I]
Het-2170
TABLE 3-continued
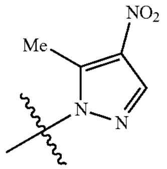 [SMILES: *n1ncc([N+](=O)[O-])c1C]
Het-2171
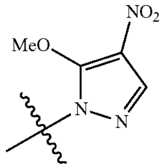 [SMILES: *n1ncc([N+](=O)[O-])c1OC]
Het-2172
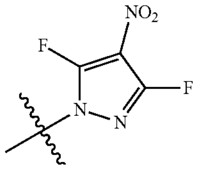
Het-2173
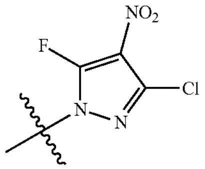 [SMILES: *n1nc(Cl)c([N+](=O)[O-])c1F]
Het-2174
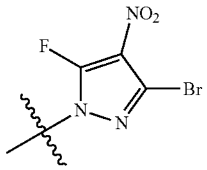 [SMILES: *n1nc(Br)c([N+](=O)[O-])c1F]
Het-2175
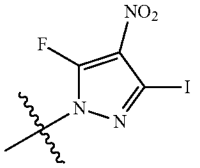 [SMILES: *n1nc(I)c([N+](=O)[O-])c1F]
Het-2176
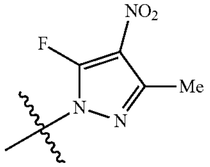
Het-2177
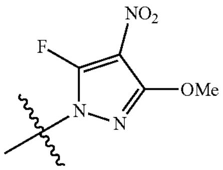 [SMILES: *n1nc(OC)c([N+](=O)[O-])c1F]
Het-2178
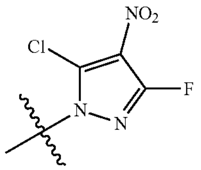 [SMILES: *n1nc(F)c([N+](=O)[O-])c1Cl]
Het-2179

TABLE 3-continued
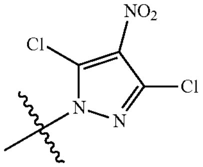 [SMILES: *n1nc(Cl)c([N+](=O)[O-])c1Cl]
Het-2180
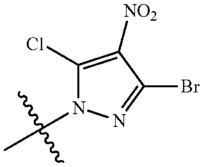 [SMILES: *n1nc(Br)c([N+](=O)[O-])c1Cl]
Het-2181
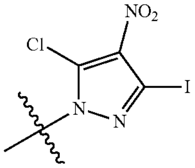 [SMILES: *n1nc(I)c([N+](=O)[O-])c1Cl]
Het-2182
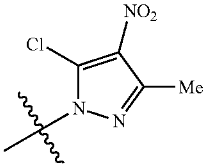 [SMILES: *n1nc(C)c([N+](=O)[O-])c1Cl]
Het-2183
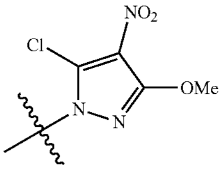 [SMILES: *n1nc(OC)c([N+](=O)[O-])c1Cl]
Het-2184
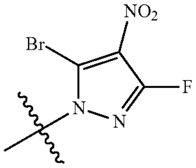 [SMILES: *n1nc(F)c([N+](=O)[O-])c1Br]
Het-2185
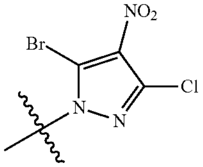 [SMILES: *n1nc(Cl)c([N+](=O)[O-])c1Br]
Het-2186
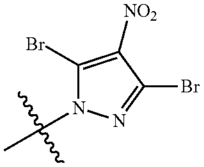 [SMILES: *n1nc(Br)c([N+](=O)[O-])c1Br]
Het-2187
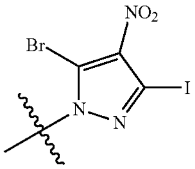 [SMILES: *n1nc(I)c([N+](=O)[O-])c1Br]
Het-2188
TABLE 3-continued
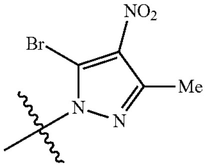 [SMILES: *n1nc(C)c([N+](=O)[O-])c1Br]
Het-2189
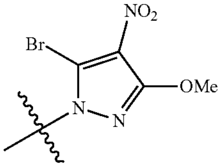 [SMILES: *n1nc(OC)c([N+](=O)[O-])c1Br]
Het-2190
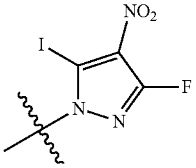 [SMILES: *n1nc(F)c([N+](=O)[O-])c1I]
Het-2191
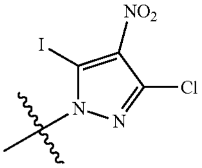 [SMILES: *n1nc(Cl)c([N+](=O)[O-])c1I]
Het-2192
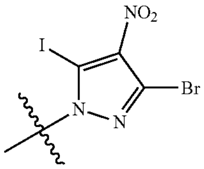 [SMILES: *n1nc(Br)c([N+](=O)[O-])c1I]
Het-2193
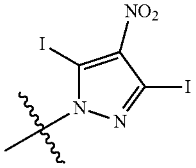 [SMILES: *n1nc(I)c([N+](=O)[O-])c1I]
Het-2194
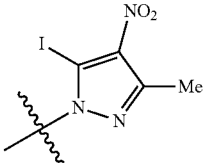 [SMILES: *n1nc(C)c([N+](=O)[O-])c1I]
Het-2195
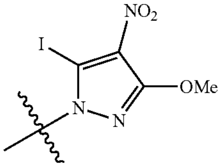 [SMILES: *n1nc(OC)c([N+](=O)[O-])c1I]
Het-2196
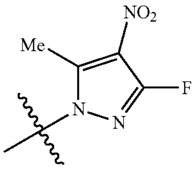 [SMILES: *n1nc(F)c([N+](=O)[O-])c1C]
Het-2197

TABLE 3-continued
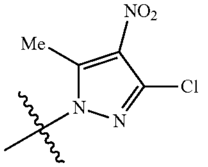 [SMILES: *n1nc(Cl)c([N+](=O)[O-])c1C]
Het-2198
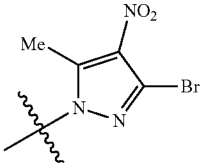 [SMILES: *n1nc(Br)c([N+](=O)[O-])c1C]
Het-2199
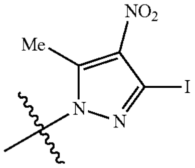 [SMILES: *n1nc(I)c([N+](=O)[O-])c1C]
Het-2200
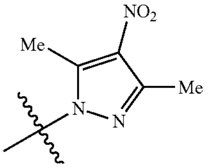 [SMILES: *n1nc(C)c([N+](=O)[O-])c1C]
Het-2201
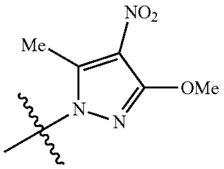 [SMILES: *n1nc(OC)c([N+](=O)[O-])c1C]
Het-2202
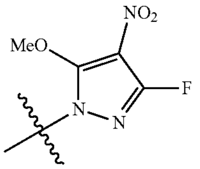 [SMILES: *n1nc(F)c([N+](=O)[O-])c1OC]
Het-2203
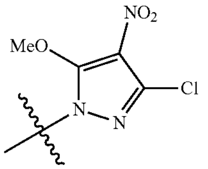 [SMILES: *n1nc(Cl)c([N+](=O)[O-])c1OC]
Het-2204
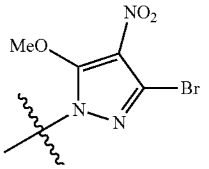 [SMILES: *n1nc(Br)c([N+](=O)[O-])c1OC]
Het-2205
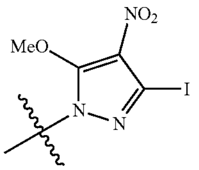 [SMILES: *n1nc(I)c([N+](=O)[O-])c1OC]
Het-2206
TABLE 3-continued
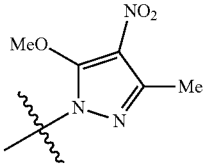 [SMILES: *n1nc(C)c([N+](=O)[O-])c1OC]
Het-2207
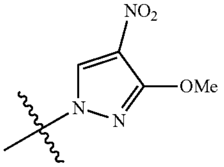 [SMILES: *n1cc([N+](=O)[O-])c(OC)n1]
Het-2208
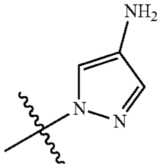 [SMILES: *n1cc(N)cn1]
Het-2209
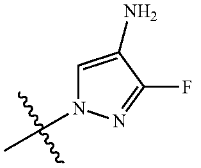 [SMILES: *n1cc(N)c(F)n1]
Het-2210
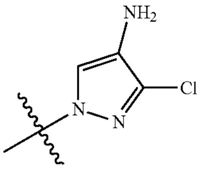 [SMILES: *n1cc(N)c(Cl)n1]
Het-2211
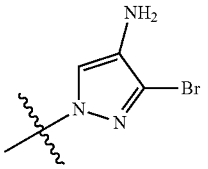 [SMILES: *n1cc(N)c(Br)n1]
Het-2212
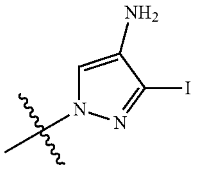 [SMILES: *n1cc(N)c(I)n1]
Het-2213
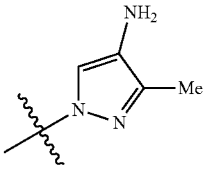 [SMILES: *n1cc(N)c(C)n1]
Het-2214
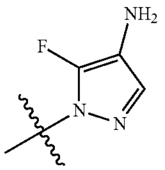 [SMILES: *n1ncc(N)c1F]
Het-2215

TABLE 3-continued
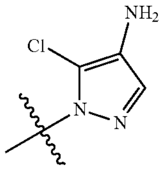 [SMILES: *n1ncc(N)c1Cl]
Het-2216
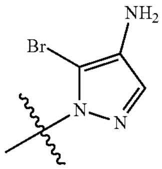 [SMILES: *n1ncc(N)c1Br]
Het-2217
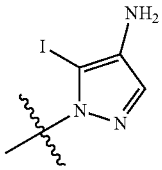 [SMILES: *n1ncc(N)c1I]
Het-2218
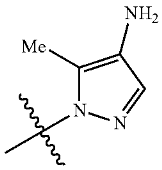 [SMILES: *n1ncc(N)c1C]
Het-2219
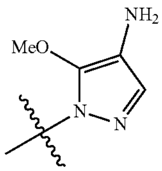 [SMILES: *n1ncc(N)c1OC]
Het-2220
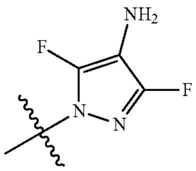
Het-2221
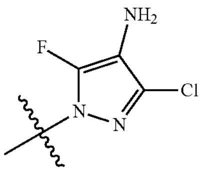 [SMILES: *n1nc(Cl)c(N)c1F]
Het-2222
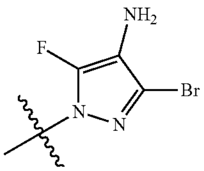 [SMILES: *n1nc(Br)c(N)c1F]
Het-2223
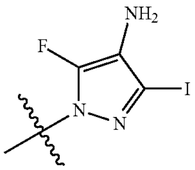 [SMILES: *n1nc(I)c(N)c1F]
Het-2224
TABLE 3-continued
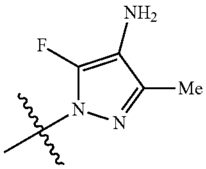
Het-2225
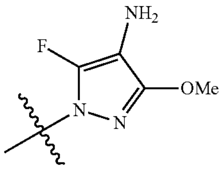 [SMILES: *n1nc(OC)c(N)c1F]
Het-2226
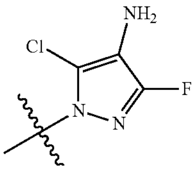 [SMILES: *n1nc(F)c(N)c1Cl]
Het-2227
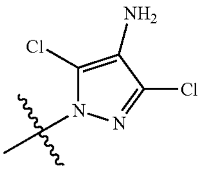 [SMILES: *n1nc(Cl)c(N)c1Cl]
Het-2228
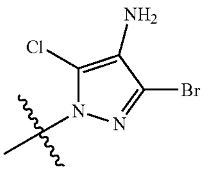 [SMILES: *n1nc(Br)c(N)c1Cl]
Het-2229
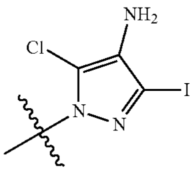 [SMILES: *n1nc(I)c(N)c1Cl]
Het-2230
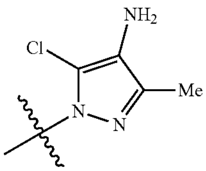 [SMILES: *n1nc(C)c(N)c1Cl]
Het-2231
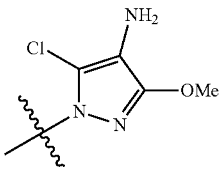 [SMILES: *n1nc(OC)c(N)c1Cl]
Het-2232
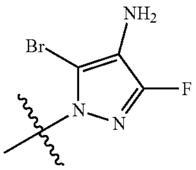 [SMILES: *n1nc(F)c(N)c1Br]
Het-2233

TABLE 3-continued
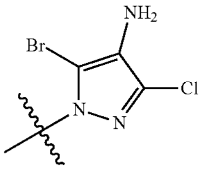 [SMILES: *n1nc(Cl)c(N)c1Br]
Het-2234
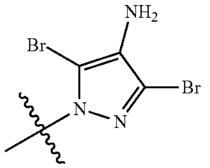 [SMILES: *n1nc(Br)c(N)c1Br]
Het-2235
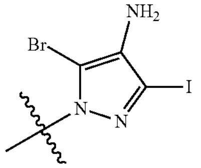 [SMILES: *n1nc(I)c(N)c1Br]
Het-2236
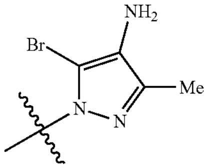 [SMILES: *n1nc(C)c(N)c1Br]
Het-2237
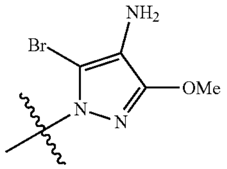
Het-2238
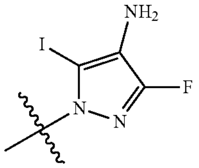 [SMILES: *n1nc(F)c(N)c1I]
Het-2239
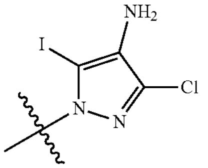 [SMILES: *n1nc(Cl)c(N)c1I]
Het-2240
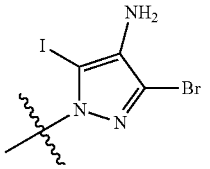 [SMILES: *n1nc(Br)c(N)c1I]
Het-2241
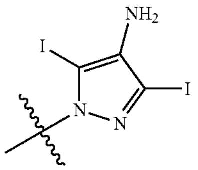 [SMILES: *n1nc(I)c(N)c1I]
Het-2242
TABLE 3-continued
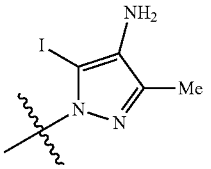 [SMILES: *n1nc(C)c(N)c1I]
Het-2243
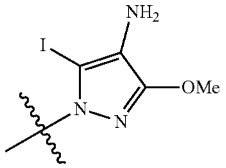 [SMILES: *n1nc(OC)c(N)c1I]
Het-2244
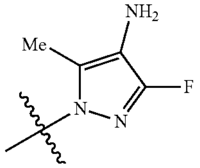 [SMILES: *n1nc(F)c(N)c1C]
Het-2245
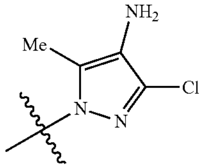 [SMILES: *n1nc(Cl)c(N)c1C]
Het-2246
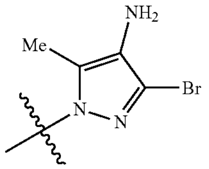 [SMILES: *n1nc(Br)c(N)c1C]
Het-2247
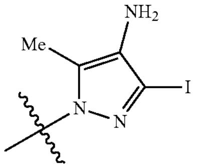 [SMILES: *n1nc(I)c(N)c1C]
Het-2248
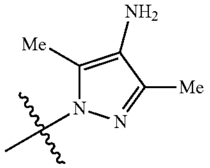 [SMILES: *n1nc(C)c(N)c1C]
Het-2249
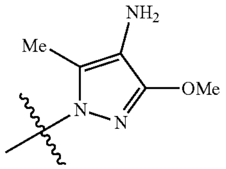 [SMILES: *n1nc(OC)c(N)c1C]
Het-2250
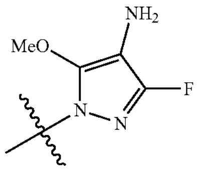 [SMILES: *n1nc(F)c(N)c1OC]
Het-2251

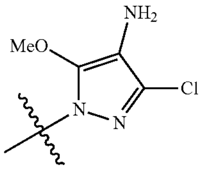 [SMILES: *n1nc(Cl)c(N)c1OC]
Het-2252
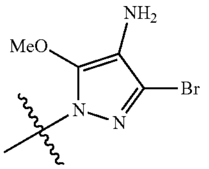 [SMILES: *n1nc(Br)c(N)c1OC]
Het-2253
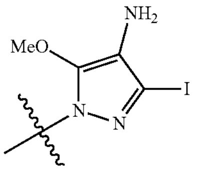 [SMILES: *n1nc(I)c(N)c1OC]
Het-2254
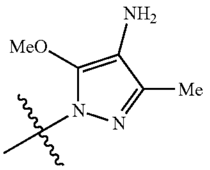 [SMILES: *n1nc(C)c(N)c1OC]
Het-2255
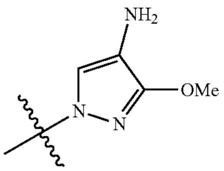 [SMILES: *n1cc(N)c(OC)n1]
Het-2256
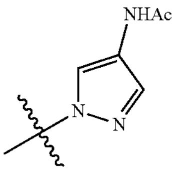 [SMILES: *n1cc(NC(C)=O)cn1]
Het-2257
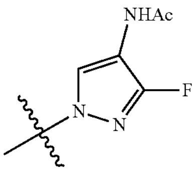 [SMILES: *n1cc(NC(C)=O)c(F)n1]
Het-2258
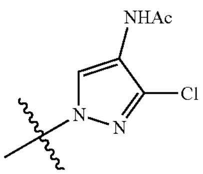 [SMILES: *n1cc(NC(C)=O)c(Cl)n1]
Het-2259
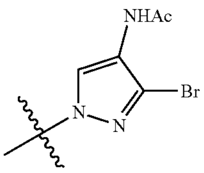 [SMILES: *n1cc(NC(C)=O)c(Br)n1]
Het-2260
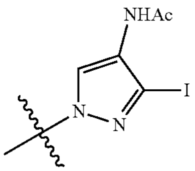 [SMILES: *n1cc(NC(C)=O)c(I)n1]
Het-2261
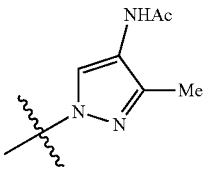 [SMILES: *n1cc(NC(C)=O)c(C)n1]
Het-2262
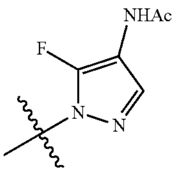 [SMILES: *n1ncc(NC(C)=O)c1F]
Het-2263
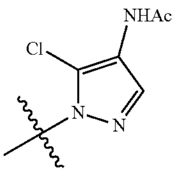 [SMILES: *n1ncc(NC(C)=O)c1Cl]
Het-2264
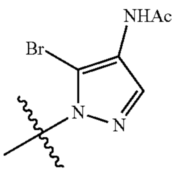 [SMILES: *n1ncc(NC(C)=O)c1Br]
Het-2265
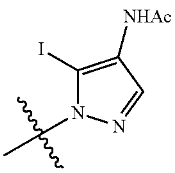 [SMILES: *n1ncc(NC(C)=O)c1I]
Het-2266
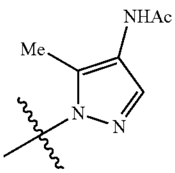 [SMILES: *n1ncc(NC(C)=O)c1C]
Het-2267
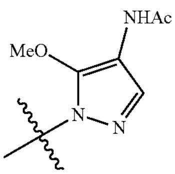 [SMILES: *n1ncc(NC(C)=O)c1OC]
Het-2268
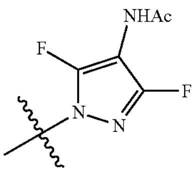
Het-2269

TABLE 3-continued
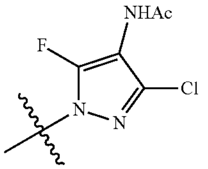 [SMILES: *n1nc(Cl)c(NC(C)=O)c1F]
Het-2270
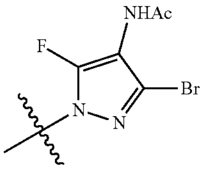 [SMILES: *n1nc(Br)c(NC(C)=O)c1F]
Het-2271
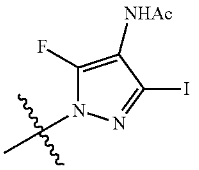 [SMILES: *n1nc(I)c(NC(C)=O)c1F]
Het-2272
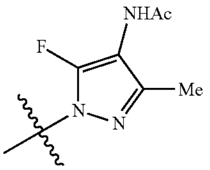
Het-2273
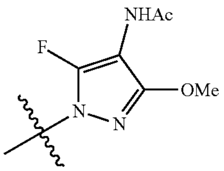
Het-2274
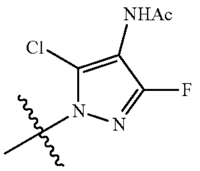
Het-2275
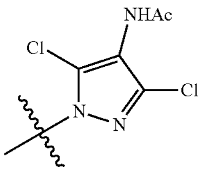 [SMILES: *n1nc(Cl)c(NC(C)=O)c1Cl]
Het-2276
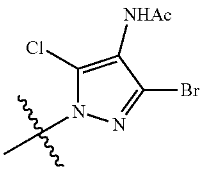 [SMILES: *n1nc(Br)c(NC(C)=O)c1Cl]
Het-2277
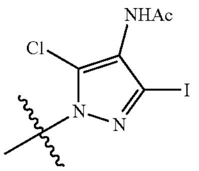 [SMILES: *n1nc(I)c(NC(C)=O)c1Cl]
Het-2278
TABLE 3-continued
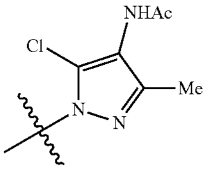 [SMILES: *n1nc(C)c(NC(C)=O)c1Cl]
Het-2279
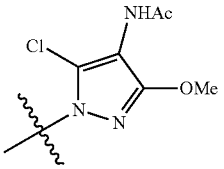 [SMILES: *n1nc(OC)c(NC(C)=O)c1Cl]
Het-2280
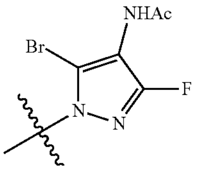 [SMILES: *n1nc(F)c(NC(C)=O)c1Br]
Het-2281
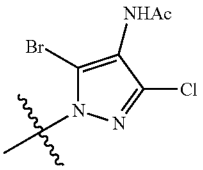 [SMILES: *n1nc(Cl)c(NC(C)=O)c1Br]
Het-2282
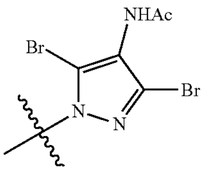 [SMILES: *n1nc(Br)c(NC(C)=O)c1Br]
Het-2283
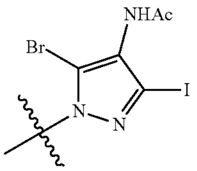 [SMILES: *n1nc(I)c(NC(C)=O)c1Br]
Het-2284
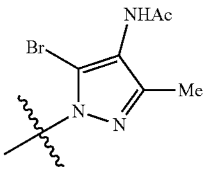 [SMILES: *n1nc(C)c(NC(C)=O)c1Br]
Het-2285
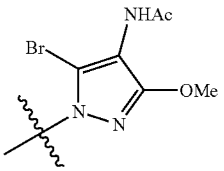 [SMILES: *n1nc(OC)c(NC(C)=O)c1Br]
Het-2286
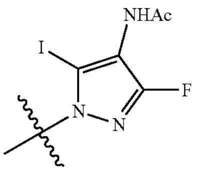 [SMILES: *n1nc(F)c(NC(C)=O)c1I]
Het-2287

TABLE 3-continued
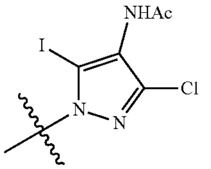 [SMILES: *n1nc(Cl)c(NC(C)=O)c1I]
Het-2288
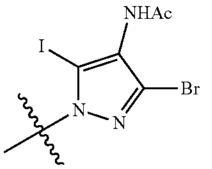 [SMILES: *n1nc(Br)c(NC(C)=O)c1I]
Het-2289
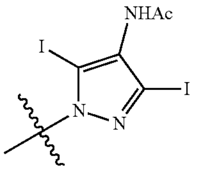 [SMILES: *n1nc(I)c(NC(C)=O)c1I]
Het-2290
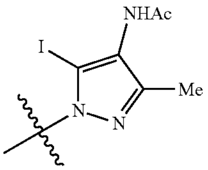 [SMILES: *n1nc(C)c(NC(C)=O)c1I]
Het-2291
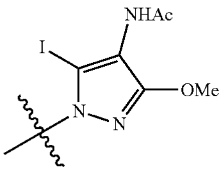 [SMILES: *n1nc(OC)c(NC(C)=O)c1I]
Het-2292
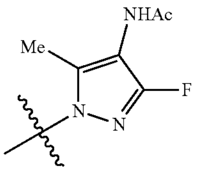 [SMILES: *n1nc(F)c(NC(C)=O)c1C]
Het-2293
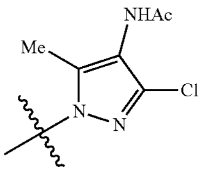 [SMILES: *n1nc(Cl)c(NC(C)=O)c1C]
Het-2294
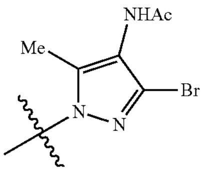 [SMILES: *n1nc(Br)c(NC(C)=O)c1C]
Het-2295
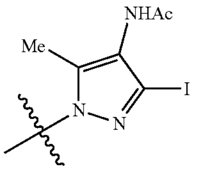 [SMILES: *n1nc(I)c(NC(C)=O)c1C]
Het-2296
TABLE 3-continued
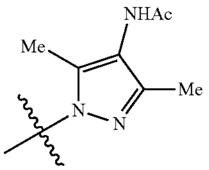 [SMILES: *n1nc(C)c(NC(C)=O)c1C]
Het-2297
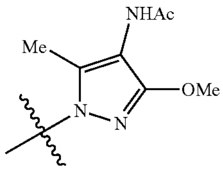 [SMILES: *n1nc(OC)c(NC(C)=O)c1C]
Het-2298
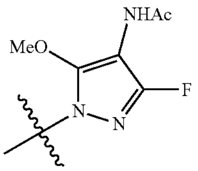 [SMILES: *n1nc(F)c(NC(C)=O)c1OC]
Het-2299
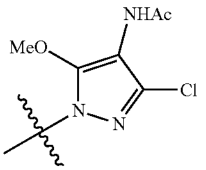 [SMILES: *n1nc(Cl)c(NC(C)=O)c1OC]
Het-2300
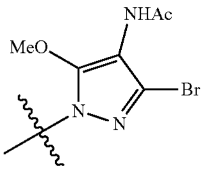 [SMILES: *n1nc(Br)c(NC(C)=O)c1OC]
Het-2301
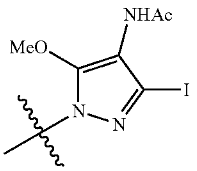 [SMILES: *n1nc(I)c(NC(C)=O)c1OC]
Het-2302
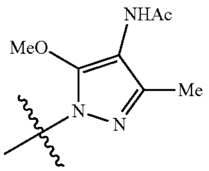 [SMILES: *n1nc(C)c(NC(C)=O)c1OC]
Het-2303
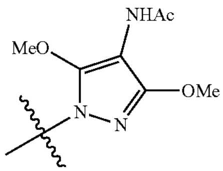 [SMILES: *n1nc(OC)c(NC(C)=O)c1OC]
Het-2304
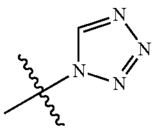 [SMILES: *n1cnnn1]
Het-2305

TABLE 3-continued
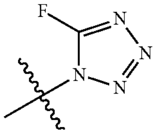 [SMILES: *n1nnnc1I]
Het-2306
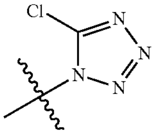
Het-2307
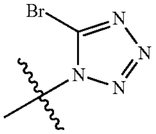
Het-2308
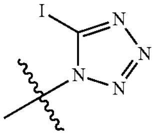
Het-2309
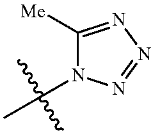 [SMILES: *n1nnnc1C]
Het-2310
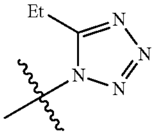 [SMILES: *n1nnnc1CC]
Het-2311
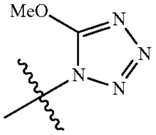 [SMILES: *n1nnnc1OC]
Het-2312
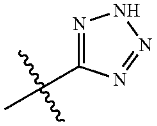 [SMILES: *c1nn[nH]n1]
Het-2313
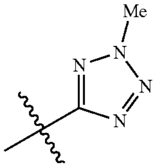 [SMILES: *c1nnn(C)n1]
Het-2314
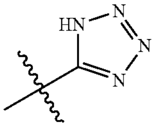 [SMILES: *c1nnn[nH]1]
Het-2315
TABLE 3-continued
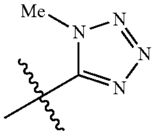 [SMILES: *c1nnnn1C]
Het-2316
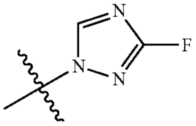 [SMILES: *n1cnc(F)n1]
Het-2317
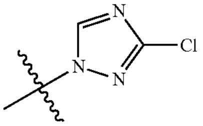 [SMILES: *n1cnc(Cl)n1]
Het-2318
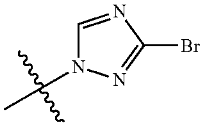 [SMILES: *n1cnc(Br)n1]
Het-2319
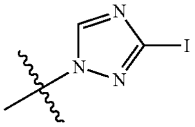 [SMILES: *n1cnc(I)n1]
Het-2320
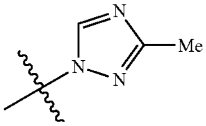 [SMILES: *n1cnc(C)n1]
Het-2321
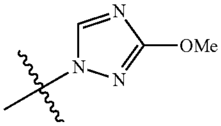 [SMILES: *n1cnc(OC)n1]
Het-2322
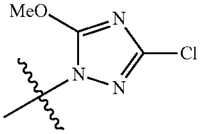 [SMILES: *n1nc(Cl)nc1OC]
Het-2323
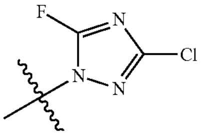 [SMILES: *n1nc(Cl)nc1F]
Het-2324
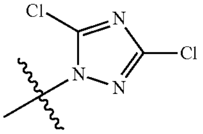
Het-2325
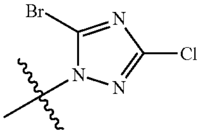 [SMILES: *n1nc(Cl)nc1Br]
Het-2326

TABLE 3-continued
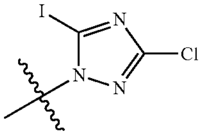 [SMILES: *n1nc(Cl)nc1I]
Het-2327
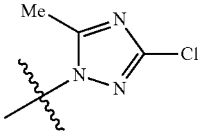 [SMILES: *n1nc(Cl)nc1C]
Het-2328
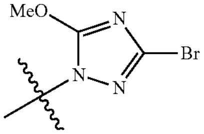 [SMILES: *n1nc(Br)nc1OC]
Het-2329
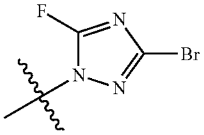 [SMILES: *n1nc(Br)nc1F]
Het-2330
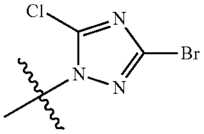
Het-2331
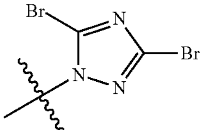 [SMILES: *n1nc(Br)nc1Br]
Het-2332
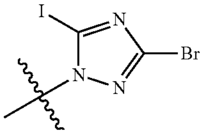 [SMILES: *n1nc(Br)nc1I]
Het-2333
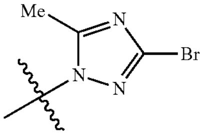 [SMILES: *n1nc(Br)nc1C]
Het-2334
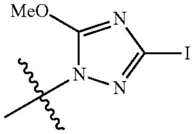 [SMILES: *n1nc(I)nc1OC]
Het-2335
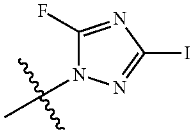 [SMILES: *n1nc(I)nc1F]
Het-2336
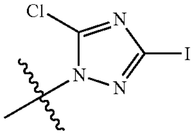
Het-2337
TABLE 3-continued
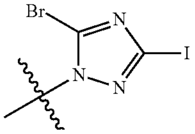 [SMILES: *n1nc(I)nc1Cl]
Het-2338
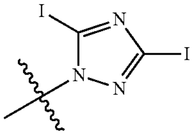 [SMILES: *n1nc(I)nc1I]
Het-2339
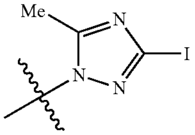 [SMILES: *n1nc(I)nc1C]
Het-2340
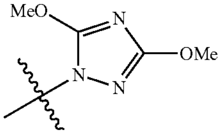 [SMILES: *n1nc(OC)nc1OC]
Het-2341
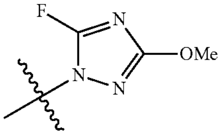 [SMILES: *n1nc(OC)nc1Cl]
Het-2342
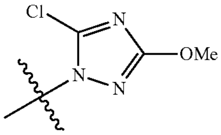
Het-2343
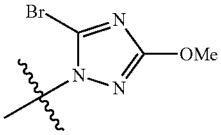 [SMILES: *n1nc(OC)nc1Br]
Het-2344
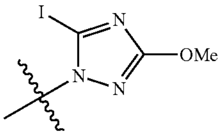 [SMILES: *n1nc(OC)nc1I]
Het-2345
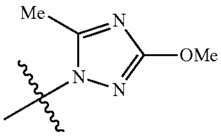 [SMILES: *n1nc(OC)nc1C]
Het-2346
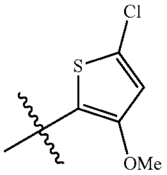 [SMILES: *c1sc(Cl)cc1OC]
Het-2347

TABLE 3-continued
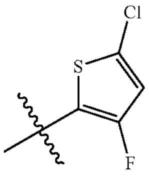 [SMILES: *c1sc(Cl)cc1F]
Het-2348
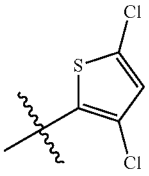
Het-2349
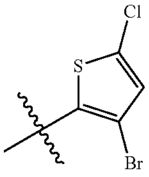 [SMILES: *c1sc(Cl)cc1Br]
Het-2350
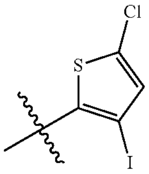 [SMILES: *c1sc(Cl)cc1I]
Het-2351
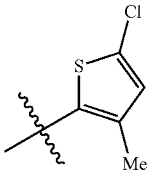 [SMILES: *c1sc(Cl)cc1C]
Het-2352
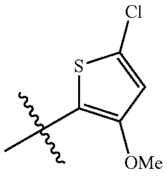 [SMILES: *c1sc(Cl)cc1OC]
Het-2353
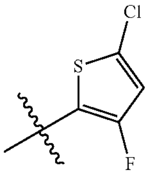 [SMILES: *c1sc(Cl)cc1F]
Het-2354
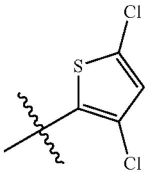
Het-2355
TABLE 3-continued
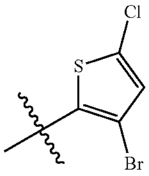 [SMILES: *c1sc(Cl)cc1Br]
Het-2356
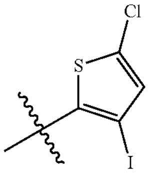
Het-2357
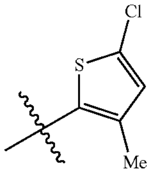 [SMILES: *c1sc(Cl)cc1C]
Het-2358
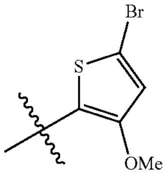 [SMILES: *c1sc(Br)cc1OC]
Het-2359
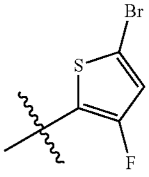 [SMILES: *c1sc(Br)cc1F]
Het-2360
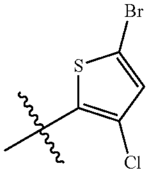 [SMILES: *c1sc(Br)cc1Cl]
Het-2361
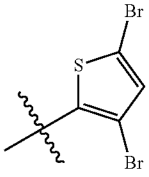 [SMILES: *c1sc(Br)cc1Br]
Het-2362
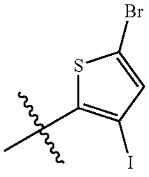 [SMILES: *c1sc(Br)cc1I]
Het-2363

TABLE 3-continued
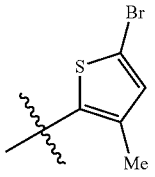 [SMILES: *c1sc(Br)cc1C]
Het-2364
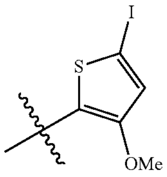 [SMILES: *c1sc(I)cc1OC]
Het-2365
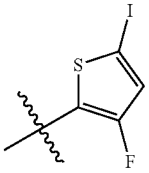 [SMILES: *c1sc(I)cc1F]
Het-2366
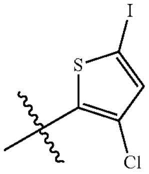 [SMILES: *c1sc(I)cc1Cl]
Het-2367
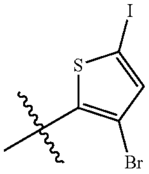 [SMILES: *c1sc(I)cc1Br]
Het-2368
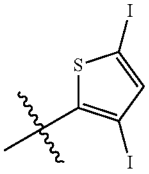 [SMILES: *c1sc(I)cc1I]
Het-2369
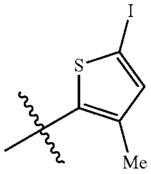 [SMILES: *c1sc(I)cc1C]
Het-2370
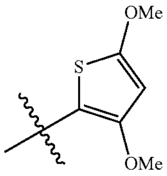 [SMILES: *c1sc(OC)cc1OC]
Het-2371
TABLE 3-continued
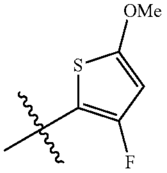 [SMILES: *c1sc(OC)cc1F]
Het-2372
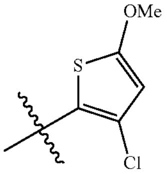 [SMILES: *c1sc(OC)cc1Cl]
Het-2373
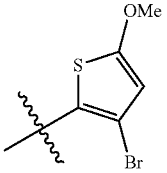 [SMILES: *c1sc(OC)cc1Br]
Het-2374
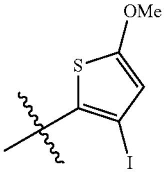 [SMILES: *c1sc(OC)cc1I]
Het-2375
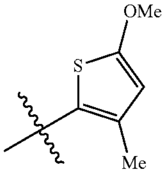 [SMILES: *c1sc(OC)cc1C]
Het-2376
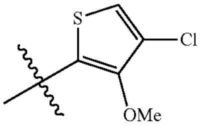 [SMILES: *c1scc(Cl)c1OC]
Het-2377
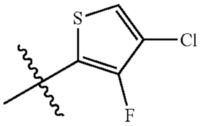 [SMILES: *c1scc(Cl)c1F]
Het-2378
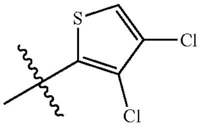 [SMILES: *c1scc(Cl)c1Cl]
Het-2379
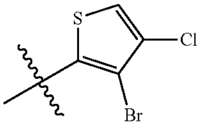 [SMILES: *c1scc(Cl)c1Br]
Het-2380
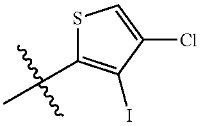 [SMILES: *c1scc(Cl)c1I]
Het-2381

TABLE 3-continued
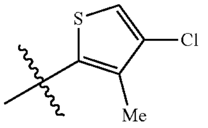 [SMILES: *c1scc(Cl)c1C]
Het-2382
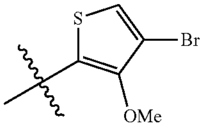 [SMILES: *c1scc(Br)c1OC]
Het-2383
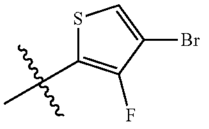
Het-2384
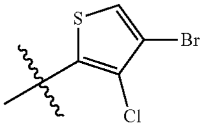 [SMILES: *c1scc(Br)c1Cl]
Het-2385
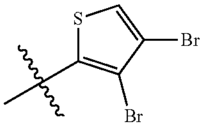 [SMILES: *c1scc(Br)c1Br]
Het-2386
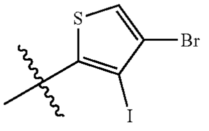 [SMILES: *c1scc(Br)c1I]
Het-2387
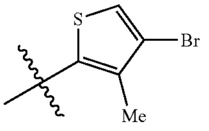 [SMILES: *c1scc(Br)c1C]
Het-2388
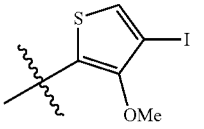 [SMILES: *c1scc(I)c1OC]
Het-2389
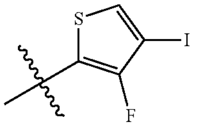
Het-2390
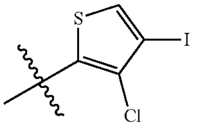 [SMILES: *c1scc(I)c1Cl]
Het-2391
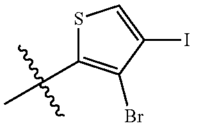 [SMILES: *c1scc(I)c1Br]
Het-2392
TABLE 3-continued
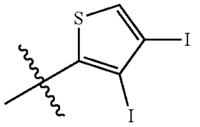
Het-2393
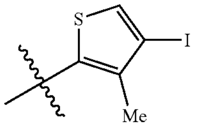 [SMILES: *c1scc(I)c1C]
Het-2394
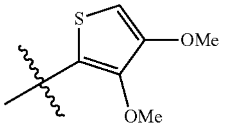 [SMILES: *c1scc(OC)c1OC]
Het-2395
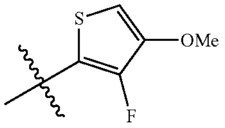
Het-2396
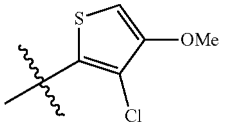 [SMILES: *c1scc(OC)c1Cl]
Het-2397
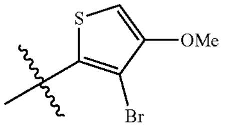
Het-2398
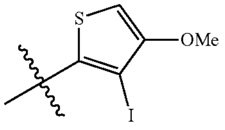 [SMILES: *c1scc(OC)c1I]
Het-2399
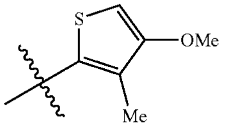 [SMILES: *c1scc(OC)c1C]
Het-2400
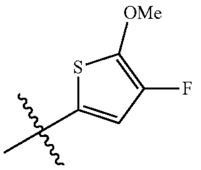
Het-2401
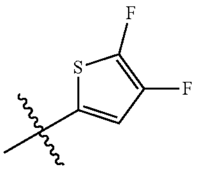
Het-2402

TABLE 3-continued
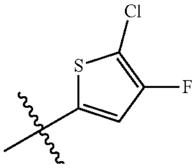 [SMILES: *c1cc(F)c(Cl)s1]
Het-2403
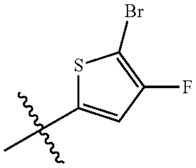
Het-2404
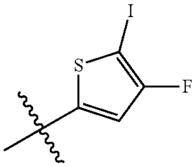 [SMILES: *c1cc(F)c(I)s1]
Het-2405
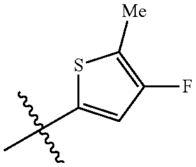 [SMILES: *c1cc(F)c(C)s1]
Het-2406
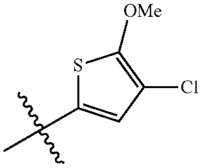 [SMILES: *c1cc(Cl)c(OC)s1]
Het-2407
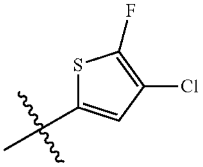 [SMILES: *c1cc(Cl)c(F)s1]
Het-2408
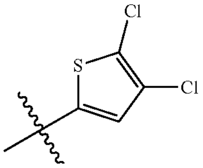 [SMILES: *c1cc(Cl)c(Cl)s1]
Het-2409
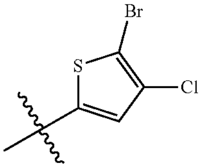 [SMILES: *c1cc(Cl)c(Br)s1]
Het-2410
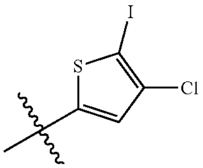 [SMILES: *c1cc(Cl)c(I)s1]
Het-2411
TABLE 3-continued
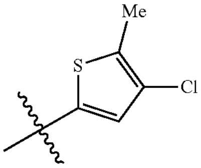 [SMILES: *c1cc(Cl)c(C)s1]
Het-2412
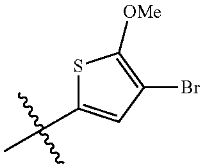 [SMILES: *c1cc(Br)c(OC)s1]
Het-2413
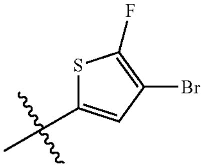 [SMILES: *c1cc(Br)c(F)s1]
Het-2414
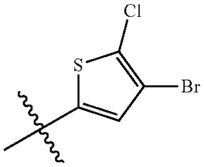 [SMILES: *c1cc(Br)c(Cl)s1]
Het-2415
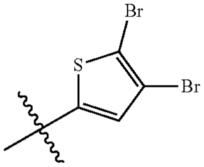 [SMILES: *c1cc(Br)c(Br)s1]
Het-2416
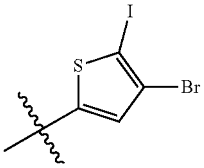 [SMILES: *c1cc(Br)c(I)s1]
Het-2417
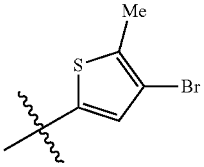 [SMILES: *c1cc(Br)c(C)s1]
Het-2418
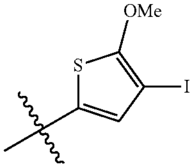 [SMILES: *c1cc(I)c(OC)s1]
Het-2419

TABLE 3-continued
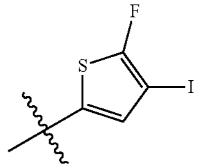
Het-2420
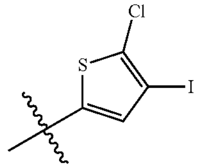 [SMILES: *c1cc(I)c(Cl)s1]
Het-2421
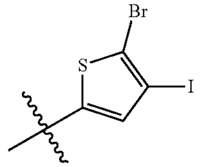 [SMILES: *c1cc(I)c(Br)s1]
Het-2422
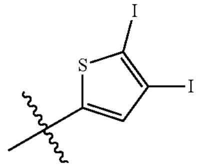 [SMILES: *c1cc(I)c(I)s1]
Het-2423
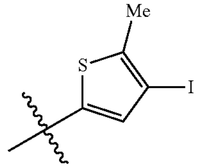 [SMILES: *c1cc(I)c(C)s1]
Het-2424
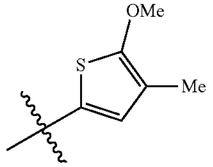 [SMILES: *c1cc(C)c(OC)s1]
Het-2425
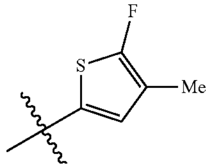 [SMILES: *c1cc(C)c(F)s1]
Het-2426
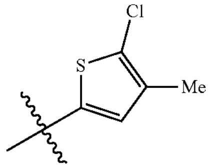 [SMILES: *c1cc(C)c(Cl)s1]
Het-2427
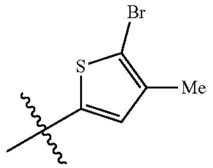 [SMILES: *c1cc(C)c(Br)s1]
Het-2428
TABLE 3-continued
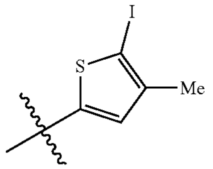 [SMILES: *c1cc(C)c(I)s1]
Het-2429
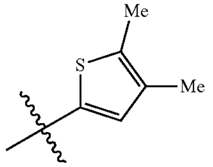 [SMILES: *c1cc(C)c(C)s1]
Het-2430
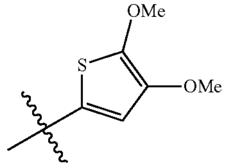 [SMILES: *c1cc(OC)c(OC)s1]
Het-2431
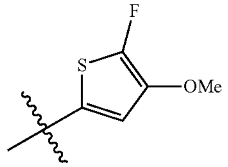
Het-2432
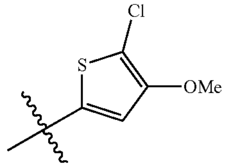 [SMILES: *c1cc(OC)c(Cl)s1]
Het-2433
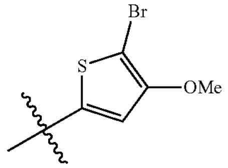 [SMILES: *c1cc(OC)c(Br)s1]
Het-2434
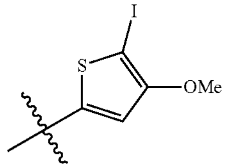 [SMILES: *c1cc(OC)c(I)s1]
Het-2435
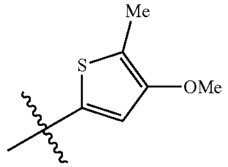 [SMILES: *c1cc(OC)c(C)s1]
Het-2436
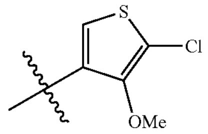 [SMILES: *c1csc(Cl)c1OC]
Het-2437

TABLE 3-continued
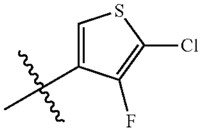 [SMILES: *c1csc(Cl)c1F]
Het-2438
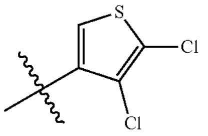 [SMILES: *c1csc(Cl)c1Cl]
Het-2439
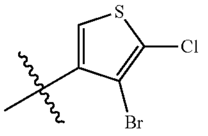 [SMILES: *c1csc(Cl)c1Br]
Het-2440
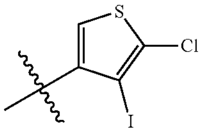 [SMILES: *c1csc(Cl)c1I]
Het-2441
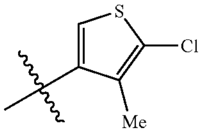 [SMILES: *c1csc(Cl)c1C]
Het-2442
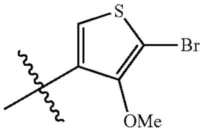 [SMILES: *c1csc(Br)c1OC]
Het-2443
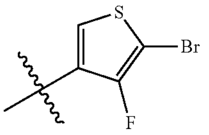
Het-2444
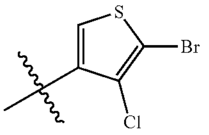 [SMILES: *c1csc(Br)c1Cl]
Het-2445
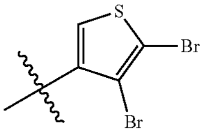 [SMILES: *c1csc(Br)c1Br]
Het-2446
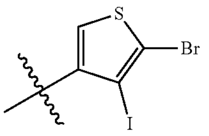 [SMILES: *c1csc(Br)c1I]
Het-2447
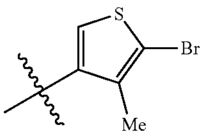 [SMILES: *c1csc(Br)c1C]
Het-2448
TABLE 3-continued
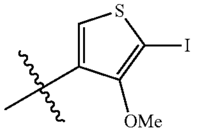 [SMILES: *c1csc(I)c1OC]
Het-2449
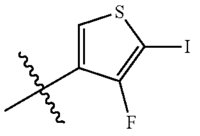
Het-2450
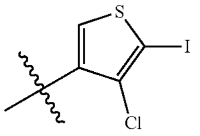 [SMILES: *c1csc(I)c1Cl]
Het-2451
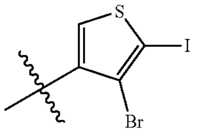 [SMILES: *c1csc(I)c1Br]
Het-2452
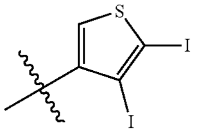 [SMILES: *c1csc(I)c1I]
Het-2453
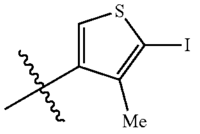 [SMILES: *c1csc(I)c1C]
Het-2454
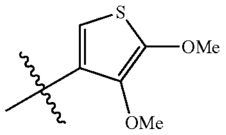 [SMILES: *c1csc(OC)c1OC]
Het-2455
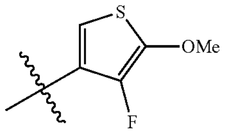
Het-2456
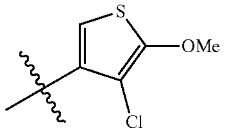 [SMILES: *c1csc(OC)c1Cl]
Het-2457
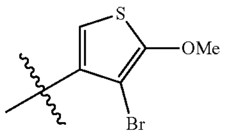 [SMILES: *c1csc(OC)c1Br]
Het-2458
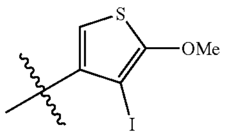 [SMILES: *c1csc(OC)c1I]
Het-2459

TABLE 3-continued
| | |
|---|---|
| 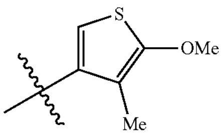 [SMILES: *c1csc(OC)c1C] | Het-2460 |
| 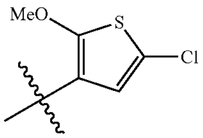 [SMILES: *c1cc(Cl)sc1OC] | Het-2461 |
| 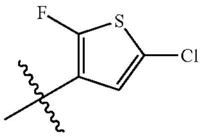 [SMILES: *c1cc(Cl)sc1F] | Het-2462 |
| 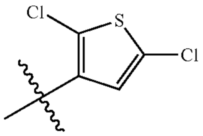 | Het-2463 |
| 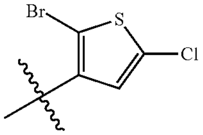 [SMILES: *c1cc(Cl)sc1Br] | Het-2464 |
| 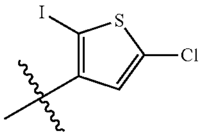 [SMILES: *c1cc(Cl)sc1I] | Het-2465 |
| 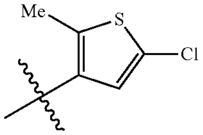 [SMILES: *c1cc(Cl)sc1C] | Het-2466 |
| 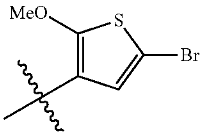 [SMILES: *c1cc(Br)sc1OC] | Het-2467 |
| 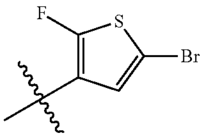 [SMILES: *c1cc(Br)sc1F] | Het-2468 |
| 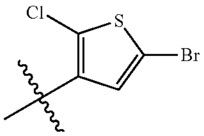 [SMILES: *c1cc(Br)sc1Cl] | Het-2469 |
TABLE 3-continued
| | |
|---|---|
| 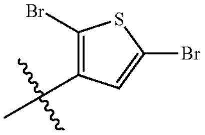 [SMILES: *c1cc(Br)sc1Br] | Het-2470 |
| 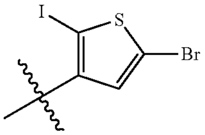 [SMILES: *c1cc(Br)sc1I] | Het-2471 |
| 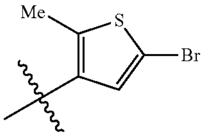 [SMILES: *c1cc(Br)sc1C] | Het-2472 |
| 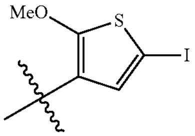 [SMILES: *c1cc(I)sc1OC] | Het-2473 |
| 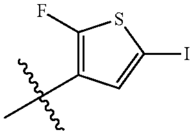 [SMILES: *c1cc(I)sc1F] | Het-2474 |
| 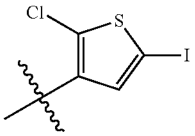 [SMILES: *c1cc(I)sc1Cl] | Het-2475 |
| 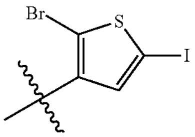 [SMILES: *c1cc(I)sc1Br] | Het-2476 |
| 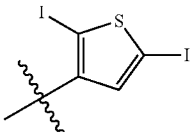 [SMILES: *c1cc(I)sc1I] | Het-2477 |
| 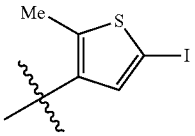 [SMILES: *c1cc(I)sc1C] | Het-2478 |
| 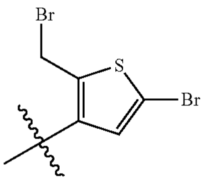 [SMILES: *c1cc(Br)sc1CBr] | Het-2479 |

TABLE 3-continued
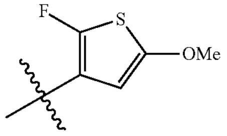
Het-2480
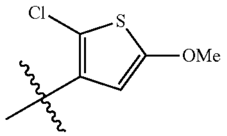
Het-2481
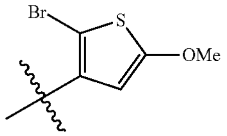 [SMILES: *c1cc(OC)sc1Br]
Het-2482
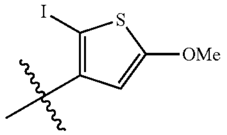 [SMILES: *c1cc(OC)sc1I]
Het-2483
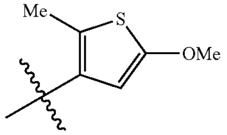 [SMILES: *c1cc(OC)sc1C]
Het-2484
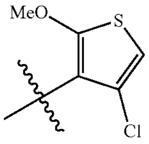 [SMILES: *c1c(Cl)csc1OC]
Het-2485
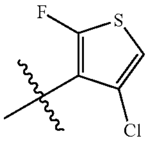 [SMILES: *c1c(Cl)csc1F]
Het-2486
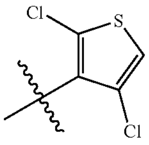 [SMILES: *c1c(Cl)csc1Cl]
Het-2487
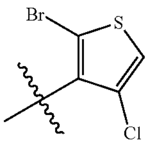 [SMILES: *c1c(Cl)csc1Br]
Het-2488
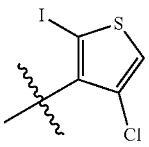 [SMILES: *c1c(Cl)csc1I]
Het-2489
TABLE 3-continued
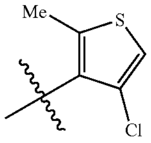 [SMILES: *c1c(Cl)csc1C]
Het-2490
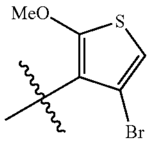 [SMILES: *c1c(Br)csc1OC]
Het-2491
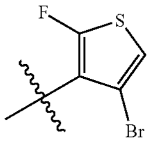
Het-2492
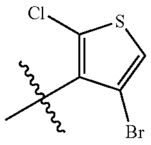 [SMILES: *c1c(Br)csc1Cl]
Het-2493
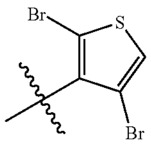 [SMILES: *c1c(Br)csc1Br]
Het-2494
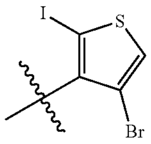 [SMILES: *c1c(Br)csc1I]
Het-2495
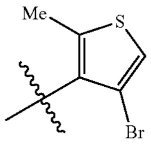 [SMILES: *c1c(Br)csc1C]
Het-2496
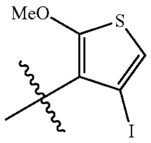 [SMILES: *c1c(I)csc1OC]
Het-2497
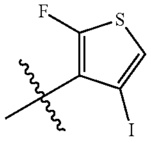 [SMILES: *c1c(I)csc1F]
Het-2498
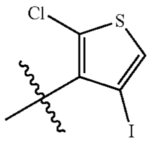 [SMILES: *c1c(I)csc1Cl]
Het-2499

TABLE 3-continued
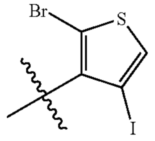 [SMILES: *c1c(I)csc1Br]
Het-2500
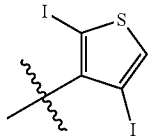 [SMILES: *c1c(I)csc1I]
Het-2501
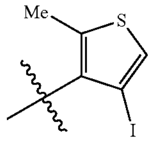 [SMILES: *c1c(I)csc1C]
Het-2502
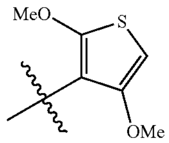 [SMILES: *c1c(OC)csc1OC]
Het-2503
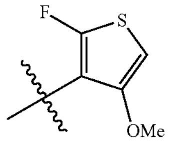 [SMILES: *c1c(OC)csc1F]
Het-2504
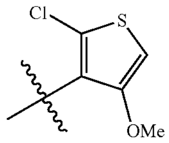
Het-2505
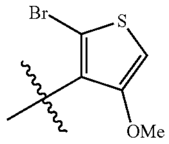 [SMILES: *c1c(OC)csc1Cl]
Het-2506
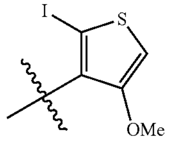 [SMILES: *c1c(OC)csc1I]
Het-2507
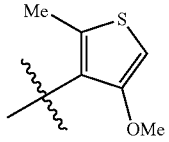 [SMILES: *c1c(OC)csc1C]
Het-2508
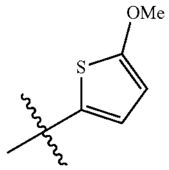 [SMILES: *c1ccc(OC)s1]
Het-2509
TABLE 3-continued
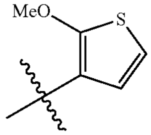 [SMILES: *c1ccsc1OC]
Het-2510
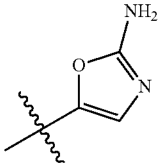 [SMILES: *c1cnc(N)o1]
Het-2511
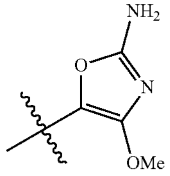 [SMILES: *c1oc(N)nc1OC]
Het-2512
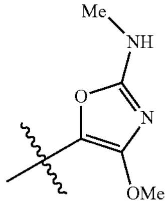 [SMILES: *c1oc(NC)nc1OC]
Het-2513
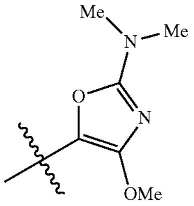 [SMILES: *c1oc(N(C)C)nc1OC]
Het-2514
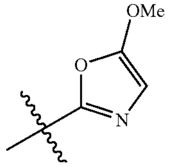 [SMILES: *c1ncc(OC)o1]
Het-2515
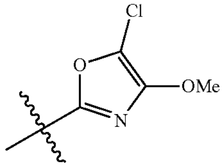 [SMILES: *c1nc(OC)c(Cl)o1]
Het-2516
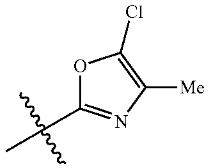 [SMILES: *c1nc(C)c(Cl)o1]
Het-2517

TABLE 3-continued
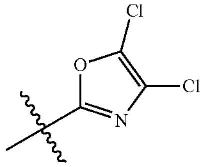 [SMILES: *c1nc(Cl)c(Cl)o1]
Het-2518
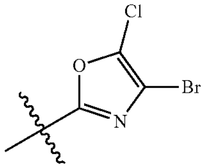 [SMILES: *c1nc(Br)c(Cl)o1]
Het-2519
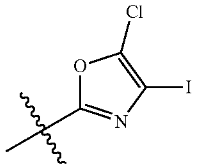 [SMILES: *c1nc(I)c(Cl)o1]
Het-2520
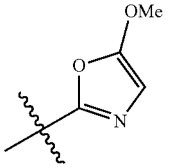 [SMILES: *c1ncc(OC)o1]
Het-2521
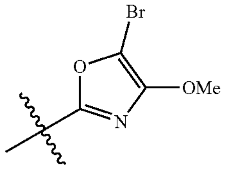 [SMILES: *c1nc(OC)c(Br)o1]
Het-2522
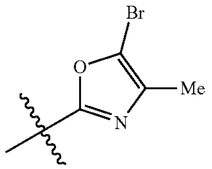 [SMILES: *c1nc(C)c(Br)o1]
Het-2523
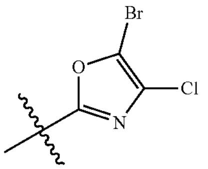 [SMILES: *c1nc(Cl)c(Br)o1]
Het-2524
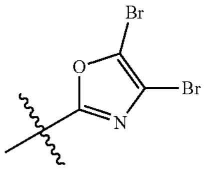 [SMILES: *c1nc(Br)c(Br)o1]
Het-2525
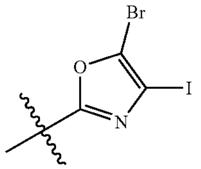 [SMILES: *c1nc(I)c(Br)o1]
Het-2526
TABLE 3-continued
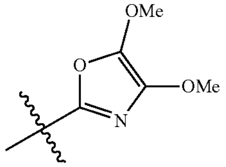 [SMILES: *c1nc(OC)c(OC)o1]
Het-2527
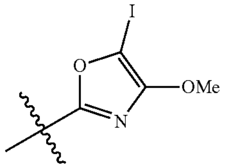 [SMILES: *c1nc(OC)c(I)o1]
Het-2528
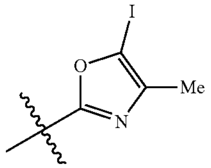 [SMILES: *c1nc(C)c(I)o1]
Het-2529
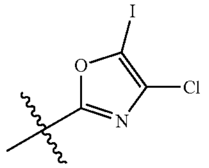 [SMILES: *c1nc(Cl)c(I)o1]
Het-2530
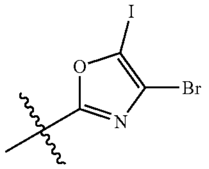 [SMILES: *c1nc(Br)c(I)o1]
Het-2531
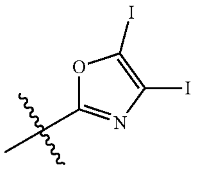 [SMILES: *c1nc(I)c(I)o1]
Het-2532
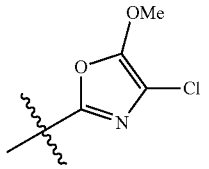 [SMILES: *c1nc(Cl)c(OC)o1]
Het-2533
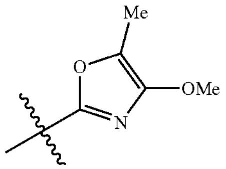 [SMILES: *c1nc(OC)c(C)o1]
Het-2534
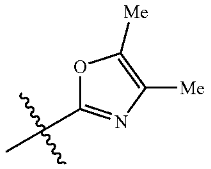 [SMILES: *c1nc(C)c(C)o1]
Het-2535

TABLE 3-continued
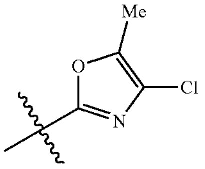 [SMILES: *c1nc(Cl)c(C)o1]
Het-2536
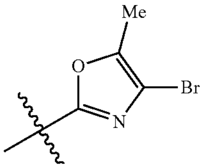 [SMILES: *c1nc(Br)c(C)o1]
Het-2537
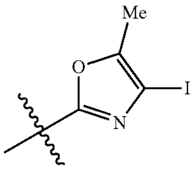 [SMILES: *c1nc(I)c(C)o1]
Het-2538
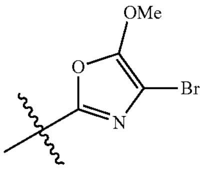 [SMILES: *c1nc(Br)c(OC)o1]
Het-2539
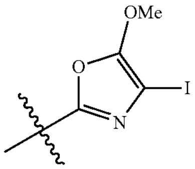 [SMILES: *c1nc(I)c(OC)o1]
Het-2540
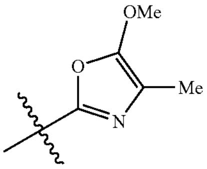 [SMILES: *c1nc(C)c(OC)o1]
Het-2541
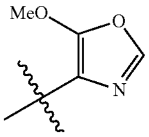 [SMILES: *c1ncoc1OC]
Het-2542
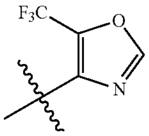 [SMILES: *c1ncoc1C(F)(F)F]
Het-2543
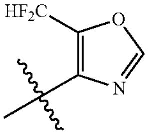 [SMILES: *c1ncoc1C(F)F]
Het-2544
TABLE 3-continued
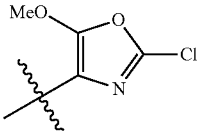 [SMILES: *c1nc(Cl)oc1OC]
Het-2545
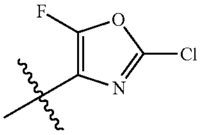 [SMILES: *c1nc(Cl)oc1F]
Het-2546
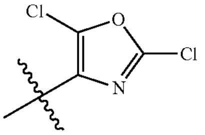 [SMILES: *c1nc(Cl)oc1Cl]
Het-2547
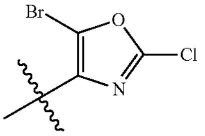 [SMILES: *c1nc(Cl)oc1Br]
Het-2548
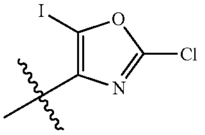 [SMILES: *c1nc(Cl)oc1I]
Het-2549
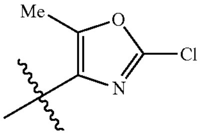 [SMILES: *c1nc(Cl)oc1C]
Het-2550
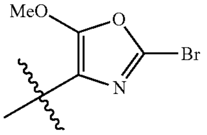 [SMILES: *c1nc(Br)oc1OC]
Het-2551
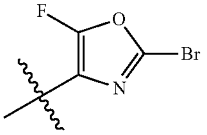 [SMILES: *c1nc(Br)oc1F]
Het-2552
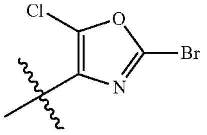 [SMILES: *c1nc(Br)oc1Cl]
Het-2553
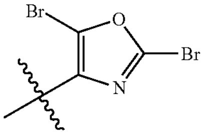 [SMILES: *c1nc(Br)oc1Br]
Het-2554
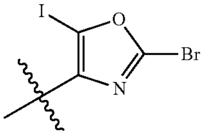 [SMILES: *c1nc(Br)oc1I]
Het-2555

TABLE 3-continued
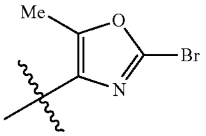 [SMILES: *c1nc(Br)oc1C]
Het-2556
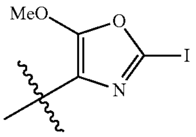 [SMILES: *c1nc(I)oc1OC]
Het-2557
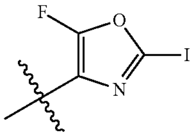 [SMILES: *c1nc(I)oc1F]
Het-2558
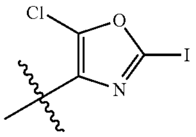 [SMILES: *c1nc(I)oc1Cl]
Het-2559
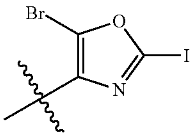 [SMILES: *c1nc(I)oc1Br]
Het-2560
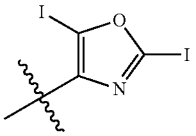 [SMILES: *c1nc(I)oc1I]
Het-2561
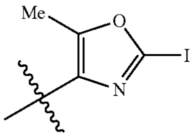 [SMILES: *c1nc(I)oc1C]
Het-2562
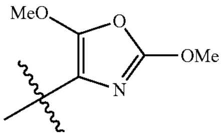 [SMILES: *c1nc(OC)oc1OC]
Het-2563
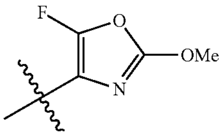
Het-2564
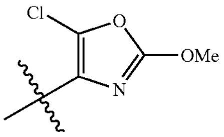 [SMILES: *c1nc(OC)oc1Cl]
Het-2565
TABLE 3-continued
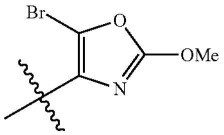 [SMILES: *c1nc(OC)oc1Br]
Het-2566
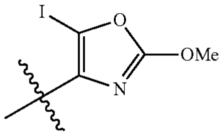 [SMILES: *c1nc(OC)oc1I]
Het-2567
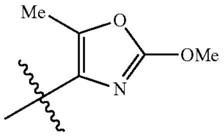 [SMILES: *c1nc(OC)oc1C]
Het-2568
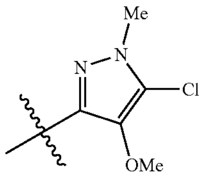 [SMILES: *c1nn(C)c(Cl)c1OC]
Het-2569
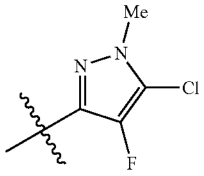 [SMILES: *c1nn(C)c(Cl)c1F]
Het-2570
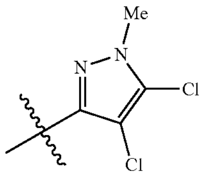 [SMILES: *c1nn(C)c(Cl)c1Cl]
Het-2571
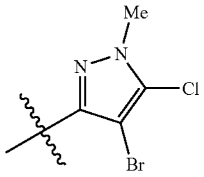 [SMILES: *c1nn(C)c(Cl)c1Br]
Het-2572
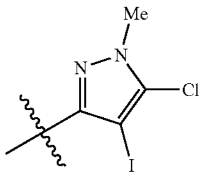 [SMILES: *c1nn(C)c(Cl)c1I]
Het-2573
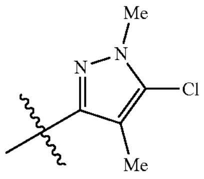 [SMILES: *c1nn(C)c(Cl)c1C]
Het-2574

TABLE 3-continued
Het-2575
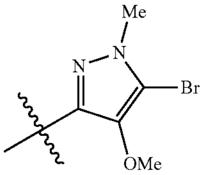 [SMILES: *c1nn(C)c(Br)c1OC]
Het-2576
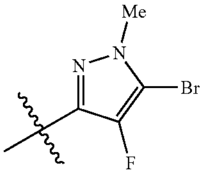
Het-2577
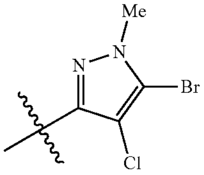 [SMILES: *c1nn(C)c(Br)c1Cl]
Het-2578
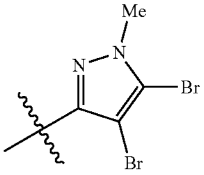 [SMILES: *c1nn(C)c(Br)c1Br]
Het-2579
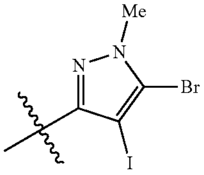 [SMILES: *c1nn(C)c(Br)c1I]
Het-2580
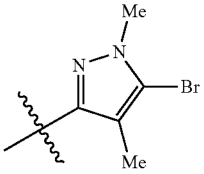 [SMILES: *c1nn(C)c(Br)c1C]
Het-2581
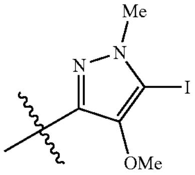 [SMILES: *c1nn(C)c(I)c1OC]
Het-2582
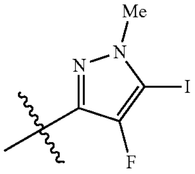
TABLE 3-continued
Het-2583
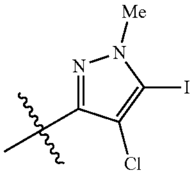 [SMILES: *c1nn(C)c(I)c1Cl]
Het-2584
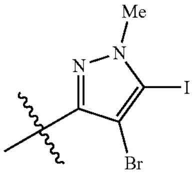 [SMILES: *c1nn(C)c(I)c1Br]
Het-2585
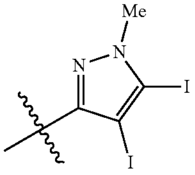 [SMILES: *c1nn(C)c(I)c1I]
Het-2586
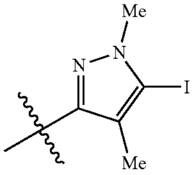 [SMILES: *c1nn(C)c(I)c1C]
Het-2587
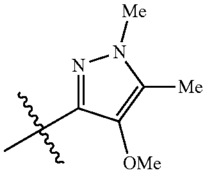 [SMILES: *c1nn(C)c(C)c1OC]
Het-2588
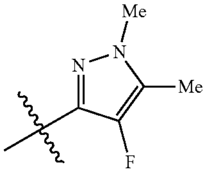
Het-2589
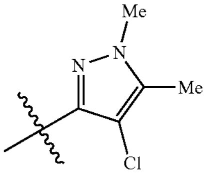 [SMILES: *c1nn(C)c(C)c1Cl]
Het-2590
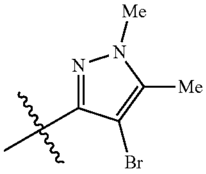 [SMILES: *c1nn(C)c(C)c1Br]

TABLE 3-continued
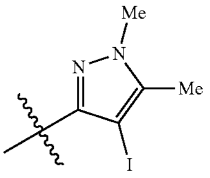 [SMILES: *c1nn(C)c(C)c1I]
Het-2591
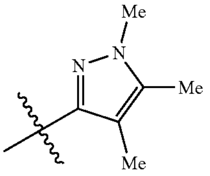 [SMILES: *c1nn(C)c(C)c1C]
Het-2592
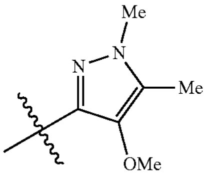 [SMILES: *c1nn(C)c(C)c1OC]
Het-2593
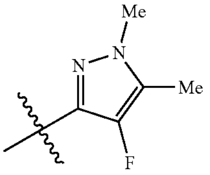 [SMILES: *c1nn(C)c(C)c1F]
Het-2594
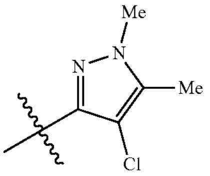 [SMILES: *c1nn(C)c(C)c1Cl]
Het-2595
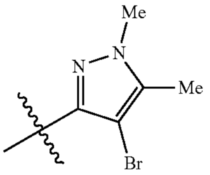 [SMILES: *c1nn(C)c(C)c1Br]
Het-2596
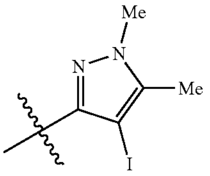 [SMILES: *c1nn(C)c(C)c1I]
Het-2597
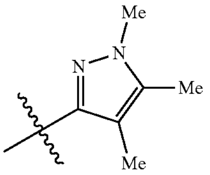 [SMILES: *c1nn(C)c(C)c1C]
Het-2598
TABLE 3-continued
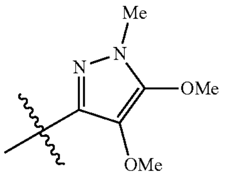 [SMILES: *c1nn(C)c(OC)c1OC]
Het-2599
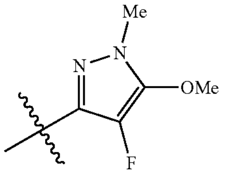
Het-2600
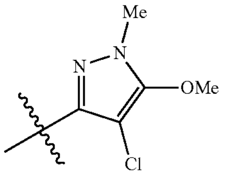 [SMILES: *c1nn(C)c(OC)c1Cl]
Het-2601
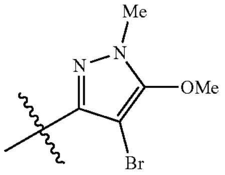 [SMILES: *c1nn(C)c(OC)c1Br]
Het-2602
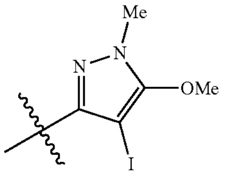 [SMILES: *c1nn(C)c(OC)c1I]
Het-2603
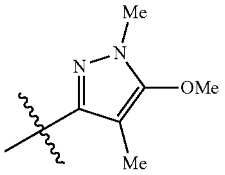 [SMILES: *c1nn(C)c(OC)c1C]
Het-2604
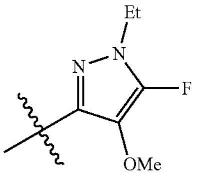 [SMILES: *c1nn(CC)c(F)c1OC]
Het-2605
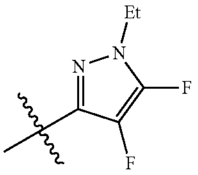 [SMILES: *c1nn(CC)c(F)c1I]
Het-2606

TABLE 3-continued
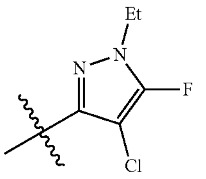
Het-2607
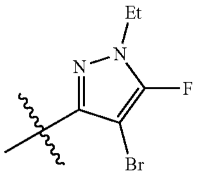
Het-2608
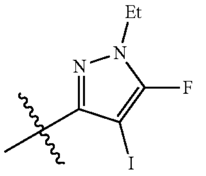
Het-2609
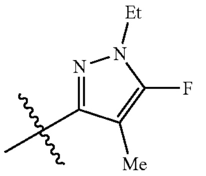 [SMILES: *c1nn(CC)c(F)c1C]
Het-2610
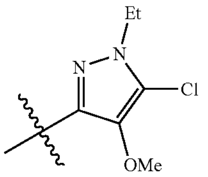 [SMILES: *c1nn(CC)c(Cl)c1OC]
Het-2611
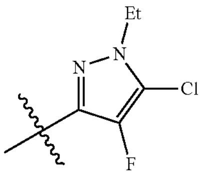 [SMILES: *c1nn(CC)c(Cl)c1F]
Het-2612
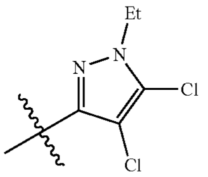 [SMILES: *c1nn(CC)c(Cl)c1Cl]
Het-2613
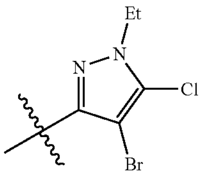 [SMILES: *c1nn(CC)c(Cl)c1Br]
Het-2614
TABLE 3-continued
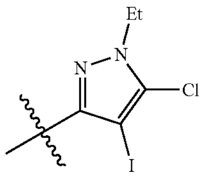 [SMILES: *c1nn(CC)c(Cl)c1I]
Het-2615
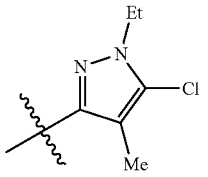 [SMILES: *c1nn(CC)c(Cl)c1C]
Het-2616
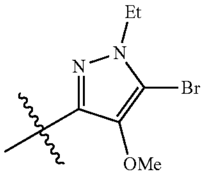 [SMILES: *c1nn(CC)c(Br)c1OC]
Het-2617
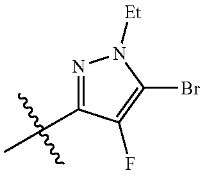 [SMILES: *c1nn(CC)c(Br)c1F]
Het-2618
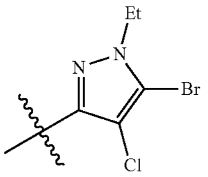 [SMILES: *c1nn(CC)c(Br)c1Cl]
Het-2619
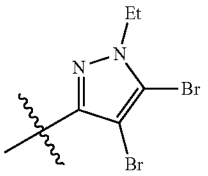 [SMILES: *c1nn(CC)c(Br)c1Br]
Het-2620
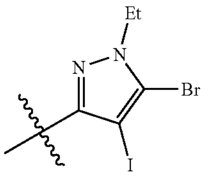 [SMILES: *c1nn(CC)c(Br)c1I]
Het-2621
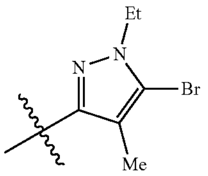 [SMILES: *c1nn(CC)c(Br)c1C]
Het-2622

TABLE 3-continued
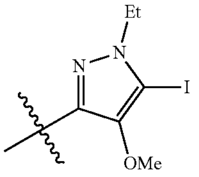 [SMILES: *c1nn(CC)c(I)c1OC]
Het-2623
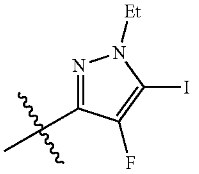
Het-2624
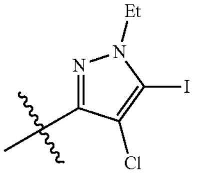 [SMILES: *c1nn(CC)c(I)c1Cl]
Het-2625
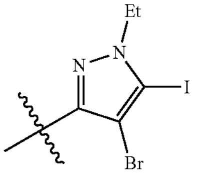 [SMILES: *c1nn(CC)c(I)c1Br]
Het-2626
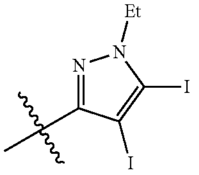 [SMILES: *c1nn(CC)c(I)c1I]
Het-2627
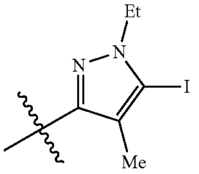 [SMILES: *c1nn(CC)c(I)c1C]
Het-2628
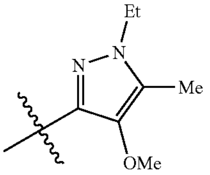 [SMILES: *c1nn(CC)c(C)c1OC]
Het-2629
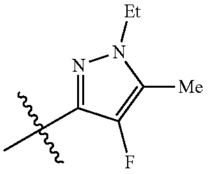 [SMILES: *c1nn(CC)c(C)c1F]
Het-2630
TABLE 3-continued
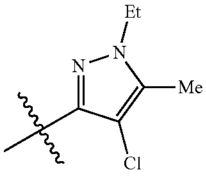 [SMILES: *c1nn(CC)c(C)c1Cl]
Het-2631
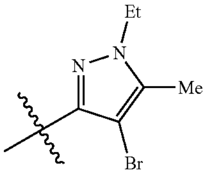 [SMILES: *c1nn(CC)c(C)c1Br]
Het-2632
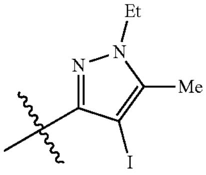 [SMILES: *c1nn(CC)c(C)c1I]
Het-2633
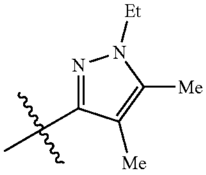 [SMILES: *c1nn(CC)c(C)c1C]
Het-2634
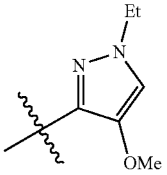 [SMILES: *c1nn(CC)cc1OC]
Het-2635
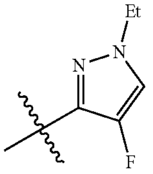 [SMILES: *c1nn(CC)cc1F]
Het-2636
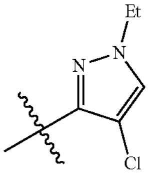 [SMILES: *c1nn(CC)cc1Cl]
Het-2637
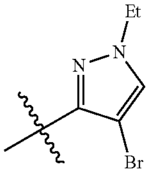 [SMILES: *c1nn(CC)cc1Br]
Het-2638

TABLE 3-continued
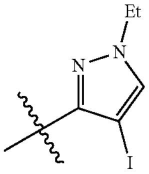 [SMILES: *c1nn(CC)cc1I]
Het-2639
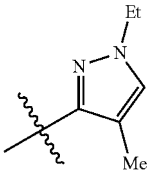 [SMILES: *c1nn(CC)cc1C]
Het-2640
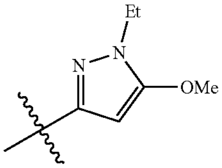 [SMILES: *c1cc(OC)n(CC)n1]
Het-2641
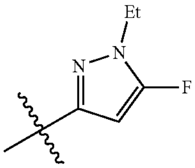 [SMILES: *c1cc(F)n(CC)n1]
Het-2642
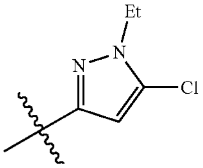 [SMILES: *c1cc(Cl)n(CC)n1]
Het-2643
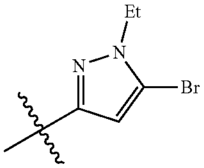 [SMILES: *c1cc(Br)n(CC)n1]
Het-2644
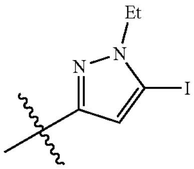 [SMILES: *c1cc(I)n(CC)n1]
Het-2645
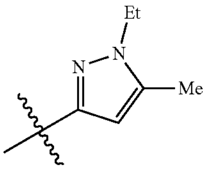 [SMILES: *c1cc(C)n(CC)n1]
Het-2646
TABLE 3-continued
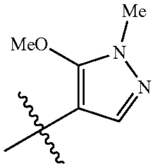 [SMILES: *c1cnn(C)c1OC]
Het-2647
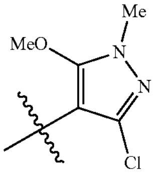 [SMILES: *c1c(Cl)nn(C)c1OC]
Het-2648
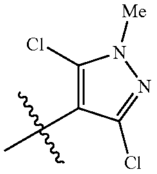 [SMILES: *c1c(Cl)nn(C)c1Cl]
Het-2649
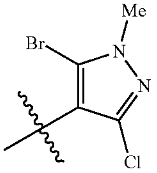 [SMILES: *c1c(Cl)nn(C)c1Br]
Het-2650
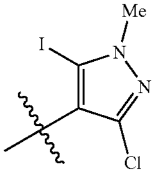 [SMILES: *c1c(Cl)nn(C)c1I]
Het-2651
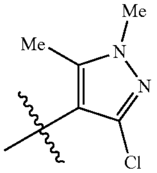 [SMILES: *c1c(Cl)nn(C)c1C]
Het-2652
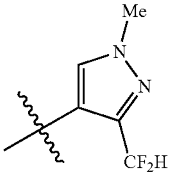 [SMILES: *c1cn(C)nc1C(F)F]
Het-2653
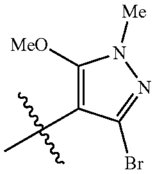 [SMILES: *c1c(Br)nn(C)c1OC]
Het-2654

TABLE 3-continued
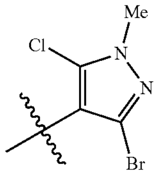 [SMILES: *c1c(Br)nn(C)c1Cl]
Het-2655
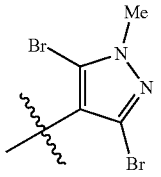
Het-2656
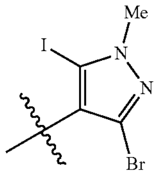 [SMILES: *c1c(Br)nn(C)c1I]
Het-2657
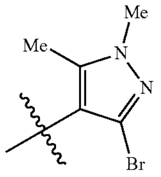 [SMILES: *c1c(Br)nn(C)c1C]
Het-2658
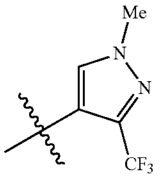 [SMILES: *c1cn(C)nc1C(F)(F)F]
Het-2659
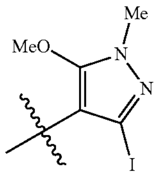 [SMILES: *c1c(I)nn(C)c1OC]
Het-2660
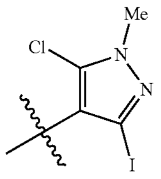 [SMILES: *c1c(I)nn(C)c1Cl]
Het-2661
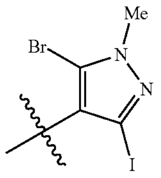
Het-2662
TABLE 3-continued
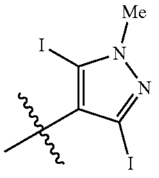 [SMILES: *c1c(I)nn(C)c1I]
Het-2663
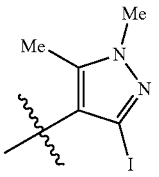 [SMILES: *c1c(I)nn(C)c1C]
Het-2664
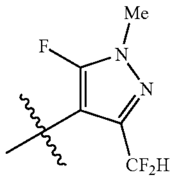 [SMILES: *c1c(C(F)F)nn(C)c1F]
Het-2665
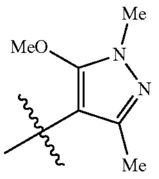 [SMILES: *c1c(C)nn(C)c1OC]
Het-2666
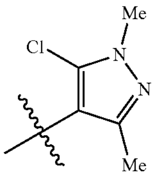 [SMILES: *c1c(C)nn(C)c1Cl]
Het-2667
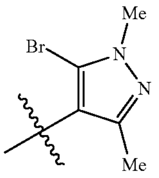 [SMILES: *c1c(C)nn(C)c1Br]
Het-2668
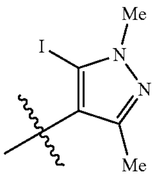 [SMILES: *c1c(C)nn(C)c1I]
Het-2669
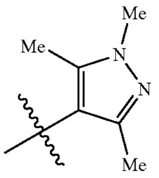 [SMILES: *c1c(C)nn(C)c1C]
Het-2670

TABLE 3-continued
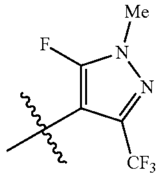 [SMILES: *c1c(C(F)(F)F)nn(C)c1F]
Het-2671
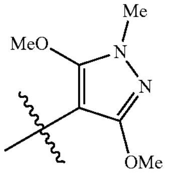 [SMILES: *c1c(OC)nn(C)c1OC]
Het-2672
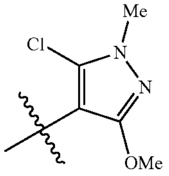
Het-2673
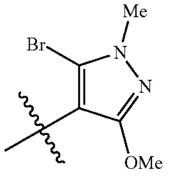 [SMILES: *c1c(OC)nn(C)c1Br]
Het-2674
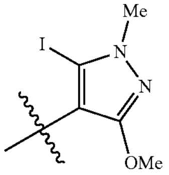 [SMILES: *c1c(OC)nn(C)c1I]
Het-2675
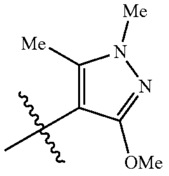 [SMILES: *c1c(OC)nn(C)c1C]
Het-2676
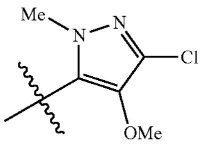 [SMILES: *c1c(OC)c(Cl)nn1C]
Het-2677
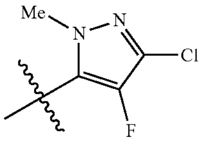 [SMILES: *c1c(F)c(Cl)nn1C]
Het-2678
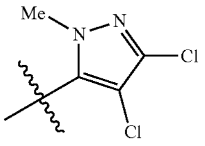 [SMILES: *c1c(Cl)c(Cl)nn1C]
Het-2679
TABLE 3-continued
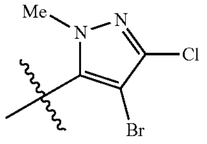 [SMILES: *c1c(Br)c(Cl)nn1C]
Het-2680
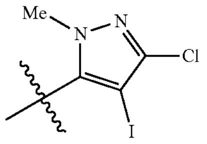 [SMILES: *c1c(I)c(Cl)nn1C]
Het-2681
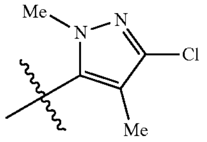 [SMILES: *c1c(C)c(Cl)nn1C]
Het-2682
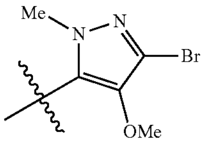 [SMILES: *c1c(OC)c(Br)nn1C]
Het-2683
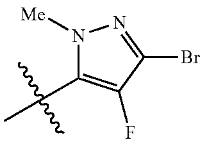 [SMILES: *c1c(F)c(Br)nn1C]
Het-2684
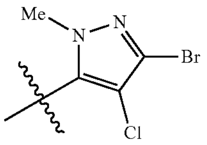 [SMILES: *c1c(Cl)c(Br)nn1C]
Het-2685
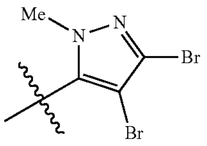
Het-2686
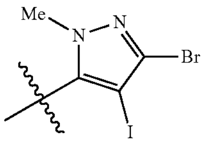 [SMILES: *c1c(I)c(Br)nn1C]
Het-2687
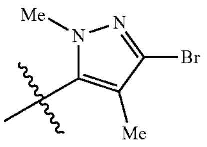 [SMILES: *c1c(C)c(Br)nn1C]
Het-2688
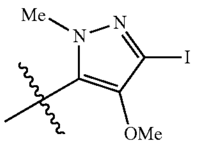 [SMILES: *c1c(OC)c(I)nn1C]
Het-2689

TABLE 3-continued
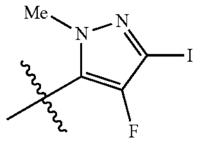
Het-2690
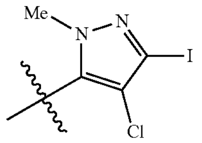 [SMILES: *c1c(Cl)c(I)nn1C]
Het-2691
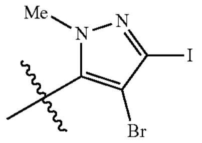 [SMILES: *c1c(Br)c(I)nn1C]
Het-2692
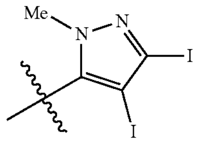 [SMILES: *c1c(I)c(I)nn1C]
Het-2693
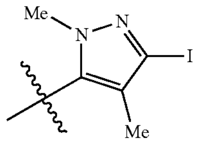 [SMILES: *c1c(C)c(I)nn1C]
Het-2694
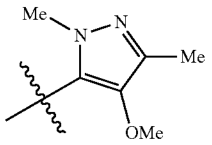 [SMILES: *c1c(OC)c(C)nn1C]
Het-2695
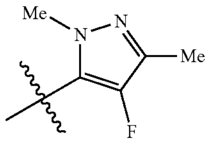
Het-2696
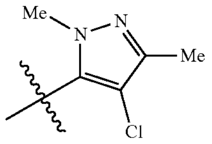 [SMILES: *c1c(Cl)c(C)nn1C]
Het-2697
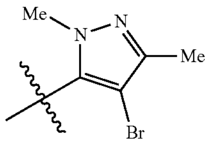 [SMILES: *c1c(Br)c(C)nn1C]
Het-2698
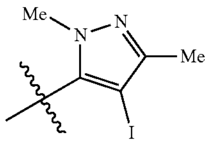 [SMILES: *c1c(I)c(C)nn1C]
Het-2699
TABLE 3-continued
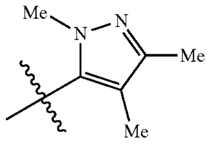 [SMILES: *c1c(C)c(C)nn1C]
Het-2700
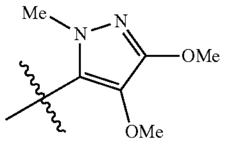 [SMILES: *c1c(OC)c(OC)nn1C]
Het-2701
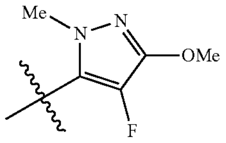
Het-2702
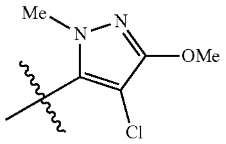 [SMILES: *c1c(Cl)c(OC)nn1C]
Het-2703
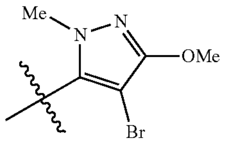 [SMILES: *c1c(Br)c(OC)nn1C]
Het-2704
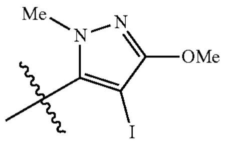 [SMILES: *c1c(I)c(OC)nn1C]
Het-2705
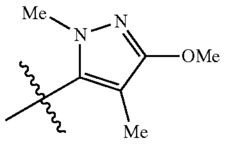 [SMILES: *c1c(C)c(OC)nn1C]
Het-2706
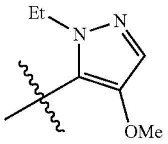 [SMILES: *c1c(OC)cnn1CC]
Het-2707
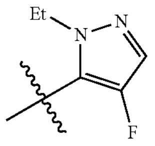 [SMILES: *c1c(F)cnn1CC]
Het-2708
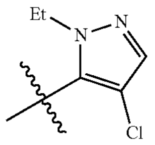 [SMILES: *c1c(Cl)cnn1CC]
Het-2709

TABLE 3-continued
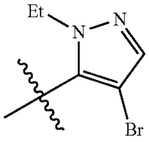 [SMILES: *c1c(Br)cnn1CC]
Het-2710
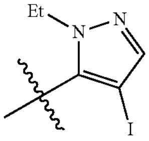 [SMILES: *c1c(I)cnn1CC]
Het-2711
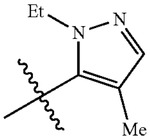 [SMILES: *c1c(C)cnn1CC]
Het-2712
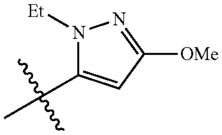 [SMILES: *c1cc(OC)nn1CC]
Het-2713
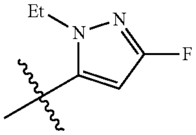 [SMILES: *c1cc(F)nn1CC]
Het-2714
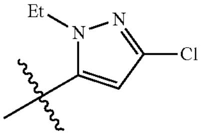 [SMILES: *c1cc(Cl)nn1CC]
Het-2715
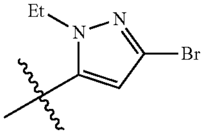 [SMILES: *c1cc(Br)nn1CC]
Het-2716
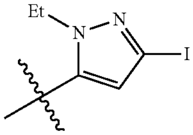 [SMILES: *c1cc(I)nn1CC]
Het-2717
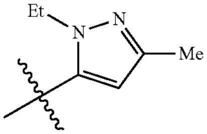 [SMILES: *c1cc(C)nn1CC]
Het-2718
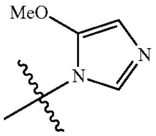 [SMILES: *n1cncc1OC]
Het-2719
TABLE 3-continued
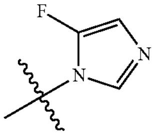 [SMILES: *n1cncc1F]
Het-2720
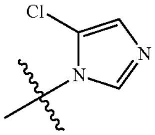 [SMILES: *n1cncc1Cl]
Het-2721
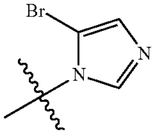 [SMILES: *n1cncc1Br]
Het-2722
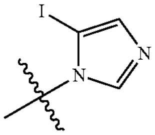 [SMILES: *n1cncc1I]
Het-2723
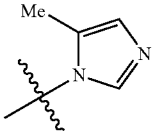 [SMILES: *n1cncc1C]
Het-2724
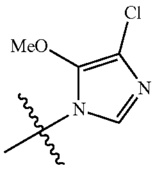
Het-2725
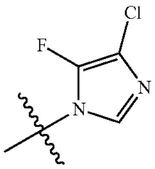
Het-2726
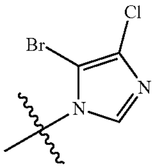
Het-2727
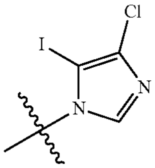 [SMILES: *n1cnc(Cl)c1I]
Het-2728

TABLE 3-continued
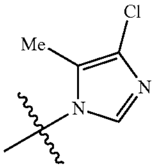 [SMILES: *n1cnc(Cl)c1C]
Het-2729
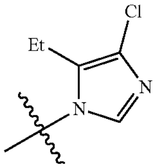 [SMILES: *n1cnc(Cl)c1CC]
Het-2730
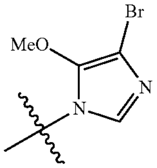 [SMILES: *n1cnc(Br)c1OC]
Het-2731
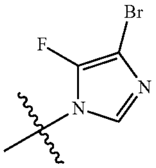 [SMILES: *n1cnc(Br)c1F]
Het-2732
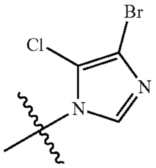 [SMILES: *n1cnc(Br)c1Cl]
Het-2733
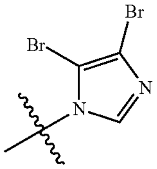
Het-2734
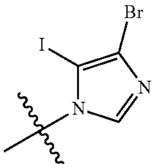 [SMILES: *n1cnc(Br)c1I]
Het-2735
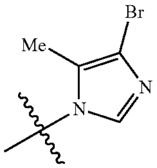 [SMILES: *n1cnc(Br)c1C]
Het-2736
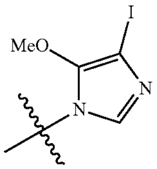 [SMILES: *n1cnc(I)c1OC]
Het-2737
TABLE 3-continued
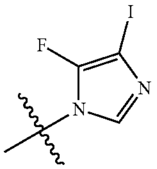
Het-2738
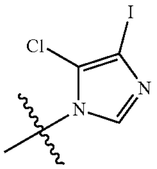 [SMILES: *n1cnc(I)c1Cl]
Het-2739
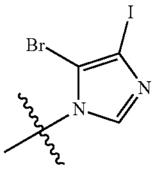 [SMILES: *n1cnc(I)c1Br]
Het-2740
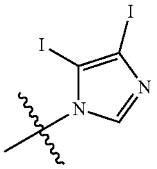 [SMILES: *n1cnc(I)c1I]
Het-2741
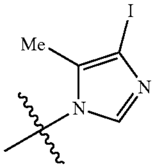 [SMILES: *n1cnc(I)c1C]
Het-2742
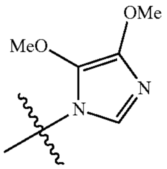 [SMILES: *n1cnc(OC)c1OC]
Het-2743
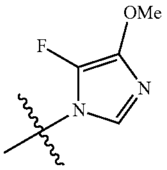 [SMILES: *n1cnc(OC)c1F]
Het-2744
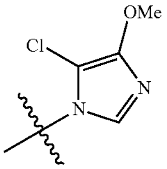 [SMILES: *n1cnc(OC)c1Cl]
Het-2745

TABLE 3-continued
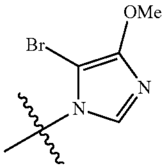 [SMILES: *n1cnc(OC)c1Br]
Het-2746
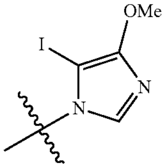 [SMILES: *n1cnc(OC)c1I]
Het-2747
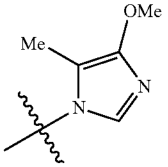 [SMILES: *n1cnc(OC)c1C]
Het-2748
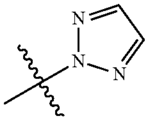 [SMILES: *n1nccn1]
Het-2749
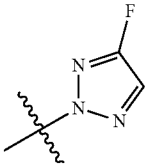 [SMILES: *n1ncc(F)n1]
Het-2750
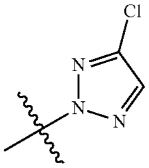
Het-2751
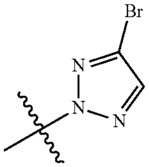 [SMILES: *n1ncc(Br)n1]
Het-2752
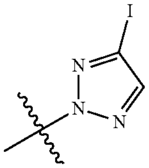 [SMILES: *n1ncc(I)n1]
Het-2753
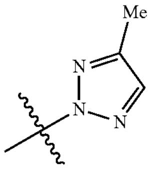 [SMILES: *n1ncc(C)n1]
Het-2754
TABLE 3-continued
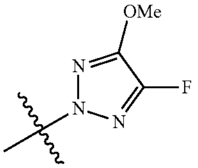 [SMILES: *n1nc(F)c(OC)n1]
Het-2755
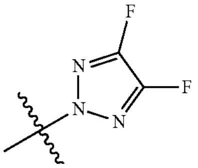
Het-2756
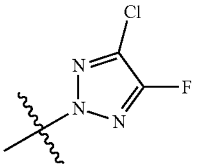
Het-2757
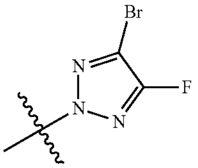 [SMILES: *n1nc(F)c(Br)n1]
Het-2758
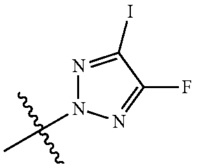 [SMILES: *n1nc(F)c(I)n1]
Het-2759
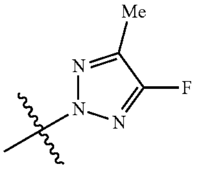 [SMILES: *n1nc(C)c(F)n1]
Het-2760
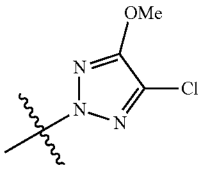 [SMILES: *n1nc(Cl)c(OC)n1]
Het-2761
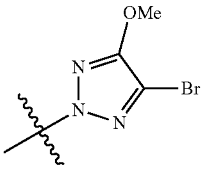 [SMILES: *n1nc(Br)c(OC)n1]
Het-2762
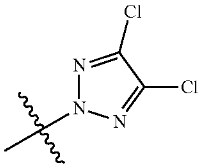 [SMILES: *n1nc(Cl)c(Cl)n1]
Het-2763

TABLE 3-continued
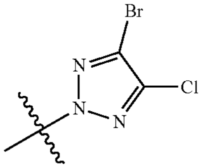 [SMILES: *n1nc(Cl)c(Br)n1]
Het-2764
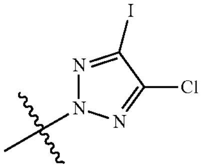 [SMILES: *n1nc(Cl)c(I)n1]
Het-2765
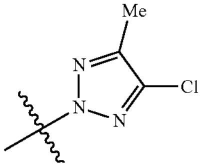 [SMILES: *n1nc(C)c(Cl)n1]
Het-2766
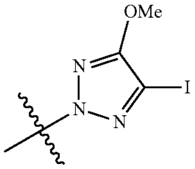 [SMILES: *n1nc(I)c(OC)n1]
Het-2767
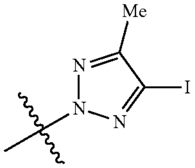 [SMILES: *n1nc(C)c(I)n1]
Het-2768
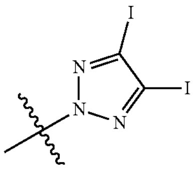 [SMILES: *n1nc(I)c(I)n1]
Het-2769
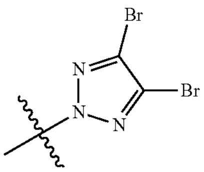 [SMILES: *n1nc(Br)c(Br)n1]
Het-2770
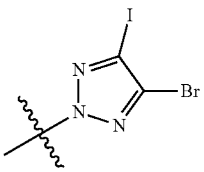 [SMILES: *n1nc(Br)c(I)n1]
Het-2771
TABLE 3-continued
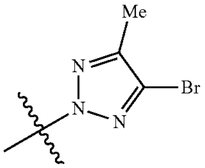 [SMILES: *n1nc(C)c(Br)n1]
Het-2772
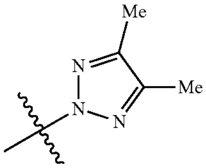 [SMILES: *n1nc(C)c(C)n1]
Het-2773
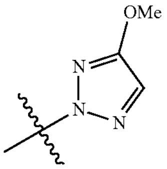 [SMILES: *n1ncc(OC)n1]
Het-2774
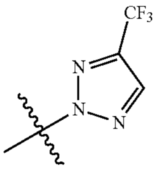 [SMILES: *n1ncc(C(F)(F)F)n1]
Het-2775
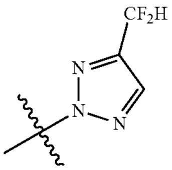 [SMILES: *n1ncc(C(F)F)n1]
Het-2776
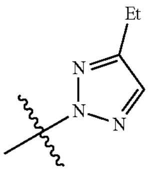 [SMILES: *n1ncc(CC)n1]
Het-2777
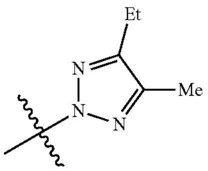 [SMILES: *n1nc(C)c(CC)n1]
Het-2778
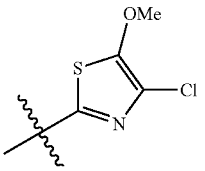 [SMILES: *c1nc(Cl)c(OC)s1]
Het-2779
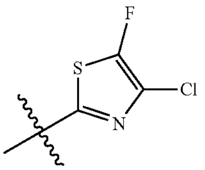 [SMILES: *c1nc(Cl)c(F)s1]
Het-2780

TABLE 3-continued
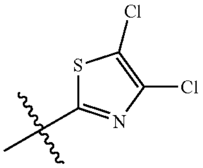
Het-2781
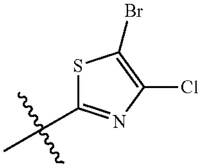 [SMILES: *c1nc(Cl)c(Br)s1]
Het-2782
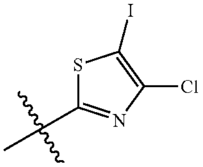 [SMILES: *c1nc(Cl)c(I)s1]
Het-2783
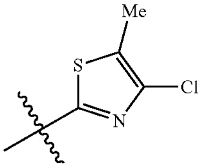 [SMILES: *c1nc(Cl)c(C)s1]
Het-2784
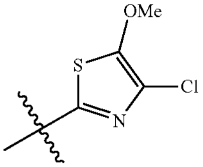 [SMILES: *c1nc(Cl)c(OC)s1]
Het-2785
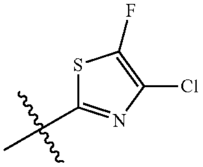 [SMILES: *c1nc(Cl)c(F)s1]
Het-2786
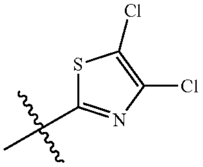
Het-2787
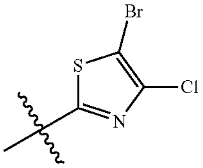 [SMILES: *c1nc(Cl)c(Br)s1]
Het-2788
TABLE 3-continued
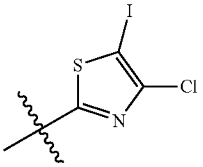 [SMILES: *c1nc(Cl)c(I)s1]
Het-2789
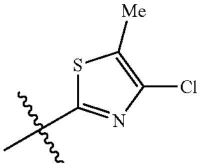 [SMILES: *c1nc(Cl)c(C)s1]
Het-2790
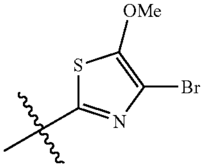 [SMILES: *c1nc(Br)c(OC)s1]
Het-2791
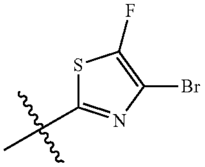 [SMILES: *c1nc(Br)c(F)s1]
Het-2792
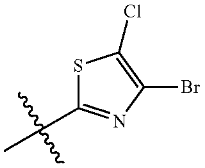 [SMILES: *c1nc(Br)c(Cl)s1]
Het-2793
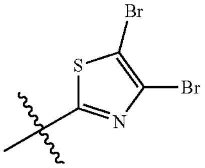
Het-2794
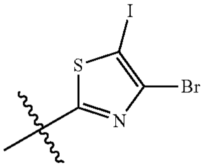 [SMILES: *c1nc(Br)c(I)s1]
Het-2795
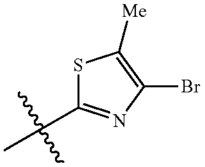 [SMILES: *c1nc(Br)c(C)s1]
Het-2796
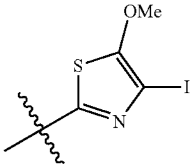 [SMILES: *c1nc(I)c(OC)s1]
Het-2797

TABLE 3-continued
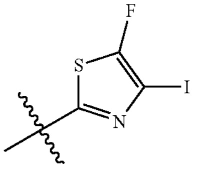
Het-2798
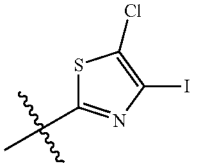 [SMILES: *c1nc(I)c(F)s1]
Het-2799
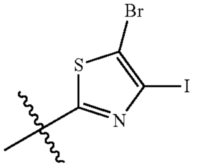 [SMILES: *c1nc(I)c(Br)s1]
Het-2800
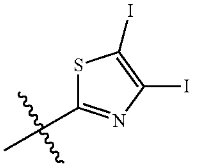 [SMILES: *c1nc(I)c(I)s1]
Het-2801
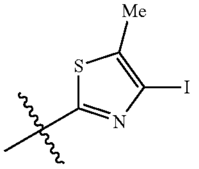
Het-2802
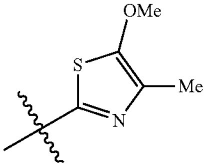 [SMILES: *c1nc(C)c(OC)s1]
Het-2803
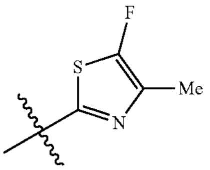 [SMILES: *c1nc(C)c(F)s1]
Het-2804
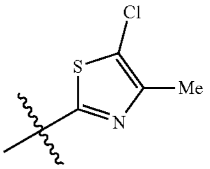 [SMILES: *c1nc(C)c(Cl)s1]
Het-2805
TABLE 3-continued
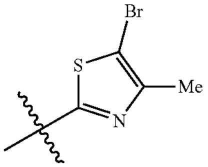 [SMILES: *c1nc(C)c(Br)s1]
Het-2806
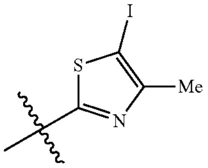 [SMILES: *c1nc(C)c(I)s1]
Het-2807
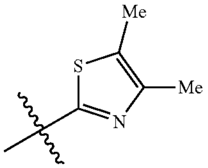 [SMILES: *c1nc(C)c(C)s1]
Het-2808
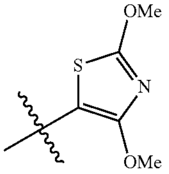 [SMILES: *c1sc(OC)nc1OC]
Het-2809
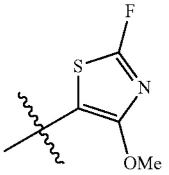 [SMILES: *c1sc(F)nc1OC]
Het-2810
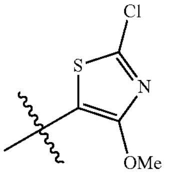 [SMILES: *c1sc(Cl)nc1OC]
Het-2811
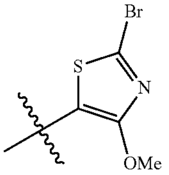 [SMILES: *c1sc(Br)nc1OC]
Het-2812
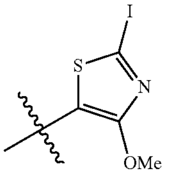 [SMILES: *c1sc(I)nc1OC]
Het-2813

TABLE 3-continued
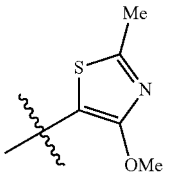 [SMILES: *c1sc(C)nc1OC]
Het-2814
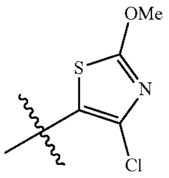 [SMILES: *c1sc(OC)nc1Cl]
Het-2815
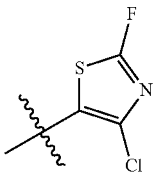
Het-2816
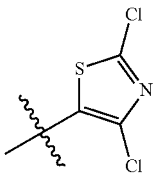 [SMILES: *c1sc(Cl)nc1Cl]
Het-2817
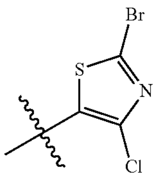
Het-2818
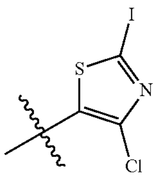 [SMILES: *c1sc(I)nc1Cl]
Het-2819
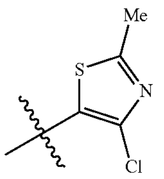 [SMILES: *c1sc(C)nc1Cl]
Het-2820
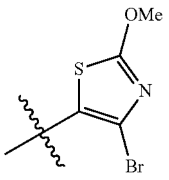 [SMILES: *c1sc(OC)nc1Br]
Het-2821
TABLE 3-continued
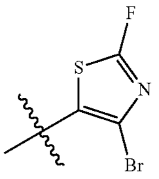
Het-2822
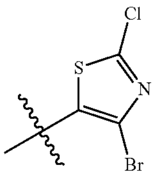 [SMILES: *c1sc(F)nc1Br]
Het-2823
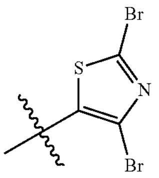 [SMILES: *c1sc(Br)nc1Br]
Het-2824
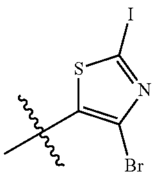 [SMILES: *c1sc(I)nc1Br]
Het-2825
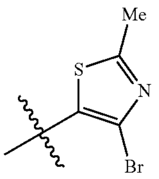
Het-2826
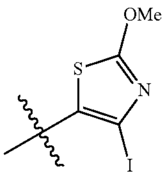 [SMILES: *c1sc(OC)nc1I]
Het-2827
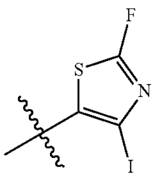
Het-2828
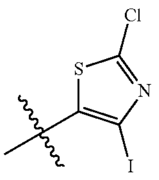
Het-2829

TABLE 3-continued
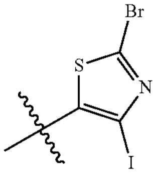 [SMILES: *c1sc(Br)nc1I]
Het-2830
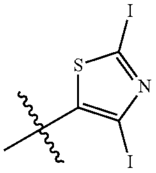 [SMILES: *c1sc(I)nc1I]
Het-2831
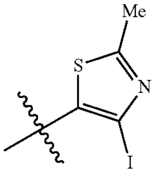 [SMILES: *c1sc(C)nc1I]
Het-2832
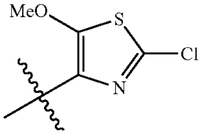
Het-2833
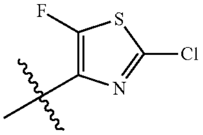 [SMILES: *c1nc(Cl)sc1F]
Het-2834
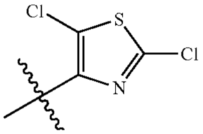
Het-2835
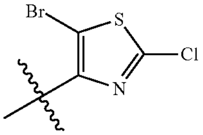 [SMILES: *c1nc(Cl)sc1Br]
Het-2836
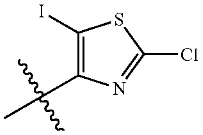 [SMILES: *c1nc(Cl)sc1I]
Het-2837
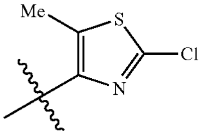 [SMILES: *c1nc(Cl)sc1C]
Het-2838
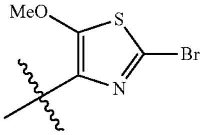
Het-2839
TABLE 3-continued
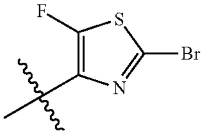
Het-2840
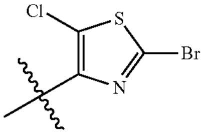
Het-2841
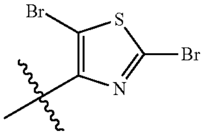 [SMILES: *c1nc(Br)sc1Br]
Het-2842
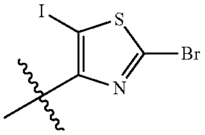
Het-2843
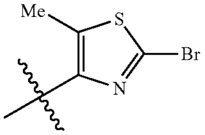
Het-2844
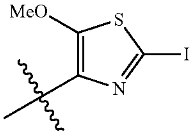 [SMILES: *c1nc(I)sc1OC]
Het-2845
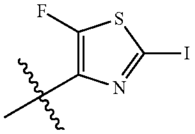 [SMILES: *c1nc(I)sc1F]
Het-2846
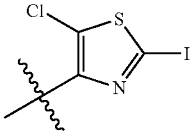
Het-2847
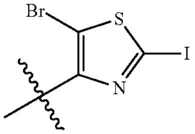 [SMILES: *c1nc(I)sc1Br]
Het-2848
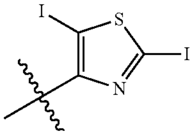 [SMILES: *c1nc(I)sc1I]
Het-2849
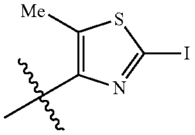 [SMILES: *c1nc(I)sc1C]
Het-2850

TABLE 3-continued
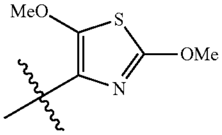 [SMILES: *c1nc(OC)sc1OC]
Het-2851
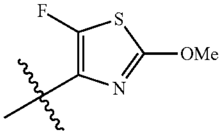
Het-2852
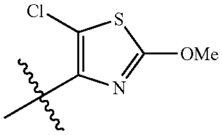
Het-2853
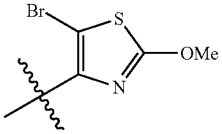 [SMILES: *c1nc(OC)sc1Br]
Het-2854
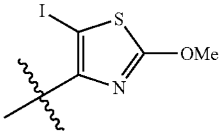
Het-2855
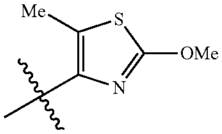 [SMILES: *c1nc(OC)sc1C]
Het-2856
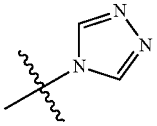 [SMILES: *n1cnnc1]
Het-2857
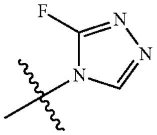 [SMILES: *n1cnnc1F]
Het-2858
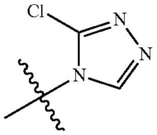
Het-2859
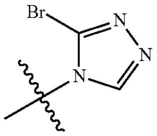 [SMILES: *n1cnnc1Br]
Het-2860
TABLE 3-continued
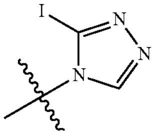 [SMILES: *n1cnnc1I]
Het-2861
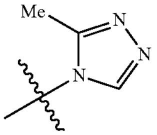 [SMILES: *n1cnnc1C]
Het-2862
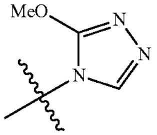 [SMILES: *n1cnnc1OC]
Het-2863
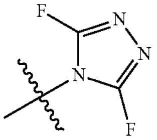
Het-2864
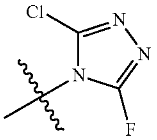
Het-2865
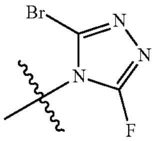 [SMILES: *n1c(F)nnc1Cl]
Het-2866
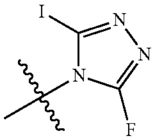
Het-2867
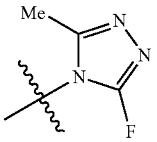 [SMILES: *n1c(C)nnc1F]
Het-2868
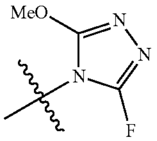 [SMILES: *n1c(F)nnc1OC]
Het-2869
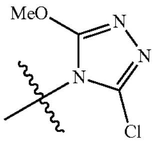 [SMILES: *n1c(Cl)nnc1OC]
Het-2870

TABLE 3-continued

| | |
|---|---|
| 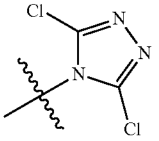 | Het-2871 |
| 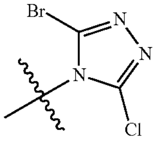 [SMILES: *n1c(Cl)nnc1Br] | Het-2872 |
| 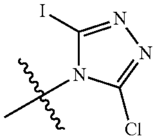 [SMILES: *n1c(Cl)nnc1I] | Het-2873 |
| 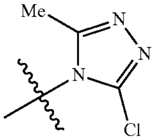 [SMILES: *n1c(C)nnc1Cl] | Het-2874 |
| 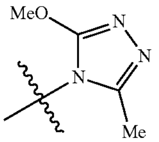 [SMILES: *n1c(C)nnc1OC] | Het-2875 |
| 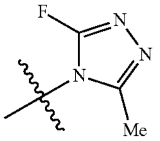 | Het-2876 |
| 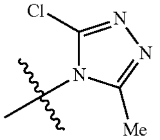 | Het-2877 |
| 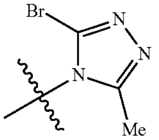 [SMILES: *n1c(C)nnc1Cl] | Het-2878 |
| 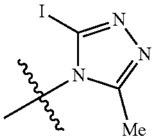 [SMILES: *n1c(C)nnc1I] | Het-2879 |
| 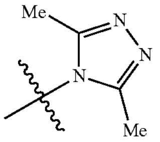 [SMILES: *n1c(C)nnc1C] | Het-2880 |

In the following, examples of the methods for producing the compounds represented by Formula (1) will be illustrated. The methods for producing the compounds of the present invention are not limited to Production Method A to Production Method AJ.

[Production Method A]

[Chem. 83]

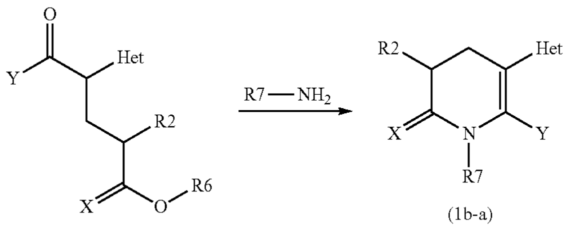

(3) (1b-a)

In the formula, R7 represents a hydrogen atom, a hydroxyl group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group or RaRbN— (wherein Ra and Rb each independently represents a hydrogen atom, a C1-C6 alkyl group optionally substituted with substituent(s) B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group), R6 represents a hydrogen atom or a C1-C6 alkyl group, and R2, Het, X and Y are the same as defined hereinabove.

Production Method A is a method for obtaining a compound represented by Formula (1b-a) including a compound of the present invention and a production intermediate of a compound of the present invention, and includes reacting a compound represented by Formula (3) with $R7NH_2$ in the presence of an acid.

The $R7NH_2$ used in the present reaction can be obtained as a commercially available product or produced by a conventionally known method. The $R7NH_2$ may be a material which forms a salt with an acidic compound such as hydrochloric acid and acetic acid, and is not particularly limited as long as the target reaction proceeds.

The $R7NH_2$ used in the present reaction may be 1 equivalent or more relative to the compound represented by Formula (3), and is not particularly limited as long as the target reaction proceeds, and is preferably 1 equivalent or more and 200 equivalents or less.

The acids used in the present reaction may be exemplified by an inorganic acid such as hydrochloric acid, sulfuric acid and the like, and an organic acid such as acetic acid, methanesulfonic acid, p-toluenesulfonic acid and the like, and is not particularly limited as long as the target reaction proceeds, and preferably acetic acid. In addition, when a salt of the $R7NH_2$ and the acidic compound is used, use of the acid is not essential.

An amount of the acid used in the present reaction may be 1 equivalent or more relative to the $R7NH_2$, and is not particularly limited as long as the target reaction proceeds, and preferably 1 equivalent or more and 200 equivalents or less. In addition, when the acid to be used is a liquid, it is possible to use it as a solvent.

A solvent may be used in the present reaction, but it is not essential.

The solvent to be used in the present reaction is not particularly limited as long as the target reaction proceeds, and may include acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, and the like. These solvents may be used singly, or two or more kinds may be used in combination in an optional ratio. As the solvents, among others, acidic solvents are preferably mentioned, and acetic acid is more preferably mentioned.

An amount of the solvent used in the present reaction is not particularly limited as long as the target reaction proceeds, and is usually 3 times by weight to 200 times by weight relative to the amount of the compound represented by Formula (3).

A temperature to carry out the present reaction is not particularly limited as long as the target reaction proceeds, and is usually 50° C. or higher and 180° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio.

The number of times of the liquid separation is not particularly limited, and may be carried out in accordance with the purity and yield to be desired.

The reaction mixture obtained above which contains the compound represented by Formula (1b-a) may be dehydrated with a drying agent such as sodium sulfate and magnesium sulfate, but this is not essential.

The reaction mixture obtained above which contains the compound represented by Formula (1b-a) may be distilled under reduced pressure to remove the solvent as long as the compound is not decomposed.

The reaction mixture obtained after distillation of the solvent which contains the compound represented by Formula (1b-a) may be purified by washing, reprecipitation, recrystallization, column chromatography and the like, using a suitable solvent. It may be optionally set in accordance with the desired purity.

According to Production Method A, a compound represented by Formula (2) which can be produced when R7 in a compound represented by Formula (1b-a) represents a hydrogen atom can be a useful production intermediate for obtaining a compound represented by Formula (1b) among the compounds of the present invention.

Specific examples of the production intermediate represented by Formula (2) are shown by combinations of the structural formulae (I-1 to I-12) illustrated in Table 4, Y illustrated in Table 2, Het illustrated in Table 3, and X which is an oxygen atom or a sulfur atom. These compounds are only illustrative, and the present invention is not limited by these.

[Table 4]

TABLE 4

| | |
|---|---|
| 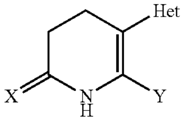 | I-1 |
| 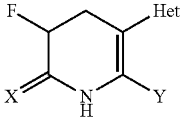 | I-2 |
| 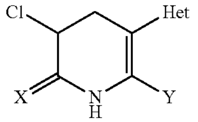 | I-3 |
| 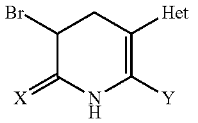 | I-4 |
| 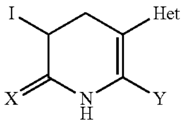 | I-5 |
| 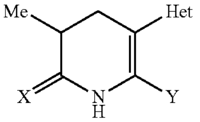 | I-6 |
| 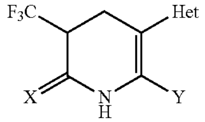 | I-7 |
| 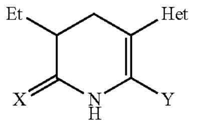 | I-8 |

TABLE 4-continued

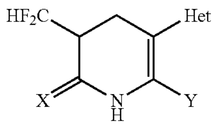

I-9

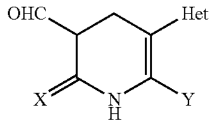

I-10

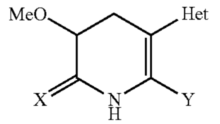

I-11

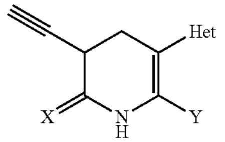

I-12

A method for obtaining Formula (1b) of the present invention by utilizing the compound represented by Formula (2) as a production intermediate is described.

[Production Method B]

[Chem. 84]

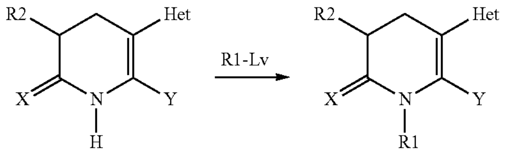

(2)

(1b)

In the formula, Lv represents a leaving group such as a methanesulfonyl group, a trifluoromethanesulfonyl group, a p-toluenesulfonyl group or a halogen atom, and R1, R2, Het, X and Y are the same as defined hereinabove.

Production Method B is a method for obtaining a compound represented by Formula (1b), and is a production method which comprises reacting a production intermediate represented by Formula (2) with R1-Lv in the presence of a base in a solvent.

The R1-Lv to be used in the present reaction can be obtained as a commercially available product or produced by a conventionally known method.

An amount of the R1-Lv to be used in the present reaction may be 1 equivalent or more relative to the compound represented by Formula (2), which is not particularly limited as long as the target reaction proceeds, and preferably 1 equivalent or more and 10 equivalents or less.

The base to be used in the present reaction may be exemplified by inorganic bases such as sodium hydroxide, potassium hydroxide, sodium carbonate, potassium carbonate, cesium carbonate and sodium hydride, which is not particularly limited as long as the target reaction proceeds.

An amount of the base to be used in the present reaction may be 1 equivalent or more relative to the compound represented by Formula (2), which is not particularly limited as long as the target reaction proceeds, preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like.

These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (2).

A temperature to carry out the present reaction is not particularly limited as long, as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1b) may be dehydrated with a drying agent such as sodium sulfate and magnesium sulfate, but this is not essential.

The reaction mixture obtained above which contains the compound represented by Formula (1b) may be distilled under reduced pressure to remove the solvent as long as the compound is not decomposed.

The reaction mixture obtained after distillation of the solvent which contains the compound represented by Formula (1b) may be purified by washing, reprecipitation, recrystallization, column chromatography and the like, using a suitable solvent. It may be optionally set in accordance with the desired purity.

[Production Method C]

[Chem. 85]

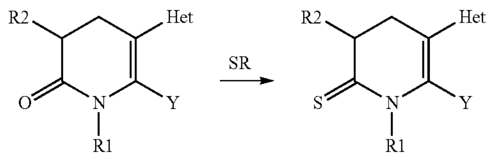

(1b-b) (1b-c)

In the formula, SR represents a sulfurizing agent, and R1, R2, Het and Y are the same as defined hereinabove.

Production Method C is a production method for obtaining a compound represented by Formula (1b-c) which belongs to the compounds represented by Formula (1b), and is a production method which comprises reacting a compound represented by Formula (1b-b) and a sulfurizing agent (SR) in a solvent.

An example of the sulfurizing agent to be used in the present reaction may include Lawesson's reagent (2,4-bis (4-methoxyphenyl)-1,3-dithia-2,4-diphosphetane-2,4-disulfide) and the like.

An amount of the sulfurizing agent to be used in the present reaction may be 0.5 equivalent or more relative to a compound represented by Formula (1b-b), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1b-b).

A temperature to carry out the present reaction is not particularly limited as long as the target reaction proceeds, and is usually 50° C. or higher and 180° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. Also, in the present reaction, the liquid separating operation is not essential.

The reaction mixture obtained above which contains the compound represented by Formula (1b-c) may be dehydrated with a drying agent such as sodium sulfate and magnesium sulfate, but this is not essential.

The reaction mixture obtained above which contains the compound represented by Formula (1b-c) may be distilled under reduced pressure to remove the solvent as long as the compound is not decomposed.

The reaction mixture obtained after distillation of the solvent which contains the compound represented by Formula (1b-c) may be purified by washing, reprecipitation, recrystallization, column chromatography and the like, using a suitable solvent. It may be optionally set in accordance with the desired purity.

[Production Method D]

[Chem. 86]

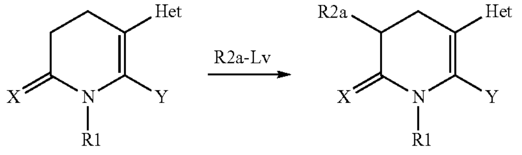

(1b-d) (1b-e)

In the formula, R2a represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A or C2-C6 haloalkynyl group, and R1, Het, Lv, X and Y are the same as defined hereinabove.

Production Method D is a synthetic method of a compound represented by Formula (1b-e), which belongs to the compounds represented by Formula (1b), wherein R2a is a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A or a C2-C6 haloalkynyl group, and is a production method which comprises reacting a compound represented by Formula (1b-d) and R2a-Lv in the presence of a base in a solvent.

The R2a-Lv to be used in the present reaction can be obtained as a commercially available product or produced by a conventionally known method.

An amount of the R2a-Lv to be used in the present reaction may be 1 equivalent or more relative to the compound represented by Formula (1b-d), which is not particularly limited as long as the target reaction proceeds, and preferably 1 equivalent or more and 1.8 equivalents or less.

The base to be used in the present reaction may be exemplified by metal hydrides such as sodium hydride, organolithiums such as methyllithium, butyllithium, sec-butyllithium, t-butyllithium and hexyllithium, metal amides such as lithium diisopropylamide, hexamethyldisilazane lithium, hexamethyldisilazane sodium and hexamethyldisilazane potassium.

An amount of the base to be used in the present reaction may be 1 equivalent or more relative to the compound represented by Formula (1b-d), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1b-d).

A temperature to carry out the present reaction is not particularly limited as long as the target reaction proceeds, and is usually −80° C. or higher and 100° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane and chloroform, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1b-e) may be dehydrated with a drying agent such as sodium sulfate and magnesium sulfate, but this is not essential.

The reaction mixture obtained above which contains the compound represented by Formula (1b-e) may be distilled under reduced pressure to remove the solvent as long as the compound is not decomposed.

The reaction mixture obtained after distillation of the solvent which contains the compound represented by Formula (1b-e) may be purified by washing, reprecipitation, recrystallization, column chromatography and the like, using a suitable solvent. It may be optionally set in accordance with the desired purity.

[Production Method E]

[Chem. 87]

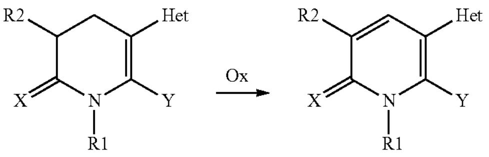

(1b) (1a)

In the formula, Ox represents an oxidizing agent, and R1, R2, Het, X and Y are the same as defined hereinabove.

Production Method E is a method for obtaining a compound represented by Formula (1a), and is a production method which comprises reacting a compound represented by Formula (1b) and an oxidizing agent (Ox) in a solvent.

The oxidizing agent to be used in the present reaction may include metal oxides such as manganese dioxide, benzoquinones such as 2,3-dichloro-5,6-dicyano-p-benzoquinone, a combination of a radical initiator such as azobisisobutyronitrile, 2,2'-azobis(4-methoxy-2,4-dimethylvaleryonitrile) and benzoyl peroxide, and a halogenating agent such as N-chlorosuccinimide, N-bromosuccinimide, N-iodosuccinimide, 1,3-dichloro-5,5-dimethylhydantoin, 1,3-dibromo-5,5-dimethylhydantoin and 1,3-diiodo-5,5-dimethylhydantoin.

In the following, a method in which the oxidizing agent is a metal oxide will be described.

An amount of the oxidizing agent to be used in the present reaction may be 1 equivalent or more relative to the compound represented by Formula (1b), which is not particularly limited as long as the target reaction proceeds, and is usually 1 equivalent or more and 200 equivalents or less.

The solvent to be used in the present reaction is not particularly limited as long as the target reaction proceeds, and may include benzene based solvents such as benzene, toluene, xylene, mesitylene, chlorobenzene and dichlorobenzene, halogen based solvents such as dichloromethane, dichloroethane, chloroform and carbon tetrachloride, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1b).

A temperature to carry out the present reaction is not particularly limited as long as the target reaction proceeds, and is usually 0° C. or higher and 150° C. or lower or a boiling point of the solvent or lower.

As a post treatment after the reaction; it is possible to remove undissolved metal by filtration. Further, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents, such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. Also, in the present reaction, the liquid separating operation is not essential.

The reaction mixture obtained above which contains the compound represented by Formula (1a) may be dehydrated with a drying agent such as sodium sulfate and magnesium sulfate, but this is not essential.

The reaction mixture obtained above which contains the compound represented by Formula (1a) may be distilled off under reduced pressure to remove the solvent as long as the compound is not decomposed.

The reaction mixture obtained after distillation of the solvent which contains the compound represented by Formula (1a) may be purified by washing, reprecipitation, recrystallization, column chromatography and the like, using a suitable solvent. It may be optionally set in accordance with the desired purity.

In the following, a method in which the oxidizing agent is a benzoquinone will be described.

An amount of the oxidizing agent to be used in the present reaction may be 1 equivalent or more relative to the compound represented by Formula (1b), which is not particularly limited as long as the target reaction proceeds, and is usually 1 equivalent or more and 20 equivalents or less.

The solvent to be used in the present reaction is not particularly limited as long as the target reaction proceeds, and may include benzene based solvents such as benzene, toluene, xylene, mesitylene, chlorobenzene and dichlorobenzene, halogen based solvents such as dichloromethane, dichloroethane, chloroform and carbon tetrachloride, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1b).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. Also, in the present reaction, the liquid separating operation is not essential.

The reaction mixture obtained above which contains the compound represented by Formula (1a) may be dehydrated with a drying agent such as sodium sulfate and magnesium sulfate, but this is not essential.

The reaction mixture obtained above which contains the compound represented by Formula (1a) may be distilled under reduced pressure to remove the solvent as long as the compound is not decomposed.

The reaction mixture obtained after distillation of the solvent which contains the compound represented by Formula (1a) may be purified by washing, reprecipitation, recrystallization, column chromatography and the like, using a suitable solvent. It may be optionally set in accordance with the desired purity.

In the following, a method in which the oxidizing agent is a combination of a radical initiator and a halogenating agent will be described.

Each amount of the radical initiator and the halogenating agent to be used in the present reaction is 0.01 equivalent or more and 1.0 equivalent or more relative to the compound represented by Formula (1b), respectively, and is not particularly limited as long as the target reaction proceeds. The radical initiator is preferably 0.01 equivalent or more and 1 equivalent or less, and the halogenating agent is 1 equivalent or more and 3 equivalents or less.

The solvent to be used in the present reaction is not particularly limited as long as the target reaction proceeds, and may include halogenated benzene solvents such as chlorobenzene and dichlorobenzene, ester solvents such as ethyl acetate, isopropyl acetate and butyl acetate, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1b).

A temperature to carry out the present reaction is not particularly limited as long as the target reaction proceeds, and is usually 20° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane and chloroform, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a) may be dehydrated with a drying agent such as sodium sulfate and magnesium sulfate, but this is not essential.

The reaction mixture obtained above which contains the compound represented by Formula (1a) may be distilled under reduced pressure to remove the solvent as long as the compound is not decomposed.

The reaction mixture obtained after distillation of the solvent which contains the compound represented by Formula (1a) may be purified by washing, reprecipitation, recrystallization, column chromatography and the like, using a suitable solvent. It may be optionally set in accordance with the desired purity.

[Production Method F]

[Chem. 88]

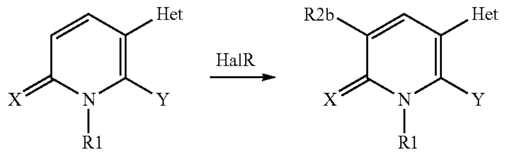

(1a-a) (1a-b)

In the formula, R2b represents a halogen atom, HalR represents a halogenating agent, and R1, Het, X and Y are the same as defined hereinabove.

Production Method F is a production method for obtaining a compound represented by Formula (1a-b), which belongs to the compounds represented by Formula (1a), wherein R2b represents a halogen atom, and is a production method which comprises reacting a compound represented by Formula (1a-a) and a halogenating agent (HalR) in a solvent.

The halogenating agent to be used in the present reaction may include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

An amount of the halogenating agent to be used in the present reaction may be 1 equivalent or more relative to the compound represented by Formula (1a-a), which is not particularly limited as long as the target reaction proceeds, and preferably 1 equivalent or more and 10 equivalents or less. If the amount of the halogenating agent including hydantoin is 0.5 equivalent or more, it is not particularly limited as long as the target reaction proceeds, and preferably 1 equivalent or more and 5 equivalents or less.

When the halogenating agent to be used in the present reaction is an iodinating agent, an acid including an inorganic acid such as hydrochloric acid, sulfuric acid or the like, or an organic acid such as acetic acid, trifluoroacetic acid, methanesulfonic acid, trifluoromethanesulfonic acid or the like may be added.

An amount of the acid to be used when the halogenating agent to be used in the present reaction is the iodinating agent may be 0.01 equivalent or more relative to the compound represented by Formula (1a-a), which is not particularly limited as long as the target reaction proceeds, and preferably 0.1 equivalent or more and 3 equivalents or less.

The solvent to be used in the present reaction is not particularly limited as long as the target reaction proceeds, and may include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, and the like.

These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-a).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution, is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a-b) may be dehydrated with a drying agent such as sodium sulfate and magnesium sulfate, but this is not essential.

The reaction mixture obtained above which contains the compound represented by Formula (1a-b) may be distilled under reduced pressure to remove the solvent as long as the compound is not decomposed.

The reaction mixture obtained after distillation of the solvent which contains the compound represented by Formula (1a-b) may be purified by washing, reprecipitation, recrystallization, column chromatography and the like, using a suitable solvent. It may be optionally set in accordance with the desired purity.

[Production Method G]

[Chem. 89]

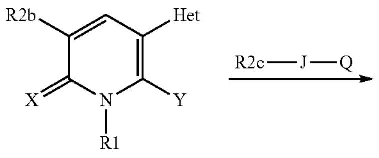

(1a-b)

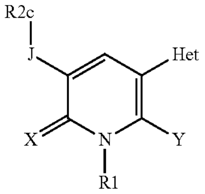

(1a-c)

In the formula, J represents an oxygen atom or a sulfur atom, when J is an oxygen atom, R2c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A or a C3-C6 haloalkynyl group, when J is a sulfur atom, R2c represents a C1-C6 alkyl group or a C1-C6 haloalkyl group, Q represents a hydrogen atom or a metal, and R1, Het, R2b, X and Y are the same as defined hereinabove.

Production Method G is a synthetic method of a compound represented by Formula (1a-c), which belongs to the compounds represented by Formula (1a), wherein J represents an oxygen atom or a sulfur atom, when J is an oxygen atom, R2c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A or a C3-C6 haloalkynyl group, and when J is a sulfur atom, R2c represents a C1-C6 alkyl group or a C1-C6 haloalkyl group, and is a production method which comprises a coupling reaction wherein a compound represented by Formula (1a-b) and R2c-J-Q are reacted in the presence of a transition metal and a base in a solvent.

Among the compounds represented by Formula (1a-b), preferable R2b is a chlorine atom, a bromine atom or an iodine atom.

The R2c-J-Q to be used in the present reaction can be obtained as a commercially available product or produced by a conventionally known method. Preferable Q is a hydrogen atom or an alkali metal such as sodium, potassium and the like.

An amount of the R2c-J-Q to be used in the present reaction may be 1 equivalent or more relative to the compound represented by Formula (1a-b), and is not particularly limited as long as the target reaction proceeds. When Q is a hydrogen atom, it can be also used as a solvent.

The transition metal to be used in the present reaction may have a ligand, and may include palladiums such as palladium acetate, [1,1'-bis(diphenylphosphine)ferrocene]palladium dichloride, tris(dibenzylideneacetone)dipalladium, tetrakis(triphenylphosphine)palladium, bis(triphenylphosphine)palladium dichloride and the like.

An amount of the transition metal to be used in the present reaction may be 0.001 equivalent or more and 1 equivalent or less relative to the compound represented by Formula (1a-b), and is not particularly limited as long as the target reaction proceeds.

In order to proceed the present reaction efficiently, a phosphine ligand such as triphenylphosphine, 1,1'-bis(diphenylphosphine)ferrocene, 2-dicyclohexylphosphino-2'4'6'-triisopropylbiphenyl, 2-di-t-butylphosphino-2'4'6'-triisopropylbiphenyl and the like may be added.

An amount of the phosphine ligand to be used in the present reaction may be 0.001 equivalent or more and 1 equivalent or less relative to the compound represented by Formula (1a-b), and is not particularly limited as long as the target reaction proceeds.

The base to be used in the present reaction may include inorganic bases such as sodium carbonate, potassium carbonate and cesium carbon and organic bases such as triethylamine, tributylamine and diisopropylethylamine.

An amount of the base to be used in the present reaction may be 1 equivalent or more relative to the compound represented by Formula (1a-b), which is not particularly limited as long as the target reaction proceeds, and preferably 1 equivalent or more and 50 equivalents or less.

The solvent to be used in the present reaction is not particularly limited as long as the target reaction proceeds, and may include alcohol solvents represented by R2c-J-H (wherein R2c is the same as defined hereinabove, and J is an oxygen atom), ether solvents such as diethyl ether, diisopropyl ether, methyl-t-butyl ether, dimethoxyethane, tetrahydrofuran and dioxane, and benzene based solvents such as benzene, toluene, xylene, mesitylene, chlorobenzene and dichlorobenzene, and the like.

These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-b).

A temperature to carry out the present reaction is not particularly limited as long as the target reaction proceeds, and is usually 30° C. or higher and 200° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. In addition, it is also possible to remove insoluble materials by subjecting to filtration operation but it is not essential.

The reaction mixture obtained above which contains the compound represented by Formula (1a-c) may be dehydrated with a drying agent such as sodium sulfate and magnesium sulfate, but this is not essential.

The reaction mixture obtained above which contains the compound represented by Formula (1a-c) may be distilled under reduced pressure to remove the solvent as long as the compound is not decomposed.

The reaction mixture obtained after distillation of the solvent which contains the compound represented by Formula (1a-c) may be purified by washing, reprecipitation, recrystallization, column chromatography and the like, using a suitable solvent. It may be optionally set in accordance with the desired purity.

[Production Method H]

[Chem. 90]

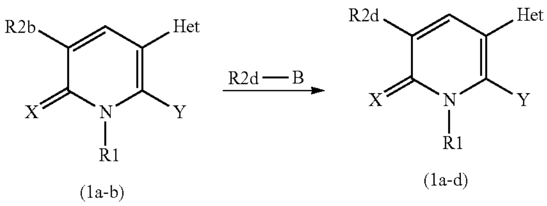

(1a-b)

(1a-d)

In the formula, R2d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A or a C2-C6 haloalkenyl group, R2d-B represents organic boronic acids, and R1, Het, R2b, X and Y are the same as defined hereinabove.

Production Method H is a synthetic method of a compound represented by Formula (1a-d), which belongs to the compounds represented by Formula (1a), wherein R2d is a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A or a C2-C6 haloalkenyl group, and is a production method which comprises Suzuki-Miyaura coupling wherein a compound represented by Formula (1a-b) and an organic boronic acid (R2d-B) are reacted in the presence of a transition metal and a base in a solvent.

In Formula (1a-b), preferable R2b is a chlorine atom, a bromine atom or an iodine atom.

The R2d-B to be used in the present reaction represents organic boronic acids such as an organic boronic acid, organic boronic acid ester and the like, and can be obtained as a commercially available product or produced by a conventionally known method.

An amount of the R2d-B to be used in the present reaction may be 1 equivalent or more relative to the compound represented by Formula (1a-b), which is not particularly limited as long as the target reaction proceeds, and preferably 1 equivalent or more and 10 equivalents or less.

The transition metal to be used in the present reaction may be palladium, nickel, ruthenium and the like, which may have a ligand(s). It may preferably include palladiums such as palladium acetate, [1,1'-bis(diphenylphosphine)ferrocene]palladium dichloride, tris(dibenzylideneacetone)dipalladium, tetrakis(triphenylphosphine)palladium, bis(triphenylphosphine)palladium dichloride and the like.

An amount of the transition metal to be used in the present reaction may be 0.001 equivalent or more and 1 equivalent or less relative to the compound represented by Formula (1a-b), and is not particularly limited as long as the target reaction proceeds.

In order to proceed the reaction efficiently, a phosphine ligand such as triphenylphosphine, tricyclohexylphosphine and the like may be added.

An amount of the phosphine ligand to be used in the present reaction may be 0.001 equivalent or more and 1 equivalent or less relative to the compound represented by Formula (1a-b), and is not particularly limited as long as the target reaction proceeds.

The base to be used in the present reaction may include inorganic bases such as sodium carbonate, potassium carbonate, cesium carbonate and tripotassium phosphate, and metal alkoxides such as sodium methoxide, sodium ethoxide and potassium t-butoxide.

An amount of the base to be used in the present reaction may be 1 equivalent or more relative to the compound represented by Formula (1a-b), which is not particularly limited as long as the target reaction proceeds, and preferably 1 equivalent or more and 50 equivalents or less.

The solvent to be used in the present reaction is not particularly limited as long as the target reaction proceeds, and may include water solvent, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-b).

A temperature to carry out the present reaction is not particularly limited as long as the target reaction proceeds, and is usually 30° C. or higher and 200° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. In addition, it is also possible to remove insoluble materials by subjecting to filtration operation but it is not essential.

The reaction mixture obtained above which contains the compound represented by Formula (1a-d) may be dehydrated with a drying agent such as sodium sulfate and magnesium sulfate, but this is not essential.

The reaction mixture obtained above which contains the compound represented by Formula (1a-d) may be distilled under reduced pressure to remove the solvent as long as the compound is not decomposed.

The reaction mixture obtained after distillation of the solvent which contains the compound represented by Formula (1a-d) may be purified by washing, reprecipitation, recrystallization, column chromatography and the like, using a suitable solvent. It may be optionally set in accordance with the desired purity.

[Production Method I]

[Chem. 91]

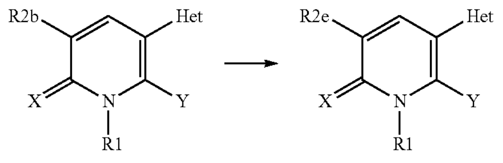

(1a-b) (1a-e)

In the formula, R2e represents a C2-C6 alkynyl group optionally substituted with substituent(s) A or a C2-C6 haloalkynyl group, and R1, Het, R2b, X and Y are the same as defined hereinabove.

Production Method I is a synthetic method of a compound represented by Formula (1a-e), among the compounds represented by Formula (1a), wherein R2e is a C2-C6 alkynyl group optionally substituted with substituent(s) A or a C2-C6 haloalkynyl group, and is a production method which comprises Sonogashira coupling wherein a compound represented by (1a-b) and a terminal-alkyne compound are reacted in the presence of a transition metal and a base in a solvent.

In Formula (1a-b), preferable R2b is a chlorine atom, a bromine atom or an iodine atom.

The terminal-alkyne compound to be used in the present reaction can be obtained as a commercially available product or produced by a conventionally known method. In addition, as the terminal-alkyne compound, trimethylsilylacetylene may be also used. In such a case, after introducing trimethylsilylethynyl group into the compound represented by Formula (1a-b), desilylation is required to be carried out.

With regard to the desilylation, it may be carried out with reference to Non-Patent Documents such as Journal of the American Chemical Society, vol. 131, No. 2, pp. 634-643 (2009) and Journal of Organometallic Chemistry, vol. 696, No. 25, pp. 4039-4045 (2011).

An amount of the terminal-alkyne compound to be used in the present reaction may be 1 equivalent or more relative to the compound represented by Formula (1a-b), which is not particularly limited as long as the target reaction proceeds, and preferably 1 equivalent or more and 10 equivalents or less.

The transition metal to be used in the present reaction may have a ligand, and may include palladiums such as palladium acetate, [1,1'-bis(diphenyl-phosphine)ferrocene]palladium dichloride, tris(dibenzylideneacetone)dipalladium, tetrakis(triphenylphosphine)palladium, bis(triphenylphosphine)palladium dichloride and the like. In addition, coppers such as copper chloride, copper bromide, copper iodate and the like may also be used simultaneously.

With regard to an amount of the transition metal to be used in the present reaction, palladiums and coppers each may be used in 0.001 equivalent or more relative to the compound represented by Formula (1a-b), and is not particularly limited as long as the target reaction proceeds. Preferable amounts thereof are each 0.001 equivalent or more and 1 equivalent or less.

The base to be used in the present reaction may include organic amines such as triethylamine, tributylamine, isopropylamine, diethylamine, diisopropylamine and diisopropylethylamine, inorganic bases such as sodium carbonate, potassium carbonate and cesium carbonate and the like.

An amount of the base to be used in the present reaction may be 1 equivalent or more relative to the compound represented by Formula (1a-b), which is not particularly limited as long as the target reaction proceeds, and preferably 1 equivalent or more and 50 equivalents or less. In addition, the organic bases which is in a liquid state can be also used as a solvent.

In order to proceed the reaction efficiently, a phosphine ligand such as tri-t-butyl phosphine, 2-dicyclohexylphosphino-2'4'6'-triisopropylbiphenyl and the like may be added, but this is not essential.

An amount of the phosphine ligand to be used in the present reaction may be 0.001 equivalent or more and 1 equivalent or less relative to the compound represented by Formula (1a-b), and is not particularly limited as long as the target reaction proceeds.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, an organic amine solvent such as triethylamine, tributylamine, isopropylamine, diethylamine, diisopropylamine and diisopropylethylamine, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-b).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired. In addition, it is also possible to remove insoluble materials by subjecting to filtration operation but it is not essential.

The reaction mixture obtained above which contains the compound represented by Formula (1a-e) may be dehydrated with a drying agent such as sodium sulfate and magnesium sulfate, but this is not essential.

The reaction mixture obtained above which contains the compound represented by Formula (1a-e) may be distilled under reduced pressure to remove the solvent as long as the compound is not decomposed.

The reaction mixture obtained after distillation of the solvent which contains the compound represented by Formula (1a-e) may be purified by washing, reprecipitation, recrystallization, column chromatography and the like, using a suitable solvent. It may be optionally set in accordance with the desired purity.

[Production Method J]

[Chem. 92]

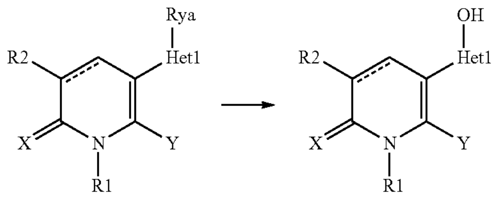

(1-a) (1-b)

In the formula, Rya represents a C1-C6 alkoxy group, Het1 represents a 5 to 6-membered heterocyclic group or the 8 to 10-membered heterocyclic group, the 5 to 6-membered heterocyclic group or the 8 to 10-membered heterocyclic group is optionally substituted with 0 to 5 substituents R3 (with the proviso that when two or more substituents R3 are present, each R3 represents an independent substituent), and R1, R2, X, Y and the broken line are the same as defined hereinabove.

Production Method J is a synthetic method of a compound represented by Formula (1-b) having a hydroxyl group which belongs to the compounds represented by Formula (1), and is a production method which comprises reacting a compound represented by Formula (1-a) wherein Rya is a C1-C6 alkoxy group and an acid in a solvent.

The acid to be used in the present reaction may include boron halides such as boron trichloride and boron tribromide.

An amount of the acid to be used in the present reaction may be 1 equivalent or more relative to the compound represented by Formula (1-a), which is not particularly limited as long as the target reaction proceeds, and preferably 1 equivalent or more and 10 equivalents or less.

The solvent to be used in the present reaction is not particularly limited as long as the target reaction proceeds, and may include benzene based solvents such as benzene, toluene, xylene, mesitylene, chlorobenzene and dichlorobenzene, nitrile solvents such as acetonitrile, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-a).

A temperature to carry out the present reaction is not particularly limited as long as the target reaction proceeds, and is usually −80° C. or higher and 100° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-b) may be dehydrated with a drying agent such as sodium sulfate and magnesium sulfate, but this is not essential.

The reaction mixture obtained above which contains the compound represented by Formula (1-b) may be distilled under reduced pressure to remove the solvent as long as the compound is not decomposed.

The reaction mixture obtained after distillation of the solvent which contains the compound represented by Formula (1-b) may be purified by washing, reprecipitation, recrystallization, column chromatography and the like, using a suitable solvent. It may be optionally set in accordance with the desired purity.

[Production Method K]

[Chem. 93]

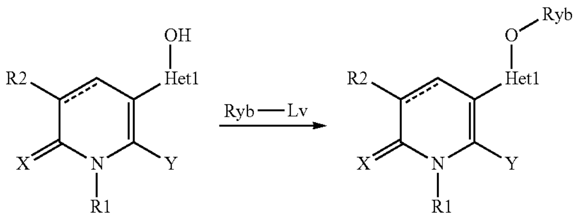

(1-b) (1-c)

In the formula, Ryb represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, an aryl group optionally substituted with substituent(s) D, a heteroaryl group optionally substituted with substituent(s) D, an aralkyl group optionally substituted with substituent(s) D or Rx1C(═O)—, and Lv, R1, R2, Het1, Rx1, X, Y and the broken line are the same as defined hereinabove.

Production Method K is a synthetic method of a compound represented by Formula (1-c), which belongs to the compounds represented by Formula (1), wherein Ryb-O— represents a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryloxy group optionally substituted with substituent(s) D, a heteroaryloxy group optionally substituted with substituent(s) D, an aralkyloxy group optionally substituted with substituent(s) D or Rx1C(═O)O— (Rx1 is the same as defined hereinabove), and is a production method which comprises reacting a compounds represented by Formula (1-b) and Ryb-Lv in the presence of a base in a solvent.

The Ryb-Lv to be used in the present reaction can be obtained as a commercially available product or produced by a conventionally known method.

The Ryb-Lv to be used in the present reaction may be 1 equivalent or more relative to the compounds represented by Formula (i-b), which is not particularly limited as long as the target reaction proceeds, and preferably 1 equivalent or more and 10 equivalents or less.

The base to be used in the present reaction may be exemplified by inorganic bases such as sodium carbonate, potassium carbonate, cesium carbonate and sodium hydride, and organic bases such as triethylamine, tributylamine, diisopropylethylamine, pyridine, 4-dimethylaminopyridine, collidine and lutidine, and is not particularly limited as long as the target reaction proceeds.

The base to be used in the present reaction may be 1 equivalent or more relative to the compound represented by Formula (1-b), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-b).

A temperature to carry out the present reaction is not particularly limited as long as the target reaction proceeds, and is usually −20° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-c) may be dehydrated with a drying agent such as sodium sulfate and magnesium sulfate, but this is not essential.

The reaction mixture obtained above which contains the compound represented by Formula (1-c) may be distilled under reduced pressure to remove the solvent as long as the compound is not decomposed.

The reaction mixture obtained after distillation of the solvent which contains the compound represented by Formula (1-c) may be purified by washing, reprecipitation, recrystallization, column chromatography and the like, using a suitable solvent. It may be optionally set in accordance with the desired purity.

[Production Method L].

[Chem. 94]

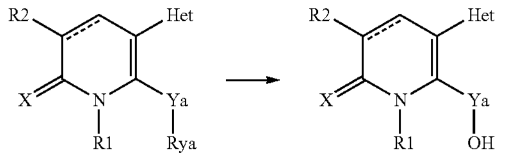

(1-d) (1-e)

In the formula, Ya represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, wherein when the phenyl group is substituted with the Rya at the ortho-position, the group is further optionally substituted with 0 to 4 substituents R5 (with the proviso that when two or more substituents R5 are present, each R5 represents an independent substituent), and when R4 is positioned at the ortho-position, the group is further optionally substituted with 0 to 3 substituents R5 (with the proviso that when two or more substituents R5 are present, each R5 represents an independent substituent), and when the pyridyl group, the pyrazinyl group, the pyrimidinyl group, the pyridazinyl group, the a triazinyl group or the tetrazinyl group is substituted with the Rya at the ortho-position, the group is further optionally substituted with 0 to 3 substituents R5 (with the proviso that when two or more substituents R5 are present, each R5 represents an independent substituent), and when R4 is positioned at the ortho-position, the group is further optionally substituted with 0 to 2 substituents R5 (with the proviso that when two substituents R5 are present, each R5 represents an independent substituent), and R1, R2, Rya, X, Het and the broken line are the same as defined hereinabove.

Production Method L is a synthetic method of a compound represented by Formula (1-e) having a hydroxyl group at Y which belongs to the compounds represented by Formula (1), and is a production method which comprises reacting a compound represented by Formula (1-d) and an acid in a solvent.

By using the compound represented by Formula (1-d) in place of the compound represented by Formula (1-a) in Production Method J, Production Method L can be carried out in accordance with Production Method J.

[Production Method M]

[Chem. 95]

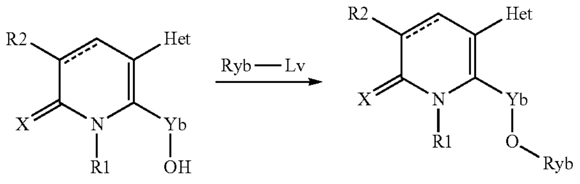

(1-e) (1-f)

In the formula, Yb represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, wherein when the phenyl group is substituted with a hydroxyl group at the ortho-position, the group is further optionally substituted with 0 to 4 substituents R5 (with the proviso that when two or more substituents R5 are present, each R5 represents an independent substituent), and when R4 is positioned at the ortho-position, the group is further optionally substituted with 0 to 3 substituents R5 (with the proviso that when two or more substituents R5 are present, each R5 represents an independent substituent), and when the pyridyl group, the pyrazinyl group, the pyrimidinyl group, the pyridazinyl group, the a triazinyl group or the tetrazinyl group is substituted with hydroxyl group at the ortho-position, the group is further optionally substituted with 0 to 3 substituents R5 (with the proviso that when two or more substituents R5 are present, each R5 represents an independent substituent), and when R4 is positioned at the ortho-position, the group is further optionally substituted with 0 to 2 substituents R5 (with the proviso that when two substituents R5 are present, each R5 represents an independent substituent), and Lv, R1, R2, Het, Ryb, X and the broken line are the same as defined hereinabove. The hydroxyl group in the compound represented by Formula (1-e) and the Ryb-O— in the compound represented by Formula (1-f) represent a substituent corresponding to either of R4 or R5, or each other's substituents.

Production Method M is a synthetic method of a compound represented by Formula (1-f) which belongs to the compounds represented by Formula (1), and is a production method which comprises reacting a compound represented by Formula (1-e) and Ryb-Lv in the presence of a base in a solvent.

By using the compound represented by Formula (1-e) in place of the compound represented by Formula (1-b) in Production Method K, Production Method M can be carried out in accordance with Production Method K.

[Production Method N]

[Chem. 96]

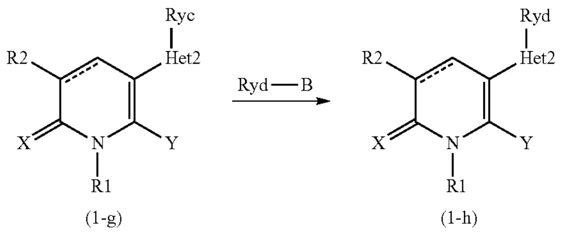

In the formula, Ryc represents a halogen atom, Ryd represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, an aryl group optionally substituted with substituent(s) D or a heteroaryl group optionally substituted with substituent(s) D, Het2 represents a 5 to 6-membered heterocyclic group or a 8 to 10-membered heterocyclic group, the 5 to 6-membered heterocyclic group or the 8 to 10-membered heterocyclic group is optionally substituted with 0 to 5 substituents R3 (with the proviso that when two or more substituents R3 are present, each R3 represents an independent substituent), Ryd-B represents an organic boronic acid, and R1, R2, X, Y and the broken line are the same as defined hereinabove.

Production Method N is a synthetic method of a compound represented by Formula (1-h), which belongs to the compounds represented by Formula (1), wherein Ryd is a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, an aryl group optionally substituted with substituent(s) D or a heteroaryl group optionally substituted with substituent(s) D, and is a production method which comprises Suzuki-Miyaura coupling wherein a compound represented by Formula (1-g) and an organic boronic acid (Ryd-B) are reacted in the presence of a transition metal and a base in a solvent.

In the compound represented by Formula (1-g), preferable Ryc is a chlorine atom, a bromine atom or an iodine atom.

The Ryd-B to be used in the present reaction represents organic boronic acids such as an organic boronic acid and an organic boronic acid ester, and can be obtained as a commercially available product or produced by a conventionally known method.

By using the compound represented by Formula (1-g) and Ryd-B in place of the compound represented by Formula (1a-b) and R2d-B in Production Method H, respectively, Production Method N can be carried out in accordance with Production Method H.

[Production Method O]

[Chem. 97]

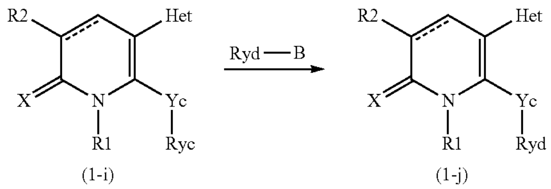

In the formula, Yc represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, wherein when the phenyl group is substituted with Ryc at the ortho-position, the group is further optionally substituted with 0 to 4 substituents R5 (with the proviso that when two or more substituents R5 are present, each R5 represents an independent substituent), and when R4 is positioned at the ortho-position, the group is further optionally substituted with 0 to 3 substituents R5 (with the proviso that when two or more substituents R5 are present, each R5 represents an independent substituent), and when the pyridyl group, the pyrazinyl group, the pyrimidinyl group, the pyridazinyl group, the a triazinyl group or the tetrazinyl group is substituted with Ryc at the ortho-position, the group is further optionally substituted with 0 to 3 substituents R5 (with the proviso that when two or more substituents R5 are present, each R5 represents an independent substituent), and when R4 is positioned at the ortho-position, the group is further optionally substituted with 0 to 2 substituents R5 (with the proviso that when two substituents R5 are present, each R5 represents an independent substituent), and Ryc, Ryd, Ryd-B, R1, R2, X, Het and the broken line are the same as defined hereinabove. The Ryc in the compound represented by Formula (1-i) and the Ryd in the compound represented by Formula (1-j) represent a substituent corresponding to either of R4 or R5, or each other's substituents.

Production Method O is a synthetic method of a compound represented by Formula (1-j) which belongs to the compounds represented by Formula (1), and is a production method which comprises Suzuki-Miyaura coupling wherein a compound represented by Formula (1-i) and an organic boronic acid (Ryd-B) are reacted in the presence of a transition metal and a base in a solvent.

In the compounds represented by Formula (1-i), preferable Ryc is a chlorine atom, a bromine atom or an iodine atom.

By using the compound represented by Formula (1-i) and Ryd-B in place of the compound represented by Formula (1a-b) and R2d-B in Production Method H, respectively, Production Method O can be carried out in accordance with Production Method H.

[Production Method P]

[Chem. 98]

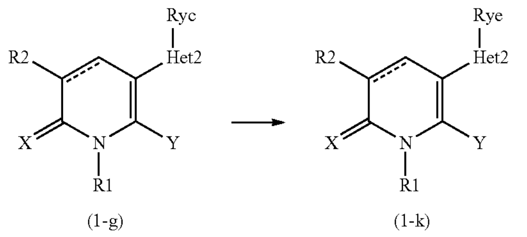

In the formula, Rye represents a C2-C6 alkynyl group optionally substituted with substituent(s) C or a C2-C6 haloalkynyl group, and Ryc, R1, R2, X, Y, Het2 and the broken line are the same as defined hereinabove.

Production Method P is a synthetic method of a compound represented by Formula (1-k), which belongs to the compounds represented by Formula (1), wherein Rye is a C2-C6 alkynyl group optionally substituted with substituent(s) C or a C2-C6 haloalkynyl group, and is a production method which comprises Sonogashira coupling wherein a compound represented by Formula (1-g) and a terminal-alkyne compound are reacted in the presence of a transition metal and a base in a solvent.

Among the compounds represented by Formula (1-g), preferable Ryc is a chlorine atom, a bromine atom or an iodine atom.

By using the compound represented by Formula (1-g) in place of the compound represented by Formula (1a-b) in Production Method I, Production Method P can be carried out in accordance with Production Method I.

[Production Method Q]

[Chem. 99]

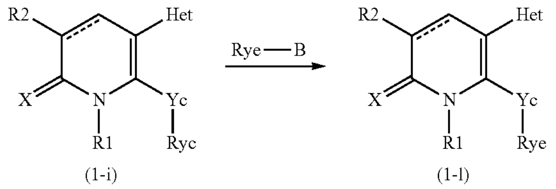

In the formula, Ryc, Rye, R1, R2, X, Yc, Het and the broken line are the same as defined hereinabove. The Ryc in the compound represented by Formula (1-i) and the Rye in the compound represented by Formula (1-1) represent a substituent corresponding to either of R4 or R5, or each other's substituents.

Production Method Q is a synthetic method of a compound represented by Formula (1-1) which belongs to the compounds represented by Formula (1), and is a production method which comprises Sonogashira coupling wherein a compound represented by Formula (1-i) and a terminal-alkyne compound are reacted in the presence of a transition metal and a base in a solvent.

In the compound represented by Formula (1-i), preferable Ryc is a chlorine atom, a bromine atom or an iodine atom.

By using the compound represented by Formula (1-i) in place of the compound represented by Formula (1a-b) in Production Method I, Production Method Q can be carried out in accordance with Production Method I.

[Production Method R]

[Chem. 100]

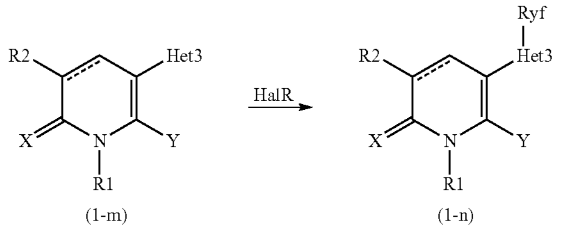

In the formula, Ryf represents a halogen atom, Het3 represents a 5 to 6-membered heterocyclic group or a 8 to 10-membered heterocyclic group, the 5 to 6-membered heterocyclic group or the 8 to 10-membered heterocyclic group is optionally substituted with 0 to 5 substituents R3 (with the proviso that when two or more substituents R3 are present, each R3 represents an independent substituent), and HalR, R1, R2, X, Y and the broken line are the same as defined hereinabove.

Production Method R is a production method of a compound represented by Formula (1-n), which belongs to the compounds represented by Formula (1), wherein Ryf is a halogen atom, and is a production method which comprises reacting a compound represented by Formula (1-m) and a halogenating agent (HalR) in a solvent.

A base or a radical initiator may be added to the present reaction. It may be optionally set so that the target reaction proceeds.

In the following, a method of reacting a compound represented by Formula (1-m) and a halogenating agent (HalR) in a solvent will be described.

The halogenating agent to be used in the present reaction may include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like, An amount of the halogenating agent to be used in the present reaction may be 1 equivalent or more relative to the compound represented by Formula (1-m), which is not particularly limited as long as the target reaction proceeds, and preferably 1 equivalent or more and 10 equivalents or less. If the amount of the halogenating agent including hydantoin is 0.5 equivalent or more, it is not particularly limited as long as the target reaction proceeds, and preferably 1 equivalent or more and 5 equivalents or less.

When the halogenating agent to be used in the present reaction is an iodinating agent, an acid including an inorganic acid such as hydrochloric acid, sulfuric acid or the like, or an organic acid such as acetic acid, trifluoroacetic acid, methanesulfonic acid, trifluoromethanesulfonic acid or the like may be added.

An amount of the acid to be used when the halogenating agent to be used in the present reaction is the iodinating agent may be 0.01 equivalent or more relative to the compound represented by Formula (1-m), which is not particularly limited as long as the target reaction proceeds, and preferably 0.1 equivalent or more and 3 equivalents or less.

The solvent to be used in the present reaction is not particularly limited as long as the target reaction proceeds, and may include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, and the like.

These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-m).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-n) may be dehydrated with a drying agent such as sodium sulfate and magnesium sulfate, but this is not essential.

The reaction mixture obtained above which contains the compound represented by Formula (1-n) may be distilled under reduced pressure to remove the solvent as long as the compound is not decomposed.

The reaction mixture obtained after distillation of the solvent which contains the compound represented by Formula (1-n) may be purified by washing, reprecipitation, recrystallization, column chromatography and the like, using a suitable solvent. It may be optionally set in accordance with the desired purity.

In the following, a method of reacting a compound represented by Formula (1-m) and a halogenating agent (HalR) in the presence of a base in a solvent will be described.

The halogenating agent to be used in the present reaction may include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, hexachloro-ethane, bromine, iodine and the like.

An amount of the halogenating agent to be used in the present reaction may be 1 equivalent or more relative to the compound represented by Formula (1-m), which is not particularly limited as long as the target reaction proceeds, and preferably 1 equivalent or more and 10 equivalents or less. If the amount of the halogenating agent including hydantoin is 0.5 equivalent or more, it is not particularly limited as long as the target reaction proceeds, and preferably 1 equivalent or more and 5 equivalents or less.

The base to be used in the present reaction may be exemplified by metal hydrides such as sodium hydride, organolithiums such as methyllithium, butyllithium, sec-butyllithium, t-butyllithium and hexyllithium, metal amides such as lithium diisopropylamide, hexamethyldisilazane lithium, hexamethyldisilazane sodium and hexamethyldisilazane potassium, and it is not particularly limited as long as the target reaction proceeds.

An amount of the base to be used in the present reaction may be 1 equivalent or more relative to the compound represented by Formula (1-m), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, amide solvents such as N-methylpyrrolidone, N,N-dimethylformamide and N,N-dimethylacetamide, urea solvents such as 1,3-dimethyl-2-imidazolidinone, benzene based solvents such as benzene, toluene, xylene, mesitylene, chlorobenzene and dichlorobenzene, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-m).

A temperature to carry out the present reaction is not particularly limited as long as the target reaction proceeds, and is usually −80° C. or higher and 100° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur, atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane and chloroform, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-n) may be dehydrated with a drying agent such as sodium sulfate and magnesium sulfate, but this is not essential.

The reaction mixture obtained above which contains the compound represented by Formula (1-n) may be distilled under reduced pressure to remove the solvent as long as the compound is not decomposed.

The reaction mixture obtained after distillation of the solvent which contains the compound represented by Formula (1-n) may be purified by washing, reprecipitation, recrystallization, column chromatography and the like, using a suitable solvent. It may be optionally set in accordance with the desired purity.

In the following, a method of reacting a compound represented by Formula (1-m), a halogenating agent (HalR) and a radical initiator in a solvent will be described.

The radical initiator to be used in the present reaction may include azobisisobutyronitrile, 2,2'-azobis(4-methoxy-2,4-dimethylvaleryonitrile), benzoyl peroxide and the like.

An amount of the radical initiator to be used in the present reaction is not particularly limited as long as the target reaction proceeds, and is usually 0.01 equivalent or more and 1.0 equivalent or less relative to the compound represented by Formula (1-m).

The halogenating agent to be used in the present reaction may include N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin and the like.

An amount of the halogenating agent to be used in the present reaction may be 1 equivalent or more relative to the compound represented by Formula (1-m), which is not particularly limited as long as the target reaction proceeds, and is usually 1 equivalent or more and 1.8 equivalents or less.

The solvent to be used in the present reaction is not particularly limited as long as the target reaction proceeds, and may include halogenated benzene solvents such as chlorobenzene and dichlorobenzene, ester solvents such as ethyl acetate, isopropyl acetate and butyl acetate, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-m).

A temperature to carry out the present reaction is not particularly limited as long as the target reaction proceeds, and is usually 20° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane and chloroform, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-n) may be dehydrated with a drying agent such as sodium sulfate and magnesium sulfate, but this is not essential.

The reaction mixture obtained above which contains the compound represented by Formula (1-n) may be distilled under reduced pressure to remove the solvent as long as the compound is not decomposed.

The reaction mixture obtained after distillation of the solvent which contains the compound represented by Formula (1-n) may be purified by washing, reprecipitation, recrystallization, column chromatography and the like, using a suitable solvent. It may be optionally set in accordance with the desired purity.

[Production Method S]

[Chem. 101]

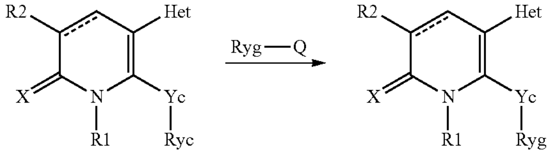

(1-i) (1-o)

In the formula, Ryg represents a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (here, Ra and Rb are the same as defined hereinabove), Rc-L- (wherein Rc and L are the same as defined hereinabove.) or Rx4Rx5C═N—O— (here, Rx4 and Rx5 are the same as defined hereinabove), and R1, R2, Ryc, Het, X, Yc, Q and the broken line are the same as defined hereinabove. The Ryc in the compound represented by Formula (1-i) and the Ryg in the compound represented by Formula (1-o) represent a substituent corresponding to either of R4 or R5, or each other's substituents.

Production Method S is a method of obtaining a compound represented by Formula (1-o), which belongs to the compounds represented by Formula (1) wherein Ryg is a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (here, Ra and Rb are the same as defined hereinabove), Rc-L- (wherein Rc and L are the same as defined hereinabove.) or Rx4Rx5C═N—O— (here, Rx4 and Rx5 are the same as defined hereinabove), and is a production method which comprises reacting a compound represented by Formula (1-i) and Ryg-Q in the presence of a base in a solvent.

In the compounds represented by Formula (1-i), preferable Ryc is a fluorine atom, a chlorine atom or a bromine atom.

The Ryg-Q to be used in the present reaction can be obtained as a commercially available product or produced by a conventionally known method. Preferable Q is a hydrogen atom or an alkali metal such as sodium, potassium and the like.

An amount of the Ryg-Q to be used in the present reaction may be 1 equivalent or more relative to the compound represented by Formula (1-i), which is not particularly limited as long as the target reaction proceeds, and is usually 1 equivalent or more and 30 equivalents or less. Also, when Q represents a hydrogen atom, it may be used as a solvent.

The base to be used in the present reaction is preferably inorganic bases such as sodium carbonate, potassium carbonate, cesium carbonate and sodium hydride. In addition, when Q is an alkali metal, use of the base is not essential.

An amount of the base to be used in the present reaction may be 1 equivalent or more relative to the compound represented by Formula (1-i), which is not particularly limited as long as the target reaction proceeds, and is usually 1 equivalent or more and 30 equivalents or less.

The solvent to be used in the present reaction is not particularly limited as long as the target reaction proceeds, and may include alcohol solvents represented by Ryg-H (wherein Ryg is the same as defined hereinabove), ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents, such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-i).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-o) may be dehydrated with a drying agent such as sodium sulfate and magnesium sulfate, but this is not essential.

The reaction mixture obtained above which contains the compound represented by Formula (1-o) may be distilled under reduced pressure to remove the solvent as long as the compound is not decomposed.

The reaction mixture obtained after distillation of the solvent which contains the compound represented by Formula (1-o) may be purified by washing, reprecipitation, recrystallization, column chromatography and the like, using a suitable solvent. It may be optionally set in accordance with the desired purity.

[Production Method T]

[Chem. 102]

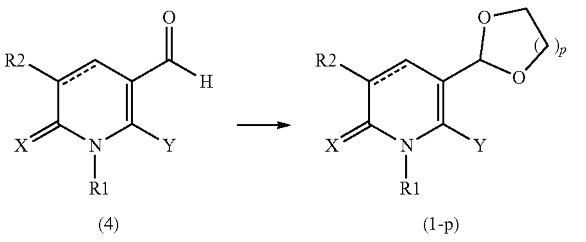

In the formula, p represents an integer of 1 to 2, and R1, R2, X, Y and the broken line are the same as defined hereinabove.

Production Method T is a synthetic method of a compound represented by Formula (1-p), which belongs to atoms among the compounds represented by Formula (1) wherein Het is a 3 to 6-membered ring group containing 1 to 2 oxygen, and is a production method which comprises reacting a compound represented by Formula (4) and a glycol in the presence of an acid in a solvent.

The compound represented by Formula (4) to be used in the present reaction can be obtained with reference to Reference Examples.

The acid to be used in the present reaction may be exemplified by an inorganic acid such as hydrochloric acid and sulfuric acid, and an organic acid such as p-toluenesulfonic acid and the like, which is not particularly limited as long as the target reaction proceeds.

An amount of the acid to be used in the present reaction may be 0.01 equivalent or more relative to the compound represented by Formula (4), which is not particularly limited as long as the target reaction proceeds, and preferably 0.1 equivalent or more and 1 equivalent or less.

The glycols to be used in the present reaction may be exemplified by ethylene glycol and propylene glycol, and can be obtained as commercially available products or produced by a conventionally known method.

An amount of the glycols to be used in the present reaction may be 1 equivalent or more relative to the compound represented by Formula (4), which is not particularly limited as long as the target reaction proceeds, and preferably 1 equivalent or more and 30 equivalent or less.

The solvent to be used in the present reaction is not particularly limited as long as the target reaction proceeds, and may include benzene based solvents such as benzene, toluene, xylene, mesitylene, chlorobenzene and dichlorobenzene, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 1 time by weight or more and 200 times by weight or less relative to the compound represented by Formula (4).

A temperature to carry out the present reaction is not particularly limited as long as the target reaction proceeds, and is usually −80° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-p) may be dehydrated with a drying agent such as sodium sulfate and magnesium sulfate, but this is not essential.

The reaction mixture obtained above which contains the compound represented by Formula (1-p) may be distilled off under reduced pressure to remove the solvent as long as the compound is not decomposed.

The reaction mixture obtained after distillation of the solvent which contains the compound represented by Formula (1-p) may be purified by washing, reprecipitation, recrystallization, column chromatography and the like, using a suitable solvent. It may be optionally set in accordance with the desired purity.

[Production Method U]

[Chem. 103]

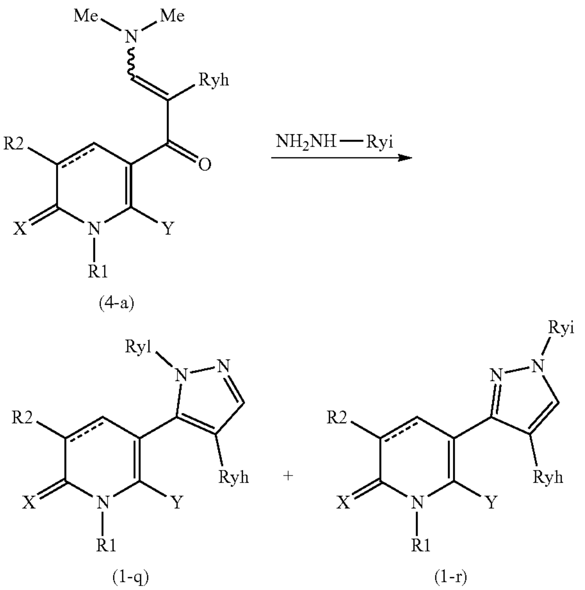

In the formula, Ryh represents a hydrogen atom, a hydroxyl group, a cyano group, a halogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, an aryl group optionally substituted with substituent(s) D, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, Rx1C(═O)— (wherein Rx1 is the same as defined hereinabove.) or Rx1C(═O)O— (wherein Rx1 is the same as defined hereinabove), Ryi represents a hydrogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, an aryl group optionally substituted with substituent(s) D or a heteroaryl group optionally substituted with substituent(s) D, and R1, R2, X, Y and the broken line are the same as defined hereinabove.

The production method U is a synthetic method of a compound represented by Formula (I-q) and a compound represented by Formula (1-r) which belong to the compounds represented by Formula (1), and is a production method which comprises reacting a compound represented by Formula (4-a) and NH2NH-Ryi in a solvent.

A ratio of the compound represented by Formula (1-q) and the compound represented by Formula (1-r) may be either one, thereof alone or a mixture thereof with an optional ratio, which is not particularly limited.

The compound represented by Formula (4-a) to be used in the present reaction can be obtained with reference to Reference Examples.

The $NH_2NH$-Ryi to be used in the present reaction can be obtained as a commercially available product or produced by a conventionally known method. The $NH_2NH$-Ryi may form a salt with an acidic compound such as hydrochloric acid and acetic acid, and is not particularly limited as long as the target reaction proceeds.

An amount of the $NH_2NH$-Ryi to be used in the present reaction may be 1 equivalent or more relative to the compound represented by Formula (4-a), which is not particularly limited as long as the target reaction proceeds, and is usually 1 equivalent or more and 30 equivalents or less.

The solvent to be used in the present reaction is not particularly limited as long as the target reaction proceeds, and may include alcohol solvents such as methanol, ethanol, propanol and butanol, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (4-a).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-q) and the compound represented by Formula (1-r) may be dehydrated with a drying agent such as sodium sulfate and magnesium sulfate, but this is not essential.

The reaction mixture obtained above which contains the compound represented by Formula (1-q) and the compound represented by Formula (1-r) may be distilled under reduced pressure to remove the solvent as long as the compound is not decomposed.

The reaction mixture obtained after distillation of the solvent which contains the compound represented by Formula (1-q) and the compound represented by Formula (1-r) may be purified by washing, reprecipitation, recrystallization, column chromatography and the like, using a suitable solvent. It may be optionally set in accordance with the desired purity.

[Production Method V]

[Chem. 104]

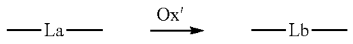

(La) (Lb)

In the formula, La represents S, Lb represents SO or $SO_2$, and Ox' represents an oxidizing agent.

The production method V is a production method of a compounds represented by Formula (Lb), which belongs to in the compounds represented by Formula (1) represented by the formula (1) wherein Lb contained in R2, R3, R4, R5, substituent(s) A and substituent(s) C is SO or $SO_2$, and is a production method which comprises reacting a compound represented by Formula (La), which belongs to the compounds represented by Formula (1) wherein La contained in R2, R3, R4, R5, substituent(s) A and substituent(s) C is S and an oxidizing agent (Ox') in a solvent.

The oxidizing agent to be used in the present reaction may include a peroxide such as aqueous hydrogen peroxide, meta-chloroperbenzoic acid and the like. In addition, a transition metal such as sodium tungstate may be added.

An amount of the oxidizing agent to be used in the present reaction may be usually 1.0 equivalent or more and 1.2 equivalents or less relative to the compound represented by Formula (La) when SO is produced, and is usually 2 equivalents or more and 10 equivalents or less when $SO_2$ is produced. In addition, when the transition metal is to be added, it is usually used in 0.001 equivalent or more and 1 equivalent or less.

The solvent to be used in the present reaction is not particularly limited as long as the target reaction proceeds, and may include water solvent, an acidic solvent such as acetic acid, benzene based solvents such as benzene, toluene, xylene, mesitylene, chlorobenzene and dichlorobenzene, nitrile solvents such as acetonitrile, halogen based solvents such as dichloromethane, dichloroethane, chloroform and carbon tetrachloride, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (La).

A temperature to carry out the present reaction is not particularly limited as long as the target reaction proceeds, and is usually −10° C. or higher and 120° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like.

In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (Lb) may be dehydrated with a drying agent such as sodium sulfate and magnesium sulfate, but this is not essential.

The reaction mixture obtained above which contains the compound represented by Formula (Lb) may be distilled under reduced pressure to remove the solvent as long as the compound is not decomposed.

The reaction mixture obtained after distillation of the solvent which contains the compound represented by Formula (Lb) may be purified by washing, reprecipitation, recrystallization, column chromatography and the like, using a suitable solvent. It may be optionally set in accordance with the desired purity.

Next, a synthetic method of the compound represented by Formula (3) described in Production Method A will be described.

[Production Method W]

[Chem. 105]

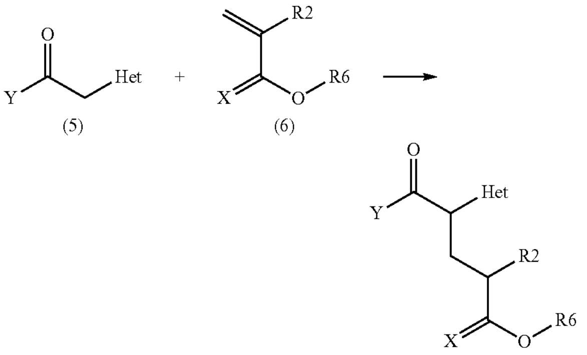

(5) (6) (3)

In the formula, R2, R6, Het, X and Y are the same as defined hereinabove.

The production method W is a production method of a production intermediate represented by the compound of Formula (3), and is a production method which comprises reacting a compound represented by Formula (5) and a compound represented by Formula (6) in the presence of a base in a solvent.

The compound represented by Formula (5) to be used in the present reaction can be synthesized in accordance with Reference Examples. In addition, it can be synthesized with reference to Green Chemistry, vol. 41, pp. 580-585, The Journal of Organic Chemistry, vol. 65, No. 20, pp. 6458-6461 (2000) or U.S. Pat. No. 5,922,718.

The compound represented by Formula (6) to be used in the present reaction can be obtained as a commercially available product or produced by a conventionally known method.

An amount of the compound represented by Formula (6) to be used in the present reaction may be 1 equivalent or more relative to the compound represented by Formula (5), which is not particularly limited as long as the target reaction proceeds, and preferably 1 equivalent or more and 3 equivalents or less.

The base to be used in the present reaction may include inorganic bases such as sodium carbonate, potassium carbonate, cesium carbonate and tripotassium phosphate, or metal alkoxides such as sodium methoxide, sodium ethoxide and potassium t-butoxide.

The base to be used in the present reaction can be carried out with a catalytic amount, which is not particularly limited as long as the target reaction proceeds, and preferably 0.01 equivalent or more and 3 equivalents or less relative to the compound represented by Formula (5).

The solvents to be used in the present reaction may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (5).

A temperature to carry out the present reaction is not particularly limited as long as the target reaction proceeds, and is usually −50° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid or the like is dissolved, an alkaline aqueous solution in which potassium hydroxide, sodium hydroxide, sodium carbonate, potassium carbonate, sodium hydrogen carbonate, potassium hydrogen carbonate or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (3) may be dehydrated with a drying agent such as sodium sulfate and magnesium sulfate, but this is not essential.

The reaction mixture obtained above which contains the compound represented by Formula (3) may be distilled under reduced pressure to remove the solvent as long as the compound is not decomposed.

The reaction mixture obtained after distillation of the solvent which contains the compound represented by Formula (3) may be purified by washing, reprecipitation, recrystallization, column chromatography and the like, using a suitable solvent. It may be optionally set in accordance with the desired purity.

[Production Method X]

[Chem. 106]

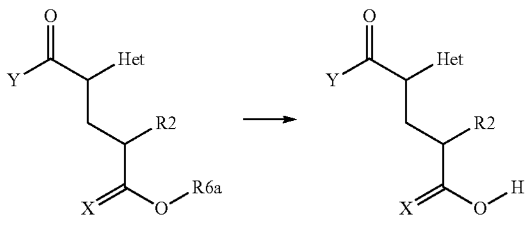

(3a) (3b)

In the formula, R6a represents a C1-C6 alkyl group, and R2, Het, X and Y are the same as defined hereinabove.

Production Method X is a production method of a production intermediate represented by Formula (3b) which belongs to the compounds represented by Formula (3), and is a production method which comprises reacting a compound represented by Formula (3a) under acidic conditions or basic conditions in a solvent.

First, the reaction under acidic conditions will be described.

The acid to be used in the present reaction may be exemplified by inorganic acids such as hydrochloric acid, hydrobromic acid and phosphoric acid, and organic acids such as acetic acid, methanesulfonic acid, p-toluenesulfonic acid and trifluoroacetic acid. It is not particularly limited as long as the target reaction proceeds.

An amount of the acid to be used in the present reaction may be a catalytic amount, which is not particularly limited as long as the target reaction proceeds, and preferably 0.01 equivalent or more relative to the compound represented by Formula (3a). In addition, with regard to a liquid state acid, it is also possible to use it as a solvent.

The solvent to be used in the present reaction is not particularly limited as long as the target reaction proceeds, and may include water solvent, acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (3a).

A temperature to carry out the present reaction is not particularly limited as long as the target reaction proceeds, and is usually 0° C. or higher and 180° C. or lower or a boiling point of the solvent or lower.

Next, the reaction under basic conditions will be described.

The base to be used in the present reaction may be exemplified by inorganic bases such as lithium hydroxide, sodium hydroxide and potassium hydroxide, and is not particularly limited as long as the target reaction proceeds.

The base to be used in the present reaction may be 1 equivalent or more relative to the compound represented by Formula (3a), which is not particularly limited as long as the target reaction proceeds, and preferably 1 equivalent or more and 30 equivalents or less.

The solvent to be used in the present reaction is not particularly limited as long as the target reaction proceeds, and may include water solvent, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (3a).

A temperature to carry out the present reaction is not particularly limited as long as the target reaction proceeds, and is usually −20° C. or higher and 180° C. or lower or a boiling point of the solvent or lower.

A post treatment after the reaction can be carried out in the same way as the reaction under acidic conditions and the reaction under basic conditions. It is possible to carry out a liquid separating operation by adding water or a suitable aqueous solution to the reaction mixture. When an aqueous solution is to be used, an acidic aqueous solution in which hydrochloric acid, sulfuric acid or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, and a saline solution can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (3b) may be dehydrated with a drying agent such as sodium sulfate and magnesium sulfate, but this is not essential.

The reaction mixture obtained above which contains the compound represented by Formula (3b) may be distilled under reduced pressure to remove the solvent as long as the compound is not decomposed.

The reaction mixture obtained after distillation of the solvent which contains the compound represented by Formula (3b) may be purified by washing, reprecipitation, recrystallization, column chromatography and the like, using a suitable solvent. It may be optionally set in accordance with the desired purity.

The compound represented by Formula (3b) contains an isomer represented by Formula (3b')

[Chem. 107]

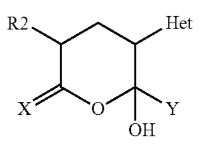

(3b')

(wherein R2, Het, X and Y are the same as defined hereinabove).

The compound represented by Formula (3b') can be handled similar to the compound represented by Formula (3b), and Production Method A can be applied.

Also, the compound represented by Formula (3b') contains an asymmetric carbon, and a mixed ratio of the isomers may be a single isomer alone or a mixture with an optional ratio. Further, it may be a mixture of the compound represented by Formula (3b) and the compound represented by Formula (3b'), and a mixed ratio of the isomers may be a single isomer alone or a mixture with an optional ratio.

[Production Method Y]

[Chem. 108]

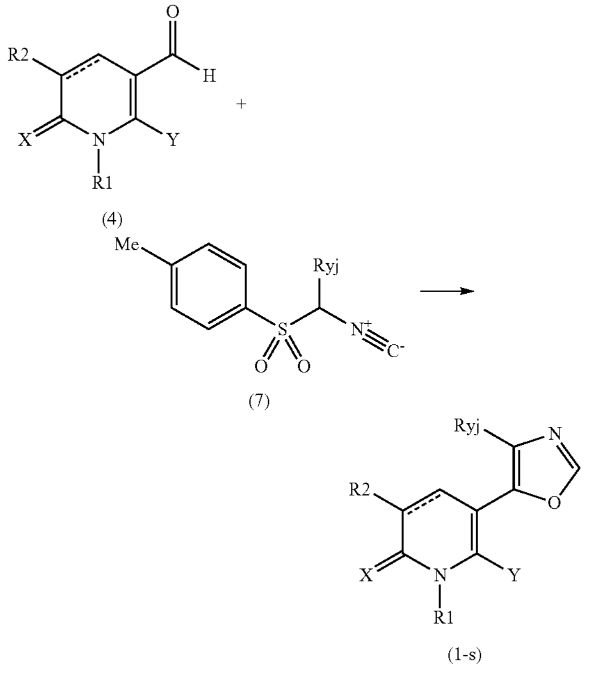

In the formula, Ryj represents a hydrogen atom, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, an aryl group optionally substituted with substituent(s) D or a heteroaryl group optionally substituted with substituent(s) D, and R1, R2, X, Y and the broken line are the same as defined hereinabove.

Production Method Y is a synthetic method of a compound represented by Formula (1-s) which belongs to the compounds represented by Formula (1), and is a production method which comprises reacting a compound represented by Formula (4) and a compound represented by Formula (7) in the presence of a base in a solvent.

The compound represented by Formula (4) to be used in the present reaction can be obtained with reference to Reference Examples.

The compound represented by Formula (7) to be used in the present reaction can be obtained as a commercially available product or produced by a conventionally known method.

An amount of the compound represented by Formula (7) to be used in the present reaction may be 1 equivalent or more relative to the compound represented by Formula (4), which is not particularly limited as long as the target reaction proceeds, and is usually 1 equivalent or more and 10 equivalents or less.

The base to be used in the present reaction may be exemplified by inorganic bases such as sodium hydride, lithium hydroxide, sodium hydroxide, potassium hydroxide, sodium carbonate, potassium carbonate, cesium carbonate and tripotassium phosphate, and metal alkoxides such as sodium methoxide, sodium ethoxide and potassium t-butoxide, and is not particularly limited as long as the target reaction proceeds.

An amount of the base to be used in the present reaction may be 1 equivalent or more relative to the compound represented by Formula (4), which is not particularly limited as long as the target reaction proceeds, and is usually 1 equivalent or more and 10 equivalents or less.

The solvent to be used in the present reaction is not particularly limited as long as the target reaction proceeds, and may include alcohol solvents such as methanol, ethanol, propanol and butanol, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (4).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-s) may be dehydrated with a drying agent such as sodium sulfate and magnesium sulfate, but this is not essential.

The reaction mixture obtained above which contains the compound represented by Formula (1-s) may be distilled under reduced pressure to remove the solvent as long as the compound is not decomposed.

The reaction mixture, obtained after distillation of the solvent which contains the compound represented by Formula (1-s) may be purified by washing, reprecipitation, recrystallization, column chromatography and the like, using a suitable solvent. It may be optionally set in accordance with the desired purity.

[Production Method Z]

[Chem. 109]

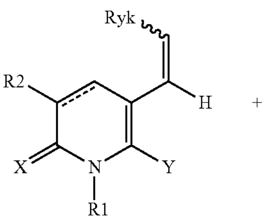

(8)

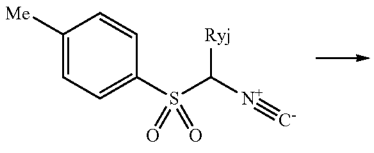

(7)

-continued

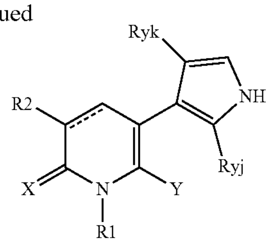

(1-t)

In the formula, Ryk represents a hydrogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group or Rx1C(═O)— (wherein Rx1 is the same as defined hereinabove), and R1, R2, Ryj, X, Y and the broken line are the same as defined hereinabove.

The production method Z is a synthetic method of a compound represented by Formula (1-t) which belongs to the compounds represented by Formula (1), and is a production method which comprises reacting a compound represented by Formula (8) and a compound represented by Formula (7) in the presence of a base in a solvent.

The compound represented by Formula (8) to be used in the present reaction can be obtained with reference to Reference Examples. The compound represented by Formula (8) contains geometric isomers, a mixed ratio of the isomers may be a single isomer alone or a mixture with an optional ratio, and is not particularly limited as long as the target reaction proceeds.

The compound represented by Formula (7) to be used in the present reaction can be obtained as a commercially available product or produced by a conventionally known method.

An amount of the compound represented by Formula (7) to be used in the present reaction may be 1 equivalent or more relative to the compound represented by Formula (8), which is not particularly limited as long as the target reaction proceeds, and is usually 1 equivalent or more and 10 equivalents or less.

The base to be used in the present reaction may be exemplified by inorganic bases such as sodium hydride, lithium hydroxide, sodium hydroxide, potassium hydroxide, sodium carbonate, potassium carbonate, cesium carbonate and tripotassium phosphate, and metal alkoxides such as sodium methoxide, sodium ethoxide and potassium t-butoxide, and is not particularly limited as long as the target reaction proceeds.

An amount of the base to be used in the present reaction may be 1 equivalent or more relative to the compound represented by Formula (8), which is not particularly limited as long as the target reaction proceeds, and is usually 1 equivalent or more and 10 equivalents or less.

The solvent to be used in the present reaction is not particularly limited as long as the target reaction proceeds, and may include alcohol solvents such as methanol, ethanol, propanol and butanol, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (8).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-t) may be dehydrated with a drying agent such as sodium sulfate and magnesium sulfate, but this is not essential.

The reaction mixture obtained above which contains the compound represented by Formula (1-t) may be distilled under reduced pressure to remove the solvent as long as the compound is not decomposed.

The reaction mixture obtained after distillation of the solvent which contains the compound represented by Formula (1-t) may be purified by washing, reprecipitation, recrystallization, column chromatography and the like, using a suitable solvent. It may be optionally set in accordance with the desired purity.

[Production Method AA]

[Chem. 110]

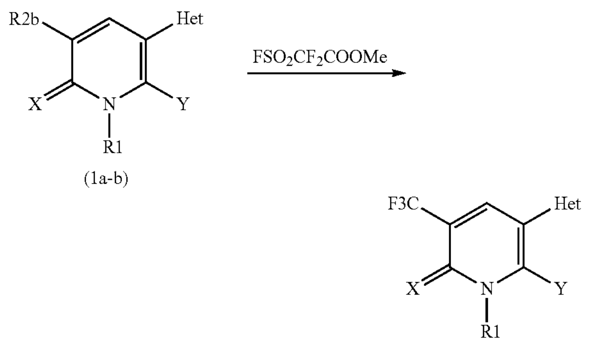

(1a-b)

(1a-f)

In the formula, R1, Het, R2b, X and Y are the same as defined hereinabove.

Production Method AA is a synthetic method of a compound represented by Formula (1a-f) having a trifluoromethyl group which belongs to the compounds represented by Formula (1a), and is a production method which comprises reacting a compound represented by Formula (1a-b) and methyl difluoro(fluorosulfonyl)acetate in the presence of a transition metal.

In the compound represented by Formula (1a-b), preferable R2b is a chlorine atom, a bromine atom or an iodine atom.

Methyl difluoro(fluorosulfonyl)acetate to be used in the present reaction can be obtained as a commercially available product or produced by a conventionally known method.

An amount of methyl difluoro(fluorosulfonyl)acetate to be used in the present reaction may be 1 equivalent or more relative to the compound represented by Formula (1a-b), which is not particularly limited as long as the target reaction proceeds, and preferably 1 equivalent or more and 50 equivalents or less.

The transition metal to be used in the present reaction is copper and the like. It is preferably copper bromide, copper iodide and the like.

An amount of the transition metal to be used in the present reaction may be 1 equivalent or more relative to the compound represented by Formula (1a-b), which is not particularly limited as long as the target reaction proceeds, and preferably 1 equivalent or more and 50 equivalents or less.

In order to proceed the reaction efficiently, an additive such as ethyldiisopropylamine and hexamethylphosphoric triamide, but it is not essential.

An amount of the additive to be used in the present reaction may be 50 equivalents or less relative to the compound represented by Formula (1a-b), and is not particularly limited as long as the target reaction proceeds.

The solvent to be used in the present reaction is not particularly limited as long as the target reaction proceeds, and may include amide solvents such as N-methylpyrrolidone, N,N-dimethylformamide and N,N-dimethylacetamide, sulfur solvents such as dimethylsulfoxide and sulforane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-b).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which ammonia, potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a-f) may be dehydrated with a drying agent such as sodium sulfate and magnesium sulfate, but this is not essential.

The reaction mixture obtained above which contains the compound represented by Formula (1a-f) may be distilled under reduced pressure to remove the solvent as long as the compound is not decomposed.

The reaction mixture obtained after distillation of the solvent which contains the compound represented by Formula (1a-f) may be purified by washing, reprecipitation, recrystallization, column chromatography and the like, using a suitable solvent. It may be optionally set in accordance with the desired purity.

[Production Method AB]

[Chem. 111]

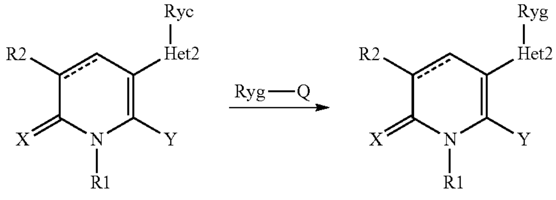

(1-g) (1-u)

In the formula, R1, R2, Ryc, Ryg, Het2, X, Y, Q and the broken line are the same as defined hereinabove.

Production Method AB is a method of obtaining a compound represented by Formula (1-u), which belongs to the compounds represented by Formula (1), wherein Ryg is a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, a heteroaryl group optionally substituted with substituent(s) D, an aryloxy group optionally substituted with substituent(s) D, a heteroaryloxy group optionally substituted with substituent(s) D, an aralkyloxy group optionally substituted with substituent(s) D, RaRbN— (here, Ra and Rb are the same as defined hereinabove), Rc-L- (wherein Rc and L are the same as defined hereinabove.) or Rx4Rx5C═N—O— (here, Rx4 and Rx5 are the same as defined hereinabove), and is a production method which comprises reacting a compound represented by Formula (1-g) and Ryg-Q in the presence of a base in a solvent.

In the compound represented by Formula (1-g), preferable Ryc is a fluorine atom, a chlorine atom or a bromine atom.

The Ryg-Q to be used in the present reaction can be obtained as a commercially available product or produced by a conventionally known method. Preferable Q is a hydrogen atom or an alkali metal such as sodium, potassium and the like.

An amount of the Ryg-Q to be used in the present reaction may be 1 equivalent or more relative to the compound represented by Formula (1-g), which is not particularly limited as long as the target reaction proceeds, and is usually 1 equivalent or more and 30 equivalents or less. Also, when Q represents a hydrogen atom, it may be used as a solvent.

The base to be used in the present reaction is preferably inorganic bases such as sodium carbonate, potassium carbonate, cesium carbonate and sodium hydride. Also, when the Q is an alkali metal, then use of the base is not essential.

An amount of the base to be used in the present reaction may be 1 equivalent or more relative to the compound represented by Formula (1-g), which is not particularly limited as long as the target reaction proceeds, and is usually 1 equivalent or more and 30 equivalents or less.

The solvent to be used in the present reaction is not particularly limited as long as the target reaction proceeds, and may include alcohol solvents represented by Ryg-H (wherein Ryg is the same as defined hereinabove), ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1-g).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride; hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1-u) may be dehydrated with a drying agent such as sodium sulfate and magnesium sulfate, but this is not essential.

The reaction mixture obtained above which contains the compound represented by Formula (1-u) may be distilled under reduced pressure to remove the solvent as long as the compound is not decomposed.

The reaction mixture obtained after distillation of the solvent which contains the compound represented by Formula (1-u) may be purified by washing, reprecipitation, recrystallization, column chromatography and the like, using a suitable solvent. It may be optionally set in accordance with the desired purity.

[Production Method AC]

[Chem. 112]

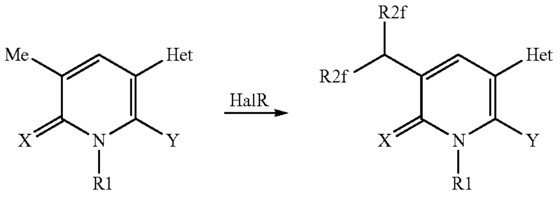

(1a-g)

(1a-h)

In the formula, R2f represents a halogen atom, and HalR, R1, Het, X and Y are the same as defined hereinabove.

Production Method AC is a method of obtaining a compound represented by Formula (1a-h), which belongs to the compounds represented by Formula (1a), wherein R2f is a halogen atom, and is a production method which comprises reacting a compound represented by Formula (1a-g) using a radical initiator and a halogenating agent (HalR) in a solvent.

In Formula (1a-h), preferable R2f is a chlorine atom, a bromine atom or an iodine atom.

The radical initiator to be used in the present reaction may include azobisisobutyronitrile, 2,2'-azobis(4-methoxy-2,4-dimethylvaleryonitrile), benzoyl peroxide and the like.

An amount of the radical initiator to be used in the present reaction is not particularly limited as long as the target reaction proceeds, and is usually 0.01 equivalent or more and 1.0 equivalent or less relative to the compound represented by Formula (1a-g).

The halogenating agent to be used in the present reaction may include N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin and the like.

An amount of the halogenating agent to be used in the present reaction may be 2 equivalents or more relative to the compound represented by Formula (1a-g), which is not particularly limited as long as the target reaction proceeds, and is usually 2 equivalents or more and 2.8 equivalents or less.

The solvent to be used in the present reaction is not particularly limited as long as the target reaction proceeds, and may include halogenated benzene solvents such as chlorobenzene and dichlorobenzene, ester solvents such as ethyl acetate, isopropyl acetate and butyl acetate, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-g).

A temperature to carry out the present reaction is not particularly limited as long as the target reaction proceeds, and is usually 20° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane and chloroform, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a-h) may be dehydrated with a drying agent such as sodium sulfate and magnesium sulfate, but this is not essential.

The reaction mixture obtained above which contains the compound represented by Formula (1a-h) may be distilled under reduced pressure to remove the solvent as long as the compound is not decomposed.

The reaction mixture obtained after distillation of the solvent which contains the compound represented by Formula (1a-h) may be purified by washing, reprecipitation, recrystallization, column chromatography and the like, using a suitable solvent. It may be optionally set in accordance with the desired purity.

[Production Method AD]

[Chem. 113]

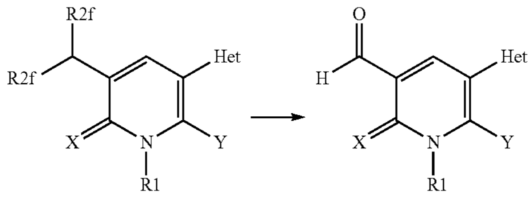

(1a-h) (1a-i)

In the formula, R1, R2f, Het, X and Y are the same as defined hereinabove.

Production Method AD is a method of obtaining a compound represented by Formula (1a-i) which belongs to the compounds represented by Formula (1a), and is a production method which comprises hydrolyzing a compound represented by Formula (1a-h) in the presence of water in a solvent.

In Formula (1a-h), preferable R2f is a chlorine atom, a bromine atom or an iodine atom.

In the present reaction, water is essential. Also, in order to proceed the present reaction smoothly, silver nitrate may be used.

When an amount of water to be used in the present reaction is 1 equivalent or more relative to the compound represented by Formula (1a-h), it is not limited as long as the target reaction proceeds. In addition, water can be used as a solvent.

When an amount of the silver nitrate to be used in the present reaction is 2 equivalents or more relative to the compound represented by Formula (1a-h), it is not limited as long as the target reaction proceeds, and it is usually 2 equivalents or more and 10 equivalents or less.

The solvent to be used in the present reaction is not particularly limited as long as the target reaction proceeds, and may include water solvent, ether solvents such as diethyl ether, diisopropyl ether, methyl-t-butyl ether, dimethoxyethane, tetrahydrofuran and dioxane, nitrile solvents such as acetonitrile, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-h).

A temperature to carry out the present reaction is not particularly limited as long as the target reaction proceeds, and is usually −10° C. or higher and 100° C. or lower or a boiling point of the solvent or lower.

As a post treatment after the reaction, it is possible to remove undissolved metal by filtration. Further, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a-i) may be dehydrated with a drying agent such as sodium sulfate and magnesium sulfate, but this is not essential.

The reaction mixture obtained above which contains the compound represented by Formula (1a-i) may be distilled under reduced pressure to remove the solvent as long as the compound is not decomposed.

The reaction mixture obtained after distillation of the solvent which contains the compound represented by Formula (1a-i) may be purified by washing, reprecipitation, recrystallization, column chromatography and the like, using a suitable solvent. It may be optionally set in accordance with the desired purity.

[Production Method AE]

[Chem. 114]

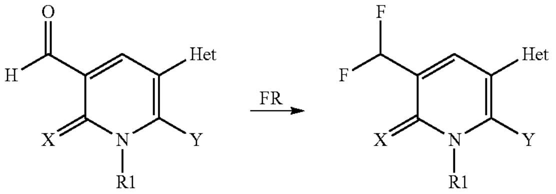

(1a-i) (1a-j)

In the formula, FR represents a fluorinating agent, and R1, Het, X and Y are the same as defined hereinabove.

Production Method AE is a method of obtaining a compound represented by Formula (1a-j) having a fluorine atom which belongs to the compounds represented by Formula (1a), and is a production method which comprises reacting a compound represented by Formula (1a-i) and a fluorinating agent (FR) in a solvent.

The fluorinating agent to be used in the present reaction may include (diethylamino)sulfur trifluoride, bis(2-methoxyethyl)aminosulfur trifluoride, N,N-diethyl-1,1,2,3,3,3-hexafluoropropylamine, 2,2-difluoro-1,3-dimethylimidazolidine and the like.

An amount of the fluorinating agent to be used in the present reaction may be 2 equivalents or more relative to the compound represented by Formula (1a-i), which is not particularly limited as long as the target reaction proceeds, and is usually 2 equivalents or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, nitrile solvents such as acetonitrile, halogen based solvents such as dichloromethane, dichloroethane, chloroform and carbon tetrachloride, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (1a-i).

A temperature to carry out the present reaction is not particularly limited as long as the target reaction proceeds, and is usually −80° C. or higher and 100° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (1a-j) may be dehydrated with a drying agent such as sodium sulfate and magnesium sulfate, but this is not essential.

The reaction mixture obtained above which contains the compound represented by Formula (1a-j) may be distilled under reduced pressure to remove the solvent as long as the compound is not decomposed.

The reaction mixture obtained after distillation of the solvent which contains the compound represented by Formula (1a-j) may be purified by washing, reprecipitation, recrystallization, column chromatography and the like, using a suitable solvent. It may be optionally set in accordance with the desired purity.

[Production Method AF]

[Chem. 115]

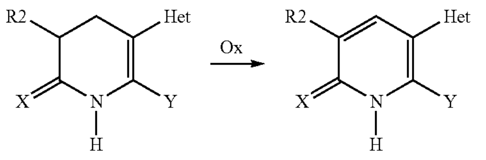

(2) (2-a)

In the formula, Ox represents an oxidizing agent, and R2, Het, X and Y are the same as defined hereinabove.

Production Method AF is a method of obtaining a compound represented by Formula (2-a), and is a production method which comprises reacting a compound represented by Formula (2) and an oxidizing agent (Ox) in a solvent.

By using the compound represented by Formula (2) in place of the compound represented by Formula (1b) in Production Method E, Production Method AF can be carried out in accordance with Production Method E.

[Production Method AG]

[Chem. 116]

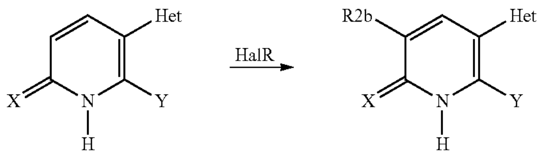

(2-b) (2-c)

In the formula, R2b represents a halogen atom, HalR represents a halogenating agent, and Het, X and Y are the same as defined hereinabove.

Production Method AG is a production method of obtaining a compound represented by Formula (2-c), which belongs to the compounds represented by Formula (2-a), wherein R2b represents a halogen atom, and is a production method which comprises reacting a compound represented by Formula (2-b) and a halogenating agent (HalR) in a solvent.

By using the compound represented by Formula (2-b) in place of the compound represented by Formula (1a-a) in Production Method F, Production Method AG can be carried out in accordance with Production Method F.

[Production Method AH]

[Chem. 117]

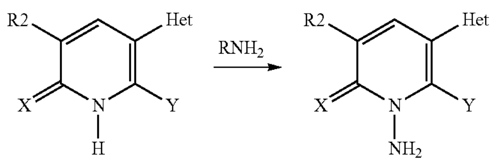

(2-a) (2-d)

In the formula, $RNH_2$ represents an aminating agent, and R2, Het, X and Y are the same as defined hereinabove.

Production Method AH is a method of obtaining a compound represented by Formula (2-d), and is a production method which comprises a compound represented by Formula (2-a) and an aminating agent ($RNH_2$) in the presence of a base in a solvent.

The aminating agent to be used in the present reaction may include diphenyl-phosphineamide, O-(4-nitrobenzoyl) hydroxylamine, O-(2,4-dinitrophenyl)-hydroxylamine, O-(diphenylphosphinyl)hydroxylamine and the like.

An amount of the aminating agent to be used in the present reaction may be 1 equivalent or more relative to the compound represented by Formula (2-a), which is not particularly limited as long as the target reaction proceeds, and is usually 1 equivalent or more and 5 equivalents or less.

The base to be used in the present reaction may be exemplified by inorganic bases such as lithium hydroxide, sodium hydroxide, potassium hydroxide, sodium carbonate, potassium carbonate, cesium carbonate and tripotassium phosphate, metal alkoxides such as sodium methoxide, sodium ethoxide and potassium t-butoxide, metal hydrides such as sodium hydride, and metal amides such as lithium diisopropylamide, hexamethyldisilazane lithium, hexamethyldisilazane sodium and hexamethyldisilazane potassium, and is not particularly limited as long as the target reaction proceeds.

An amount of the base to be used in the present reaction a base may be 1 equivalent or more relative to the compound represented by Formula (2-a), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, nitrile solvents such as acetonitrile, halogen based solvents such as dichloromethane, dichloroethane, chloroform and carbon tetrachloride, amide solvents such as N-methylpyrrolidone, N,N-dimethylformamide and N,N-dimethylacetamide, urea solvents such as 1,3-dimethyl-2-imidazolidinone, hydrocarbon solvents such as hexane, heptane, cyclohexane and methylcyclohexane, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (2-a).

A temperature to carry out the present reaction is not particularly limited as long as the target reaction proceeds, and is usually −80° C. or higher and 100° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (2-d) may be dehydrated with a drying agent such as sodium sulfate and magnesium sulfate, but this is not essential.

The reaction mixture obtained above which contains the compound represented by Formula (2-d) may be distilled under reduced pressure to remove the solvent as long as, the compound is not decomposed.

The reaction mixture obtained after distillation of the solvent which contains the compound represented by Formula (2-d) may be purified by washing, reprecipitation, recrystallization, column chromatography and the like, using a suitable solvent. It may be optionally set in accordance with the desired purity.

[Production Method AI]

[Chem. 118]

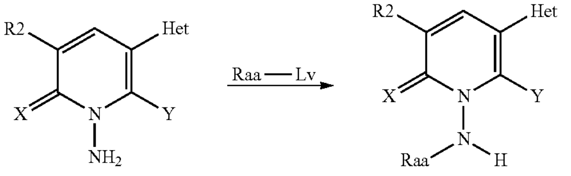

(2-d) (2-e)

In the formula, Raa represents a C1-C6 alkyl group optionally substituted with substituent(s) B, a C1-C6 haloalkyl group or a C3-C8 cycloalkyl group, and R2, Het, Lv, X and Y are the same as defined hereinabove.

Production Method AI is a method of obtaining a compound represented by Formula (2-e), and is a production method which comprises reacting a compound represented by Formula (2-d) and Raa-Lv in the presence of a base in a solvent.

The Raa-Lv to be used in the present reaction can be obtained as a commercially available product or produced by a conventionally known method.

An amount of the Raa-Lv to be used in the present reaction may be 1 equivalent or more relative to the compound represented by Formula (2-d), which is not particularly limited as long as the target reaction proceeds, and preferably 1 equivalent or more and 10 equivalents or less.

The base to be used in the present reaction may be exemplified by inorganic bases such as sodium hydroxide, potassium hydroxide, sodium carbonate, potassium carbonate, cesium carbonate and sodium hydride, and is not particularly limited as long as the target reaction proceeds.

An amount of the base to be used in the present reaction may be 1 equivalent or more relative to the compound represented by Formula (2-d), which is not particularly limited as long as the target reaction proceeds, and preferably 1 equivalent or more and 10 equivalents or less.

The solvent to be used in the present reaction is not particularly limited as long as the target reaction proceeds, and may include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen based solvents such as dichloromethane, dichloroethane, chloroform and carbon tetrachloride, sulfur solvents such as dimethylsulfoxide and sulforane, ketone solvents such as acetone, methyl ethyl ketone and methyl isobutyl ketone and water solvent, and the like. These solvents may be used singly, or two or more kinds may be used in combination in an optional ratio.

An amount of the solvent to be used in the present reaction is not particularly limited as long as the target reaction proceeds, and is usually 3 times by weight or more and 200 times by weight or less relative to the compound represented by Formula (2-d).

A temperature to carry out the present reaction is not particularly limited as long as the target reaction proceeds, and is usually 0° C. or higher and 150° C. or lower or a boiling point of the solvent or lower.

As a post treatment after the reaction, it is possible to carry out a liquid separating operation by adding water or a suitable aqueous solution to the reaction mixture. When an aqueous solution is to be used, an acidic aqueous solution in which hydrochloric acid, sulfuric acid, ammonium chloride or the like is dissolved, an alkaline aqueous solution in which potassium hydroxide, sodium hydroxide, sodium carbonate, potassium carbonate, sodium hydrogen carbonate, potassium hydrogen carbonate or the like is dissolved, an aqueous solution in which a salt containing a sulfur atom such as sodium thiosulfate, sodium sulfite or the like is dissolved or a saline solution or the like can be optionally used. At the time of the liquid separating operation, if necessary, it is possible to add a solvent which is immiscible with water including benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen based solvents such as dichloromethane, dichloroethane, chloroform and carbon tetrachloride, hydrocarbon solvents such as hexane, heptane, cyclohexane and methylcyclohexane, and the like. In addition, it is possible to use these solvents singly or to mix two or more kinds with an optional ratio. The number of times of the liquid separation is not particularly limited, and may be carried out in accordance with the purity and yield to be desired.

The reaction mixture obtained above which contains the compound represented by Formula (2-e) may be dehydrated with a drying agent such as sodium sulfate and magnesium sulfate, but this is not essential.

The reaction mixture obtained above which contains the compound represented by Formula (2-e) may be distilled under reduced pressure to remove the solvent as long as the compound is not decomposed.

The reaction mixture obtained after distillation of the solvent which contains the compound represented by Formula (2-e) may be purified by washing, reprecipitation, recrystallization, column chromatography and the like, using a suitable solvent. It may be optionally set in accordance with the desired purity.

[Production Method AJ]

[Chem. 119]

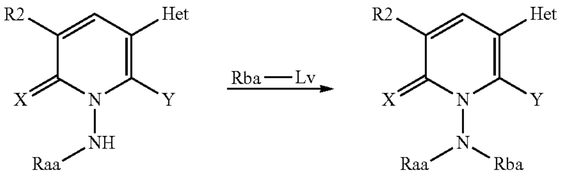

(2-e) (2-f)

In the formula, Rba represents a C1-C6 alkyl group optionally substituted with substituent(s) B, a C1-C6 haloalkyl group or a C3-C8 cycloalkyl group, and R2, Het, Lv, X and Y are the same as defined hereinabove.

Production Method AJ is a method of obtaining a compound represented by Formula (2-f), and is a production method which comprises reacting a compound represented by Formula (2-e) and Rba-Lv in the presence of a base in a solvent.

The Rba-Lv to be used in the present reaction can be obtained as a commercially available product or produced by a conventionally known method.

By using the compound represented by Formula (2-e) in place of the compound represented by Formula (2-d) in Production Method AI, Production Method AJ can be carried out in accordance with Production Method AI. Also, when Raa and Rba are the same, by using 2 equivalents or more of Raa-Lv relative to Formula (2-d) in Production Method AI, the compound represented by Formula (2-f) can be synthesized.

The compounds represented by Formula (1) can be produced by optionally combining Production Method A to Production Method AJ shown hereinabove. Or else, the compounds represented by Formula (1) can be produced even when the conventionally known method and Production Method A to Production Method AJ are optionally combined.

The compounds of the present invention can protect plants from harmful organisms and thus may be used as agricultural chemicals. Specifically, examples thereof includes fungicides, insecticides, herbicides, plant growth regulators and the like. It is preferably fungicides.

The compounds of the present invention can be used as an agricultural and horticultural fungicide in farms, paddy fields, tea gardens, orchards, meadows, grasses, forests, gardens, roadside trees, etc., for prevention and treatment of plant diseases.

Plant diseases referred to in the present invention mean that systemic, abnormal pathological symptoms such as wilting, damping-off, yellowing, dwarfism, and spindly growth, or partial pathological symptoms such as spotting, leaf blight, mosaic pattern, leaf rolling, die back, root rot, club root, and knotting are induced in plants such as crops, flowering plants, flowering trees and shrubs, and trees. That is, the plants are to get sick. As pathogens that cause plant diseases, there may be mainly mentioned fungi, bacteria, spiroplasmas, phytoplasmas, viruses, viroids, parasitic higher plants, nematodes and the like. The compounds of the present invention are effective against fungi, but it is not limited thereto.

Diseases caused by fungi are mainly fungal diseases. Examples of fungi (pathogens) that cause fungal diseases include *Plasmodiophora, Oomycetes, Zygomycetes, Ascomycetes, Basidiomycetes* and *Deuteromycetes*. For example, *Plasmodiophora* may include club root fungus, potato powdery scab fungus and beet necrotic yellow vein virus, *Oomycetes* may include blight fungus, downy mildew fungus, *Pythium* species fungus and *Aphanomyces* species fungus, *Zygomycetes* may include *Rhizopus* species fungus, *Ascomycetes* may include peach leaf curl fungus, corn brown spot fungus, rice blast fungus, powdery mildew fungus, anthracnose fungus, *Fusarium* head blight fungus, bakanae disease fungus and sclerotial disease fungus, *Basidiomycetes* may include rust disease fungus, smut fungus, violet root rot fungus, blister blight fungus and rice sheath blight fungus, and *Deuteromycetes* may include gray mold fungus, *Alternaria* species fungus, *Fusarium* species fungus, *Penicillium* species fungus, *Rhizoctonia* species fungus, southern blight fungus and the like.

The compounds of the present invention are effective against various plant diseases. The following provides specific examples of disease names and pathogens thereof.

Rice: blast (*Magnaporthe grisea*), sheath blight (*Thanatephorus cucumeris*), brown sclerotial disease (*Ceratobasidium setariae*), small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), *Cercospora* leaf spot (*Sphaerulina oryzina*), bakanae disease (*Gibberella fujikuroi*), seedling damping-off (*Pythium* spp., *Fusarium* spp., *Trichoderma* spp., *Rhizopus* spp., *Rhizoctonia solani, Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seedling damping-off (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* fsp. *hordei*; fsp. *tritici*), rust (*Puccinia striiformis, Puccinia graminis, Puccinia recondita, Puccinia hordei*), barley stripe (*Pyrenophora graminea*), net blotch (*Pyrenophora

*teres*), *Fusarium* head blight (*Gibberella zeae, Fusarium culmorum, Fusarium avenaceum, Monographella nivalis*), *Typhula* snow blight (*Typhula incarnata, Typhula ishikariensis, Monographella nivalis*), loose kernel smut (*Ustilago nuda*), stinking smut (*Tilletia* caries, *Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), seedling blight (*Gaeumannomyces graminis*), anthracnose (*Colletotrichum graminicola*), ergot (*Claviceps purpurea*), leaf spot (*Cochliobolus sativus*), bacterial black node (*Pseudoronas syringae* pv. *syringae*);

corn: leaf rust (*Gibberella zeae*, etc.), damping-off (*Fusarium avenaceum, Penicillium* spp., *Pythium* spp., *Rhizoctonia* spp.), rust (*Puccinia sorghi*), brown spot (*Cochliobolus heterostrophus*), loose smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe amnpelina*), ripe rot (*Glomerella cingulata, Colletotrichum acutatum*), black rot (*Guignardia bidwellii*), *Phomopsis* leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), *Alternaria* leaf spot (*Alternaria mali*), rust (*Gymnosporangium yamadae*), blossom blight (*Monilinia mali*), apple canker (*Valsa ceratosperma*), ring spot (*Botyosphaeria berengeriana*), anthracnose (*Colletotrichurn acutatum, Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*);

Japanese pears: black spot (*Alternaria kikuchiana*), pear scab (*Venturia nashicola*), rust (*Gymnosporangium asiaticum*), ring spot (*Botryosphaeria berengeriana* fsp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudomonas syringae* pv. *syringae*); European pears: blight (*Phytophthora cactorum, Phytophthora syringae*), bacterial shoot blight (*Erwinia* sp.); peaches: black spot (*Cladosporium carpophilum*), *Phomopsis* rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis. (*Pseudomonas syringae* pv. *syringae*); persimmons: anthracnose (*Glomerella cingulata*), brown stem rot (*Cercospora kaki; Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*); tomato, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce and the like: sclerotial disease (*Sclerotinia sclerotiorum*); various vegetables such as tomatoes, cucumbers, beans, radishes, watermelons, eggplants, rapeseed, green peppers, spinach, beets and the like: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*, etc.), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus);

tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridiflava*), soft rot (*Erwinia carotovora* subsp. *carotovora*), bacterial leaf gall (*Crynebacterium* sp.), yellowing wilt (*Phytoplasma asteris*), yellow dwarfism (Tobacco leaf curl subgroup III geminivirus); eggplants: powdery mildew (*Sphaerotheca fidiginea*, etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysantherni*), soft rot (*Erwinia carotovora* subsp. *carotovora*), bacterial spot (*Pseudomonas* sp.); rapeseed: black spot (*Alternaria brassicae*), black rot (*Xhanthomonas campestris* pv. *campestris*), bacterial black spot (*Pseudomonas syringae* pv. *maculicola*), soft rot (*Erwinia carotovora*); cruciferous vegetables: black spot (*Alternaria brassicae*, etc.), white spot (*Cercosporella brassicae*), black leg (*Phoma lingam*), club root (*Plasmodiophora brassicae*), downy mildew (*Peronospora parasitica*), black rot (*Xhanthomonas campestris* pv. *campestris*), bacterial black spot (*Pseudomonas syringae* pv. *maculicola*), soft rot (*Erwinia carotovora* subsp. *carotovora*);

cabbage: club foot (*Thanatephorus cucumeris*), yellowing wilt (*Fusarium oxysporum*), *alternaria* sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), *Rhizoctonia* root rot (*Rhizoctonia solani*), stem rot (*Phytophthora sojae*), downy mildew (*Peronospora manshurica*), rust (*Phakopsora pachyrhizi*), anthracnose (*Colletotrichum truncatum*, etc.), leaf scald (*Xhanthomonas campestris* pv. *glycines*), bacterial spot (*Pseudomonas syringae* pv. *glycinea*); green beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*); peanuts: leaf spot (*Mycosphaerella berkeleyi*), brown spot (*Mycosphaerella arachidis*), bacterial wilt (*Ralstonia solanacearum*); peas: powdery mildew (*Erysiphe pisi*), downy mildew (*Peronospora pisi*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces* scabies, *Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces* scabies), bacterial spot (*Pseudomonas syringae* pv. *aptata*);

carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae*, etc.), anthracnose (*Glomerella cingulata*, etc.), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), damping-off (*Ralstonia solanacearum*), tobacco mosaic virus (Tobacco mosaic virus);

coffee: rust disease (*Hemileia vastatrix*); banana: black sigatoka (*Mycosphaerella fijiensis*), panama disease (*Fusarium oxysporum* fsp *cubense*); cotton: damping-off (*Fusarium oxysporum*), frosty mildew (*Ramularia areola*); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa*, etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), *chrysanthemum* virescence (*Phytoplasma aurantifolia*); grasses: brown patch disease (*Rhizoctonia solani*), dollar spot disease (*Sclerotinia homoeocarpa*), *curvularia* leaf blight (*Curvularia* sp.), rust (*Puccinia zoysiae*), *helminthosporium* leaf blight (*Cochliobolus* sp.), scald (*Rhynchosporium secalis*), damping-off (*Gaeumannomyces graminis*), anthracnose (*Colletotrichum* sp.), *Typhula* brown snow blight (*Typhula incarnata*), *Typhula* black snow blight (*Typhula ishikariensis*), *Sclerotinia* (*Myriosclerotinia borealis*), fairy ring disease (*Marasmius oreades*, etc.), *Pythium* blight (*Pythium aphanidermatum*, etc.), blast (*Pyricularia grisea*) and the like.

The compounds of the present invention may be used singly, but preferably can be used as a composition such as powder, wettable powder, granular wettable powder, water-soluble powder, granular water-soluble powder, granules, an emulsion, a liquid, a microemulsion, an aqueous suspension preparation, an aqueous emulsion preparation, or a suspoemulsion preparation by mixing with a solid carrier, liquid carrier, gas carrier, surfactant, adhesive agent, dispersant, stabilizer, or the like. The compositions are not limited thereto as long as the effects are demonstrated.

The followings show specific formulating examples, but which are not limitative.

Preparation Example 1: Flowable

The compounds of the present invention (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 part by mass), and ion exchanged water (78.7 parts by mass) are mixed to make a slurry, and further the slurry is wet milled with Dyno-Mill KDL using glass beads having a diameter of 1.0 mm to obtain a flowable.

Preparation Example 2: Emulsion

The compounds of the present invention (5 parts by mass) is dissolved in a mixed solution of xylene (40 parts by mass) and cyclohexane (35 parts by mass), and Tween 20 (20 parts by mass) is added to this solution, and the mixture is mixed to obtain an emulsion.

Preparation Example 3: Wettable Powder

The compounds of the present invention (10 parts by mass), white carbon (10 parts by mass), polyvinyl alcohol (2 parts by mass), dioctylsulfosuccinic acid sodium salt (0.5 part by mass), alkylbenzene sulfonic acid sodium salt (5 parts by mass), calcined diatomaceous earth (10 parts by mass) and kaolinite clay (62.5 parts by mass) are mixed thoroughly, and the mixture is pulverized by an air mill to obtain a wettable powder.

In the following, the application of the composition of the present invention (agricultural and horticultural pest control agents, and agricultural and horticultural fungicides) will be described.

As the method for applying the composition containing the compound of the present invention, there may be mentioned a method of bringing the composition into contact with a plant body or seeds, or a method of bringing cultivation soil containing the composition into contact with the roots or underground stem of a plant. Specific examples thereof may include a treatment of spraying the composition onto the stem and leaves of a plant individual, an injection treatment, a treatment of seedling nursery boxes, a cell tray treatment, a treatment of spraying the composition to plant seeds, a treatment of coating the composition to plant seeds, a treatment of immersing the composition to plant seeds, a treatment of dressing the composition to plant seeds, a treatment of spraying the composition onto the surface of soil, soil mixing after a treatment of spraying the composition to the surface of the soil, a treatment of injecting the composition into soil, soil mixing after a treatment of injecting the composition into the soil, a treatment of irrigating the composition into soil, soil mixing after a treatment of irrigating the composition into the soil and the like. The composition demonstrates adequate effects when applied by any method usually used by a person skilled in the art.

A "plant" referred to in the present invention means a matter which thrives by photosynthesis without moving. Specific examples thereof include rice, wheat, barley, corn, coffee, bananas, grapes, apples, pears, peaches, cherries, citrus fruits, soybeans, kidney beans, cotton, strawberries, potatoes, cabbage, lettuce, tomatoes, cucumbers, eggplants, watermelons, sugar beets, spinach, field peas, squash, sugar cane, tobacco, green peppers, sweet potatoes, taro potatoes, konjak, cotton, sunflowers, roses, tulips, chrysanthemums, turf grasses and the like, and F1 hybrids thereof, and the like. In addition, gene recombinant crops that are created by artificially manipulating gene, etc., and are inherently not present in nature are also included and, for example, may include agricultural and horticultural crops such as soybeans, corn, cotton and the like to which resistance to herbicides had been imparted, rice, tobacco and the like which are acclimated to cold climates, corn, cotton and the like to which an ability to produce insecticidal substances had been imparted, and the like. Further, there may be mentioned trees such as pines, ash trees, ginkgos, maples, oaks, poplars, zelkova and the like. Also, a "plant body" referred to in the present invention means that all the sites constituting the above-mentioned plant individual are collectively called and, for example, there may be mentioned stems, leaves, roots, seeds, flowers, fruits and the like.

A "seed" referred to in the present invention means a matter which stores nutrients for germination of young plant and is used for agricultural breeding. Specific examples thereof include seeds of corn, soybeans, cotton, rice, sugar beets, wheat, barley, sunflowers, tomato, cucumbers, eggplants, spinach, field peas, squash, sugar cane, tobacco, green peppers, rape and the like, and F1 hybrids thereof and the like, seed tubers of taro potatoes, potatoes, sweet potatoes, konjak and the like, bulbs of edible lilies, tulips and the like, seed bulbs of scallions, etc., and seeds and tubers of gene recombinant crops and the like.

An application amount and an application concentration of the composition containing the compound of the present invention may vary depending on the target crop, target disease, degree of progression of the disease, dosage form of the compound, application method and various environmental conditions and the like, and in the case of spraying or irrigating, it is suitably 0.1 to 10,000 g per hectare as an amount of active ingredient and preferably 10 to 1,000 g per hectare. In addition, an amount used in the case of seed treatment is 0.0001 to 1,000 g per 1 kg of seeds as an amount of active ingredient and preferably 0.001 to 100 g. When the composition containing the compound of the present invention is used for a treatment of spraying the composition onto the stem and leaves of a plant individual, a treatment of spraying the composition onto the surface of soil, a treatment of injecting the composition into soil or a treatment of irrigating the composition into soil, the treatment may be carried out after having diluted to a suitable concentration in a suitable carrier. When the composition containing the compound of the present invention is bringing into contact with the plant seeds, after diluting to a suitable concentration, the plant seeds may be subjected to immersion, dressing, spraying or coating treatment. An amount of the composition when subjecting to immersion, dressing, spraying or coating treatment as the amount of the active ingredient is usually about 0.05 to 50% based on the dry weight of the plant seeds, and is preferably 0.1 to 30%, but is not limited thereto, and the amount may be appropriately set depending on the form of the composition or the kind of the plant seeds targeted for the treatment.

The composition-containing the compound of the present invention can be used by mixing with other agricultural chemicals as necessary, for example, including agricultural chemicals such as fungicides, insecticides, acaricides, nematicides, herbicides, biological pesticides and plant growth regulators, disease control agents containing nucleic acids as an active ingredient (WO 2014/062775), soil improvers, or fertilizing substances. As a method for using the compounds of the present invention and other agricultural chemicals by mixing, there may be mentioned a method of using the compounds of the present invention and other agricultural chemicals in one dosage form into which they are formulated, a method of using them in such a manner as to formulate each of them into separate dosage form and then mix the dosage forms immediately before use, a method of using them in such a manner as to formulate each of them into separate dosage form and then simultaneously use the dosage forms, or a method of using them in such a manner as to formulate each of them into separate dosage form and then use either one of them and thereafter use the other.

Specific components contained in the fungicides which can be used in combination with the compounds of the present invention are exemplified in the following Group b, including these salts, isomers and N-oxides. The known fungicides are not limited to these.

Group b:

b-1: Phenylamide-Based Fungicides

As phenylamide-based fungicides, there are [b-1.1]: benalaxyl, [b-1.2] benalaxyl-Mor kiralaxyl, [b-1.3] furalaxyl, [b-1.4] metalaxyl, [b-1.5] metalaxyl-Mor mefenoxam, [b-1.6] oxadixyl, [b-1.7] ofurace, and the like.

b-2: Karyokinesis and Cell Division Inhibitors

As karyokinesis and cell division inhibitors, there are [b-2.1] benomyl, [b-2.2]carbendazim, [b-2.3] fuberidazole, [b-2.4] thiabendazole, [b-2.5] thiophanate, [b-2.6]thiophanate-methyl, [b-2.7] diethofencarb, [b-2,8] zoxamide, [b-2.9] ethaboxam, [b-2.10] pencycuron, [b-2.11] fluopicolide, [b-2.12] phenamacril, and the like.

b-3: Succinate Dehydrogenase Inhibitors (SDHI Agent)

As succinate dehydrogenase inhibitors (SDHI agent), there are [b-3.1] benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14]oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid, and the like.

b-4: Quinone Outside Inhibitors (QoI Agent)

As quinone outside inhibitors (QoI agent), there are [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin, [b-4.8] flufenoxystrobin, [b-4.9] fluoxastrobin, [b-4.10] kresoxim-methyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19]triclopyricarb, [b-4.20] trifloxystrobin, and the like.

b-5: Quinone Inside Inhibitors (QiI Agent)

As quinone inside inhibitors (QiI agent), there are [b-5.1] cyazofamid, [b-5.2] amisulbrom, and the like.

b-6: Oxidative Phosphorylation Decoupling Inhibitors

As oxidative phosphorylation decoupling inhibitors, there are [b-6.1] binapacryl, [b-6.2] meptyldinocap, [b-6.3] dinocap, [b-6.4] fluazinam, and the like.

b-7: Quinone Outside Stigmaterin Binding Subsite Inhibitors (QoSI Agent)

As quinone outside stigmaterin binding subsite inhibitors (QoSIagent), there are [b-7.1] ametoctradin, and the like.

b-8: Amino Acid Biosynthesis Inhibitors

As amino acid biosynthesis inhibitors, there are [b-8.1] cyprodinil, [b-8.2] mepanipyrim, [b-8.3] pyrimethanil, and the like.

b-9: Protein Biosynthesis Inhibitors

As protein biosynthesis inhibitors, there are [b-9.1] streptomycin, [b-9.2] blasticidin-S, [b-9.3] kasugamycin, [b-9.4] oxytetracycline, and the like.

b-10: Signal Transduction Inhibitors

As signal transduction inhibitors, there are [b-10.1] fenpiclonil, [b-10.2] fludioxonil, [b-10.3] quinoxyfen, [b-10.4] proquinazid, [b-10.5] chlozolinate, [b-10.6]dimethachlone, [b-10.7] iprodione, [b-10.8] procymidone, [b-10.9] vinclozolin, and the like.

b-11: Lipid and Cell Membrane Biosynthesis Inhibitors

As lipid and cell membrane biosynthesis inhibitors, there are [b-11.1] edifenphos, [b-11.2] iprobenfos, [b-11.3] pyrazophos, [b-11.4] isoprothiolane, [b-11.5]biphenyl, [b-11.6] chloroneb, [b-11.7] dicloran, [b-11.8] quintozene, [b-11.9] tecnazene, [b-11.10] tolclofos-methyl, [b-11.11] echlomezol or etridiazole, [b-11.12] iodocarb, [b-11.13] propamocarb, [b-11.14] prothiocarb, and the like.

b-12: Demethylation Inhibitors (DMI Agent)

As demethylation inhibitors (DMI agent), there are [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36]triadimenol, [b-12.37] triflumizole, [b-12.38] triforine, [b-12.39] triticonazole, [b-12.40] mefentrifluconazole, [b-12.41] ipfentrifluconazole, and the like.

b-13: Amine-Based Fungicides

As amine-based fungicides, there are [b-13.1] aldimorph, [b-13.2] dodemorph, [b-13.3] fenpropimorph, [b-13.4] tridemorph, [b-13.5] fenpropidin, [b-13.6] piperalin, [b-13.7] spiroxamine, and the like.

b-14: 3-Ketoreductase Inhibitors in C4-Position Demethylation of Sterol Biosynthesis As 3-ketoreductase inhibitors in C4-position demethylation of sterol biosynthesis, there are [b-14.1] fenhexamid, [b-14.2] fenpyrazamine, and the like.

b-15: Squalene Epoxidase Inhibitors of Sterol Biosynthesis

As squalene epoxidase inhibitors of sterol biosynthesis, there are [b-15.1]pyributicarb, [b-15.2] naftifine, [b-15.3] terbinafine, and the like.

b-16: Cell Wall Biosynthesis Inhibitors

As cell wall biosynthesis inhibitors, there are [b-16.1] polyoxins, [b-16.2]dimethomorph, [b-16.3] flumorph, [b-16.4] pyrimorph, [b-16.5] benthiavalicarb, [b-16.6] benthivalicarb-isopropyl, [b-16.7] iprovalicarb, [b-16.8] mandipropamid, [b-17.9] valifenalate, and the like.

b-17: Melanine Biosynthesis Inhibitors

As melanine biosynthesis inhibitors, there are [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb, and the like.

b-18: Host Plant Resistance Inducers

As host plant resistance inducers, there are [b-18.1] acibenzolar-S-methyl, [b-18.2] probenazole, [b-18.3] tiadinil, [b-18.4] isotianil, [b-18.5] laminarin, and the like.

b-19: Dithiocarbamate-Based Fungicides

As dithiocarbamate-based fungicides, there are [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam, and the like.

b-20: Phthalimide-Based Fungicides

As phthalimide-based fungicides, there are [b-20.1] captan, [b-20.2] captafol, [b-20.3] folpet, [b-20.4] fluorofolpet, and the like.

b-21: Guanidine-Based Fungicides

As guanidine-based fungicides, there are [b-21.1] guazatine, [b-21.2]iminoctadine, [b-21.3] iminoctadine albesilate, [b-21.4] iminoctadine triacetate, and the like.

b-22: Multi-Site Contact Activity Type Ungicides

As multi-site contact activity type fungicides, there are [b-22.1] basic copper chloride (copper oxychloride), [b-22.2] copper(II) hydroxide, [b-22.3] basic copper sulfate (copper hydroxide sulfate), [b-22.4] organocopper compound, [b-22.5]dodecylbenzenesulfonic acid bisethylenediamine copper[II] complex salt (Dodecylbenzenesulphonic acid bisethylcnediamine copper[II] salt, DBEDC), [b-22.6] sulphur, [b-22.7] fluoroimide, [b-22.8] chlorothalonil, [b-22.9] dichlofluanid, [b-22.10] tolylfluanid, [b-22.11] anilazine, [b-22.12] dithianon, [b-22.13] chinomethionat or quinomethionate, [b-22.14] Extract from cotyledon of lupine seedling (BLAD), and the like.

b-23: Other Fungicides

As the other fungicides, there are [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] triphenyl tin acetate (fentin acetate), [b-23.8] triphenyltin chloride (fentin chloride), [b-23.9] triphenyltin hydroxide (fentin hydroxide), [b-23.10]oxolinic acid, [b-23.11] hymexazol, [b-23.12] octhilinone, [b-23.13] fosetyl, [b-23.14]phosphorous acid), [b-23.15] sodium phosphite, [b-23.16] ammonium phosphite, [b-23.17] potassium phosphite, [b-23.18] tecloftalam, [b-23.19] triazoxide,

[b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27]pyriofenone, [b-23.28] dodine, [b-23.29] flutianil, [b-23.30] ferimzone, [b-23.31]oxathiapiprolin, [b-23.32] tebufloquin, [b-23.33] picarbutrazox, [b-23.34] validamycins, [b-23.35] cymoxanil, [b-23.36] quinofumelin,

[b-23.37] a compound represented by Formula (s1)

[Chem. 120]

(s1)

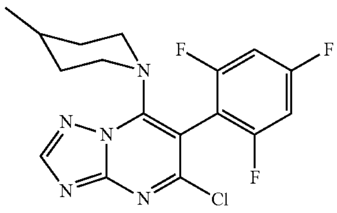

(see WO98/046607),

[b-23.38] a compound represented by Formula (s2)

[Chem. 121]

(s2)

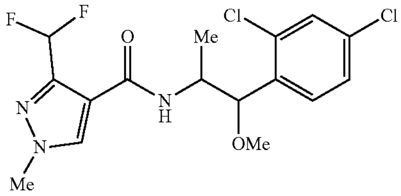

(see WO 08/148570),

[b-23.39] a compound represented by Formula (s3)

[Chem. 122]

(s3)

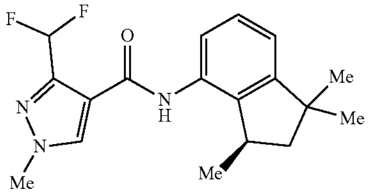

(see WO92/012970),

[b-23.40] a compound represented by Formula (s4)

[Chem. 123]

(s4)

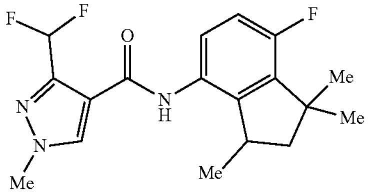

(see WO 12/084812),

[b-23.41] a compound represented by Formula (s5)

[Chem. 124]

(s5)

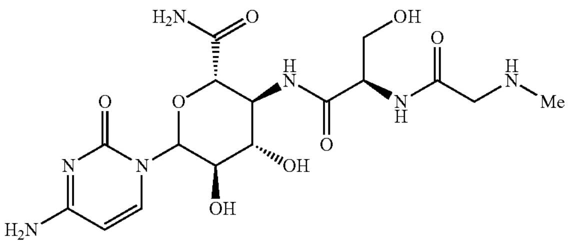

(gougerotiri),

[b-23.42] a compound represented by Formula (s6)

[Chem. 125]

(s6)

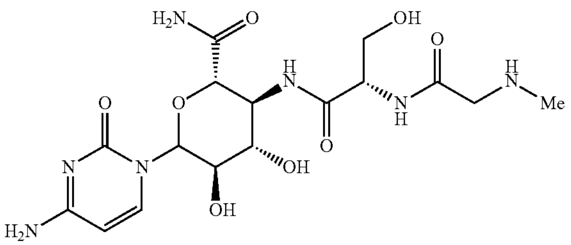

(ningnanmycin),

[b-23.43] a compound represented by Formula (s7)

[Chem. 126]

(s7)

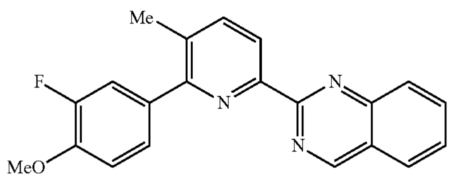

(see WO 10/136475),
[b-23.44] a compound represented by Formula (s8)
[Chem. 127]
(s8)
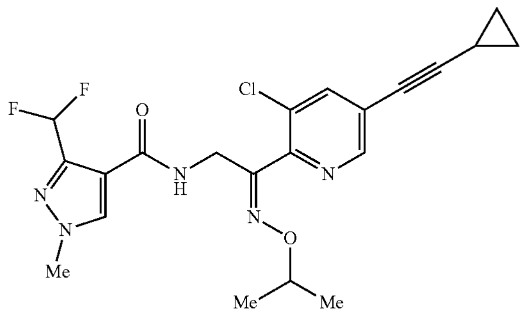
(see WO 14/010737),
[b-23.45] a compound represented by Formula (s9)
[Chem. 128]
(s9)
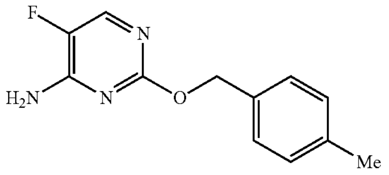
(see WO 11/085084),
[b-23.46] a compound represented by Formula (s10)
[Chem. 129]
(s10)
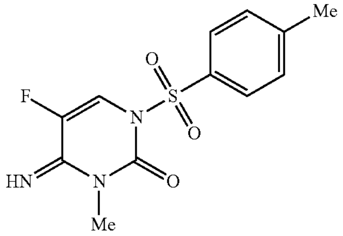
(see WO 11/137002),
[b-23.47] a compound represented by Formula (s11)
[Chem. 130]
(s11)
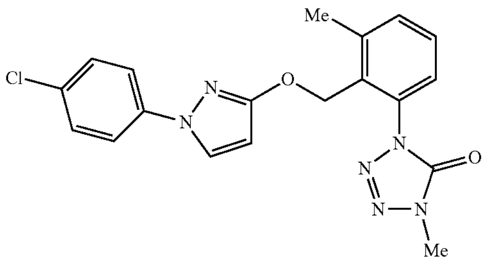
(see WO 13/162072),
[b-23.48] a compound represented by Formula (s12)
[Chem. 131]
(s12)
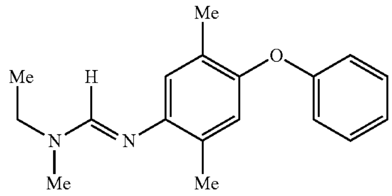
(see WO 08/110313),
[b-23.49] a compound represented by Formula (s13)
[Chem. 132]
(s13)
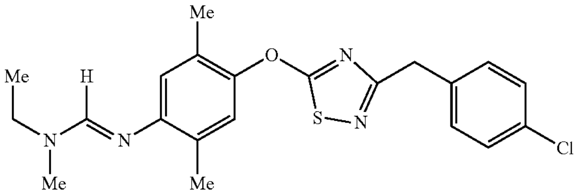
(see WO 09/156098),
[b-23.50] a compound represented by Formula (s14)
[Chem. 133]
(s14)
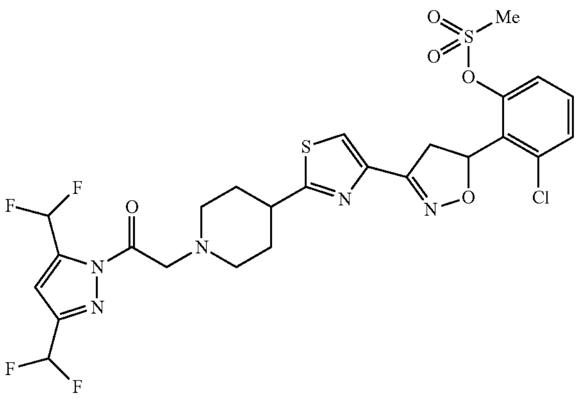

(see WO 12/025557),

[b-23.51] a compound represented by Formula (s15)

[Chem. 134]

(s15)

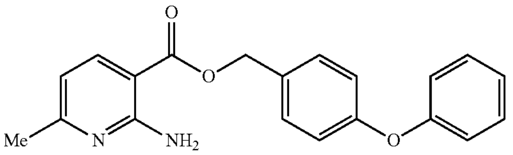

(see WO 14/006945),

[b-23.52] a compound represented by Formula (s16)

[Chem. 135]

(s16)

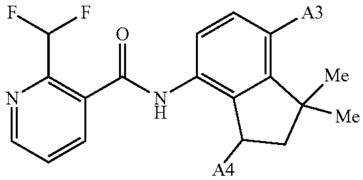

[wherein A3 represents a hydrogen atom, a halogen atom, a C1-C6 alkyl group, a C1-C6 haloalkyl group or a cyano group, A4 represents a hydrogen atom, a C1-C6 alkyl group, a C1-C6 haloalkyl group or a C3-C8 cycloalkyl group.] (see WO 14/095675),

[b-23.53] a compound represented by Formula (s17)

[Chem. 136]

(s17)

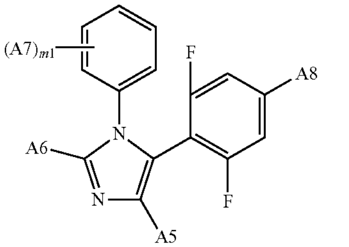

[wherein m1 represents an integer of 0 to 3, A5 and A6 each independently represents a halogen atom or a C1-C6 alkyl group, A7 and A8 each independently represents a halogen atom or a C1-C6 alkoxy group, and when m1 is 2 or more, the 2 or more of A7's each represents independent substituents, which may be the same as or different from each other.] (see WO 09/137538 and WO 09/137651),

[b-23.54] a compound represented by Formula (s18)

[Chem. 137]

(s18)

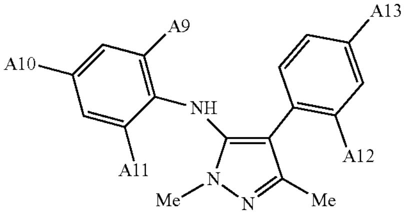

[wherein A9 and A10 each independently represents a hydrogen atom or halogen atom, A11 represents a halogen atom, A12 represents a halogen atom or a C1-C6 alkyl group, A13 represents a halogen atom, a cyano group, a C1-C6 alkyl group or a C1-C6 alkoxy group.] (see WO 12/031061),

[b-23.55] a compound represented by Formula (s19)

[Chem. 138]

(s19)

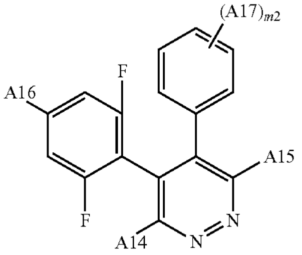

[wherein m2 represents an integer of 0 to 6, A14 and A15 each independently represents a halogen atom, a cyano group or C1-C6 alkyl group, A16 represents a hydrogen atom, a halogen atom or a C1-C6 alkoxy group, A17 represents a halogen atom or a C1-C6 alkoxy group, when m2 is 2 or more, the 2 or more A17's each represents independent substituents, which may be the same as or different from each other.] (see WO 05/121104),

[b-23.56] a compound represented by Formula (s20)

[Chem. 139]

(s20)

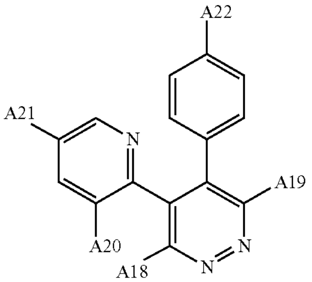

[wherein A18 and A19 each independently represents a halogen atom, a cyano group or a C1-C6 alkyl group, A20, A21 and A22 each independently represents a hydrogen atom, a halogen atom or a C1-C6 alkoxy group.] (see WO 07/066601),

[b-23.57] a compound represented by Formula (s21)

[Chem. 140]

(s21)

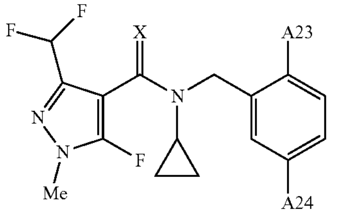

[wherein A23 and A24 each independently represents a hydrogen atom, a halogen atom, a C1-C6 alkyl group or a C3-C8 cycloalkyl group, X represents an oxygen atom or a sulfur atom.] (see WO 07/087906, WO 09/016220 and WO 10/130767),

[b-23.58] a compound represented by Formula (s22)

[Chem. 141]

(s22)

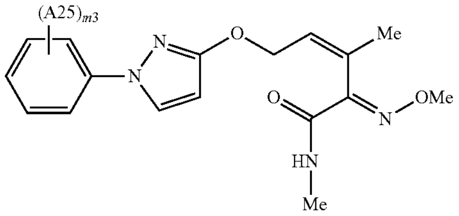

[wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group, when m3 is 2 or more, the 2 or more A25's each represent independent substituents, which may be the same as or different from each other.] (see WO 13/092224),

[b-23.59] a compound represented by Formula (s23)

[Chem. 142]

(s23)

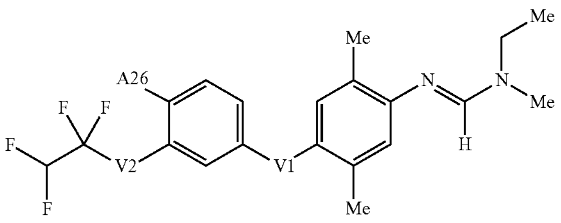

[wherein A26 represents a hydrogen atom or a halogen atom, V1 and V2 each independently represents an oxygen atom or a sulfur atom.] (see WO 12/025450),

[b-23.60] a compound represented by Formula (s24) or Formula (s25)

[Chem. 143]

(s24)

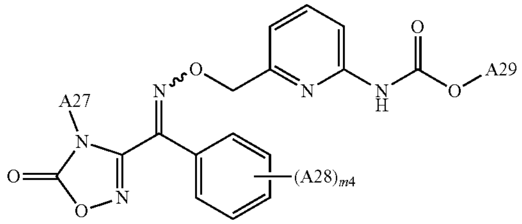

(s25)

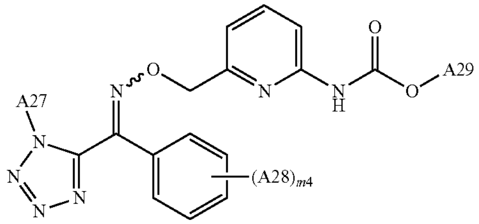

[wherein m4 represents an integer of 0 to 5, A27 represents a C1-C6 alkyl group, A28 represents a halogen atom, a cyano group, a C1-C6 alkyl group or a C1-C6 haloalkyl group, when m4 is 2 or more, the 2 or more A28's each represent independent substituents, which may be the same as or different from each other, and A29 represents a C1-C6 alkyl group, a C2-C6 alkenyl group or a C3-C6 alkynyl group.] (see WO 13/037717),

[b-23.61] a compound represented by Formula (s26) or Formula (s27)

[Chem. 144]

(s26)

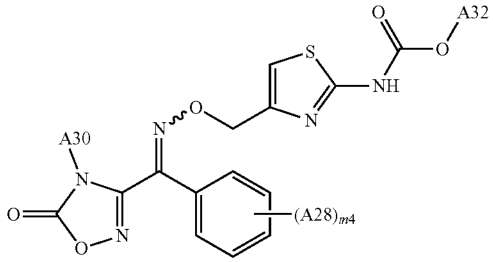

(s27)

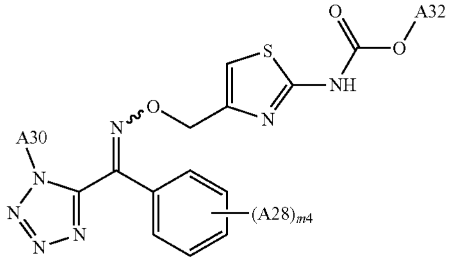

[wherein m5 represents an integer of 0 to 5, A30 represents a C1-C6 alkyl group, A31 represents a halogen atom, a cyano group, a C1-C6 alkyl group or a C1-C6 haloalkyl group, when m5 is 2 or more, the 2 or more A31 's each represent independent substituents, which may be the same as or different from each other, and A32 represents a C1-C6 alkyl group, a C2-C6 alkenyl group or a C3-C6 alkynyl group.] (see WO 13/037717),

[b-23.62] a compound represented by Formula (s28)

[Chem. 145]

(s28)

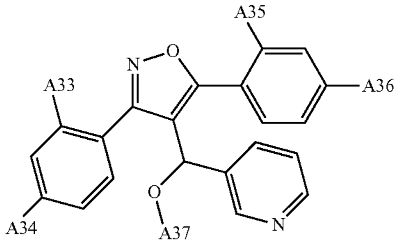

[wherein A33, A34, A35 and A36 each independently represents a hydrogen atom or a halogen atom, A37 represents a hydrogen-atom, an acetyl group or a benzoyl group.] (see WO 06/031631, WO 10/069882),

[b-23.63] a compound represented by Formula (s29)

[Chem. 146]

(s29)

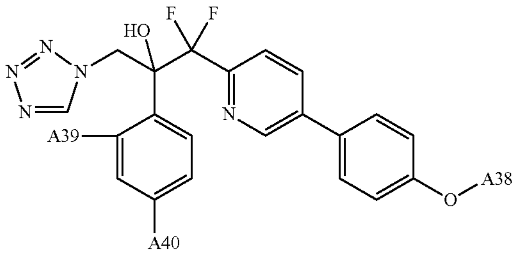

[wherein A38 represents a C1-C6 alkyl group or a C1-C6 haloalkyl group, A39 and A40 each independently represents a hydrogen atom or halogen atom.] (see WO 14/043376),

[b-23.64] a compound represented by Formula (s30)

[Chem. 147]

(s30)

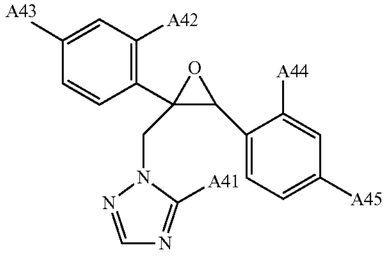

[wherein A41 represents a hydrogen atom, a sulfhydryl group (—SH), a thiocyanate group (—SCN) or a C1-C6 alkylthio group, A42, A43, A44 and A45 each independently represents a hydrogen atom or a halogen atom.] (see WO 09/077443),

[b-23.65] a compound represented by Formula (s31) or Formula (s32)

[Chem. 148]

(s31)

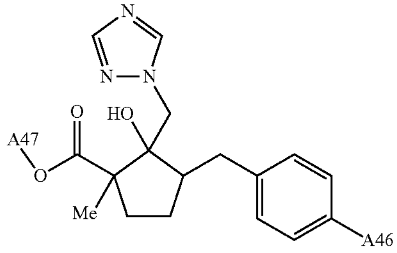

(s32)

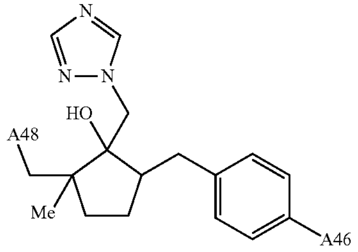

[wherein A46 represents a hydrogen atom or halogen atom, A47 represents a C1-C6 alkyl group, and A48 represents a halogen atom.] (see WO 11/070771),

[b-23.66] a compound represented by Formula (s33)

[Chem. 149]

(s33)

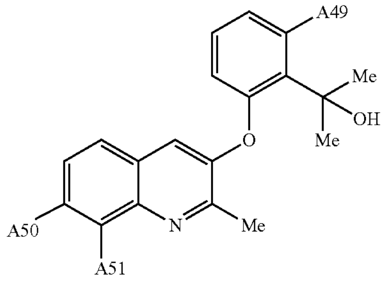

[wherein A49, A50 and A51 each independently represents a hydrogen atom or a halogen atom.] (see WO 11/081174), and the like.

Specific components contained in insecticides that can be used in combination with the compounds of the present invention are exemplified in the following Group c, including these salts, isomers and N-oxides. The known insecticides are not limited to these.

Group c:

c-1: Carbamate-Based Acetylcholine Esterase (AChE) Inhibitors

As carbamate-based acetylcholine esterase (AChE) inhibitors, there are [c-1.1]phosphocarb, [c-1.2] alanycarb, [c-1.3] butocarboxim, [c-1.4] butoxycarboxim, [c-1.5]thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12] carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20] oxamyl, [c-1.21] pirimicarb, [c-1.22] propoxur, [c-1.23] trimethacarb, [c-1.24] XMC (3,5-xylyl methylcarbamate), [c-1.25] allyxycarb, [c-1.26] aldoxycarb,

[c-1.27] bufencarb, [c-1.28] butacarb, [c-1.29]carbanolate, [c-1.30] metolcarb, [c-1.31] xylylcarb, [c-1.32] fenothiocarb, [c-1.33] xylylcarb, [c-1.34] bendiocarb, and the like.

c-2: Organic Phosphorus-Based Acetylcholine Esterase (AChE) Inhibitors

As organic phosphorus-based acetylcholine esterase (AChE) inhibitors, there are [c-2.1] acephate, [c-2.2] azamethiphos, [c-2.3] azinphos-methyl, [c-2.4]azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] O-ethyl O-4-nitrophenyl phenylphosphonothioate, [c-2.23] ethion, [c-2.24] ethoprophos, [c-2.25] famphur, [c-2.26] fenamiphos, [c-2.27] fenitrothion, [c-2.28] fenthion, [c-2.29] fosthiazate, [c-2.30] heptenophos, [c-2.31] isofenphos-methyl, [c-2.32] Isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63]triazophos, [c-2.64] trichlorfon, [c-2.65] vamidothion, [c-2.66] chlorothion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78]dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86]thionazin, [c-2.87] fosthietan, and the like.

c-3: GABAergic Chlorine Ion Channel Blockers

As GABAergic chlorine ion channel blockers, there are [c-3.1] chlordane, [c-3.2] endosulfan, [c-3.3] lindane, [c-3.4] dienochlor, [c-3.5] ethiprole, [c-3.6] fipronil, [c-3.7] acetoprole, and the like.

c-4: Sodium Channel Modulators

As sodium channel modulators, there are [c-4.1] acrinathrin, [c-4.2] allethrin [(1R)-isomer], [c-4.3] bifenthrin, [c-4.4] bioallethrin, [c-4.5] bioallethrin S-cyclo-pentenyl isomer, [c-4.6] bioresmethrin, [c-4.7] cycloprothrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypennmethrin, [c-4.14] alpha-cypermethrin, [c-4.15] beta-cypermethrin, [c-4.16] theta-cypennethrin, [c-4.17] zeta-cypermethrin, [c-4.18] cyphenothrin [(1R)-trans-isomer], [c-4.19] deltamethrin, [c-4.20] empenthrin [(EZ)-(1R)-isomer], [c-4:21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] pennethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin [(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzeneacetate), [c-4.47] biopermethrin, [c-4.48] furamethrin, [c-4.49] profluthrin, [c-4.50] flubrocythrinate, [c-4.51] dimefluthrin, [c-4.52] DDT (dichlorodiphenyl-trichloroethane), [c-4.53] methoxychlor, [c-4.54] phenothrin, [c-4.55] fluvalinate, and the like.

c-5: Nicotinic Acetylcholine. Receptor (nAChR) Competitive Modulators

As nicotinic acetylcholine receptor (nAChR) competitive modulators, there are [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8] nicotine, [c-5.9]nicotine sulfate, [c-5.10] sulfoxaflor, [c-5.11] flupyradifurone, [c-5.12] triflumezopyrim, and the like.

c-6: Nicotinic Acetylcholine Receptor (nAChR) Allosteric Modulators

As nicotinic acetylcholine receptor (nAChR) allosteric modulators, there are [c-6.1] spinosad, [c-6.2] spinetoram, and the like.

c-7: Glutamate-Gated Chloride Channel (GluCl) Allosteric Modulators

As glutamate-gated chloride channel (GluCl) allosteric modulators, there are [c-7.1] abamectin, [c-7.2] emamectin benzoate, [c-7.3] lepimectin, [c-7.4] milbemectin, and the like.

c-8: Juvenile Hormone Analogues

As juvenile hormone analogues, there are [c-8.1] hydroprene, [c-8.2] kinoprene, [c-8.3] methoprene, [c-8.4] fenoxycarb, [c-8.5] pyriproxyfen, and the like.

c-9: Nonspecific (Multisite) Inhibitors

As nonspecific (multisite) inhibitors, there are [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] antimony potassium tartrate (tartar emetic), [c-9.10] dazomet, [c-9.11] metam, [c-9.12] carbam sodium salt (metham sodium), and the like.

c-10: Chordotonal Organ TRPV Channel Modulators

Chordotonal organ TRPV channel modulators, there are [c-10.1] pymetrozine, [c-10.2] Pyrifluquinazon, and the Like.

c-11: Acari Growth Inhibitors

As acari growth inhibitors, there are [c-11.1] clofentezine, [c-11.2] diflovidazin, [c-11.3] hexythiazox, [c-11.4] etoxazole, and the like.

c-12: Mitochondrial ATP Synthase Inhibitors

As mitochondrial ATP synthase inhibitors, there are [c-12.1] diafenthiuron, [c-12.2] azocyclotin, [c-12.3] cyhexatin, [c-12.4] fenbutatin oxide, [c-12.5] propargite, [c-12.6] tetradifon, and the like.

c-13: Unicouplers of Oxidative Phosphorylation Via Disruption of Proton Gradient As unicouplers of oxidative phosphorylation via disruption of proton gradient, there are [c-13.1] chlorfenapyl, [c-13.2] DNOC (dinitro-ortho-cresol), [c-13.3] binapacryl, [c-13.4] sulfluramid, and the like.

c-14: Nicotinic Acetylcholine Receptor (nAChR) Channel Blockers

As nicotinic acetylcholine receptor (nAChR) channel blockers, there are [c-14.1] bensultap, [c-14.2] cartap hydrochloride, [c-14.3] thiocyclam, [c-14.4] monosultap, and the like.

c-15: Chitin Biosynthesis Inhibitors Type 0

As chitin biosynthesis inhibitors type 0, there are [c-15.1] bistrifluron, [c-15.2] chlorfluazuron, [c-15.3] diflubenzuron,

[c-15.4] flucycloxuron, [c-15.5] flufenoxuron, [c-15.6] hexaflumuron, [c-15.7] lufenuron, [c-15.8] novaluron, [c-15.9] noviflumuron, [c-15.10] teflubenzuron, [c-15.11] triflumuron, and the like.

c-16: Chitin Biosynthesis Inhibitor Type 1

As chitin biosynthesis inhibitor type 1, there are [c-16.1] buprofezin, and the like.

c-17: Diptera Insect Molting Inhibitors

As diptera insect molting inhibitors, there are [c-17.1] cyromazine, and the like.

c-18: Molting Hormone (Ecdysone) Receptor Agonists

As molting hormone (ecdysone) receptor agonists, there are [c-18.1]chromafenozide, [c-18.2] halofenozide, [c-18.3] methoxyfenozide, [c-18.4] tebufenozide, and the like.

c-19: Octopamine Receptor Agonists

As octopamine receptor agonists, there are [c-19.1] amitraz, and the like.

c-20: Mitochondrial electron transport system complex III inhibitors

As mitochondrial electron transport system complex III inhibitors, there are [c-20.1] hydramethylnon, [c-20.2] acequinocyl, [c-20.3] fluacrypyrim, [c-20.4] bifenazate, and the like.

c-21: Mitochondrial Electron Transport System Complex I Inhibitors (METI)

As mitochondrial electron transport system complex I inhibitors (METI), there are [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone, and the like.

c-22: Voltage-Gated Sodium Channel Blockers

As voltage-gated sodium channel blockers, there are [c-22.1] indoxacarb, [c-22.2] metaflumizone, and the like.

c-23: Acetyl CoA Carboxylase Inhibitors

As acetyl CoA carboxylase inhibitors, there are [c-23.1] spirodiclofen, [c-23.2] spiromesifen, [c-23.3] spirotetramat, and the like.

c-24: Mitochondrial Electron Transport System Complex IV Inhibitors

As mitochondrial electron transport system complex IV inhibitors, there are [c-24.1] aluminum phosphide, [c-24.2] calcium phosphide, [c-24.3] hydrogen phosphide (phosphine), [c-24.4] zinc phosphide, [c-24.5] calcium cyanide, [c-24.6] sodium cyanide, [c-24.7] potassium cyanide, and the like.

c-25: Mitochondrial Electron Transport System Complex II Inhibitors

As mitochondrial electron transport system complex II inhibitors, there are [c-25.1] cyenopyrafen, [c-25.2] cyflumetofen, [c-25.3] pyflubumide, and the like.

c-26: Ryanodine Receptor Modulators

As ryanodine receptor modulators, there are [c-26.1] chlorantraniliprole, [c-26.2] cyantraniliprole, [c-26.3] flubendiamide, and the like.

c-27: Target Site-Unspecified Chordotonal Organ Modulators

As target site-unspecified chordotonal organ modulators, there are [c-27.1] flonicamid, and the like.

c-28: Other Insecticideinsecticides

As the other insecticides, there are [c-28.1] azadirachtin, [c-28.2] benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyliodide, [c-28.14]karanjin, [c-28.15] mercury chloride, [c-28.16] methyl isothiocyanate, [c-28.17]pentachlorophenol, [c-28.18] phosphine, [c-28.19] piperonyl butoxide (piperonylbutoxide), [c-28.20] polynactin complex (polynactins), [c-28.21] sabadilla, [c-28.22] sulcofuron salt (sulcofuron-sodium), [c-28.23] tribufos, [c-28.24] aldrin, [c-28.25] amidithion, [c-28.26] amidothioate, [c-28.27] aminocarb, [c-28.28] amiton, [c-28.29] aramite, [c-28.30] athidathion, [c-28.31] azothoate, [c-28.32] barium polysulphide, [c-28.33] benclothiaz, [c-28.34]5-(1,3-benzodioxol-5-yl)-3-hexylcyclohexa-2-enone, [c-28.35]1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] hydrochloric acid levamisol (levamisol), [c-28.49] amidoflumet, [c-28.50]pyrafluprole, [c-28.51] pyriprole, [c-28.52] tralopyril, [c-28.53] flupyrazofos, [c-28.54] diofenolan, [c-28.55] chlorobenzilate, [c-28.56] flufenzine, [c-28.57] benzomate, [c-28.58] flufenerim, [c-28.59] albendazole, [c-28.60] oxibendazole, [c-28.61] fenbendazole, [c-28.62] metam-sodium, [c-28.63] 1,3-dichloropropene, [c-28.64] flometoquin, [c-28.65] cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl)ether, [c-28.72] 1-bromo-2-chloroethane, [c-28.73]3-bromo-1-chloroprop-1-ene, [c-28.74] bromocyclen, [c-28.75] carbon disulfide, [c-28.76] carbon tetrachloride (tetrachloromethane), [c-28.77] nemadectin, [c-28.78] cymiazole, [c-28.79] calcium polysulfide, [c-28.80] cytokinin, [c-28.81]2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] insect flower (pyrethrum), [c-28.89] rape seed oil, [c-28.90] soybean lecithin, [c-28.91] starch, [c-28.92] hydroxypropyl starch (hydroxypropylstarch), [c-28.93] fatty acid glyceride (decanoyloctanoylglycerol), [c-28.94] propylene glycol monofatty acid ester (propylene glycol fatty acid ester), [c-28.95] diatomaceous earth (diatomite), [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107] cycloxaprid, [c-28.108] fluensulfone, [c-28.109] TPIC (tripropyl isocyanurate), [c-28.110] D-D (1,3-Dichloropropene), [c-28.111] peroxocarbonate, [c-28.112] MB-599 (verbutin), [c-28.113] bis(2,3,3,3-tetrachloropropyl) ether, [c-28.114] DCIP (bis(2-chloro-1-methylethyl) ether), [c-28.115] ENT-8184 (N-(2-Ethylhexyl)bicyclo[2.2.1]hept-5-ene-2,3-dicarboximide), [c-28.116] Bayer 22408 (O,O-diethyl O-naphthalimidophosphorothioate), [c-28.117] Bayer 32394 (tris(1-dodecyl-3-methyl-2-phenylbenzimidazolium)hexacyanoferrate),

[c-28.118] a compound represented by Formula (s34)

[Chem. 150]

(s34)

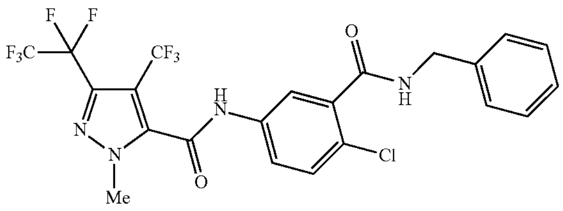

(see WO 10/051926),

[c-28.119] a compound represented by Formula (s35)

[Chem. 151]

(s35)

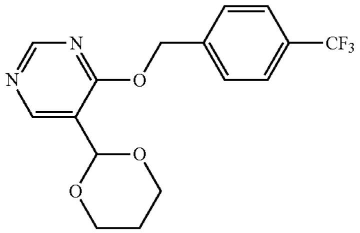

(see WO 13/115391),

[c-28.120] a compound represented by Formula (s36)

[Chem. 152]

(s36)

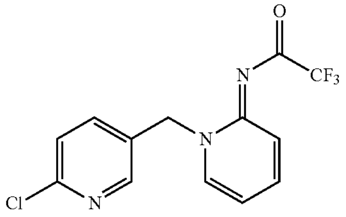

(see WO 12/029672),

[c-28.121] a compound represented by Formula (s37)

[Chem. 153]

(s37)

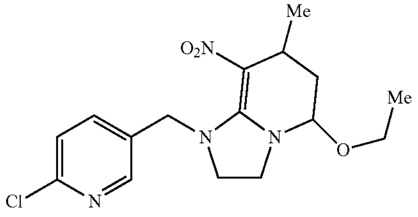

(see WO 06/056108),

[c-28.122] a compound represented by Formula (s38)

[Chem. 154]

(s38)

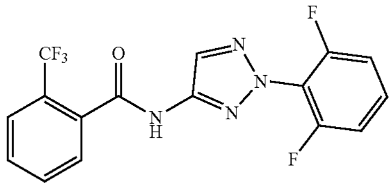

(see WO 14/053450, and WO 15/144683),

[c-28.123] a compound represented by Formula (s39)

[Chem. 155]

(s39)

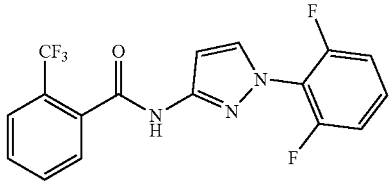

(see WO 14/053450, and WO 15/144683),

[c-28.124] a compound represented by Formula (s40)

[Chem. 156]

(s40)

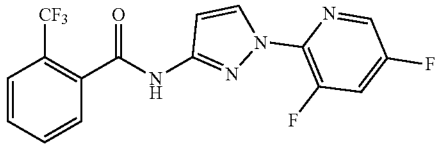

(see WO 14/053450, and WO 15/144683),

[c-28.125] a compound represented by Formula (s41)

[Chem. 157]

(s41)

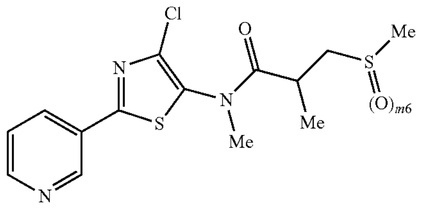

[wherein m6 represents an integer of 0 to 2.] (see WO 10/129497),

[c-28.126] a compound represented by Formula (s42)

[Chem. 158]

(s42)

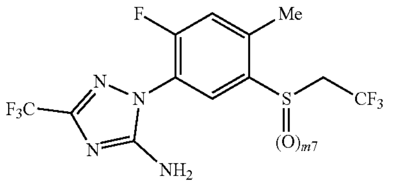

[wherein m7 represents an integer of 0 to 2.] (see WO 11/152320),

[c-28.127] a compound represented by Formula (s43)

[Chem. 159]

(s43)

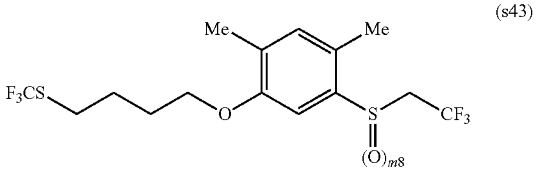

[wherein m8 represents an integer of 0 to 2.] (see JP Hei27-160813A),

[c-28.128] a compound represented by Formula (s44)

[Chem. 160]

(s44)

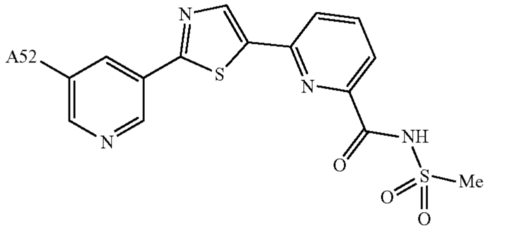

[wherein A52 represents a hydrogen atom or a fluorine atom;] (see WO 11/134964, and WO 14/005982),

[c-28.129] a compound represented by Formula (s45)

[Chem. 161]

(s45)

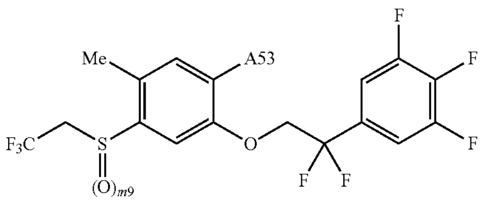

[wherein m9 represents an integer of 0 to 2, and A53 represents a fluorine atom or a chlorine atom.] (see WO 15/025826),

[c-28.130] a compound represented by Formula (s46)

[Chem. 162]

(s46)

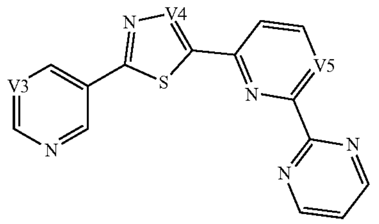

[wherein V3 represents a nitrogen atom, a carbon atom or C—F, and V4 and V5 each independently represents a nitrogen atom or a carbon atom.] (see WO 11/134964, and WO 14/005982),

[c-28.131] a compound represented by Formula (s47)

[Chem. 163]

(s47)

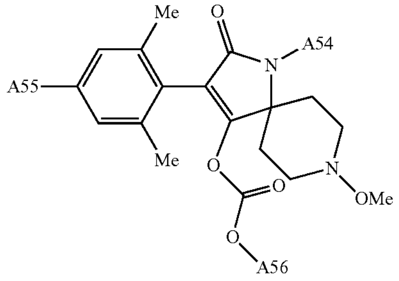

[wherein A54 represents a hydrogen atom, a methyl group, a methoxy group or an ethoxy group, A55 represents a chlorine atom or a methyl group, and A56 represents a methyl group or an ethyl group:] (see WO 09/049851),

[c-28.132] a compound represented by Formula (s48)

[Chem. 164]

(s48)

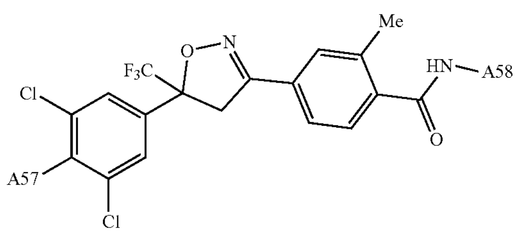

[wherein A57 represents a hydrogen atom, a fluorine atom or a chlorine atom, A58 represents one kind of a partial structure selected from the group consisting of

[Chem. 165]

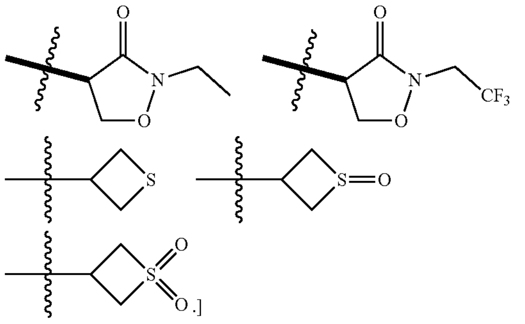

(see WO 11/067272),

[c-28.133] a compound represented by Formula (s49)

[Chem. 166]

(s49)

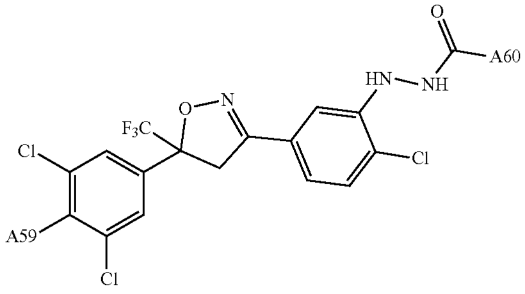

[wherein A59 represents a hydrogen atom, a fluorine atom or a chlorine atom, A60 represents a partial structure selected from the group consisting of

[Chem. 167]

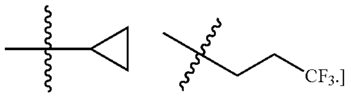

(see WO 10/090344),

[c-28.134] a compound represented by Formula (s50)

[Chem. 168]

(s50)

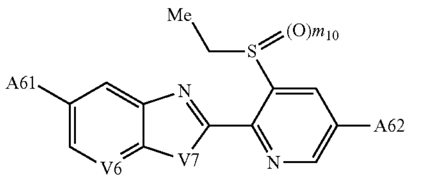

[wherein m10 represents an integer of 0 to 2, A61 represents a trifluoromethyl group, a trifluoromethylthio group, a trifluoromethylsulfinyl group or a trifluoromethylsulfonyl group, A62 represents a hydrogen atom or a trifluoromethyl group, V6 represents a nitrogen atom or a carbon atom, and V7 represents an oxygen atom or an N-methyl group.] (see WO 14/104407),

[c-28.135] a compound represented by Formula (s51)

[Chem. 169]

(s51)

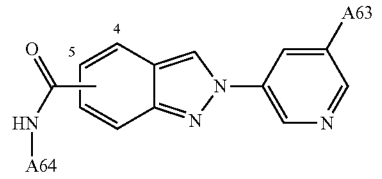

[wherein A63 represents a hydrogen atom or a fluorine atom, an amide group is bonded to the 4-position or 5-position, and A64 represents a partial structure selected from the group consisting of

[Chem. 170]

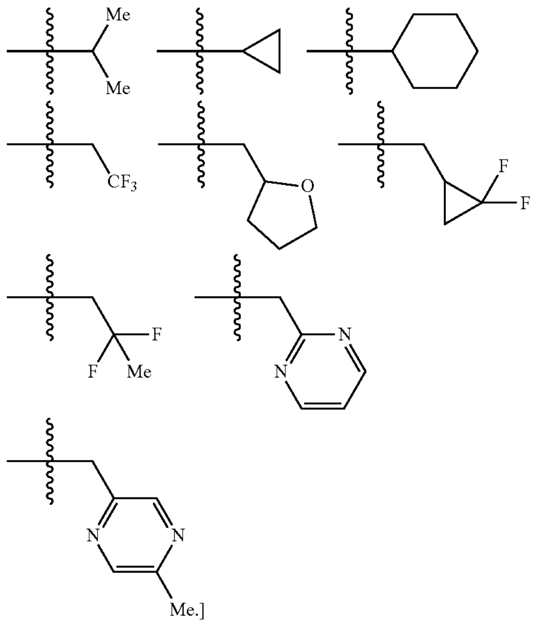

(see WO 15/038503, WO 16/144351, and WO 16/144678),

[c-28.136] a compound represented by Formula (s52)

[Chem. 171]

(s52)

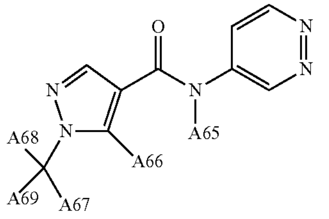

[wherein A65 represents a hydrogen atom, a C1-C6 alkyl group or a C1-C6 haloalkyl group, A66 represents a hydrogen atom, a halogen atom or a C1-C6 alkyl group, A67 and A68 each independently represents a hydrogen atom, a C1-C6 alkyl group optionally substituted with a cyano group, an alkyl group optionally substituted with a methoxy group, an alkyl group optionally substituted with an ethoxy group or a C3-C8 cycloalkyl group, and A69 represents a hydrogen atom, a cyano group, a C1-C6 haloalkyl group optionally substituted with a cyano group, a C1-C6 alkyl group or a C3-C8 cycloalkyl group.] (see WO 12/143317, and WO 16/016369),

[c-28.137] a compound represented by Formula (s53) or Formula (s54)

[Chem. 172]

(s53)

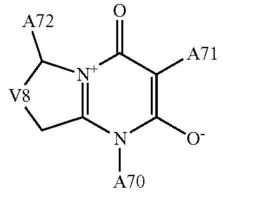

(s54)

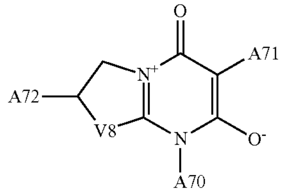

[wherein A70 represents a methyl group, an ethyl group, an isopropyl group, a 2,2,2-trifluoroethyl group or a phenyl group, A71 represents a partial structure selected from the group consisting of

[Chem. 173]

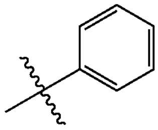

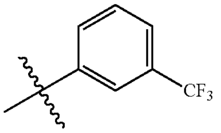

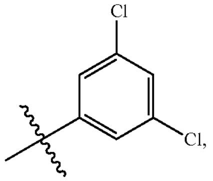

A72 represents a partial structure selected from the group consisting of

[Chem. 174]

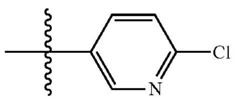

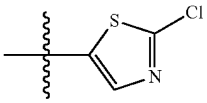

and V8 represents an oxygen atom, a sulfur atom, $—CH_2—$ or $—CH_2CH—$.] (see WO 14/167084, and WO 16/055431),

[c-28.138] a compound represented by Formula (s55)

[Chem. 175]

(s55)

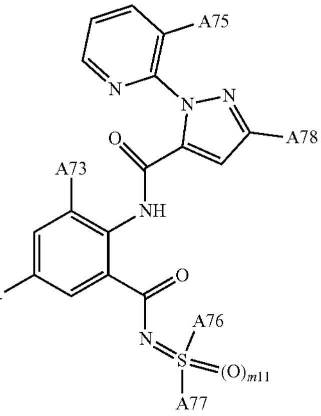

[wherein m11 represents an integer of 0 to 1, A73 represents a chlorine atom, a bromine atom, a methyl group or a trifluoromethyl group, A74 represents a hydrogen atom, a chlorine atom, a bromine atom, a cyano group or a trifluoromethyl group, A75 represents a hydrogen atom, a chlorine atom or a bromine atom, A76 and A77 each independently represents a C1-C6 alkyl group or a C3-C8 cycloalkyl group, and A78 represents a chlorine atom, a bromine atom, a cyano group, a nitro group, a difluoromethyl group or a trifluoromethyl group.] (see WO 13/024009),

[c-28.139] a compound represented by Formula (s56)

[Chem. 176]

(s56)

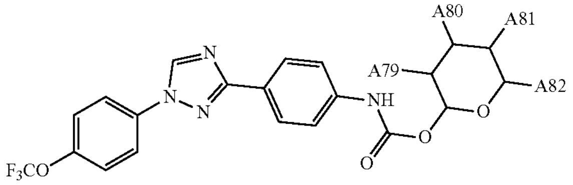

[wherein A79, A80, A81 and A82 each independently represents a hydrogen atom, a halogen atom, a C1-C6 alkyl group, a C1-C6 haloalkyl group, a C1-C6 alkoxy group or a C3-C8 cycloalkoxy group.] (see WO 12/027521),

[c-28.140] a compound represented by Formula (s57)

[Chem. 177]

(s57)

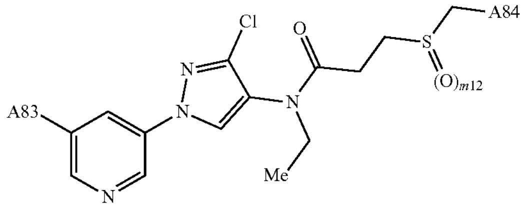

[wherein m12 represents an integer of 0 to 2, A83 represents a hydrogen atom or a fluorine atom, A84 represents a partial structure selected from the group consisting of

[Chem. 178]

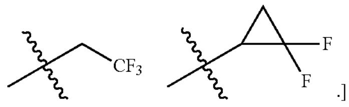

.]

(see WO 13/162715),

[c-28.141] acynonapyr,

[c-28.142] a compound represented by Formula (s59)

[Chem. 179]

(s59)

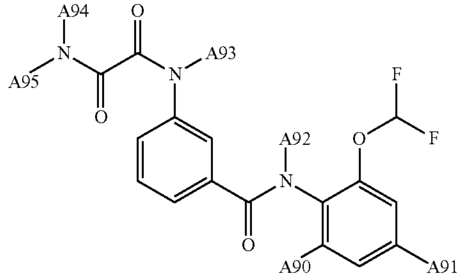

[A90 represents a halogen atom, a C1-C6 alkyl group or a C1-C6 haloalkyl group, A91 represents a C1-C6 haloalkyl group, A92 and A93 each independently represents a hydrogen atom, a C1-C6 alkyl group, an acetyl group, a propionoyl group, a methanesulfonylethyl group, a methoxycarbonyl group or an ethoxycarbonyl group, and A94 and A95 each independently represents a hydrogen atom, a C1-C6 alkyl group or a C1-C6 haloalkyl group.] (see WO 12/164698), and the like.

A mixing ratio of the compound(s) of the present invention and a pest control agent is not particularly limited as long as the effects are developed, and the pest control agent is usually used in a weight ratio of 0.001 to 1,000 relative to that of the compound(s) of the present invention, and preferably a ratio of 0.01 to 100.

EXAMPLES

In the following, the present invention will be shown in more detail by referring to Synthetic Examples, Reference Examples and Test Examples, but the present invention is not limited by these.

Synthetic Example 1

Step 1: Synthesis of 6-(2,6-difluorophenyl)-5-(thiophen-2-yl)-3,4-dihydropyridine 2(1H)-one

[Chem. 180]

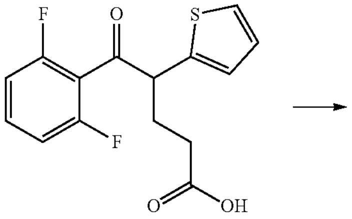

-continued

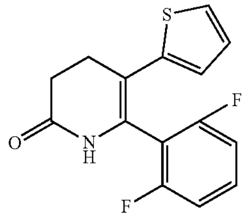

To 8.64 g of 5-(2,6-difluorophenyl)-5-oxo-4-(thiophen-2-yl)pentanoic acid obtained in Reference Example 3 were added 107.31 g of ammonium acetate and 43 ml of acetic acid, and the mixture was stirred at 100° C. for 4 hours. After cooling to room temperature, water and ethyl acetate were added to the reaction mixture and the liquids were separated. Water was added to the obtained organic layer, then, the mixture was neutralized by adding sodium carbonate. After separating the liquids to the organic layer and the aqueous layer, the obtained organic layer was washed with saturated brine, and dried over magnesium sulfate. After distilling off the solvent under reduced pressure, the obtained residue was purified by silica gel column chromatography. The title compound was obtained as 4.98 g of dark brown solid.

$^1$H-NMR ($CDCl_3$) δ: 7.42 (1H, m), 7.06 (1H, m), 6.97 (2H, m), 6.86 (2H, m), 6.77 (1H, m), 2.99 (2H, m), 2.72 (2H, m).

Step 2: Synthesis of 6-(2,6-difluorophenyl)-1-ethyl-5-(thiophen-2-yl)-3,4-dihydropyridin-2(1H)-one (Compound No.: 2)

[Chem. 181]

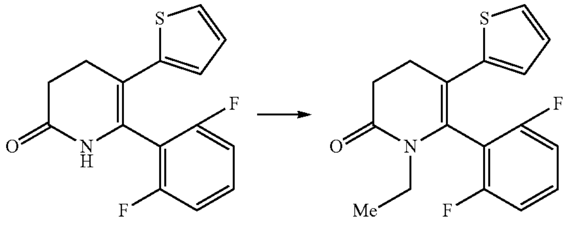

20 ml of DMF containing 2.00 g of 6-(2,6-difluorophenyl)-5-(thiophen-2-yl)-3,4-dihydropyridine 2(1-H)-one, 1.65 ml of ethyl iodide and 6.71 g of cesium carbonate was stirred at 50° C. for 3 hours. After cooling the mixture to room temperature, water and ethyl acetate were added to the reaction mixture and the liquids were separated. The obtained organic layer was successively washed with an aqueous sodium thiosulfate solution and saturated brine, and dried over magnesium sulfate. After the solvent was distilled off under reduced pressure, the obtained residue was purified by silica gel column chromatography. The title compound was obtained as 1.92 g of brown oily product.

Synthetic Example 2

Synthesis of 6-(2,6-difluorophenyl)-1-ethyl-5-(thiophen-2-yl)pyridin-2(1H)-one (Compound No.: 5)

[Chem. 182]

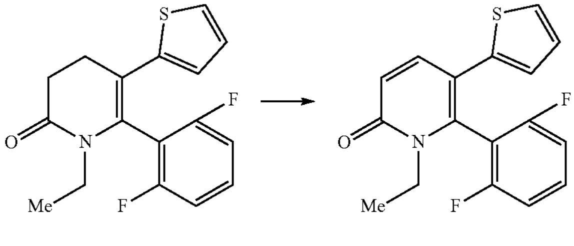

To 15 ml of a dichloromethane solution containing 520 mg of 6-(2,6-difluorophenyl)-1-ethyl-5-(thiophen-2-yl)-3,4-dihydropyridin-2(1H)-one was added 7.08 g of manganese dioxide, and the mixture was stirred under reflux by heating for 16 hours. 3.54 g of manganese dioxide was further added and the resulting mixture was stirred under reflux by heating for 6 hours. After cooling the mixture to room temperature, the reaction mixture was filtered through Celite, and the residue was washed with ethyl acetate. After the solvent was distilled off under reduced pressure, the obtained residue was purified by silica gel column chromatography. The title compound was obtained as 212 mg of a white solid.

Synthetic Example 3

Synthesis of 5-(5-chlorothiophen-2-yl)-6-(2,6-difluorophenyl)-1-ethylpyridin-2(1H)-one (Compound No.: 6)

[Chem. 183]

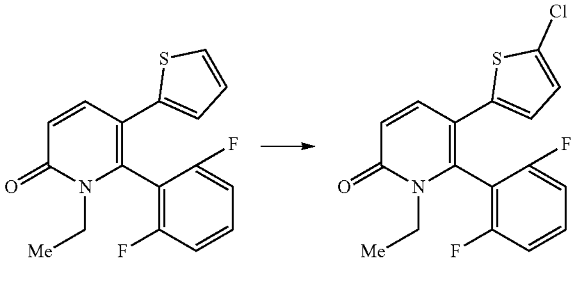

3 ml of a DMF solution containing 85 mg of 6-(2,6-difluorophenyl)-1-ethyl-5-(thiophen-2-yl)pyridin-2(1H)-one and 39 mg of N-chlorosuccinimide was stirred at 80° C. for 2 hours. After cooling the mixture to room temperature, water and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography, and then the precipitates were washed with a solution in which diisopropyl ether and hexane had been mixed. The title compound was obtained as 66 mg of a white solid.

Synthetic Example 4

Synthesis of 3-chloro-5-(5-chlorothiophen-2-yl)-6-(2,6-difluorophenyl)-1-ethylpyridin-2(1H)-one (Compound No.: 7)

[Chem. 184]

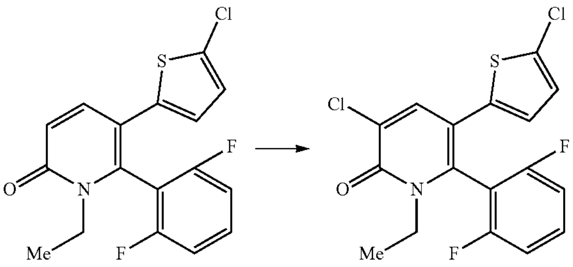

3 ml of a DMF solution containing 97 mg of 5-(5-chlorothiophen-2-yl)-6-(2,6-difluorophenyl)-1-ethylpyridin-2(1H)-one and 41 mg of N-chlorosuccinimide was stirred at 80° C. for 2 hours. 21 mg of N-chlorosuccinimide was further added, and the resulting mixture was stirred at 120° C. for 5 hours. After cooling the mixture to room temperature, water and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 32 mg of a white solid.

Synthetic Example 5

Step 1: Synthesis of 2-chloro-2-(2,6-difluorophenyl)-4,5-dihydro-[3,3'-bipyridin]-6(1H)-one

[Chem. 185]

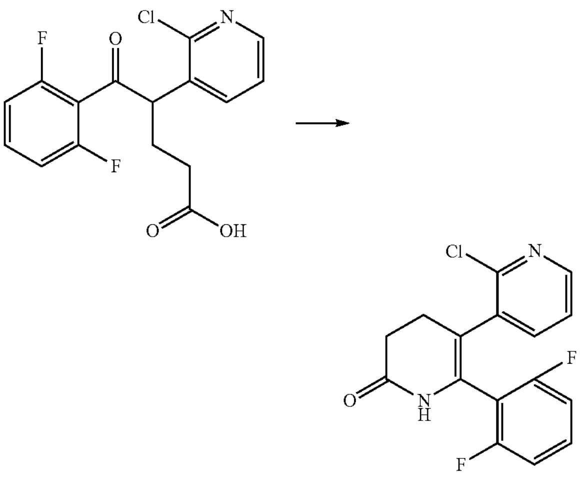

To 280 mg of 4-(2-chloropyridin-3-yl)-5-(2,6-difluorophenyl)-5-oxopentanoic acid obtained in Reference Example 6 were added 2.80 g of ammonium acetate and 5 ml of acetic acid, and the mixture was stirred at 100° C. for 5 hours. After cooling the mixture to room temperature, water and ethyl acetate were added to the reaction mixture and the liquids were separated. Water was added to the obtained organic layer, and then, the mixture was neutralized by adding potassium carbonate. After separating the liquids to the organic layer and the aqueous layer, the obtained organic layer was successively washed with water and saturated brine, and dried over sodium sulfate. After the solvent was distilled off under reduced pressure, the obtained residue was purified by silica gel column chromatography. The title compound was obtained as 39.5 mg of a brown solid.

$^1$H-NMR ($CDCl_3$) δ: 8.21 (1H, dd, J=4.7, 1.8 Hz), 7.34 (1H, dd, J=7.6, 1.8 Hz), 7.26-7.23 (1H, m), 7.02 (1H, dd, J=7.6, 4.7 Hz), 6.83-6.81 (3H, m), 3.15-2.65 (4H, m).

Step 2: Synthesis of 2-chloro-2-(2,6-difluorophenyl)-1-ethyl-4,5-dihydro-[3,3'-bipyridin]-6(1H)-one

[Chem. 186]

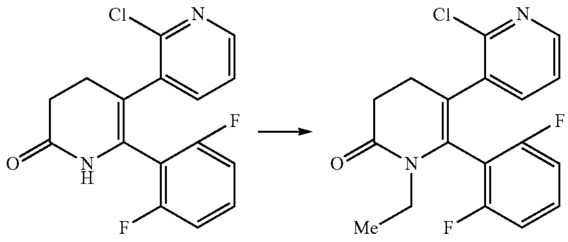

3 ml of DMF containing 39.5 mg of 2-chloro-2-(2,6-difluorophenyl)-4,5-dihydro-[3,3'-bipyridin]-6(1H)-one, 29.3 μl of ethyl iodide and 120.2 mg of cesium carbonate was stirred at 60° C. for 3 hours. After cooling the mixture to room temperature, water and ethyl acetate were added to the reaction mixture and the liquids were separated. The obtained organic layer was successively washed with water and saturated brine, and dried over sodium sulfate. After the solvent was distilled off under reduced pressure, the obtained residue was purified by silica gel column chromatography. The title compound was obtained as 37.5 mg of a pale yellow solid.

$^1$H-NMR ($CDCl_3$) δ: 8.17 (1H, dd, J=4.9, 1.8 Hz), 7.37-7.35 (1H, m), 7.24-7.21 (1H, m), 6.99 (1H, dd, J=7.6, 4.9 Hz), 6.82-6.77 (2H, m), 3.52-3.46 (1H, m), 3.41-3.33 (1H, m), 2.92-2.83 (2H, m), 2.75-2.69 (1H, m), 2.62-2.56 (1H, m), 0.99 (3H, t, J=7.2 Hz).

Synthetic Example 6

Synthesis of 2-chloro-2-(2,6-difluorophenyl)-1-ethyl-[3,3'-bipyridin]-6(1H)-one (Compound No.: 17)

[Chem. 187]

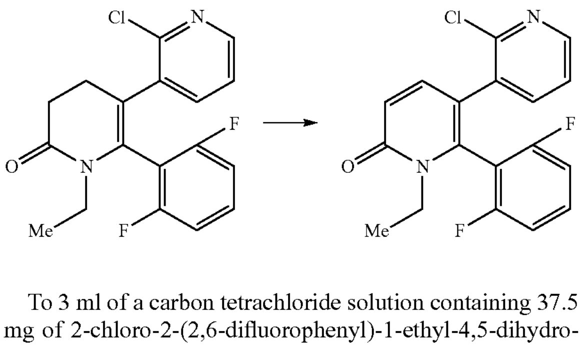

To 3 ml of a carbon tetrachloride solution containing 37.5 mg of 2-chloro-2-(2,6-difluorophenyl)-1-ethyl-4,5-dihydro-[3,3'-bipyridin]-6(1H)-one were added 20.1 mg of N-bromosuccinimide and 1.8 mg of azobisisobutyronitrile, and the mixture was stirred at 80° C. for 1 hour. After cooling the mixture to room temperature, an aqueous sodium thiosulfate solution was added. Water and ethyl acetate were added to the resulting reaction mixture and the liquids were separated. The obtained organic layer was washed with saturated brine, and dried over sodium sulfate. The solvent was distilled off under reduced pressure, and the title compound was obtained as 32.3 mg of a solid.

Synthetic Example 7

Synthesis of 2,5-dichloro-2-(2,6-difluorophenyl)-1-ethyl-[3,3'-bipyridin]-6(1H)-one (Compound No.: 18)

[Chem. 188]

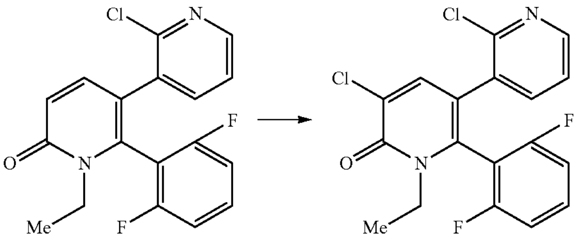

3 ml of a DMF solution containing 12.3 mg of 2-chloro-2-(2,6-difluoro-phenyl)-1-ethyl-[3,3'-bipyridin]-6(1H)-one and 11.4 mg of N-chlorosuccinimide was stirred at 60° C. for 10.5 hours. After cooling the mixture to room temperature, water and ethyl acetate were added to the reaction mixture and the liquids were separated. The obtained organic layer was washed with water and saturated brine, and dried over sodium sulfate. After the solvent was distilled off under reduced pressure, the obtained residue was purified by silica gel column chromatography. The title compound was obtained as 10.7 mg of a white solid.

Synthetic Example 8

Synthesis of 3-chloro-1-ethyl-5-(1-methyl-1H-pyrazol-5-yl)-6-(2,4,6-trifluorophenyl)pyridin-2(1H)-one (Compound No.: 20)

[Chem. 189]

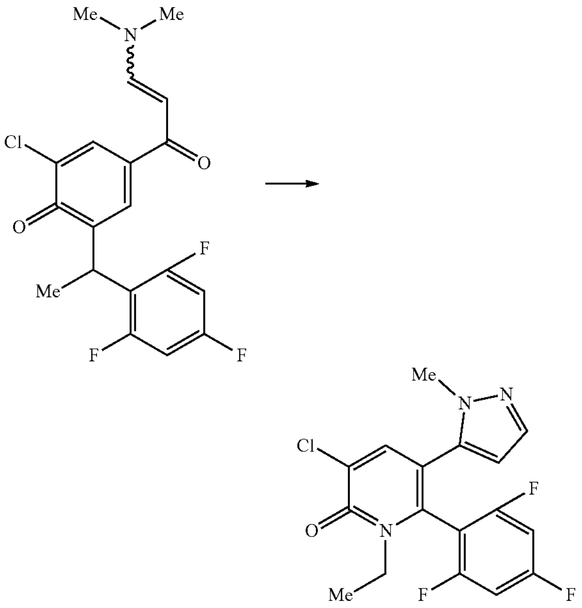

5 ml of an ethanol solution containing 400 mg of 3-chloro-5-(3-(dimethyl-amino)acryloyl)-1-ethyl-6-(2,4,6-trifluorophenyl)pyridin-2(1H)-one obtained in Reference Example 16 and 165 μl of methylhydrazine was stirred at 60° C. for 2 hours. After cooling the mixture to room temperature, 1N hydrochloric acid and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 250 mg of a yellow solid.

Synthetic Example 9

Synthesis of 5-(4-bromo-1-methyl-1H-pyrazol-5-yl)-3-chloro-1-ethyl-6-(2,4,6-trifluorophenyl)pyridin-2(1H)-one (Compound No.: 21)

[Chem. 190]

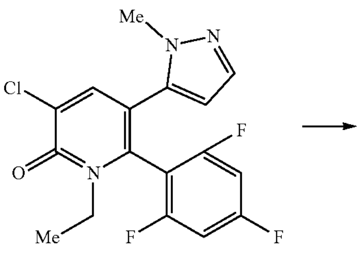

-continued

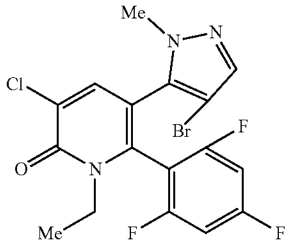

3 ml of a DMF solution containing 100 mg of 3-chloro-1-ethyl-5-(1-methyl-1H-pyrazol-5-yl)-6-(2,4,6-trifluorophenyl)pyridin-2(1H)-one and 53 mg of N-bromosuccinimide was stirred at 60° C. for 2 hours. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 117 mg of a white solid.

Synthetic Example 10

Synthesis of 5-(4-bromo-1-methyl-1H-pyrazol-5-yl)-3-chloro-6-(2,6-difluoro-4-methoxyphenyl)-1-ethylpyridin-2(1H)-one (Compound No.: 23)

[Chem. 191]

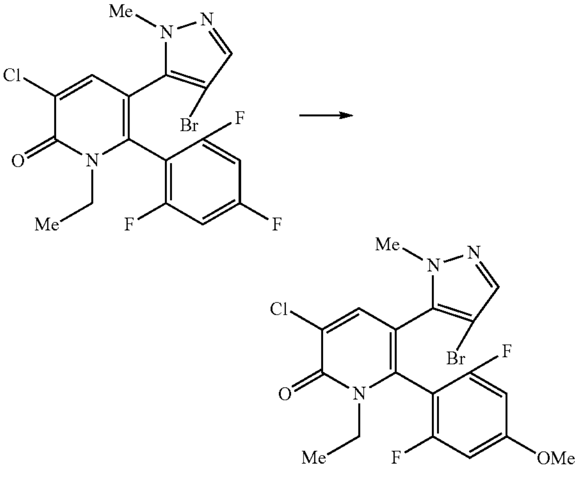

3 ml of a methanol solution containing 69 mg of 5-(4-bromo-1-methyl-1H-pyrazol-5-yl)-3-chloro-1-ethyl-6-(2,4,6-trifluorophenyl)pyridin-2(1H)-one and 149 μl of 28% sodium methoxide methanol solution was stirred under reflux by heating for 5 hours. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 59 mg of a white solid.

Synthetic Example 11

Step 1: Synthesis of 3-chloro-1-ethyl-5-(1-methyl-1H-pyrazol-3-yl)-6-(2,4,6-trifluorophenyl)pyridin-2(1H)-one

[Chem. 192]

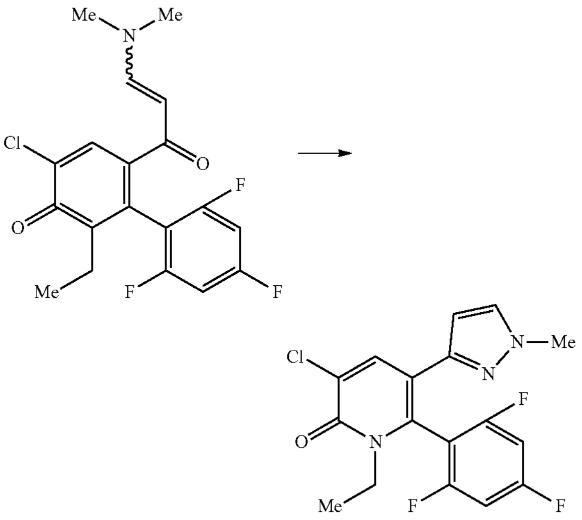

4 ml of acetone containing 546 μl of methylhydrazine was stirred at room temperature for 1 hour. Then, 1 ml of an acetone solution containing 400 mg of 3-chloro-5-(3-(dimethylamino)acryloyl)-1-ethyl-6-(2,4,6-trifluorophenyl)pyridin-2(1H)-one obtained in Reference Example 16 was added and the mixture was stirred under reflux by heating for 3 hours. After cooling the mixture to room temperature, the solvent was distilled off under reduced pressure. To the resulting reaction mixture were added 3 ml of ethanol and 0.5 ml of conc. hydrochloric acid and the mixture was stirred at 60° C. for 8 hours. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 29 mg of a yellow oily product.

$^1$H-NMR ($CDCl_3$) δ: 8.09 (1H, s), 7.14 (1H, d, J=2.4 Hz), 6.81-6.79 (2H, m), 5.47 (1H, d, J=2.4 Hz), 3.95 (2H, q, J=7.1 Hz), 3.80 (3H, s), 1.17 (3H, t, J=7.1 Hz).

Step 2: Synthesis of 5-(4-bromo-1-methyl-1H-pyrazol-3-yl)-3-chloro-1-ethyl-6-(2,4,6-trifluorophenyl)pyridin-2(1H)-one (Compound No.: 24)

[Chem. 193]

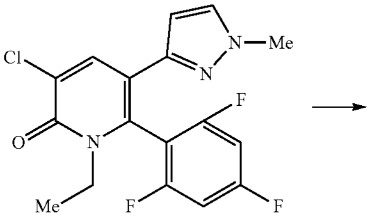

-continued

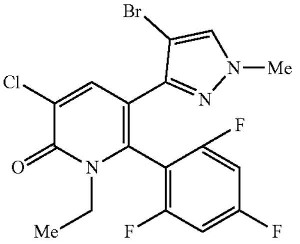

2 ml of a DMF solution containing 29 mg of 3-chloro-1-ethyl-5-(1-methyl-1H-pyrazol-3-yl)-6-(2,4,6-trifluorophenyl)pyridin-2(1H)-one and 15 mg of N-bromosuccinimide was stirred at 60° C. for 2 hours. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 29 mg of a white solid.

Synthetic Example 12

Synthesis of 3-chloro-5-(1,3-dioxan-2-yl)-1-ethyl-6-(2,4,6-trifluorophenyl)-pyridin-2(1H)-one (Compound No.: 8)

[Chem. 194]

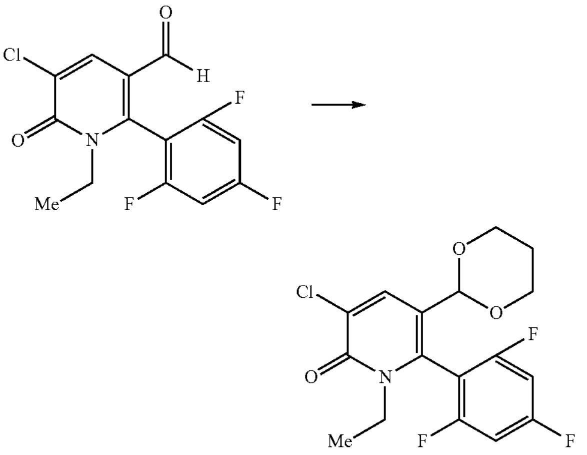

5 ml of a toluene solution containing 150 mg of 5-chloro-1-ethyl-6-oxo-2-(2,4,6-trifluorophenyl)-1,6-dihydropyridin-3-carboaldehyde obtained in Reference Example 13, 52 μl of 1,3-propandiol and 8 mg of p-toluenesulfonic acid monohydrate was stirred under reflux by heating for 4 hours. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 153 mg of a white solid.

Synthetic Example 13

Step 1: Synthesis of 5-(1H-1,2,4-triazol-1-yl)-6-(2,4,6-trifluorophenyl)-3,4-dihydropyridin-2(1H)-one

[Chem. 195]

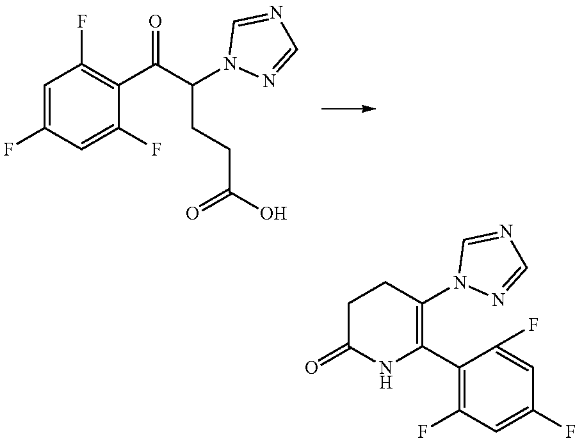

To 914 mg of 5-oxo-4-(1H-1,2,4-triazol-1-yl)-5-(2,4,6-trifluorophenyl)-pentanoic acid were added 4.50 g of ammonium acetate and 9.14 ml of acetic acid, and the mixture was stirred under reflux by heating for 30 minutes. After cooling the mixture to room temperature, an aqueous saturated sodium hydrogen carbonate solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 547 mg of a brown solid.

$^1$H-NMR ($CDCl_3$) δ: 7.92 (1H, s), 7.81 (1H, s), 6.84 (1H, s), 6.72-6.69 (2H, m), 3.06-3.05 (2H, m), 2.89-2.88 (2H, m).

Step 2: Synthesis of 1-ethyl-5-(1H-1,2,4-triazol-1-yl)-6-(2,4,6-trifluorophenyl)-3,4-dihydropyridin-2(1H)-one

[Chem. 196]

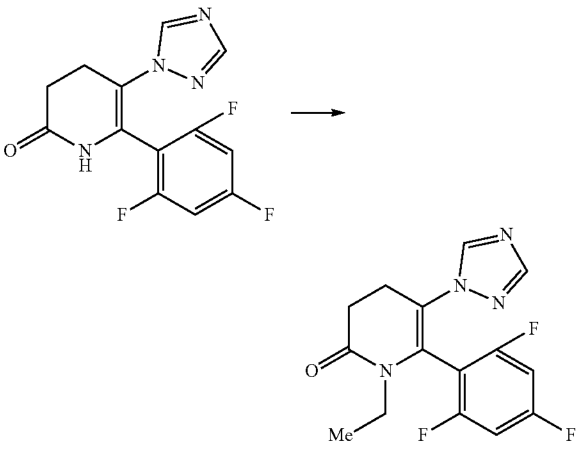

5 ml of DMF containing 547 mg of 5-(1H-1,2,4-triazol-1-yl)-6-(2,4,6-trifluorophenyl)-3,4-dihydropyridin-2(1H)-one, 446 μl of ethyl iodide and 1.82 g of cesium carbonate was stirred at 50° C. for 1.5 hours. After cooling the mixture to room temperature, an aqueous saturated ammonium chloride solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 482 mg of a white solid.

$^1$H-NMR ($CDCl_3$) δ: 7.87 (1H, s), 7.83 (1H, s), 6.71-6.68 (2H, m), 3.42 (2H, q, J=7.1 Hz), 2.90-2.89 (4H, m), 0.99 (3H, t, J=7.1 Hz).

Step 3: Synthesis of 1-ethyl-5-(1H-1,2,4-triazol-1-yl)-6-(2,4,6-trifluorophenyl)-pyridin-2(1H)-one

[Chem. 197]

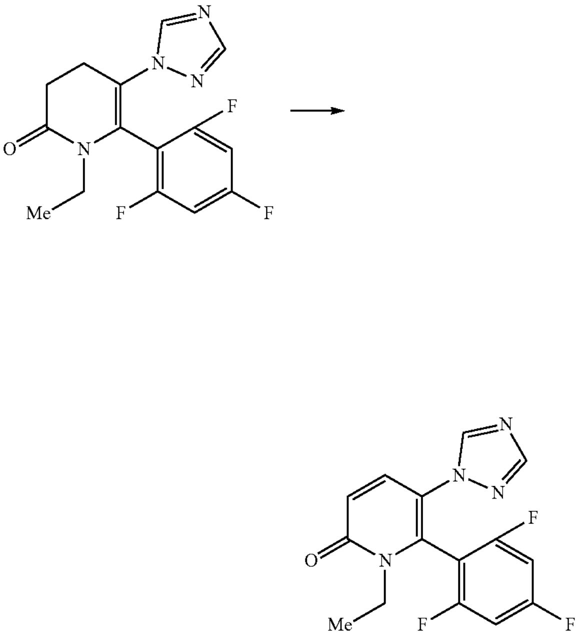

5 ml of a toluene solution containing 482 mg of 1-ethyl-5-(1H-1,2,4-triazol-1-yl)-6-(2,4,6-trifluorophenyl)-3,4-dihydropyridin-2(1H)-one and 1.02 g of 2,3-dichloro-5,6-dicyano-p-benzoquinone was stirred under reflux by heating for 5 hours. 340 mg of 2,3-dichloro-5,6-dicyano-p-benzoquinone was further added to the reaction mixture, and the mixture was stirred under reflux by heating for 4.5 hours. After cooling the mixture to room temperature, the solvent was distilled off under reduced pressure. The obtained residue was purified by silica gel column chromatography. The title compound was obtained as 97 mg of a brown solid.

$^1$H-NMR ($CDCl_3$) δ: 7.99 (1H, s), 7.86 (1H, s), 7.42 (1H, d, J=9.8 Hz), 6.79 (1H, d, J=9.8 Hz), 6.75-6.73 (2H, m), 3.89 (2H, q, J=7.2 Hz), 1.18 (3H, t, J=7.2 Hz).

Step 4: Synthesis of 3-chloro-1-ethyl-5-(1H-1,2,4-triazol-1-yl)-6-(2,4,6-trifluorophenyl)pyridin-2(1H)-one (Compound No.: 34)

[Chem. 198]

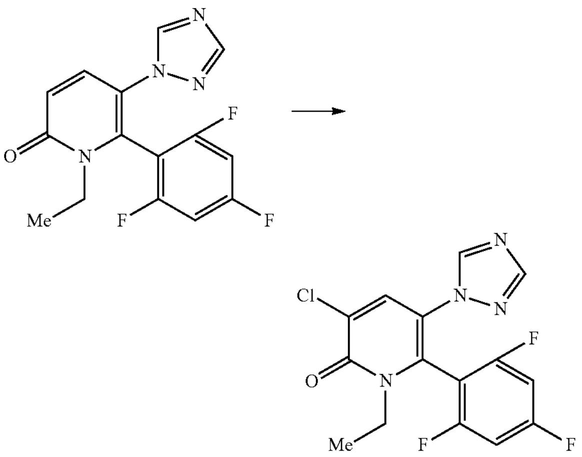

3 ml of a DMF solution containing 97 mg of 1-ethyl-5-(1H-1,2,4-triazol-1-yl)-6-(2,4,6-trifluorophenyl)pyridin-2(1H)-one and 49 mg of N-chlorosuccinimide was stirred at 70° C. for 4 hours. 32 mg of N-chlorosuccinimide was further added to the reaction mixture, and the mixture was stirred at 70° C. for 1 hour. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 86 mg of a white solid.

Synthetic Example 14

Synthesis of 5-(5-bromo-1H-1,2,4-triazol-1-yl)-3-chloro-1-ethyl-6-(2,4,6-trifluorophenyl)pyridin-2(1H)-one (Compound No.: 35)

[Chem. 199]

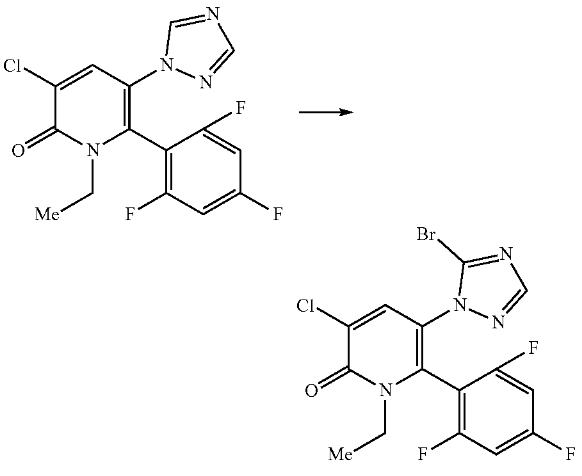

To 2 ml of a carbon tetrachloride solution containing 58 mg of 3-chloro-1-ethyl-5-(1H-1,2,4-triazol-1-yl)-6-(2,4,6-trifluorophenyl)pyridin-2(1H)-one were added 35 mg of N-bromosuccinimide and 5 mg of azobisisobutyronitrile, and the mixture was stirred under reflux by heating for 2 hours. 39 mg of N-bromosuccinimide and 5.4 mg of azobisisobutyronitrile were further added to the reaction mixture, and the mixture was stirred under reflux by heating for 3.5 hours. After cooling the mixture to room temperature, an aqueous sodium thiosulfate solution was added. Water and ethyl acetate were added to the resulting reaction mixture and the liquids were separated. The obtained organic layer was washed with saturated brine, and dried over sodium sulfate. The solvent was distilled off under reduced pressure to obtain the title compound as 34 mg of a white solid.

Synthetic Example 15

Step 1: Synthesis of 5-(1H-pyrazol-1-yl)-6-(2,4,6-trifluorophenyl)-3,4-dihydropyridin-2(1H)-one

[Chem. 200]

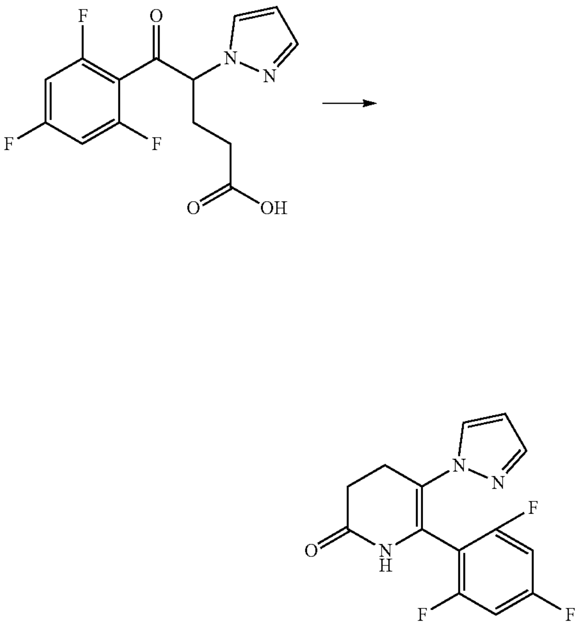

To 3.66 g of 5-oxo-4-(1H-pyrazol-1-yl)-5-(2,4,6-trifluorophenyl)pentanoic acid obtained in Reference Example 24 were added 9.03 g of ammonium acetate and 36.6 ml of acetic acid, and the mixture was stirred at 120° C. for 1.5 hours. After cooling the mixture to room temperature, an aqueous saturated sodium hydrogen carbonate solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 1.10 g of a brown solid.

$^1$H-NMR ($CDCl_3$) δ: 7.53 (1H, dd, J=1.8, 0.6 Hz), 7.10 (1H, d, J=2.4 Hz), 6.72-6.65 (2H, m), 6.71 (1H, br s), 6.16 (1H, dd, J=2.4, 1.8 Hz), 3.10-3.09 (2H, m), 2.86-2.84 (2H, m).

Step 2: Synthesis of 1-ethyl-5-(1H-pyrazol-1-yl)-6-(2,4,6-trifluorophenyl)-3,4-dihydropyridin-2(1H)-one (Compound No.: 25)

[Chem. 201]

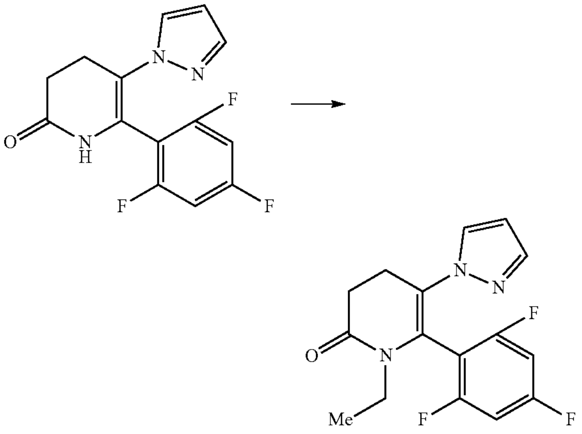

4.5 ml of DMF containing 448 mg of 5-(1H-pyrazol-1-yl)-6-(2,4,6-trifluoro-phenyl)-3,4-dihydropyridin-2(1H)-one, 244 μl of ethyl iodide and 996 mg of cesium carbonate was stirred at 50° C. for 30 minutes. After cooling the mixture to room temperature, an aqueous saturated ammonium chloride solution and ethyl acetate were added to the reaction mixture and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 430 mg of a brown solid.

Synthetic Example 16

Synthesis of 1-ethyl-5-(1H-pyrazol-1-yl)-6-(2,4,6-trifluorophenyl)pyridin-2(1H)-one (Compound No.: 26)

[Chem. 202]

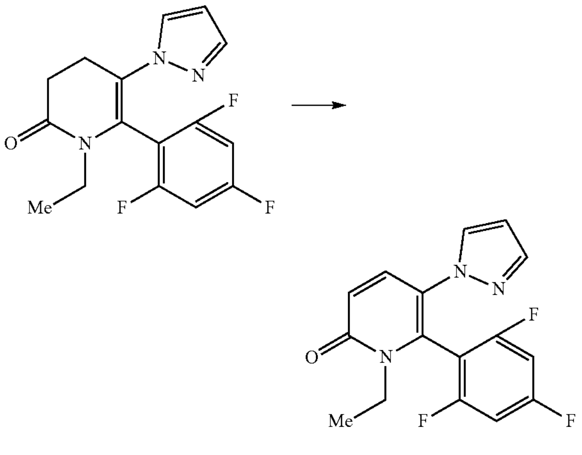

8 ml of a toluene solution containing 430 mg of 1-ethyl-5-(1H-pyrazol-1-yl)-6-(2,4,6-trifluorophenyl)-3,4-dihydropyridin-2(1H)-one and 1.22 g of 2,3-dichloro-5,6-dicyano-p-benzoquinone was stirred under reflux by heating for 4 hours. After cooling the mixture to room temperature, the solvent was distilled off under reduced pressure. The obtained residue was purified by silica gel column chromatography. The title compound was obtained as 315 mg of a brown solid.

Synthetic Example 17

Step 1: Synthesis of 5-(4-bromo-1H-pyrazol-1-yl)-1-ethyl-6-(2,4,6-trifluoro-phenyl)pyridin-2(1H)-one

[Chem. 203]

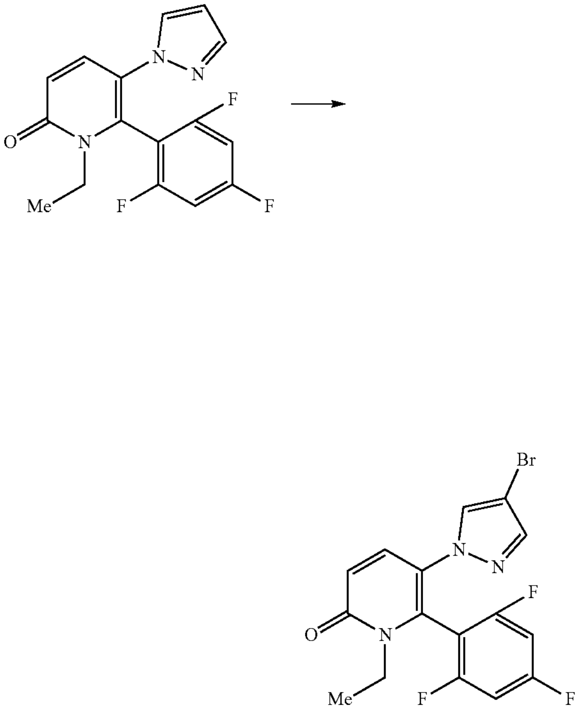

3 ml of a DMF solution containing 136 mg of 1-ethyl-5-(H-pyrazol-1-yl)-6-(2,4,6-trifluorophenyl)pyridin-2(1H)-one and 83 mg of N-bromosuccinimide was stirred at 60° C. for 15 minutes. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 153 mg of a white solid.

$^1$H-NMR ($CDCl_3$) δ: 7.41 (1H, d, J=9.5 Hz), 7.40 (1H, d, J=0.7 Hz), 7.34 (1H, s), 6.76-6.71 (2H, m), 6.75 (1H, d, J=9.5 Hz), 3.88 (2H, q, J=7.1 Hz), 1.17 (3H, t, J=7.1 Hz).

Step 2: Synthesis of 5-(4-bromo-1H-pyrazol-1-yl)-3-chloro-1-ethyl-6-(2,4,6-trifluorophenyl)pyridin-2(1H)-one (Compound No.: 70)

[Chem. 204]

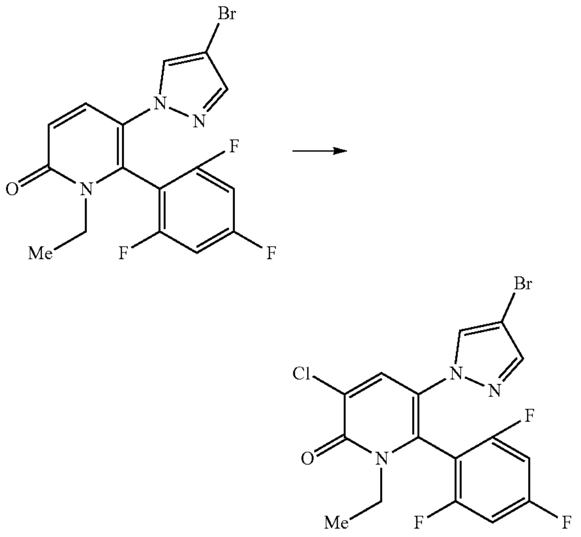

3 ml of a DMF solution containing 153 mg of 5-(4-bromo-1H-pyrazol-1-yl)-1-ethyl-6-(2,4,6-trifluorophenyl)pyridin-2(1H)-one and 56 mg of N-chlorosuccinimide was stirred at 80° C. for 3 hours. 56 mg of N-chlorosuccinimide was further added to the reaction mixture, and the mixture was stirred at 80° C. for 55 minutes. After cooling the mixture to room temperature, an aqueous sodium thiosulfate solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 154 mg of a white solid.

Synthetic Example 18

Synthesis of 5-(4-bromo-1H-pyrazol-1-yl)-3-chloro-6-(2,6-difluoro-4-methoxyphenyl)-1-ethylpyridin-2(1H)-one (Compound No.: 72)

[Chem. 205]

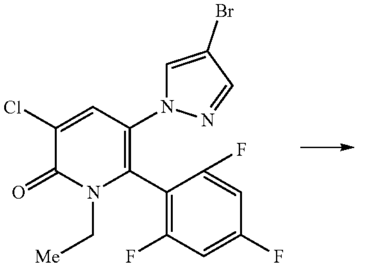

-continued

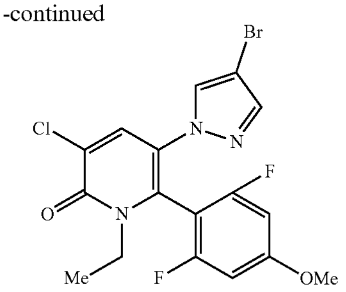

3 ml of a methanol solution containing 51 mg of 5-(4-bromo-1H-pyrazol-1-yl)-3-chloro-1-ethyl-6-(2,4,6-trifluorophenyl)pyridin-2(1H)-one and 118 μl of a 5M sodium methoxide-methanol solution was stirred at 60° C. for 1 hour. After cooling the mixture to room temperature, an aqueous ammonium chloride solution and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 44 mg of a white solid.

Synthetic Example 19

Synthesis of 3-chloro-1-ethyl-5-(oxazol-5-yl)-6-(2,4,6-trifluorophenyl)pyridin-2(1H)-one (Compound No.: 36)

[Chem. 206]

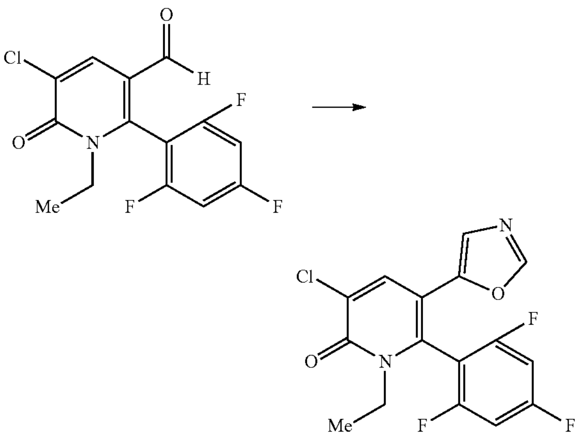

20 ml of a methanol solution containing 2.00 g of 5-chloro-1-ethyl-6-oxo-2-(2,4,6-trifluorophenyl)-1,6-dihydropyridin-3-carboaldehyde, 1.36 g of p-toluenesulfonylmethyl isocyanide and 1.76 g of potassium carbonate was stirred at room temperature for 2 hours. Then, the reaction mixture was stirred at 50° C. for 30 minutes. After cooling the mixture to room temperature, water and ethyl acetate were added to the reaction mixture and the liquids were separated. The obtained organic layer was washed with saturated brine, and dried over magnesium sulfate. The solvent was distilled off under reduced pressure, and the obtained residue was purified by silica gel column chromatography. The title compound was obtained as 1.50 g of a white solid.

Synthetic Example 20

Synthesis of 3-chloro-5-(4-chlorooxazol-5-yl)-1-ethyl-6-(2,4,6-trifluoro-phenyl)pyridin-2(1H)-one (Compound No.: 112)

[Chem. 207]

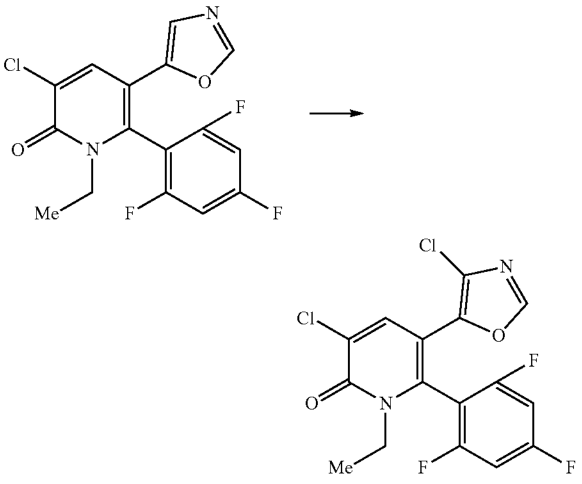

To 2 ml of a DMF solution containing 100 mg of 3-chloro-1-ethyl-5-(oxazol-5-yl)-6-(2,4,6-trifluorophenyl) pyridin-2(1H)-one was added dropwise 0.23 ml of a 1.3 mol/L hexamethyldisilazane lithium-THF solution at −60° C. and the mixture was stirred at 1 hour. Then, after adding 38 mg of N-chlorosuccinimide to the reaction mixture, the resulting mixture was stirred at room temperature for 3 hours. An aqueous sodium thiosulfate solution and ethyl acetate were added to the reaction mixture and the liquids were separated. The obtained organic layer was washed with 1N hydrochloric acid and saturated brine, and dried over magnesium sulfate. The solvent was distilled off under reduced pressure, and the obtained residue was purified by silica gel column chromatography. The title compound was obtained as 62 mg of a pale yellow solid.

Synthetic Example 21

Synthesis of 3-chloro-6-(2,6-difluorophenyl)-1-ethyl-5-(4-methyloxazol-5-yl)pyridin-2(1H)-one (Compound No.: 43)

[Chem. 208]

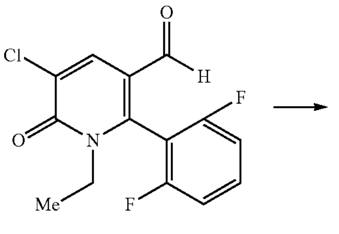

-continued

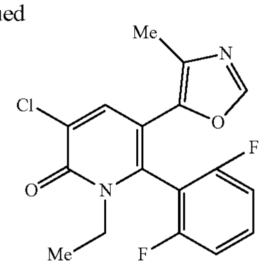

3 ml of a methanol solution containing 100 mg of 5-chloro-2-(2,6-difluoro-phenyl)-1-ethyl-6-oxo-1,6-dihydropyridin-3-carboaldehyde, 77 mg of 1-((1-isocyano-ethyl) sufonyl)-4-methylbenzene and 93 mg of potassium carbonate was stirred under reflux by heating for 5.5 hours. After cooling the mixture to room temperature, an aqueous saturated ammonium chloride solution and ethyl acetate were added to the reaction mixture and the liquids were separated. The obtained organic layer was washed with saturated brine, and dried over magnesium sulfate. The solvent was distilled off under reduced pressure, and the obtained residue was purified by silica gel column chromatography. The title compound was obtained as 55 mg of an orange solid.

Synthetic Example 22

Synthesis of 4-(5-chloro-1-ethyl-6-oxo-2-(2,6-difluorophenyl)-1,6-dihydro-pyridin-3-yl)-1H-pyrrol-3-carbonitrile (Compound No.: 88)

[Chem. 209]

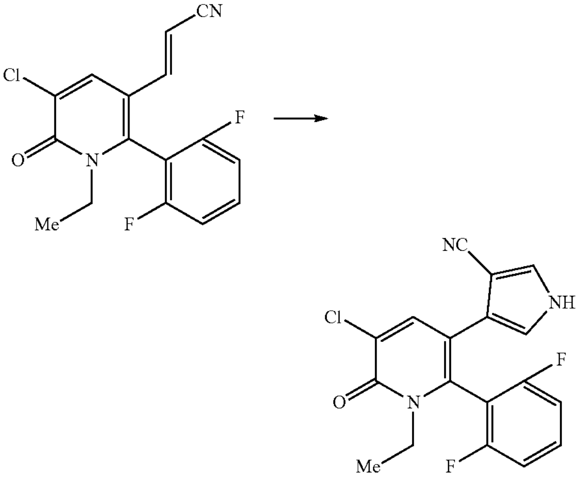

A solution comprising 3 ml of diethyl ether and 1 ml of dimethylsulfoxide which contains 150 mg of (E)-3-(5-chloro-1-ethyl-6-oxo-2-(2,6-difluorophenyl)-1,6-dihydropyridin-3-yl)acrylonitrile obtained in Reference Example 31, 109 mg of p-toluenesulfonylmethylisocyanide and 26 mg of 60% sodium hydride was stirred under room temperature for 2.5 hours. Water and ethyl acetate were added to the reaction mixture and the liquids were separated. The obtained organic layer was washed with saturated brine, and dried over magnesium sulfate. The solvent was distilled off under reduced pressure, and the obtained residue was purified by silica gel column chromatography. The title compound was obtained as 88 mg of a brown solid.

Synthetic Example 23

Step 1: Synthesis of 5-(4,5-dichloro-1H-imidazol-1-yl)-6-(2,4,6-trifluoro-phenyl)-3,4-dihydropyridin-2(1H)-one

[Chem. 210]

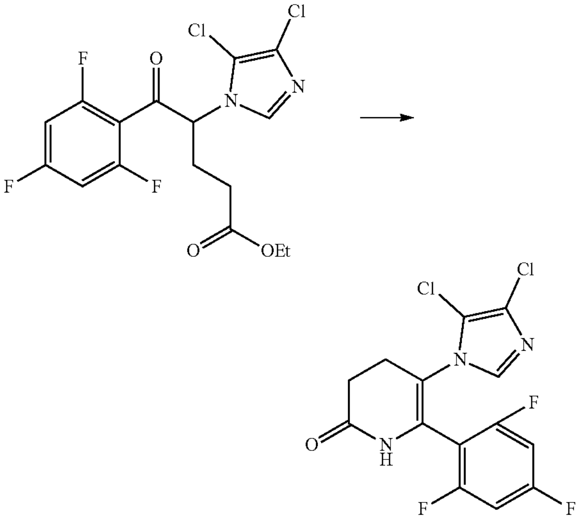

To 2.61 g of ethyl 4-(4,5-dichloro-1H-imidazol-1-yl)-5-oxo-5-(2,4,6-trifluoro-phenyl)pentanoate obtained in Reference Example 33 were added 9.77 g of ammonium acetate and 25.0 ml of acetic acid, and the mixture was stirred at 120° C. for 7 hours. After cooling the mixture to room temperature, an aqueous saturated sodium hydrogen carbonate solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 1.05 g of a brown solid.

$^1$H-NMR ($CDCl_3$) δ: 7.17 (1H, s), 6.78 (1H, s), 6.71-6.69 (2H, m), 2.87-2.85 (4H, m).

Step 2: Synthesis of 5-(4,5-dichloro-1H-imidazol-1-yl)-1-ethyl-6-(2,4,6-trifluorophenyl)-3,4-dihydropyridin-2(1H)-one

[Chem. 211]

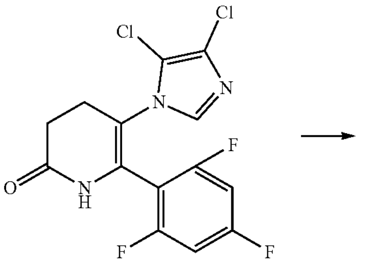

-continued

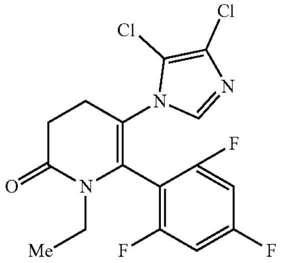

4.2 ml of DMF containing 419 mg of 5-(4,5-dichloro-1H-imidazol-1-yl)-6-(2,4,6-trifluorophenyl)-3,4-dihydropyridin-2(1H)-one, 139 μl of ethyl iodide and 565 mg of cesium carbonate was stirred at 50° C. for 40 minutes. After cooling the mixture to room temperature, an aqueous saturated ammonium chloride solution and ethyl acetate were added to the reaction mixture and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 388 mg of a brown solid.

$^1$H-NMR ($CDCl_3$) δ: 7.17 (1H, s), 6.71-6.69 (2H, m), 3.41 (2H, s), 2.83-2.74 (4H, m), 0.99 (3H, t, J=7.1 Hz).

Step 3: Synthesis of 5-(4,5-dichloro-1H-imidazol-1-yl)-1-ethyl-6-(2,4,6-trifluorophenyl)pyridin-2(1H)-one (Compound No.: 136)

[Chem. 212]

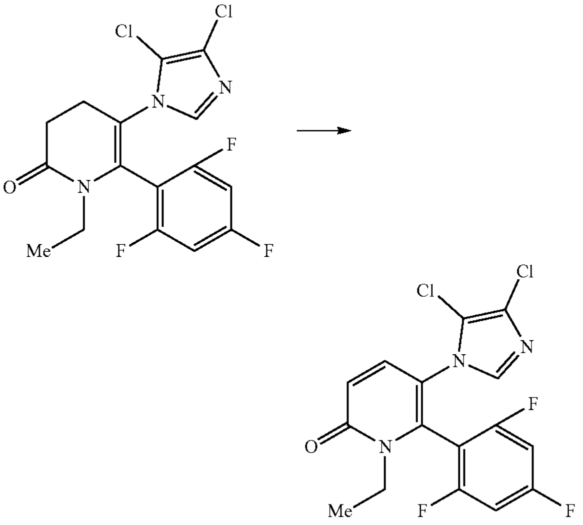

To 7.8 ml of a carbon tetrachloride solution containing 388 mg of 5-(4,5-dichloro-1H-imidazol-1-yl)-6-(2,4,6-trifluorophenyl)-3,4-dihydropyridin-2(1H)-one were added 194 mg of N-bromosuccinimide and 16 mg of azobisisobutyronitrile, and the mixture was stirred at 90° C. for 30 minutes. An aqueous saturated ammonium chloride solution and ethyl acetate were added to the reaction mixture and the liquids were separated. The obtained organic layer was successively washed with an aqueous sodium thiosulfate solution and saturated brine, and dried over sodium sulfate.

After the solvent was distilled off under reduced pressure, the obtained residue was purified by silica gel column chromatography. The title compound was obtained as 284 mg of a brown solid.

Synthetic Example 24

Synthesis of 3-chloro-5-(4,5-dichloro-1H-imidazol-1-yl)-1-ethyl-6-(2,4,6-trifluorophenyl)pyridin-2(1H)-one (Compound No.: 138)

[Chem. 213]

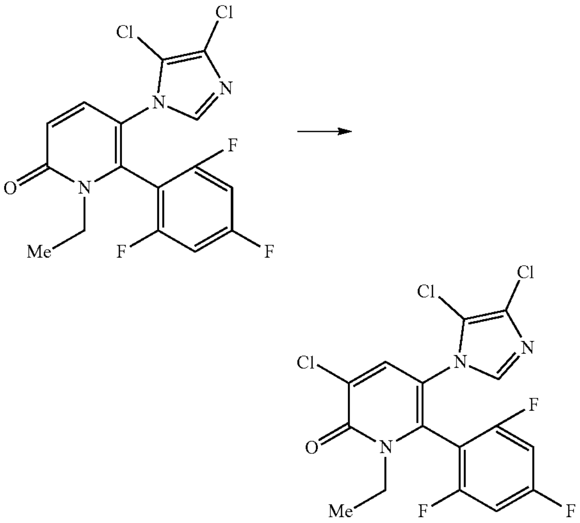

3 ml of a DMF solution containing 122 mg of 5-(4,5-dichloro-1H-imidazol-1-yl)-1-ethyl-6-(2,4,6-trifluorophenyl)pyridin-2(1H)-one and 55 mg of N-chlorosuccinimide was stirred at 80° C. for 1 hour. After cooling the mixture to room temperature, water and ethyl acetate were added to the reaction mixture and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 79 mg of a white solid.

Synthetic Example 25

Synthesis of 5-(4-chloro-1H-pyrazol-1-yl)-1-ethyl-6-(2,4,6-trifluorophenyl)-pyridin-2(1H)-one (Compound No.: 27)

[Chem. 214]

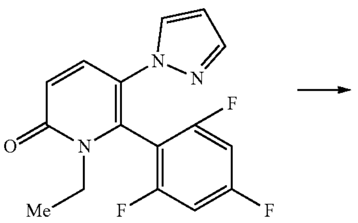

-continued

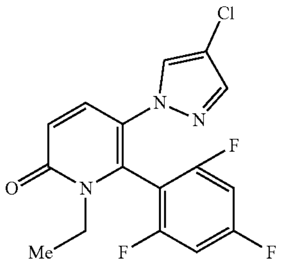

3 ml of a DMF solution containing 176 mg of 1-ethyl-5-(1H-pyrazol-1-yl)-6-(2,4,6-trifluorophenyl)pyridin-2(1H)-one and 82.3 mg of N-chlorosuccinimide was stirred at 70° C. for 50 minutes. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 163 mg of a white solid.

Synthetic Example 26

Synthesis of 5-(4-chloro-1H-pyrazol-1-yl)-1-ethyl-3-iodo-6-(2,4,6-trifluoro-phenyl)pyridin-2(1H)-one (Compound No.: 140)

[Chem. 215]

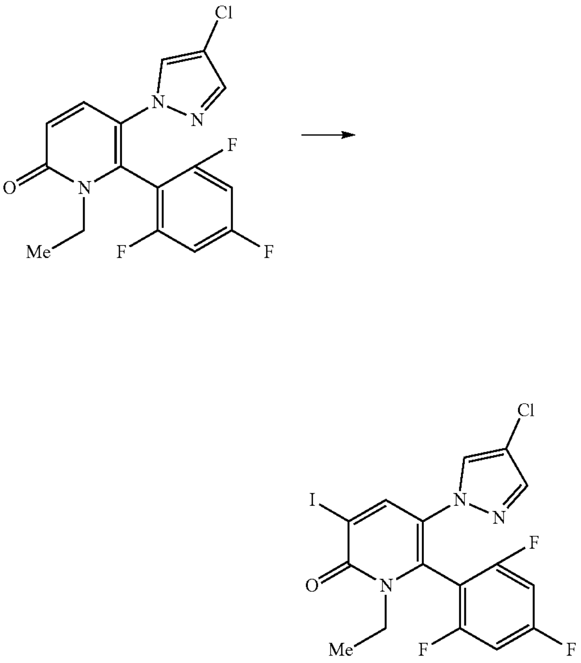

14 ml of a methanol solution containing 750 mg of 5-(4-chloro-1H-pyrazol-1-yl)-1-ethyl-6-(2,4,6-trifluorophenyl)pyridin-2(1H)-one, 954 mg of N-iodosuccinimide and 113 μl of sulfuric acid was stirred at 60° C. for 5 hours. Then, 954 mg of N-iodosuccinimide and 113 μl of sulfuric acid were added to the solution, and the resulting mixture was stirred at 60° C. for 2 hours. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 954 mg of a pale yellow solid.

Synthetic Example 27

Step 1: Synthesis of 5-(4-chloro-1H-pyrazol-1-yl)-1-ethyl-6-(2,4,6-trifluoro-phenyl)-3-((trimethylsilyl)ethynyl)pyridin-2(1H)-one

[Chem. 216]

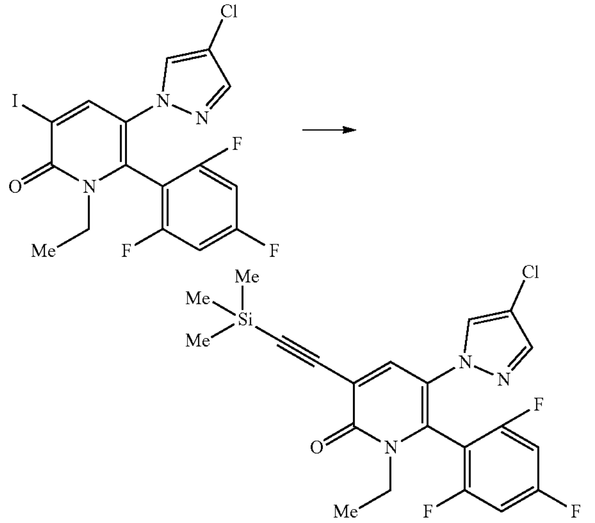

To 1 ml of a DMF solution containing 300 mg of 5-(4-chloro-1H-pyrazol-1-yl)-1-ethyl-3-iodo-6-(2,4,6-trifluorophenyl)pyridin-2(1H)-one obtained in Synthetic Example 26, 865 μl of trimethylsilylacetylene, 44 mg of dichlorobis(triphenylphosphine)palladium(II) and 12 mg of copper iodide was added 3 ml of triethylamine, and the resulting mixture was stirred at room temperature for 1 hour. 1N Hydrochloric acid and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 258 mg of a yellow solid.

$^1$H-NMR ($CDCl_3$) δ: 7.64 (1H, s), 7.35 (1H, s), 7.32 (1H, s), 6.75-6.71 (2H, m), 3.89 (2H, q, J=7.1 Hz), 1.18 (3H, t, J=7.1 Hz), 0.26 (9H, s).

Step 2: Synthesis of 5-(4-chloro-1H-pyrazol-1-yl)-1-ethyl-3-ethynyl-6-(2,4,6-trifluorophenyl)pyridin-2(1H)-one (Compound No.: 223)

[Chem. 217]

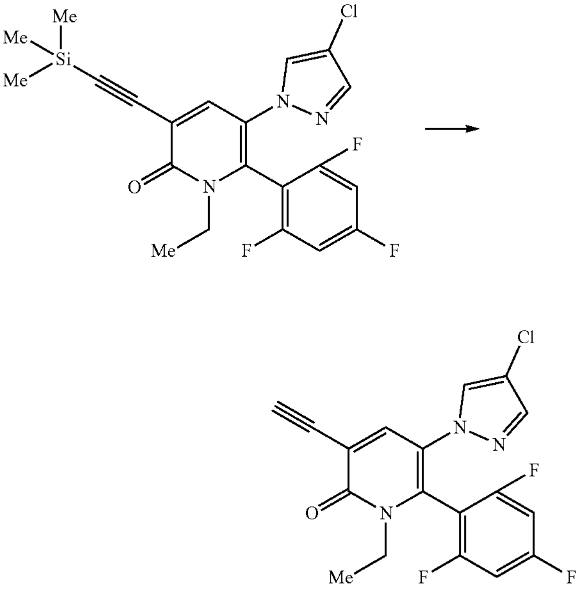

5 ml of a methanol solution containing 255 mg of 5-(4-chloro-1H-pyrazol-1-yl)-1-ethyl-6-(2,4,6-trifluorophenyl)-3-((trimethylsilyl)ethyny 1)pyridin-2(1H)-one and 391 mg of potassium carbonate was stirred at room temperature for 15 minutes. An aqueous saturated ammonium chloride solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 161 mg of a yellow solid.

Synthetic Example 28

Synthesis of 5-(4-chloro-1H-pyrazol-1-yl)-1-ethyl-3-methoxy-6-(2,4,6-trifluorophenyl)pyridin-2(1H)-one (Compound No.: 225)

[Chem. 218]

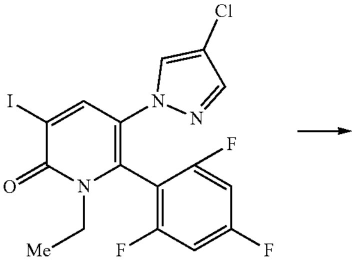

-continued

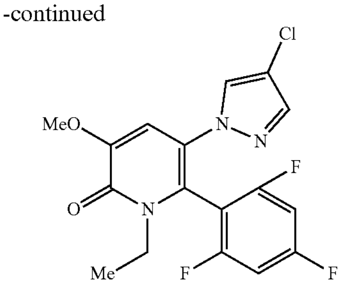

3 ml of a toluene solution containing 143 mg of 5-(4-chloro-1H-pyrazol-1-yl)-1-ethyl-3-iodo-6-(2,4,6-trifluoro-phenyl)pyridin-2(1H)-one obtained in Synthetic Example 26, 6.7 mg of palladium(II) acetate, 32 mg of 2-di-t-butylphosphino-2,4,6-triisopropylbiphenyl, 147 mg of cesium carbonate and 1 ml of methanol was stirred at 60° C. for 4 hours. 1N Hydrochloric acid and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 33 mg of a white solid.

Synthetic Example 29

Synthesis of 5-(4-chloro-1H-pyrazol-1-yl)-1-ethyl-3-bromo-6-(2,4,6-trifluoro-phenyl)pyridin-2(1H)-one (Compound No.: 71)

[Chem. 219]

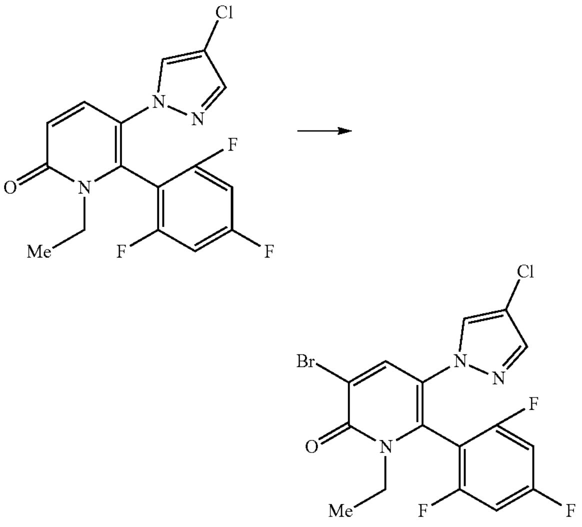

7 ml of a DMF solution containing 730 mg of 5-(4-chloro-1H-pyrazol-1-yl)-1-ethyl-6-(2,4,6-trifluorophenyl)pyridin-2(1H)-one and 551 mg of N-bromosuccinimide was stirred at 80° C. for 1 hour. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 836 mg of a white solid.

Synthetic Example 30

Synthesis of 5-(4-chloro-1H-pyrazol-1-yl)-1-ethyl-3-methyl-6-(2,4,6-trifluoro-phenyl)pyridin-2(1H)-one (Compound No.: 206)

[Chem. 220]

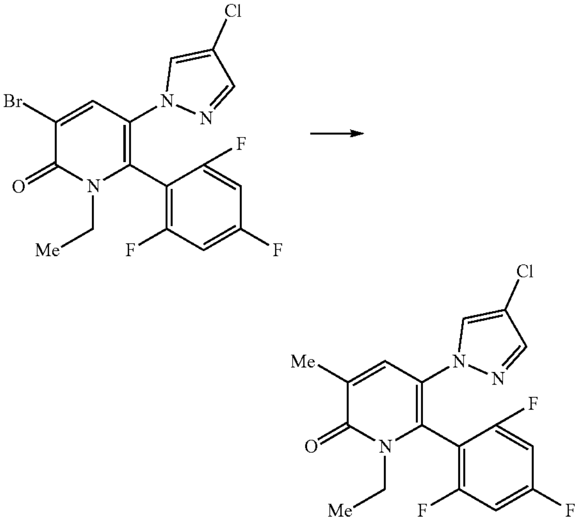

A mixed solution of 6.8 ml of toluene containing 836 mg of 5-(4-chloro-1H-pyrazol-1-yl)-1-ethyl-3-bromo-6-(2,4,6-trifluorophenyl)pyridin-2(1H)-one, 463 mg of methylboronic acid, 43 mg of palladium(II) acetate, 1.44 g of tripotassium phosphate and 108 mg of tricyclohexylphosphine, and 1.7 ml of water was stirred under reflux by heating for 20 minutes. After cooling the mixture to room temperature, water and ethyl acetate were added to the reaction mixture and the liquids were separated. The obtained organic layer was washed with saturated brine, and then, dried over sodium sulfate. After the solvent was distilled off under reduced pressure, the obtained residue was purified by silica gel column chromatography. The title compound was obtained as 559 mg of a brown solid.

Synthetic Example 31

Step 1: Synthesis of 5-(4-chloro-1H-pyrazol-1-yl)-3-(dibromomethyl)-1-ethyl-6-(2,4,6-trifluorophenyl) pyridin-2(1H)-one

[Chem. 221]

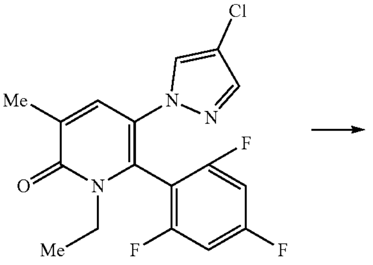

-continued

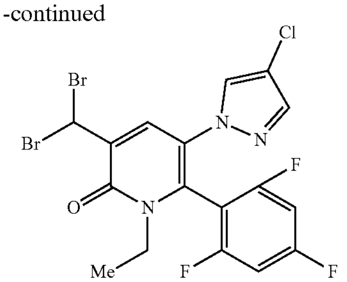

To 11.2 ml of chlorobenzene solution containing 559 mg of 5-(4-chloro-1H-pyrazol-1-yl)-1-ethyl-3-methyl-6-(2,4,6-trifluorophenyl)pyridin-2(1H)-one were added 568 mg of N-bromosuccinimide and 25 mg of azobisisobutyronitrile, and the mixture was stirred at 110° C. for 20 minutes. After cooling the mixture to room temperature, water and ethyl acetate were added to the reaction mixture and the liquids were separated. The obtained organic layer was successively washed with an aqueous sodium thiosulfate solution and saturated brine, and dried over sodium sulfate. Then, the solvent was distilled off under reduced pressure to obtain 829 mg of the yellow oily product containing the title compound.

$^1$H-NMR ($CDCl_3$) δ: 8.05 (1H, s), 7.39 (1H, s), 7.38 (1H, s), 6.96 (1H, s), 6.77-6.75 (2H, m), 3.93 (2H, q, J=7.1 Hz), 1.19 (3H, t, J=7.1 Hz).

Step 2: Synthesis of 5-(4-chloro-1H-pyrazol-1-yl)-1-ethyl-2-oxo-6-(2,4,6-trifluorophenyl)-1,2-dihydro-pyridin-3-carboaldehyde (Compound No.: 265)

[Chem. 222]

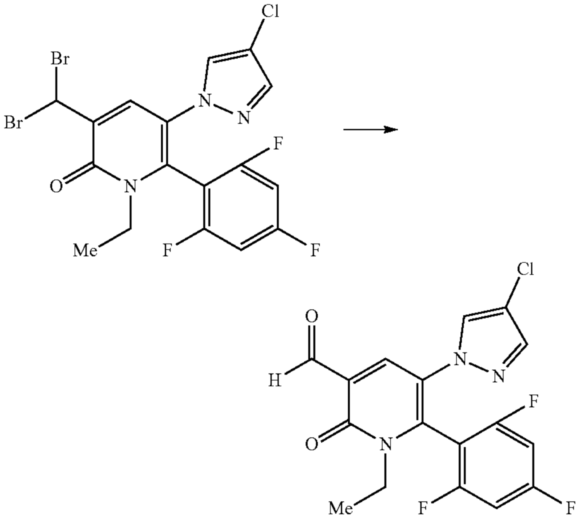

To 8 ml of acetonitrile solution containing 829 mg of 5-(4-chloro-1H-pyrazol-1-yl)-3-(dibromomethyl)-1-ethyl-6-(2,4,6-trifluorophenyl)pyridin-2(1H)-one obtained in Step 1 of Synthetic Example 30 was added 4 ml of an aqueous solution containing 536 mg of silver nitrate, and the mixture was stirred under room temperature for 10 minutes. The reaction mixture was filtered through Celite, and washed with ethyl acetate. The obtained organic layer was successively washed with water, 1N hydrochloric acid and saturated brine, and dried over sodium sulfate. After the solvent was distilled off under reduced pressure, the obtained residue was purified by silica gel column chromatography. The title compound was obtained as 505 mg of a white solid.

Synthetic Example 32

Synthesis of 5-(4-chloro-H-pyrazol-1-yl)-3-(difluoromethyl)-1-ethyl-6-(2,4,6-trifluorophenyl)pyridin-2(1H)-one (Compound No.: 266)

[Chem. 223]

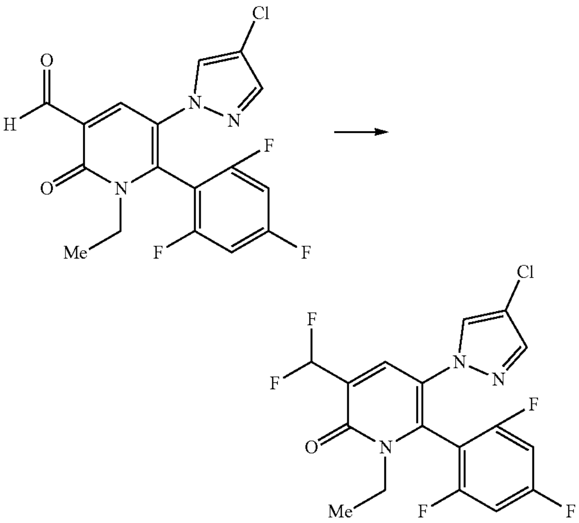

3 ml of a dichloromethane solution containing 208 mg of 5-(4-chloro-1H-pyrazol-1-yl)-1-ethyl-2-oxo-6-(2,4,6-trifluorophenyl)-1,2-dihydropyridin-3-carboaldehyde and 286 μl of (diethylamino)sulfur trifluoride was stirred under room temperature for 30 minutes. Then, 1N hydrochloric acid and ethyl acetate were added to the reaction mixture and the liquids were separated. The obtained organic layer was washed with saturated brine, and then, dried over sodium sulfate. After the solvent was distilled off under reduced pressure, the obtained residue was purified by silica gel column chromatography. The title compound was obtained as 169 mg of a white solid.

Synthetic Example 33

Synthesis of 3-chloro-5-(4-chloro-1H-pyrazol-1-yl)-1-ethyl-6-(2,4,6-trifluoro-phenyl)pyridin-2(1H)-one (Compound No.: 40)

[Chem. 224]

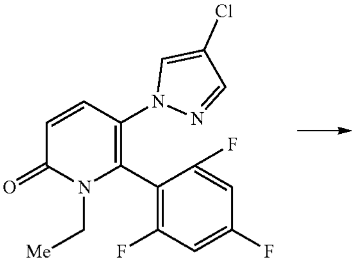

-continued

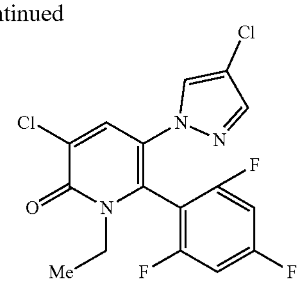

12 ml of a DIF solution containing 1.19 g of 1-ethyl-5-(1H-pyrazol-1-yl)-6-(2,4,6-trifluorophenyl)pyridin-2(1H)-one and 1.49 g of N-chlorosuccinimide was stirred at 80° C. for 40 minutes. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 1.13 g of a white solid.

Synthetic Example 34

Synthesis of 3-chloro-5-(4-chloro-1H-pyrazol-1-yl)-6-(2,6-difluoro-4-methoxyphenyl)-1-ethylpyridin-2(1H)-one (Compound No.: 41)

[Chem. 225]

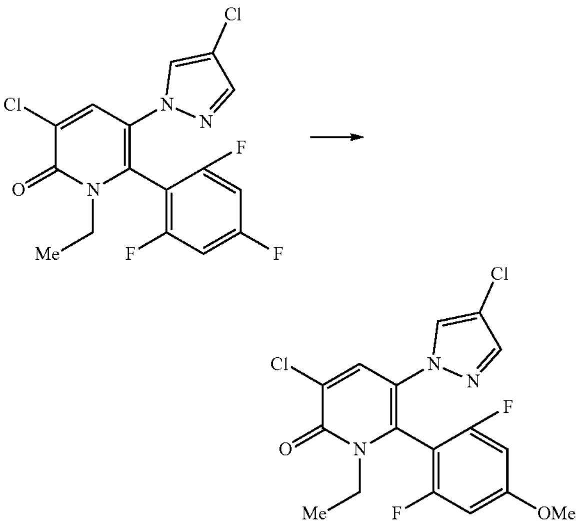

6 ml of a methanol solution containing 578 mg of 3-chloro-5-(4-chloro-1H-pyrazol-1-yl)-1-ethyl-6-(2,4,6-trifluorophenyl)pyridin-2(1H)-one and 402 mg of sodium methoxide was stirred at 0.60° C. for 5 hours. Then, 402 mg of sodium methoxide was added thereto, and the mixture was further stirred at 60° C. for 2 hours. After cooling the mixture to room temperature, an aqueous ammonium chloride solution and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 520 mg of a white solid.

Synthetic Example 35

Synthesis of 3-chloro-5-(4-chloro-1H-pyrazol-1-yl)-6-(2,6-difluoro-4-hydroxyphenyl)-1-ethylpyridin-2(1H)-one (Compound No.: 184)

[Chem. 226]

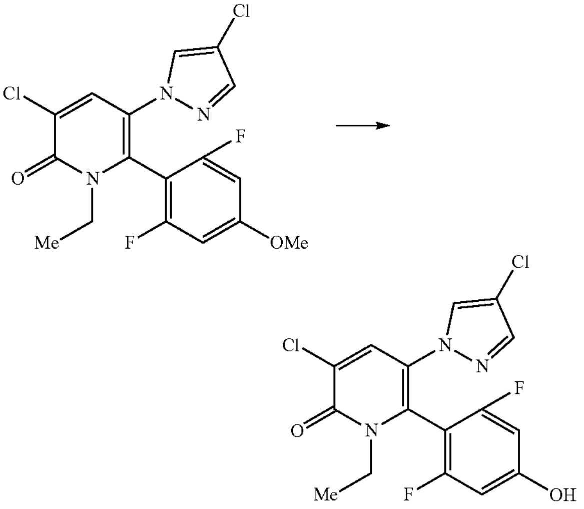

2 ml of an acetic acid solution containing 27 mg of 3-chloro-5-(4-chloro-1H-pyrazol-1-yl)-6-(2,6-difluoro-4-methoxyphenyl)-1-ethylpyridin-2(1H)-one and 2 ml of hydrobromic acid and the mixture was stirred at 110° C. for 7 hours. After cooling the mixture to room temperature, the mixture was neutralized by adding an aqueous sodium hydrogen carbonate solution. Ethyl acetate was added to the mixture and the liquids were separated, the obtained organic layer was washed with saturated brine, and dried over sodium sulfate. After the solvent was distilled off under reduced pressure, the obtained residue was purified by silica gel column chromatography. The title compound was obtained as 22 mg of a white solid.

Synthetic Example 36

Synthesis of 4-(5-chloro-3-(4-chloro-1H-pyrazol-1-yl)-1-ethyl-6-oxo-1,6-dihydropyridin-2-yl)-3,5-difluorophenylacetic acid (Compound No.: 205)

[Chem. 227]

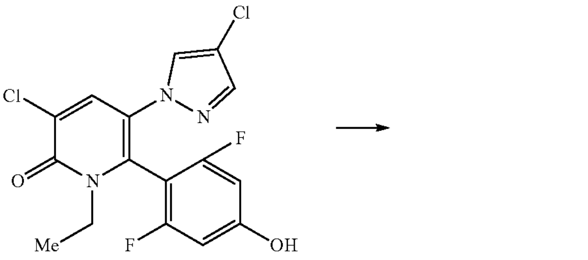

-continued

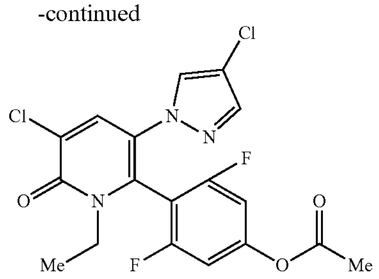

2 ml of a dichloroethane solution containing 80 mg of 3-chloro-5-(4-chloro-1H-pyrazol-1-yl)-6-(2,6-difluoro-4-hydroxyphenyl)-1-ethylpyridin-2(1H)-one, 98 μl of anhydrous acetic acid and 33 μl of pyridine was stirred at room temperature for 3 hours. 1N hydrochloric acid and dichloromethane were added to the reaction mixture; and the liquids were separated. The obtained organic layer was washed with saturated brine, and dried over sodium sulfate. After the solvent was distilled off under reduced pressure, the obtained residue was purified by silica gel column chromatography. The title compound was obtained as 70 mg of an orange white solid.

Synthetic Example 37

Synthesis of 6-(4-(allyloxy)-2,6-difluorophenyl)-3-chloro-5-(4-chloro-1H-pyrazol-1-yl)-1-ethylpyridin-2(1H)-one (Compound No.: 202)

[Chem. 228]

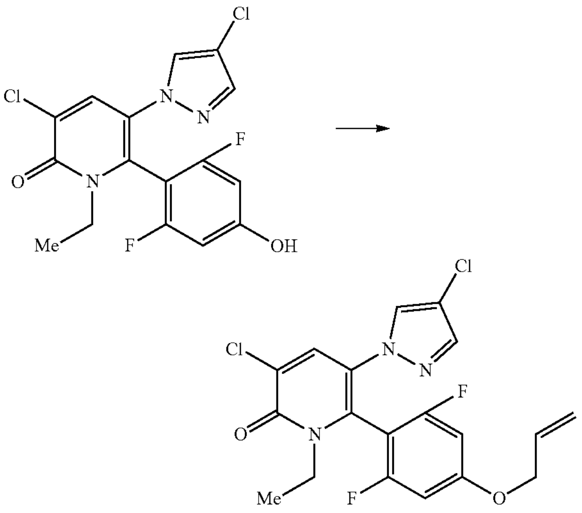

2 ml of an acetonitrile solution containing 70 mg of 3-chloro-5-(4-chloro-1H-pyrazol-1-yl)-6-(2,6-difluoro-4-hydroxyphenyl)-1-ethylpyridin-2(1H)-one, 23 μl of allyl bromide and 89 mg of cesium carbonate was stirred at room temperature for 3 hours. Then, 31 μl of allyl bromide was added, and the mixture was stirred at room temperature for 1 hour. An aqueous ammonium chloride solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 49 mg of a yellowish white solid.

Synthetic Example 38

Synthesis of 3-chloro-5-(4-chloro-1H-pyrazol-1-yl)-6-(2,6-difluoro-4-(propargyloxy)phenyl)-1-ethyl pyridin-2(1H)-one (Compound No.: 201)

[Chem. 229]

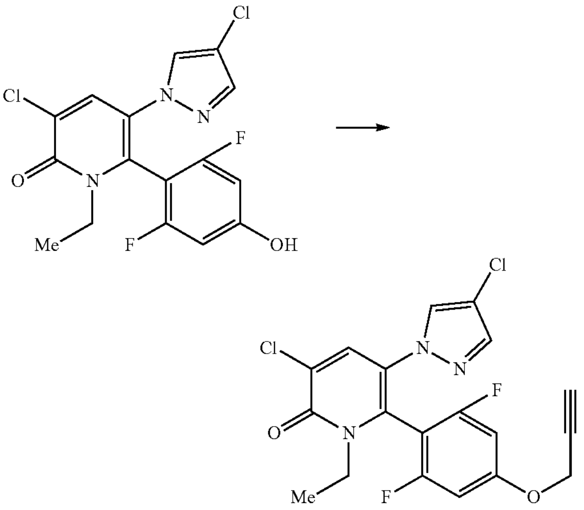

2 ml of an acetonitrile solution containing 70 mg of 3-chloro-5-(4-chloro-1H-pyrazol-1-yl)-6-(2,6-difluoro-4-hydroxyphenyl)-1-ethylpyridin-2(1H)-one, 20 μl of propargyl bromide and 85 mg of cesium carbonate was stirred at room temperature for 3 hours. Then, 27 μl of propargyl bromide was added thereto, and the mixture was stirred at room temperature for 1 hour. An aqueous ammonium chloride solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 64 mg of a yellowish white solid.

Synthetic Example 39

Synthesis of 3-chloro-5-(4-chloro-1H-pyrazol-1-yl)-6-(2,6-difluoro-4-(2-methoxyethoxy)phenyl)-1-ethylpyridin-2(1H)-one (Compound No.: 204)

[Chem. 230]

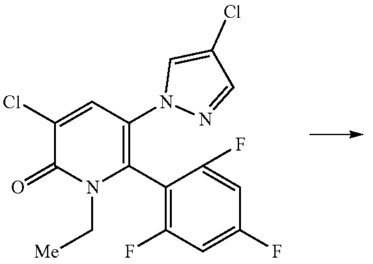

-continued

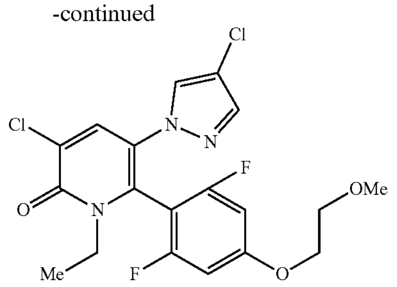

4 ml of a THF solution containing 75 mg of 3-chloro-5-(4-chloro-1H-pyrazol-1-yl)-1-ethyl-6-(2,4,6-trifluorophenyl)pyridin-2(1H)-one, 23 mg of 60% sodium hydride and 46 μl of 2-methoxyethanol was stirred at room temperature for 2 hours. An aqueous ammonium chloride solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 65 mg of a white solid.

Synthetic Example 40

Step 1: Synthesis of 6-(2,4-difluorophenyl)-5-(4-methyl-1H-pyrazol-1-yl)-3,4-dihydropyridin-2(1H)-one

[Chem. 231]

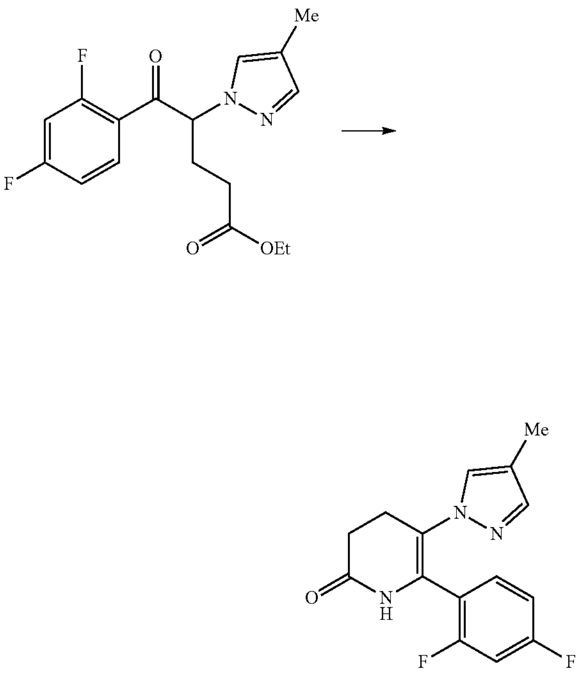

To 4.79 g of ethyl 5-(2,4-difluorophenyl)-4-(4-methyl-1H-pyrazol-1-yl)-5-oxopentanoate obtained in Reference Example 35 were added 21.8 g of ammonium acetate and 24.0 ml of acetic acid, and the mixture was stirred at 120° C. for 1.5 hours. After cooling the mixture to room temperature, an aqueous potassium carbonate solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 2.42 g of a brown solid.

$^1$H-NMR ($CDCl_3$) δ: 7.35 (1H, s), 7.06-7.00 (1H, m), 6.87-6.78 (2H, m), 6.75 (1H, s), 6.71 (1H, s), 3.03-3.01 (2H, m), 2.83-2.79 (2H, m), 1.93 (3H, s).

Step 2: Synthesis of 6-(2,4-difluorophenyl)-1-ethyl-5-(4-methyl-1H-pyrazol-1-yl)-3,4-dihydropyridin-2(1H)

[Chem. 232]

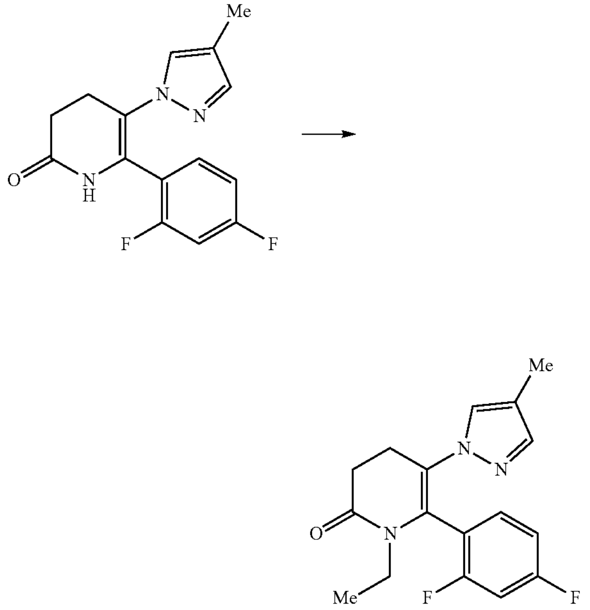

5 ml of DMF containing 513 mg of 6-(2,4-difluorophenyl)-5-(4-methyl-1H-pyrazol-1-yl)-3,4-dihydropyridin-2(1H)-one, 211 μl of ethyl iodide and 859 mg of cesium carbonate was stirred at 50° C. for 1.5 hours. Further, 70.3 μl of ethyl iodide and 286 mg of cesium carbonate were added thereto, and the mixture was stirred at 50° C. for 30 minutes. After cooling the mixture to room temperature, an aqueous saturated ammonium chloride solution and ethyl acetate were added to the reaction mixture and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 463 mg of a brown solid.

$^1$H-NMR ($CDCl_3$) δ: 7.28-7.25 (1H, m), 7.13-7.07 (1H, m), 6.87-6.79 (2H, m), 6.74 (1H, s), 3.62-3.55 (1H, m), 3.22-3.18 (1H, m), 3.01-2.94 (1H, m), 2.83-2.72 (3H, m), 1.90 (3H, s), 0.94 (3H, t, J=7.1 Hz).

Step 3: Synthesis of 6-(2,4-difluorophenyl)-1-ethyl-5-(4-methyl-1H-pyrazol-1-yl)pyridin-2(1H)-one (Compound No.: 505)

[Chem. 233]

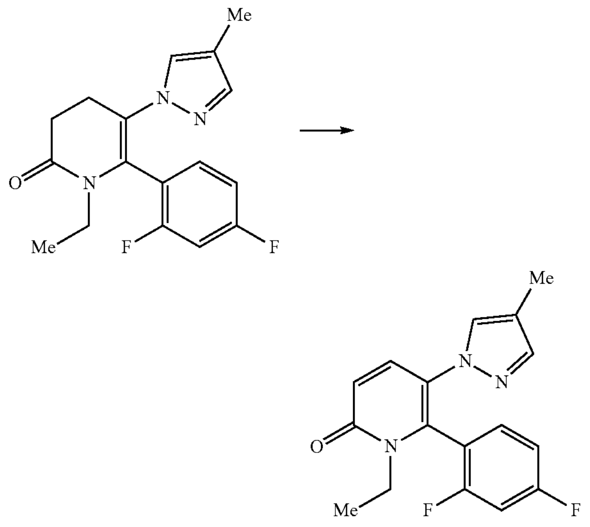

To 9.0 ml of a carbon tetrachloride solution containing 463 mg of 6-(2,4-difluorophenyl)-1-ethyl-5-(4-methyl-1H-pyrazol-1-yl)-3,4-dihydropyridin-2(1H)-one were added 312 mg of N-bromosuccinimide and 68 mg of 2,2'-azobis (4-methoxy-2,4-dimethylvaleryonitrile), and the mixture was stirred at 40° C. for 1.5 hours. Water and ethyl acetate were added to the reaction mixture and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 249 mg of a white solid.

Synthetic Example 41

Synthesis of 3-bromo-6-(2,4-difluorophenyl)-1-ethyl-5-(4-methyl-1H-pyrazol-1-yl)pyridin-2(1H)-one (Compound No.: 226)

[Chem. 234]

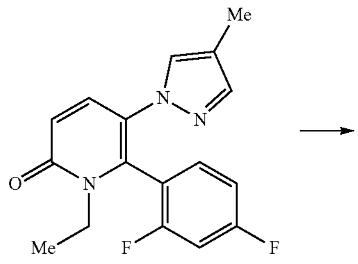

-continued

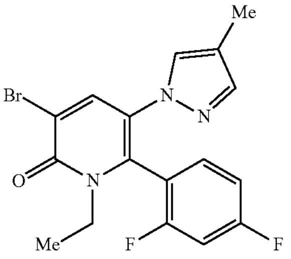

4 ml of an acetonitrile solution containing 249 mg of 6-(2,4-difluorophenyl)-1-ethyl-5-(4-methyl-1H-pyrazol-1-yl)pyridin-2(1H)-one and 169 mg of N-bromosuccinimide was stirred at 50° C. for 10 minutes. After cooling the mixture to room temperature, an aqueous sodium thiosulfate solution and ethyl acetate were added to the reaction mixture and the liquids were separated. The obtained organic layer was washed with saturated brine, and dried over sodium sulfate. The solvent was distilled off under reduced pressure, and the obtained residue was purified by silica gel column chromatography. The title compound was obtained as 230 mg of a white solid.

Synthetic Example 42

Synthesis of 3-bromo-5-(5-chloro-4-methyl-1H-pyrazol-1-yl)-6-(2,4-difluoro-phenyl)-1-ethylpyridin-2(1H)-one (Compound No.: 228)

[Chem. 235]

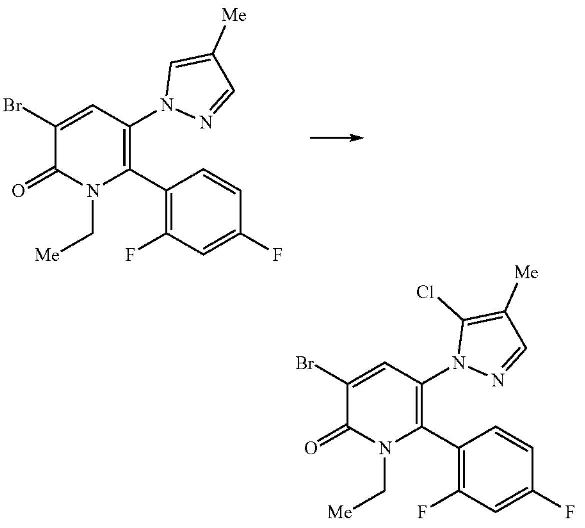

3 ml of an acetonitrile solution containing 184 mg of 3-bromo-6-(2,4-difluorophenyl)-1-ethyl-5-(4-methyl-1H-pyrazol-1-yl)pyridin-2(1H)-one and 81 mg of N-chlorosuccinimide was stirred at 80° C. for 30 minutes. Further, 19 mg of N-chlorosuccinimide was added thereto at 50° C., and the mixture was stirred at 80° C. for 10 minutes. After cooling the mixture to room temperature; water and ethyl acetate were added to the reaction mixture and the liquids were separated. The obtained organic layer was successively washed with an aqueous sodium thiosulfate solution and saturated brine, and dried over sodium, sulfate. The solvent was distilled off under reduced pressure, and the obtained residue was purified by silica gel column chromatography. The title compound was obtained as 64 mg of a white solid.

Reference Example 1

Synthesis of 1-(2,6-difluorophenyl)-2-(thiophen-2-yl)ethan-1-one

[Chem. 236]

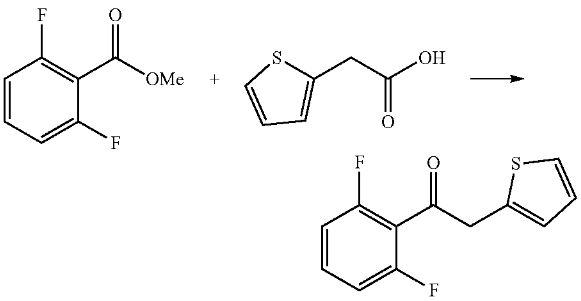

To 100 ml of a THF solution containing 10.00 g of 2-(thiophen-2-yl)acetic acid was added dropwise 118.5 ml of a 1.9 mol/L THF solution of hexamethyldisilazane sodium at −78° C. and the mixture was stirred for 1 hour. Then, 20 ml of a THF solution containing 12.11 g of methyl 2,6-difluorobenzoate was added dropwise thereto, then, the temperature of the mixture was raised from −78° C. to room temperature and stirred for 2.5 hours. To the mixture was added an aqueous saturated ammonium chloride solution followed by stirring for 1 hour. Thereafter, ethyl acetate were added and the liquids were separated. The obtained organic layer was washed with saturated brine, and dried over magnesium sulfate. After the solvent was distilled off under reduced pressure, the obtained residue was purified by silica gel column chromatography. The title compound was obtained as 10.35 g of a red oily product.

$^1$H-NMR ($CDCl_3$) δ: 7.39 (1H, m), 7.22 (1H, m), 6.95 (4H, m), 4.36 (1H, s).

Reference Example 2

Synthesis of ethyl 5-(2,6-difluorophenyl)-5-oxo-4-(thiophen-2-yl)pentanoate

[Chem. 237]

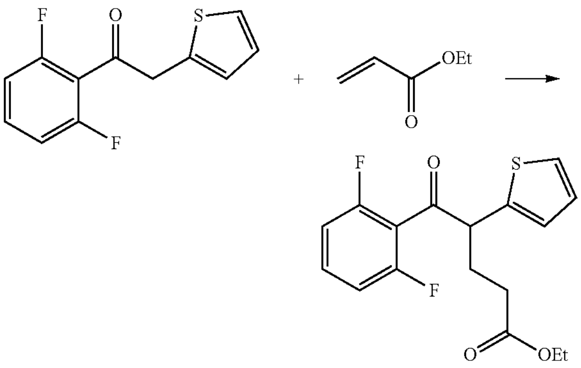

To 104 ml of a THF solution containing 10.35 g of 1-(2,6-difluorophenyl)-2-(thiophen-2-yl)ethan-1-one obtained in Reference Example 1 were added 730 mg of potassium t-butoxide and 5.20 ml of ethyl acrylate, and the mixture was stirred at −3° C. for 23 hours. To the mixture were added 1N hydrochloric acid and ethyl acetate and after separating the liquids, the obtained organic layer was washed with saturated brine, and dried over magnesium sulfate. The solvent was distilled off under reduced pressure to obtain 12.79 g of a red oily product containing the title compound. The product was used in the next reaction without further purification.

Reference Example 3

Synthesis of 5-(2,6-difluorophenyl)-5-oxo-4-(thiophen-2-yl)pentanoic acid

[Chem. 238]

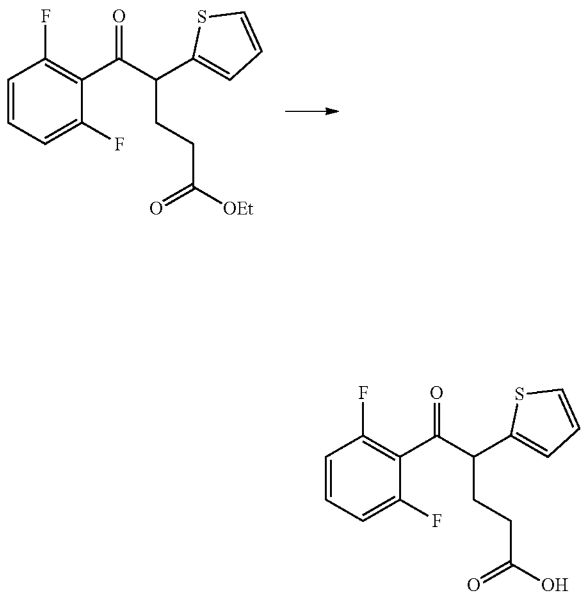

To a mixed solution of 102 ml of THF containing 3.37 g of ethyl 5-(2,6-difluorophenyl)-5-oxo-4-(thiophen-2-yl)pentanoate obtained in Reference Example 2 and 26 ml of water was added 7.93 g of lithium hydroxide monohydrate, and the mixture was stirred at 50° C. for 2.5 hours. After cooling the mixture to room temperature, the solvent of the reaction mixture was distilled off until the amount of the liquid became about a half. To the residue were added water and diethyl ether and the liquids were separated, conc. hydrochloric acid and ethyl acetate were added to the obtained aqueous layer and the liquids were separated. The obtained organic layer was washed with saturated brine, and dried over magnesium sulfate. Then, the solvent was distilled off under reduced pressure to obtain 8.64 g of a pale yellowish oily product containing the title compound. The product was used in the next reaction without further purification.

Reference Example 4

Synthesis of 2-(2-chloropyridin-3-yl)-1-(2,6-difluorophenyl)ethan-1-one

[Chem. 239]

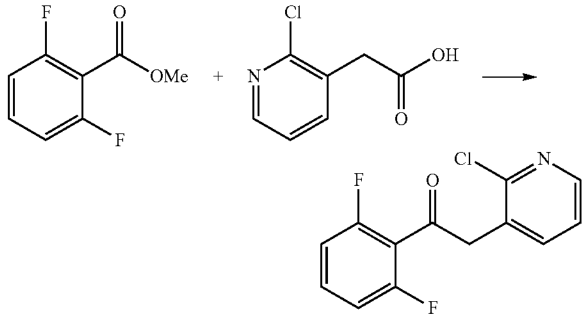

To 30 ml of a THF solution containing 700 mg of 2-(2-chloropyridin-3-yl)acetic acid was added dropwise 7.75 ml of a 1.9 mol/L THF solution of hexamethyldisilazane sodium at −78° C. and the mixture was stirred for 10 minutes. Then, 616 μl of methyl 2,6-difluorobenzoate was added dropwise thereto, and then, the temperature of the mixture was raised from −78° C. to room temperature and stirred for 1 hour. To the mixture was added an aqueous saturated ammonium chloride solution followed by stirring the mixture for 1 hour. Thereafter, ethyl acetate was added thereto and the liquids were separated. The obtained organic layer was washed with saturated brine, and dried over sodium sulfate. After the solvent was distilled off under reduced pressure, the obtained residue was purified by silica gel column chromatography. The title compound was obtained as 450 mg of a transparent oily product.

$^1$H-NMR ($CDCl_3$) δ: 8.35 (1H, dd, J=4.7, 1.8 Hz), 7.66 (1H, dd, J=7.6, 1.8 Hz), 7.44-7.43 (1H, m), 7.25 (2H, dd, J=7.6, 4.7 Hz), 7.00-6.96 (2H, m).

Reference Example 5

Synthesis of ethyl 4-(2-chloropyridin-3-yl)-5-(2,6-difluorophenyl)-5-oxopentanoate

[Chem. 240]

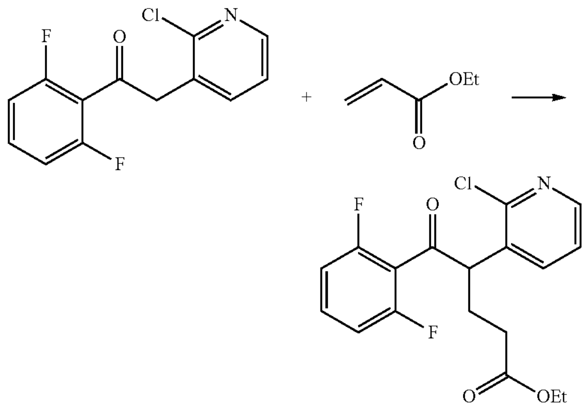

To 10 ml of a THF solution containing 450 mg of 2-(2-chloropyridin-3-yl)-1-(2,6-difluorophenyl)ethan-1-one were added 84 mg of potassium t-butoxide and 192 μl of ethyl acrylate, and the mixture was stirred at room temperature for 2.5 hours. Further, 28 mg of potassium t-butoxide and 154 μl of ethyl acrylate were added thereto, and the mixture was stirred at 60° C. for 7 hours. After cooling the mixture to room temperature, 1N hydrochloric acid and ethyl acetate were added thereto followed by separating the liquids. Thereafter, the obtained organic layer was washed with saturated brine, and dried over sodium sulfate. The solvent was distilled off under reduced pressure to obtain 589 mg of a yellow oily product containing the title compound. The product was used in the next reaction without further purification.

Reference Example 6

Synthesis of 4-(2-chloropyridin-3-yl)-5-(2,6-difluorophenyl)-5-oxopentanoic acid

[Chem. 241]

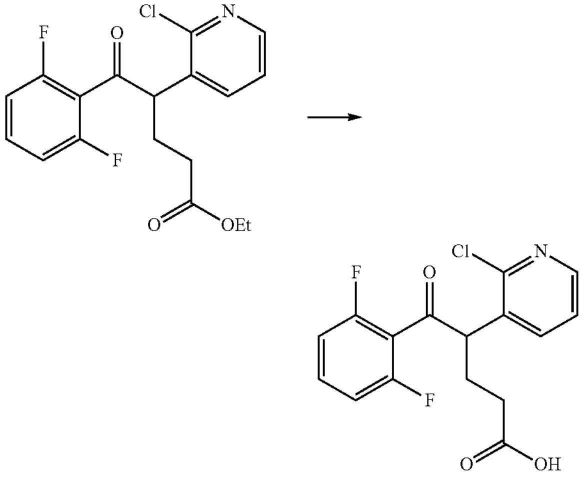

To a mixed solution of 15 ml of THF containing 589 mg of ethyl 4-(2-chloropyridin-3-yl)-5-(2,6-difluorophenyl)-5-oxopentanoate obtained in Reference Example 5 and 15 ml of water was added 335 mg of lithium hydroxide monohydrate, and the mixture was stirred at 60° C. for 3.5 hours. After cooling the mixture to room temperature, an aqueous saturated sodium hydrogen carbonate solution and diethyl ether were added thereto to separate the liquids, then, conc. hydrochloric acid and ethyl acetate were added to the obtained aqueous layer and the liquids were separated. The obtained organic layer was washed with saturated brine, and dried over magnesium sulfate. Then, the solvent was distilled off under reduced pressure to in 250 mg of a yellow oily product containing the title compound. The product was used in the next reaction without further purification.

$^1$H-NMR ($CDCl_3$) δ: 8.30 (1H, dd, J=4.6, 1.8 Hz), 7.67 (1H, dd, J=7.6, 1.8 Hz), 7.36-7.34 (1H, m), 7.28-7.24 (1H, m), 6.90-6.85 (2H, m), 4.92 (1H, t, J=7.2 Hz), 2.63-2.26 (5H, m).

Reference Example 7

Synthesis of N-phenyl-1-(2,4,6-trifluorophenyl)propan-1-imine

[Chem. 242]

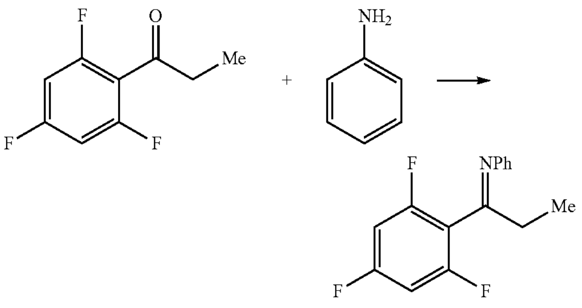

To 30 ml of a dichloromethane solution containing 3.64 ml of aniline and 7.41 ml of triethylamine was added dropwise 15 ml of a dichloromethane solution containing 4.37 ml of titanium tetrachloride at 00° C., and the mixture was stirred for 15 minutes. Then, 10 ml of a dichloromethane solution containing 5.00 g of 1-(2,4,6-trifluoro-phenyl) propan-1-one was added thereto at 000° C., and the mixture was stirred under room temperature for 3.5 hours. 1N hydrochloric acid and dichloromethane were added to the obtained reaction mixture and the liquids were separated. The obtained organic layer was washed with water, and dried over sodium sulfate. The solvent was distilled off under reduced pressure to obtain 7.08 g of a yellow oily product containing the title compound.

$^1$H-NMR ($CDCl_3$) δ: 7.16-7.11 (2H, m), 6.96-6.92 (1H, m), 6.69-6.67 (2H, m), 6.52-6.49 (2H, m), 2.73 (2H, q, J=7.4 Hz), 1.25 (3H, t, J=7.4 Hz).

Reference Example 8

Synthesis of 5-methyl-6-(2,4,6-trifluorophenyl)-3,4-dihydropyridin-2(1H)-one

[Chem. 243]

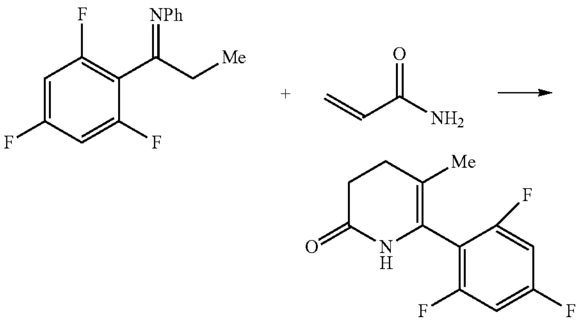

To 70 ml of 1,4-dioxane containing 7.08 g of N-phenyl-1-(2,4,6-trifluoro-phenyl)propan-1-imine obtained in Reference Example 7 were added 3.90 g of aluminum chloride and 2.08 g of acrylamide, and the mixture was stirred at 90° C. for 5 hours. After cooling the mixture to room temperature, 1N hydrochloric acid and ethyl acetate were added thereto and the liquids were separated. The obtained organic layer was washed with saturated brine, and dried over sodium sulfate. After the solvent was distilled off under reduced pressure, the obtained residue was purified by silica gel column chromatography. The title compound was obtained as 3.86 g of a white solid.

$^1$H-NMR ($CDCl_3$) δ: 6.76-6.72 (2H, m), 6.58 (1H, s), 2.60-2.57 (2H, ni), 2.47-2.45 (2H, m), 1.61 (3H, s).

Reference Example 9

Synthesis of 1-ethyl-5-methyl-6-(2,4,6-trifluorophenyl)-3,4-dihydropyridin-2(1H)-one

[Chem. 244]

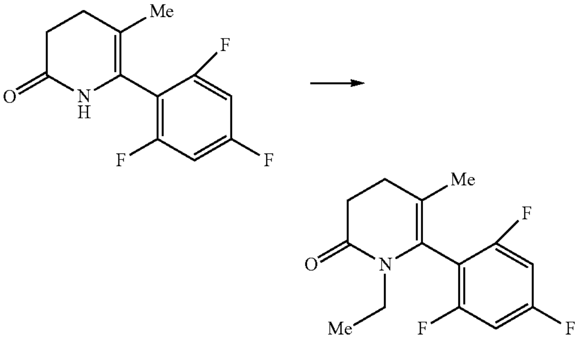

40 ml of DMF containing 3.86 g of 5-methyl-6-(2,4,6-trifluorophenyl)-3,4-dihydropyridin-2(1H)-one, 5.12 ml of ethyl iodide and 20.85 g of cesium carbonate was stirred at 60° C. for 10 hours. After cooling the mixture to room temperature, water and ethyl acetate were added to the reaction mixture and the liquids were separated. The obtained organic layer was washed with saturated brine, and dried over sodium sulfate. After the solvent was distilled off under reduced pressure, the obtained solid was washed with diisopropyl ether. The title compound was obtained as 4.01 g of a white solid.

$^1$H-NMR ($CDCl_3$) δ: 6.77-6.72 (2H, m), 3.32 (2H, q, J=7.1 Hz), 2.59-2.56 (2H, m), 2.37-2.35 (2H, m), 0.92 (3H, t, J=7.1 Hz).

Reference Example 10

Synthesis of 1-ethyl-5-methyl-6-(2,4,6-trifluorophenyl)pyridin-2(1H)-one

[Chem. 245]

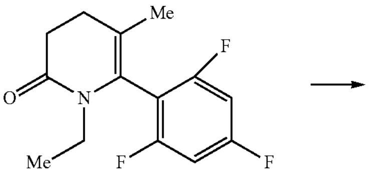

-continued

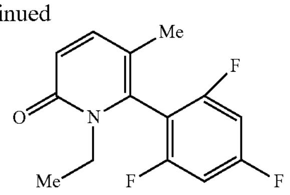

60 ml of a toluene solution containing 4.00 g of 1-ethyl-5-methyl-6-(2,4,6-trifluorophenyl)-3,4-dihydropyridin-2(1H)-one obtained in Reference Example 9 and 6.75 g of 2,3-dichloro-5,6-dicyano-p-benzoquinone was stirred at 120° C. for 5 hours. Further, 1.69 g of 2,3-dichloro-5,6-dicyano-p-benzoquinone was added to the reaction mixture, and the mixture was stirred at 120° C. for 2 hours. After cooling the mixture to room temperature, the obtained reaction mixture was filtered. After the solvent of the organic layer was distilled off under reduced pressure, the obtained residue was purified by silica gel column chromatography, and then, the solid was washed with diisopropyl ether. The title compound was obtained as 3.50 g of a white solid.

$^1$H-NMR ($CDCl_3$) δ: 7.26 (1H, d, J=9.5 Hz), 6.88-6.84 (2H, m), 6.64 (1H, d, J=9.5 Hz), 3.82 (2H, q, J=7.1 Hz), 1.81 (3H, s), 1.10 (3H, t, J=7.1 Hz).

Reference Example 11

Synthesis of 3-chloro-1-ethyl-5-methyl-6-(2,4,6-trifluorophenyl)pyridin-2(1H)-one

[Chem. 246]

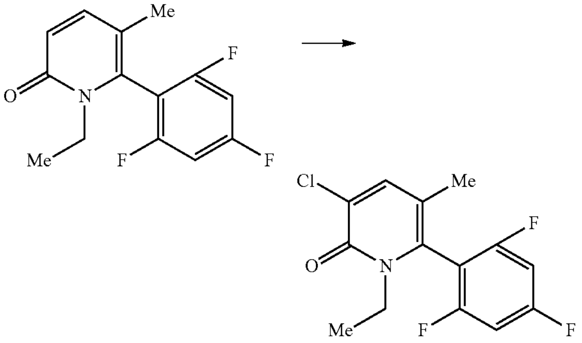

3 ml of DMF solution containing 97 mg of 1-ethyl-5-methyl-6-(2,4,6-trifluorophenyl)pyridin-2(1H)-one and 49 mg of N-chlorosuccinimide was stirred at 70° C. for 4 hours. Further, 32 mg of N-chlorosuccinimide was added to the reaction mixture, and the mixture was stirred at 70° C. for 1 hour. After cooling the mixture to room temperature, water and ethyl acetate were added and the liquids were separated. The obtained organic layer was washed with saturated brine, and dried over sodium sulfate. After the solvent was distilled off under reduced pressure, the obtained residue was purified by silica gel column chromatography. The title compound was obtained as 86 mg of a white solid.

$^1$H-NMR ($CDCl_3$) δ: 7.50 (1H, s), 6.89-6.85 (2H, m), 3.87 (2H, q, J=7.1 Hz), 1.82 (3H, s), 1.13 (3H, t, J=7.1 Hz).

Reference Example 12

Synthesis of 3-chloro-5-(dibromomethyl)-1-ethyl-6-(2,4,6-trifluorophenyl)-pyridin-2-one

[Chem. 247]

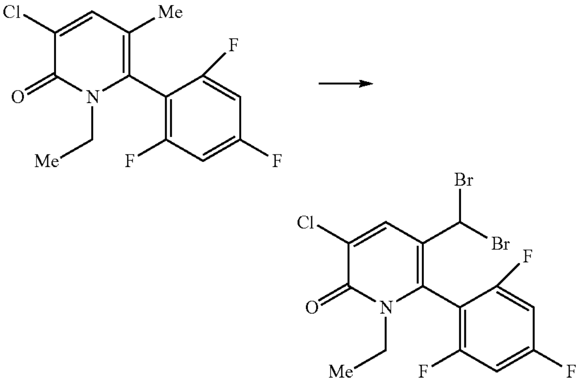

To 70 ml of chlorobenzene solution containing 3.86 g of 3-chloro-1-ethyl-5-methyl-6-(2,4,6-trifluorophenyl)pyridin-2(1H)-one were added 4.78 g of N-bromosuccinimide and 113.9 mg of azobisisobutyronitrile, and the mixture was stirred at 110° C. for 1 hour. After cooling the mixture to room temperature, water and dichloromethane were added thereto and the liquids were separated. The obtained organic layer was successively washed with an aqueous sodium thiosulfate solution and saturated brine, and dried over sodium sulfate. After the solvent was distilled off under reduced pressure, the obtained residue was purified by silica gel column chromatography. The title compound was obtained as 5.40 g of brown oily product.

$^1$H-NMR ($CDCl_3$) δ: 8.13 (1H, s), 6.97-6.93 (2H, m), 5.96 (1H, s), 3.81 (2H, q, J=7.1 Hz), 1.14 (3H, t, J=7.1 Hz).

Reference Example 13

Synthesis of 5-chloro-1-ethyl-6-oxo-2-(2,4,6-trifluorophenyl)-1,6-dihydro-pyridin-3-carboaldehyde

[Chem. 248]

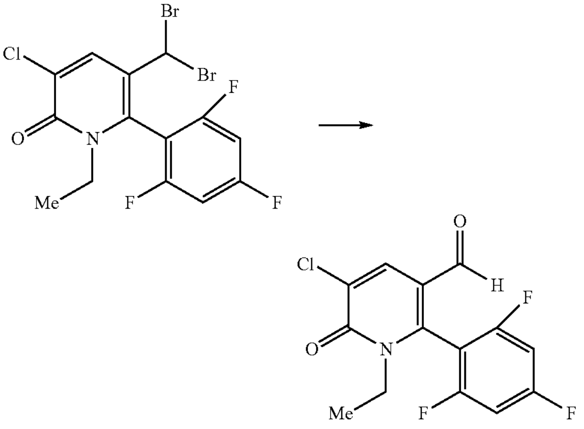

To 95 ml of acetonitrile solution containing 5.40 g of 3-chloro-5-(dibromomethyl)-1-ethyl-6-(2,4,6-trifluorophenyl)pyridin-2-one was added 47 ml of an aqueous solution containing 5.99 g of silver nitrate, and the mixture was stirred under room temperature for 1 hour. The reaction mixture was filtered through Celite, and washed with ethyl acetate. The obtained organic layer was successively washed with water, 1N hydrochloric acid and saturated brine, and dried over sodium sulfate. After the solvent was distilled off under reduced pressure, the obtained solid was washed with diisopropyl ether. The title compound was obtained as 3.56 g of a white solid.

$^1$H-NMR ($CDCl_3$) δ: 9.23 (1H, s), 8.12 (1H, s), 6.97-6.94 (2H, m), 3.94 (2H, q, J=7.1 Hz), 1.20 (3H, t, J=7.1 Hz).

Reference Example 14

Synthesis of 3-chloro-1-ethyl-5-(1-hydroxyethyl)-6-(2,4,6-trifluorophenyl)-pyridin-2(1H)-one

[Chem. 249]

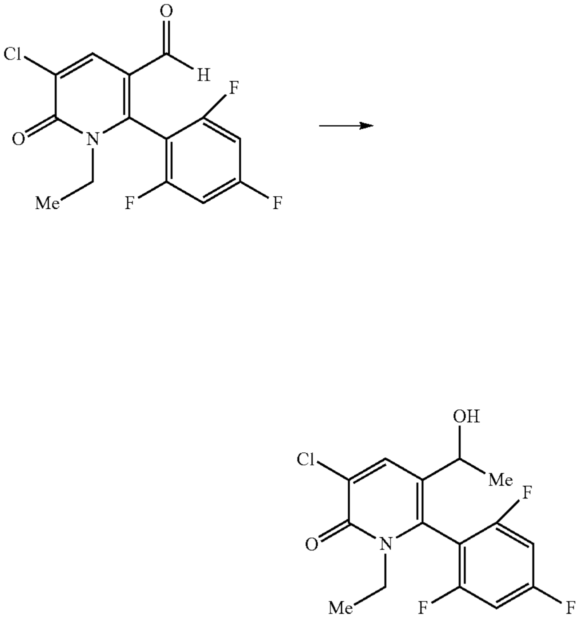

To 12 ml of a THF solution containing 1.13 g of 5-chloro-1-ethyl-6-oxo-2-(2,4,6-trifluorophenyl)-1,6-dihydropyridin-3-carboaldehyde was added dropwise 1.32 ml of a 3 mol/l THF solution of methylmagnesium chloride at −78° C. and stirred for 20 minutes. An aqueous saturated ammonium chloride solution and ethyl acetate were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 920 mg of a white solid.

$^1$H-NMR ($CDCl_3$) δ: 7.85 (1H, s), 6.92-6.86 (2H, m), 4.24 (1H, dq, J=2.8, 6.4 Hz), 3.85-3.81 (2H, m), 1.64 (1H, d, J=2.8 Hz), 1.30 (3H, d, J=6.4 Hz), 1.13 (3H, t, J=7.0 Hz).

Reference Example 15

Synthesis of 5-acetyl-3-chloro-1-ethyl-6-(2,4,6-trifluorophenyl)pyridin-2(1H)-one

[Chem. 250]

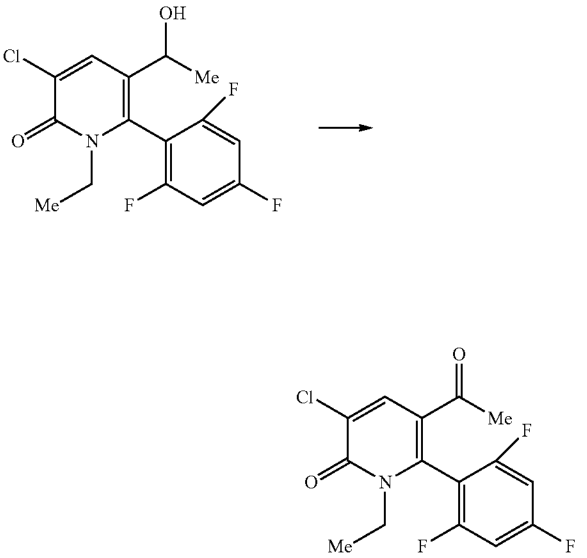

To 18 ml of a dichloromethane solution containing 910 mg of 3-chloro-1-ethyl-5-(1-hydroxyethyl)-6-(2,4,6-trifluorophenyl)pyridin-2(1H)-one was added 1.28 g of Dess-Martin periodinane (1,1,1-triacetoxy-1,1-dihydro-1,2-benziodoxol-3-(1H)-one), and the mixture was stirred at room temperature for 1 hour. Ethyl acetate was added to the reaction mixture and the mixture was filtered through Celite. After the solvent of the organic layer was distilled off under reduced pressure, the obtained residue was purified by silica gel column chromatography. The title compound was obtained as 870 mg of a white solid.

$^1$H-NMR ($CDCl_3$) δ: 8.02 (1H, s), 6.83-6.81 (2H, m), 3.91 (2H, q, J=7.1 Hz), 2.31 (3H, s), 1.14 (3H, t, J=7.1 Hz).

Reference Example 16

Synthesis of 3-chloro-5-(3-(dimethylamino)acryloyl)-1-ethyl-6-(2,4,6-trifluorophenyl)pyridin-2(1H)-one

[Chem. 251]

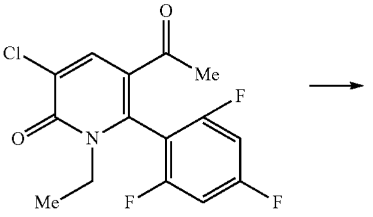

-continued

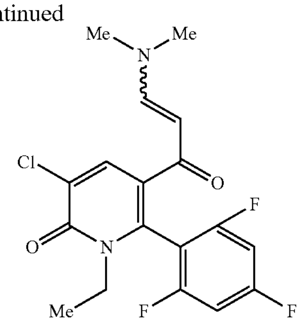

To 870 mg of 5-acetyl-3-chloro-1-ethyl-6-(2,4,6-trifluorophenyl)pyridin-2(1H)-one was added 8 ml of N,N-dimethylformamide dimethylacetal, and the mixture was stirred at 100° C. for 5 hours. After cooling the mixture to room temperature, ethyl acetate and water were added to the reaction mixture and the liquids were separated. The obtained organic layer was washed with saturated brine, and dried over sodium sulfate. After the solvent was distilled off under reduced pressure, the obtained residue was purified by silica gel column chromatography. The title compound was obtained as 859 mg of a yellow solid.

$^1$H-NMR ($CDCl_3$) δ: 7.88 (1H, s), 7.48 (1H, d, J=12.2 Hz), 6.79-6.77 (2H, m), 5.08 (1H, d, J=12.2 Hz), 3.92 (2H, q, J=7.1 Hz), 3.08 (3H, s), 2.81 (3H, s), 1.16 (3H, t, J=7.1 Hz).

Reference Example 17

Synthesis of 2-bromo-1-(2,4,6-trifluorophenyl)ethan-1-one

[Chem. 252]

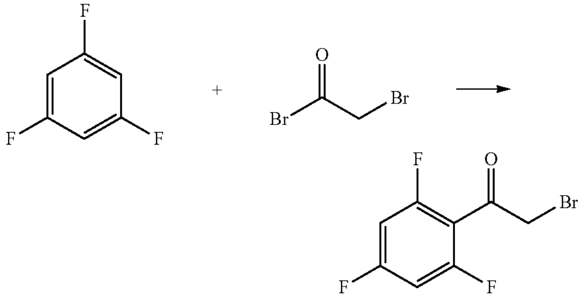

To 100 ml of a dichloromethane solution containing 5.50 g of 1,3,5-trifluorobenzene and 11.1 g of aluminum chloride was added dropwise 4.33 ml of bromoacetyl bromide at 0° C., and the reaction mixture was stirred under reflux by heating for 15 hours. After cooling the mixture to room temperature, an aqueous saturated sodium hydrogen carbonate solution and dichloromethane were added thereto and the mixture was filtered through Celite. After separating the liquids to the organic layer and the aqueous layer, the obtained organic layer was washed with saturated brine, and dried over sodium sulfate. After the solvent was distilled off under reduced pressure, the obtained residue was purified by silica gel column chromatography. The title compound was obtained as 4.26 g of an oily product.

$^1$H-NMR ($CDCl_3$) δ: 6.79-6.76 (2H, m), 4.33-4.33 (2H, m).

Reference Example 18

Synthesis of 2-(1H-1,2,4-triazol-1-yl)-1-(2,4,6-trifluorophenyl)ethan-1-one

[Chem. 253]

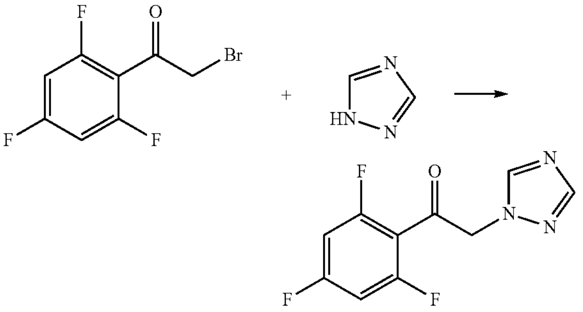

An ethyl acetate solution containing 4.26 g of 2-bromo-1-(2,4,6-trifluorophenyl)ethan-1-one, 2.56 g of 1H-1,2,4-triazole and 2.37 ml of triethylamine was stirred under reflux by heating for 1.5 hours. After cooling the mixture to room temperature, the reaction mixture was filtered through Celite, and washed with ethyl acetate. After the solvent was distilled off under reduced pressure, the obtained residue was purified by silica gel column chromatography. The title compound was obtained as 1.22 g of a brown solid.

$^1$H-NMR ($CDCl_3$) δ: 8.22 (1H, s), 7.99 (1H, s), 6.81-6.79 (2H, m), 5.46-5.45 (2H, m).

Reference Example 19

Synthesis of ethyl 5-oxo-4-(1H-1,2,4-triazol-1-yl)-5-(2,4,6-trifluorophenyl)-pentanoate

[Chem. 254]

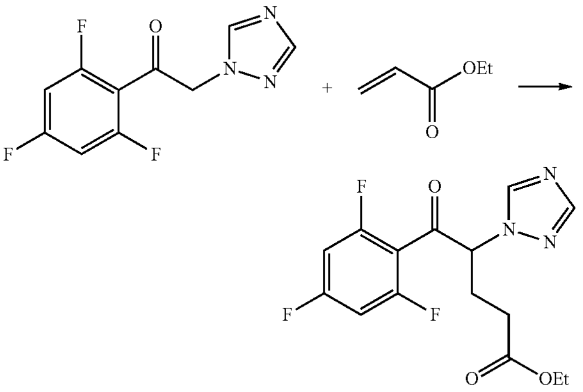

To 14 ml of a THF solution containing 1.43 g of 2-(1H-1,2,4-triazol-1-yl)-1-(2,4,6-trifluorophenyl)ethan-1-one were added 133 mg of potassium t-butoxide and 712 μl of ethyl acrylate, and the mixture was stirred under room temperature for 40 minutes. An aqueous saturated ammonium chloride solution and ethyl acetate were added to the mixture followed by separating the liquids. Thereafter, the obtained organic layer was washed with saturated brine, and dried over sodium sulfate. After the solvent was distilled off under reduced pressure, the obtained residue was purified by silica gel column chromatography. The title compound was obtained as 828 mg of a brown oily product.

$^1$H-NMR ($CDCl_3$) δ: 8.22 (1H, s), 7.90 (1H, s), 6.71-6.65 (2H, m), 5.79-5.76 (1H, m), 4.13 (2H, q, J=7.2 Hz), 2.67-2.63 (1H, m), 2.43-2.35 (2H, m), 2.12-2.07 (1H, m), 1.25 (3H, t, J=7.2 Hz).

Reference Example 20

Synthesis of 5-oxo-4-(1H-1,2,4-triazol-1-yl)-5-(2,4,6-trifluorophenyl)pentanoic acid

[Chem. 255]

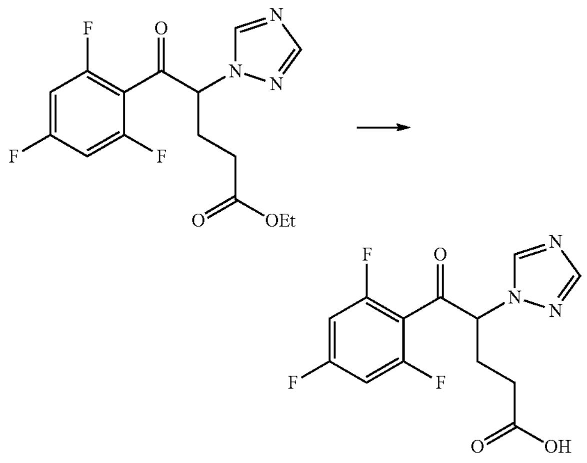

305 mg of lithium hydroxide monohydrate was added to a mixed solution comprising 8 ml of THF containing 828 mg of ethyl 5-oxo-4-(1H-1,2,4-triazol-1-yl)-5-(2,4,6-trifluorophenyl)pentanoate and 4 ml of water, and the mixture was stirred under room temperature for 1.5 hours. Diethyl ether was added to the reaction mixture followed by separation of the liquids, conc. hydrochloric acid and ethyl acetate were added to the obtained aqueous layer and the liquids were separated. The obtained organic layer was washed with saturated brine, and dried over sodium sulfate. Then, the solvent was distilled off under reduced pressure to obtain 709 mg of a brown solid containing the title compound. The product was used in the next reaction without further purification.

$^1$H-NMR ($CDCl_3$) δ: 8.26 (1H, s), 7.91 (1H, s), 6.70-6.67 (2H, m), 5.77-5.75 (1H, m), 3.52 (1H, br s), 2.68-2.65 (1H, m), 2.51-2.44 (2H, m), 2.25-2.18 (1H, m).

Reference Example 21

Synthesis of 2-chloro-1-(2,4,6-trifluorophenyl)ethan-1-one

[Chem. 256]

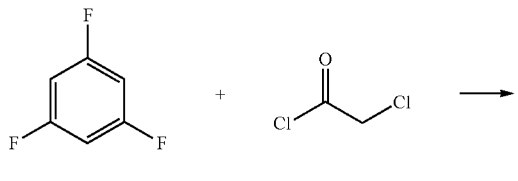

-continued

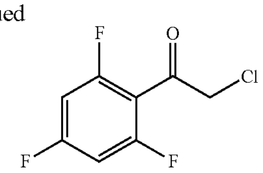

28.0 ml of dichloroethane solution containing 12.0 ml of 1,3,5-trifluorobenzene, 30.9 g of aluminum chloride and 11.1 ml of chloroacetyl chloride was stirred at 70° C. for 1 hour. After cooling the mixture to room temperature, iced water and ethyl acetate were added to the reaction mixture and the liquids were separated. The obtained organic layer was successively washed with an aqueous saturated sodium hydrogen carbonate solution and saturated brine, and dried over sodium sulfate. After the solvent was distilled off under reduced pressure, 24.8 g of a pale yellowish solid containing the title compound was obtained. The product was used in the next reaction without further purification.

$^1$H-NMR ($CDCl_3$) δ: 6.80-6.76 (2H, m), 4.51 (2H, t, J=1.1 Hz).

Reference Example 22

Synthesis of 2-(1H-pyrazol-1-yl)-1-(2,4,6-trifluorophenyl)ethan-1-one

[Chem. 257]

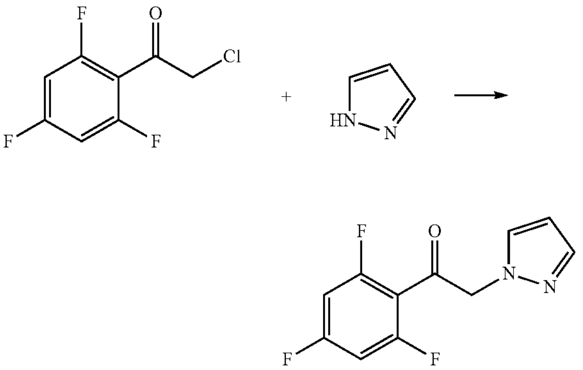

70.0 ml of a methyl isobutyl ketone solution containing 7.28 g of 2-chloro-1-(2,4,6-trifluorophenyl)ethan-1-one obtained in Reference Example 21 and 11.9 g of 1H-pyrazole was stirred at 120° C. for 5.5 hours. After cooling the mixture to room temperature, ethyl acetate and 1N hydrochloric acid were added to the reaction mixture and the liquids were separated. The obtained organic layer was successively washed with an aqueous saturated sodium hydrogen carbonate solution and saturated brine, and dried over sodium sulfate. After the solvent was distilled off under reduced pressure, the obtained residue was purified by silica gel column chromatography. The title compound was obtained as 3.74 g of a brown solid.

$^1$H-NMR ($CDCl_3$) δ: 7.55 (1H, d, J=1.7 Hz), 7.49 (1H, d, J=2.2 Hz), 6.77-6.72 (2H, m), 6.34 (1H-1, dd, J=2.2, 1.7 Hz), 5.37 (2H, t, J=1.2 Hz).

Reference Example 23

Synthesis of ethyl 5-oxo-4-(1H-pyrazol-1-yl)-5-(2,4,6-trifluorophenyl)-pentanoate

[Chem. 258]

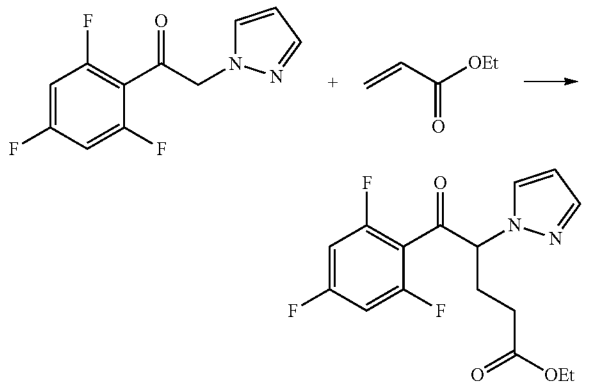

To 37.0 ml of a THF solution containing 3.74 g of 2-(1H-pyrazol-1-yl)-1-(2,4,6-trifluorophenyl)ethan-1-one were added 349 mg of potassium t-butoxide and 1.86 ml of ethyl acrylate, and the mixture was stirred at 40° C. for 55 minutes. After cooling the mixture to room temperature, an aqueous saturated ammonium chloride solution and ethyl acetate were added and the liquids were separated. The obtained organic layer was washed with saturated brine, and dried over sodium sulfate. The solvent was distilled off under reduced pressure to obtain 5.33 g of a reddish brown oily product containing the title compound. The product was used in the next reaction without further purification.

$^1$H-NMR ($CDCl_3$) δ: 7.47 (1H, d, J=2.4 Hz), 7.45 (1H, d, J=1.8 Hz), 6.64-6.59 (2H, m), 6.22 (1H, dd, J=2.4, 1.8 Hz), 5.57 (1H, dd, J=10.4, 4.9 Hz), 4.13 (2H, q, J=7.1 Hz), 2.66-2.59 (1H, m), 2.43-2.41 (1H, m), 2.33-2.31 (1H, m), 2.15-2.11 (1H, m), 1.25 (3H, t, J=7.1 Hz).

Reference Example 24

Synthesis of 5-oxo-4-(1H-pyrazol-1-yl)-5-(2,4,6-trifluorophenyl)pentanoic acid

[Chem. 259]

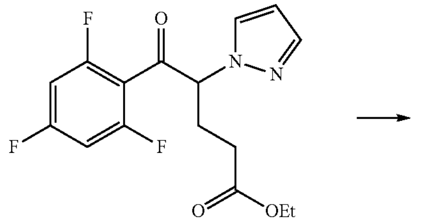

-continued

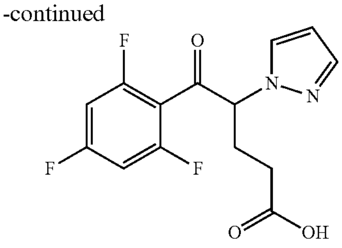

To 20 ml of THF containing 5.33 g of ethyl 5-oxo-4-(1H-pyrazol-1-yl)-5-(2,4,6-trifluorophenyl)pentanoate obtained in Reference Example 23 was added 10 ml of an aqueous solution containing 1.96 g of lithium hydroxide monohydrate, and the mixture was stirred at room temperature for 25 minutes. Diethyl ether was added to the reaction mixture followed by separation of the liquids, conc. hydrochloric acid and ethyl acetate were added to the obtained aqueous layer and the liquids were separated. The obtained organic layer was washed with saturated brine, and dried over sodium sulfate. Then, the solvent was distilled off under reduced pressure to obtain 3.66 g of a brown solid containing the title compound. The product was used in the next reaction without further purification.

$^1$H-NMR ($CDCl_3$) δ: 7.49 (1H, d, J=2.4 Hz), 7.48 (1H, d, J=1.8 Hz), 6.65-6.62 (2H, m), 6.25 (1H, dd, J=2.4, 1.8 Hz), 5.63 (1H, dd, J=10.2, 4.7 Hz), 2.69-2.61 (1H, m), 2.44-2.37 (2H, m), 2.21-2.15 (1H, m).

Reference Example 25

[Chem. 260]

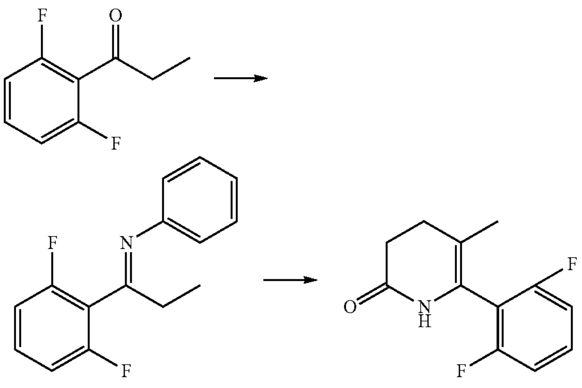

Step 1: Synthesis of 1-(2,6-difluorophenyl)-N-phenylpropan-1-imine

To 100 ml of a methylene chloride solution containing 11.74 g of aniline and 17.01 g of triethylamine was added dropwise 50 ml of a methylene chloride solution containing 23.91 g of titanium tetrachloride under ice-cooling. After 30 ml of a methylene chloride solution containing 14.30 g of 1-(2,6-difluorophenyl)propan-1-one was added dropwise to the reaction mixture, a temperature of the mixture was raised from ice-cooling to room temperature and the mixture was stirred overnight. To the obtained reaction mixture was added 1N hydrochloric acid followed by separation of the liquids, and the organic layer was dried over sodium sulfate. The solvent was distilled off under reduced pressure to obtain 21.10 g of a dark green oily product containing the title compound. The product was used in the next reaction without further purification.

Step 2: Synthesis of 6-(2,6-difluorophenyl)-5-methyl-3,4-dihydropyridin-2(1H)-one To 200 ml of a dioxane solution containing 21.10 g of 1-(2,6-difluorophenyl)-N-phenylpropan-1-imine obtained in Step 1 and 12.33 g of aluminum chloride was added 6.57 g of an acrylamide monomer, and the mixture was stirred at 90° C. for 3 hours. After the solvent of the reaction mixture was distilled off under reduced pressure until the amount of the liquid became about a half, 1N hydrochloric acid and ethyl acetate were added thereto and the liquids were separated. The obtained organic layer was washed with saturated brine, and dried over sodium sulfate. After the solvent was distilled off under reduced pressure, the obtained residue was purified by silica gel column chromatography. The obtained solid was washed with isopropyl ether, and the title compound was obtained as 11.65 g of a white solid.

$^{1}$H-NMR ($CDCl_3$) δ: 7.36-7.34 (1H, m), 6.97-6.94 (2H, m), 6.52 (1H, br s), 2.61-2.59 (2H, m), 2.48-2.47 (2H, m), 1.63 (3H, s).

Reference Example 26

Synthesis of 6-(2,6-difluorophenyl)-1-ethyl-5-methyl-3,4-dihydropyridin-2(1H)-one

[Chem. 261]

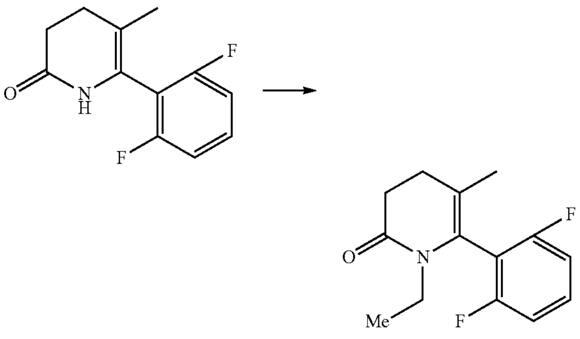

120 ml of a DMF solution containing 12.40 g of 6-(2,6-difluorophenyl)-5-methyl-3,4-dihydropyridin-2(1H)-one, 54.30 g of cesium carbonate and 25.99 g of ethyl iodide was stirred at 50° C. for 3.5 hours. Then, 27.15 g of cesium carbonate and 13.01 g of ethyl iodide were additionally added thereto, and then, the mixture was stirred at 50° C. for 2 hours, and further stirred at 60° C. for 1.5 hours. After cooling to room temperature, the reaction mixture was filtered to remove the insoluble materials. After the solvent of the filtrate was distilled off under reduced pressure, ethyl acetate and water were added to the residue and the liquids were separated. The obtained organic layer was successively washed with an aqueous sodium thiosulfate solution and saturated brine, and dried over sodium sulfate. After the solvent was distilled off under reduced pressure, the obtained solid was washed with isopropyl ether. The title compound was obtained as 11.98 g of a white solid.

$^{1}$H-NMR ($CDCl_3$) δ: 7.38-7.35 (1H, m), 6.97-6.96 (2H, m), 3.33 (2H, q, J=7.1 Hz), 2.60-2.58 (2H, m), 2.38-2.36 (2H, m), 1.59 (3H, s), 0.91 (3H, t, J=7.1 Hz).

Reference Example 27

Synthesis of 6-(2,6-difluorophenyl)-1-ethyl-5-methylpyridin-2(1H)-one

[Chem. 262]

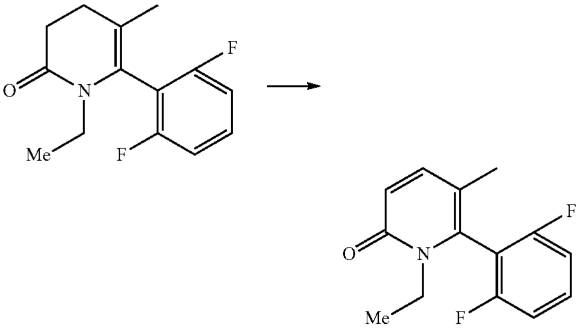

170 ml of a toluene solution containing 11.98 g of 6-(2,6-difluorophenyl)-1-ethyl-5-methyl-3,4-dihydropyridin-2(1H)-one and 21.65 g of 2,3-dichloro-5,6-dicyano-p-benzoquinone was stirred at 120° C. for 1.5 hours. After cooling the mixture to room temperature, the reaction mixture was filtered to remove the insoluble materials. After the solvent of the filtrate was distilled off under reduced pressure, the obtained residue was purified by silica gel column chromatography. The obtained solid was washed with isopropyl ether, and the title compound was obtained as 9.34 g of a pale yellow solid.

$^{1}$H-NMR ($CDCl_3$) δ: 7.50-7.49 (1H, m), 7.27 (2H, d, J=9.5 Hz), 7.09-7.06 (2H, m), 6.63 (1H, d, J=9.5 Hz), 3.83 (2H, q, J=7.1 Hz), 1.80 (3H, s), 1.10 (3H, t, J=7.1 Hz).

Reference Example 28

Synthesis of 3-chloro-6-(2,6-difluorophenyl)-1-ethyl-5-methylpyridin-2(1H)-one

[Chem. 263]

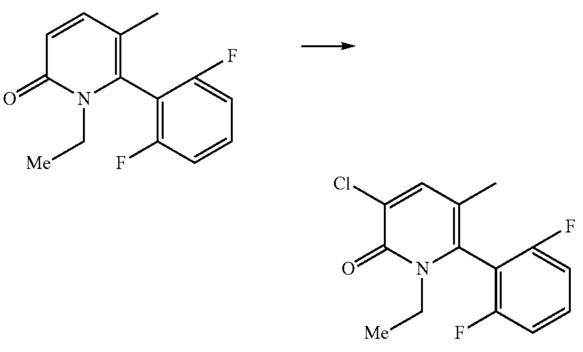

110 ml of a DMF solution containing 11.36 g of 6-(2,6-difluorophenyl)-1-ethyl-5-methylpyridin-2(1H)-one and 6.69 g of N-chlorosuccinimide was stirred at 70° C. for 50 minutes. After cooling the mixture to room temperature, the solvent of the reaction mixture was distilled off under reduced pressure. Ethyl acetate and water were added thereto followed by separation of the liquids. Thereafter, the obtained organic layer was successively washed with an aqueous sodium thiosulfate solution and saturated brine, and dried over sodium sulfate. After the solvent was distilled off under reduced pressure, the obtained solid was washed with isopropyl ether. The title compound was obtained as 11.41 g of a white solid.

$^1$H-NMR ($CDCl_3$) δ: 7.53-7.49 (1H, m), 7.50 (1H, s), 7.09-7.07 (2H, m), 3.88 (2H, q, J=7.1 Hz), 1.81 (3H, s), 1.12 (3H, t, J=7.1 Hz).

Reference Example 29

Synthesis of 3-chloro-5-(dibromomethyl)-6-(2,6-difluorophenyl)-1-ethyl-pyridin-2(1H)-one

[Chem. 264]

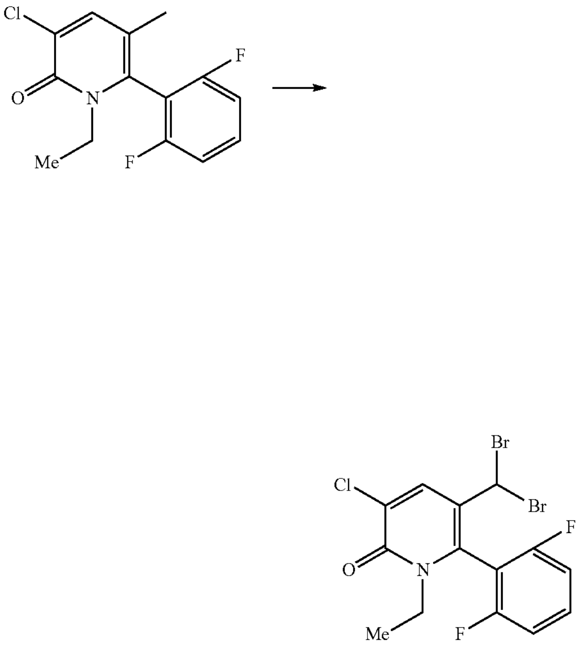

To 230 ml of a chlorobenzene solution containing 12.65 g of 3-chloro-6-(2,6-difluorophenyl)-1-ethyl-5-methylpyridin-2(1H)-one were added 16.67 g of N-bromosuccinimide and 366 mg of azobisisobutyronitrile, and the mixture was stirred at 110° C. for 50 minutes. After cooling the mixture to room temperature, water and dichloromethane were added to the reaction mixture and the liquids were separated. The obtained organic layer was washed with an aqueous sodium thiosulfate solution, and dried over sodium sulfate. After the solvent was distilled off under reduced pressure, the obtained solid was washed with isopropyl ether. The title compound was obtained as 16.88 g of a pale brown solid.

$^1$H-NMR ($CDCl_3$) δ: 8.13 (1H, s), 7.65-7.63 (1H, m), 7.18 (2H, dd, J=8.5, 6.8 Hz), 5.96 (1H, s), 3.82 (2H, q, J=7.1 Hz), 1.13 (3H, t, J=7.1 Hz).

Reference Example 30

Synthesis of 5-chloro-2-(2,6-difluorophenyl)-1-ethyl-6-oxo-1,6-dihydro-pyridin-3-carboaldehyde

[Chem. 265]

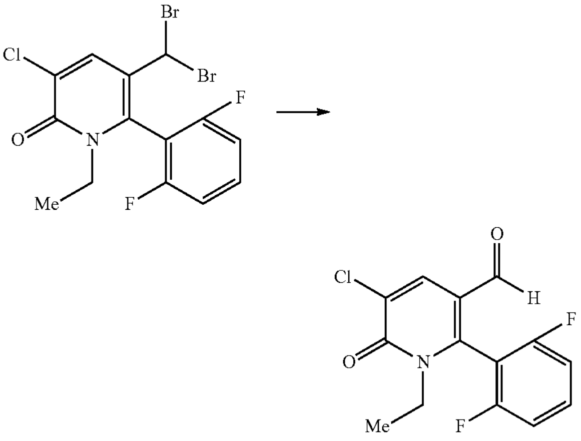

To 380 ml of acetonitrile containing 18.95 g of 3-chloro-5-(dibromomethyl)-6-(2,6-difluorophenyl)-1-ethylpyridin-2(1H)-one was added 190 ml of an aqueous solution containing 21.87 g of silver nitrate, and the mixture was stirred at room temperature for 15 minutes. The obtained reaction mixture was filtered to remove insoluble materials. After the solvent of the filtrate was distilled off under reduced pressure, water and ethyl acetate were added and the liquids were separated. The obtained organic layer was washed with 1N hydrochloric acid and saturated brine, and dried over sodium sulfate. After the solvent was distilled off under reduced pressure, the obtained solid was washed with isopropyl ether. The title compound was obtained as 11.37 g of a pale yellow solid.

$^1$H-NMR ($CDCl_3$) δ: 9.19 (1H, t, J=1.0 Hz), 8.13 (1H, s), 7.67-7.63 (1H, m), 7.18-7.16 (2H, m), 3.94 (2H, q, J=7.1 Hz), 1.19 (3H, t, J=7.1 Hz).

Reference Example 31

Synthesis of (E)-3-(5-chloro-1-ethyl-6-oxo-2-(2,6-difluorophenyl)-1,6-dihydropyridin-3-yl)acrylonitrile

[Chem. 266]

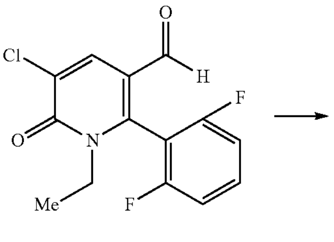

-continued

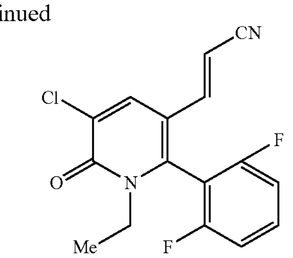

To 10 ml of a THF solution containing 202 mg of 60% sodium hydride was added 792 μl of diethyl cyanomethylphosphonate and the mixture was stirred at 0° C. for 30 minutes. Then, 500 mg of 5-chloro-2-(2,6-difluorophenyl)-1-ethyl-6-oxo-1,6-dihydropyridin-3-carboaldehyde was added thereto, and the mixture was stirred at 0° C. for 4 hours. An aqueous saturated ammonium chloride solution and ethyl acetate were added to the reaction mixture and the liquids were separated. The obtained organic layer was washed with saturated brine, and dried over magnesium sulfate. After the solvent was distilled off under reduced pressure, the obtained residue was purified by silica gel column chromatography. The title compound was obtained as 343 mg of a white solid.

$^1$H-NMR ($CDCl_3$) δ: 7.78 (1H, s), 7.67-7.63 (1H, m), 7.18-7.16 (2H, m), 6.58 (1H, d, J=16.4 Hz), 5.59 (1H, d, J=16.4 Hz), 3.89 (2H, q, J=7.1 Hz), 1.15 (3H, t, J=7.1 Hz).

Reference Example 32

Synthesis of 2-(4,5-dichloro-1H-imidazol-1-yl)-1-(2,4,6-trifluorophenyl)ethan-1-one

[Chem. 267]

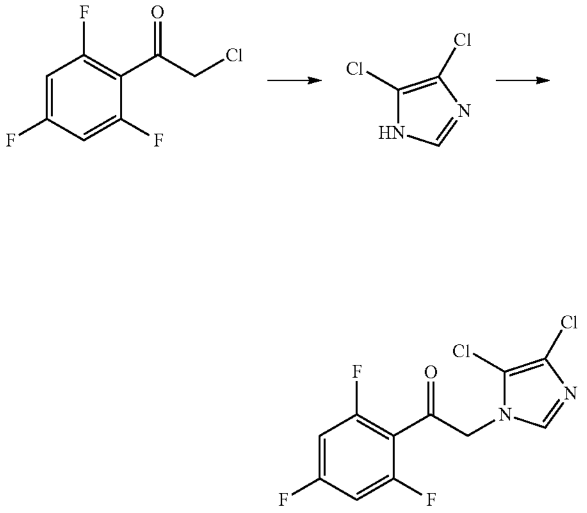

20.0 ml of a ethyl acetate solution containing 2.12 g of 2-chloro-1-(2,4,6-trifluorophenyl)ethan-1-one obtained in Reference Example 21, 1.70 g of 4,5-dichloroimidazole and 1.45 ml of triethylamine was stirred at 90° C. for 3 hours. Then, 1.70 g of 4,5-dichloroimidazole was added to the solution, and the mixture was stirred at 90° C. for 2 hours. After cooling the mixture to room temperature, ethyl acetate and 1N hydrochloric acid were added to the reaction mixture and the liquids were separated. The obtained organic layer was successively washed with an aqueous saturated sodium hydrogen carbonate solution and saturated brine, and dried over sodium sulfate. After the solvent was distilled off under reduced pressure, the obtained residue was purified by silica gel column chromatography. The title compound was obtained as 1.96 g of a white solid.

$^1$H-NMR ($CDCl_3$) δ: 7.44 (1H, s), 6.84-6.82 (2H, m), 5.14 (2H, s).

Reference Example 33

Synthesis of ethyl 4-(4,5-dichloro-1H-imidazol-1-yl)-5-oxo-5-(2,4,6-trifluoro-phenyl)pentanoate

[Chem. 268]

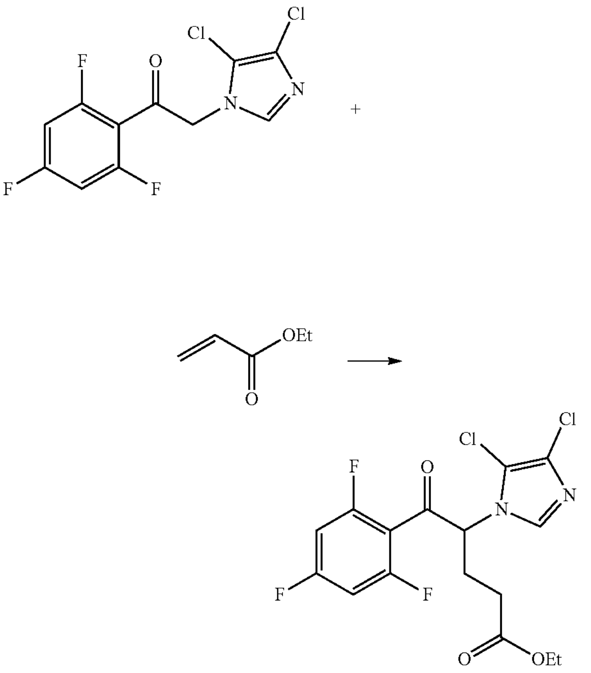

To 20.0 ml of a THF solution containing 1.96 g of 2-(4,5-dichloro-1H-imidazol-1-yl)-1-(2,4,6-trifluorophenyl)ethan-1-one obtained in Reference Example 32 were added 142 mg of potassium t-butoxide and 0.73 ml of ethyl acrylate, and the mixture was stirred at room temperature for 5.5 hours. Then, 71 mg of potassium t-butoxide and 173 μl of ethyl acrylate were added to the solution, and the mixture was stirred at room temperature for 1 hour. An aqueous saturated ammonium chloride solution and ethyl acetate were added to the obtained solution and the liquids were separated. The obtained organic layer was washed with saturated brine, and dried over sodium sulfate. After the solvent was distilled off under reduced pressure, 2.61 g of reddish black oily product containing the title compound was obtained. The product was used in the next reaction without further purification.

$^1$H-NMR ($CDCl_3$) δ: 7.48 (1H, s), 6.76-6.74 (2H, m), 5.59 (1H, dd, J=10:3, 4.6 Hz), 4.19-4.10 (2H, m), 2.63-2.58 (1H, m), 2.41-2.36 (1H, m), 2.28-2.16 (2H, m), 1.28-1.23 (3H, m).

Reference Example 34

Synthesis of 1-(2,4-difluorophenyl)-2-(4-methyl-1H-pyrazol-1-yl)ethan-1-one

[Chem. 269]

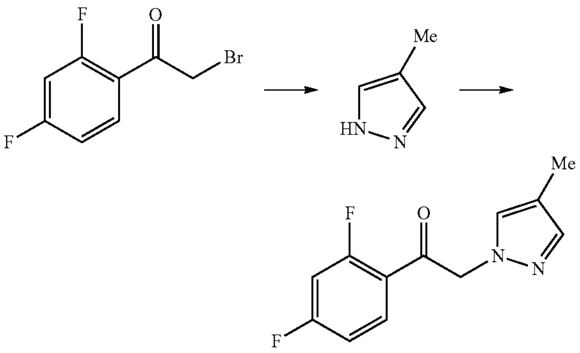

30.0 ml of a methyl isobutyl ketone solution containing 10.1 g of 2-bromo-1-(2,4-difluorophenyl)ethan-1-one and 4.23 g of 4-methyl-1H-pyrazole was stirred at 120° C. for 1 hour. After cooling the mixture to room temperature, ethyl acetate and an aqueous saturated sodium hydrogen carbonate solution were added to the reaction mixture and the liquids were separated. The obtained organic layer was washed with saturated brine, and dried over sodium sulfate. After the solvent was distilled off under reduced pressure, the obtained residue was washed with isopropyl ether. The title compound was obtained as 4.78 g of a brown solid.

$^1$H-NMR ($CDCl_3$) δ: 8.02 (1H, td, J=8.5, 6.4 Hz), 7.40 (1H, s), 7.25-7.25 (1H, m), 7.04-7.00 (1H, m), 6.97-6.92 (1H, m), 5.45 (2H, d, J=3.7 Hz), 2.13 (3H, s).

Reference Example 35

Synthesis of ethyl 5-(2,4-difluorophenyl)-4-(4-methyl-1H-pyrazol-1-yl)-5-oxopentanoate

[Chem. 270]

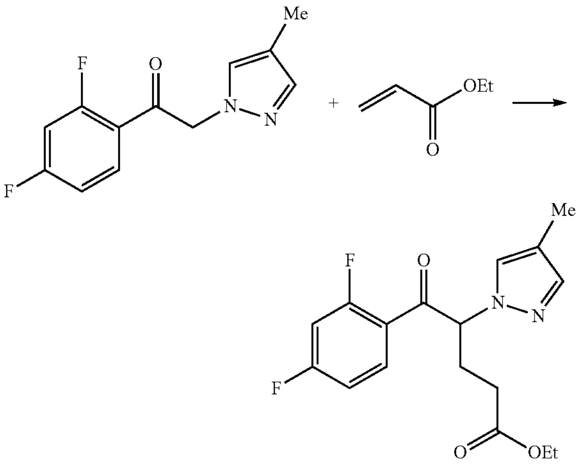

To 40.0 ml of a THF solution containing 4.69 g of 1-(2,4-difluorophenyl)-2-(4-methyl-1H-pyrazol-1-yl)ethan-1-one obtained in Reference Example 34 were added 2.94 ml of 1,8-diazabicyclo[5.4.0]-7-undecene and 2.25 ml of ethyl acrylate, and the mixture was stirred at room temperature for 1.5 hours. An aqueous saturated ammonium chloride solution and ethyl acetate were added to the obtained solution and the liquids were separated. The obtained organic layer was washed with saturated brine, and dried over sodium sulfate. After the solvent was distilled off under reduced pressure, 4.79 g of a blackish red oily product containing the title compound was obtained. The product was used in the next reaction without further purification.

$^1$H-NMR ($CDCl_3$) δ: 7.87 (1H, td, J=8.6, 6.4 Hz), 7.32 (1H, s), 7.28 (1H, s), 6.97-6.93 (1H, m), 6.85-6.81 (1H, m), 5.74 (1H, dd, J=10.4, 4.3 Hz), 4.13 (2H, q, J=7.2 Hz), 2.50-2.47 (1H, m), 2.32-2.25 (3H, m), 2.06 (31-, s), 1.25 (3H, t, J=7.2 Hz).

Compounds synthesized according to the above-mentioned Examples are shown in Table 5, but the present invention is not limited to these.

In Table 5, Ph represents a phenyl group, 2-Thio represents a thiophen-2-yl group, 3-Thio represents a thiophen-3-yl group, 3-Py represents a pyridin-3-yl group, 3-Pyra represents a 1H-pyrazol-3-yl group, 5-Pyra represents a 1H-pyrazol-5-yl group, 1-Pyra represents a 1H-pyrazol-1-yl group, 5-Oxa represents an oxazol-5-yl group, 2-Oxa represents an oxazol-2-yl group, 1H-1,2,4-triazol-1-yl represents a 1H-1,2,4-triazol-1-yl group, 1-Pyrrolyl represents a 1H-pyrrol-1-yl group, 4-Pyrrolyl represents a 1H-pyrrol-4-yl group, 1-Imida represents a 1H-imidazol-1-yl group, and 1H-tetrazol-1-yl represents a 1H-tetrazol-1-yl group.

For example, the description "2,4,6-tri-F-Ph" in Table 5 means that it is a phenyl group in which fluorine atoms are bound to the 2-position, 4-position and 6-position, and the description "2-Cl-3-Py" means that it is a pyridin-3-yl group in which a chlorine atom is bound to the 2-position, and the other descriptions are also the same.

In Table 5, Structure A indicates the following.

[Chem. 271]

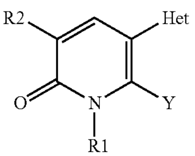

In Table 5, Structure B indicates the following.

[Chem. 272]

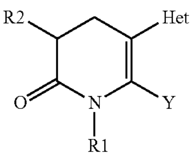

In Table 5, Structure C indicates the following.

[Chem. 273]

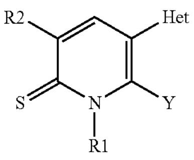

In Table 5, Structure D indicates the following.

[Chem. 274]

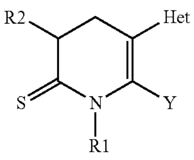

TABLE 5

| Compound | Structure | R1 | R2 | Het | Y |
|---|---|---|---|---|---|
| 1 | B | Me | H | 2-Thio | 2,6-di-F—Ph |
| 2 | B | Et | H | 2-Thio | 2,6-di-F—Ph |
| 3 | B | Me | H | 3-Thio | 2,6-di-F—Ph |
| 4 | B | Et | H | 3-Thio | 2,6-di-F—Ph |
| 5 | A | Et | H | 2-Thio | 2,6-di-F—Ph |
| 6 | A | Et | H | 5-Cl-2-Thio | 2,6-di-F—Ph |
| 7 | A | Et | Cl | 5-Cl-2-Thio | 2,6-di-F—Ph |
| 8 | A | Et | Cl | 1,3-dioxan-2-yl | 2,4,6-tri-F—Ph |
| 9 | A | Et | Cl | 1,3-dioxolan-2-yl | 2,4,6-tri-F—Ph |
| 10 | A | Et | Cl | 1,3-dioxan-2-yl | 2,6-di-F-4-MeO—Ph |
| 11 | A | Et | Cl | 1,3-dioxan-2-yl | 2,6-di-F—Ph |
| 12 | A | Et | Cl | 1,3-dioxolan-2-yl | 2,6-di-F-4-MeO—Ph |
| 13 | A | Et | Cl | 1,3-dioxolan-2-yl | 2,6-di-F—Ph |
| 14 | A | Me | H | 2-Thio | 2,6-di-F—Ph |
| 15 | A | Me | H | 3-Thio | 2,6-di-F—Ph |
| 16 | A | Et | H | 3-Thio | 2,6-di-F—Ph |
| 17 | A | Et | H | 2-Cl-3-Py | 2,6-di-F—Ph |
| 18 | A | Et | Cl | 2-Cl-3-Py | 2,6-di-F—Ph |
| 19 | A | Et | Cl | 1,4-di-Me-3-Pyra | 2,4,6-tri-F—Ph |
| 20 | A | Et | Cl | 1-Me-5-Pyra | 2,4,6-tri-F—Ph |
| 21 | A | Et | Cl | 4-Br-1-Me-5-Pyra | 2,4,6-tri-F—Ph |
| 22 | A | Et | Cl | 4-Cl-1-Me-5-Pyra | 2,4,6-tri-F—Ph |
| 23 | A | Et | Cl | 4-Br-1-Me-5-Pyra | 2,6-di-F-4-MeO—Ph |
| 24 | A | Et | Cl | 4-Br-1-Me-3-Pyra | 2,4,6-tri-F—Ph |
| 25 | B | Et | H | 1-Pyra | 2,4,6-tri-F—Ph |
| 26 | A | Et | H | 1-Pyra | 2,4,6-tri-F—Ph |
| 27 | A | Et | H | 4-Cl-1-Pyra | 2,4,6-tri-F—Ph |
| 28 | A | Et | Cl | 1-Me-5-Pyra | 2,6-di-F-4-MeO—Ph |
| 29 | A | Et | Cl | 4-Cl-1-Me-5-Pyra | 2,6-di-F-4-MeO—Ph |
| 30 | B | Et | H | 1-Pyra | 2,6-di-F—Ph |
| 31 | A | Et | H | 1-Pyra | 2,6-di-F—Ph |
| 32 | A | Et | Cl | 5-Oxa | 2-Cl-4-F—Ph |
| 33 | A | Et | Cl | 5-Oxa | 2-Cl-4-MeO—Ph |
| 34 | A | Et | Cl | 1H-1,2,4-triazol-1-yl | 2,4,6-tri-F—Ph |
| 35 | A | Et | Cl | 5-Br-1H-1,2,4-triazol-1-yl | 2,4,6-tri-F—Ph |
| 36 | A | Et | Cl | 5-Oxa | 2,4,6-tri-F—Ph |
| 37 | A | Et | Cl | 5-Oxa | 2,6-di-F-4-MeO—Ph |
| 38 | A | Et | Cl | 4-Me-5-Oxa | 2-Cl-4-F—Ph |
| 39 | A | Et | Cl | 4-Me-5-Oxa | 2-Cl-4-MeO—Ph |
| 40 | A | Et | Cl | 4-Cl-1-Pyra | 2,4,6-tri-F—Ph |
| 41 | A | Et | Cl | 4-Cl-1-Pyra | 2,6-di-F-4-MeO—Ph |
| 42 | A | Et | Cl | 5-Oxa | 2,6-di-F—Ph |
| 43 | A | Et | Cl | 4-Me-5-Oxa | 2,6-di-F—Ph |
| 44 | A | Et | H | 2-Br-3-Thio | 2,6-di-F—Ph |
| 45 | A | Et | Cl | 2-Br-3-Thio | 2,6-di-F—Ph |
| 46 | A | Et | Br | 5-Br-1H-1,2,4-triazol-1-yl | 2,4,6-tri-F—Ph |
| 47 | A | Et | Br | 1H-1,2,4-triazol-1-yl | 2,4,6-tri-F—Ph |
| 48 | A | Et | Cl | 5-I-1H-1,2,4-triazol-1-yl | 2,4,6-tri-F—Ph |
| 49 | A | Et | Cl | 4-Br-5-Oxa | 2,6-di-F—Ph |
| 50 | A | Et | Cl | 4-Cl-5-Oxa | 2,6-di-F—Ph |
| 51 | A | Et | Cl | 4-F-5-Oxa | 2,6-di-F—Ph |
| 52 | A | Et | H | 4-Cl-1-Pyra | 2,6-di-F—Ph |
| 53 | A | Et | Cl | 4-Cl-1-Pyra | 2,6-di-F—Ph |
| 54 | A | Et | Br | 2-Br-3-Thio | 2,6-di-F—Ph |
| 55 | A | Et | Br | 2-Cl-3-Py | 2,6-di-F—Ph |
| 56 | A | F2CHCH2— | H | 2-Cl-3-Py | 2,6-di-F—Ph |
| 57 | A | F2CHCH2— | Cl | 2-Cl-3-Py | 2,6-di-F—Ph |
| 58 | A | F3CCH2— | H | 2-Cl-3-Py | 2,6-di-F—Ph |
| 59 | A | F2CHCH2— | Br | 2-Cl-3-Py | 2,6-di-F—Ph |
| 60 | A | F3CCH2— | Cl | 2-Cl-3-Py | 2,6-di-F—Ph |
| 61 | A | Et | H | 2-Cl-3-Py | 2,4,6-tri-F—Ph |
| 62 | A | Et | Cl | 2-Cl-3-Py | 2,4,6-tri-F—Ph |

TABLE 5-continued

| Compound | Structure | R1 | R2 | Het | Y |
|---|---|---|---|---|---|
| 63 | A | Et | Br | 2-Cl-3-Py | 2,4,6-tri-F—Ph |
| 64 | A | F3CCH2— | Br | 2-Cl-3-Py | 2,6-di-F—Ph |
| 65 | A | Et | I | 2-Cl-3-Py | 2,6-di-F—Ph |
| 66 | A | Et | Me | 2-Cl-3-Py | 2,6-di-F—Ph |
| 67 | A | F2CHCH2— | H | 2-Cl-3-Py | 2,4,6-tri-F—Ph |
| 68 | A | F2CHCH2— | Cl | 2-Cl-3-Py | 2,4,6-tri-F—Ph |
| 69 | A | F2CHCH2— | Br | 2-Cl-3-Py | 2,4,6-tri-F—Ph |
| 70 | A | Et | Cl | 4-Br-1-Pyra | 2,4,6-tri-F—Ph |
| 71 | A | Et | Br | 4-Cl-1-Pyra | 2,4,6-tri-F—Ph |
| 72 | A | Et | Cl | 4-Br-1-Pyra | 2,6-di-F-4-MeO—Ph |
| 73 | A | Et | Br | 4-Cl-1-Pyra | 2,6-di-F-4-MeO—Ph |
| 74 | A | Et | Cl | 4-I-5-Oxa | 2,6-di-F—Ph |
| 75 | A | Et | Cl | 2,4-di-I-5-Oxa | 2,6-di-F—Ph |
| 76 | A | Et | H | 4-Br-3,5-di-Me-1-Pyra | 2,4,6-tri-F—Ph |
| 77 | A | Et | Br | 4-Br-1-Pyra | 2,4,6-tri-F—Ph |
| 78 | A | Et | Br | 4-Br-1-Pyra | 2,6-di-F-4-MeO—Ph |
| 79 | A | Et | H | 2-Cl-3-Py | 2,6-di-F-4-MeO—Ph |
| 80 | A | Et | Cl | 2-Cl-3-Py | 2,6-di-F-4-MeO—Ph |
| 81 | A | Et | Br | 2-Cl-3-Py | 2,6-di-F-4-MeO—Ph |
| 82 | A | Et | H | 5-Cl-4-Me-1-Pyra | 2,4,6-tri-F—Ph |
| 83 | A | Et | Cl | 5-Cl-4-Me-1-Pyra | 2,4,6-tri-F—Ph |
| 84 | A | Et | Cl | 1-Pyra | 2,4,6-trl-F—Ph |
| 85 | A | Et | Cl | 4-Me-1-Pyra | 2,4,6-tri-F—Ph |
| 86 | A | Et | Me | 4-Me-1-Pyra | 2,4,6-tri-F—Ph |
| 87 | A | Et | Cl | 2-Cl-5-Oxa | 2,6-di-F—Ph |
| 88 | A | Et | Cl | 3-N≡C-4-Pyrrolyl | 2,6-di-F—Ph |
| 89 | A | Et | Br | 5-Oxa | 2,4,6-tri-F—Ph |
| 90 | A | Et | Br | 5-Oxa | 2,6-di-F-4-MeO—Ph |
| 91 | A | Et | Cl | 4-MeO-5-Oxa | 2,6-di-F—Ph |
| 92 | A | Et | Cl | 2-I-5-Oxa | 2,6-di-F—Ph |
| 93 | A | Et | H | 3,5-di-Me-1-Pyra | 2,4,6-tri-F—Ph |
| 94 | A | Et | H | 3,5-di-Me-1-Pyra | 2,6-di-F-4-MeO—Ph |
| 95 | A | Et | H | 4-Cl-3,5-di-Me-1-Pyra | 2,4,6-tri-F—Ph |
| 96 | A | Et | Br | 2,4-di-Br-5-Oxa | 2,4,6-tri-F—Ph |
| 97 | A | Et | Br | 4-Br-5-Oxa | 2,4,6-tri-F—Ph |
| 98 | A | Me | H | 2-Cl-3-Py | 2,4,6-tri-F—Ph |
| 99 | A | Me | H | 2-Cl-3-Py | 2,6-di-F—Ph |
| 100 | A | Me | Cl | 2-Cl-3-Py | 2,4,6-tri-F—Ph |
| 101 | A | Et | Br | 4-Me-1-Pyra | 2,4,6-tri-F—Ph |
| 102 | A | Et | Br | 2,4-di-Br-5-Oxa | 2,6-di-F-4-MeO—Ph |
| 103 | A | Et | Br | 4-Br-5-Oxa | 2,6-di-F-4-MeO—Ph |
| 104 | A | Me | Br | 2-Cl-3-Py | 2,4,6-tri-F—Ph |
| 105 | A | Me | Cl | 2-Cl-3-Py | 2,6-di-F—Ph |
| 106 | A | Me | Br | 2-Cl-3-Py | 2,6-di-F—Ph |
| 107 | A | Et | Br | 4-Cl-5-Oxa | 2,4,6-tri-F—Ph |
| 108 | A | Et | H | 4-Br-3-Me-1-Pyra | 2,4,6-tri-F—Ph |
| 109 | A | Et | H | 3,4-di-Me-1-Pyra | 2,4,6-tri-F—Ph |
| 110 | A | F2CHCH2— | Cl | 4-Cl-1-Pyra | 2,4,6-tri-F—Ph |
| 111 | A | F2CHCH2— | Cl | 4-Cl-1-Pyra | 2,6-di-F-4-MeO—Ph |
| 112 | A | Et | Cl | 4-Cl-5-Oxa | 2,4,6-tri-F—Ph |
| 113 | A | Et | Cl | 4-Br-5-Oxa | 2,4,6-tri-F—Ph |
| 114 | A | Et | Cl | 2,4-di-Cl-5-Oxa | 2,6-di-F-4-MeO—Ph |
| 115 | A | Et | Cl | 4-Cl-5-Oxa | 2,6-di-F-4-MeO—Ph |
| 116 | A | Et | Cl | 2,4-di-Br-5-Oxa | 2,6-di-F-4-MeO—Ph |
| 117 | A | Et | Br | 4-Br-3,5-di-Me-1-Pyra | 2,4,6-tri-F—Ph |
| 118 | A | Et | Cl | 4-Br-5-Oxa | 2,6-di-F-4-MeO—Ph |
| 119 | A | Et | Cl | 5-Oxa | 2,6-di-F-4-MeHN—Ph |
| 120 | A | Et | Cl | 4-F-5-Oxa | 2,4,6-tri-F—Ph |
| 121 | A | F3CCH2— | Cl | 4-Cl-1-Pyra | 2,4,6-tri-F—Ph |
| 122 | A | F3CCH2— | Cl | 4-Cl-1-Pyra | 2,6-di-F-4-MeO—Ph |
| 123 | A | Et | Cl | 4-HC(═O)-1-Pyra | 2,4,6-tri-F—Ph |
| 124 | A | Et | Cl | 4-F2HC-1-Pyra | 2,4,6-tri-F—Ph |
| 125 | A | Et | Cl | 2,5-di-Me-1-Pyrrolyl | 2,4,6-tri-F—Ph |
| 126 | A | Et | Cl | 2,5-di-Me-1-Pyrrolyl | 2,6-di-F-4-MeO—Ph |
| 127 | A | Et | Cl | 4-F-5-Oxa | 2,6-di-F-4-MeO—Ph |
| 128 | A | Et | Cl | 4-MeO-1-Pyra | 2,4,6-tri-F—Ph |
| 129 | A | Et | Cl | 5-EtOC(═O)-1-Imida | 2,4,6-tri-F—Ph |
| 130 | A | Et | Cl | 2-MeO-5-Oxa | 2,6-di-F—Ph |
| 131 | A | Et | Cl | 2-Me2N-5-Oxa | 2,6-di-F—Ph |
| 132 | A | Et | Cl | 1-Pyrrolyl | 2,4,6-tri-F—Ph |
| 133 | A | Et | Cl | 2,5-di-Cl-1-Pyrrolyl | 2,4,6-tri-F—Ph |
| 134 | A | Et | Cl | 2-MeNH-5-Oxa | 2,6-di-F—Ph |
| 135 | A | Et | Cl | 2-H2N-5-Oxa | 2,6-di-F—Ph |
| 136 | A | Et | H | 4,5-di-Cl-1-Imida | 2,4,6-tri-F—Ph |
| 137 | A | Et | Cl | 2,4,5-tri-Cl-1-Imida | 2,4,6-tri-F—Ph |
| 138 | A | Et | Cl | 4,5-di-Cl-1-Imida | 2,4,6-tri-F—Ph |
| 139 | A | Et | Br | 4,5-di-Cl-1-Imida | 2,4,6-tri-F—Ph |
| 140 | A | Et | I | 4-Cl-1-Pyra | 2,4,6-tri-F—Ph |

TABLE 5-continued

| Compound | Structure | R1 | R2 | Het | Y |
|---|---|---|---|---|---|
| 141 | A | Et | H | 4-Cl-3-Me-1-Pyra | 2,4,6-tri-F—Ph |
| 142 | A | Et | Cl | 4-Cl-3-Me-1-Pyra | 2,4,6-tri-F—Ph |
| 143 | A | Et | Cl | 4-Cl-3-Me-1-Pyra | 2,6-di-F-4-MeO—Ph |
| 144 | A | Et | Br | 4-Cl-3-Me-1-Pyra | 2,4,6-tri-F—Ph |
| 145 | A | Et | H | 4-Cl-1-Pyra | 2,4-di-F—Ph |
| 146 | A | Et | Br | 4-Cl-3-Me-1-Pyra | 2,6-di-F-4-MeO—Ph |
| 147 | A | Et | Br | 4-Br-3-Me-1-Pyra | 2,4,6-tri-F—Ph |
| 148 | A | Et | Cl | 4-Cl-1-Pyra | 2,4-di-F—Ph |
| 149 | A | Et | Cl | 4-Cl-1-Pyra | 2-F-4-MeO—Ph |
| 150 | A | Et | Br | 4-Cl-1-Pyra | 2,4-di-F—Ph |
| 151 | A | Et | Br | 4-Br-3-Me-1-Pyra | 2,6-di-F-4-MeO—Ph |
| 152 | A | Et | Br | 4-Cl-1-Pyra | 2-F-4-MeO—Ph |
| 153 | A | Et | H | 5-Cl-4-Me-1-Pyra | 2,6-di-F—Ph |
| 154 | A | Et | F3C— | 4-F3C-1-Pyra | 2,4,6-tri-F—Ph |
| 155 | A | Et | Cl | 4-F3C-1-Pyra | 2,4,6-tri-F—Ph |
| 156 | A | Et | H | 4-Cl-1-Pyra | 2-Cl-4-F—Ph |
| 157 | A | Et | Cl | 4-Cl-1-Pyra | 2-Cl-4-F—Ph |
| 158 | A | Et | Br | 4-Cl-1-Pyra | 2-Cl-4-F—Ph |
| 159 | A | Et | Cl | 4-Cl-1-Pyra | 2-Cl-4-MeO—Ph |
| 160 | A | Et | Cl | 4-I-1-Pyra | 2,4,6-tri-F—Ph |
| 161 | A | Et | Cl | 4-NO2-1-Pyra | 2,4,6-tri-F—Ph |
| 162 | A | Et | Cl | 5-MeO-2-Oxa | 2,6-di-F—Ph |
| 163 | A | Et | Cl | 4-MeC(=O)NH-1-Pyra | 2,4,6-tri-F—Ph |
| 164 | A | Et | H | 4-Cl-1-Pyra | 2-Br-4-F—Ph |
| 165 | A | Et | Cl | 4-Cl-1-Pyra | 2-Br-4-F—Ph |
| 166 | A | Et | Br | 4-Cl-1-Pyra | 2-Br-4-F—Ph |
| 167 | A | Et | Cl | 4-Cl-1-Pyra | 2-Br-4-MeO—Ph |
| 168 | A | Et | H | 4-Cl-1-Pyra | 4-F-2-Me—Ph |
| 169 | A | Et | H | 4-Cl-1-Pyra | 2-Cl—Ph |
| 170 | A | Et | Cl | 4-Cl-1-Pyra | 4-F-2-Me—Ph |
| 171 | A | Et | Br | 4-Cl-1-Pyra | 4-F-2-Me—Ph |
| 172 | A | Et | Cl | 4-Cl-1-Pyra | 2-Cl—Ph |
| 173 | A | Et | Br | 4-Cl-1-Pyra | 2-Cl—Ph |
| 174 | A | Me | H | 4-Cl-1-Pyra | 2,4,6-tri-F—Ph |
| 175 | A | Me | Cl | 4-Cl-1-Pyra | 2,4,6-tri-F—Ph |
| 176 | A | Me | Br | 4-Cl-1-Pyra | 2,4,6-tri-F—Ph |
| 177 | A | Me | Cl | 4-Cl-1-Pyra | 2,6-di-F-4-MeO—Ph |
| 178 | A | Me | Br | 4-Cl-1-Pyra | 2,6-di-F-4-MeO—Ph |
| 179 | A | Et | Cl | 5-Cl-4-Me-1-Pyra | 2-Cl—Ph |
| 180 | A | Et | Br | 4-Me-1-Pyra | 2-Cl—Ph |
| 181 | A | Et | Br | 5-Cl-4-Me-1-Pyra | 2-Cl—Ph |
| 182 | A | Et | Cl | 5-Cl-4-Me-1-Pyra | 2,4-di-F—Ph |
| 183 | A | Et | H | 4-Cl-1-Pyra | 2-Br—Ph |
| 184 | A | Et | Cl | 4-Cl-1-Pyra | 2,6-di-F-4-OH—Ph |
| 185 | C | Et | H | 4-Cl-1-Pyra | 2,4,6-tri-F—Ph |
| 186 | A | F2CHCH2— | H | 4-Me-1-Pyra | 2,6-di-F—Ph |
| 187 | A | Me | Cl | 5-Cl-4-Me-1-Pyra | 2,6-di-F—Ph |
| 188 | A | Me | Br | 4-Me-1-Pyra | 2,6-di-F—Ph |
| 189 | A | Me | Br | 5-Cl-4-Me-1-Pyra | 2,6-di-F—Ph |
| 190 | A | F2CHCH2— | Cl | 5-Cl-4-Me-1-Pyra | 2,6-di-F—Ph |
| 191 | A | Et | H | 4-F-1-Pyra | 2,4,6-tri-F—Ph |
| 192 | A | Et | Cl | 4-F-1-Pyra | 2,4,6-tri-F—Ph |
| 193 | A | F2CHCH2— | Br | 5-Cl-4-Me-1-Pyra | 2,6-di-F—Ph |
| 194 | A | Et | Br | 4-F-1-Pyra | 2,4,6-tri-F—Ph |
| 195 | A | Et | Cl | 4-Cl-1-Pyra | 2-Br—Ph |
| 196 | A | Et | Br | 4-Cl-1-Pyra | 2-Br—Ph |
| 197 | A | Et | H | 4-Cl-1-Pyra | 2-Cl-6-F—Ph |
| 198 | A | Et | Cl | 4-Cl-1-Pyra | 2-Cl-6-F—Ph |
| 199 | A | Et | Br | 4-Cl-1-Pyra | 2-Cl-6-F—Ph |
| 200 | A | Et | Cl | 4-Cl-1-Pyra | 2,6-di-F-4-EtO—Ph |
| 201 | A | Et | Cl | 4-Cl-1-Pyra | 2,6-di-F-4-HC≡C—CH2O—Ph |
| 202 | A | Et | Cl | 4-Cl-1-Pyra | 2,6-di-F-4-H2C=CH—CH2O—Ph |
| 203 | A | Et | Cl | 4-Cl-1-Pyra | 6-di-F-4-MeOCH2O—Ph |
| 204 | A | Et | Cl | 4-Cl-1-Pyra | 2,6-di-F-4-MeOCH2—CH2O—Ph |
| 205 | A | Et | Cl | 4-Cl-1-Pyra | 2,6-di-F-4-MeC(=O)O—Ph |
| 206 | A | Et | Me | 4-Cl-1-Pyra | 2,4,6-tri-F—Ph |
| 207 | A | F2CHCH2— | Br | 4-Cl-1-Pyra | 2,4,6-tri-F—Ph |
| 208 | A | Et | H | 4,5-di-Cl-1-Imida | 2-Cl—Ph |
| 209 | A | Et | Cl | 4,5-di-Cl-1-Imida | 2-Cl—Ph |
| 210 | A | Et | Br | 4,5-di-Cl-1-Imida | 2-Cl—Ph |
| 211 | A | F2CHCH2— | H | 4-Cl-1-Pyra | 2,4-di-F—Ph |
| 212 | A | F2CHCH2— | Cl | 4-Cl-1-Pyra | 2,4-di-F—Ph |
| 213 | A | F2CHCH2— | Cl | 4-Cl-1-Pyra | 2-F-4-MeO—Ph |

TABLE 5-continued

| Compound | Structure | R1 | R2 | Het | Y |
|---|---|---|---|---|---|
| 214 | A | F2CHCH2— | Br | 4-Cl-1-Pyra | 2,4-di-F—Ph |
| 215 | A | F2CHCH2— | Br | 4-Cl-1-Pyra | 2-F-4-MeO—Ph |
| 216 | A | Et | H | 4-Cl-1-Pyra | 2-Br-6-F—Ph |
| 217 | A | Et | H | 4-Cl-1-Pyra | 2-F—Ph |
| 218 | A | Et | Cl | 4-Cl-1-Pyra | 2-Br-6-F—Ph |
| 219 | A | Et | Br | 4-Cl-1-Pyra | 2-Br-6-F—Ph |
| 220 | A | Et | Cl | 4-Cl-1-Pyra | 2-F—Ph |
| 221 | A | Et | Br | 4-Cl-1-Pyra | 2-F—Ph |
| 222 | A | F2CHCH2— | Br | 4-Cl-1-Pyra | 2,6-di-F-4-MeO—Ph |
| 223 | A | Et | HCC- | 4-Cl-1-Pyra | 2,4,6-tri-F—Ph |
| 224 | A | Et | HCEC- | 4-Cl-1-Pyra | 2,6-di-F-4-MeO—Ph |
| 225 | A | Et | MeO- | 4-Cl-1-Pyra | 2,4,6-tri-F—Ph |
| 226 | A | Et | Br | 4-Me-1-Pyra | 2,4-di-F—Ph |
| 227 | A | F2CHCH2— | H | 4-Me-1-Pyra | 2-Cl—Ph |
| 228 | A | Et | Br | 5-Cl-4-Me-1-Pyra | 2,4-di-F—Ph |
| 229 | A | F2CHCH2— | Cl | 5-Cl-4-Me-1-Pyra | 2-Cl—Ph |
| 230 | A | F2CHCH2— | Br | 5-Cl-4-Me-1-Pyra | 2-Cl—Ph |
| 231 | A | F2CHCH2— | H | 4,5-di-Cl-1-Imida | 2-Cl—Ph |
| 232 | A | F2CHCH2— | Cl | 4,5-di-Cl-1-Imida | 2-Cl—Ph |
| 233 | A | F2CHCH2— | H | 4-Cl-1-Pyra | 2-Cl-4-F—Ph |
| 234 | A | F2CHCH2— | Cl | 4-Cl-1-Pyra | 2-Cl-4-F—Ph |
| 235 | A | F2CHCH2— | Br | 4-Cl-1-Pyra | 2-Cl-4-F—Ph |
| 236 | A | F2CHCH2— | Br | 4,5-di-Cl-1-Imida | 2-Cl—Ph |
| 237 | A | Et | Br | 4-Me-1-Pyra | 2-Me—Ph |
| 238 | A | Et | H | 4-Cl-1-Pyra | 2,6-di-F-4-MeO—Ph |
| 239 | A | F2CHCH2— | Cl | 4-Cl-1-Pyra | 2-Cl-4-MeO—Ph |
| 240 | A | F2CHCH2— | Br | 4-Cl-1-Pyra | 2-Cl-4-MeO—Ph |
| 241 | A | Et | Br | 4-Cl-1-Pyra | 2-MeO—Ph |
| 242 | A | Et | H | 4-Cl-1-Pyra | 2-MeO—Ph |
| 243 | A | Et | Cl | 4-Cl-1-Pyra | 2-MeO—Ph |
| 244 | A | Et | Cl | 5-Cl-4-Me-1-Pyra | 2-Me—Ph |
| 245 | A | Et | Br | 5-Cl-4-Me-1-Pyra | 2-Me—Ph |
| 246 | A | Et | H | 4-Me-1-Pyra | 2-MeO—Ph |
| 247 | A | Et | Br | 4-Me-1-Pyra | 2-MeO—Ph |
| 248 | A | Et | Cl | 5-Cl-4-Me-1-Pyra | 2-MeO—Ph |
| 249 | A | Et | Br | 5-Cl-4-Me-1-Pyra | 2-MeO—Ph |
| 250 | A | Et | H | 4-F-1-Pyra | 2,4-di-F—Ph |
| 251 | A | Et | Cl | 4-F-1-Pyra | 2,4-di-F—Ph |
| 252 | A | Et | Br | 4-F-1-Pyra | 2,4-di-F—Ph |
| 253 | A | Et | I | 4-Cl-1-Pyra | 2,6-di-F-3-I-4-MeO—Ph |
| 254 | A | F2CHCH2— | H | 4-Me-1-Pyra | 2,4-di-F—Ph |
| 255 | A | F2CHCH2— | Cl | 5-Cl-4-Me-1-Pyra | 2,4-di-F—Ph |
| 256 | A | F2CHCH2— | Br | 5-Cl-4-Me-1-Pyra | 2,4-di-F—Ph |
| 257 | A | Et | Br | 4-Cl-1-Pyra | 2-NO2—Ph |
| 258 | A | Et | Cl | 4-Cl-1-Pyra | 2-NO2—Ph |
| 259 | A | Et | H | 4-Me-1-Pyra | 2-F—Ph |
| 260 | A | Et | Br | 4-Me-1-Pyra | 2-F—Ph |
| 261 | A | Et | Cl | 3-Cl-1H-1,2,4-triazol-1-yl | 2,4,6-tri-F—Ph |
| 262 | A | Et | Br | 3-Cl-1H-1,2,4-triazol-1-yl | 2,4,6-tri-F—Ph |
| 263 | A | Et | Cl | 5-Cl-4-Me-1-Pyra | 2-F—Ph |
| 264 | A | Et | Br | 5-Cl-4-Me-1-Pyra | 2-F—Ph |
| 265 | A | Et | HC(═O)— | 4-Cl-1-Pyra | 2,4,6-tri-F—Ph |
| 266 | A | Et | F2CH— | 4-Cl-1-Pyra | 2,4,6-tri-F—Ph |
| 267 | A | Et | Cl | 3-Cl-1H-1,2,4-triazol-1-yl | 2,6-di-F-4-MeO—Ph |
| 268 | A | Et | H | 4-Me-1-Pyra | 2-Br—Ph |
| 269 | A | Et | Br | 4-Me-1-Pyra | 2-Br—Ph |
| 270 | A | Et | Br | 5-Br-4-Me-1-Pyra | 2,4-di-F—Ph |
| 271 | A | Et | Br | 5-Cl-4-Me-1-Pyra | 2-Br—Ph |
| 272 | A | Et | Cl | 5-Cl-4-Me-1-Pyra | 2-Br—Ph |
| 273 | A | F2CHCH2— | H | 4-Cl-1-Pyra | 2-Br-4-F—Ph |
| 274 | A | F2CHCH2— | Cl | 4-Cl-1-Pyra | 2-Br-4-F—Ph |
| 275 | A | F2CHCH2— | Br | 4-Cl-1-Pyra | 2-Br-4-F—Ph |
| 276 | A | F2CHCH2— | H | 4-Cl-1-Pyra | 2-F—Ph |
| 277 | A | F2CHCH2— | Cl | 4-Cl-1-Pyra | 2-F—Ph |
| 278 | A | F2CHCH2— | Br | 4-Cl-1-Pyra | 2-F—Ph |
| 279 | A | Et | Cl | 4-Cl-1-Pyra | 4-N≡C-2-F—Ph |
| 280 | A | Et | Br | 4-Cl-1-Pyra | 4-N≡C-2-F—Ph |
| 281 | A | Et | H | 1H-tetrazol-1-yl | 2,4,6-tri-F—Ph |
| 282 | A | F2CHCH2— | H | 4-F-1-Pyra | 2,4,6-tri-F—Ph |
| 283 | A | F2CHCH2— | Br | 4-F-1-Pyra | 2,4,6-tri-F—Ph |
| 284 | A | F2CHCH2— | H | 4-F-1-Pyra | 2,4-di-F—Ph |
| 285 | A | F2CHCH2— | Cl | 4-F-1-Pyra | 2,4-di-F—Ph |
| 286 | A | F2CHCH2— | Br | 4-F-1-Pyra | 2,4-di-F—Ph |
| 287 | A | F2CHCH2— | Cl | 4-Cl-1-Pyra | 2-Br-4-MeO—Ph |
| 288 | A | F2CHCH2— | Br | 4-Cl-1-Pyra | 2-Br-4-MeO—Ph |
| 289 | A | F2CHCH2— | H | 4-Cl-1-Pyra | 2-Br—Ph |
| 290 | A | F2CHCH2— | Cl | 4-Cl-1-Pyra | 2-Br—Ph |
| 291 | A | F2CHCH2— | Br | 4-Cl-1-Pyra | 2-Br—Ph |

TABLE 5-continued

| Compound | Structure | R1 | R2 | Het | Y |
|---|---|---|---|---|---|
| 292 | A | F2CHCH2— | H | 4-Cl-1-Pyra | 2-Cl—Ph |
| 293 | A | F2CHCH2— | Cl | 4-Cl-1-Pyra | 2-Cl—Ph |
| 294 | A | F2CHCH2— | Br | 4-Cl-1-Pyra | 2-Cl—Ph |
| 295 | B | Et | H | 2-Cl-3-Thio | 2,6-di-F—Ph |
| 296 | A | Et | H | 2-Cl-3-Thio | 2,6-di-F—Ph |
| 297 | A | Et | Cl | 2,5-di-Cl-3-Thio | 2,6-di-F—Ph |
| 298 | A | Et | Cl | 2-Cl-3-Thio | 2,6-di-F—Ph |
| 299 | A | Et | Br | 2-Cl-3-Thio | 2,6-di-F—Ph |
| 300 | A | Et | H | 4-F-1-Pyra | 2-F-4-MeO—Ph |
| 301 | A | Et | Cl | 4-F-1-Pyra | 2-F-4-MeO—Ph |
| 302 | A | Et | Br | 4-F-1-Pyra | 2-F-4-MeO—Ph |
| 303 | A | F2CHCH2— | H | 4-Me-1-Pyra | 2-Me—Ph |
| 304 | A | F2CHCH2— | Br | 4-Me-1-Pyra | 2-Me—Ph |
| 305 | A | F2CHCH2— | H | 4-Me-1-Pyra | 2-F—Ph |
| 306 | A | F2CHCH2— | Cl | 5-Cl-4-Me-1-Pyra | 2-Me—Ph |
| 307 | A | F2CHCH2— | Br | 5-Cl-4-Me-1-Pyra | 2-Me—Ph |
| 308 | A | Et | H | 4-F-1-Pyra | 2,6-di-F-4-MeO-Ph |
| 309 | A | F2CHCH2— | Br | 4-Me-1-Pyra | 2-F—Ph |
| 310 | A | F2CHCH2— | Cl | 5-Cl-4-Me-1-Pyra | 2-F—Ph |
| 311 | A | Et | H | 4-F-1-Pyra | 2,6-di-F-4-EtO—Ph |
| 312 | A | F2CHCH2— | Br | 5-Cl-4-Me-1-Pyra | 2-F—Ph |
| 313 | A | Et | Br | 4-F-1-Pyra | 2-Cl—Ph |
| 314 | A | Et | Cl | 4-F-1-Pyra | 2,6-di-F-4-MeO—Ph |
| 315 | A | Et | Br | 4-F-1-Pyra | 2,6-di-F-4-MeO—Ph |
| 316 | A | Et | Cl | 4-F-1-Pyra | 2,6-di-F-4-EtO—Ph |
| 317 | A | Et | Br | 4-F-1-Pyra | 2,6-di-F-4-EtO—Ph |
| 318 | A | Et | H | 4-F-1-Pyra | 2,6-di-F—Ph |
| 319 | A | Et | Cl | 4-F-1-Pyra | 2,6-di-F—Ph |
| 320 | A | Et | Br | 4-F-1-Pyra | 2,6-di-F—Ph |
| 321 | A | Et | Br | 4-Me-1-Pyra | 2-Et—Ph |
| 322 | A | Et | Br | 5-Cl-4-Me-1-Pyra | 2-Et—Ph |
| 323 | A | F2CHCH2— | H | 2-Br-3-Thio | 2,6-di-F—Ph |
| 324 | A | F2CHCH2— | H | 2,5-di-Br-3-Thio | 2,6-di-F—Ph |
| 325 | A | F2CHCH2— | Br | 2,5-di-Br-3-Thio | 2,6-di-F—Ph |
| 326 | A | Et | H | 4-F-1-Pyra | 2-Br-4-F—Ph |
| 327 | A | Et | H | 4-F-1-Pyra | 2-Cl-4-F—Ph |
| 328 | A | Et | Cl | 4-F-1-Pyra | 2-Cl-4-F—Ph |
| 329 | A | Et | Br | 4-F-1-Pyra | 2-Cl-4-F—Ph |
| 330 | A | Et | H | 4-Me-1-Pyra | 2-Br-4-F—Ph |
| 331 | A | Et | Cl | 5-Cl-4-Me-1-Pyra | 2-Br-4-F—Ph |
| 332 | A | Et | Br | 4-Me-1-Pyra | 2-Br-4-F—Ph |
| 333 | A | Et | Br | 5-Cl-4-Me-1-Pyra | 2-Br-4-F—Ph |
| 334 | A | Et | H | 4-Me-1-Pyra | 2-Cl-4-F—Ph |
| 335 | A | Et | Br | 4-Me-1-Pyra | 2-Cl-4-F—Ph |
| 336 | A | Et | Cl | 5-Cl-4-Me-1-Pyra | 2-Cl-4-F—Ph |
| 337 | A | Et | Br | 5-Cl-4-Me-1-Pyra | 2-Cl-4-F—Ph |
| 338 | A | F2CHCH2— | H | 4-Me-1-Pyra | 2-Br-4-F—Ph |
| 339 | A | F2CHCH2— | Br | 4-Me-1-Pyra | 2-Br-4-F—Ph |
| 340 | A | F2CHCH2— | Cl | 5-Cl-4-Me-1-Pyra | 2-Br-4-F—Ph |
| 341 | A | F2CHCH2— | Br | 5-Cl-4-Me-1-Pyra | 2-Br-4-F—Ph |
| 342 | A | F2CHCH2— | H | 4-Me-1-Pyra | 2-Cl-4-F—Ph |
| 343 | A | F2CHCH2— | Cl | 5-Cl-4-Me-1-Pyra | 2-Cl-4-F—Ph |
| 344 | A | F2CHCH2— | Br | 4-Me-1-Pyra | 2-Cl-4-F—Ph |
| 345 | A | F2CHCH2— | Br | 5-Cl-4-Me-1-Pyra | 2-Cl-4-F—Ph |
| 346 | A | F2CHCH2— | Br | 2-Br-3-Thio | 2,6-di-F—Ph |
| 347 | A | F2CHCH2— | Cl | 2-Br-3-Thio | 2,6-di-F—Ph |
| 348 | A | F2CHCH2— | H | 2-Br-5-Cl-3-Thio | 2,6-di-F—Ph |
| 349 | A | F2CHCH2— | Cl | 2-Br-5-Cl-3-Thio | 2,6-di-F—Ph |
| 350 | A | Et | H | 4-F-1-Pyra | 2-Cl—Ph |
| 351 | A | Et | Cl | 4-F-1-Pyra | 2-Cl—Ph |
| 352 | A | Et | Cl | 4-F-1-Pyra | 2-Br-4-F—Ph |
| 353 | A | Et | Br | 4-F-1-Pyra | 2-Br-4-F—Ph |
| 354 | A | Et | H | 4-F-1-Pyra | 2-Br-4-MeO—Ph |
| 355 | A | Et | Cl | 4-F-1-Pyra | 2-Br-4-MeO—Ph |
| 356 | A | Et | H | 4-F-1-Pyra | 2-Br—Ph |
| 357 | A | Et | Cl | 4-F-1-Pyra | 2-Br—Ph |
| 358 | A | Et | Br | 4-F-1-Pyra | 2-Br—Ph |
| 359 | A | Et | H | 3-Me-2-Thio | 2,6-di-F—Ph |
| 360 | A | Et | H | 4-F-1-Pyra | 2-Br-6-F—Ph |
| 361 | A | Et | Cl | 4-F-1-Pyra | 2-Cl-4-MeO—Ph |
| 362 | A | Et | H | 4-F-1-Pyra | 2-Cl-4-MeO—Ph |
| 363 | A | Et | Br | 4-F-1-Pyra | 2-Cl-4-MeO—Ph |
| 364 | A | Et | H | 3-Br-2-Thio | 2,6-di-F—Ph |
| 365 | A | Et | Cl | 3-Br-2-Thio | 2,6-di-F—Ph |
| 366 | A | F2CHCH2— | H | 2-Cl-3-Thio | 2,6-di-F—Ph |
| 367 | A | Et | H | 4-Me-1-Pyra | 4-F-2-Me—Ph |
| 368 | A | Et | Br | 5-Cl-4-Me-1-Pyra | 2-F-4-MeNH—Ph |
| 369 | A | Et | Cl | 5-Cl-4-Me-1-Pyra | 4-F-2-Me—Ph |

TABLE 5-continued

| Compound | Structure | R1 | R2 | Het | Y |
|---|---|---|---|---|---|
| 370 | A | Et | Br | 4-Me-1-Pyra | 4-F-2-Me—Ph |
| 371 | A | Et | Br | 5-Cl-4-Me-1-Pyra | 4-F-2-Me—Ph |
| 372 | A | Et | H | 4-Me-1-Pyra | 2-F3C—Ph |
| 373 | A | Et | Br | 5-Cl-4-Me-1-Pyra | 2-F-4-MeS—Ph |
| 374 | A | Et | Br | 4-Me-1-Pyra | 2-F3C—Ph |
| 375 | A | Et | Cl | 5-Cl-4-Me-1-Pyra | 2-F3C—Ph |
| 376 | A | NH2 | Br | 5-Cl-4-Me-1-Pyra | 2,4-di-F—Ph |
| 377 | A | Et | H | 2-Me-3-Thio | 2,6-di-F—Ph |
| 378 | A | Et | H | 4-F-1-Pyra | 2-Cl-6-F—Ph |
| 379 | A | Et | Cl | 4-F-1-Pyra | 2-Cl-6-F—Ph |
| 380 | A | Et | Br | 4-F-1-Pyra | 2-Cl-6-F—Ph |
| 381 | A | Et | Cl | 3-Me-2-Thio | 2,6-di-F—Ph |
| 382 | A | Et | H | 4-F-1-Pyra | 2-F—Ph |
| 383 | A | Et | Cl | 4-F-1-Pyra | 2-F—Ph |
| 384 | A | Et | Br | 4-F-1-Pyra | 2-F—Ph |
| 385 | A | F2CHCH2— | H | 3-Me-2-Thio | 2,6-di-F—Ph |
| 386 | A | Et | H | 5-Br-3-Me-2-Thio | 2,6-di-F—Ph |
| 387 | A | Et | Cl | 5-Br-3-Me-2-Thio | 2,6-di-F—Ph |
| 388 | A | Et | Br | 5-Br-3-Me-2-Thio | 2,6-di-F—Ph |
| 389 | A | Et | Br | 3-Me-2-Thio | 2,6-di-F—Ph |
| 390 | A | Et | Cl | 2-Me-3-Thio | 2,6-di-F—Ph |
| 391 | A | Et | Cl | 4-F-1-Pyra | 2-Br-6-F—Ph |
| 392 | A | Et | Br | 4-F-1-Pyra | 2-Br-6-F—Ph |
| 393 | A | Et | H | 3-Cl-2-Thio | 2,6-di-F—Ph |
| 394 | A | F2CHCH2— | H | 3-Cl-2-Thio | 2,6-di-F—Ph |
| 395 | A | Et | Cl | 3-Cl-2-Thio | 2,6-di-F—Ph |
| 396 | A | Et | Cl | 3,5-di-Cl-2-Thio | 2,6-di-F—Ph |
| 397 | A | Et | Br | 3-Cl-2-Thio | 2,6-di-F—Ph |
| 398 | A | Et | Br | 5-Br-3-Cl-2-Thio | 2,6-di-F—Ph |
| 399 | A | NH2 | Br | 2-Cl-3-Thio | 2,6-di-F—Ph |
| 400 | A | F2CHCH2— | Br | 5-Br-2-Cl-3-Thio | 2,6-di-F—Ph |
| 401 | A | F2CHCH2— | H | 5-Br-2-Cl-3-Thio | 2,6-di-F—Ph |
| 402 | A | F2CHCH2— | Br | 2-Cl-3-Thio | 2,6-di-F—Ph |
| 403 | A | F2CHCH2— | Cl | 5-Br-2-Cl-3-Thio | 2,6-di-F—Ph |
| 404 | A | F2CHCH2— | Cl | 2-Cl-3-Thio | 2,6-di-F—Ph |
| 405 | A | F2CHCH2— | H | 4-Me-1-Pyra | 2-Br—Ph |
| 406 | A | Me | H | 4-Me-1-Pyra | 2,4-di-F—Ph |
| 407 | A | F2CHCH2— | Cl | 5-Cl-4-Me-1-Pyra | 2-Br—Ph |
| 408 | A | F2CHCH2— | Br | 4-Me-1-Pyra | 2-Br—Ph |
| 409 | A | F2CHCH2— | Br | 5-Cl-4-Me-1-Pyra | 2-Br—Ph |
| 410 | A | Me | Cl | 5-Cl-4-Me-1-Pyra | 2,4-di-F—Ph |
| 411 | A | Me | Br | 4-Me-1-Pyra | 2,4-di-F—Ph |
| 412 | A | Me | Br | 5-Cl-4-Me-1-Pyra | 2,4-di-F—Ph |
| 413 | A | Me | H | 4-F-1-Pyra | 2,6-di-F—Ph |
| 414 | A | MeNH | Br | 5-Cl-4-Me-1-Pyra | 2,4-di-F—Ph |
| 415 | A | Et | Br | 3,5-di-Br-2-Thio | 2,6-di-F—Ph |
| 416 | A | Et | Br | 3-Br-2-Thio | 2,6-di-F—Ph |
| 417 | A | Et | H | 3,5-di-Br-2-Thio | 2,6-di-F—Ph |
| 418 | A | F2CHCH2— | H | 3-Br-2-Thio | 2,6-di-F—Ph |
| 419 | A | F2CHCH2— | Cl | 3-Br-5-Cl-2-Thio | 2,6-di-F—Ph |
| 420 | A | F2CHCH2— | Cl | 3-Br-2-Thio | 2,6-di-F—Ph |
| 421 | A | F2CHCH2— | H | 3-Br-5-Cl-2-Thio | 2,6-di-F—Ph |
| 422 | A | F2CHCH2— | Br | 3,5-di-Br-2-Thio | 2,6-di-F—Ph |
| 423 | A | F2CHCH2— | Br | 3-Br-2-Thio | 2,6-di-F—Ph |
| 424 | A | F2CHCH2— | H | 2-Me-3-Thio | 2,6-di-F—Ph |
| 425 | A | F2CHCH2— | H | 4-F-1-Pyra | 2-Cl-4-F—Ph |
| 426 | A | F2CHCH2— | Cl | 4-F-1-Pyra | 2-Cl-4-F—Ph |
| 427 | A | Et | Br | 4-Cl-1-Pyra | 2-Cl-4-MeO—Ph |
| 428 | A | Et | H | 4-Cl-1-Pyra | 2-Cl-4-MeO—Ph |
| 429 | A | Me | Cl | 2-Br-3-Thio | 2,6-di-F—Ph |
| 430 | A | Me | Br | 2-Br-3-Thio | 2,6-di-F—Ph |
| 431 | A | Me | H | 2-Me-3-Thio | 2,6-di-F—Ph |
| 432 | A | F2CHCH2— | Br | 5-Br-3-Cl-2-Thio | 2,6-di-F—Ph |
| 433 | A | F2CHCH2— | Br | 3-Cl-2-Thio | 2,6-di-F—Ph |
| 434 | A | F2CHCH2— | H | 5-Br-3-Cl-2-Thio | 2,6-di-F—Ph |
| 435 | A | Me | H | 3-Cl-2-Thio | 2,6-di-F—Ph |
| 436 | A | F2CHCH2— | Cl | 3,5-di-Cl-2-Thio | 2,6-di-F—Ph |
| 437 | A | F2CHCH2— | Cl | 3-Cl-2-Thio | 2,6-di-F—Ph |
| 438 | A | F2CHCH2— | H | 3,5-di-Cl-2-Thio | 2,6-di-F—Ph |
| 439 | A | Me | Cl | 3-Cl-2-Thio | 2,6-di-F—Ph |
| 440 | A | Me | Cl | 3,5-di-Cl-2-Thio | 2,6-di-F—Ph |
| 441 | A | Me | Br | 3-Cl-2-Thio | 2,6-di-F—Ph |
| 442 | A | Me | Br | 5-Br-3-Cl-2-Thio | 2,6-di-F—Ph |
| 443 | A | F2CHCH2— | H | 5-Br-3-Me-2-Thio | 2,6-di-F—Ph |
| 444 | A | Et | Br | 2-Me-3-Thio | 2,6-di-F—Ph |
| 445 | A | F2CHCH2— | Cl | 3-Me-2-Thio | 2,6-di-F—Ph |
| 446 | A | F2CHCH2— | Br | 3-Me-2-Thio | 2,6-di-F—Ph |
| 447 | A | F2CHCH2— | H | 4-F-1-Pyra | 2-Br-4-F—Ph |

TABLE 5-continued

| Compound | Structure | R1 | R2 | Het | Y |
|---|---|---|---|---|---|
| 448 | A | F2CHCH2— | Cl | 4-F-1-Pyra | 2-Br-4-F—Ph |
| 449 | A | F2CHCH2— | Br | 4-F-1-Pyra | 2-Br4-F—Ph |
| 450 | A | F2CHCH2— | Br | 4-F-1-Pyra | 2-Br-4-MeO—Ph |
| 451 | A | Me | H | 4-Cl-1-Pyra | 2-Cl-4-F—Ph |
| 452 | A | Me | Cl | 4-Cl-1-Pyra | 2-Cl-4-F—Ph |
| 453 | A | Me | Br | 4-Cl-1-Pyra | 2-Cl-4-F—Ph |
| 454 | B | Me | H | 2-Br-3-Thio | 2,6-di-F—Ph |
| 455 | A | Me2N | Br | 2-Cl-3-Thio | 2,6-di-F—Ph |
| 456 | A | Me | H | 2-Br-3-Thio | 2,6-di-F—Ph |
| 457 | B | Me | H | 3-Me-2-Thio | 2,6-di-F—Ph |
| 458 | A | Et | H | 2-Cl-3-Thio | 2-Cl-4-F—Ph |
| 459 | A | Et | Br | 2-Cl-3-Thio | 2-Cl-4-F—Ph |
| 460 | A | Et | Cl | 2-Cl-3-Thio | 2-Cl-4-F—Ph |
| 461 | A | Me | Cl | 4-F-1-Pyra | 2,6-di-F—Ph |
| 462 | A | Me | Br | 4-F-1-Pyra | 2,6-di-F—Ph |
| 463 | A | Me | H | 4-F-1-Pyra | 2,4-di-F—Ph |
| 464 | A | Me | Cl | 4-F-1-Pyra | 2,4-di-F—Ph |
| 465 | A | Me | Br | 4-F-1-Pyra | 2,4-di-F—Ph |
| 466 | A | Et | Br | 5-Cl-4-Me-1-Pyra | 2-F-4-(pyrrolidin-1-yl)-Ph |
| 467 | A | NH2 | Br | 4-F-1-Pyra | 2,6-di-F—Ph |
| 468 | A | MeNH | Br | 4-F-1-Pyra | 2,6-di-F—Ph |
| 469 | A | Et | Br | 5-Cl-4-Me-1-Pyra | 2-F-4-(piperidin-1-yl)-Ph |
| 470 | A | Me2N | Br | 5-Cl-4-Me-1-Pyra | 2,4-di-F—Ph |
| 471 | A | Et | Br | 4-Me-1-Pyra | 2-N≡C—Ph |
| 472 | A | Et | Br | 5-Cl-4-Me-1-Pyra | 2-N≡C—Ph |
| 473 | A | NH2 | Br | 5-Cl-4-Me-1-Pyra | 2,6-di-F—Ph |
| 474 | A | Me | H | 4-Me-1-Pyra | 2-Cl-4-F—Ph |
| 475 | A | MeNH | Br | 5-Cl-4-Me-1-Pyra | 2,6-di-F—Ph |
| 476 | A | Me | Cl | 5-Cl-4-Me-1-Pyra | 2-Cl-4-F—Ph |
| 477 | A | NH2 | Br | 5-Cl-4-Me-1-Pyra | 2-Cl-4-F—Ph |
| 478 | A | MeNH | Br | 5-Cl-4-Me-1-Pyra | 2-Cl-4-F—Ph |
| 479 | A | Me2N | Br | 5-Cl-4-Me-1-Pyra | 2-Cl-4-F—Ph |
| 480 | A | F2CHCH2— | Cl | 2-Me-3-Thio | 2,6-di-F—Ph |
| 481 | A | Me | H | 4-F-1-Pyra | 2-Cl-4-F—Ph |
| 482 | A | Me | Cl | 4-F-1-Pyra | 2-Cl-4-F—Ph |
| 483 | A | Me | Br | 4-F-1-Pyra | 2-Cl-4-F—Ph |
| 484 | A | Me | Cl | 2-Me-3-Thio | 2,6-di-F—Ph |
| 485 | A | Et | H | 4-Me-1-Pyra | 4-Br-2-F—Ph |
| 486 | A | Et | Br | 5-Cl-4-Me-1-Pyra | 2-N≡C-4-F—Ph |
| 487 | A | Me | H | 4-Me-1-Pyra | 2-F—Ph |
| 488 | A | Me | Cl | 5-Cl-4-Me-1-Pyra | 2-F—Ph |
| 489 | A | Me | Br | 4-Me-1-Pyra | 2-F—Ph |
| 490 | A | Me | Br | 5-Cl-4-Me-1-Pyra | 2-F—Ph |
| 491 | A | Me | H | 5-Br-2-Me-3-Thio | 2,6-di-F—Ph |
| 492 | A | Me | Br | 2-Me-3-Thio | 2,6-di-F—Ph |
| 493 | A | F2CHCH2— | H | 3-Thio | 2,6-di-F—Ph |
| 494 | A | F2CHCH2— | Br | 5-Br-2-Me-3-Thio | 2,6-di-F—Ph |
| 495 | A | F2CHCH2— | Br | 5-Br-2-BrCH2-3-Thio | 2,6-di-F—Ph |
| 496 | A | Me | H | 3-Me-2-Thio | 2,6-di-F—Ph |
| 497 | A | Et | H | 2-Cl-3-Thio | 2-Cl-4-MeO—Ph |
| 498 | A | Me | Cl | 3-Me-2-Thio | 2,6-di-F—Ph |
| 499 | A | Et | Br | 2-Br-3-Thio | 2,4-di-F—Ph |
| 500 | A | Et | H | 2-Br-3-Thio | 2,4-di-F—Ph |
| 501 | A | Et | Cl | 2-Br-3-Thio | 2,4-di-F—Ph |
| 502 | A | Et | Cl | 2-Cl-3-Thio | 2-Cl-4-MeO—Ph |
| 503 | A | Et | H | 2-Me-3-Thio | 2,4-di-F—Ph |
| 504 | A | Et | Br | 2-Cl-3-Thio | 2-Cl-4-MeO—Ph |
| 505 | A | Et | H | 4-Me-1-Pyra | 2,4-di-F—Ph |
| 506 | A | Et | H | 5-Cl-4-Me-1-Pyra | 2,4-di-F—Ph |
| 507 | A | Et | Cl | 5-Cl-4-Me-1-Pyra | 4-N≡C-2-F—Ph |
| 508 | A | Et | Cl | 4-F-1-Pyra | 4-N≡C-2-F—Ph |
| 509 | A | Me | Cl | 4-F-1-Pyra | 2-Cl-6-F—Ph |
| 510 | A | Me | Br | 4-F-1-Pyra | 2-Cl-6-F—Ph |
| 511 | A | Me | H | 4-Me-1-Pyra | 4-F-2-Me—Ph |
| 512 | A | Me | Cl | 5-Cl-4-Me-1-Pyra | 4-F-2-Me—Ph |
| 513 | A | Me | Br | 4-Me-1-Pyra | 4-F-2-Me—Ph |
| 514 | A | Me | Br | 5-Cl-4-Me-1-Pyra | 4-F-2-Me—Ph |
| 515 | A | Me | Br | 5-Cl-4-Me-1-Pyra | 2-Cl-4-F—Ph |

Next, with regard to the compounds shown in Table 5, H-NMR data thereof are shown in Table 6.

TABLE 6

| Compound | $^1$H-NMR |
|---|---|
| 1 | $^1$H-NMR CDCl$_3$) δ: 7.45-7.43 (1H, m), 7.04 (1H, dd, J = 5.3, 1.1 Hz), 6.98 (2H, dd, J = 8.2, 6.9 Hz), 6.84 (1H, dd, J = 5.0, 3.7 Hz), 6.76 (1H, dd, J = 3.7, 0.9 Hz), 2.92 (2H, dd, J = 8.9, 6.2 Hz), 2.88 (3H, s), 2.75 (2H, dd, J = 8.9, 6.2 Hz). |
| 2 | $^1$H-NMR (CDCl$_3$) δ: 7.45-7.43 (1H, m), 7.03 (1H, dd, J = 5.0, 1.4 Hz), 6.97 (2H, dd, J = 8.5, 7.1 Hz), 6.83 (1H, dd, J = 5.0, 3.7 Hz), 6.73 (1H, dd, J = 3.7, 0.9 Hz), 3.42 (2H, q, J = 7.2 Hz), 2.90 (2H, dd, J = 9.4, 6.2 Hz), 2.73 (2H, dd, J = 8.7, 6.0 Hz), 0.97 (3H, t, J = 7.1 Hz). |
| 3 | $^1$H-NMR (CDCl$_3$) δ: 7.35-7.33 (1H, m), 7.09 (1H, dd, J = 5.0, 3.2 Hz), 6.90 (2H, dd, J = 8.5, 7.1 Hz), 6.74 (1H, dd, J = 3.2, 1.4 Hz), 6.63 (1H, dd, J = 5.0, 1.4 Hz), 2.87 (3H, s), 2.83-2.69 (4H, m). |
| 4 | $^1$H-NMR (CDCl$_3$) δ: 7.35-7.33 (1H, m), 7.08 (1H, dd, J = 5.0, 2.7 Hz), 6.89 (2H, dd, J = 8.2, 6.9 Hz), 6.71 (1H, dd, J = 3.2, 1.4 Hz), 6.63 (1H, dd, J = 5.0, 1.4 Hz), 3.41 (2H, q, J = 7.0 Hz), 2.81-2.69 (4H, m), 0.95 (3H, q, J = 7.9 Hz). |
| 5 | $^1$H-NMR (CDCl$_3$) δ: 7.53 (1H, d, J = 9.5 Hz), 7.43 (1H, tt, J = 8.6, 6.3 Hz), 7.12 (1H, dd, J = 5.1, 1.2 Hz), 6.99-6.94 (2H, m), 6.83 (1H, dd, J = 5.1, 3.7 Hz), 6.73 (1H, dd, J = 3.7, 1.2 Hz), 6.72 (1H, d, J = 9.5 Hz), 3.90 (2H, q, J = 7.1 Hz), 1.15 (3H, t, J = 7.1 Hz). |
| 6 | $^1$H-NMR (CDCl$_3$) δ: 7.48-7.45 (2H, m), 7.00 (2H, dd, J = 8.5, 7.1 Hz), 6.71 (1H, d, J = 9.5 Hz), 6.65 (1H, d, J = 3.9 Hz), 6.52 (1H, d, J = 3.9 Hz), 3.87 (2H, q, J = 7.1 Hz), 1.14 (3H, t, J = 7.1 Hz). |
| 7 | $^1$H-NMR (CDCl$_3$) δ: 7.70 (1H, s), 7.49 (1H, tt, J = 8.5, 6.4 Hz), 7.00 (2H, dd, J = 8.5, 7.1 Hz), 6.66 (1H, d, J = 3.9 Hz), 6.56 (1H, d, J = 3.9 Hz) 3.92 (2H, q, J = 7.1 Hz), 1.16 (3H, 1, J = 7.1 Hz). |
| 8 | $^1$H-NMR (CDCl$_3$) δ: 7.91 (1H, s), 6.88-6.84 (2H, m), 4.75 (1H, s), 4.09-4.07 (2H, m), 3.85 (2H, q, J = 7.1 Hz), 3.60-3.57 (2H, m), 2.07-2.02 (1H, m), 1.30-1.27 (1H, m), 1.14 (3H, t, J = 7.1 Hz). |
| 9 | $^1$H-NMR (CDCl$_3$) δ: 7.77 (1H, s), 6.87 (2H, td, J = 8.6, 1.8 Hz), 5.09 (1H, s), 4.06-4.02 (2H, m), 3.87-3.84 (4H, m), 1.15 (3H, t, J = 7.1 Hz). |
| 10 | $^1$H-NMR (CDCl$_3$) δ: 7.91 (1H, s), 6.63-6.59 (2H, m), 4.77 (1H, s), 4.11-4.08 (2H, m), 3.89 (3H, s), 3.87 (2H, q, J = 7.1 Hz), 3.62-3.59 (2H, m), 2.10-2.06 (1H, m), 1.30-1.26 (1H, m), 1.13 (3H, t, J = 7.1 Hz). |
| 11 | $^1$H-NMR (CDCl$_3$) δ: 7.93 (1H, s), 7.55 (1H, tt, J = 8.4, 6.4 Hz), 7.10-7.07 (2H, m), 4.74 (1H, s), 4.08-4.06 (2H, m), 3.86 (2H, q, J = 7.1 Hz), 3.56-3.53 (2H, m), 2.08-2.03 (1H, m), 1.28-1.24 (1H, m), 1.14 (3H, t, J = 7.1 Hz). |
| 12 | $^1$H-NMR (CDCl$_3$) δ: 7.75 (1H, s), 6.62-6.60 (2H, m), 5.11 (1H, s), 4.07-4.05 (2H, m), 3.88-3.86 (7H, m), 1.14 (3H, t, J = 7.1 Hz). |
| 13 | $^1$H-NMR (CDCl$_3$) δ: 7.77 (1H, s), 7.54 (1H, tt, J = 8.5, 6.4 Hz), 7.09 (2H, dd, J = 8.5, 7.0 Hz), 5.08 (1H, s), 4.05-4.03 (2H, m), 3.87-3.83 (4H, m), 1.14 (3H, t, J = 7.1 Hz). |
| 14 | $^1$H-NMR (CDCl$_3$) δ: 7.56 (1H, d, J = 9.5 Hz), 7.45-7.43 (1H, m), 7.12 (1H, dd, J = 5.2, 1.2 Hz), 6.99-6.95 (2H, m), 6.84 (1H, dd, J = 5.0, 3.5 Hz), 6.74-6.73 (2H, m), 3.37 (3H, s). |
| 15 | $^1$H-NMR (CDCl$_3$) δ: 7.47 (1H, d, J = 9.5 Hz), 7.40-7.38 (1H, m), 7.13 (1H, dd, J = 5.0, 3.1 Hz), 6.96-6.90 (2H, m), 6.89 (1H, dd, J = 2.9, 1.2 Hz), 6.75-6.72 (2H, m), 3.38 (3H, s). |
| 16 | $^1$H-NMR (CDCl$_3$) δ: 7.44 (1H, d, J = 9.5 Hz), 7.39-7.37 (1H, m), 7.11 (1H, dd, J = 5.0, 2.9 Hz), 6.93-6.91 (2H, m), 6.89 (1H, dd, J = 2.9, 1.4 Hz), 6.75 (1H, dd, J = 4.9, 1.2 Hz), 6.72 (1H, d, J = 9.5 Hz), 3.90 (2H, q, J = 7.0 Hz), 1.14 (3H, t, J = 7.0 Hz). |
| 17 | $^1$H-NMR (CDCl$_3$) δ: 8.23 (1H, dd, J = 4.9, 2.0 Hz), 7.42 (1H, dt, J = 7.6, 2.0 Hz), 7.36-7.29 (2H, m), 7.04 (1H, dd, J = 7.6, 4.9 Hz), 6.91-6.83 (2H, m), 6.76 (1H, d, J = 9.3 Hz), 3.96-3.87 (2H, m), 1.16 (3H, t, J = 7.1 Hz). |
| 18 | $^1$H-NMR (CDCl$_3$) δ: 8.25 (1H, dd, J = 4.8, 1.9 Hz), 7.57 (1H, s), 7.43 (1H, dt, J = 7.6, 1.9 Hz), 7.38-7.30 (1H, m), 7.06 (1H, dd, J = 7.6, 4.8 Hz) 6.91-6.85 (2H, m), 4.01-3.92 (2H, m), 1.19 (3H, t, J = 7.1 Hz). |
| 19 | $^1$H-NMR (CDCl$_3$) δ: 7.60 (1H, s), 6.99 (1H, s), 6.67-6.65 (2H, m), 3.97 (2H, q, J = 7.2 Hz), 3.64 (3H, s), 1.87 (3H, d, J = 0.5 Hz), 1.18 (3H, t, J = 7.2 Hz). |
| 20 | $^1$H-NMR (CDCl$_3$) δ: 7.53 (1H, s), 7.28 (1H, d, J = 2.0 Hz), 6.71-6.69 (2H, m), 5.93 (1H, d, J = 2.0 Hz), 3.94 (2H, q, J = 7.1 Hz), 3.69 (3H, s), 1.19 (3H, t, J = 7.1 Hz). |
| 21 | $^1$H-NMR (CDCl$_3$) δ: 7.47 (1H, s), 7.32 (1H, s), 6.77-6.76 (1H, m), 6.69-6.64 (1H, m), 4.19-4.13 (1H, m), 3.87-3.81 (1H, m), 3.69 (3H, d, J = 1.5 Hz), 1.18 (3H, t, J = 7.1 Hz). |
| 22 | $^1$H-NMR (CDCl$_3$) δ: 7.48 (1H, s), 7.28 (1H, s), 6.78-6.76 (1H, m), 6.67-6.64 (1H, m), 4.19 (1H, dq, J = 13.5, 7.0 Hz), 3.81 (1H, dq, J = 13.5, 7.0 Hz), 3.68 (3H, d, J = 1.2 Hz), 1.19 (3H, t, J = 7.0 Hz). |
| 23 | $^1$H-NMR (CDCl$_3$) δ: 7.45 (1H, s), 7.32 (1H, s), 6.48 (1H, dt, J = 11.2, 1.8 Hz), 6.41 (1H, dt, J = 11.2, 1.8 Hz), 4.12 (1H, dq, J = 13.5, 7.0 Hz), 3.91 (1H, dq, J = 13.5, 7.0 Hz), 3.80 (3H, s), 3.66 (3H, d, J = 1.2 Hz), 1.18 (3H, t, J = 7.0 Hz). |

TABLE 6-continued

| Compound | $^1$H-NMR |
|---|---|
| 24 | $^1$H-NMR ($CDCl_3$) δ: 7.71 (1H, s), 7.26 (1H, s), 6.69-6.67 (2H, m), 3.97 (2H, q, J = 7.1 Hz), 3.69 (3H, s), 1.18 (3H, t, J = 7.1 Hz). |
| 25 | $^1$H-NMR ($CDCl_3$) δ: 7.47 (1H, d, J = 2.0 Hz), 7.14 (1H, d, J = 2.2 Hz), 6.69-6.63 (2H, m), 6.11 (1H, dd, J = 2.2, 2.0 Hz), 3.42 (2H, q, J = 7.2 Hz), 2.95-2.90 (2H, m), 2.88-2.83 (2H, m), 0.98 (3H, t, J = 7.2 Hz). |
| 26 | $^1$H-NMR ($CDCl_3$) δ: 7.46-7.45 (2H, m), 7.29 (1H, d, J = 2.4 Hz), 6.75 (1H, d, J = 9.8 Hz), 6.72-6.68 (2H, m), 6.19-6.18 (1H, m), 3.89 (2H, q, J = 7.2 Hz), 1.17 (3H, t, J = 7.2 Hz). |
| 27 | $^1$H-NMR ($CDCl_3$) δ: 7.40 (1H, d, J = 9.8 Hz), 7.37 (1H, s), 7.31 (1H, s), 6.75-6.72 (3H, m), 3.88 (2H, q, J = 7.0 Hz), 1.17 (3H, t, J = 7.0 Hz). |
| 28 | $^1$H-NMR ($CDCl_3$) δ: 7.51 (1H, s), 7.28 (1H, d, J = 1.8 Hz), 6.44-6.42 (2H, m), 5.96 (1H, d, J = 1.8 Hz), 3.97 (2H, q, J = 7.1 Hz), 3.79 (3H, s), 3.68 (3H, s), 1.18 (3H, t, J = 7.1 Hz). |
| 29 | $^1$H-NMR ($CDCl_3$) δ: 7.46 (1H, s), 7.28 (1H, s), 6.49 (1H, ddd, J = 10.7, 2.2, 1.5 Hz), 6.40 (1H, ddd, J = 11.0, 2.2, 1.5 Hz), 4.17-4.10 (1H, m), 3.90-3.87 (1H, m), 3.80 (3H, s), 3.66 (3H, d, J = 1.2 Hz), 1.18 (3H, t, J = 7.1 Hz). |
| 30 | $^1$H-NMR ($CDCl_3$) δ: 7.47 (1H, d, J = 1.8 Hz), 7.34-7.32 (1H, m), 7.11 (1H, d, J = 2.4 Hz), 6.90-6.88 (2H, m), 6.06-6.06 (1H, m), 3.42 (2H, q, J = 7.0 Hz). 2.95-2.93 (2H, m), 2.88-2.85 (2H, m), 0.98 (3H, t, J = 7.0 Hz). |
| 31 | $^1$H-NMR ($CDCl_3$) δ: 7.48 (1H, d, J = 9.5 Hz), 7.44 (1H, dd, J = 1.8, 0.9 Hz), 7.40-7.38 (1H, m), 7.27-7.27 (1H, m), 6.95-6.91 (2H, m), 6.75 (1H, d, J = 9.5 Hz), 6.14 (1H, dd, J = 2.4, 1.8 Hz), 3.89 (2H, q, J = 7.2 Hz), 1.17 (3H, t, J = 7.2 Hz). |
| 32 | $^1$H-NMR ($CDCl_3$) δ: 8.00 (1H, s), 7.76 (1H, s), 7.37 (1H, dd, J = 8.3, 2.6 Hz), 7.31 (1H, dd, J = 8.6, 5.8 Hz), 7.21 (1H, ddd, J = 8.6, 7.6, 2.6 Hz), 5.77 (1H, s), 4.23-4.16 (1H, m), 3.62-3.56 (1H, m), 1.18 (3H, t, J = 7.0 Hz). |
| 33 | $^1$H-NMR ($CDCl_3$) δ: 8.03 (1H, s), 7.76 (1H, s), 7.18 (1H, d, J = 8.6 Hz), 7.12 (1H, d, J = 2.8 Hz), 6.99 (1H, dd, J = 8.6, 2.8 Hz), 5.66 (1H, s), 4.23-4.16 (1H, m), 3.90 (3H, s), 3.68-3.61 (1H, m), 1.18 (3H, t, J = 7.0 Hz). |
| 34 | $^1$H-NMR ($CDCl_3$) δ: 7.99 (1H, s), 7.87 (1H, s), 7.68 (1H, s), 6.76-6.74 (2H, m), 3.95 (2H, q, J = 7.2 Hz), 1.21 (3H, t, J = 7.2 Hz). |
| 35 | $^1$H-NMR ($CDCl_3$) δ: 7.76 (1H, s), 7.60 (1H, s), 6.75-6.73 (2H, m), 3.97 (2H, q, J = 7.2 Hz), 1.22 (3H, t, J = 7.2 Hz). |
| 36 | $^1$H-NMR ($CDCl_3$) δ: 7.94 (1H, s), 7.77 (1H, s), 6.93-6.86 (2H, m), 6.19 (1H, s), 3.95 (2H, q, J = 7.1 Hz), 1.19 (3H, t, J = 7.1 Hz). |
| 37 | $^1$H-NMR ($CDCl_3$) δ: 7.98 (1H, s), 7.78 (1H, s), 6.66-6.61 (2H, m), 6.04 (1H, s), 3.98 (2H, q, J = 7.1 Hz), 3.89 (3H, s), 1.19 (3H, t, J = 7.1 Hz). |
| 38 | $^1$H-NMR ($CDCl_3$) δ: 7.57 (1H, s), 7.53 (1H, s), 7.24 (1H, dd, J = 8.6, 5.8 Hz), 7.19 (1H, dd, J = 8.3, 2.4 Hz), 7.04 (1H, ddd, J = 8.6, 8.0, 2.4 Hz), 4.29-4.22 (1H, m), 3.60-3.53 (1H, m), 2.05 (3H, s), 1.15 (3H, t, J = 7.0 Hz). |
| 39 | $^1$H-NMR ($CDCl_3$) δ: 7.55 (1H, s), 7.55 (1H, s), 7.11 (1H, d, J = 8.5 Hz), 6.93 (1H, d, J = 2.4 Hz), 6.80 (1H, dd, J = 8.5, 2.4 Hz), 4.30-4.22 (1H, m), 3.82 (3H, s), 3.65-3.57 (1H, m), 2.02 (3H, s), 1.14 (3H, t, J = 7.1 Hz). |
| 40 | $^1$H-NMR ($CDCl_3$) δ: 7.66 (1H, s), 7.38 (1H, s), 7.32 (1H, s), 6.76-6.74 (2H, m), 3.94 (2H, q, J = 7.2 Hz), 1.19 (3H, t, J = 7.2 Hz). |
| 41 | $^1$H-NMR ($CDCl_3$) δ: 7.67 (1H, s), 7.40 (1H, s), 7.28 (1H, s), 6.51-6.48 (2H, m), 3.95 (2H, q, J = 7.2 Hz), 3.83 (3H, s), 1.18 (3H, t, J = 7.2 Hz). |
| 42 | $^1$H-NMR ($CDCl_3$) δ: 7.98 (1H, s), 7.75 (1H, s), 7.63-7.56 (1H, m), 7.15-7.10 (2H, m), 6.01 (1H, s), 3.96 (2H, q, J = 7.1 Hz), 1.19 (3H, t, J = 7.1 Hz). |
| 43 | $^1$H-NMR ($CDCl_3$) δ: 7.59 (1H, s), 7.56 (1H, s), 7.43 (1H, tt, J = 8.6, 6.4 Hz), 6.99-6.94 (2H, m), 3.97 (2H, q, J = 7.1 Hz), 1.99 (3H, s), 1.17 (3H, t, J = 7.1 Hz). |
| 44 | $^1$H-NMR ($CDCl_3$) δ: 7.38-7.32 (2H, m), 7.00 (1H, d, J = 5.8 Hz), 6.91-6.89 (2H, m), 6.76 (1H, d, J = 9.5 Hz), 6.54 (1H, d, J = 5.8 Hz), 3.91 (2H, q, J = 7.0 Hz), 1.16 (3H, t, J = 7.0 Hz). |
| 45 | $^1$H-NMR ($CDCl_3$) δ: 7.59 (1H, s), 7.37 (1H, tt, J = 8.6, 6.4 Hz), 7.01 (1H, d, J = 5.8 Hz), 6.92-6.90 (2H, m), 6.55 (1H, d, J = 5.8 Hz), 3.96 (2H, q, J = 7.1 Hz), 1.18 (3H, t, J = 7.1 Hz). |
| 46 | $^1$H-NMR ($CDCl_3$) δ: 7.80 (1H, s), 7.76 (1H, s), 6.76-6.72 (2H, m), 3.97 (2H, q, J = 7.0 Hz), 1.22 (3H, t, J = 7.0 Hz). |
| 47 | $^1$H-NMR ($CDCl_3$) δ: 7.99 (1H, s), 7.88 (1H, s), 7.87 (1H, s), 6.77-6.73 (2H, m), 3.95 (2H, q, J = 7.2 Hz), 1.21 (3H, t, J = 7.2 Hz). |
| 48 | $^1$H-NMR ($CDCl_3$) δ: 7.79 (1H, s), 7.60 (1H, s), 6.74-6.72 (2H, m), 3.97 (2H, q, J = 72 Hz), 1.23 (3H, t, J = 7.2 Hz). |
| 49 | $^1$H-NMR ($CDCl_3$) δ: 7.74 (1H, s), 7.57 (1H, s), 7.49-7.43 (1H, m), 7.01-6.97 (2H, m), 3.97 (2H, q, J = 7.1 Hz), 1.18 (3H, t, J = 7.1 Hz). |
| 50 | $^1$H-NMR ($CDCl_3$) δ: 7.75 (1H, s), 7.56 (1H, s), 7.47 (1H, tt, J = 8.5, 6.3 Hz), 7.03-6.97 (2H, m), 3.97 (2H, q, J = 7.1 Hz), 1.17 (3H, t, J = 7.1 Hz). |
| 51 | $^1$H-NMR ($CDCl_3$) δ: 7.75 (1H, s), 7.51 (1H, tt, J = 8.5, 6.3 Hz), 7.43 (1H, d, J = 2.0 Hz), 7.06-7.00 (2H, m), 3.95 (2H, q, J = 7.1 Hz), 1.17 (3H, t, J = 7.1 Hz). |
| 52 | $^1$H-NMR ($CDCl_3$) δ: 7.44-7.42 (2H, m), 7.35 (1H, s), 7.28 (1H, s), 6.98-6.96 (2H, m), 6.74 (1H, d, J = 9.8 Hz), 3.88 (2H, q, J = 7.2 Hz), 1.16 (3H, t, J = 7.2 Hz). |

TABLE 6-continued

| Compound | $^1$H-NMR |
|---|---|
| 53 | $^1$H-NMR ($CDCl_3$) δ: 7.68 (1H, s), 7.46-7.43 (1H, m), 7.36 (1H, s), 7.28 (1H, s), 6.99-6.97 (2H, m), 3.94 (2H, q, J = 7.2 Hz), 1.19 (3H, t, J = 7.2 Hz). |
| 54 | $^1$H-NMR ($CDCl_3$) δ: 7.80 (1H, s), 7.37 (1H, tt, J = 8.4, 6.4 Hz), 7.01 (1H, d, J = 5.8 Hz), 6.91 (2H, dd, J = 8.4, 7.2 Hz), 6.54 (1H, d, J = 5.8 Hz), 3.96 (2H, q, J = 7.2 Hz), 1.17 (3H, t, J = 7.2 Hz). |
| 55 | $^1$H-NMR ($CDCl_3$) δ: 8.25 (1H, dd, J = 4.8, 2.0 Hz), 7.78 (1H, s), 7.43 (1H, dt, J = 7.6, 1.7 Hz), 7.38-7.30 (1H, m), 7.07 (1H, dd, J = 7.6, 4.8 Hz), 6.91-6.85 (2H, m), 4.01-3.92 (2H, m), 1.18 (3H, t, J = 7.2 Hz). |
| 56 | $^1$H-NMR ($CDCl_3$) δ: 8.25 (1H, dd, J = 4.9, 2.0 Hz), 7.44 (1H, dt, J = 7.6, 2.0 Hz), 7.42-7.33 (2H, m), 7.08 (1H, dd, J = 7.6, 4.9 Hz), 6.90-6.85 (2H, m), 6.79 (1H, d, J = 9.5 Hz), 6.16 (1H, tt, J = 56.4, 4.6 Hz), 4.28-4.08 (2H, m). |
| 57 | $^1$H-NMR ($CDCl_3$) δ: 8.28 (1H, dd, J = 4.8, 2.0 Hz), 7.63 (1H, s), 7.47 (1H, dt, J = 7.5, 2.0 Hz), 7.41-7.35 (1H, m), 7.10 (1H, dd, J = 7.5, 4.8 Hz), 6.91-6.87 (2H, m), 6.19 (1H, tt, J = 56.4, 4.5 Hz), 4.34-4.25 (1H, m), 4.20-4.10 (1H, m). |
| 58 | $^1$H-NMR ($CDCl_3$) δ: 8.24 (1H, dd, J = 4.9, 2.0 Hz), 7.45-7.41 (1H, m), 7.38-7.30 (2H, m), 7.07 (1H, dd, J = 7.6, 4.9 Hz), 6.88-6.79 (3H, m), 4.70 (1H, br s), 4.53 (1H, br s). |
| 59 | $^1$H-NMR ($CDCl_3$) δ: 8.27 (1H, dd, J = 4.7, 1.9 Hz), 7.83 (1H, s), 7.46 (1H, dt, J = 7.6, 1.9 Hz), 7.41-7.34 (1H, m), 7.10 (1H, dd, J = 7.6, 4.7 Hz), 6.91-6.86 (2H, m), 6.19 (1H, tt, J = 56.3, 4.5 Hz), 4.35-4.24 (1H, m), 4.21-4.10 (1H, m). |
| 60 | $^1$H-NMR ($CDCl_3$) δ: 8.28 (1H, dd, J = 4.7, 2.0 Hz), 7.60 (1H, s), 7.50-7.46 (1H, m), 7.42-7.34 (1H, m), 7.12 (1H, dd, J = 7.6, 4.7 Hz), 6.92-6.85 (2H, m), 4.88-4.75 (1H, br m), 4.60-4.49 (1H, br m). |
| 61 | $^1$H-NMR ($CDCl_3$) δ: 8.28 (1H, dd, J = 4.8, 1.7 Hz), 7.42 (1H, dt, J = 7.5, 1.7 Hz), 7.33 (1H, d, J = 9.3 Hz), 7.10 (1H, dd, J = 7.5, 4.8 Hz), 6.77 (1H, d, J = 9.3 Hz), 6.69-6.62 (2H, m), 3.96-3.86 (2H, m), 1.16 (3H, t, J = 7.0 Hz). |
| 62 | $^1$H-NMR ($CDCl_3$) δ: 8.30 (1H, dd, J = 4.8, 1.9 Hz), 7.56 (1H, s), 7.43 (1H, dt, J = 7.6, 1.9 Hz), 7.12 (1H, dd, J = 7.6, 4.8 Hz), 6.69-6.64 (2H, m), 4.03-3.89 (2H, m), 1.19 (3H, t, J = 7.2 Hz). |
| 63 | $^1$H-NMR ($CDCl_3$) δ: 8.29 (1H, dd, J = 4.8, 1.9 Hz), 7.76 (1H, s), 7.43 (1H, dt, J = 7.6, 1.9 Hz), 7.12 (1H, dd, J = 7.6, 4.8 Hz), 6.69-6.64 (2H, m) 4.03-3.89 (2H, m), 1.19 (3H, t, J = 7.0 Hz). |
| 64 | $^1$H-NMR ($CDCl_3$) δ: 8.28 (1H, dd, J = 4.9, 1.8 Hz), 7.81 (1H, s), 7.49-7.46 (1H, m), 7.41-7.35 (1H, m), 7.12 (1H, dd, J = 7.6, 4.9 Hz), 6.92-6.85 (2H, m), 4.88-4.77 (1H, br m), 4.60-4.49 (1H, br m). |
| 65 | $^1$H-NMR ($CDCl_3$) δ: 8.24 (1H, dd, J = 4.9, 1.9 Hz), 8.00 (1H, s), 7.43 (1H, dt, J = 7.6, 1.9 Hz), 7.38-7.30 (1H, m), 7.06 (1H, dd, J = 7.6, 4.9 Hz), 6.91-6.85 (2H, m), 4.01-3.91 (2H, m), 1.17 (3H, t, J = 7.1 Hz). |
| 66 | $^1$H-NMR ($CDCl_3$) δ: 8.22 (1H, dd, J = 4.9, 2.0 Hz), 7.42 (1H, dt, J = 7.6, 2.0 Hz), 7.33-7.28 (1H, m), 7.23-7.22 (1H, m), 7.04 (1H, dd, J = 7.6, 4.9 Hz), 6.89-6.83 (2H, m), 3.92 (2H, q, J = 7.2 Hz), 2.27 (3H, d, J = 1.2 Hz), 1.16 (3H, t, J = 7.2 Hz). |
| 67 | $^1$H-NMR ($CDCl_3$) δ: 8.30 (1H, dd, J = 4.9, 2.0 Hz), 7.44 (1H, dt, J = 7.5, 2.0 Hz), 7.39 (1H, d, J = 9.5 Hz), 7.13 (1H, dd, J = 7.6, 4.6 Hz), 6.80 (1H, d, J = 9.5 Hz), 6.68-6.63 (2H, m), 6.16 (1H, tt, J = 56.6, 4.4 Hz), 4.28-4.19 (1H, m), 4.14-4.05 (1H, m). |
| 68 | $^1$H-NMR ($CDCl_3$) δ: 8.32 (1H, dd, J = 4.7, 2.0 Hz), 7.62 (1H, s), 7.46 (1H, dt, J = 7.6, 2.0 Hz), 7.15 (1H, dd, J = 7.6, 4.7 Hz), 6.70-6.63 (2H, m), 6.18 (1H, tt, J = 56.4, 4.4 Hz), 4.37-4.25 (1H, m), 4.16-4.06 (1H, m). |
| 69 | $^1$H-NMR ($CDCl_3$) δ: 8.31 (1H, dd, J = 4.9, 2.0 Hz), 7.82 (1H, s), 7.46 (1H, dt, J = 7.6, 2.0 Hz), 7.15 (1H, dd, J = 7.6, 4.9 Hz), 6.70-6.62 (2H, m), 6.18 (1H, tt, J = 56.4, 4.5 Hz), 4.37-4.26 (1H, m), 4.16-4.05 (1H, m). |
| 70 | $^1$H-NMR ($CDCl_3$) δ: 7.66 (1H, s), 7.41 (1H, s), 7.34 (1H, s), 6.76-6.74 (2H, m), 3.94 (2H, q, J = 7.1 Hz), 1.20 (3H, t, J = 7.1 Hz). |
| 71 | $^1$H-NMR ($CDCl_3$) δ: 7.86 (1H, s), 7.38 (1H, s), 7.31 (1H, s), 6.78-6.72 (2H, m), 3.94 (2H, q, J = 7.1 Hz), 1.19 (3H, t, J = 7.1 Hz). |
| 72 | $^1$H-NMR ($CDCl_3$) δ: 7.66 (1H, s), 7.43 (1H, s), 7.31 (1H, s), 6.50-6.49 (2H, m), 3.95 (2H, q, J = 7.0 Hz), 3.83 (3H, s), 1.19 (3H, t, J = 7.0 Hz). |
| 73 | $^1$H-NMR ($CDCl_3$) δ: 7.87 (1H, s), 7.40 (1H, s), 7.28 (1H, s), 6.51-6.48 (2H, m), 3.95 (2H, q, J = 7.2 Hz), 3.83 (3H, s), 1.18 (3H, t, J = 7.2 Hz). |
| 74 | $^1$H-NMR ($CDCl_3$) δ: 7.72 (1H, s), 7.58 (1H, s), 7.48-7.42 (1H, m), 7.00-6.96 (2H, m), 3.97 (2H, q, J = 7.1 Hz), 1.18 (3H, t, J = 7.1 Hz). |
| 75 | $^1$H-NMR ($CDCl_3$) δ: 7.72 (1H, s), 7.52-7.46 (1H, m), 7.04-6.99 (2H, m), 3.98 (2H, q, J = 7.1 Hz), 1.19 (3H, t, J = 7.1 Hz). |
| 76 | $^1$H-NMR ($CDCl_3$) δ: 7.26 (1H, d, J = 9.5 Hz), 6.73-6,68 (3H, m), 3.88 (2H, q, J = 7.0 Hz), 2.08 (3H, s), 2.04 (3H, s), 1.17 (3H, t, J = 7,0 Hz). |
| 77 | $^1$H-NMR ($CDCl_3$) δ: 7.86 (1H, s), 7.41 (1H, s), 7.34 (1H, s), 6.77-6.73 (2H, m), 3.94 (2H, q, J = 7.1 Hz), 1.19 (3H, t, J = 7.1 Hz). |
| 78 | $^1$H-NMR ($CDCl_3$) δ: 7.86 (1H, s), 7.43 (1H, s), 7.31 (1H, s), 6.50-6.48 (2H, m), 3.95 (2H, q, J = 7.2 Hz), 3.83 (3H, s), 1.19 (3H, t, J = 7.2 Hz), |
| 79 | $^1$H-NMR ($CDCl_3$) δ: 8.25 (1H, dd, J = 4.8, 1.8 Hz), 7.42 (1H, dt, J = 7.6, 1.8 Hz), 7.32 (1H, d, J = 9.5 Hz), 7.08 (1H, dd, J = 7.6, 4.8 Hz), 6.74 |

TABLE 6-continued

| Compound | $^1$H-NMR |
|---|---|
| | (1H, d, J = 9.5 Hz), 6.43-6.36 (2H, m), 3.93 (2H, q, J = 7.1 Hz), 3.76 (3H, s), 1.16 (3H, t, J = 7.1 Hz). |
| 80 | $^1$H-NMR ($CDCl_3$) δ: 8.25 (1H, dd, J = 4.9, 1.8 Hz), 7.53 (1H, s), 7.41 (1H, dt, J = 7.6, 1.8 Hz), 7.08 (1H, dd, J = 7.6, 4.9 Hz), 6.40-6.34 (2H, m), 4.02-3.88 (2H, m), 3.74 (3H, s), 1.16 (3H, t, J = 7.1 Hz). |
| 81 | $^1$H-NMR ($CDCl_3$) δ: 8.27 (1H, dd, J = 4.8, 1.9 Hz), 7.75 (1H, s), 7.43 (1H, dt, J = 7.6, 1.9 Hz), 7.10 (1H, dd, J = 7.6, 4.8 Hz), 6.42-6.37 (2H, m), 4.04-3.91 (2H, m), 3.76 (3H, s), 1.18 (3H, t, J = 7.0 Hz). |
| 82 | $^1$H-NMR ($CDCl_3$) δ: 7.32 (1H, d, J = 9.5 Hz), 7.24 (1H, s), 6.73-6.68 (3H, m), 3.90 (2H, q, J = 7.2 Hz), 1.93 (3H, s), 1.18 (3H, t, J = 7.2 Hz). |
| 83 | $^1$H-NMR ($CDCl_3$) δ: 7.57 (1H, s), 7.25 (1H, s), 6.73-6.67 (2H, m), 3.96 (2H, q, J = 7.1 Hz), 1.93 (3H, s). 1.20 (3H, t, J = 7.1 Hz). |
| 84 | $^1$H-NMR ($CDCl_3$) δ: 7.71 (1H, s), 7.46 (1H, d, J = 2.0 Hz), 7.29 (1H, d, J = 2.4 Hz), 6.72-6.70 (2H, m), 6.20 (1H, dd, J = 2.4, 2.0 Hz), 3.95 (2H, g, J = 7.1 Hz), 1.20 (3H, t, J = 7.1 Hz). |
| 85 | $^1$H-NMR ($CDCl_3$) δ: 7.68 (1H, s), 7.25 (1H, s), 7.04 (1H, s), 6.74-6.69 (2H, m), 3.94 (2H, q, J = 7.2 Hz), 1.97 (3H, s). 1.19 (3H, t, J = 7.2 Hz). |
| 86 | $^1$H-NMR ($CDCl_3$) δ: 7.33 (1H, d, J = 1.2 Hz), 7.24 (1H, s), 7.03 (1H, s), 6.70-6.69 (2H, m), 3.88 (2H, q, J = 7.0 Hz), 2.24 (3H, d, J = 1.2 Hz), 1.97 (3H, s). 1.16 (3H, t, J = 7.0 Hz). |
| 87 | $^1$H-NMR ($CDCl_3$) δ: 7.90 (1H, s), 7.64-7.57 (1H, m), 7.16-7.10 (2H, m), 5.96 (1H, s), 3.95 (2H, q, J = 7.1 Hz), 1.19 (3H, t, J = 7.1 Hz). |
| 88 | $^1$H-NMR ($CDCl_3$) δ: 8.90 (1H, br s), 7.69 (1H, s), 7.44-7.36 (1H, m), 7.17 (1H, dd, J = 3.2, 2.0 Hz), 6.97-6.91 (2H, m), 6.42-6.41 (1H, m), 3.95 (2H, q, J = 7.1 Hz), 1.16 (4H, t, J = 7.1 Hz). |
| 89 | $^1$H-NMR ($CDCl_3$) δ: 8.15 (1H, s), 7.77 (1H, s), 6.92-6.87 (2H, m), 6.19 (1H, s), 3.95 (2H, q, J = 7.2 Hz), 1.19 (3H, t, J = 7.2 Hz). |
| 90 | $^1$H-NMR ($CDCl_3$) δ: 8.18 (1H, s), 7.78 (1H, s), 6.65-6.61 (2H, m), 6.05 (1H, s), 3.98 (2H, q, J = 7.1 Hz), 3.89 (3H, s), 1.19 (3H, t, J = 7.1 Hz). |
| 91 | $^1$H-NMR ($CDCl_3$) δ: 7.90 (1H, s), 7.51-7.44 (1H, m), 7.34 (1H, s), 7.03-6.97 (2H, m), 3.94 (2H, q, J = 7.1 Hz), 3.78 (3H, s), 1.15 (3H, t, J = 7.1 Hz). |
| 92 | $^1$H-NMR ($CDCl_3$) δ: 7.92 (1H, s), 7.63-7.57 (1H, m), 7.15-7.10 (2H, m), 5.96 (1H, s), 3.95 (2H, q, J = 7.0 Hz), 1.19 (3H, t, J = 7.0 Hz). |
| 93 | $^1$H-NMR ($CDCl_3$) δ: 7.31 (1H, d, J = 9.8 Hz), 6.72 (1H, d, J = 9.8 Hz), 6.69-6.66 (2H, m), 5.71 (1H, s), 3.89 (2H, q, J = 7.2 Hz), 2.07 (3H, s), 2.02 (3H, s), 1.17 (3H, t, J = 7.2 Hz). |
| 94 | $^1$H-NMR ($CDCl_3$) δ: 7.30 (1H, d, J = 9.5 Hz), 6.69 (1H, d, J = 9.5 Hz), 6.44-6.42 (2H, m), 5.70 (1H, s), 3.91 (2H, q, J = 7.0 Hz), 3.80 (3H, s), 2.052 (3H, s), 2.048 (3H, s), 1.16 (3H, t, J = 7.0 Hz). |
| 95 | $^1$H-NMR ($CDCl_3$) δ: 7.26 (1H, d, J = 9.5 Hz), 6.74-6.68 (3H, m), 3.89 (2H, q, J = 7.2 Hz), 2.07 (3H, s), 2.03 (3H, s), 1.17 (3H, t, J = 7.2 Hz). |
| 96 | $^1$H-NMR ($CDCl_3$) δ: 7.93 (1H, s), 6.84-6.79 (2H, m), 3.97 (2H, q, J = 7.1 Hz), 1.18 (3H, t, J = 7.1 Hz). |
| 97 | $^1$H-NMR ($CDCl_3$) δ: 7.94 (1H, s), 7.62 (1H, s), 6.80-6.75 (2H, m), 3.96 (2H, q, J = 7.1 Hz), 1.18 (3H, t, J = 7.1 Hz). |
| 98 | $^1$H-NMR ($CDCl_3$) δ: 8.28 (1H, dd, J = 4.6, 1.9 Hz), 7.41 (1H, dt, J = 7.6, 1.9 Hz), 7.34 (1H, d, J = 9.5 Hz), 7.11 (1H, dd, J = 7.6, 4.6 Hz), 6.79 (1H, d, J = 9.5 Hz), 6.69-6.63 (2H, m), 3.39 (3H, s). |
| 99 | $^1$H-NMR ($CDCl_3$) δ: 8.24 (1H, dd, J = 4.6, 1.9 Hz), 7.40 (1H, dt, J = 7.6, 1.9 Hz), 7.37-7.29 (2H, m), 7.06 (1H, dd, J = 7.6, 4.9 Hz), 6.91-6.82 (2H, m), 6.78 (1H, d, J = 9.3 Hz), 3.39 (3H, s). |
| 100 | $^1$H-NMR ($CDCl_3$) δ: 8.31 (1H, dd, J = 4.8, 1.9 Hz), 7.58 (1H, s), 7.43 (1H, dt, J = 7.6, 1.9 Hz), 7.14 (1H, dd, J = 7.6, 4.8 Hz), 6.70-6.64 (2H, m), 3.46 (3H, s). |
| 101 | $^1$H-NMR ($CDCl_3$) δ: 7.88 (1H, s), 7.25 (1H, s), 7.04 (1H, s), 6.73-6.70 (2H, m), 3.94 (2H, q, J = 7.1 Hz), 1.97 (3H, s). 1.19 (3H, t, J = 7.1 Hz). |
| 102 | $^1$H-NMR ($CDCl_3$) δ: 7.90 (1H, s), 6.55-6.51 (2H, m), 3.99 (2H, q, J = 7.1 Hz), 3.85 (3H, s), 1.18 (3H, t, J = 7.1 Hz). |
| 103 | $^1$H-NMR ($CDCl_3$) δ: 7.91 (1H, s), 7.62 (1H, s), 6.52-6.48 (2H, m), 3.99 (2H, q, J = 7.0 Hz). 3.83 (3H, s), 1.17 (3H, t, J = 7.0 Hz). |
| 104 | $^1$H-NMR ($CDCl_3$) δ: 8.30 (1H, dd, J = 4.7, 1.9 Hz), 7.78 (1H, s), 7.43 (1H, dt, J = 7.7, 1.9 Hz), 7.13 (1H, dd, J = 7.7, 4.7 Hz), 6.70-6.63 (2H, m), 3.46 (3H, s). |
| 105 | $^1$H-NMR ($CDCl_3$) δ: 8.26 (1H, dd, J = 4.9, 2.0 Hz), 7.59 (1H, s), 7.44-7.41 (1H, m), 7.39-7.32 (1H, m), 7.08 (1H, dd, J = 7.6, 4.9 Hz), 6.91-6.86 (2H, m), 3.46 (3H, s). |
| 106 | $^1$H-NMR ($CDCl_3$) δ: 8.26 (1H, dd, J = 4.9, 1.9 Hz), 7.79 (1H, s), 7.42 (1H, dt, J = 7.5, 1.9 Hz), 7.39-7.31 (1H, m), 7.08 (1H, dd, J = 7.5, 4.9 Hz), 6.90-6.86 (2H, m), 3.46 (3H, s). |
| 107 | $^1$H-NMR ($CDCl_3$) δ: 7.95 (1H, s), 7.61 (1H, s), 6.80-6.75 (2H, m), 3.96 (2H, q, J = 7.1 Hz), 1.18 (3H, t, J = 7.1 Hz). |
| 108 | $^1$H-NMR ($CDCl_3$) δ: 7.40 (1H, d, J = 9.8 Hz), 7.23 (1H, s), 6.78-6.72 (3H, m), 3.87 (2H, q, J = 7.2 Hz), 2.12 (3H, s), 1.16 (3H, t, J = 7.2 Hz). |
| 109 | $^1$H-NMR ($CDCl_3$) δ: 7.43 (1H, d, J = 9.5 Hz), 6.92 (1H, s), 6.73-6.70 (3H, m), 3.86 (2H, q, J = 7.1 Hz), 2.06 (3H, s), 1.87 (3H, s), 1.15 (3H, t, J = 7.1 Hz). |
| 110 | $^1$H-NMR ($CDCl_3$) δ: 7.74 (1H, s), 7.40 (1H, s), 7.32 (1H, s), 6.77-6.75 (2H, m), 6.17 (1H, tt, J = 56.3, 4.6 Hz), 4.19 (2H, td, J = 12.6, 4.6 Hz). |

TABLE 6-continued

| Compound | $^1$H-NMR |
|---|---|
| 111 | $^1$H-NMR ($CDCl_3$) δ: 7.75 (1H, s), 7.42 (1H, s), 7.27 (1H, s), 6.52-6.49 (2H, m), 6.17 (1H, tt, J = 56.5, 4.4 Hz), 4.21 (2H, td, J = 12.6, 4.4 Hz), 3.84 (3H, s). |
| 112 | $^1$H-NMR ($CDCl_3$) δ: 7.75 (1H, s), 7.62 (1H, s), 6.81-6.75 (2H, m), 3.96 (2H, q, J = 7.1 Hz), 1.18 (3H, t, J = 7.1 Hz). |
| 113 | $^1$H-NMR ($CDCl_3$) δ: 7.74 (1H, s), 7.62 (1H, s), 6.80-6.74 (2H, m), 3.96 (2H, q, J = 7.1 Hz), 1.18 (3H, t, J = 7.1 Hz). |
| 114 | $^1$H-NMR ($CDCl_3$) δ: 7.70 (1H, s), 6.56-6.52 (2H, m), 3.99 (2H, q, J = 7.1 Hz), 3.85 (3H, s), 1.17 (3H, t, J = 7.1 Hz). |
| 115 | $^1$H-NMR ($CDCl_3$) δ: 7.72 (1H, s), 7.61 (1H, s), 6.53-6.48 (2H, m), 3.99 (2H, q, J = 7.1 Hz), 3.84 (3H, s), 1.17 (3H, t, J = 7.1 Hz). |
| 116 | $^1$H-NMR ($CDCl_3$) δ: 7.70 (1H, s), 6.56-6.51 (2H, m), 3.99 (2H, q, J = 7.1 Hz), 3.85 (3H, s), 1.18 (3H, t, 3 = 7.1 Hz). |
| 117 | $^1$H-NMR ($CDCl_3$) δ: 7.71 (1H, s), 6.74-6.68 (2H, m), 3.94 (2H, q, J = 7.1 Hz), 2.09 (3H, s), 2.04 (3H, s), 1.20 (3H, t, J = 7.1 Hz). |
| 118 | $^1$H-NMR ($CDCl_3$) δ: 7.71 (1H, s), 7.62 (1H, s), 6.62-6.48 (2H, m), 3.98 (2H, q, J = 7.1 Hz), 3.83 (3H, s), 1.17 (3H, t, J = 7.1 Hz). |
| 119 | $^1$H-NMR ($CDCl_3$) δ: 8.00 (1H, s), 7.79 (1H, s), 6.24 (2H, d, J = 10.0 Hz), 6.05 (1H, s), 4.42-4.38 (1H, m), 4.02 (2H, q, J = 7.1 Hz), 2.90 (3H, d, J = 5.1 Hz), 1.20 (3H, t, J = 7.1 Hz). |
| 120 | $^1$H-NMR ($CDCl_3$) δ: 7.75 (1H, s), 7.47 (1H, d, J = 2.0 Hz), 6.85-6.78 (2H, m), 3.94 (2H, q, J = 7.1 Hz), 1.17 (3H, t, J = 7.1 Hz). |
| 121 | $^1$H-NMR ($CDCl_3$) δ: 7.71 (1H, s), 7.39 (1H, s), 7.33 (1H, s), 6.77-6.75 (2H, m), 4.63-4.61 (2H, br m). |
| 122 | $^1$H-NMR ($CDCl_3$) δ: 7.72 (1H, s), 7.42 (1H, s), 7.27 (1H, s), 6.51-6.49 (2H, m), 4.66-4.64 (2H, br m), 3.84 (3H, s). |
| 123 | $^1$H-NMR ($CDCl_3$) δ: 9.81 (1H, s), 7.90 (1H, s), 7.85 (1H, s), 7.70 (1H, s), 6.75-6.74 (2H, m), 3.95 (2H, q, J = 7.2 Hz), 1.21 (3H, t, J = 7.2 Hz). |
| 124 | $^1$H-NMR ($CDCl_3$) δ: 7.69 (1H, s), 7.58 (1H, s), 7.50 (1H, s), 6.76-6.47 (3H, m), 3.95 (2H, q, J = 7.2 Hz), 1.20 (3H, t, J = 7.2 Hz). |
| 125 | $^1$H-NMR ($CDCl_3$) δ: 7.45 (1H, s), 6.73-6.71 (2H, m), 5.68 (2H, s), 3.96 (2H, q, J = 7.2 Hz), 1.96 (6H, s), 1.19 (3H, t, J = 7.2 Hz). |
| 126 | $^1$H-NMR ($CDCl_3$) δ: 7.43 (1H, s), 6.47-6.45 (2H, m), 5.68 (2H, s), 3.98 (2H, q, J = 7.2 Hz), 3.79 (3H, s), 1.96 (6H, s), 1.18 (3H, t, J = 7.2 Hz). |
| 127 | $^1$H-NMR ($CDCl_3$) δ: 7.73 (1H, s), 7.47 (1H, d, J = 1.8 Hz), 6.56-6.52 (2H, m), 3.97 (2H, q, J = 7.0 Hz), 3.86 (3H, s), 1.17 (3H, t, J = 7.0 Hz). |
| 128 | $^1$H-NMR ($CDCl_3$) δ: 7.83 (1H, s), 7.81 (1H, s), 7.68 (1H, s), 6.75-6.73 (2H, m), 3.95 (2H, q, J = 7.1 Hz), 3.81 (3H, s), 1.20 (3H, t, J = 7.1 Hz). |
| 129 | $^1$H-NMR ($CDCl_3$) δ: 7.63 (1H, s), 7.61 (1H, s), 7.41 (1H, s), 6.76-6.74 (1H, m), 6.69-6.67 (1H, m), 4.29-4.19 (2H, m), 3.91 (2H, q, J = 7.2 Hz), 1.26 (3H, t, J = 7.2 Hz), 1.19 (3H, t, J = 7.2 Hz). |
| 130 | $^1$H-NMR ($CDCl_3$) δ: 7.88 (1H, s), 7.60-7.54 (1H, m), 7.13-7.09 (2H, m), 5.67 (1H, s), 3.99 (3H, s), 3.93 (2H, q, J = 7.1 Hz), 1.18 (3H, t, J = 7.1 Hz). |
| 131 | $^1$H-NMR ($CDCl_3$) δ: 7.83 (1H, s), 7.57-7.50 (1H, m), 7.12-7.06 (2H, m), 5.81 (1H, s), 3.92 (2H, q, J = 7.1 Hz), 2.95 (6H, s), 1.17 (3H, t, J = 7.1 Hz). |
| 132 | $^1$H-NMR ($CDCl_3$) δ: 7.63 (1H, s), 6.71-6.69 (2H, m), 6.49 (2H, t, J = 2.1 Hz), 6.05 (2H, t, J = 2.1 Hz), 3.92 (2H, q, J = 7.2 Hz), 1.19 (3H, t, J = 7.2 Hz). |
| 133 | $^1$H-NMR ($CDCl_3$) δ: 7.48 (1H, s), 6.73-6.72 (2H, m), 5.95 (2H, s), 4.00 (2H, q, J = 7.0 Hz), 1.19 (3H, t, J = 7.0 Hz). |
| 134 | $^1$H-NMR ($CDCl_3$) δ: 7.85 (1H, s), 7.59-7.52 (1H, m), 7.13-7.07 (2H, m), 5.67 (1H, s), 4.51-4.47 (1H, m), 3.93 (2H, q, J = 7.1 Hz), 2.90 (3H, d, J = 5.1 Hz), 1.17 (3H, t, J = 7.1 Hz). |
| 135 | $^1$H-NMR ($CDCl_3$) δ: 7.86 (1H, s), 7.61-7.52 (1H, m), 7.13-7.08 (2H, m), 5.59 (1H, s), 4.61 (2H, br s), 3.93 (2H, q, J = 7.1 Hz), 1.17 (3H, t, J = 7.1 Hz). |
| 136 | $^1$H-NMR ($CDCl_3$) δ: 7.28-7.26 (2H, m), 7.24 (1H, s), 6.79-6.78 (3H, m), 3.96-3.94 (1H, m), 3.82-3.80 (1H, m), 1.17 (3H, t, J = 7.2 Hz). |
| 137 | $^1$H-NMR ($CDCl_3$) δ: 7.47 (1H, s), 6.81-6.80 (2H, m), 4.01-3.94 (2H, m), 1.20 (3H, t, J = 7.0 Hz). |
| 138 | $^1$H-NMR ($CDCl_3$) δ: 7.54 (1H, s), 7.25 (1H, s), 6.80-6.78 (2H, m), 4.03-4.01 (1H, m), 3.88-3.86 (1H, m), 1.20 (3H, t, J = 7.0 Hz). |
| 139 | $^1$H-NMR ($CDCl_3$) δ: 7.74 (1H, s), 7.25 (1H, s), 6.80-6.78 (2H, m), 4.03-4.01 (1H, m), 3.88-3.85 (1H, m), 1.20 (3H, t, J = 7.1 Hz). |
| 140 | $^1$H-NMR ($CDCl_3$) δ: 8.08 (1H, s), 7.37 (1H, s), 7.31 (1H, s), 6.75-6.73 (2H, m), 3.93 (2H, q, J = 7.2 Hz), 1.18 (3H, t, J = 7.2 Hz). |
| 141 | $^1$H-NMR ($CDCl_3$) δ: 7.40 (1H, d, J = 9.8 Hz), 7.20 (1H, s), 6.76-6.73 (3H, m), 3.86 (2H, q, J = 7.2 Hz), 2.12 (3H, s), 1.16 (3H, t, J = 7.2 Hz). |
| 142 | $^1$H-NMR ($CDCl_3$) δ: 7.66 (1H, s), 7.20 (1H, s), 6.77-6.76 (2H, m), 3.93 (2H, q, J = 7.2 Hz), 2.12 (3H, s), 1.19 (3H, t, J = 7.2 Hz). |
| 143 | $^1$H-NMR ($CDCl_3$) δ: 7.68 (1H, s), 7.15 (1H, s), 6.52-6.50 (2H, m), 3.94 (2H, q, J = 7.2 Hz), 3.84 (3H, s), 2.15 (3H, s), 1.17 (3H, t, J = 7.2 Hz). |
| 144 | $^1$H-NMR ($CDCl_3$) δ: 7.86 (1H, s), 7.20 (1H, s), 6.77-6.75 (2H, m), 3.92 (2H, q, J = 7.0 Hz), 2.12 (3H, s), 1.18 (3H, t, J = 7.0 Hz). |

TABLE 6-continued

| Compound | $^1$H-NMR |
|---|---|
| 145 | $^1$H-NMR ($CDCl_3$) δ: 7.40 (1H, d, J = 9.8 Hz), 7.36 (1H, s), 7.20 (1H, s), 7.17-7.14 (1H, m), 6.92-6.89 (2H, m), 6.71 (1H, d, J = 9.8 Hz), 4.03-3.98 (1H, m), 3.73-3.69 (1H, m), 1.14 (3H, t, J = 7.1 Hz). |
| 146 | $^1$H-NMR ($CDCl_3$) δ: 7.88 (1H, s), 7.15 (1H, s), 6.52-6.50 (2H, m), 3.94 (2H, q, J = 7.2 Hz), 3.84 (3H, s), 2.15 (3H, s), 1.17 (3H, t, J = 7.2 Hz). |
| 147 | $^1$H-NMR ($CDCl_3$) δ: 7.86 (1H, s), 7.22 (1H, s), 6.78-6.74 (2H, m), 3.92 (2H, q, J = 7.1 Hz), 2.12 (3H, s), 1.18 (3H, t, J = 7.1 Hz). |
| 148 | $^1$H-NMR ($CDCl_3$) δ: 7.66 (1H, s), 7.38 (1H, s), 7.19 (1H, s), 7.16-7.14 (1H, m), 6.95-6.88 (2H, m), 4.11-4.02 (1H, m), 3.79-3.76 (1H, m), 1.16 (3H, t, J = 7.1 Hz). |
| 149 | $^1$H-NMR ($CDCl_3$) δ: 7.67 (1H, s), 7.39 (1H, s), 7.16 (1H, s), 7.05-7.01 (1H, m), 6.70-6.67 (2H, m), 4.09-4.06 (1H, m), 3.83-3.78 (4H, m), 1.15 (3H, t, J = 7.2 Hz). |
| 150 | $^1$H-NMR ($CDCl_3$) δ: 7.86 (1H, s), 7.38 (1H, s), 7.20 (1H, s), 7.19-7.14 (1H, m), 6.95-6.89 (2H, m), 4.07-4.04 (1H, m), 3.79-3.76 (1H, m), 1.16 (3H, t, J = 7.0 Hz). |
| 151 | $^1$H-NMR ($CDCl_3$) δ: 7.87 (1H, s), 7.18 (1H, s), 6.52-6.49 (2H, m), 3.94 (2H, q, J = 7.2 Hz), 3.84 (3H, s), 2.15 (3H, s), 1.17 (3H, t, J = 7.2 Hz). |
| 152 | $^1$H-NMR ($CDCl_3$) δ: 7.87 (1H, s), 7.39 (1H, s), 7.16 (1H, s), 7.03-7.01 (1H, m), 6.69-6.67 (2H, m), 4.11-4.05 (1H, m), 3.82-3.79 (4H, m), 1.15 (3H, t, J = 7.1 Hz). |
| 153 | $^1$H-NMR ($CDCl_3$) δ: 7.41-7.38 (1H, m), 7.33 (1H, d, J = 9.8 Hz), 7.20 (1H, s), 6.92-6.90 (2H, m), 6.73 (1H, d, J = 9.8 Hz), 3.91 (2H, q, J = 7.2 Hz), 1.91 (3H, s), 1.17 (3H, t, J = 7.2 Hz). |
| 154 | $^1$H-NMR ($CDCl_3$) δ: 7.86 (1H, s), 7.66 (1H, s), 7.64 (1H, s), 6.78-6.77 (2H, m), 3.95 (2H, q, J = 7.0 Hz), 1.22 (3H, t, J = 7.0 Hz). |
| 155 | $^1$H-NMR ($CDCl_3$) δ: 7.70 (1H, s), 7.64 (1H, s), 7.61 (1H, s), 6.76-6.74 (2H, m), 3.95 (2H, q, J = 7.1 Hz), 1.22 (3H, t, J = 7.1 Hz). |
| 156 | $^1$H-NMR ($CDCl_3$) δ: 7.42 (1H, d, J = 9.8 Hz), 7.37 (1H, s), 7.27-7.24 (1H, m), 7.23-7.21 (2H, m), 7.03-6.99 (1H, m), 6.71 (1H, d, J = 9.8 Hz), 4.27-4.20 (1H, m), 3.46-3.38 (1H, m), 1.12 (3H, t, J = 7.0 Hz). |
| 157 | $^1$H-NMR ($CDCl_3$) δ: 7.67 (1H, s), 7.38 (1H, s), 7.26-7.22 (2H, m), 7.21 (1H, s), 7.05-7.00 (1H, m), 4.30-4.25 (1H, m), 3.53-3.46 (1H, m), 1.14 (3H, t, J = 7.0 Hz). |
| 158 | $^1$H-NMR ($CDCl_3$) δ: 7.87 (1H, s), 7.38 (1H, d, J = 0.6 Hz), 7.26-7.22 (2H, m), 7.21 (1H, d, J = 0.6 Hz), 7.04-7.00 (1H, m), 4.30-4.23 (1H, m), 3.53-3.46 (1H, m), 1.14 (3H, t, J = 7.0 Hz). |
| 159 | $^1$H-NMR ($CDCl_3$) δ: 7.69 (1H, s), 7.40 (1H, s), 7.18 (1H, s), 7.11 (1H, d, J = 8.6 Hz), 6.99 (1H, d, J = 2.7 Hz), 6.80 (1H, dd, J = 8.6, 2.7 Hz), 4.31-4.24 (1H, m), 3.84 (3H, s), 3.57-3.50 (1H, m), 1.13 (3H, t, J = 7.0 Hz). |
| 160 | $^1$H-NMR ($CDCl_3$) δ: 7.65 (1H, s), 7.45 (1H, s), 7.36 (1H, s), 6.75-6.73 (2H, m), 3.94 (2H, q, J = 7.2 Hz), 1.19 (3H, t, J = 7.2 Hz). |
| 161 | $^1$H-NMR ($CDCl_3$) δ: 8.07 (1H, s), 8.00 (1H, s), 7.69 (1H, s), 6.79-6.77 (2H, m), 3.95 (2H, q, J = 7.0 Hz), 1.21 (3H, t, J = 7.0 Hz). |
| 162 | $^1$H-NMR ($CDCl_3$) δ: 8.25 (1H, s), 7.57-7.51 (1H, m), 7.10-7.05 (2H, m), 5.99 (1H, s), 3.94 (2H, q, J = 7.1 Hz), 3.72 (3H, s), 1.17 (3H, t, J = 7.1 Hz). |
| 163 | $^1$H-NMR ($CDCl_3$) δ: 7.65 (1H, s), 7.45 (1H, s), 7.36 (1H, s), 6.75-6.73 (2H, m), 3.94 (2H, q, J = 7.2 Hz), 1.19 (3H, t, J = 7.2 Hz). |
| 164 | $^1$H-NMR ($CDCl_3$) δ: 7.43-7.37 (3H, m), 7.28-7.27 (1H, m), 7.25 (1H, d, J = 0.7 Hz), 7.08-7.04 (1H, m), 6.71 (1H, d, J = 9.5 Hz), 4.32-4.24 (1H, m), 3.41-3.33 (1H, m), 1.12 (3H, t, J = 7.1 Hz). |
| 165 | $^1$H-NMR ($CDCl_3$) δ: 7.67 (1H, s), 7.42-7.37 (2H, m), 7.28-7.24 (4H, m), 7.10-7.05 (1H, m), 4.37-4.28 (1H, m), 3.49-3.40 (1H, m), 1.14 (3H, t, J = 7.1 Hz). |
| 166 | $^1$H-NMR ($CDCl_3$) δ: 7.87 (1H, s), 7.41-7.37 (2H, m), 7.28-7.24 (2H, m), 7.10-7.04 (1H, m), 4.36-4.28 (1H, m), 3.49-3.41 (1H, m), 1.14 (3H, t, J = 7.0 Hz). |
| 167 | $^1$H-NMR ($CDCl_3$) δ: 7.69 (1H, s), 7.40 (1H, d, J = 0.6 Hz), 7.22 (1H, d, J = 0.6 Hz), 7.16 (1H, d, J = 2.4 Hz), 7.13 (1H, d, J = 8.6 Hz), 6.85 (1H, dd, J = 8.6, 2.4 Hz), 4.36-4.29 (1H, m), 3.84 (3H, s), 3.53-3.46 (1H, m), 1.13 (3H, t, J = 7.0 Hz). |
| 168 | $^1$H-NMR ($CDCl_3$) δ: 7.45 (1H, d, J = 9.8 Hz), 7.36 (1H, d, J = 0.6 Hz), 7.17-7.13 (1H, m), 7.01 (1H, d, J = 0.6 Hz), 6.97-6.91 (2H, m), 6.68 (1H, d, J = 9.8 Hz), 4.21-4.11 (1H, m), 3.48-3.39 (1H, m), 2.13 (3H, s), 1.10 (3H, t, J = 7.1 Hz). |
| 169 | $^1$H-NMR ($CDCl_3$) δ: 7.47-7.43 (2H, m), 7.39 (1H, td, J = 7.7, 1.8 Hz), 7.36 (1H, s), 7.29 (1H, dd, J = 7.7, 1.3 Hz), 7.23 (1H, dd, J = 7.7, 1.8 Hz), 7.18 (1H, s), 6.71 (1H, d, J = 9.8 Hz), 4.28-4.19 (1H, m), 3.48-3.40 (1H, m), 1.11 (3H, t, J = 7.0 Hz). |
| 170 | $^1$H-NMR ($CDCl_3$) δ: 7.72 (1H, s), 7.37 (1H, d, J = 0.7 Hz), 7.17-7.12 (1H, m), 7.00 (1H, d, J = 0.7 Hz), 6.97-6.93 (2H, m), 4.27-4.17 (1H, m), 3.55-3.47 (1H, m), 2.12 (3H, s), 1.13 (3H, t, J = 7.1 Hz). |
| 171 | $^1$H-NMR ($CDCl_3$) δ: 7.91 (1H, s), 7.37 (1H, d, J = 0.6 Hz), 7.17-7.12 (1H, m), 7.00 (1H, d, J = 0.6 Hz), 6.97-6.93 (2H, m), 4.26-4.17 (1H, m), 3.55-3.46 (1H, m), 2.13 (3H, s), 1.12 (3H, t, J = 7.1 Hz). |
| 172 | $^1$H-NMR ($CDCl_3$) δ: 7.70 (1H, s), 7.48 (1H, dd, J = 8.0, 1.0 Hz), 7.42 (1H, td, J = 7.5, 1.8 Hz), 7.37 (1H, d, J = 0.7 Hz), 7.30 (1H, td, J = 7.5, |

TABLE 6-continued

| Compound | $^1$H-NMR |
|---|---|
| | 1.0 Hz), 7.22 (1H, dd, J = 7.5, 1.8 Hz), 7.17 (1H, d, J = 0.7 Hz), 4.32-4.25 (1H, m), 3.54-3.48 (1H, m), 1.14 (3H, t, J = 7.0 Hz). |
| 173 | $^1$H-NMR ($CDCl_3$) δ: 7.90 (1H, s), 7.48 (1H, dd, J = 8.0, 1.5 Hz), 7.42 (1H, td, J = 7.6, 1.5 Hz), 7.37 (1H, d, J = 0.6 Hz), 7.29 (1H, td, J = 7.6, 1.2 Hz), 7.23 (1H, dd, J = 7.6, 1.2 Hz), 7.17 (1H, d, J = 0.6 Hz), 4.31-4.24 (1H, m), 3.55-3.48 (1H, m), 1.14 (3H, t, J = 7.0 Hz). |
| 174 | $^1$H-NMR ($CDCl_3$) δ: 7.43 (1H, d, J = 9.8 Hz), 7.38 (1H, s), 7.31 (1H, s), 6.76-6.74 (3H, m), 3.38 (3H, s). |
| 175 | $^1$H-NMR ($CDCl_3$) δ: 7.69 (1H, s), 7.39 (1H, s), 7.31 (1H, s), 6.79-6.74 (2H, m), 3.45 (3H, s). |
| 176 | $^1$H-NMR ($CDCl_3$) δ: 7.72 (1H, s), 7.25-7.24 (3H, m), 7.04-7.02 (2H, m), 3.95-3.93 (2H, br m), 1.86 (3H, s), 1.17 (3H, t, J = 7.0 Hz). |
| 177 | $^1$H-NMR (DMSO-D6) δ: 8.15 (1H, s), 8.09 (1H, s), 7.58 (1H, s), 6.89-6.86 (2H, m), 3.80 (3H, s), 3.34 (3H, s). |
| 178 | $^1$H-NMR (DMSO-D6) δ: 8.29 (1H, s), 8.09 (1H, s), 7.58 (1H, s), 6.89-6.87 (2H, m), 3.80 (3H, s), 3.34 (3H, s). |
| 179 | $^1$H-NMR ($CDCl_3$) δ: 7.54 (1H, s), 7.40 (1H, dd, J = 8.2, 1.3 Hz), 7.36-7.30 (2H, m), 7.24-7.22 (1H, m), 7.20 (1H, s), 4.36-4.32 (1H, m), 3.55-3.50 (1H, m), 1.87 (3H, s), 1.15 (3H, t, J = 7.1 Hz). |
| 180 | $^1$H-NMR ($CDCl_3$) δ: 7.92 (1H, s), 7.46-7.44 (1H, m), 7.39-7.37 (1H, m), 7.26-7.24 (3H, m), 6.91 (1H, s), 4.31-4.28 (1H, m), 3.52-3.49 (1H, m), 1.88 (3H, s), 1.13 (3H, t, J = 7.0 Hz). |
| 181 | $^1$H-NMR ($CDCl_3$) δ: 7.74 (1H1 s), 7.40-7.39 (1H, m), 7.35-7.30 (2H, m), 7.24-7.23 (1H, m), 7.21 (1H, s), 4.35-4.32 (1H, m), 3.54-3.52 (1H, m), 1.87 (3H, s), 1.14 (3H, t, J = 7.2 Hz). |
| 182 | $^1$H-NMR ($CDCl_3$) δ: 7.55 (1H, s), 7.26 (1H, s), 7.19-7.18 (1H, m), 6.87-6.84 (2H, m), 4.16-4.14 (1H, m), 3.76-3.73 (1H, m), 1.89 (3H, s), 1.16 (3H, t, J = 7.2 Hz). |
| 183 | $^1$H-NMR ($CDCl_3$) δ: 7.64 (1H, dd, J = 7.0, 2.1 Hz), 7.44 (1H, d, J = 9.6 Hz), 7.36 (1H, d, J = 0.6 Hz), 7.35-7.29 (2H, m), 7.26-7.24 (1H, m), 7.22 (1H, d, J = 0.6 Hz), 6.71 (1H, d, J = 9.6 Hz), 4.32-4.25 (1H, m), 3.43-3.36 (1H, m), 1.12 (3H, t, J = 7.0 Hz). |
| 184 | $^1$H-NMR ($CDCl_3$) δ: 7.70 (1H, s), 7.42 (1H, s), 7.28 (1H, br s), 7.13 (1H, br s), 6.50-6.48 (2H, m), 3.98 (2H, q, J = 7.1 Hz), 1.20 (3H, t, J = 7.1 Hz). |
| 185 | $^1$H-NMR ($CDCl_3$) δ: 7.84 (1H, d, J = 9.3 Hz), 7.39 (1H, s), 7.33 (1H, s), 7.20 (1H, d, J = 9.3 Hz), 6.78-6.76 (2H, m), 4.52 (2H, q, J = 7.1 Hz), 1.27 (3H, t, J = 7.1 Hz). |
| 186 | $^1$H-NMR ($CDCl_3$) δ: 7.54 (1H, d, J = 9.8 Hz), 7.47-7.40 (1H, m), 7.24 (1H, s), 7.01 (1H, s), 6.96-6.94 (2H, m), 6.76 (1H, d, J = 9.8 Hz), 6.15 (1H, tt, J = 56.6, 4.6 Hz), 4.14 (2H, td, J = 12.8, 4.6 Hz), 1.94 (3H, s). |
| 187 | $^1$H-NMR ($CDCl_3$) δ: 7.60 (1H, s), 7.41-7.39 (1H, m), 7.24 (1H, s), 6.94-6.92 (2H, m), 3.47 (3H, s), 1.91 (3H, s). |
| 188 | $^1$H-NMR ($CDCl_3$) δ: 7.94 (1H, s), 7.44-7.42 (1H, m), 7.26 (1H, s), 6.99 (1H, s), 6.97-6.95 (2H, m), 3.45 (3H, s), 1.94 (3H, s). |
| 189 | $^1$H-NMR ($CDCl_3$) δ: 7.79 (1H, s), 7.41-7.39 (1H, m), 7.24 (1H, s), 6.94-6.92 (2H, m), 3.47 (3H, s), 1.91 (3H, s). |
| 190 | $^1$H-NMR ($CDCl_3$) δ: 7.65 (1H, s), 7.44-7.40 (1H, m), 7.24 (1H, s), 6.94-6.92 (2H, m), 6.17 (1H, tt, J = 56.3, 4.5 Hz), 4.23 (2H, td, J = 12.6, 4.5 Hz), 1.92 (3H, s). |
| 191 | $^1$H-NMR ($CDCl_3$) δ: 7.42 (1H, d, J = 9.8 Hz), 7.31-7.30 (1H, m), 7.21-7.20 (1H, m), 6.75-6.73 (3H, m), 3.87 (2H, q, J = 7.0 Hz), 1.17 (3H, t, J = 7.0 Hz). |
| 192 | $^1$H-NMR ($CDCl_3$) δ: 7.68 (1H, s), 7.33-7.32 (1H, m), 7.22-7.21 (1H, m), 6.76-6.74 (2H, m), 3.94 (2H, q, J = 7.2 Hz), 1.19 (3H, t, J = 7.2 Hz). |
| 193 | $^1$H-NMR ($CDCl_3$) δ: 7.85 (1H, s), 7.47-7.40 (1H, m), 7.24 (1H, s), 6.94-6.92 (2H, m), 6.17 (1H, tt, J = 56.3, 4.5 Hz), 4.23 (2H, td, J = 12.6, 4.5 Hz), 1.91 (3H, s). |
| 194 | $^1$H-NMR ($CDCl_3$) δ: 7.88 (1H, s), 7.324-7.315 (1H, m), 7.22-7.21 (1H, m), 6.77-6.73 (2H, m), 3.94 (2H, q, J = 7.2 Hz), 1.19 (3H, t, J = 7.2 Hz). |
| 195 | $^1$H-NMR ($CDCl_3$) δ: 7.70 (1H, s), 7.66-7.64 (1H, m), 7.37 (1H, d, J = 0.6 Hz), 7.36-7.33 (2H, m), 7.25-7.23 (1H, m), 7.21 (1H, d, J = 0.6 Hz), 4.37-4.30 (1H, m), 3.50-3.43 (1H, m), 1.14 (3H, t, J = 7.2 Hz). |
| 196 | $^1$H-NMR ($CDCl_3$) δ: 7.90 (1H, s), 7.67-7.63 (1H, m), 7.37 (1H, d, J = 0.6 Hz), 7.36-7.32 (2H, m), 7.25-7.23 (1H, m), 7.21 (1H, d, J = 0.6 Hz), 4.36-4.29 (1H, m), 3.51-3.44 (1H, m), 1.14 (3H, t, J = 7.0 Hz). |
| 197 | $^1$H-NMR ($CDCl_3$) δ: 7.44 (1H, d, J = 9.8 Hz), 7.42-7.38 (1H, m), 7.36 (1H, d, J = 0.6 Hz), 7.29 (1H, s), 7.27-7.25 (1H, m), 7.09 (1H, td, J = 8.4, 0.9 Hz), 6.75 (1H, d, J = 9.8 Hz), 4.13-4.05 (1H, m), 3.64-3.57 (1H, m), 1.17 (3H, t, J = 7.0 Hz). |
| 198 | $^1$H-NMR ($CDCl_3$) δ: 7.70 (1H, s), 7.44-7.40 (1H, m), 7.37 (1H, d, J = 0.6 Hz), 7.28-7.27 (2H, m), 7.10 (1H, td, J = 8.4, 0.9 Hz), 4.18-4.11 (1H, m), 3.71-3.64 (1H, m), 1.19 (3H, t, J = 7.2 Hz). |
| 199 | $^1$H-NMR ($CDCl_3$) δ: 7.90 (1H, s), 7.44-7.40 (1H, m), 7.37 (1H, d, J = 0.6 Hz), 7.28-7.26 (2H, m), 7.10 (1H, td, J = 8.4, 0.9 Hz), 4.17-4.10 (1H, m), 3.71-3.64 (1H, m), 1.19 (3H, t, J = 7.2 Hz). |

TABLE 6-continued

| Compound | $^1$H-NMR |
|---|---|
| 200 | $^1$H-NMR ($CDCl_3$) δ: 7.67 (1H, s), 7.40 (1H, s), 7.27 (1H, s), 6.48-6.46 (2H, m), 4.02 (2H, q, J = 7.0 Hz), 3.95 (2H, q, J = 7.0 Hz), 1.44 (3H, t, J = 7.0 Hz), 1.18 (3H, t, J = 7.0 Hz). |
| 201 | $^1$H-NMR ($CDCl_3$) δ: 7.67 (1H, s), 7.40 (1H, s), 7.28 (1H, s), 6.60-6.59 (2H, m), 4.71 (2H, d, J = 2.1 Hz), 3.96 (2H, q, J = 7.1 Hz), 2.62 (1H, t, J = 2.1 Hz) 1.19 (3H, t, J = 7.1 Hz). |
| 202 | $^1$H-NMR ($CDCl_3$) δ: 7.67 (1H, s), 7.40 (1H, s), 7.27 (1H, s), 6.52-6.50 (2H, m), 6.00 (1H, ddt, J = 17.4, 10.5, 5.3 Hz), 5.42 (1H, dq, J = 17.4, 1.5 Hz), 5.36 (1H, dq, J = 10.5, 1.0 Hz), 4.53 (2H, dt, J = 5.3, 1.5 Hz), 3.95 (2H, q, J = 7.0 Hz), 1.19 (3H, t, J = 7.0 Hz). |
| 203 | $^1$H-NMR ($CDCl_3$) δ: 7.67 (1H, s), 7.41 (1H, s), 7.27 (1H, s), 6.66-6.64 (2H, m), 5.17 (2H, s), 3.96 (2H, q, J = 7.1 Hz), 3.49 (3H, s), 1.20 (3H, t, J = 7.1 Hz). |
| 204 | $^1$H-NMR ($CDCl_3$) δ: 7.67 (1H, s), 7.40 (1H, s), 7.28 (1H, s), 6.54-6.52 (2H, m), 4.11-4.10 (2H, m), 3.94 (2H, q, J = 7.1 Hz), 3.76-3.75 (2H, m), 3.45 (3H, s), 1.18 (3H, t, J = 7.1 Hz). |
| 205 | $^1$H-NMR ($CDCl_3$) δ: 7.67 (1H, s), 7.39 (1H, s), 7.30 (1H, s), 6.87-6.81 (2H, m), 3.96 (2H, q, J = 7.1 Hz), 2.32 (3H, s), 1.20 (3H, t, J = 7.1 Hz). |
| 206 | $^1$H-NMR ($CDCl_3$) δ: 7.37 (1H, s), 7.31 (1H, q, J = 0.9 Hz), 7.30 (1H, s), 6.75-6.71 (2H, m), 3.88 (2H, q, J = 7.1 Hz), 2.25 (3H, d, J = 0.9 Hz), 1.16 (3H, t, J = 7.1 Hz). |
| 207 | $^1$H-NMR ($CDCl_3$) δ: 7.94 (1H, s), 7.39 (1H, s), 7.32 (1H, s), 6.77-6.75 (2H, m), 6.17 (1H, tt, J = 56.4, 4.5 Hz), 4.18 (2H, td, J = 12.6, 4.5 Hz). |
| 208 | $^1$H-NMR ($CDCl_3$) δ: 7.47-7.45 (1H, m), 7.41 (1H, td, J = 7.7, 1.5 Hz), 7.31-7.28 (3H, m), 7.20-7.18 (1H, br m), 6.73 (1H, d, J = 9.5 Hz), 4.19-4.17 (1H, br m), 3.47-3.45 (1H, br m), 1.15 (3H, t, J = 7.0 Hz). |
| 209 | $^1$H-NMR ($CDCl_3$) δ: 7.53 (1H, s), 7.48-7.47 (1H, m), 7.43 (1H, td, J = 7.7, 1.6 Hz), 7.35-7.20 (3H, m), 4.24-4.23 (1H, br m), 3.55-3.53 (1H, br m), 1.18 (3H, t, J = 7.0 Hz). |
| 210 | $^1$H-NMR ($CDCl_3$) δ: 7.73 (1H, s), 7.46-7.43 (2H, m), 7.35-7.20 (3H, m), 4.24-4.21 (1H, br m), 3.56-3.53 (1H, br m), 1.17 (3H, t, J = 7.1 Hz). |
| 211 | $^1$H-NMR ($CDCl_3$) δ: 7.50 (1H, d, J = 9.8 Hz), 7.39 (1H, s), 7.18-7.15 (2H, m), 6.94-6.90 (2H, m), 6.75 (1H, d, J = 9.8 Hz), 6.19 (1H, tdd, J = 56.7, 5.9, 3.3 Hz), 4.43-4.34 (1H, m), 3.86-3.81 (1H, m). |
| 212 | $^1$H-NMR ($CDCl_3$) δ: 7.75 (1H, s), 7.40 (1H, s), 7.18-7.16 (2H, m), 6.94-6.93 (2H, m), 6.21 (1H, tdd, J = 56.6, 5.9, 3.3 Hz), 4.48-4.39 (1H, m), 3.91-3.86 (1H, m). |
| 213 | $^1$H-NMR ($CDCl_3$) δ: 7.76 (1H, s), 7.42 (1H, s), 7.14 (1H, s), 7.04-7.02 (1H, m), 6.71-6.68 (2H, m), 6.21 (1H, tdd, J = 56.8, 5.9, 3.4 Hz), 4.46-4.40 (1H, m), 3.98-3.92 (1H, m), 3.84 (3H, s). |
| 214 | $^1$H-NMR ($CDCl_3$) δ: 7.95 (1H, s), 7.40 (1H, s), 7.19-7.15 (2H, m), 6.94-6.92 (2H, m), 6.21 (1H, tdd, J = 56.6, 5.9, 3.3 Hz), 4.46-4.40 (1H, m), 3.91-3.87 (1H, m). |
| 215 | $^1$H-NMR ($CDCl_3$) δ: 7.96 (1H, s), 7.41 (1H, s), 7.14 (1H, s), 7.05-7.03 (1H, m), 6.71-6.67 (2H, m), 6.21 (1H, tdd, J = 56.7, 5.8, 3.4 Hz), 4.45-4.39 (1H, m), 4.02-3.91 (1H, m), 3.84 (3H, s). |
| 216 | $^1$H-NMR ($CDCl_3$) δ: 7.45-7.41 (2H, m), 7.36 (1H, d, J = 0.6 Hz), 7.35-7.32 (1H, m), 7.31 (1H, s), 7.14 (1H, td, J = 8.5, 1.0 Hz), 6.75 (1H, d, J = 9.5 Hz), 4.17-4.10 (1H, m), 3.59-3.52 (1H, m), 1.18 (3H, t, J = 7.0 Hz). |
| 217 | $^1$H-NMR ($CDCl_3$) δ: 7.47-7.41 (2H, m), 7.36-7.35 (1H, br m), 7.18-7.13 (4H, m), 6.70 (1H, d, J = 9.8 Hz), 4.06-3.97 (1H, m), 3.77-3.68 (1H, m), 1.13 (3H, t, J = 7.1 Hz). |
| 218 | $^1$H-NMR ($CDCl_3$) δ: 7.70 (1H, s), 7.45-7.42 (1H, m), 7.38-7.32 (2H, m), 7.30 (1H, s), 7.15 (1H, td, J = 8.4, 1.1 Hz), 4.23-4.10 (1H, m), 3.67-3.58 (1H, m), 1.20 (3H, t, J = 7.1 Hz). |
| 219 | $^1$H-NMR ($CDCl_3$) δ: 7.90 (1H, s), 7.44-7.42 (1H, m), 7.37 (1H, d, J = 0.6 Hz), 7.36-7.33 (1H, m), 7.30 (1H, s), 7.14 (1H, td, J = 8.3, 0.9 Hz), 4.21-4.15 (1H m), 3.66-3.59 (1H, m), 1.20 (3H, t, J = 7.0 Hz). |
| 220 | $^1$H-NMR ($CDCl_3$) δ: 7.69 (1H, s), 7.49-7.44 (1H, m), 7.37 (1H, d, J = 0.6 Hz), 7.19-7.14 (4H, m), 4.09-4.01 (1H, m), 3.83-3.76 (1H, m), 1.16 (3H, t, J = 7.0 Hz). |
| 221 | $^1$H-NMR ($CDCl_3$) δ: 7.89 (1H, s), 7.49-7.44 (1H, m), 7.37 (1H, s), 7.19-7.13 (4H, m), 4.10-4.03 (1k, m), 3.83-3.76 (1H, m), 1.16 (3H, t, J = 7.2 Hz). |
| 222 | $^1$H-NMR ($CDCl_3$) δ: 7.95 (1H, s), 7.42 (1H, s), 7.28 (1H, s), 6.51-6.49 (2H, m), 6.17 (1H, tt, J = 56.5, 4.5 Hz), 4.21 (2H, td, J = 12.6, 4.5 Hz), 3.84 (3H, s). |
| 223 | $^1$H-NMR ($CDCl_3$) δ: 7.66 (1H, s), 7.37 (1H, s), 7.32 (1H, s), 6.75-6.74 (2H, m), 3.91 (2H, q, J = 7.0 Hz), 3.45 (1H, s), 1.19 (3H, t, J = 7.0 Hz). |
| 224 | $^1$H-NMR ($CDCl_3$) δ: 7.67 (1H, s), 7.39 (1H, s), 7.29 (1H, s), 6.50-6.48 (2H, m), 3.92 (2H, q, J = 7.1 Hz), 3.82 (2H, s), 3.43 (1H, s), 1.18 (3H, t, J = 7.1 Hz). |
| 225 | $^1$H-NMR ($CDCl_3$) δ: 7.40 (1H, s), 7.32 (1H, s), 6.75-6.71 (3H, m), 3.91 (2H, q, J = 7.0 Hz), 3.89 (3H, s), 1.16 (3H, t, J = 7.0 Hz). |
| 226 | $^1$H-NMR ($CDCl_3$) δ: 7.88 (1H, s), 7.25 (1H, s), 7.17-7.15 (1H, m), 6.92-6.85 (3H, m), 4.09-4.06 (1H, m), 3.78-3.75 (1H, m), 1.93 (3H, s), 1.15 (3H, t, J = 7.2 Hz). |
| 227 | $^1$H-NMR ($CDCl_3$) δ: 7.57 (1H, d, J = 9.8 Hz), 7.46 (1H, dd, J = 8.2, 0.9 Hz), 7.38 (1H, ddd, J = 8.6, 6.8, 1.3 Hz), 7.26-7.21 (3H, m), 6.86 (1H, s), |

TABLE 6-continued

| Compound | $^1$H-NMR |
|---|---|
| | 6.73 (1H, d, J = 9.8 Hz), 6.35-6.04 (1H, m), 4.62-4.50 (1H, m), 3.62-3.57 (1H, m). |
| 228 | $^1$H-NMR ($CDCl_3$) δ: 7.75 (1H, s), 7.26 (1H, s), 7.19-7.18 (1H, br m), 6.87-6.84 (2H, m), 4.16-4.14 (1H, br m), 3.76-3.74 (1H, br m), 1.89 (3H, s), 1.16 (3H, t, J = 7.0 Hz). |
| 229 | $^1$H-NMR ($CDCl_3$) δ: 7.62 (1H, s), 7.42-7.41 (1H, m), 7.37-7.35 (1H, m), 7.26-7.22 (3H, m), 6.29-6.13 (1H, m), 4.71-4.61 (1H, m), 3.73-3.65 (1H, m), 1.88 (3H, s). |
| 230 | $^1$H-NMR ($CDCl_3$) δ: 7.82 (1H, s), 7.42-7.41 (1H, m), 7.38-7.33 (1H, m), 7.26-7.23 (3H, m), 6.28-6.14 (1H, m), 4.67-4.62 (1H, m), 3.72-3.67 (1H, m), 1.88 (3H, s). |
| 231 | $^1$H-NMR ($CDCl_3$) δ: 7.46-7.43 (2H, m), 7.36-7.32 (2H, m), 7.21-7.19 (2H, m), 6.77 (1H, d, J = 9.8 Hz), 6.37-6.06 (1H, m), 4.60-4.49 (1H, m), 3.59-3.57 (1H, br m). |
| 232 | $^1$H-NMR ($CDCl_3$) δ: 7.61 (1H, s), 7.47-7.45 (2H, m), 7.36-7.34 (1H, m), 7.22-7.20 (2H, m), 6.31-6.16 (1H, m), 4.63-4.56 (1H, m), 3.66-3.64 (1H, br m). |
| 233 | $^1$H-NMR ($CDCl_3$) δ: 7.52 (1H, d, J = 9.8 Hz), 7.39 (1H, d, J = 0.6 Hz), 7.25-7.20 (2H, m), 7.17 (1H, d, J = 0.6 Hz), 7.05-7.00 (1H, m), 6.75 (1H, d, J = 9.8 Hz), 6.32-6.06 (1H, m), 4.61-4.51 (1H, m), 3.60-3.51 (1H, m). |
| 234 | $^1$H-NMR ($CDCl_3$) δ: 7.77 (1H, s), 7.40 (1H, d, J = 0.7 Hz), 7.26-7.20 (2H, m), 7.16 (1H, d, J = 0.7 Hz), 7.06-7.01 (1H, m), 6.37-6.05 (1H, m), 4.67-4.54 (1H, m), 3.67-3.57 (1H, m). |
| 235 | $^1$H-NMR ($CDCl_3$) δ: 7.96 (1H, s), 7.40 (1H, d, J = 0.7 Hz), 7.25-7.20 (2H, m), 7.16 (1H, d, J = 0.7 Hz), 7.06-7.01 (1H, m), 6.37-6.05 (1H, m), 4.65-4.53 (1H, m), 3.68-3.57 (1H, m). |
| 236 | $^1$H-NMR ($CDCl_3$) δ: 7.81 (1H, s), 7.48-7.44 (2H, m), 7.35-7.33 (1H, m), 7.22-7.20 (2H, m), 6.39-6.08 (1H, m), 4.64-4.53 (1H, m), 3.66-3.64 (1H, br m). |
| 237 | $^1$H-NMR ($CDCl_3$) δ: 7.98 (1H, s), 7.33 (1H, td, J = 7.5, 1.6 Hz), 7.23-7.18 (4H, m), 6.67 (1H, s), 4.24-4.19 (1H, m), 3.57-3.52 (1H, m), 2.10 (3H, s) 1.86 (3H, s), 1.12 (3H, t, J = 7.0 Hz). |
| 238 | $^1$H-NMR ($CDCl_3$) δ: 7.41 (1H, d, J = 9.5 Hz), 7.39 (1H, s), 7.28 (1H, s), 6.72 (1H, d, J = 9.5 Hz), 6.50-6.48 (2H, m), 3.89 (2H, q, J = 7.1 Hz), 3.82 (3H, s), 1.16 (3H, t, J = 7.1 Hz). |
| 239 | $^1$H-NMR ($CDCl_3$) δ: 7.78 (1H, s), 7.42 (1H, d, J = 0.6 Hz), 7.12 (1H, d, J = 0.6 Hz), 7.09 (1H, dd, J = 8.6, 2.0 Hz), 7.00 (1H, d, J = 2.5 Hz), 6.81 (1H, dd, J = 8.6, 2.5 Hz), 6.37-6.06 (1H, m), 4.63-4.52 (1H, m), 3.85 (3H, s), 3.73-3.67 (1H, m). |
| 240 | $^1$H-NMR ($CDCl_3$) δ: 7.98 (1H, s), 7.42 (1H, d, J = 0.7 Hz), 7.13 (1H, d, J = 0.7 Hz), 7.09 (1H, dd, J = 8.7, 2.1 Hz), 7.00 (1H, d, J = 2.4 Hz), 6.81 (1H, dd, J = 8.7, 2.4 Hz), 6.37-6.06 (1H, m), 4.62-4.51 (1H, m), 3.84 (3H, s), 3.76-3.65 (1H, m). |
| 241 | $^1$H-NMR ($CDCl_3$) δ: 7.90 (1H, s), 7.44-7.40 (1H, m), 7.36 (1H, s), 7.04-7.01 (2H, m), 6.96-6.91 (2H, m), 4.16-4.09 (1H, m), 3.84 (3H, s), 3.69-3.60 (1H, m), 1.11 (3H, t, J = 7.3 Hz). |
| 242 | $^1$H-NMR ($CDCl_3$) δ: 7.45 (1H, d, J = 9.8 Hz), 7.42-7.38 (1H, m), 7.35 (1H, d, J = 0.6 Hz), 7.04-7.02 (2H, m), 6.95-6.90 (2H, m), 6.66 (1H, d, J = 9.8 Hz), 4.12-4.04 (1H, m), 3.84 (3H, s), 3.61-3.53 (1H, m), 1.09 (3H, t, J = 7.0 Hz). |
| 243 | $^1$H-NMR ($CDCl_3$) δ: 7.71 (1H, s), 7.44-7.40 (1H, m), 7.37 (1H, d, J = 0.6 Hz), 7.04-7.01 (2H, m), 6.96-6.92 (2H, m), 4.17-4.09 (1H, m), 3.84 (3H, s), 3.68-3.60 (1H, m), 1.11 (3H, t, J = 7.0 Hz). |
| 244 | $^1$H-NMR ($CDCl_3$) δ: 7.53 (1H, s), 7.29-7.25 (1H, m), 7.19-7.12 (4H, m), 4.29-4.26 (1H, m), 3.48-3.43 (1H, m), 2.21 (3H, s), 1.86 (3H, s), 1.13 (3H, t, J = 7.1 Hz). |
| 245 | $^1$H-NMR ($CDCl_3$) δ: 7.72 (1H, s), 7.29-7.25 (1H, m), 7.17-7.14 (4H, m), 4.27-4.25 (1H, m), 3.48-3.43 (1H, m), 2.21 (3H, s), 1.86 (3H, s), 1.12 (3H, t, J = 7.0 Hz). |
| 246 | $^1$H-NMR ($CDCl_3$) δ: 7.47 (1H, d, J = 9.8 Hz), 7.38-7.36 (1H, m), 7.23 (1H, s), 7.03 (1H, dd, J = 7.5, 1.7 Hz), 6.91-6.88 (21-1, m), 6.77 (1H, s), 6.65 (1H, d, J = 9.8 Hz), 4.13-4.10 (1H, m), 3.83 (3H, s), 3.57-3.54 (1H, m), 1.86 (3H, s), 1.08 (3H, t, J = 7.2 Hz). |
| 247 | $^1$H-NMR ($CDCl_3$) δ: 7.93 (1H, s), 7.39-7.38 (1H, m), 7.24 (1H, s), 7.03 (1H, dd, J = 7.5, 1.7 Hz), 6.93-6.88 (2H, m), 6.75 (1H, s), 4.17-4.14 (1H, m), 3.83 (3H, s), 3.64-3.61 (1H, m), 1.86 (3H, s), 1.10 (3H, t, J = 7.0 Hz). |
| 248 | $^1$H-NMR ($CDCl_3$) δ: 7.53 (1H, s), 7.34-7.32 (1H, m), 7.20 (1H, s), 7.11-7.09 (1H, br m), 6.87-6.84 (2H, m), 4.23-4.22 (1H, br m), 3.78 (3H, s), 3.66-3.61 (1H, m), 1.85 (3H, s), 1.12 (3H, t, J = 7.0 Hz). |
| 249 | $^1$H-NMR ($CDCl_3$) δ: 7.72 (1H, s), 7.35-7.32 (1H, m), 7.20 (1H, s), 7.12-7.10 (1H, br m), 6.87-6.84 (2H, m), 4.23-4.21 (1H, br m), 3.78 (3H, s), 3.66-3.63 (1H, m), 1.85 (3H, s), 1.12 (3H, t, J = 7.0 Hz). |
| 250 | $^1$H-NMR ($CDCl_3$) δ: 7.42 (1H, d, J = 9.5 Hz), 7.31-7.30 (1H, m), 7.19-7.14 (1H, m), 7.10-7.09 (1H, m), 6.94-6.88 (2H, m), 6.71 (1H, d, J = 9.5 Hz), 4.02-4.00 (1H, m), 3.72-3.69 (1H, m), 1.13 (3H, t, J = 7.2 Hz). |
| 251 | $^1$H-NMR ($CDCl_3$) δ: 7.68 (1H, s), 7.32 (1H, d, J = 4.9 Hz), 7.18-7.14 (1H, m), 7.09 (1H, d, J = 4.9 Hz), 6.95-6.88 (2H, m), 4.08-4.05 (1H, m), 3.79-3.76 (1H, m), 1.16 (3H, t, J = 7.1 Hz). |

TABLE 6-continued

| Compound | $^1$H-NMR |
|---|---|
| 252 | $^1$H-NMR ($CDCl_3$) δ: 7.88 (1H, s), 7.31 (1H, d, J = 4.9 Hz), 7.19-7.14 (1H, m), 7.09 (1H, d, J = 4.9 Hz), 6.95-6.89 (2H, m), 4.07-4.05 (1H, m), 3.79-3.76 (1H, m), 1.16 (3H, t, J = 7.0 Hz). |
| 253 | $^1$H-NMR ($CDCl_3$) δ: 8.08 (1H, s), 7.37 (1H, s), 7.29 (1H, s), 6.48 (1H, dd, J = 10.5, 1.7 Hz), 3.95-3.85 (5H, m), 1.17 (3H, t, J = 7.0 Hz). |
| 254 | $^1$H-NMR ($CDCl_3$) δ: 7.52 (1H, d, J = 9.8 Hz), 7.26 (1H, s), 7.18-7.14 (1H, m), 6.91-6.86 (3H, m), 6.77 (1H, s), 6.73 (1H, d, J = 9.8 Hz), 6.34-6.03 (1H, m), 4.42-4.36 (1H, m), 3.83-3.81 (1H, br m), 1.93 (3H, s). |
| 255 | $^1$H-NMR ($CDCl_3$) δ: 7.63 (1H, s), 7.28 (1H, s), 7.19-7.17 (1H, m), 6.88-6.85 (2H, m), 6.32-6.07 (1H, m), 4.57-4.54 (1H, m), 3.89-3.81 (1H, m), 1.89 (3H, s). |
| 256 | $^1$H-NMR ($CDCl_3$) δ: 7.82 (1H, s), 7.28 (1H, s), 7.20-7.16 (1H, m), 6.88-6.85 (2H, m), 6.35-6.04 (1H, m), 4.61-4.51 (1H, m), 3.87-3.84 (1H, m), 1.89 (3H, s). |
| 257 | $^1$H-NMR ($CDCl_3$) δ: 8.22-8.20 (1H, m), 7.81 (1H, s), 7.71-7.64 (2H, m), 7.37-7.35 (1H, m), 7.25 (1H, d, J = 0.6 Hz), 7.17 (1H, d, J = 0.6 Hz), 4.22-4.14 (1H, m), 3.53-3.45 (1H, m), 1.16 (3H, t, J = 7.2 Hz), |
| 258 | $^1$H-NMR ($CDCl_3$) δ: 8.22-8.20 (1H, m), 7.71-7.64 (2H, m), 7.61 (1H, s), 7.37-7.35 (1H, m), 7.25 (1H, d, J = 0.6 Hz), 7.17 (1H, d, J = 0.6 Hz), 4.22-4.15 (1H, m), 3.52-3.45 (1H, m), 1.17 (3H, t, J = 7.0 Hz). |
| 259 | $^1$H-NMR ($CDCl_3$) δ: 7.45 (1H, d, J = 9.8 Hz), 7.43-7.38 (1H, m) 7.23 (1H, s), 7.17-7.10 (3H, m), 6.90 (1H, s), 6.69 (1H, d, J = 9.8 Hz), 4.05-4.02 (1H, m), 3.72-3.70 (1H, m), 1.89 (3H, s), 1.13 (3H, t, J = 7.0 Hz). |
| 260 | $^1$H-NMR ($CDCl_3$) δ: 7.91 (1H, s), 7.45-7.40 (1H, m), 7.24 (1H, s), 7.15-7.13 (3H, m), 6.89 (1H, s), 4.12-4.06 (1H, m), 3.79-3.77 (1H, m), 1.89 (3H, s), 1.15 (3H, t, J = 7.0 Hz). |
| 261 | $^1$H-NMR ($CDCl_3$) δ: 7.87 (1H, s), 7.67 (1H, s), 6.82-6.79 (2H, m), 3.94 (2H, q, J = 7.0 Hz), 1.20 (3H, t, J = 7.0 Hz). |
| 262 | $^1$H-NMR ($CDCl_3$) δ: 7.87 (1H, s), 7.86 (1H, s), 6.81-6.79 (2H, m), 3.94 (2H, q, J = 7.2 Hz), 1.20 (3H, t, J = 7.2 Hz). |
| 263 | $^1$H-NMR ($CDCl_3$) δ: 7.56 (1H, s), 7.41-7.38 (1H, m), 7.23 (1H, s), 7.19-7.17 (1H, m), 7.13-7.07 (2H, m), 4.18-4.15 (1H, m), 3.78-3.75 (1H, m), 1.86 (3H, s), 1.16 (3H, t, J = 7.1 Hz). |
| 264 | $^1$H-NMR ($CDCl_3$) δ: 7.75 (1H, s), 7.42-7.36 (1H, m), 7.23 (1H, s), 7.19-7.17 (1H, m), 7.13-7.07 (2H, m), 4.18-4.11 (1H, m), 3.79-3.75 (1H, m), 1.86 (3H, s), 1.16 (3H, t, J = 7.1 Hz). |
| 265 | $^1$H-NMR ($CDCl_3$) δ: 10.40 (1H, s), 8.06 (1H, s), 7.372 (1H, s), 7.367 (1H, s), 6.78-6.76 (2H, m), 3.98 (2H, q, J = 7.0 Hz), 1.23 (3H, t, J = 7.0 Hz) |
| 266 | $^1$H-NMR ($CDCl_3$) δ: 7.76 (1H, t, J = 1.2 Hz), 7.38 (1H, s), 7.35 (1H, s), 7.01-6.74 (3H, m), 3.92 (2H, q, J = 7.2 Hz), 1.19 (3H, t, J = 7.2 Hz). |
| 267 | $^1$H-NMR ($CDCl_3$) δ: 7.81 (1H, s), 7.69 (1H, s), 6.54-6.51 (2H, m), 3.96 (2H, q, J = 7.1 Hz), 3.84 (3H, s), 1.19 (3H, t, J = 7.1 Hz). |
| 268 | $^1$H-NMR ($CDCl_3$) δ: 7.62-7.61 (1H, m), 7.46 (1H, d, J = 9.6 Hz), 7.32-7.24 (4H, m), 6.96 (1H, s), 6.70 (1H, d, J = 9.6 Hz), 4.32-4.29 (1H, m), 3.40-3.37 (1H, m), 1.88 (3H, s), 1.10 (3H, t, J = 7.1 Hz). |
| 269 | $^1$H-NMR ($CDCl_3$) δ: 7.92 (1H, s), 7.63-7.61 (1H, m), 7.33-7.29 (2H, m), 7.26-7.25 (2H, m), 6.94 (1H, s), 4.36-4.33 (1H, m), 3.48-3.45 (1H, m), 1.88 (3H, s), 1.13 (3H, t, J = 7.0 Hz). |
| 270 | $^1$H-NMR ($CDCl_3$) δ: 7.87 (1H, s, minor), 7.74 (1H, s, major), 7.22-7.15 (1H, m, mixture), 6.91-6.84 (2H, m, mixture), 4.16-4.13 (1H, br m, major), 4.10-4.03 (1H, m, minor), 3.76-3.73 (1H, m, mixture), 1.89 (3H, s, major), 1.87 (3H, s, minor), 1.16-1.15 (3H, m, mixture). |
| 271 | $^1$H-NMR ($CDCl_3$) δ: 7.74 (1H, s), 7.58-7.57 (1H, m), 7.32-7.23 (3H, m), 7.21 (1H, s), 4.38-4.36 (1H, m), 3.51-3.47 (1H, m), 1.88 (3H, s), 1.15 (3H, t, J = 7.0 Hz). |
| 272 | $^1$H-NMR ($CDCl_3$) δ: 7.58-7.57 (1H, m), 7.54 (1H, s), 7.34-7.23 (3H, m), 7.20 (1H, s), 4.39-4.36 (1H, m), 3.50-3.47 (1H, m), 1.88 (3H, s), 1.15 (3H, t, J = 7.1 Hz). |
| 273 | $^1$H-NMR ($CDCl_3$) δ: 7.52 (1H, d, J = 9.8 Hz), 7.41-7.39 (2H, m), 7.25-7.22 (1H, m), 7.20 (1H, d, J = 0.6 Hz), 7.07 (1H, ddd, J = 9.5, 7.0, 1.5 Hz), 6.75 (1H, d, J = 9.8 Hz), 6.32-6.07 (1H, m), 4.60-4.56 (1H, m), 3.55-3.52 (1H, m). |
| 274 | $^1$H-NMR ($CDCl_3$) δ: 7.77 (1H, s), 7.43-7.41 (2H, m), 7.25-7.22 (1H, m), 7.19 (1H, d, J = 0.6 Hz), 7.09-7.08 (1H, m), 6.34-6.10 (1H, m), 4.65-4.59 (1H, m), 3.61-3.58 (1H, m). |
| 275 | $^1$H-NMR ($CDCl_3$) δ: 7.97 (1H, s), 7.42-7.41 (2H, m), 7.25-7.22 (1H, m), 7.19 (1H, d, J = 0.6 Hz), 7.09-7.08 (1H, m), 6.34-6.10 (1H, m), 4.66-4.57 (1H, m), 3.63-3.58 (1H, m). |
| 276 | $^1$H-NMR ($CDCl_3$) δ: 7.52 (1H, d, J = 9.8 Hz), 7.49-7.46 (1H, m), 7.38 (1H, d, J = 0.5 Hz), 7.20-7.14 (4H, m), 6.74 (1H, d, J = 9.8 Hz), 6.19 (1H, t dd, J = 56.8, 5.9, 3.4 Hz), 4.41-4.36 (1H, m), 3.92-3.82 (1H, m). |
| 277 | $^1$H-NMR ($CDCl_3$) δ: 7.78 (1H, s), 7.53-7.47 (1H, m), 7.39 (1H, d, J = 0.5 Hz), 7.19-7.15 (4H, m), 6.21 (1H, tdd, J = 56.6, 5.9, 3.4 Hz), 4.50-4.38 (1H, m), 3.94-3.90 (1H, m). |
| 278 | $^1$H-NMR ($CDCl_3$) δ: 7.97 (1H, s), 7.52-7.47 (1H, m), 7.39 (1H, d, J = 0.7 Hz), 7.21-7.13 (4H, m), 6.21 (1H, tdd, J = 56.7, 5.8, 3.3 Hz), 4.49-4.37 (1H, m), 3.94-3.91 (1H, m). |

TABLE 6-continued

| Compound | $^1$H-NMR |
|---|---|
| 279 | $^1$H-NMR ($CDCl_3$) δ: 7.65 (1H, s), 7.49-7.46 (2H, m), 7.36-7.32 (2H, m), 7.25 (1H, br s), 4.07-4.00 (1H, m), 3.78-3.70 (1H, m), 1.17 (3H, t, J = 7.0 Hz). |
| 280 | $^1$H-NMR ($CDCl_3$) δ: 7.85 (1H, s), 7.49-7.46 (2H, m), 7.36-7.32 (2H, m), 7.25 (1H, s), 4.07-4.00 (1H, m), 3.78-3.71 (1H, m), 1.17 (3H, t, J = 7.0 Hz). |
| 281 | $^1$H-NMR ($CDCl_3$) δ: 8.52 (1H, s), 7.40 (1H, d, J = 9.8 Hz), 6.84 (1H, d, J = 9.8 Hz), 6.79-6.72 (2H, m), 3.91 (2H, q, J = 7.1 Hz), 1.19 (3H, t, J = 7.1 Hz). |
| 282 | $^1$H-NMR ($CDCl_3$) δ: 7.50 (1H, d, J = 9.8 Hz), 7.32 (1H, d, J = 4.9 Hz), 7.22 (1H, d, J = 4.9 Hz), 6.78-6.74 (3H, m), 6.22-6.07 (1H, m), 4.14-4.12 (2H, m). |
| 283 | $^1$H-NMR ($CDCl_3$) δ: 7.96 (1H, s), 7.34 (1H, d, J = 4.9 Hz), 7.22 (1H, d, J = 4.9 Hz), 6.77-6.75 (2H, m), 6.29-6.05 (1H, m), 4.20-4.17 (2H, m). |
| 284 | $^1$H-NMR ($CDCl_3$) δ: 7.52 (1H, d, J = 9.8 Hz), 7.32 (1H, d, J = 4.9 Hz), 7.19-7.15 (1H, m), 7.08 (1H, d, J = 4.9 Hz), 6.95-6.89 (2H, m), 6.75 (1H, d, J = 9.8 Hz), 6.18 (1H, tdd, J = 56.8, 5.9, 3.2 Hz), 4.42-4.36 (1H, m), 3.85-3.81 (1H, m). |
| 285 | $^1$H-NMR ($CDCl_3$) δ: 7.77 (1H, s), 7.34 (1H, d, J = 4.9 Hz), 7.19-7.16 (1H, m), 7.07 (1H, d, J = 4.9 Hz), 6.96-6.91 (2H, m), 6.21 (1H, tdd, J = 56.6, 6.0, 3.2 Hz), 4.46-4.42 (1H, m), 3.90-3.87 (1H, m). |
| 286 | $^1$H-NMR ($CDCl_3$) δ: 7.96 (1H, s), 7.34 (1H, d, J = 4.9 Hz), 7.19-7.16 (1H, m), 7.07 (1H, d, J = 4.9 Hz), 6.96-6.91 (2H, m), 6.21 (1H, tdd, J = 56.7, 5.9, 3.3 Hz), 4.48-4.39 (1H, m), 3.91-3.88 (1H, m). |
| 287 | $^1$H-NMR ($CDCl_3$) δ: 7.78 (1H, s), 7.42 (1H, d, J = 0.6 Hz), 7.18-7.17 (1H, m), 7.16 (1H, d, J = 0.6 Hz), 7.11 (1H, dd, J = 8.6, 2.1 Hz), 6.86 (1H, dd, J = 8.6, 2.4 Hz), 6.27-6.16 (1H, m), 4.62-4.57 (1H, m), 3.84 (3H, s), 3.70-3.66 (1H, m). |
| 288 | $^1$H-NMR ($CDCl_3$) δ: 7.98 (1H, s), 7.42 (1H, d, J = 0.6 Hz), 7.17-7.17 (1H, m), 7.16 (1H, d, J = 0.6 Hz), 7.11 (1H, dd, J = 8.6, 2.1 Hz), 6.86 (1H, dd, J = 8.7, 2.6 Hz), 6.34-6.10 (1H, m), 4.62-4.54 (1H, m), 3.84 (3H, s), 3.71-3.67 (1H, m). |
| 289 | $^1$H-NMR ($CDCl_3$) δ: 7.66-7.65 (1H, m), 7.55 (1H, d, J = 9.8 Hz), 7.39 (1H, d, J = 0.6 Hz), 7.35-7.34 (2H, m), 7.23-7.21 (1H, m), 7.16 (1H, d, J = 0.6 Hz), 6.75 (1H, d, J = 9.8 Hz), 6.32-6.08 (1H, m), 4.61-4.53 (1H, m), 3.61-3.53 (1H, m). |
| 290 | $^1$H-NMR ($CDCl_3$) δ: 7.80 (1H, s), 7.68-7.67 (1H, m), 7.40 (1H, d, J = 0.6 Hz), 7.37-7.34 (2H, m), 7.23-7.20 (1H, m), 7.14 (1H, d, J = 0.6 Hz), 6.30-6.13 (1H, m), 4.63-4.60 (1H, m), 3.65-3.63 (1H, m). |
| 291 | $^1$H-NMR ($CDCl_3$) δ: 8.00 (1H, s), 7.68-7.65 (1H, m), 7.40 (1H, d, J = 0.6 Hz), 7.38-7.34 (2H, m), 7.23-7.21 (1H, m), 7.15 (1H, d, J = 0.6 Hz), 6.29-6.15 (1H, m), 4,65-4.56 (1H, m), 3.67-3.62 (1H, m). |
| 292 | $^1$H-NMR ($CDCl_3$) δ: 7.55 (1H, d, J = 9.5 Hz), 7.48 (1H, dd, J = 8.1, 1.2 Hz), 7.44-7.41 (1H, m), 7.38 (1H, d, J = 0.6 Hz), 7.29 (1H, td, J = 7.5, 1.2 Hz), 7.21-7.20 (1H, m), 7.13 (1H, d, J = 0.6 Hz), 6.75 (1H, d, J = 9.5 Hz), 6.32-6.07 (1H, m), 4.60-4.51 (1H, m), 3.63-3.55 (1H, m). |
| 293 | $^1$H-NMR ($CDCl_3$) δ: 7.80 (1H, s), 7.50 (1H, dd, J = 7.8, 1.1 Hz), 7.46-7.44 (1H, m), 7.40 (1H, d, J = 0.6 Hz), 7.31 (1H, td, J = 7.5, 1.1 Hz), 7.21-7.20 (1H, m), 7.11 (1H, d, J = 0.6 Hz), 6.29-6.14 (1H, m), 4.63-4.57 (1H, m), 3.68-3.62 (1H, m). |
| 294 | $^1$H-NMR ($CDCl_3$) δ: 7.99 (1H, s), 7.48-7.45 (2H, m), 7.39 (1H, s), 7.32-7.30 (1H, m), 7.21-7.19 (1H, m), 7.11 (1H, s), 6.36-6.07 (1H, m), 4.64-4.53 (1H, m), 3.69-3.63 (1H, m). |
| 295 | $^1$H-NMR ($CDCl_3$) δ: 7.28-7.25 (1H, m), 6.85-6.80 (3H, m), 6.48 (1H, d, J = 5.6 Hz), 3.43 (2H, q, J = 7.1 Hz), 2.76-2.67 (4H, m), 0.97 (3H, t, J = 5.6 Hz). |
| 296 | $^1$H-NMR ($CDCl_3$) δ: 7.39-7.32 (1H, m), 7.36 (1H, d, J = 9.5 Hz), 6.90 (2H, dd, J = 8.4, 7.2 Hz), 6.85 (1H, d, J = 5.6 Hz), 6.73 (1H, d, J = 9.5 Hz), 6.53 (1H, d, J = 5.6 Hz), 3.91 (2H, q, J = 7.1 Hz), 1.15 (3H, t, J = 7.1 Hz). |
| 297 | $^1$H-NMR ($CDCl_3$) δ: 7.55 (1H, s), 7.43 (1H, tt, J = 8.6, 6.4 Hz), 6.98-6.96 (2H, m), 6.41 (1H, s), 3.95 (2H, q, J = 7.1 Hz), 1.17 (3H, t, J = 7.1 Hz). |
| 298 | $^1$H-NMR ($CDCl_3$) δ: 7.60 (1H, s), 7.38 (1H, tt, J = 8.4, 6.4 Hz), 6.92-6.90 (2H, m), 6.87 (1H, d, J = 5.8 Hz), 6.54 (1H, d, J = 5.8 Hz), 3.96 (2H, g, J = 7.0 Hz), 1.17 (3H, t, J = 7.0 Hz). |
| 299 | $^1$H-NMR ($CDCl_3$) δ: 7.80 (1H, s), 7.37 (1H, tt, J = 8.4, 6.4 Hz), 6.92-6.90 (2H, m), 6.87 (1H, d, J = 5.8 Hz), 6.54 (1H, d, J = 5.8 Hz), 3.96 (2H, g, J = 7.1 Hz), 1.17 (3H, t, J = 7.1 Hz). |
| 300 | $^1$H-NMR ($CDCl_3$) δ: 7.43 (1H, d, J = 9.5 Hz), 7.32 (1H, dd, J = 3.9, 0.7 Hz), 7.06-7.01 (2H, m), 6.69-6.67 (3H, m), 4.04-4.01 (1H, m), 3.83 (3H, s), 3.37-3.71 (1H, m), 1.13 (3H, t, J = 7.0 Hz). |
| 301 | $^1$H-NMR ($CDCl_3$) δ: 7.70 (1H, s), 7.33 (1H, dd, J = 4.0, 0.6 Hz), 7.06-7.01 (2H, m), 6.70-6.67 (2H, m), 4.12-4.01 (1H, m), 3.82-3.77 (4H, m), 1.15 (3H, t, J = 7.1 Hz). |
| 302 | $^1$H-NMR ($CDCl_3$) δ: 7.89 (1H, s), 7.34-7.33 (1H, m), 7.05-7.02 (2H, m), 6.69-6.67 (2H, m), 4.09-4.06 (1H, m), 3.81-3.79 (4H, m), 1.15 (3H, t, J = 7.0 Hz). |
| 303 | $^1$H-NMR ($CDCl_3$) δ: 7.64 (1H, d, J = 9.8 Hz), 7.34-7.33 (1H, m), 7.26-7.18 (4H, m), 6.71-6.69 (1H, m), 6.67-6.66 (1H, m), 6.25 (1H, tdd, |

TABLE 6-continued

| Compound | $^1$H-NMR |
|---|---|
| | J = 57.1, 5.7, 3.6 Hz), 4.35-4.26 (1H, m), 3.85-3.82 (1H, m), 2.05 (3H, s), 1.86 (3H, s). |
| 304 | $^1$H-NMR ($CDCl_3$) δ: 8.10 (1H, s), 7.37-7.35 (1H, m), 7.27-7.26 (2H, m), 7.23-7.22 (1H, m), 7.19-7.18 (1H, m), 6.64 (1H, s), 6.28 (1H, tdd, J = 57.0, 5.6, 3.6 Hz), 4.37-4.32 (1H, m), 3.91-3.88 (1H, m), 2.04 (3H, s), 1.86 (3H, s). |
| 305 | $^1$H-NMR ($CDCl_3$) δ: 7.55 (1H, d, J = 9.8 Hz), 7.45-7.43 (1H, m), 7.25 (1H, s), 7.15-7.13 (3H, m), 6.87 (1H, s), 6.73 (1H, d, J = 9.8 Hz), 6.19 (1H, tdd, J = 56.7, 5.8, 3.3 Hz), 4.45-4.35 (1H, m), 3.90-3.83 (1H, m), 1.89 (3H, s). |
| 306 | $^1$H-NMR ($CDCl_3$) δ: 7.60 (1H, s), 7.31-7.28 (1H, m), 7.21-7.15 (4H, m), 6.31-6.20 (1H, m), 4.42-4.39 (1H, br m), 3.83-3.75 (1H, m), 2.18 (3H, s), 1.86 (3H, s). |
| 307 | $^1$H-NMR ($CDCl_3$) δ: 7.80 (1H, s), 7.31-7.26 (1H, m), 7.20-7.14 (4H, m), 6.33-6.19 (1H, m), 4.44-4.39 (1H, m), 3.84-3.74 (1H, m), 2.18 (3H, s), 1.86 (3H, s). |
| 308 | $^1$H-NMR ($CDCl_3$) δ: 7.43 (1H, d, J = 9.5 Hz), 7.33 (1H, d, J = 4.2 Hz), 7.17 (1H, d, J = 4.2 Hz), 6.72 (2H, d, J = 9.5 Hz), 6.50-6.47 (2H, m), 3.89 (2H, q, J = 7.2 Hz), 3.82 (3H, s), 1.16 (3H, t, J = 7.2 Hz). |
| 309 | $^1$H-NMR ($CDCl_3$) δ: 8.00 (1H, s), 7.47-7.45 (1H, m), 7.26 (1H, s), 7.16-7.13 (3H, m), 6.86 (1H, s), 6.21 (1H, tdd, J = 56.6, 6.0, 3.2 Hz), 4.49-4.40 (1H, m), 3.93-3.90 (1H, m), 1.89 (3H, s). |
| 310 | $^1$H-NMR ($CDCl_3$) δ: 7.63 (1H, s), 7.44-7.41 (1H, m), 7.26 (1H, s), 7.18-7.16 (1H, m), 7.12-7.10 (2H, m), 6.35-6.04 (1H, m), 4.59-4.54 (1H, m), 3.91-3.86 (1H, m), 1.86 (3H, s). |
| 311 | $^1$H-NMR ($CDCl_3$) δ: 7.43 (1H, d, J = 9.8 Hz), 7.33 (1H, d, J = 4.6 Hz), 7.17 (1H, d, J = 4.6 Hz), 6.71 (2H, d, J = 9.8 Hz), 6.48-645 (2H, m), 4.01 (2H, q, J = 7.0 Hz), 3.89 (2H, q, J = 7.0 Hz), 1.43 (3H, t, J = 7.0 Hz) 1.16 (3H, t, J = 7.0 Hz). |
| 312 | $^1$H-NMR ($CDCl_3$) δ: 7.83 (1H, s), 7.45-7.39 (1H, m), 7.26 (1H, s), 7.18-7.17 (1H, m), 7.13-7.09 (2H, m), 6.35-6.04 (1H, m), 4.61-4.51 (1H, m), 3.91-3.88 (1H, m), 1.86 (3H, s). |
| 313 | $^1$H-NMR ($CDCl_3$) δ: 7.92 (1H, s), 7.49-7.47 (1H, m), 7.42-7.41 (1H, m), 7.31-7.28 (2H, m), 7.23-7.22 (1H, m), 7.08-7.07 (1H, m), 4.30-4.25 (1H, m), 3.54-3.49 (1H, m), 1.13 (3H, t, J = 7.0 Hz). |
| 314 | $^1$H-NMR ($CDCl_3$) δ: 7.69 (1H, s), 7.34 (1H, d, J = 4.9 Hz), 7.17 (1H, d, J = 4.9 Hz), 6.51-6.48 (2H, m), 3.95 (2H, q, J = 7.1 Hz), 3.83 (3H, s), 1.18 (3H, t, J = 7.1 Hz). |
| 315 | $^1$H-NMR ($CDCl_3$) δ: 7.89 (1H, s), 7.34 (1H, d, J = 4.9 Hz), 7.17 (1H, d, J = 4.9 Hz), 6.51-6.49 (2H, m), 3.95 (2H, q, J = 7.0 Hz), 3.83 (3H, s), 1.18 (3H, t, J = 7.0 Hz). |
| 316 | $^1$H-NMR ($CDCl_3$) δ: 7.69 (1H, s), 7.34 (1H, d, J = 4.9 Hz), 7.16 (1H, d, J = 4.9 Hz), 6.49-6.46 (2H, m), 4.02 (2H, q, J = 7.0 Hz), 3.95 (2H, q, J = 7.2 Hz), 1.44 (3H, t, J = 7.0 Hz), 1.18 (3H, t, J = 7.2 Hz). |
| 317 | $^1$H-NMR ($CDCl_3$) δ: 7.89 (1H, s), 7.34 (1H, d, J = 4.9 Hz), 7.16 (1H, d, J = 4.9 Hz), 6.48-6.46 (2H, m), 4.02 (2H, q, J = 7.0 Hz), 3.95 (2H, q, J = 7.2 Hz), 1.44 (3H, t, J = 7.0 Hz), 1.18 (3H, t, J = 7.2 Hz). |
| 318 | $^1$H-NMR ($CDCl_3$) δ: 7.45-7.43 (2H, m), 7.29 (1H, d, J = 4.9 Hz), 7.18 (1H, d, J = 4.9 Hz), 6.97-6.96 (2H, m), 6.73 (1H, d, J = 9.8 Hz), 3.88 (2H, q, J = 7.0 Hz), 1.16 (3H, t, J = 7.0 Hz). |
| 319 | $^1$H-NMR ($CDCl_3$) δ: 7.70 (1H, s), 7.47-7.45 (1H, m), 7.30 (1H, d, J = 4.9 Hz), 7.18 (1H, d, J = 4.9 Hz), 7.00-6.96 (2H, m), 3.94 (2H, q, J = 7.2 Hz), 1.19 (3H, t, J = 7.2 Hz). |
| 320 | $^1$H-NMR ($CDCl_3$) δ: 7.90 (1H, s), 7.46-7.44 (1H, m), 7.30 (1H, d, J = 4.9 Hz), 7.18 (1H, d, J = 4.9 Hz), 7.00-6.95 (2H, m), 3.94 (2H, q, J = 7.2 Hz), 1.18 (3H, t, J = 7.2 Hz). |
| 321 | $^1$H-NMR ($CDCl_3$) δ: 8.00 (1H, s), 7.42-7.38 (1H, m), 7.30-7.20 (4H, m), 6.66 (1H, s), 4.22-4.15 (1H, m), 3.54-3.49 (1H, m), 2.38-2.34 (2H, m), 1.86 (3H, s) 1.14 (3H, t, J = 7.1 Hz), 1.07 (3H, t, J = 7.6 Hz). |
| 322 | $^1$H-NMR ($CDCl_3$) δ: 7.71 (1H, s), 7.36-7.32 (1H, m), 7.25 (1H, s), 7.19-7.14 (3H, m), 4.28-4.23 (1H, m), 3.47-3.38 (1H, m), 2.59-2.57 (1H, m), 2.44-2.40 (1H, m), 1.86 (3H, s) 1.19 (3H, t, J = 7.6 Hz), 1.14 (3H, t, J = 7.1 Hz). |
| 323 | $^1$H-NMR ($CDCl_3$) δ: 7.43 (1H, d, J = 9.5 Hz), 7.39-7.37 (1H, m), 7.02 (1H, d, J = 5.8 Hz), 6.91-6.90 (2H, m), 6.76 (1H, d, J = 9.5 Hz), 6.55 (1H, d, J = 5.8 Hz), 6.16 (1H, tt, J = 56.7, 4.5 Hz), 4.17 (2H, td, J = 13.0, 4.5 Hz). |
| 324 | $^1$H-NMR ($CDCl_3$) δ: 7.44 (1H, tt, J = 8.4, 3.5 Hz), 7.38 (1H, d, J = 9.5 Hz), 6.96-6.94 (2H, m), 6.75 (1H, d, J = 9.5 Hz), 6.55 (1H, s), 6.15 (1H, tt, J = 56.6, 4.5 Hz) 4.16 (2H, td, J = 12.9, 4.5 Hz). |
| 325 | $^1$H-NMR ($CDCl_3$) δ: 7.81 (1H, s), 7.47-7.43 (1H, m), 6.97-6.95 (2H, m), 6.56 (1H, s), 6.17 (1H, tt, J = 56.4, 4.4 Hz), 4.21 (2H, td, J = 12.7, 4.4 Hz). |
| 326 | $^1$H-NMR ($CDCl_3$) δ: 7.43 (1H, d, J = 9.8 Hz), 7.39 (1H, dd, J = 7.8, 2.4 Hz), 7.30 (1H, dd, J = 3.9, 0.7 Hz), 7.26 (1H, dd, J = 8.2, 6.0 Hz), 7.15 (1H, dd, J = 4.9, 0.7 Hz), 7.07-7.05 (1H, m), 6.71 (1H, d, J = 9.8 Hz), 4.31-4.27 (1H, m), 3.39-3.34 (1H, m), 1.11 (3H, t, J = 7.1 Hz). |
| 327 | $^1$H-NMR ($CDCl_3$) δ: 7.44 (1H, d, J = 9.6 Hz), 7.30 (1H, dd, J = 3.9, 0.7 Hz), 7.25-7.20 (2H, m), 7.11 (1H, dd, J = 4.9, 0.7 Hz), 7.04-6.98 (1H, m), |

TABLE 6-continued

| Compound | $^1$H-NMR |
|---|---|
| | 6.71 (1H, d, J = 9.6 Hz), 4.28-4.19 (1H, m), 3.46-3.36 (1H, m), 1.11 (3H, t, J = 7.1 Hz). |
| 328 | $^1$H-NMR ($CDCl_3$) δ: 7.67 (1H, s), 7.30-7.29 (1H, m), 7.23-7.20 (2H, m), 7.09-7.07 (1H, m), 7.00 (1H, td, J = 8.3, 2.5 Hz), 4.30-4.22 (1H, m), 3.50-3.42 (1H, m), 1.12 (3H, t, J = 7.0 Hz). |
| 329 | $^1$H-NMR ($CDCl_3$) δ: 7.87 (1H, s), 7.30-7.28 (1H, m), 7.23-7.20 (2H, m), 7.09-7.07 (1H, m), 7.02-6.98 (1H, m), 4.30-4.21 (1H, m), 3.51-3.42 (1H, m), 1.11 (3H, t, J = 7.0 Hz). |
| 330 | $^1$H-NMR ($CDCl_3$) δ: 7.43 (1H, d, J = 9.8 Hz), 7.37-7.35 (1H, m), 7.28-7.26 (1H, m), 7.24 (1H, s), 7.04-7.02 (1H, m), 6.98 (1H, s), 6.70 (1H, d, J = 9.8 Hz), 4.32-4.29 (1H, m), 3.37-3.35 (1H, m), 1.92 (3H, s), 1.11 (3H, t, J = 7.0 Hz). |
| 331 | $^1$H-NMR ($CDCl_3$) δ: 7.53 (1H, s), 7.35-7.32 (2H, m), 7.23 (1H, s), 7.03-7.01 (1H, m), 4.39-4.36 (1H, m), 3.48-3.45 (1H, m), 1.91 (3H, s), 1.15 (3H, t J = 7.0 Hz). |
| 332 | $^1$H-NMR ($CDCl_3$) δ: 7.89 (1H, s), 7.38-7.36 (1H, m), 7.28-7.25 (2H, m), 7.05-7.03 (1H, m), 6.97 (1H, s), 4.36-4.31 (1H, m), 3.46-3.42 (1H, m), 1.92 (3H, s), 1.13 (3H, t, J = 7.1 Hz). |
| 333 | $^1$H-NMR ($CDCl_3$) δ: 7.73 (1H, s), 7.34-7.32 (2H, m), 7.23 (1H, s), 7.03-7.01 (1H, m), 4.39-4.34 (1H, m), 3.49-3.45 (1H, m), 1.90 (3H, s), 1.15 (3H, t, J = 7.1 Hz). |
| 334 | $^1$H-NMR ($CDCl_3$) δ: 7.43 (1H, d, J = 9.8 Hz), 7.25-7.23 (2H, m), 7.20-7.18 (1H, m), 6.98-6.97 (1H, m), 6.95 (1H, s), 6.70 (1H, d, J = 9.8 Hz), 4.28-4.23 (1H, m), 3.42-3.39 (1H, m), 1.92 (3H, s), 1.11 (3H, 1, J = 7.2 Hz). |
| 335 | $^1$H-NMR ($CDCl_3$) δ: 7.89 (1H, s), 7.25-7.20 (3H, m), 7.01-6.96 (1H, m), 6.93 (1H, s), 4.32-4.27 (1H, m), 3.50-3.46 (1H, m), 1.92 (3H, s), 1.13 (3H, t, J = 7.0 Hz). |
| 336 | $^1$H-NMR ($CDCl_3$) δ: 7.54 (1H, s), 7.31-7.30 (1H, br m), 7.23 (1H, s), 7.16-7.15 (1H, m), 6.98-6.96 (1H, m), 4.36-4.33 (1H, m), 3.51-3.49 (1H, m), 1.90 (3H, s), 1.15 (3H, t, J = 7.0 Hz). |
| 337 | $^1$H-NMR ($CDCl_3$) δ: 7.74 (1H, s), 7.31-7.29 (1H, br m), 7.23 (1H, s), 7.16-7.15 (1H, m), 6.99-6.95 (1H, m), 4.35-4.32 (1H, m), 3.53-3.49 (1H, m), 1.90 (3H, s), 1.15 (3H, t, J = 7.2 Hz). |
| 338 | $^1$H-NMR ($CDCl_3$) δ: 7.54 (1H, d, J = 9.8 Hz), 7.38 (1H, dd, J = 8.0, 2.4 Hz), 7.25-7.23 (2H, m), 7.04-7.03 (1H, m), 6.93 (1H, s), 6.73 (1H, d, J = 9.8 Hz), 6.32-6.07 (1H, m), 4.63-4.54 (1H, m), 3.55-3.53 (1H, m), 1.92 (3H, s). |
| 339 | $^1$H-NMR ($CDCl_3$) δ: 7.99 (1H, s), 7.39 (1H, dd, J = 7.8, 2.4 Hz), 7.27-7.22 (2H, m), 7.06-7.04 (1H, m), 6.91 (1H, s), 6.37-6.06 (1H, m), 4.67-4.56 (1H, m), 3.66-3.56 (1H, m), 1.92 (3H, s). |
| 340 | $^1$H-NMR ($CDCl_3$) δ: 7.61 (1H, s), 7.35-7.33 (1H, m), 7.32-7.29 (1H, br m), 7.24 (1H, s), 7.03-7.01 (1H, m), 6.29-6.14 (1H, m), 4.69-4.65 (1H, m), 3.66-3.61 (1H, m), 1.91 (3H, s). |
| 341 | $^1$H-NMR ($CDCl_3$) δ: 7.81 (1H, s), 7.35-7.31 (2H, m), 7.24 (1H, s), 7.04-7.00 (1H, m), 6.34-6.09 (1H, m), 4.71-4.62 (1H, m), 3.67-3.63 (1H, m), 1.91 (3H, s). |
| 342 | $^1$H-NMR ($CDCl_3$) δ: 7.54 (1H, d, J = 9.8 Hz), 7.26 (1H, s), 7.23-7.20 (2H, m), 7.00-6.97 (1H, m), 6.90 (1H, s), 6.73 (1H, d, J = 9.8 Hz), 6.34-6.04 (1H, m), 4.63-4.51 (1H, m), 3.58-3.53 (1H, m), 1.92 (3H, s). |
| 343 | $^1$H-NMR ($CDCl_3$) δ: 7.61 (1H, s), 7.26-7.24 (2H, m), 7.18-7.16 (1H, m), 7.00-6.95 (1H, m), 6.35-6.06 (1H, m), 4.72-4.61 (1H, m), 3.67-3.62 (1H, m), 1.90 (3H, s). |
| 344 | $^1$H-NMR ($CDCl_3$) δ: 7.99 (1H, s), 7.27 (1H, s), 7.23-7.21 (2H, m), 7.01-6.99 (1H, m), 6.88 (1H, s), 6.33-6.09 (1H, m), 4.64-4.55 (1H, m), 3.63-3.60 (1H, m), 1.92 (3H, s). |
| 345 | $^1$H-NMR ($CDCl_3$) δ: 7.81 (1H, s), 7.30-7.26 (2H, m), 7.18-7.16 (1H, m), 6.98-6.96 (1H, m), 6.36-6.05 (1H, m), 4.71-4.59 (1H, m), 3.70-3.61 (1H, m), 1.90 (3H, s). |
| 346 | $^1$H-NMR ($CDCl_3$) δ: 7.86 (1H, s), 7.42-7.37 (1H, m), 7.04 (1H, d, J = 5.8 Hz), 6.93-6.89 (2H, m), 6.56 (1H, d, J = 5.8 Hz), 6.18 (1H, tt, J = 56.4, 4.6 Hz), 4.22 (2H, td, J = 12.7, 4.6 Hz). |
| 347 | $^1$H-NMR ($CDCl_3$) δ: 7.66 (1H, s), 7.44-7.36 (1H, m), 7.04 (1H, d, J = 5.9 Hz), 6.95-6.88 (2H, m), 6.56 (1H, d, J = 5.9 Hz), 6.18 (1H, tt, J = 56.5, 4.5 Hz), 4.22 (2H, td, J = 12.8, 4.5 Hz). |
| 348 | $^1$H-NMR ($CDCl_3$) δ: 7.48-7.39 (1H, m), 7.38 (1H, d, J = 9.5 Hz), 6.99-6.93 (2H, m), 6.75 (1H, d, J = 9.5 Hz), 6.42 (1H, s), 6.15 (1H, tt, J = 56.6, 4.4 Hz), 4.16 (2H, td, J = 12.9, 4.4 Hz). |
| 349 | $^1$H-NMR ($CDCl_3$) δ: 7.61 (1H, s), 7.50-7.42 (1H, m), 7.00-6.94 (2H, m), 6.43 (1H, s), 6.17 (1H, tt, J = 56.4, 4.5 Hz), 4.21 (2H, td, J = 12.8, 4.5 Hz). |
| 350 | $^1$H-NMR ($CDCl_3$) δ: 7.47-7.45 (2H, m), 7.40 (1H, td, J = 7.8, 1.8 Hz), 7.30-7.28 (2H, m), 7.23 (1H, dd, J = 7.6, 1.8 Hz), 7.09 (1H, dd, J = 4.7, 0.8 Hz), 6.70 (1H, d, J = 9.5 Hz), 4.25-4.23 (1H, m), 3.47-3.42 (1H, m), 1.11 (3H, t, J = 7.0 Hz). |
| 351 | $^1$H-NMR ($CDCl_3$) δ: 7.72 (1H, s), 7.48 (1H, dd, J = 8.1, 1.0 Hz), 7.43-7.40 (1H, m), 7.31 (1H, dd, J = 3.9, 0.7 Hz), 7.29 (1H, dd, J = 7.4, 1.3 Hz), 7.22 (1H, dd, J = 7.9, 1.6 Hz), 7.08 (1H, dd, J = 4.9, 0.7 Hz), 4.33-4.24 (1H, m), 3.55-3.46 (1H, m), 1.14 (3H, t, J = 7.1 Hz). |

TABLE 6-continued

| Compound | $^1$H-NMR |
|---|---|
| 352 | $^1$H-NMR ($CDCl_3$) δ: 7.69 (1H, s), 7.40 (1H, dd, J = 7.8, 2.4 Hz), 7.32 (1H, dd, J = 4.2, 0.7 Hz), 7.26 (1H, dd, J = 8.5, 5.6 Hz), 7.14 (1H, dd, J = 4.9, 0.7 Hz), 7.10-7.05 (1H, m), 4.38-4.29 (1H, m), 3.48-3.40 (1H, m), 1.14 (3H, t, J = 7.1 Hz). |
| 353 | $^1$H-NMR ($CDCl_3$) δ: 7.90 (1H, s), 7.40 (1H, dd, J = 7.8, 2.6 Hz), 7.32 (1H, dd, J = 4.0, 0.6 Hz), 7.27 (1H, dd, J = 8.4, 5.4 Hz), 7.15 (1H, dd, J = 4.9, 0.6 Hz), 7.10-7.05 (1H, m), 4.36-4.29 (1H, m), 3.48-3.42 (1H, m), 1.14 (3H, t, J = 7.0 Hz). |
| 354 | $^1$H-NMR ($CDCl_3$) δ: 7.45 (1H, d, J = 9.5 Hz), 7.32 (1H, dd, J = 4.2, 0.7 Hz), 7.17-7.11 (3H, m), 6.83 (1H, dd, J = 8.7, 2.6 Hz), 6.69 (1H, d, J = 9.8 Hz), 4.33-4.23 (1H, m), 3.83 (3H, s), 3.46-3.37 (1H, m), 1.11 (3H, t, J = 7.0 Hz). |
| 355 | $^1$H-NMR ($CDCl_3$) δ: 7.72 (1H, s), 7.33 (1H, dd, J = 4.2, 0.7 Hz), 7.16 (1H, d, J = 2.7 Hz), 7.14-7.11 (2H, m), 6.85 (1H, dd, J = 8.5, 2.4 Hz), 4.37-4.28 (1H, m), 3.84 (3H, s), 3.54-3.44 (1H, m), 1.13 (3H, t, J = 7.1 Hz). |
| 356 | $^1$H-NMR ($CDCl_3$) δ: 7.65-7.63 (1H, m), 7.46 (1H, d, J = 9.5 Hz), 7.35-7.29 (3H, m), 7.26-7.24 (1H, m), 7.13 (1H, dd, J = 4.9, 0.9 Hz), 6.71 (1H, d, J = 9.5 Hz), 4.29 (1H, td, J = 13.6, 7.0 Hz), 3.39 (1H, td, J = 13.6, 7.0 Hz), 1.11 (3H, t, J = 7.0 Hz). |
| 357 | $^1$H-NMR ($CDCl_3$) δ: 7.72 (1H, s), 7.66-7.64 (1H, m), 7.35-7.31 (3H, m), 7.25-7.23 (1H, m), 7.11 (1H, dd, J = 4.9, 0.7 Hz), 4.34 (1H, dt, J = 20.3, 7.1 Hz), 3.46 (1H, dt, J = 20.3, 7.1 Hz), 1.14 (3H, t, J = 7.1 Hz). |
| 358 | $^1$H-NMR ($CDCl_3$) δ: 7.92 (1H, s), 7.66-7.64 (1H, m), 7.35-7.30 (3H, m), 7.25-7.23 (1H, m), 7.12 (1H, dd, J = 4.9, 0.7 Hz), 4.33 (1H, dt, J = 20.3, 7.1 Hz), 3.47 (1H, dt, J = 20.3, 7.1 Hz), 1.13 (3H, t, J = 7.1 Hz). |
| 359 | $^1$H-NMR ($CDCl_3$) δ: 7.36-7.31 (1H, m), 7.34 (1H, d, J = 9.5 Hz), 7.00 (1H, d, J = 5.1 Hz), 6.88 (2H, dd, J = 8.3, 7.3 Hz), 6.70 (1H, d, J = 9.5 Hz), 6.69 (1H, d, J = 5.1 Hz), 3.90 (2H, q, J = 7.1 Hz), 2.04 (3H, s), 1.15 (3H, t, J = 7.1 Hz). |
| 360 | $^1$H-NMR ($CDCl_3$) δ: 7.46 (1H, d, J = 9.8 Hz), 7.44-7.42 (1H, m), 7.33 (1H, td, J = 8.3, 5.8 Hz), 7.30 (1H, dd, J = 4.0, 0.6 Hz), 7.21 (1H, dd, J = 4.9, 0.6 Hz), 7.14 (1H, td, J = 8.3, 1.0 Hz), 6.75 (1H, d, J = 9.8 Hz), 4.17-4.10 (1H, m), 3.58-3.51 (1H, m), 1.17 (3H, t, J = 7.2 Hz). |
| 361 | $^1$H-NMR ($CDCl_3$) δ: 7.71 (1H, s), 7.33 (1H, dd, J = 4.0, 0.6 Hz), 7.11 (1H, d, J = 8.6 Hz), 7.07 (1H, dd, J = 4.6, 0.6 Hz), 6.99 (1H, d, J = 2.4 Hz), 6.80 (1H, dd, J = 8.6, 2.4 Hz), 4.31-4.25 (1H, m), 3.84 (3H, s), 3.56-3.49 (1H, m), 1.13 (3H, t, J = 7.0 Hz). |
| 362 | $^1$H-NMR ($CDCl_3$) δ: 7.45 (1H, d, J = 9.8 Hz), 7.31 (1H, dd, J = 3.9, 0.7 Hz), 7.12 (1H, d, J = 8.7 Hz), 7.09 (1H, dd, J = 4.6, 0.7 Hz), 6.98 (1H, d, J = 2.4 Hz), 6.79 (1H, dd, J = 8.7, 2.4 Hz), 6.69 (1H, d, J = 9.8 Hz), 4.28-4.18 (1H, m), 3.83 (3H, s), 3.49-3.43 (1H, m), 1.10 (3H, t, J = 7.0 Hz). |
| 363 | $^1$H-NMR ($CDCl_3$) δ: 7.91 (1H, s), 7.33 (1H, dd, J = 3.9, 0.7 Hz), 7.11 (1H, d, J = 8.5 Hz), 7.08 (1H, dd, J = 4.9, 0.7 Hz), 6.99 (1H, d, J = 2.4 Hz), 6.80 (1H, dd, J = 8.5, 2.4 Hz), 4.32-4.23 (1H, m), 3.84 (3H, s), 3.58-3.48 (1H, m), 1.13 (3H, t, J = 7.1 Hz). |
| 364 | $^1$H-NMR ($CDCl_3$) δ: 7.42-7.34 (2H, m), 7.10 (1H, d, J = 5.3 Hz), 6.94-6.90 (2H, m), 6.85 (1H, d, J = 5.3 Hz), 6.73 (1H, d, J = 9.5 Hz), 3.91 (2H, q, J = 7.0 Hz), 1.16 (3H, t, J = 7.0 Hz). |
| 365 | $^1$H-NMR ($CDCl_3$) δ: 7.64 (1H, s), 7.42-7.36 (1H, m), 7.12 (1H, d, J = 5.5 Hz), 6.95-6.90 (2H, m), 6.86 (1H, d, J = 5.5 Hz), 3.96 (2H, q, J = 7.0 Hz), 1.18 (3H, t, J = 7.0 Hz). |
| 366 | $^1$H-NMR ($CDCl_3$) δ: 7.44 (1H, d, J = 9.3 Hz), 7.39 (1H, tt, J = 8.4, 6.4 Hz), 6.93-6.87 (3H, m), 6.76 (1H, d, J = 9.3 Hz), 6.55 (1H, d, J = 5.9 Hz), 6.15 (1H, tt, J = 56.6, 4.4 Hz), 4.18 (2H, td, J = 12.9, 4.4 Hz). |
| 367 | $^1$H-NMR ($CDCl_3$) δ: 7.48 (1H, d, J = 9.8 Hz), 7.24 (1H, s), 7.18-7.16 (1H, m), 6.92-6.90 (2H, m), 6.74 (1H, s), 6.67 (1H, d, J = 9.8 Hz), 4.20-4.12 (1H, m), 3.46-3.43 (1H, m), 2.12 (3H, s), 1.90 (3H, s), 1.10 (3H, t, J = 6.9 Hz). |
| 368 | $^1$H-NMR ($CDCl_3$) δ: 7.71 (1H, s), 7.29 (1H, s), 6.89-6.87 (1H, m), 6.26-6.22 (2H, m), 4.22-4.20 (1H, br m), 4.06 (1H, br s), 3.83-3.80 (1H, br m), 2.82 (3H, d, J = 5.1 Hz), 1.89 (3H, s), 1.15 (3H, t, J = 7.1 Hz). |
| 369 | $^1$H-NMR ($CDCl_3$) δ: 7.52 (1H, s), 7.21-7.18 (2H, m), 6.88-6.85 (2H, m), 4.29-4.27 (1H, br m), 3.45-3.42 (1H, m), 2.21 (3H, s), 1.88 (3H, s), 1.13 (3H, t, J = 7.1 Hz). |
| 370 | $^1$H-NMR ($CDCl_3$) δ: 7.94 (1H, s), 7.24 (1H, s), 7.18-7.14 (1H, m), 6.94-6.91 (2H, m), 6.73 (1H, s), 4.23-4.20 (1H, m), 3.54-3.49 (1H, m), 2.12 (3H, s), 1.90 (3H, s), 1.12 (3H, t, J = 7.1 Hz). |
| 371 | $^1$H-NMR ($CDCl_3$) δ: 7.72 (1H, s), 7.21-7.18 (2H, m), 6.88-6.85 (2H, m), 4.27-4.25 (1H, br m), 3.45-3.42 (1H, m), 2.21 (3H, s), 1.88 (3H, s), 1.13 (3H, t, J = 7.0 Hz). |
| 372 | $^1$H-NMR ($CDCl_3$) δ: 7.70-7.69 (1H, m), 7.58-7.55 (2H, m), 7.48-7.47 (1H, m), 7.40 (1H, d, J = 9.5 Hz), 7.18 (1H, s), 6.89 (1H, s), 6.68 (1H, d, J = 9.5 Hz), 4.29-4.25 (1H, m), 3.24-3.20 (1H, m), 1.88 (3H, s), 1.11 (3H, t, J = 7.0 Hz). |
| 373 | $^1$H-NMR ($CDCl_3$) δ: 7.73 (1H, s), 7.27 (1H, s), 7.07-7.05 (1H, m), 6.92-6.90 (2H, m), 4.17-4.15 (1H, br m), 3.78-3.76 (1H, m), 2.48 (3H, s), 1.89 (3H, s), 1.16 (3H, t, J = 7.0 Hz). |

TABLE 6-continued

| Compound | $^1$H-NMR |
|---|---|
| 374 | $^1$H-NMR ($CDCl_3$) δ: 7.86 (1H, s), 7.71-7.70 (1H, m), 7.60-7.57 (2H, m), 7.47-7.46 (1H, m), 7.18 (1H, s), 6.88 (1H, s), 4.32-4.30 (1H, m), 3.31-3.28 (1H, m), 1.88 (3H, s), 1.13 (3H, t, J = 7.0 Hz). |
| 375 | $^1$H-NMR ($CDCl_3$) δ: 7.67-7.65 (1H, m), 7.58-7.56 (2H, m), 7.53 (1H, s), 7.47-7.45 (1H, m), 7.15 (1H, s), 4.31-4.28 (1H, m), 3.38-3.35 (1H, m), 1.87 (3H, s), 1.15 (3H, t, J = 7.0 Hz). |
| 376 | $^1$H-NMR ($CDCl_3$) δ: 7.83 (1H, s), 7.36 (1H, s), 7.04-7.02 (1H, m), 6.91-6.88 (1H, m), 5.23 (2H, s), 1.90 (3H, s). |
| 377 | $^1$H-NMR ($CDCl_3$) δ: 7.36-7.26 (2H, m), 6.87 (2H, dd, J = 8.3, 7.3 Hz), 6.80 (1H, d, J = 5.2 Hz), 6.71 (1H, d, J = 9.3 Hz), 6.54 (1H, d, J = 5.2 Hz), 3.90 (2H, q, J = 7.1 Hz), 2.25 (3H, s), 1.15 (3H, t, J = 7.1 Hz). |
| 378 | $^1$H-NMR ($CDCl_3$) δ: 7.45 (1H, d, J = 9.8 Hz), 7.40 (1H, td, J = 8.3, 5.9 Hz), 7.30 (1H, dd, J = 4.0, 0.6 Hz), 7.27-7.25 (1H, m), 7.19 (1H, dd, J = 4.9, 0.6 Hz), 7.09 (1H, td, J = 8.3, 0.9 Hz), 6.74 (1H, d, J = 9.8 Hz), 4.13-4.04 (1H, m), 3.64-3.55 (1H, m), 1.16 (3H, t, J = 7.2 Hz). |
| 379 | $^1$H-NMR ($CDCl_3$) δ: 7.71 (1H, s), 7.42 (1H, td, J = 8.4, 5.9 Hz), 7.31 (1H, dd, J = 4.0, 0.9 Hz), 7.29-7.26 (1H, m), 7.18 (1H, dd, J = 4.9, 0.9 Hz), 7.10 (1H, td, J = 8.4, 0.9 Hz), 4.18-4.10 (1H, m), 3.70-3.63 (1H, m), 1.19 (3H, t, J = 7.0 Hz). |
| 380 | $^1$H-NMR ($CDCl_3$) δ: 7.91 (1H, s), 7.42 (1H, td, J = 8.4, 6.1 Hz), 7.31 (1H, dd, J = 3.9, 0.6 Hz), 7.29-7.26 (1H, m), 7.18 (1H, dd, J = 4.9, 0.6 Hz), 7.10 (1H, td, J = 8.4, 0.9 Hz), 4.18-4.11 (1H, m), 3.71-3.62 (1H, m), 1.19 (3H, t, J = 7.1 Hz). |
| 381 | $^1$H-NMR ($CDCl_3$) δ: 7.57 (1H, s), 7.38-7.32 (1H, m), 7.02 (1H, d, J = 5.0 Hz), 6.89 (2H, dd, J = 8.6, 7.0 Hz), 6.69 (1H, d, J = 5.0 Hz), 3.95 (2H, q, J = 7.1 Hz), 2.05 (3H, s), 1.18 (3H, t, J = 7.1 Hz). |
| 382 | $^1$H-NMR ($CDCl_3$) δ: 7.47-7.41 (1H, m), 7.45 (1H, d, J = 9.5 Hz), 7.29 (1H, dd, J = 4.0, 0.9 Hz), 7.18-7.13 (3H, m), 7.06 (1H, d, J = 4.9 Hz), 6.70 (1H, d, J = 9.5 Hz), 4.02 (1H, dt, J = 20.3, 7.1 Hz), 3.72 (1H, td, J = 13.7, 6.9 Hz), 1.13 (3H, t, J = 7.0 Hz). |
| 383 | $^1$H-NMR ($CDCl_3$) δ: 7.71 (1H, s), 7.49-7.44 (1H, m), 7.31 (1H, dd, J = 4.2, 0.7 Hz), 7.19-7.15 (3H, m), 7.05 (1H, d, J = 4.9 Hz), 4.07 (1H, td, J = 13.7, 7.1 Hz), 3.79 (1H, td, J = 13.7, 7.1 Hz), 1.16 (3H, t, J = 7.1 Hz). |
| 384 | $^1$H-NMR ($CDCl_3$) δ: 7.90 (1H, s), 7.49-7.44 (1H, m), 7.30 (1H, dd, J = 3.9, 0.7 Hz), 7.19-7.13 (3H, m), 7.05 (1H, d, J = 4.6 Hz), 4.07 (1H, td, J = 13.6, 7.1 Hz), 3.83-3.75 (1H, m), 1.16 (3H, t, J = 7.1 Hz). |
| 385 | $^1$H-NMR ($CDCl_3$) δ: 7.42 (1H, d, J = 9.5 Hz), 7.40-7.34 (1H, m), 7.03 (1H, d, J = 4.9 Hz), 6.91-6.88(2H, m), 6.73 (1H, d, J = 9.5 Hz), 6.70 (1H, d, J = 4.9 Hz), 6.17 (1H, tt, J = 56.7, 4.5 Hz), 4.17 (2H, td, J = 12.8, 4.5 Hz), 2.04 (3H, s). |
| 386 | $^1$H-NMR ($CDCl_3$) δ: 7.43-7.35 (1H, m), 7.29 (1H, d, J = 9.5 Hz), 6.93 (2H, dd, J = 8.4, 7.2 Hz), 6.69 (1H, d, J = 9.5 Hz), 6.66 (1H, s), 3.88 (2H, q, J = 7.1 Hz), 1.98 (3H, s), 1.14 (3H, t, J = 7.1 Hz). |
| 387 | $^1$H-NMR ($CDCl_3$) δ: 7.53 (1H, s), 7.45-7.37 (1H, m), 6.94 (2H, dd, J = 8.4, 7.2 Hz), 6.66 (1H, s), 3.93 (2H, q, J = 7.1 Hz), 1.99 (3H, s), 1.17 (3H, t, J = 7.1 Hz). |
| 388 | $^1$H-NMR ($CDCl_3$) δ: 7.74 (1H, s), 7.44-7.37 (1H, m), 6.94 (2H, dd, J = 8.5, 7.3 Hz), 6.66 (1H, s), 3.93 (2H, q, J = 7.1 Hz), 1.99 (3H, s), 1.16 (3H, t, J = 7.1 Hz). |
| 389 | $^1$H-NMR ($CDCl_3$) δ: 7.78 (1H, s), 7.39-7.31 (1H, m), 7.02 (1H, d, J = 5.1 Hz), 6.89 (2H, dd, J = 8.5, 7.1 Hz), 6,69 (1H, d, J = 5.1 Hz), 3.95 (2H, g, J = 7.1 Hz), 2.05 (3H, s), 1.17 (3H, t, J = 7.1 Hz). |
| 390 | $^1$H-NMR ($CDCl_3$) δ: 7.52 (1H, s), 7.36-7.30 (1H, m), 6.89-6.86 (2H, m), 6.81 (1H, d, J = 5.2 Hz), 6.54 (1H, d, J = 5.2 Hz), 3.95 (2H, q, J = 7.0 Hz), 2.26 (3H, s), 1.17 (3H, t, J = 7.0 Hz). |
| 391 | $^1$H-NMR ($CDCl_3$) δ: 7.72 (1H, s), 7.44 (1H, d, J = 8.3 Hz), 7.35 (1H, td, J = 8.3, 5.8 Hz), 7.32-7.31 (1H, m), 7.20 (1H, d, J = 4.9 Hz), 7.16-7.13 (1H, m), 4.22-4.15 (1H, m), 3.65-3.58 (1H, m), 1.20 (3H, t, J = 7.0 Hz). |
| 392 | $^1$H-NMR ($CDCl_3$) δ: 7.92 (1H, s), 7.44 (1H, d, J = 8.0 Hz), 7.35 (1H, td, J = 8.0, 5.8 Hz), 7.32 (1H, d, J = 4.0 Hz), 7.20 (1H, d, J = 4.9 Hz), 7.16-7.13 (1H, m), 4.22-4.15 (1H, m), 3.65-3.58 (1H, m), 1.20 (3H, t, J = 7.2 Hz). |
| 393 | $^1$H-NMR ($CDCl_3$) δ: 7.41-7.34 (1H, m), 7.41 (1H, d, J = 9.5 Hz), 7.09 (1H, d, J = 5.6 Hz), 6.95-6.89 (2H, m), 6.79 (1H, d, J = 5.6 Hz), 6.73 (1H, d, J = 9.5 Hz), 3.91 (2H, q, J = 7.1 Hz), 1.15 (3H, t, J = 7.1 Hz). |
| 394 | $^1$H-NMR ($CDCl_3$) δ: 7.49 (1H, d, J = 9.5 Hz), 7.45-7.37 (1H, m), 7.13 (1H, d, J = 5.4 Hz), 6.95-6.90 (2H, m), 6.80 (1H, d, J = 5.4 Hz), 6.76 (1H, d, J = 9.5 Hz), 6.15 (1H, tt, J = 56.6, 4.4 Hz), 4.18 (2H, td, J = 12.9, 4.4 Hz). |
| 395 | $^1$H-NMR ($CDCl_3$) δ: 7.65 (1H, s), 7.42-7.36 (1H, m), 7.12 (1H, d, J = 5.5 Hz), 6.95-6.91 (2H, m), 6.79 (1H, d, J = 5.5 Hz), 3.96 (2H, q, J = 7.1 Hz), 1.18 (3H, t, J = 7.1 Hz). |
| 396 | $^1$H-NMR ($CDCl_3$) δ: 7.60 (1H, s), 7.49-7.41 (1H, m), 7.00-6.95 (2H, m), 6.66 (1H, s), 3.95 (2H, q, J = 7.1 Hz), 1.17 (3H, t, J = 7.1 Hz). |
| 397 | $^1$H-NMR ($CDCl_3$) δ: 7.85 (1H, s), 7.43-7.36 (1H, m), 7.12 (1H, d, J = 5.4 Hz), 6.95-6.90 (2H, m), 6.79 (1H, d, J = 5.4 Hz), 3.96 (2H, q, J = 7.1 Hz), 1.17 (3H, t, J = 7.1 Hz). |

TABLE 6-continued

| Compound | $^1$H-NMR |
|---|---|
| 398 | $^1$H-NMR ($CDCl_3$) δ: 7.80 (1H, s), 7.49-7.41 (1H, m), 7.00-6.94 (2H, m), 6.78 (1H, s), 3.95 (2H, q, J = 7.1 Hz), 1.17 (3H, t, J = 7.1 Hz). |
| 399 | $^1$H-NMR ($CDCl_3$) δ: 7.85 (1H, s), 7.37 (1H, tt, J = 8.4, 6.4 Hz), 6.93 (1H, d, J = 5.8 Hz), 6.90-6.88 (2H, m), 6.57 (1H, d, J = 5.8 Hz), 5.18 (2H, s). |
| 400 | $^1$H-NMR ($CDCl_3$) δ: 7.81 (1H, s), 7.52-7.42 (1H, m), 7.00-6.95 (2H, m), 6.57 (1H, s), 6.16 (1H, tt, J = 56.5, 4.5 Hz), 4.22 (2H, td, J = 12.7, 4.5 Hz). |
| 401 | $^1$H-NMR ($CDCl_3$) δ: 7.44 (1H, tt, J = 8.5, 6.4 Hz), 7.38 (1H, d, J = 9.5 Hz), 6.97-6.95 (2H, m), 6.75 (1H, d, J = 9.5 Hz), 6.55 (1H, s), 6.14 (1H, tt, J = 56.6, 4.5 Hz), 4.19-4.13 (2H, m). |
| 402 | $^1$H-NMR ($CDCl_3$) δ: 7.86 (1H, s), 7.43-7.37 (1H, m), 6.93-6.90 (3H, m), 6.56 (1H, d, J = 5.9 Hz), 6.18 (1H, tt, J = 55.4, 4.3 Hz), 4.22 (2H, td, J = 12.8, 4.3 Hz). |
| 403 | $^1$H-NMR ($CDCl_3$) δ: 7.61 (1H, s), 7.49-7.43 (1H, m), 6.98-6.96 (2H, m), 6.57 (1H, s), 6.16 (1H, tt, J = 56.6, 4.6 Hz), 4.22 (2H, td, J = 12.7, 4.6 Hz). |
| 404 | $^1$H-NMR ($CDCl_3$) δ: 7.66 (1H, s), 7.41 (1H, tt, J = 8.4, 6.4 Hz), 6.92-6.91 (3H, m), 6.56 (1H, d, J = 5.9 Hz), 6.18 (1H, tt, J = 56.5, 4.5 Hz), 4.22 (2H, td, J = 12.8, 4.5 Hz). |
| 405 | $^1$H-NMR ($CDCl_3$) δ: 7.64-7.63 (1H, m), 7.57 (1H, d, J = 9.8 Hz), 7.31-7.29 (2H, m), 7.27 (1H, s), 7.23-7.22 (1H, m), 6.89 (1H, s), 6.73 (1H, d, J = 9.8 Hz), 6.35-6.05 (1H, m), 4.64-4.52 (1H, m), 3.63-3.53 (1H, m), 1.88 (3H, s). |
| 406 | $^1$H-NMR ($CDCl_3$) δ: 7.46 (1H, d, J = 9.8 Hz), 7.27 (1H, s), 7.10-7.08 (1H, m), 6.91-6.85 (3H, m), 6.71 (1H, d, J = 9.8 Hz), 3.34 (3H, s), 1.93 (3H, s). |
| 407 | $^1$H-NMR ($CDCl_3$) δ: 7.61 (1H, s), 7.60-7.58 (1H, m), 7.28-7.27 (3H, m), 7.22 (1H, s), 6.34-6.10 (1H, m), 4.72-4.62 (1H, m), 3.68-3.66 (1H, m), 1.88 (3H, s). |
| 408 | $^1$H-NMR ($CDCl_3$) δ: 8.02 (1H, s), 7.66-7.63 (1H, m), 7.34-7.29 (2H, m), 7.27 (1H, s), 7.24-7.21 (1H, m), 6.87 (1H, s), 6.35-6.10 (1H, m), 4.66-4.56 (1H, m), 3.67-3.63 (1H, m), 1.88 (3H, s). |
| 409 | $^1$H-NMR ($CDCl_3$) δ: 7.81 (1H, s), 7.60-7.57 (1H, m), 7.29-7.26 (3H, m), 7.22 (1H, s), 6.37-6.07 (1H, m), 4.72-4.60 (1H, m), 3.69-3.67 (1H, m), 1.88 (3H, s). |
| 410 | $^1$H-NMR ($CDCl_3$) δ: 7.58 (1H, s), 7.30 (1H, s), 7.11-7.10 (1H, m), 6.91-6.89 (1H, m), 6.83-6.81 (1H, m), 3.45 (3H, s), 1.89 (3H, s). |
| 411 | $^1$H-NMR ($CDCl_3$) δ: 7.91 (1H, s), 7.28 (1H, s), 7.10-7.08 (1H, m), 6.93-6.91 (1H, m), 6.87-6.85 (2H, m), 3.41 (3H, s), 1.93 (3H, s). |
| 412 | $^1$H-NMR ($CDCl_3$) δ: 7.78 (1H, s), 7.30 (1H, s), 7.12-7.09 (1H, m), 6.91-6.88 (1H, m), 6.83-6.81 (1H, m), 3.45 (3H, s), 1.89 (3H, s). |
| 413 | $^1$H-NMR ($CDCl_3$) δ: 7.46-7.43 (2H, m), 7.31 (1H, d, J = 4.9 Hz), 7.17 (1H, d, J = 4.9 Hz), 7.00-6.96 (2H, m), 6.76 (1H, d, J = 9.5 Hz), 3.38 (3H, s). |
| 414 | $^1$H-NMR ($CDCl_3$) δ: 7.80 (1H, s), 7.34 (1H, s), 7.12-7.08 (1H, m), 6.85-6.83 (1H, m), 6.78-6.76 (1H, m), 5.97 (1H, q, J = 5.9 Hz), 2.46 (3H, d, J = 5.9 Hz), 1.89 (3H, s). |
| 415 | $^1$H-NMR ($CDCl_3$) δ: 7.79 (1H, s), 7.47-7.42 (1H, m), 6.99-6.95 (2H, m), 6.83 (1H, s), 3.94 (2H, q, J = 7.0 Hz), 1.17 (3H, t, J = 7.0 Hz). |
| 416 | $^1$H-NMR ($CDCl_3$) δ: 7.84 (1H, s), 7.42-7.36 (1H, m), 7.12 (1H, d, J = 5.4 Hz), 6.95-6.90 (2H, m), 6.85 (1H, d, J = 5.4 Hz), 3.96 (2H, q, J = 7.0 Hz), 1.18 (3H, t, J = 7.0 Hz). |
| 417 | $^1$H-NMR ($CDCl_3$) δ: 7.46-7.39 (1H, m), 7.35 (1H, d, J = 9.3 Hz), 7.00-6.94 (2H, m), 6.83 (1H, s), 6.72 (1H, d, J = 9.3 Hz), 3.89 (2H, q, J = 7.1 Hz), 1.15 (3H, t, J = 7.0 Hz). |
| 418 | $^1$H-NMR ($CDCl_3$) δ: 7.48 (1H, d, J = 9.5 Hz), 7.43-7.37 (1H, m), 7.13 (1H, d, J = 5.2 Hz), 6.95-6.90 (2H, m), 6.86 (1H, d, J = 5.2 Hz), 6.76 (1H, d, J = 9.5 Hz), 6.16 (1H, tt, J = 56.6, 4.5 Hz), 4.18 (2H, td, J = 12.8, 4.5 Hz). |
| 419 | $^1$H-NMR ($CDCl_3$) δ: 7.66 (1H, s), 7.53-7.44 (1H, m), 7.01-6.95 (2H, m), 6.72 (1H, s), 6.16 (1H, tt, J = 56.4, 4.5 Hz), 4.20 (2H, td, J = 12.6, 4.5 Hz). |
| 420 | $^1$H-NMR ($CDCl_3$) δ: 7.71 (1H, s), 7.47-7.37 (1H, m), 7.15 (1H, d, J = 5.5 Hz), 6.95-6.90 (2H, m), 6.87 (1H, d, J = 5.5 Hz), 6.18 (1H, tt, J = 56.4, 4.5 Hz), 4.22 (2H, td, J = 13.1, 4.5 Hz). |
| 421 | $^1$H-NMR ($CDCl_3$) δ: 7.52-7.40 (2H, m), 7.00-6.95 (2H, m), 6.75 (1H, d, J = 9.5 Hz), 6.71 (1H, s), 6.14 (1H, tt, J = 56.6, 4.4 Hz), 4.16 (2H, td, J = 12.8, 4.4 Hz). |
| 422 | $^1$H-NMR ($CDCl_3$) δ: 7.86 (1H, s), 7.52-7.44 (1H, m), 7.01-6.94 (2H, m), 6.84 (1H, s), 6.16 (1H, tt, J = 56.4, 4.5 Hz), 4.20 (2H, td, J = 12.7, 4.5 Hz). |
| 423 | $^1$H-NMR ($CDCl_3$) δ: 7.91 (1H, s), 7.46-7.39 (1H, m), 7.15 (1H, d, J = 5.5 Hz), 6.95-6.90 (2H, m), 6.86 (1H, d, J = 5.5 Hz), 6.18 (1H, tt, J = 56.6, 4.5 Hz), 4.22 (2H, td, J = 12.7, 4.5 Hz). |
| 424 | $^1$H-NMR ($CDCl_3$) δ: 7.39-7.31 (2H, m), 6.91-6.85 (2H, m), 6.82 (1H, d, J = 5.1 Hz), 6.74 (1H, d, J = 9.3 Hz), 6.53 (1H, d, J = 5.1 Hz), 6.17 (1H, tt, J = 56.8, 4.5 Hz), 4.17 (2H, td, J = 12.9, 4.5 Hz), 2.24 (3H, s). |
| 425 | $^1$H-NMR ($CDCl_3$) δ: 7.54 (1H, d, J = 9.8 Hz), 7.33 (1H, dd, J = 3.9, 0.7 Hz), 7.25-7.20 (2H, m), 7.07 (1H, dd, J = 4.6, 0.7 Hz), 7.05-6.99 (1H, m), 6.75 (1H, d, J = 9.8 Hz), 6.34-6.04 (1H, m), 4.62-4.50 (1H, m), 3.61-3.50 (1H, m). |

TABLE 6-continued

| Compound | $^1$H-NMR |
|---|---|
| 426 | $^1$H-NMR ($CDCl_3$) δ: 7.79 (1H, s), 7.35 (1H, dd, J = 4.0, 0.6 Hz), 7.26-7.19 (2H, m), 7.05-7.03 (2H, m), 6.36-6.06 (1H, m), 4.66-4.54 (1H, m), 3.67-3.57 (1H, m). |
| 427 | $^1$H-NMR ($CDCl_3$) δ: 7.89 (1H, s), 7.39 (1H, d, J = 0.5 Hz), 7.18 (1H, d, J = 0.5 Hz), 7.11 (1H, d, J = 8.5 Hz), 6.99 (1H, d, J = 2.4 Hz), 6.80 (1H, dd, J = 8.5, 2.4 Hz), 4.31-4.23 (1H, m), 3.84 (3H, s), 3.57-3.50 (1H, m), 1.13 (3H, t, J = 7.1 Hz). |
| 428 | $^1$H-NMR ($CDCl_3$) δ: 7.43 (1H, d, J = 9.5 Hz), 7.38 (1H, d, J = 0.5 Hz), 7.19 (1H, d, J = 0.5 Hz), 7.12 (1H, d, J = 8.5 Hz), 6.98 (1H, d, J = 2.4 Hz), 6.79 (1H, dd, J = 8.5, 2.4 Hz), 6.69 (1H, d, J = 9.8 Hz), 4.27-4.18 (1H, m), 3.83 (3H, s), 3.51-3.41 (1H, m), 1.11 (3H, t, J = 7.1 Hz). |
| 429 | $^1$H-NMR ($CDCl_3$) δ: 7.61 (1H, s), 7.42-7.33 (1H, m), 7.03 (1H, d, J = 5.6 Hz), 6.91 (2H, t, J = 7.9 Hz), 6.53 (1H, d, J = 5.6 Hz), 3.45 (3H, s). |
| 430 | $^1$H-NMR ($CDCl_3$) δ: 7.81 (1H, s), 7.41-7.33 (1H, m), 7.03 (1H, d, J = 5.6 Hz), 6.91 (2H, dd, J = 8.4, 7.4 Hz), 6.53 (1H, d, J = 5.6 Hz), 3.45 (3H, s). |
| 431 | $^1$H-NMR ($CDCl_3$) δ: 7.35-7.29 (2H, m), 6.88 (2H, dd, J = 8.3, 7.3 Hz), 6.82 (1H, d, J = 5.2 Hz), 6.73 (1H, d, J = 9.5 Hz), 6.53 (1H, d, J = 5.2 Hz 3.38 (3H, s), 2.23 (3H, s). |
| 432 | $^1$H-NMR ($CDCl_3$) δ: 7.87 (1H, s), 7.48 (1H, tt, J = 8.5, 6.3 Hz), 7.00-6.95 (2H, m), 6.79 (1H, s), 6.16 (1H, tt, J = 56.5, 4.5 Hz), 4.21 (2H, td, J = 12.7, 4.5 Hz). |
| 433 | $^1$H-NMR ($CDCl_3$) δ: 7.92 (1H, s), 7.43 (1H, tt, J = 8.5, 6.3 Hz), 7.15 (1H, d, J = 5.4 Hz), 6.96-6.90 (2H, m), 6.80 (1H, d, J = 5.4 Hz), 6.17 (1H, tt, J = 56.5, 4.5 Hz), 4.23 (2H, td, J = 12.7, 4.5 Hz). |
| 434 | $^1$H-NMR ($CDCl_3$) δ: 7.52-7.42 (1H, m), 7.44 (1H, d, J = 9.5 Hz), 6.99-6.95 (2H, m), 6.78 (1H, s), 6.75 (1H, d, J = 9.5 Hz), 6.14 (1H, tt, J = 56.6, 4.5 Hz), 4.16 (2H, td, J = 12.9, 4.5 Hz). |
| 435 | $^1$H-NMR ($CDCl_3$) δ: 7.44 (1H, d, J = 9.5 Hz), 7.38 (1H, tt, J = 8.6, 6.4 Hz), 7.11 (1H, d, J = 5.5 Hz), 6.94-6.90 (2H, m), 6.79 (1H, d, J = 5.5 Hz), 6.75 (1H, d, J = 9.5 Hz), 3.39 (3H, s). |
| 436 | $^1$H-NMR ($CDCl_3$) δ: 7.67 (1H, s), 7.48 (1H, tt, J = 8.6, 6.4 Hz), 7.00-6.97 (2H, m), 6.67 (1H, s), 6.16 (1H, tt, J = 56.4, 4.5 Hz), 4.21 (2H, td, J = 12.6, 4.5 Hz). |
| 437 | $^1$H-NMR ($CDCl_3$) δ: 7.71 (1H, s), 7.43 (1H, tt, J = 8.5, 6.3 Hz), 7.15 (1H, d, J = 5.4 Hz), 6.95-6.91 (2H, m), 6.80 (1H, d, J = 5.4 Hz), 6.17 (1H, tt, J = 56.5, 4.5 Hz), 4.23 (2H, td, J = 12.7, 4.5 Hz). |
| 438 | $^1$H-NMR ($CDCl_3$) δ: 7.52-7.43 (1H, m), 7.44 (1H, d, J = 9.5 Hz), 7.00-6.95 (2H, m), 6.75 (1H, d, J = 9.5 Hz), 6.66 (1H, s), 6.14 (1H, tt, J = 56.5, 4.5 Hz), 4.16 (2H, td, J = 12.8, 4.5 Hz). |
| 439 | $^1$H-NMR ($CDCl_3$) δ: 7.67 (1H, s), 7.40 (1H, tt, J = 8.5, 6.3 Hz), 7.14 (1H, d, J = 5.4 Hz), 6.96-6.90 (2H, m), 6.80 (1H, d, J = 5.4 Hz), 3.46 (3H, s). |
| 440 | $^1$H-NMR ($CDCl_3$) δ: 7.62 (1H, s), 7.46 (1H, tt, J = 8.5, 6.3 Hz), 7.01-6.95 (2H, m), 6.66 (1H, s), 3.44 (3H, s). |
| 441 | $^1$H-NMR ($CDCl_3$) δ: 7.87 (1H, s), 7.40 (1H, tt, J = 8.6, 6.4 Hz), 7.14 (1H, d, J = 5.2 Hz), 6.95-6.90 (2H, m), 6.80 (1H, d, J = 5.2 Hz), 3.46 (3H, s). |
| 442 | $^1$H-NMR ($CDCl_3$) δ: 7.82 (1H, s), 7.45 (1H, tt, J = 8.6, 6.4 Hz), 6.99-6.95 (2H, m), 6.78 (1H, s), 3.44 (3H, s). |
| 443 | $^1$H-NMR ($CDCl_3$) δ: 7.46-7.39 (1H, m), 7.37 (1H, d, J = 9.4 Hz), 6.96-6.92 (2H, m), 6.72 (1H, d, J = 9.4 Hz), 6.67 (1H, s), 6.15 (1H, tt, J = 56.5, 4.5 Hz), 4.15 (2H, td, J = 12.9, 4.5 Hz), 1.98 (3H, s). |
| 444 | $^1$H-NMR ($CDCl_3$) δ: 7.72 (1H, s), 7.36-7.29 (1H, m), 6.87 (2H, dd, J = 8.5, 7.3 Hz), 6.80 (1H, d, J = 5.1 Hz), 6.53 (1H, d, J = 5.1 Hz), 3.94 (2H, q, J = 7.1 Hz), 2.25 (3H, s), 1.16 (3H, t, J = 7.1 Hz). |
| 445 | $^1$H-NMR ($CDCl_3$) δ: 7.65 (1H, s), 7.42-7.35 (1H, m), 7.05 (1H, d, J = 5.1 Hz), 6.90 (2H, dd, J = 8.5, 7.3 Hz), 6.70 (1H, d, J = 5.1 Hz), 6.19 (1H, tt, J = 56.5, 4.5 Hz), 4.21 (2H, td, J = 12.8, 4.5 Hz), 2.05 (3H, s). |
| 446 | $^1$H-NMR ($CDCl_3$) δ: 7.85 (1H, s), 7.42-7.35 (1H, m), 7.05 (1H, d, J = 5.1 Hz), 6.92-6.88 (2H, m), 6.70 (1H, d, J = 5.1 Hz), 6.19 (1H, tt, J = 56.5, 4.5 Hz), 4.21 (2H, td, J = 12.6, 4.5 Hz), 2.05 (3H, s). |
| 447 | $^1$H-NMR ($CDCl_3$) δ: 7.54 (1H, d, J = 9.8 Hz), 7.40 (1H, dd, J = 7.6, 2.4 Hz), 7.33 (1H, d, J = 4.0 Hz), 7.25-7.22 (1H, m), 7.10-7.05 (2H, m), 6.75 (1H, d, J = 9.8 Hz), 6.32-6.08 (1H, m), 4.64-4.53 (1H, m), 3.58-3.49 (1H, m). |
| 448 | $^1$H-NMR ($CDCl_3$) δ: 7.79 (1H, s), 7.42 (1H, dd, J = 7.8, 2.6 Hz), 7.35 (1H, dd, J = 4.0, 0.6 Hz), 7.25-7.22 (1H, m), 7.11-7.06 (2H, m), 6.34-6.09 (1H, m), 4.68-4.57 (1H, m), 3.64-3.56 (1H, m). |
| 449 | $^1$H-NMR ($CDCl_3$) δ: 7.99 (1H, s), 7.41 (1H, dd, J = 8.0, 2.4 Hz), 7.35 (1H, dd, J = 4.0, 0.6 Hz), 7.25-7.22 (1H, m), 7.11-7.06 (2H, m), 6.33-6.10 (1H, m), 4.66-4.57 (1H, m), 3.65-3.56 (1H, m). |
| 450 | $^1$H-NMR ($CDCl_3$) δ: 8.01 (1H, s), 7.36 (1H, dd, J = 4.0, 0.6 Hz), 7.17 (1H, d, J = 2.4 Hz), 7.10 (1H, dd, J = 8.6, 2.1 Hz), 7.05 (1H, dd, J = 4.9, 0.6 Hz), 6.86 (1H, dd, J = 8.6, 2.1 Hz), 6.34-6.09 (1H, m), 4.63-4.54 (1H, m), 3.84 (3H, s), 3.74-3.65 (1H, m). |
| 451 | $^1$H-NMR ($CDCl_3$) δ: 7.46 (1H, d, J = 9.8 Hz), 7.39 (1H, d, J = 0.5 Hz), 7.25 (1H, dd, J = 8.5, 2.6 Hz), 7.19 (1H, d, J = 0.5 Hz), 7.16 (1H, dd, J = 8.5, 5.6 Hz), 7.04-6.98 (1H, m), 6.73 (1H, d, J = 9.5 Hz), 3.29 (3H, s). |

TABLE 6-continued

| Compound | $^1$H-NMR |
|---|---|
| 452 | $^1$H-NMR ($CDCl_3$) δ: 7.72 (1H, s), 7.40 (1H, d, J = 0.6 Hz), 7.26 (1H, dd, J = 8.3, 2.4 Hz), 7.19-7.16 (2H, m), 7.05-7.00 (1H, m), 3.37 (3H, s). |
| 453 | $^1$H-NMR ($CDCl_3$) δ: 7.91 (1H, s), 7.40 (1H, d, J = 0.7 Hz), 7.25-7.24 (1H, m), 7.18-7.16 (2H, m), 7.05-6.99 (1H, m), 3.37 (3H, s). |
| 454 | $^1$H-NMR ($CDCl_3$) δ: 7.26 (1H, tt, J = 8.4, 6.4 Hz), 6.98 (1H, d, J = 5.6 Hz), 6.83-6.81 (2H, m), 6.49 (1H, d, J = 5.6 Hz), 2.89 (3H, s), 2.76-2.74 (4H, m). |
| 455 | $^1$H-NMR ($CDCl_3$) δ: 7.80 (1H, s), 7.27 (1H, tt, J = 8.4, 6.4 Hz), 6.87 (1H, d, J = 5.6 Hz), 6.85-6.83 (2H, m), 6.55 (1H, d, J = 5.6 Hz), 2.92 (6H, s). |
| 456 | $^1$H-NMR ($CDCl_3$) δ: 7.37-7.35 (2H, m), 7.01 (1H, d, J = 5.6 Hz), 6.91-6.89 (2H, m), 6.75 (1H, d, J = 9.5 Hz), 6.52 (1H, d, J = 5.6 Hz), 3.39 (3H, s). |
| 457 | $^1$H-NMR ($CDCl_3$) δ: 7.25 (1H, tt, J = 8.4, 6.4 Hz), 6.96 (1H, d, J = 4.9 Hz), 6.83-6.81 (2H, m), 6.65 (1H, d, J = 4.9 Hz), 2.89 (3H, s), 2.77-2.69 (4H, m), 2.04 (3H, s). |
| 458 | $^1$H-NMR ($CDCl_3$) δ: 7.35 (1H, d, J = 9.5 Hz), 7.22 (1H, dd, J = 8.6, 5.8 Hz), 7.15 (1H, dd, J = 8.3, 2.4 Hz), 6.98 (1H, ddd, J = 8.6, 8.0, 2.4 Hz), 6.84 (1H, d, J = 5.8 Hz), 6.71 (1H, d, J = 9.5 Hz), 6.47 (1H, d, J = 5.8 Hz), 4.23-4.18 (1H, m), 3.51-3.49 (1H, m), 1.13 (3H, t, J = 7.0 Hz). |
| 459 | $^1$H-NMR ($CDCl_3$) δ: 7.78 (1H, s), 7.21 (1H, dd, J = 8.6, 5.8 Hz), 7.15 (1H, dd, J = 8.3, 2.8 Hz), 6.99 (1H, ddd, J = 8.6, 8.0, 2.8 Hz), 6.86 (1H, d, J = 5.5 Hz), 6.48 (1H, d, J = 5.5 Hz), 4.24 (1H, dq, J = 13.8, 7.0 Hz) 3.56 (1H, dq, J = 13.8, 7.0 Hz), 1.15 (3H, t, J = 7.0 Hz). |
| 460 | $^1$H-NMR ($CDCl_3$) δ: 7.58 (1H, s), 7.21 (1H, dd, J = 8.5, 5.6 Hz), 7.16 (1H, dd, J = 8.3, 2.4 Hz), 6.99 (1H, ddd, J = 8.5, 8.3, 2.4 Hz), 6.86 (1H, d, J = 5.9 Hz), 6.48 (1H, d, J = 5.9 Hz), 4.25 (1H, dq, J = 13.7, 7.0 Hz), 3.56 (1H, dq, J = 13.7, 7.0 Hz), 1.15 (3H, t, J = 7.1 Hz). |
| 461 | $^1$H-NMR ($CDCl_3$) δ: 7.73 (1H, s), 7.52-7.43 (1H, m), 7.32 (1H, d, J = 4.9 Hz), 7.16 (1H, d, J = 4.9 Hz), 7.02-6.97 (2H, m), 3.45 (3H, s). |
| 462 | $^1$H-NMR ($CDCl_3$) δ: 7.93 (1H, s), 7.47-7.45 (1H, m), 7.32 (1H, d, J = 4.9 Hz), 7.16 (1H, d, J = 4.9 Hz), 7.00-6.98 (2H, m), 3.45 (3H, s). |
| 463 | $^1$H-NMR ($CDCl_3$) δ: 7.46 (1H, d, J = 9.8 Hz), 7.33 (1H, d, J = 4.9 Hz), 7.11-7.09 (1H, m), 7.05 (1H, d, J = 4.9 Hz), 6.95-6.93 (1H, m), 6.91-6.87 (1H, m), 6.73 (1H, d, J = 9.8 Hz), 3.34 (3H, s). |
| 464 | $^1$H-NMR ($CDCl_3$) δ: 7.71 (1H, s), 7.35 (1H, d, J = 4.9 Hz), 7.11-7.09 (1H, m), 7.04 (1H, d, J = 4.9 Hz), 6.98-6.88 (2H, m), 3.41 (3H, s). |
| 465 | $^1$H-NMR ($CDCl_3$) δ: 7.91 (1H, s), 7.34 (1H, d, J = 4.9 Hz), 7.11-7.09 (1H, m), 7.04 (1H, d, J = 4.9 Hz), 6.96-6.94 (1H, m), 6.91-6.89 (1H, m), 3.41 (3H, s). |
| 466 | $^1$H-NMR ($CDCl_3$) δ: 7.70 (1H, s), 7.30 (1H, s), 6.91-6.89 (1H, br m), 6.19-6.18 (1H, br m), 6.17-6.15 (1H, br m), 4.23-4.21 (1H, br m), 3.81-3.79 (1H, br m), 3.26-3.25 (4H, m), 2.03-2.00 (4H, m), 1.90 (3H, s), 1.15 (3H, t, J = 7.0 Hz). |
| 467 | $^1$H-NMR ($CDCl_3$) δ: 8.00 (1H, s), 7.48-7.42 (1H, m), 7.37 (1H, d, J = 4.9 Hz), 7.13 (1H, d, J = 4.9 Hz), 6.99-6.95 (2H, m), 5.15 (2H, br s). |
| 468 | $^1$H-NMR ($CDCl_3$) δ: 7.98 (1H, s), 7.47-7.40 (1H, m), 7.37 (1H, d, J = 4.6 Hz), 7.13 (1H, d, J = 4.6 Hz), 6.96-6.95 (2H, m), 5.88 (1H, q, J = 5.9 Hz), 2.55 (3H, d, J = 5.9 Hz). |
| 469 | $^1$H-NMR ($CDCl_3$) δ: 7.71 (1H, s), 7.28 (1H, s), 6.94-6.92 (1H, m), 6.55-6.52 (1H, br m), 6.51-6.50 (1H, m), 4.20-4.17 (1H, br m), 3.81-3.79 (1H, br m), 3.22-3.20 (4H, m), 1.89 (3H, s), 1.66-1.63 (6H, m), 1.15 (3H, t, J = 7.0 Hz). |
| 470 | $^1$H-NMR ($CDCl_3$) δ: 7.75 (1H, s), 7.30 (1H, s), 7.02-6.97 (1H, m), 6.83-6.81 (1H, m), 6.74-6.72 (1H, m), 3.08 (3H, s), 2.71 (3H, s), 1.88 (3H, s). |
| 471 | $^1$H-NMR ($CDCl_3$) δ: 7.87 (1H, s), 7.70-7.68 (1H, m), 7.65-7.63 (1H, m), 7.55-7.51 (1H, m), 7.48-7.47 (1H, m), 7.16 (1H, s), 7.12 (1H, s), 4.05-3.98 (1H, m), 3.74-3.71 (1H, m), 1.92 (3H, s), 1.19 (3H, t, J = 7.1 Hz). |
| 472 | $^1$H-NMR ($CDCl_3$) δ: 7.77 (1H, s), 7.71-7.69 (1H, m), 7.61-7.59 (1H, m), 7.53-7.51 (1H, m), 7.46-7.44 (1H, m), 7.20 (1H, s), 4.17-4.12 (1H, m), 3.70-3.67 (1H, m), 1.86 (3H, s), 1.19 (3H, t, J = 7.0 Hz). |
| 473 | $^1$H-NMR ($CDCl_3$) δ: 7.84 (1H, s), 7.40-7.38 (1H, m), 7.30 (1H, s), 6.92-6.90 (2H, m), 5.19 (2H, br s), 1.93 (3H, s). |
| 474 | $^1$H-NMR ($CDCl_3$) δ: 7.48 (1H, d, J = 9.8 Hz), 7.26 (1H, s), 7.23-7.21 (1H, m), 7.17-7.15 (1H, m), 6.98-6.96 (1H, m), 6.92 (1H, s), 6.71 (1H, d, J = 9.8 Hz), 3.29 (3H, s), 1.92 (3H, s). |
| 475 | $^1$H-NMR ($CDCl_3$) δ: 7.81 (1H, s), 7.37-7.35 (1H, m), 7.29 (1H, s), 6.90-6.88 (2H, m), 5.92 (1H, q, J = 5.9 Hz), 2.55 (3H, d, J = 5.9 Hz), 1.92 (3H, s). |
| 476 | $^1$H-NMR ($CDCl_3$) δ: 7.56 (1H, s), 7.25-7.17 (3H, m), 6.98-6.95 (1H, m), 3.40 (3H, s), 1.90 (3H, s). |
| 477 | $^1$H-NMR ($CDCl_3$) δ: 7.80 (1H, s), 7.29 (1H, s), 7.20-7.15 (2H, m), 6.93-6.91 (1H, m), 5.27 (2H, br s), 1.91 (3H, s). |
| 478 | $^1$H-NMR ($CDCl_3$) δ: 7.78 (1H, s), 7.30 (1H, s), 7.24-7.23 (1H, m), 7.15-7.13 (1H, m), 6.92-6.90 (1H, m), 5.97 (1H, q, J = 5.8 Hz), 2.47 (3H, d, J = 5.9 Hz), 1.91 (3H, s). |
| 479 | $^1$H-NMR ($CDCl_3$) δ: 7.73 (1H, s), 7.24 (1H, s), 7.19-7.17 (1H, m), 7.11-7.08 (1H, m), 6.92-6.90 (1H, m), 3.08 (3H, s), 2.75 (3H, s), 1.90 (3H, s). |

TABLE 6-continued

| Compound | $^1$H-NMR |
|---|---|
| 480 | $^1$H-NMR ($CDCl_3$) δ: 7.60 (1H, s), 7.41-7.32 (1H, m), 6.89 (2H, dd, J = 8.4, 7.4 Hz), 6.84 (1H, d, J = 5.1 Hz), 6.54 (1H, d, J = 5.1 Hz), 6.19 (1H, tt, J = 56.5, 4.5 Hz), 4.21 (2H, td, J = 12.8, 4.5 Hz), 2.25 (3H, s). |
| 481 | $^1$H-NMR ($CDCl_3$) δ: 7.48 (1H, d, J = 9.8 Hz), 7.32 (1H, dd, J = 3.9, 0.7 Hz), 7.25 (1H, dd, J = 8.3, 2.4 Hz), 7.17 (1H, dd, J = 8.7, 5.7 Hz), 7.09 (1H, dd, J = 4.9, 0.7 Hz), 7.04-6.98 (1H, m), 6.73 (1H, d, J = 9.8 Hz), 3.30 (3H, s). |
| 482 | $^1$H-NMR ($CDCl_3$) δ: 7.73 (1H, s), 7.34 (1H, dd, J = 3.9, 0.6 Hz), 7.26 (1H, dd, J = 7.8, 2.7 Hz), 7.16 (1H, dd, J = 8.7, 5.7 Hz), 7.08 (1H, dd, J = 4.8, 0.6 Hz), 7.04-7.00 (1H, m), 3.37 (3H, s). |
| 483 | $^1$H-NMR ($CDCl_3$) δ: 7.93 (1H, s), 7.34 (1H, dd, J = 4.0, 0.7 Hz), 726 (1H, dd, J = 8.4, 2.4 Hz), 7.17 (1H, dd, J = 8.7, 5.7 Hz), 7.08 (1H, dd, J = 4.7, 0.7 Hz), 7.05-6.99 (1H, m), 3.37 (3H, s). |
| 484 | $^1$H-NMR ($CDCl_3$) δ: 7.54 (1H, s), 7.38-7.30 (1H, m), 6.88 (2H, dd, J = 8.6, 7.3 Hz), 6.83 (1H, d, J = 5.2 Hz), 6.53 (1H, d, J = 5.2 Hz), 3.45 (3H, s), 2.24 (3H, s). |
| 485 | $^1$H-NMR ($CDCl_3$) δ: 7.41 (1H, d, J = 9.8 Hz), 7.33-7.32 (1H, m), 7.28-7.26 (1H, m), 7.24 (1H, s), 7.06-7.05 (1H, m), 6.94 (1H, s), 6.69 (1H, d, J = 9.8 Hz), 4.03-4.00 (1H, m), 3.69-3.67 (1H, m), 1.94 (3H, s), 1.13 (3H, t, J = 7.0 Hz). |
| 486 | $^1$H-NMR ($CDCl_3$) δ: 7.77 (1H, s), 7.47-7.44 (1H, m), 7.41-7.39 (1H, m), 7.32-7.30 (1H, m), 7.23 (1H, s), 4.16-4.13 (1H, m), 3.70-3.67 (1H, m), 1.89 (3H, s), 1.19 (314, t, .J = 7.1 Hz). |
| 487 | $^1$H-NMR ($CDCl_3$) δ: 7.49 (1H, d, J = 9.8 Hz), 7.44-7.38 (1H, m), 7.26 (1H, s), 7.17-7.05 (3H, m), 6.85 (1H, s), 6.71 (1H, d, J = 9.8 Hz), 3.35 (3H, s), 1.89 (3H, s). |
| 488 | $^1$H-NMR ($CDCl_3$) δ: 7.59 (1H, s), 7.42-7.39 (1H, m), 7.28 (1H, s), 7.17-7.05 (3H, m), 3.45 (3H, d, J = 1.0 Hz), 1.86 (3H, s). |
| 489 | $^1$H-NMR ($CDCl_3$) δ: 7.95 (1H, s), 7.46-7.40 (1H, m), 7.27 (1H, s), 7.18-7.05 (3H, m), 6.84 (1H, s), 3.42 (3H, d, J = 1.0 Hz), 1.89 (3H, s). |
| 490 | $^1$H-NMR ($CDCl_3$) δ: 7.79 (1H, s), 7.41-7.39 (1H, m), 7.28 (1H, s), 7.13-7.07 (3H, m), 3.45 (3H, d, J = 1.2 Hz), 1.86 (3H, s). |
| 491 | $^1$H-NMR ($CDCl_3$) δ: 7.42-7.33 (1H, m), 7.27-7.24 (1H, m), 6.93 (2H, dd, J = 8.3, 7.3 Hz), 6.72 (1H, d, J = 9.3 Hz), 6.50 (1H, s), 3.37 (3H, s), 2.15 (3H, s). |
| 492 | $^1$H-NMR ($CDCl_3$) δ: 7.75 (1H, s), 7.37-7.31 (2H, m), 6.88 (2H, dd, J = 8.6, 7.3 Hz), 6.83 (1H, d, J = 5.2 Hz), 6.53 (1H, d, J = 5.2 Hz), 3.45 (3H, s). |
| 493 | $^1$H-NMR ($CDCl_3$) δ: 7.51 (1H, d, J = 9.5 Hz), 7.41 (1H, tt, J = 8.4, 3.5 Hz), 7.15-7.12 (1H, m), 6.95-6.90 (3H, m), 6.74 (2H, dt, J = 10.3, 3.5 Hz), 6.16 (1H, tt, J = 56.6, 4.6 Hz), 4.16 (2H, td, J = 12.9, 4.6 Hz). |
| 494 | $^1$H-NMR ($CDCl_3$) δ: 7.76 (1H, s), 7.45-7.39 (1H, m), 6.96-6.92 (2H, m), 6.51 (1H, s), 6.18 (1H, tt, J = 56.6, 4.5 Hz), 4.20 (2H, td, J = 12.7, 4.5 Hz), 2.17 (3H, s). |
| 495 | $^1$H-NMR ($CDCl_3$) δ: 7.95 (1H, s), 7.48-7.40 (1H, m), 6.95 (2H, t, J = 8.3 Hz), 6.52 (1H, s), 6.18 (1H, tt, J = 56.5, 4.5 Hz), 4.43 (2H, s), 4.19 (2H, td, J = 12.3, 4.5 Hz). |
| 496 | $^1$H-NMR ($CDCl_3$) δ: 7.37-7.33 (2H, m), 7.02 (1H, d, J = 4.9 Hz), 6.90-6.88 (2H, m), 6.72 (1H, d, J = 9.5 Hz), 6.70 (1H, d, J = 4.9 Hz), 3.38 (3H, s), 2.02 (3H, s). |
| 497 | $^1$H-NMR ($CDCl_3$) δ: 7.35 (1H, d, J = 9.3 Hz), 7.10 (1H, d, J = 8.7 Hz), 6.91 (1H, d, J = 2.7 Hz), 6.82 (1H, d, J = 5.9 Hz), 6.76 (1H, dd, J = 8.7, 2.7 Hz), 6.68 (1H, d, J = 9.3 Hz), 6.47 (1H, d, J = 5.9 Hz), 4.21 (1H, d q, J = 13.2, 7.1 Hz), 3.81 (3H, s), 3.54 (1H, dq, J = 13.2, 7.1 Hz), 1.12 (3H, t, J = 7.1 Hz). |
| 498 | $^1$H-NMR ($CDCl_3$) δ: 7.59 (1H, s), 7.41-7.32 (1H, m), 7.04 (1H, d, J = 5.1 Hz), 6.92-6.89 (2H, m), 6.70 (1H, d, J = 5.1 Hz), 3.45 (3H, s), 2.03 (3H, s). |
| 499 | $^1$H-NMR ($CDCl_3$) δ: 7.76 (1H, s), 7.16-7.10 (1H, m), 7.04 (1H, d, J = 5.6 Hz), 6.88-6.81 (2H, m), 6.49 (1H, dd, J = 5.6, 0.7 Hz), 4.08-4.01 (1H, m) 3.84-3.81 (1H, m), 1.17 (3H, t, J = 7.1 Hz). |
| 500 | $^1$H-NMR ($CDCl_3$) δ: 7.32 (1H, d, J = 9.5 Hz), 7.15-7.12 (1H, m), 7.02 (1H, d, J = 5.6 Hz), 6.86-6.82 (2H, m), 6.70 (1H, d, J = 9.5 Hz), 6.48 (1H, d, J = 5.6 Hz), 4.04-3.97 (1H, m), 3.78-3.75 (1H, m), 1.14 (3H, t, J = 7.1 Hz). |
| 501 | $^1$H-NMR ($CDCl_3$) δ: 7.55 (1H, s), 7.15-7.11 (1H, m), 7.04 (1H, d, J = 5.6 Hz), 6.88-6.81 (2H, m), 6.49 (1H, d, J = 5.6 Hz), 4.00-3.88 (2H, m), 1.17 (3H, t, J = 7.1 Hz). |
| 502 | $^1$H-NMR ($CDCl_3$) δ: 7.58 (1H, s), 7.09 (1H, d, J = 8.6 Hz), 6.91 (1H, d, J = 2.4 Hz), 6.83 (1H, d, J = 5.5 Hz), 6.76 (1H, dd, J = 8.6, 2.4 Hz), 6.48 (1H, d, J = 5.5 Hz), 4.25 (1H, dq, J = 13.1, 7.0 Hz), 3.81 (3H, s), 3.60 (1H, dq, J = 13.1, 7.0 Hz), 1.14 (3H, t, J = 7.0 Hz). |
| 503 | $^1$H-NMR ($CDCl_3$) δ: 7.28-7.26 (1H, m), 7.10-7.04 (1H, m), 6.86-6.78 (3H, m), 6.68 (1H, d, J = 9.5 Hz), 6.47 (1H, d, J = 5.4 Hz), 4.04-4.00 (1H, m), 3.79-3.75 (1H, m), 2.22 (3H, s), 1.14 (3H, t, J = 7.1 Hz). |

TABLE 6-continued

| Compound | $^1$H-NMR |
|---|---|
| 504 | $^1$H-NMR ($CDCl_3$) δ: 7.78 (1H, s), 7.09 (1H, d, J = 8.6 Hz), 6.91 (1H, d, J = 2.8 Hz), 6.83 (1H, d, J = 5.8 Hz), 6.76 (1H, dd, J = 8.6, 2.4 Hz), 6.48 (1H, d, J = 5.8 Hz), 4.26-4.23 (1H, m), 3.81 (3H, s), 3.62-3.59 (1H, m), 1.14 (3H, t, J = 7.0 Hz). |
| 505 | $^1$H-NMR ($CDCl_3$) δ: 7.42 (1H, d, J = 9.5 Hz), 7.24 (1H, s), 7.17-7.15 (1H, m), 6.93 (1H, s), 6.89-6.86 (2H, m), 6.69 (1H, d, J = 9.5 Hz), 4.04-4.02 (1H, m), 3.71-3.68 (1H, m), 1.93 (3H, s), 1.13 (3H, t, J = 7.0 Hz). |
| 506 | $^1$H-NMR ($CDCl_3$) δ: 7.30 (1H, d, J = 9.8 Hz), 7.24 (1H, s), 7.19-7.18 (1H, m), 6.86-6.83 (2H, m), 6.70 (1H, d, J = 9.8 Hz), 4.12-4.11 (1H, m), 3.70-3.67 (1H, m), 1.89 (3H, s), 1.14 (3H, t, J = 7.0 Hz). |
| 507 | $^1$H-NMR ($CDCl_3$) δ: 7.57 (1H, s), 7.43 (1H, s), 7.42-7.41 (1H, m), 7.35-7.34 (1H, m), 7.24 (1H, s), 4.15-4.12 (1H, m), 3.72-3.69 (1H, m), 1.87 (3H, s), 1.17 (3H, t, J = 7.0 Hz). |
| 508 | $^1$H-NMR ($CDCl_3$) δ: 7.67 (1H, s), 7.51-7.46 (2H, m), 7.35 (1H, dd, J = 7.9, 6.7 Hz) 7.29 (1H, d, J = 4.2 Hz), 7.15 (1H, d, J = 4.9 Hz), 4.04 (1H, dq, J = 13.8, 7.1 Hz), 3.74 (1H, dq, J = 13.8, 7.1 Hz), 1.17 (3H, t, J = 7.1 Hz). |
| 509 | $^1$H-NMR ($CDCl_3$) δ: 7.75 (1H, s), 7.43 (1H, td, J = 8.3, 5.9 Hz), 7.34-7.32 (1H, m), 7.31-7.28 (1H, m), 7.17 (1H, d, J = 4.9 Hz), 7.11 (1H, td, J = 8.4, 0.9 Hz), 3.41 (3H, s). |
| 510 | $^1$H-NMR ($CDCl_3$) δ: 7.94 (1H, s), 7.43 (1H, td, J = 8.3, 6.1 Hz), 7.34-7.31 (1H, m), 7.30-7.27 (1H, m), 7.17 (1H, d, J = 4.9 Hz), 7.11 (1H, td, J = 8.3, 1.0 Hz), 3.41 (3H, s). |
| 511 | $^1$H-NMR ($CDCl_3$) δ: 7.52 (1H, d, J = 9.8 Hz), 7.25 (1H, s), 7.10-7.08 (1H, m), 6.96-6.89 (2H, m), 6.75 (1H, s), 6.69 (1H, d, J = 9.8 Hz), 3.24 (3H, s), 2.13 (3H, s), 1.91 (3H, s). |
| 512 | $^1$H-NMR ($CDCl_3$) δ: 7.56 (1H, s), 7.22 (1H, s), 7.11-7.09 (1H, br m), 6.93-6.91 (1H, m), 6.86-6.84 (1H, m), 3.31 (3H, s), 2.21 (3H, s), 1.89 (3H, s). |
| 513 | $^1$H-NMR ($CDCl_3$) δ: 7.98 (1H, s), 7.26 (1H, s), 7.10-7.07 (1H, m), 6.95-6.92 (2H, m), 6.73 (1H, s), 3.31 (3H, s), 2.12 (3H, s), 1.90 (3H, s). |
| 514 | $^1$H-NMR ($CDCl_3$) δ: 7.75 (1H, s), 7.22 (1H, s), 7.11-7.09 (1H, m), 6.93-6.90 (1H, m), 6.86-6.84 (1H, m), 3.31 (3H, s), 2.21 (3H, s), 1.89 (3H, s). |
| 515 | $^1$H-NMR ($CDCl_3$) δ: 7.76 (1H, s), 7.25 (1H, s), 7.23-7.21 (1H, br m), 7.19-7.17 (1H, m), 6.98-6.94 (1H, m), 3.40 (3H, s), 1.90 (3H, s). |

Next, it specifically shows that the compounds of the present invention are effective against plant diseases, but the invention is not limited to these examples.

[Test Example A] Blast on Rice

Seeds of a test plant (rice variety: Sachikaze) were planted and cultivated until the second leaves appeared. In the test, the compounds of the present invention were dissolved into a dimethyl sulfoxide-methanol mixture solution (volume ratio: 9/1), and the resultant solutions were diluted with well water to a concentration of 250 ppm. The dilutions thus obtained were sprayed to the test plant (2.5 ml/pot). After the dilutions dried, a conidial suspension (1-2×$10^5$ conidia/ml) of *Magnaporthe grisea* was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

[Test Example B] Gray Mold on Tomato

Seeds of a test plant (tomato variety: Oogata Fukuju) were planted and cultivated until three to five first leaves (true leaves) appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (4-8×$10^5$ conidia/ml) of *Botrytis cinerea* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

[Test Example C] *Alternaria* Sooty Spot on Cabbage

Seeds of a test plant (cabbage variety: Shikidori) were planted and cultivated until the cotyledons extended. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (4-8×$10^5$ conidia/ml) of *Alternaia brassicicola* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

[Test Example D] Powdery Mildew on Barley

Seeds of a test plant (barley variety: Akashinriki) were planted and cultivated until the first leaves appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, conidia of *Blumeria graminis* f. sp. *hordei* were inoculated to the plant by shaking off. The disease development was investigated 6 to 10 days after the inoculation, and the effectiveness of the dilutions was evaluated.

[Test Example E] Brown Rust on Wheat

Seeds of a test plant (wheat variety: Norin 61) were planted and cultivated until the first leaves appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a urediniospore suspension (1-2×$10^5$ urediniospores/ml) of *Puccinia recondita* was inoculated to the plant by spraying. After the inoculation, the plant was kept in a mist chamber at room temperature of 20 to 23° C. for about 24 hours to promote the onset of disease. The disease development was investigated 7 to 10 days after the inoculation, and the effectiveness of the dilutions was evaluated.

[Test Example F] Late Blight on Tomato

Seeds of a test plant (tomato variety: Oogata Fukuju) were planted and cultivated until three to five first leaves appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension (4-8×$10^3$ zoosporangia/ml) of *Phytophthora infestans* was inoculated to the plant by spraying. After the inoculation, the plant was kept in a mist chamber at room temperature of 20° C. for about 24 hours to promote the onset of disease. The disease development was investigated 5 to 10 days after the inoculation, and the effectiveness of the dilutions was evaluated.

[Test Example G] Downy Mildew on Vine

Seeds of a test plant (grape variety: Neomuscat) were planted and cultivated until three to four first leaves appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension (1-2×$10^4$ zoosporangia/ml) of *Plasmopara viticola* was inoculated to the plant by spraying. After the inoculation, the plant was kept in a mist chamber at room temperature of 20° C. for about 24 hours to promote the onset of disease. The disease development was investigated 7 to 10 days after the inoculation, and the effectiveness of the dilutions was evaluated.

[Test Example H] Anthracnose on Cucumber

Seeds of a test plant (cucumber variety: Sagami Hanjiro) were planted and cultivated until the first leaf appeared. In the test, the compounds of the present invention were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (2-4×$10^5$ conidia/ml) of *Colletotrichum orbiculare* was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

Disease development in Test Example described above was evaluated in increments of 0.05 by setting 0 as no incidence of disease and 3 as disease development in a plant of untreated group. In addition, control values were calculated using the following equation based on disease development.

<Control Value>

Control value=100 {1−(n/3)} n=Disease development of each treated groups

A summary of test results described above is shown in Table 7. In the table, H shows the control value more than 50%, and L shows the control value of 50% or less. Also, nt shows that no test was performed.

TABLE 7

| Compound | Test A | Test B | Test C | Test D | Test E | Test F | Test G | Test H |
|---|---|---|---|---|---|---|---|---|
| 1 | H | L | L | L | L | L | L | H |
| 2 | H | L | L | H | H | L | H | H |
| 3 | H | L | L | L | H | L | H | L |
| 4 | H | L | L | H | H | L | H | H |
| 5 | H | H | H | H | H | H | H | H |
| 6 | H | H | H | L | H | L | L | L |
| 7 | H | H | H | L | H | L | L | L |
| 8 | H | H | H | L | L | L | H | L |
| 9 | H | H | H | H | L | L | L | H |
| 10 | H | H | H | L | L | L | L | H |
| 11 | H | L | H | H | H | L | L | L |
| 12 | H | H | H | L | H | L | L | H |
| 13 | H | H | H | L | H | L | L | H |
| 14 | L | H | L | H | H | L | H | L |
| 15 | L | H | L | H | H | L | L | H |
| 16 | L | H | H | H | H | L | L | H |
| 17 | nt | H | nt | H | H | nt | nt | nt |
| 18 | H | H | H | H | H | L | L | H |
| 19 | H | H | H | H | H | L | L | H |
| 20 | H | H | H | H | H | L | L | H |
| 21 | H | H | H | H | H | L | H | H |
| 22 | H | H | H | H | H | L | H | H |
| 23 | H | H | H | H | H | L | L | H |
| 24 | H | H | H | H | H | L | H | H |
| 25 | L | L | H | H | L | L | L | H |
| 26 | H | H | H | H | H | L | L | H |
| 27 | L | H | H | H | H | L | L | H |
| 28 | H | H | H | H | H | L | L | H |
| 29 | H | H | H | H | H | L | L | H |
| 30 | L | L | L | H | L | L | L | L |
| 31 | L | H | H | H | L | L | L | H |
| 32 | L | H | H | L | H | L | L | L |
| 33 | H | L | H | L | L | L | L | L |
| 34 | H | H | H | H | H | L | L | H |
| 35 | H | H | H | H | H | L | L | H |
| 36 | H | L | H | L | H | L | L | H |
| 37 | H | H | H | L | H | L | L | H |
| 38 | H | L | L | L | L | L | L | L |
| 39 | H | H | H | L | H | L | L | H |
| 40 | H | H | H | H | H | L | L | H |
| 41 | H | H | H | H | H | L | L | H |
| 42 | L | H | H | L | H | L | L | H |
| 43 | H | H | H | H | H | L | L | H |
| 44 | H | H | H | H | H | L | H | H |
| 45 | H | H | H | H | H | L | L | L |
| 46 | H | H | H | H | H | L | H | H |
| 47 | L | H | H | H | H | L | L | H |
| 48 | H | H | H | H | H | L | H | H |
| 49 | H | H | H | H | H | L | H | H |
| 50 | H | H | H | H | H | L | H | H |
| 51 | H | H | H | H | H | L | H | H |
| 52 | H | H | H | H | H | L | L | H |

TABLE 7-continued

| Compound | Test A | Test B | Test C | Test D | Test E | Test F | Test G | Test H |
|---|---|---|---|---|---|---|---|---|
| 53 | H | H | H | L | H | L | L | H |
| 54 | H | H | H | H | H | L | L | L |
| 55 | H | H | H | H | H | L | L | H |
| 56 | H | H | H | H | H | L | H | H |
| 57 | H | H | H | H | H | L | L | H |
| 58 | H | H | L | H | H | L | L | H |
| 59 | H | H | H | H | H | L | L | H |
| 60 | L | H | L | H | L | L | L | L |
| 61 | H | H | H | H | H | L | H | H |
| 62 | H | H | H | H | H | L | H | H |
| 63 | H | H | H | H | H | L | H | H |
| 64 | H | H | L | H | H | L | L | L |
| 65 | H | H | H | H | H | L | H | H |
| 66 | H | nt | H | nt | nt | L | H | H |
| 67 | H | H | H | H | H | L | H | H |
| 68 | H | H | H | H | H | L | L | H |
| 69 | H | H | H | H | H | L | L | H |
| 70 | H | H | H | H | H | L | L | L |
| 71 | H | H | H | H | H | L | L | H |
| 72 | H | H | H | H | H | L | L | H |
| 73 | H | H | H | H | H | L | L | H |
| 74 | H | H | H | H | H | L | H | H |
| 75 | H | H | H | L | L | L | L | L |
| 76 | H | H | H | H | L | L | L | L |
| 77 | H | H | H | H | H | L | L | H |
| 78 | H | H | H | H | H | L | L | H |
| 79 | H | H | H | H | H | L | L | H |
| 80 | H | H | H | H | H | L | L | H |
| 81 | H | H | H | H | H | L | L | H |
| 82 | H | H | H | H | H | L | H | H |
| 83 | H | H | H | H | H | L | L | H |
| 84 | H | H | H | H | H | L | L | H |
| 85 | H | H | H | H | H | L | L | H |
| 86 | H | H | H | H | H | L | L | H |
| 87 | L | L | H | L | L | L | L | L |
| 88 | L | L | H | L | L | L | L | L |
| 89 | H | H | H | L | H | L | L | H |
| 90 | L | H | H | L | H | L | L | H |
| 91 | L | L | H | L | L | L | L | L |
| 92 | L | H | L | L | L | L | L | L |
| 93 | L | H | H | H | L | L | L | H |
| 94 | H | H | H | H | H | L | L | H |
| 95 | H | H | H | H | L | L | L | H |
| 96 | H | L | L | L | L | L | L | L |
| 97 | H | H | H | H | H | L | H | H |
| 98 | H | H | H | H | H | L | L | H |
| 99 | H | H | H | H | H | L | H | H |
| 100 | H | H | H | H | H | L | L | H |
| 101 | H | H | H | H | H | L | L | H |
| 102 | H | H | H | L | L | L | H | H |
| 103 | H | H | H | H | H | L | L | H |
| 104 | H | H | H | H | H | L | L | H |
| 105 | L | H | H | L | H | nt | L | H |
| 106 | H | H | H | L | H | H | H | H |
| 107 | H | H | H | H | H | L | H | H |
| 108 | H | H | H | H | H | L | L | H |
| 109 | H | H | H | H | H | L | L | H |
| 110 | H | H | H | H | H | L | L | L |
| 111 | H | H | H | H | H | L | L | H |
| 112 | H | H | H | H | H | L | H | H |
| 113 | H | H | H | H | H | L | L | H |
| 114 | H | H | H | L | H | L | L | H |
| 115 | H | H | H | L | H | L | H | H |
| 116 | H | H | H | L | H | H | H | H |
| 117 | L | L | H | L | L | L | L | L |
| 118 | H | H | H | H | H | L | H | H |
| 119 | L | L | H | L | L | L | L | L |
| 120 | H | H | H | L | H | L | L | H |
| 121 | H | L | L | L | L | L | L | L |
| 122 | H | H | H | H | H | L | L | L |
| 123 | L | H | H | L | L | L | L | L |
| 124 | H | H | H | L | L | L | L | H |
| 125 | H | H | H | L | H | L | L | H |
| 126 | H | H | H | L | H | L | L | H |
| 127 | H | H | H | H | H | L | L | H |
| 128 | L | L | H | H | H | L | H | L |
| 129 | H | L | H | L | L | L | H | L |
| 130 | L | L | H | L | L | L | L | L |
| 131 | L | L | H | L | L | L | L | L |
| 132 | H | H | H | H | H | L | H | H |
| 133 | H | H | H | H | H | L | H | H |
| 134 | L | H | L | L | L | L | L | L |
| 135 | L | L | L | L | L | L | H | L |
| 136 | H | H | H | H | H | L | H | H |
| 137 | H | H | H | H | H | L | H | H |
| 138 | H | H | H | H | H | L | L | H |
| 139 | H | H | H | H | H | L | H | H |
| 140 | L | H | H | H | H | L | L | H |
| 141 | H | H | H | H | H | L | L | H |
| 142 | H | L | H | L | L | L | L | H |
| 143 | L | H | H | L | H | L | L | H |
| 144 | H | L | H | L | L | L | L | L |
| 145 | H | H | H | H | H | L | L | H |
| 146 | H | H | H | L | H | L | H | H |
| 147 | H | L | H | L | L | L | L | L |
| 148 | H | H | H | H | H | L | L | H |
| 149 | H | H | H | H | H | L | L | H |
| 150 | H | H | H | H | H | L | L | H |
| 151 | H | H | H | L | H | L | L | L |
| 152 | H | H | H | L | H | L | L | H |
| 153 | H | H | H | H | H | L | H | H |
| 154 | H | L | L | L | L | L | L | L |
| 155 | L | L | H | L | L | L | L | H |
| 156 | H | H | H | H | H | L | L | H |
| 157 | H | H | H | H | H | L | L | H |
| 158 | H | H | H | H | H | L | L | H |
| 159 | H | H | H | H | H | L | L | H |
| 160 | L | H | H | L | L | L | L | L |
| 161 | H | H | H | L | H | L | L | L |
| 162 | L | L | L | L | L | L | H | L |
| 163 | L | L | L | L | L | L | H | L |
| 164 | H | H | H | H | H | L | L | H |
| 165 | H | H | H | H | H | L | L | H |
| 166 | H | H | H | L | H | L | H | H |
| 167 | H | H | H | L | H | L | H | H |
| 168 | H | L | H | H | H | L | L | H |
| 169 | L | H | H | H | H | L | L | H |
| 170 | H | L | H | L | L | L | L | H |
| 171 | H | L | L | L | L | L | L | L |
| 172 | H | H | H | L | H | L | L | H |
| 173 | H | H | H | H | H | L | L | H |
| 174 | H | H | H | H | H | H | L | H |
| 175 | H | H | H | H | H | H | L | H |
| 176 | H | H | H | H | H | L | L | H |
| 177 | H | H | H | H | H | L | H | H |
| 178 | H | H | H | H | H | L | H | H |
| 179 | H | H | H | H | H | L | H | H |
| 180 | H | H | H | H | H | L | L | H |
| 181 | H | H | H | H | H | H | H | H |
| 182 | H | H | H | H | H | H | H | H |
| 183 | L | H | H | H | H | L | H | H |
| 184 | L | H | H | L | H | L | H | H |
| 185 | L | H | L | H | H | L | L | L |
| 186 | H | H | H | H | H | L | L | H |
| 187 | H | H | H | H | H | L | L | H |
| 188 | H | H | H | H | H | L | L | H |
| 189 | H | H | H | H | H | L | L | H |
| 190 | H | H | H | H | H | L | L | H |
| 191 | H | H | H | H | H | L | L | H |
| 192 | H | H | H | H | H | L | H | H |
| 193 | H | H | H | H | H | L | H | H |
| 194 | H | H | H | H | H | L | L | H |
| 195 | H | H | H | L | H | L | L | H |
| 196 | H | H | H | L | H | L | L | L |
| 197 | H | H | H | H | H | L | L | H |
| 198 | L | L | H | L | L | L | L | L |
| 199 | L | L | H | L | L | L | L | L |
| 200 | H | H | H | H | H | L | L | H |
| 201 | H | H | H | H | H | L | L | H |
| 202 | H | H | H | H | H | L | L | H |
| 203 | H | H | H | H | H | L | L | H |
| 204 | L | H | H | L | L | L | L | H |
| 205 | L | H | H | L | H | L | L | L |
| 206 | H | H | H | H | H | L | L | H |

TABLE 7-continued

| Compound | Test A | Test B | Test C | Test D | Test E | Test F | Test G | Test H |
|---|---|---|---|---|---|---|---|---|
| 207 | H | H | H | H | H | L | H | H |
| 208 | H | H | H | H | H | L | L | H |
| 209 | H | H | H | H | H | L | L | H |
| 210 | L | H | L | L | H | L | L | H |
| 211 | H | L | H | H | H | L | L | L |
| 212 | H | L | H | H | L | L | L | L |
| 213 | H | H | H | H | H | L | L | H |
| 214 | H | L | H | H | H | L | H | L |
| 215 | H | H | H | H | H | H | H | H |
| 216 | L | H | H | H | H | L | L | H |
| 217 | L | H | H | H | H | L | L | L |
| 218 | H | L | H | L | L | L | L | L |
| 219 | L | L | L | L | L | L | H | L |
| 220 | H | H | H | H | H | L | L | H |
| 221 | L | L | H | L | L | L | L | L |
| 222 | H | H | H | H | H | L | L | H |
| 223 | H | L | H | L | L | L | H | L |
| 224 | L | H | H | H | H | L | H | H |
| 225 | L | L | H | H | H | L | H | L |
| 226 | H | H | H | H | H | L | H | H |
| 227 | L | H | H | H | H | L | L | L |
| 228 | H | H | H | H | H | L | L | H |
| 229 | H | H | H | H | H | L | L | H |
| 230 | H | H | H | H | H | L | H | H |
| 231 | H | H | H | H | H | L | L | L |
| 232 | H | H | H | H | H | L | L | L |
| 233 | H | H | H | H | H | L | L | L |
| 234 | L | H | H | H | H | L | L | L |
| 235 | H | H | H | H | H | L | L | L |
| 236 | H | H | H | H | H | L | H | H |
| 237 | L | L | H | L | L | L | L | L |
| 238 | H | H | H | H | H | L | L | H |
| 239 | H | H | H | H | H | L | L | H |
| 240 | L | H | H | H | H | L | L | H |
| 241 | L | H | L | L | H | L | L | L |
| 242 | L | H | L | L | L | L | L | L |
| 243 | L | H | H | L | H | L | L | L |
| 244 | H | H | H | H | H | L | L | H |
| 245 | H | H | H | H | H | L | L | H |
| 246 | L | L | L | L | L | L | L | H |
| 247 | L | H | L | L | L | L | L | L |
| 248 | H | H | H | H | H | L | L | H |
| 249 | L | H | H | H | H | L | L | L |
| 250 | H | H | H | H | H | L | L | H |
| 251 | H | H | H | H | H | L | L | H |
| 252 | H | H | H | H | H | L | L | H |
| 253 | L | H | H | L | H | L | L | L |
| 254 | H | H | H | H | H | L | H | H |
| 255 | H | H | H | H | H | L | H | H |
| 256 | H | H | H | H | H | L | L | H |
| 257 | L | H | L | L | L | L | L | H |
| 258 | L | L | L | L | H | L | L | L |
| 259 | L | L | H | H | H | L | L | L |
| 260 | L | L | H | L | L | L | L | L |
| 261 | H | H | H | H | H | L | L | H |
| 262 | H | H | H | H | H | L | L | H |
| 263 | H | H | H | H | H | L | L | H |
| 264 | H | H | H | L | H | L | L | H |
| 265 | L | L | H | H | H | L | L | L |
| 266 | H | H | H | H | H | L | H | H |
| 267 | H | H | H | H | H | L | L | H |
| 268 | L | L | H | H | H | L | L | L |
| 269 | H | H | H | H | H | L | L | L |
| 270 | H | H | H | H | H | L | L | H |
| 271 | H | H | H | H | H | L | H | H |
| 272 | H | H | H | H | H | L | L | H |
| 273 | H | H | H | H | H | L | L | L |
| 274 | H | H | H | H | H | L | L | L |
| 275 | H | H | H | H | H | L | L | L |
| 276 | L | L | H | H | L | L | L | L |
| 277 | H | H | H | H | H | L | H | L |
| 278 | H | H | H | H | H | L | H | L |
| 279 | H | H | H | L | H | L | L | H |
| 280 | H | L | H | L | H | L | L | H |
| 281 | L | L | H | H | L | L | L | L |
| 282 | H | H | H | H | H | L | L | H |
| 283 | H | H | H | H | H | L | L | H |

TABLE 7-continued

| Compound | Test A | Test B | Test C | Test D | Test E | Test F | Test G | Test H |
|---|---|---|---|---|---|---|---|---|
| 284 | H | H | H | H | H | L | L | H |
| 285 | H | H | H | H | H | L | L | H |
| 286 | H | H | H | H | H | L | L | H |
| 287 | H | H | H | L | H | L | L | H |
| 288 | H | H | H | L | H | L | L | H |
| 289 | L | L | H | H | H | L | L | L |
| 290 | L | L | H | H | H | H | L | L |
| 291 | L | L | H | L | L | L | L | L |
| 292 | L | H | H | H | H | L | L | L |
| 293 | H | H | H | H | H | L | L | L |
| 294 | H | L | H | H | H | L | L | L |
| 295 | L | H | H | H | H | L | H | L |
| 296 | H | H | H | H | H | L | H | H |
| 297 | L | L | L | L | H | L | L | L |
| 298 | H | H | H | L | H | L | L | H |
| 299 | H | H | H | L | H | L | L | H |
| 300 | H | H | H | H | H | L | L | H |
| 301 | H | H | H | H | H | L | L | H |
| 302 | H | H | H | H | H | L | H | H |
| 303 | L | L | H | H | H | L | L | L |
| 304 | L | L | H | H | L | L | L | L |
| 305 | L | L | H | H | H | L | L | L |
| 306 | H | H | H | H | H | L | L | H |
| 307 | H | H | H | H | H | L | L | H |
| 308 | H | H | H | H | H | L | L | H |
| 309 | H | H | H | H | H | L | L | L |
| 310 | H | H | H | H | H | L | L | H |
| 311 | H | H | H | H | H | L | L | H |
| 312 | H | H | H | H | H | L | L | H |
| 313 | H | H | H | H | H | L | L | H |
| 314 | H | H | H | H | H | L | L | H |
| 315 | H | H | H | H | H | L | L | H |
| 316 | H | H | H | H | H | L | L | H |
| 317 | L | H | H | L | H | L | L | H |
| 318 | L | H | H | H | H | H | L | H |
| 319 | H | H | H | H | H | L | L | H |
| 320 | H | H | H | H | H | L | L | H |
| 321 | L | L | L | L | L | L | L | H |
| 322 | L | H | H | H | H | L | L | L |
| 323 | H | H | H | H | H | H | H | H |
| 324 | L | L | L | L | L | L | H | H |
| 325 | L | L | H | L | L | L | L | L |
| 326 | H | H | H | H | H | L | L | H |
| 327 | H | H | H | H | H | L | L | H |
| 328 | H | H | H | H | H | L | L | H |
| 329 | H | H | H | L | L | L | L | H |
| 330 | H | H | H | H | H | L | L | H |
| 331 | H | H | H | H | H | L | H | H |
| 332 | H | H | H | H | H | L | H | H |
| 333 | H | H | H | H | H | L | H | H |
| 334 | H | H | H | H | H | L | L | H |
| 335 | H | H | H | H | H | L | H | H |
| 336 | H | H | H | H | H | H | H | H |
| 337 | H | H | H | H | H | H | H | H |
| 338 | H | H | H | H | H | L | L | H |
| 339 | H | H | H | H | H | L | L | H |
| 340 | H | H | H | H | H | L | H | H |
| 341 | H | H | H | H | H | H | L | H |
| 342 | H | H | H | H | H | L | L | H |
| 343 | H | H | H | H | H | L | H | H |
| 344 | H | H | H | H | H | L | H | H |
| 345 | H | H | H | H | H | L | H | H |
| 346 | H | H | H | H | H | L | H | H |
| 347 | H | H | H | H | H | L | H | H |
| 348 | H | H | H | L | H | L | L | L |
| 349 | H | H | H | L | H | L | H | H |
| 350 | L | H | H | H | H | L | H | H |
| 351 | H | H | H | H | H | L | L | H |
| 352 | H | H | H | H | H | L | L | H |
| 353 | H | H | H | H | H | L | L | H |
| 354 | H | H | H | H | H | L | H | H |
| 355 | H | H | H | L | H | L | L | H |
| 356 | L | H | H | H | H | L | L | L |
| 357 | H | H | H | H | H | L | L | H |
| 358 | H | H | H | L | H | L | L | H |
| 359 | H | H | H | H | H | H | H | H |
| 360 | H | H | H | H | H | L | L | H |

TABLE 7-continued

| Compound | Test A | Test B | Test C | Test D | Test E | Test F | Test G | Test H |
|---|---|---|---|---|---|---|---|---|
| 361 | H | H | H | H | H | L | L | H |
| 362 | H | H | H | H | H | L | H | H |
| 363 | H | H | H | L | H | L | L | H |
| 364 | H | H | H | H | H | L | H | H |
| 365 | H | H | H | H | H | L | H | H |
| 366 | H | H | H | H | H | L | H | H |
| 367 | L | L | H | H | L | L | L | L |
| 368 | L | nt | H | nt | nt | L | H | L |
| 369 | H | H | H | H | H | L | L | H |
| 370 | H | H | H | H | H | L | L | L |
| 371 | H | H | H | H | H | L | H | H |
| 372 | L | L | L | H | L | L | H | L |
| 373 | H | H | H | L | H | L | H | H |
| 374 | L | L | L | H | H | L | H | H |
| 375 | H | H | H | H | H | L | H | H |
| 376 | L | H | L | L | H | L | H | H |
| 377 | H | H | H | H | H | H | L | H |
| 378 | H | H | H | H | H | H | L | H |
| 379 | H | H | H | L | H | L | L | H |
| 380 | H | H | H | L | H | L | L | H |
| 381 | H | H | H | H | H | H | H | H |
| 382 | H | H | L | H | H | L | L | H |
| 383 | H | H | H | H | H | L | L | H |
| 384 | H | H | H | H | H | L | L | H |
| 385 | H | H | H | H | H | H | H | H |
| 386 | H | H | H | H | H | L | L | L |
| 387 | H | H | H | H | H | L | L | L |
| 388 | H | H | H | H | H | L | L | L |
| 389 | H | H | H | H | H | L | L | H |
| 390 | H | H | H | L | H | L | L | L |
| 391 | H | H | L | L | H | H | L | L |
| 392 | H | H | H | L | L | H | L | L |
| 393 | H | H | H | L | H | H | H | H |
| 394 | H | H | H | H | H | H | H | H |
| 395 | H | H | H | H | H | L | L | H |
| 396 | H | L | L | L | L | L | L | L |
| 397 | H | H | H | H | H | L | L | H |
| 398 | H | H | H | L | H | L | L | H |
| 399 | L | H | L | L | H | L | L | L |
| 400 | H | L | H | L | L | L | L | L |
| 401 | L | L | H | L | L | L | L | L |
| 402 | H | L | H | L | L | L | L | L |
| 403 | H | H | H | L | L | L | L | L |
| 404 | H | L | H | L | L | L | L | L |
| 405 | L | L | H | H | H | L | L | L |
| 406 | L | L | H | H | L | L | L | L |
| 407 | H | H | H | H | H | L | L | H |
| 408 | H | H | H | L | H | L | L | L |
| 409 | H | H | H | H | H | L | L | L |
| 410 | H | H | H | H | H | L | H | H |
| 411 | H | H | H | L | H | L | L | L |
| 412 | H | H | H | H | H | L | H | H |
| 413 | L | H | L | H | L | L | L | H |
| 414 | H | H | H | H | H | L | L | H |
| 415 | L | nt | L | nt | nt | H | L | H |
| 416 | H | H | H | H | H | L | H | H |
| 417 | H | nt | H | nt | nt | H | L | L |
| 418 | H | H | H | H | H | L | L | H |
| 419 | H | nt | H | nt | nt | L | L | H |
| 420 | H | nt | H | nt | nt | H | L | H |
| 421 | H | H | H | H | H | L | L | H |
| 422 | H | L | H | H | H | L | L | L |
| 423 | H | H | H | H | H | L | H | H |
| 424 | H | H | H | H | H | H | H | H |
| 425 | H | H | H | H | H | L | L | H |
| 426 | H | H | H | H | H | L | L | H |
| 427 | H | H | H | L | H | L | L | H |
| 428 | H | L | H | H | H | L | L | H |
| 429 | H | H | H | L | H | L | L | H |
| 430 | H | H | H | L | H | L | L | H |
| 431 | H | H | H | L | H | L | L | H |
| 432 | H | H | H | H | L | L | L | H |
| 433 | H | H | H | H | H | L | L | H |
| 434 | H | L | L | L | L | L | L | L |
| 435 | H | H | H | L | H | L | H | H |
| 436 | H | H | H | H | H | L | H | H |
| 437 | H | H | H | H | H | L | L | H |
| 438 | H | L | H | H | H | L | L | H |
| 439 | H | H | H | H | H | L | H | H |
| 440 | H | L | H | L | L | L | H | L |
| 441 | H | H | H | L | H | L | L | H |
| 442 | H | L | L | L | L | L | L | L |
| 443 | H | H | H | H | H | L | L | H |
| 444 | H | L | H | L | H | L | L | L |
| 445 | H | H | H | H | H | L | L | H |
| 446 | H | H | H | H | H | L | L | H |
| 447 | H | H | H | H | H | L | L | L |
| 448 | H | H | H | H | H | L | L | L |
| 449 | H | H | H | H | H | L | L | H |
| 450 | H | H | H | L | H | L | L | H |
| 451 | L | L | H | H | H | L | H | L |
| 452 | H | H | H | H | H | L | L | H |
| 453 | H | H | H | L | H | L | L | H |
| 454 | L | H | H | H | H | L | H | H |
| 455 | L | L | H | L | L | L | L | L |
| 456 | H | H | H | L | H | L | L | H |
| 457 | L | H | H | L | H | L | L | H |
| 458 | H | H | H | H | H | L | L | H |
| 459 | H | H | H | L | H | L | L | H |
| 460 | H | H | H | H | H | L | H | H |
| 461 | H | H | H | H | H | L | L | H |
| 462 | H | H | H | H | H | L | L | H |
| 463 | L | L | H | H | L | L | L | H |
| 464 | H | H | H | L | H | L | L | H |
| 465 | H | H | H | L | H | L | L | H |
| 466 | H | H | H | L | H | L | L | L |
| 467 | L | H | L | L | L | L | L | L |
| 468 | H | H | H | L | H | L | L | H |
| 469 | H | H | H | H | H | L | L | H |
| 470 | L | H | H | H | H | L | H | H |
| 471 | L | L | H | L | L | L | L | L |
| 472 | H | H | H | L | H | L | H | H |
| 473 | L | H | H | L | H | L | H | L |
| 474 | L | H | L | H | H | L | L | L |
| 475 | H | H | H | H | H | L | H | H |
| 476 | H | H | H | H | H | L | H | H |
| 477 | H | H | H | L | H | L | L | L |
| 478 | H | H | H | H | H | L | L | H |
| 479 | L | H | H | H | H | L | H | H |
| 480 | L | L | H | L | L | L | L | L |
| 481 | L | H | L | H | H | L | L | L |
| 482 | H | H | H | H | H | L | L | H |
| 483 | L | H | H | H | H | L | L | H |
| 484 | H | H | H | L | H | L | L | L |
| 485 | L | L | H | H | H | L | L | L |
| 486 | H | H | H | H | H | L | H | H |
| 487 | L | L | L | L | L | L | H | L |
| 488 | H | H | H | H | H | L | H | H |
| 489 | L | L | H | L | H | L | L | L |
| 490 | H | H | H | H | H | L | H | H |
| 491 | L | H | L | L | H | L | H | L |
| 492 | L | H | H | L | H | L | L | L |
| 493 | H | H | H | H | H | L | H | L |
| 494 | H | L | H | H | H | L | H | H |
| 495 | H | H | H | L | H | L | H | L |
| 496 | H | H | H | L | H | L | H | L |
| 497 | H | H | H | L | H | L | H | H |
| 498 | H | H | H | H | H | L | H | H |
| 499 | H | H | H | L | H | L | H | H |
| 500 | H | H | H | L | H | L | H | L |
| 501 | H | H | H | L | H | L | H | H |
| 502 | H | H | H | L | H | L | H | H |
| 503 | H | H | H | H | H | L | H | H |
| 504 | H | H | H | L | H | L | H | H |
| 505 | H | H | H | H | H | L | H | L |
| 506 | H | H | H | H | H | L | H | H |
| 507 | H | nt | H | nt | nt | L | H | H |
| 508 | L | L | H | L | H | L | L | H |
| 509 | L | H | H | H | H | L | H | H |
| 510 | L | H | H | H | H | L | L | H |
| 511 | L | L | L | H | L | L | L | L |
| 512 | H | H | H | H | H | L | L | H |
| 513 | L | L | H | L | H | L | L | L |

TABLE 7-continued

| Compound | Test A | Test B | Test C | Test D | Test E | Test F | Test G | Test H |
|---|---|---|---|---|---|---|---|---|
| 514 | H | H | H | H | H | L | L | H |
| 515 | H | H | H | H | H | L | H | H |

INDUSTRIAL APPLICABILITY

The pyridone compounds of the present invention are novel compounds and can treat or prevent plant diseases, thus being valuable as agricultural chemicals, for example, an agricultural and horticultural pest control agent, in particular, an agricultural and horticultural fungicide.

The entire contents of Japanese Patent Application No. 2017-78492 (filing date: Apr. 11, 2017) and Japanese Patent Application No. 2017-199795 (filing date: Oct. 13, 2017) are incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:

1. A compound represented by Formula (1)

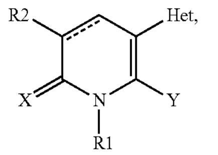

(1)

or a salt thereof wherein R1 represents a C1-C6 alkyl group optionally substituted with one substituent A, a C1-C6 haloalkyl group, or RaRbN— wherein Ra and Rb each independently represents a hydrogen atom, a C1-C6 alkyl group optionally substituted with one substituent B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group;

R2 represents a hydrogen atom, a halogen atom, a C1-C6 alkyl group optionally substituted with one substituent A, a C1-C6 haloalkyl group, a C2-C6 alkynyl group optionally substituted with one substituent A, a C1-C6 alkoxy group optionally substituted with one substituent A, or Rx1C(═O)— wherein Rx1 represents a hydrogen atom, a C1-C6 alkyl group optionally substituted with one substituent B, a C1-C6 haloalkyl group, a C3-C8 cycloalkyl group, a C1-C6 alkoxy group, a C1-C6 haloalkoxy group, a C3-C8 cycloalkoxy group or RaRbN— wherein Ra and Rb are the same as defined hereinabove;

Het represents a pyridyl group, a thienyl group, a pyrrolyl group, a pyrazolyl group, an imidazolyl group, a triazolyl group, a tetrazolyl group, an oxazolyl group or a 3 to 6-membered ring group containing 1 to 2 oxygen atoms, the pyridyl group is optionally substituted with 0 to 4 substituents R3 with the proviso that when two or more substituents R3 are present, each R3 represents an independent substituent, the thienyl group is optionally substituted with 0 to 3 substituents R3 with the proviso that when two or more substituents R3 are present, each R3 represents an independent substituent, the pyrrolyl group, the pyrazolyl group, the imidazolyl group, the triazolyl group or the tetrazolyl group is each independently and optionally substituted with 0 to 4 substituents R3 with the proviso that when two or more substituents R3 are present, each R3 represents an independent substituent, the oxazolyl group is optionally substituted with 0 to 2 substituents R3 with the proviso that when two substituents R3 are present, each R3 represents an independent substituent, R3 represents a cyano group, a nitro group, a halogen atom, a C1-C6 alkyl group optionally substituted with one substituent C, a C1-C6 haloalkyl group, a C1-C6 alkoxy group optionally substituted with one substituent C, RaRbN— wherein Ra and Rb each independently represents a hydrogen atom, a C1-C6 alkyl group optionally substituted with one substituent B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group, Rx1C(═O)— wherein Rx1 is the same as defined hereinabove, Rx2C(═O)N(Rx3)- wherein Rx2 represents a hydrogen atom, a C1-C6 alkyl group optionally substituted with one substituent B, a C1-C6 haloalkyl group, a C3-C8 cycloalkyl group, a C1-C6 alkoxy group, a C1-C6 haloalkoxy group, a C3-C8 cycloalkoxy group or RaRbN— wherein Ra and Rb are the same as defined hereinabove, Rx3 represents a hydrogen atom, a C1-C6 alkyl group optionally substituted with one substituent B, a C1-C6 haloalkyl group or a C3-C8 cycloalkyl group;

Y represents a phenyl group, the phenyl group is substituted with R4 at the ortho position and further optionally substituted with 0 to 4 substituents R5 with the proviso that when two or more substituents R5 are present, each R5 represents an independent substituent, R4 represents a cyano group, a nitro group, a halogen atom, a C1-C6 alkyl group optionally substituted with one substituent C, a C1-C6 haloalkyl group, or a C1-C6 alkoxy group optionally substituted with one substituent C, R5 represents a hydroxyl group, a cyano group, a halogen atom, a C1-C6 alkyl group optionally substituted with one substituent C, a C1-C6 alkoxy group optionally substituted with one substituent C, a C2-C6 alkenyloxy group optionally substituted with one substituent C, a C3-C6 alkynyloxy group optionally substituted with one substituent C, RaRbN— wherein Ra and Rb are the same as defined hereinabove, Rc-L- wherein Rc represents a C1-C6 alkyl group or a C1-C6 haloalkyl group and L represents S, SO or $SO_2$, or Rx1C(=O)O— wherein Rx1 is the same as defined hereinabove;

X represents an oxygen atom or a sulfur atom;

a bond containing the broken line represents a double bond or a single bond;

and the substituent A is at least one selected from the group consisting of a hydroxyl group, a cyano group, a C3-C8 cycloalkyl group, a C1-C6 alkoxy group, a C1-C6 haloalkoxy group, a C3-C8 cycloalkoxy group, RaRbN— wherein Ra and Rb are the same as defined hereinabove and Rc-L- wherein Rc and L are the same as defined hereinabove;

the substituent B is at least one selected from the group consisting of a cyano group, a C1-C6 alkoxy group, a C1-C6 haloalkoxy group and a C3-C8 cycloalkoxy group;

the substituent C is at least one selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— wherein Ra and Rb are the same as defined hereinabove, Rc-L- wherein Rc and L are the same as defined hereinabove, Rx1C(=O)— wherein Rx1 is the same as defined hereinabove and a 3 to 6-membered ring group containing 1 to 2 oxygen atoms;

the substituent D is at least one selected from the group consisting of a hydroxyl group, a cyano group, a nitro group, a halogen atom, a C1-C6 alkyl group which may be substituted with one substituent B, a C1-C6 haloalkyl group, a C3-C8 cycloalkyl group, a C1-C6 alkoxy group, a C1-C6 haloalkoxy group and a C3-C8 cycloalkoxy group.

2. A compound represented by Formula (2)

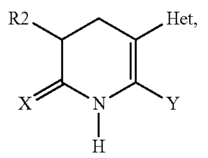

(2)

or a salt thereof wherein R2 represents a hydrogen atom, a halogen atom, a C1-C6 alkyl group optionally substituted with one substituent A, a C1-C6 haloalkyl group, a C2-C6 alkynyl group optionally substituted with one substituent A, a C1-C6 alkoxy group optionally substituted with one substituent A, or Rx1C(=O)— wherein Rx1 represents a hydrogen atom, a C1-C6 alkyl group optionally substituted with one substituent B, a C1-C6 haloalkyl group, a C3-C8 cycloalkyl group, a C1-C6 alkoxy group, a C1-C6 haloalkoxy group, a C3-C8 cycloalkoxy group or RaRbN— wherein Ra and Rb each independently represents a hydrogen atom, a C1-C6 alkyl group optionally substituted with one substituent B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group;

Het represents a pyridyl group, a thienyl group, a pyrrolyl group, a pyrazolyl group, an imidazolyl group, a triazolyl group, a tetrazolyl group, an oxazolyl group or a 3 to 6-membered ring group containing 1 to 2 oxygen atoms, the pyridyl group is optionally substituted with 0 to 4 substituents R3 with the proviso that when two or more substituents R3 are present, each R3 represents an independent substituent, the thienyl group is optionally substituted with 0 to 3 substituents R3 with the proviso that when two or more substituents R3 are present, each R3 represents an independent substituent, the pyrrolyl group, the pyrazolyl group, the triazolyl group or the tetrazolyl group is each independently and optionally substituted with 0 to 4 substituents R3 with the proviso that when two or more substituents R3 are present, each R3 represents an independent substituent, the imidazolyl group is substituted with 1 to 3 substituents R3 with the proviso that when two or more substituents R3 are present, each R3 represents an independent substituent, the oxazolyl group is optionally substituted with 0 to 2 substituents R3 with the proviso that when two substituents R3 are present, each R3 represents an independent substituent, R3 represents a cyano group, a nitro group, a halogen atom, a C1-C6 alkyl group optionally substituted with one substituent C, a C1-C6 haloalkyl group, a C1-C6 alkoxy group optionally substituted with one substituent C, RaRbN— wherein Ra and Rb each independently represents a hydrogen atom, a C1-C6 alkyl group optionally substituted with one substituent B, a C1-C6 haloalkyl group or a C3-C8 cycloalkyl group or Ra and Rb together with the nitrogen atom to which they are bonded form an aziridinyl group, an azetidinyl group, a pyrrolidinyl group, a piperidinyl group, a homopiperidinyl group or an azocanyl group, Rx1C(=O)— wherein Rx1 is the same as defined hereinabove, or Rx2C(=O)N(Rx3)- wherein Rx2 represents a hydrogen atom, a C1-C6 alkyl group optionally substituted with one substituent B, a C1-C6 haloalkyl group, a C3-C8 cycloalkyl group, a C1-C6 alkoxy group, a C1-C6 haloalkoxy group, a C3-C8 cycloalkoxy group or RaRbN— wherein Ra and Rb are the same as defined hereinabove, Rx3 represents a hydrogen atom, a C1-C6 alkyl group optionally substituted with one substituent B, a C1-C6 haloalkyl group or a C3-C8 cycloalkyl group;

Y represents a phenyl group, the phenyl group is substituted with R4 at the ortho position and further optionally substituted with 0 to 4 substituents R5 with the proviso that when two or more substituents R5 are present, each R5 represents an independent substituent, R4 represents a cyano group, a nitro group, a halogen atom, a C1-C6 alkyl group optionally substituted with one substituent C, a C1-C6 haloalkyl group, or a C1-C6 alkoxy group optionally substituted with one substituent C, R5 represents a hydroxyl group, a cyano group, a halogen atom, a C1-C6 alkyl group optionally substituted with one substituent C, a C1-C6 alkoxy group optionally substituted with one substituent C, a C2-C6 alkenyloxy group optionally substituted with one substituent C, a C3-C6 alkynyloxy group optionally substituted with one substituent C, RaRbN— wherein Ra and Rb are the same as defined hereinabove, Rc-L- wherein Rc represents a C1-C6 alkyl group or a C1-C6 haloalkyl group and L represents S, SO or $SO_2$, or Rx1C(═O)O— wherein Rx1 is the same as defined hereinabove;

X represents an oxygen atom or a sulfur atom;

and the substituent is at least one selected from the group consisting of a hydroxyl group, a cyano group, a C3-C8 cycloalkyl group, a C1-C6 alkoxy group, a C1-C6 haloalkoxy group, a C3-C8 cycloalkoxy group, RaRbN— wherein Ra and Rb are the same as defined hereinabove) and Rc-L- wherein Rc and L are the same as defined hereinabove;

the substituent B is at least one selected from the group consisting of a cyano group, a C1-C6 alkoxy group, a C1-C6 haloalkoxy group and a C3-C8 cycloalkoxy group;

the substituent C is at least one selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— wherein Ra and Rb are the same as defined hereinabove, Rc-L- wherein Rc and L are the same as defined hereinabove), Rx1C(═O)— wherein Rx1 is the same as defined hereinabove and a 3 to 6-membered ring group containing 1 to 2 oxygen atoms; and the substituent D is at least one selected from the group consisting of a hydroxyl group, a cyano group, a nitro group, a halogen atom, a C1-C6 alkyl group which may be substituted with one substituent B, a C1-C6 haloalkyl group, a C3-C8 cycloalkyl group, a C1-C6 alkoxy group, a C1-C6 haloalkoxy group and a C3-C8 cycloalkoxy group.

3. An agricultural and horticultural pest control agent containing the compound or a salt thereof according to claim 1 as an active ingredient.

4. An agricultural and horticultural fungicide containing the compound or a salt thereof according to claim 1 as an active ingredient.

5. A method for preventing and/or treating a plant disease, which comprises applying the agricultural and horticultural pest control agent according to claim 3 to a plant, a plant seed or a soil for plant cultivation.

6. A method for preventing and/or treating a plant disease, which comprises applying the agricultural and horticultural fungicides according to claim 4 to a plant, a plant seed or a soil for plant cultivation.

* * * * *